US009556169B2

(12) United States Patent
Chatterjee et al.

(10) Patent No.: US 9,556,169 B2
(45) Date of Patent: *Jan. 31, 2017

(54) COMPOUNDS AND COMPOSITIONS FOR THE TREATMENT OF PARASITIC DISEASES

(71) Applicant: NOVARTIS AG, Basel (CH)

(72) Inventors: Arnab Kumar Chatterjee, San Diego, CA (US); Advait Suresh Nagle, San Diego, CA (US); Prasuna Paraselli, San Diego, CA (US); Ravinder Reddy Kondreddi, Singapore (SG); Seh Yong Leong, Singapore (SG); Pranab Kumar Mishra, Holland, PA (US); Robert Joseph Moreau, Walnut Creek, CA (US); Jason Thomas Roland, San Diego, CA (US); Wei Lin Sandra Sim, Singapore (SG); Oliver Simon, Singapore (SG); Jocelyn Liying Tan, Singapore (SG); Bryan K S Yeung, Singapore (SG); Bin Zou, Singapore (SG); Venkatataiah Bollu, San Diego, CA (US)

(73) Assignee: Novartis AG, Basel (CH)

( * ) Notice: Subject to any disclaimer, the term of this patent is extended or adjusted under 35 U.S.C. 154(b) by 59 days.

This patent is subject to a terminal disclaimer.

(21) Appl. No.: 14/443,609

(22) PCT Filed: Nov. 18, 2013

(86) PCT No.: PCT/US2013/070601
§ 371 (c)(1),
(2) Date: May 18, 2015

(87) PCT Pub. No.: WO2014/078802
PCT Pub. Date: May 22, 2014

(65) Prior Publication Data
US 2015/0344471 A1    Dec. 3, 2015

Related U.S. Application Data

(60) Provisional application No. 61/728,018, filed on Nov. 19, 2012, provisional application No. 61/847,860, filed on Jul. 18, 2013.

(51) Int. Cl.
C07D 471/04 (2006.01)
C07D 519/00 (2006.01)

(52) U.S. Cl.
CPC ........... C07D 471/04 (2013.01); C07D 519/00 (2013.01)

(58) Field of Classification Search
None
See application file for complete search history.

(56) References Cited

U.S. PATENT DOCUMENTS

| | | | |
|---|---|---|---|
| 6,348,474 B1 | 2/2002 | Kayakiri et al. | |
| 7,074,801 B1 | 7/2006 | Yoshida et al. | |
| 7,105,550 B2 * | 9/2006 | Love | C07D 277/42 514/365 |
| 7,662,826 B2 | 2/2010 | Seno et al. | |
| 7,713,975 B1 | 5/2010 | Hellberg et al. | |
| 8,088,385 B2 | 1/2012 | Chesney et al. | |
| 2004/0209878 A1 | 10/2004 | Guzi et al. | |
| 2007/0219218 A1 | 9/2007 | Yu et al. | |
| 2008/0153813 A1 | 6/2008 | Chen et al. | |
| 2010/0184800 A1 | 7/2010 | Pracitto | |
| 2012/0059162 A1 | 3/2012 | Kusakabe et al. | |

FOREIGN PATENT DOCUMENTS

| | | |
|---|---|---|
| EP | 1217000 | 6/2002 |
| EP | 1939175 | 7/2008 |
| JP | 2001139575 | 5/2001 |
| JP | 2009298710 | 12/2009 |
| RU | 2421455 | 6/2011 |
| WO | 9634866 | 11/1996 |
| WO | 9803510 | 1/1998 |
| WO | 9900372 | 7/1999 |
| WO | 0156555 | 8/2001 |
| WO | 0156573 | 8/2001 |
| WO | 0183479 | 11/2001 |
| WO | 0210170 | 2/2002 |
| WO | 0218382 | 3/2002 |
| WO | 02088107 | 11/2002 |
| WO | 03045950 | 6/2003 |

(Continued)

OTHER PUBLICATIONS

Belanger, et al., "Discovery of imidazo[1,2-a]pyrazine-based Aurora kinase inhibitors", Bioorganic & Medicinal Chemistry Letters, 2010, pp. 5170-5174, vol. 20, Elsevier Ltd.

(Continued)

*Primary Examiner* — Timothy R Rozof
(74) *Attorney, Agent, or Firm* — Chihang Amy Smith; Genomics Institute of the Novartis Research Foundation

(57) ABSTRACT

The present invention provides compounds of formula I:

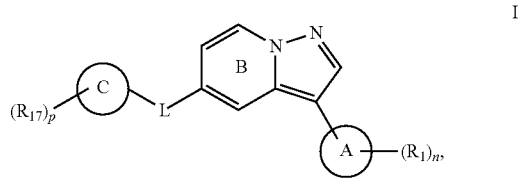

or a pharmaceutically acceptable salt, tautomer, or stereoisomer, thereof, wherein the variables are as defined herein. The present invention further provides pharmaceutical compositions comprising such compounds and methods of using such compounds for treating, preventing, inhibiting, ameliorating, or eradicating the pathology and/or symptomology of a disease caused by a *Plasmodium* parasite, such as malaria.

17 Claims, No Drawings

(56) References Cited

FOREIGN PATENT DOCUMENTS

| | | |
|---|---|---|
| WO | 03091256 | 6/2003 |
| WO | 2004026871 | 4/2004 |
| WO | 2004069837 | 8/2004 |
| WO | 2004069838 | 8/2004 |
| WO | 2006017443 | 2/2006 |
| WO | 2006044509 | 4/2006 |
| WO | 2006049339 | 5/2006 |
| WO | 2006070943 | 7/2006 |
| WO | 2007013673 | 2/2007 |
| WO | 2007025090 | 3/2007 |
| WO | 2007025540 | 3/2007 |
| WO | 2007028051 | 3/2007 |
| WO | 2007065664 | 6/2007 |
| WO | 2007067537 | 6/2007 |
| WO | 2007084415 | 7/2007 |
| WO | 2007086080 | 8/2007 |
| WO | 2007096764 | 8/2007 |
| WO | 2007100775 | 9/2007 |
| WO | 2007146087 | 12/2007 |
| WO | 2007147646 | 12/2007 |
| WO | 2007147647 | 12/2007 |
| WO | 2008025822 | 3/2008 |
| WO | 2008030579 | 3/2008 |
| WO | 2008033408 | 3/2008 |
| WO | 2008037477 | 4/2008 |
| WO | 2008052734 | 5/2008 |
| WO | 2008058126 | 5/2008 |
| WO | 2008072682 | 6/2008 |
| WO | 2008078091 | 7/2008 |
| WO | 2008094737 | 8/2008 |
| WO | 2008130570 | 10/2008 |
| WO | 2008156783 | 12/2008 |
| WO | 2009008748 | 1/2009 |
| WO | 2009012482 | 1/2009 |
| WO | 2009017954 | 2/2009 |
| WO | 2009106577 | 9/2009 |
| WO | 2009140128 | 11/2009 |
| WO | 2010002846 | 1/2010 |
| WO | 2010017046 | 2/2010 |
| WO | 2010017047 | 2/2010 |
| WO | 2010030538 | 3/2010 |
| WO | 2010034738 | 4/2010 |
| WO | 2010059836 | 5/2010 |
| WO | 2010064020 | 6/2010 |
| WO | 2010074586 | 7/2010 |
| WO | 2010090716 | 8/2010 |
| WO | 2010108074 | 9/2010 |
| WO | 2010108187 | 9/2010 |
| WO | 2010117787 | 10/2010 |
| WO | 2010118207 | 10/2010 |
| WO | 2011006143 | 1/2011 |
| WO | 2011013729 | 3/2011 |
| WO | 2011029027 | 3/2011 |
| WO | 2011038097 | 3/2011 |
| WO | 2011101640 | 8/2011 |
| WO | 2014078813 | 5/2014 |

OTHER PUBLICATIONS

Borbely, et al., "Small-Molecule Inhibitors of NADPH Oxidase 4", J. Med. Chem., 2010, pp. 6758-6762, vol. 53, No. 18, American Chemical Society.

Bullock, et al., "Structural Basis of Inhibitor Specificity of the Human Protooncogene Proviral Insertion Site in Moloney Murine Leukemia Virus (PIM-1) Kinase", J. Med. Chem., 2005, pp. 7604-7614, vol. 48, No. 24, American Chemical Society.

Lubbers, et al., "Design, Synthesis, and Structure-Activity Relationship Studies of ATP Analogues as DNA Gyrase Inhibitors", Bioorganic & Medicinal Chemistry Letters, 2000, pp. 821-826, vol. 10, Elsevier Science Ltd.

Merckx, et al., "Structures of P. Falciparum Protein Kinase 7 Identify an Activation Motif and Leads for Inhibitors Design", Structure, 2008, pp. 228-238, vol. 16, Elsevier Ltd.

Michalska, "Novel Synthesis of Azaindolizines by Reaction of Isonitrosoflavanone Esters with Pyridine Bases", Tetrahedron Letters, 1971, pp. 2667-2668, vol. 28, Pergamon Press, Great Britain.

Ren, et al., "Discovery of Novel Pim-1 Kinase Inhibitors by a Hierarchical Multistage Virtual Screening Approach Based on SVM Model, Pharmacophore, and Molecular Docking", Journal of Chemical Information and Modeling, 2011, pp. 1364-1375, vol. 51, American Chemical Society.

Shaaban, "Microwave-assistaed synthesis of fused heterocycles incorporating trifluoromethyl moiety", Journal of Fluorine Chemistry, 2008, pp. 1156-1161, vol. 129, Elsevier Ltd.

Williamson, et al., "Structure-guided design of pyrazolo[1,5-a]pyrimidines as inhibitors of human cyclin-dependent kinase 2", Bioorganic & Medicinal Chemistry Letters, 2005, pp. 863-867, vol. 15, Elsevier Ltd.

Akkaoui, et al., "Development of New Access Roads to the Imidazo[1,2-b]Pyridazins Di- and Trisubstituted", Scientific Study & Research, 2008, pp. 259-264. vol. IX, No. 2, in French.

Blanco-Aparicio, et al., "Pim 1 kinase inhibitor ETP-45299 suppresses cellular proliferation and synergizes with P13K inhibition", Cancer Letters, 2011, pp. 145-153, vol. 300, Elsevier Ireland Ltd.

Bouloc, et al., "Synthesis and in vitro evaluation of imidazopyridazines as novel inhibitors of the malarial kinase PfPK7", Bioorganic & Medicinal Chemistry Letters, 2008, pp. 5294-5298, vol. 18, Elsevier Ltd.

Calderon, et al., "An Invitation to Open Innovation in malaria Drug Discovery: 47 Quality Starting Points from the TCAMS", Medicinal Chemistry Letters, 2011, pp. 741-746, vol. 2, American Chemical Society.

El Akkaoui, et al., "Direct Arylation of Imidazo[1,2-b]pyridazines: Microwave-Assisted One-Pot Suzuki Coupling/Pd-Catalysed Arylation", European Journal of Organic Chemistry, 2010, pp. 862-871, Wiley-VCH Verlag GMBH & Co. KGaA, Weinheim.

El Akkaoui, et al., "Efficient and regioselective functionalization of imidzo[1,2-b]pyridazines via palladium catalyzed cross-coupling reaction and SNAR", Tetrahedron Letters, 2008, pp. 2472-2475, vol. 49.

Gamo, et al., "Thousands of chemical starting points for antimalarial lead identification", Nature, May 20, 2010, pp. 305-312, vol. 465, Macmillan Publishers Limited.

Hamdouchi, et al., "Imidazo[1,2-b]pyridazines, Novel Nucleus with Potent and Broad Spectrum Activity against Human Picomaviruses: Design, Synthesis and Biological Evaluation", J. Med. Chem., 2003, pp. 4333-4341, vol. 46, American Chemical Society.

Lemercier, et al., "Identification and Characterization of Novel Small Molecules as Potent Inhibitors of the Plasmodial Calcium-Dependent Protein Kinase", Biochemistry, 2009, pp. 6379-6389, vol. 48, American Chemical Society.

Madhavan, et al., "QSAR analysis on PfPK7 inhibitors using HQSAR, CoMFA, and CoMSIA", Med. Chem. Res., 2011, pp. 1-13.

Shimizu, et al., "Discovery of imidazo[1,2-b]pyridazine derivatives as IKKB inhibitors. Part 1: Hit-to-lead study and structure-activity relationship", Bioorganic & Medicinal Chemistry Letters, 2010, pp. 5113-5118, vol. 20, Elsevier Ltd.

\* cited by examiner

COMPOUNDS AND COMPOSITIONS FOR THE TREATMENT OF PARASITIC DISEASES

CROSS-REFERENCED TO RELATED APPLICATIONS

This application claims the benefit of priority to PCT Application Number PCT/US2013/070601, filed on 18 Nov. 2013 and claiming priority to U.S. Provisional Patent Application No. 61/728,018, filed 19 Nov. 2012 and U.S. Provisional Application No. 61/847,860 filed 18 Jul. 2013. The full disclosures of these applications are incorporated herein by reference in its entirety and for all purposes.

BACKGROUND OF THE INVENTION

Field of the Invention

The invention provides a class of compounds, pharmaceutical compositions comprising such compounds and methods of using such compounds to treat or prevent malaria.

Background

Malaria is an infectious disease caused by four protozoan parasites: *Plasmodium falciparum; Plasmodium vivax; Plasmodium ovale*; and *Plasmodium malaria. These four parasites are typically transmitted by the bite of an infected female Anopheles* mosquito. Malaria is a problem in many parts of the world and over the last few decades the malaria burden has steadily increased. An estimated 1-3 million people die every year from malaria—mostly children under the age of 5. This increase in malaria mortality is due in part to the fact that *Plasmodium falciparum*, the deadliest malaria parasite, has acquired resistance against nearly all available antimalarial drugs, with the exception of the artemisinin derivatives. Further for true causal prophylaxis and interrupt transmission of the disease, prevention of liver stage development is crucial, because development of the proceeding infectious blood stage gametocytes would be block. A single drug effective against hepatichypnozoites, primaquine, is available, but its deployment is curtailed by its potential side effects.

Leishmaniasis is caused by one or more than 20 varieties of parasitic protozoa that belong to the genus *Leishmania*, and is transmitted by the bite of female sand flies. Leishmaniasis is endemic in about 88 countries, including many tropical and sub-tropical areas.

There are four main forms of Leishmaniasis. Visceral leishmaniasis, also called kala-azar, is the most serious form and is caused by the parasite *Leishmania donovani*. Patients who develop visceral leishmaniasis can die within months unless they receive treatment. The two main therapies for visceral leishmaniasis are the antimony derivatives sodium stibogluconate (Pentostam®) and meglumine antimoniate (Glucantim®). Sodium stibogluconate has been used for about 70 years and resistance to this drug is a growing problem. In addition, the treatment is relatively long and painful, and can cause undesirable side effects.

Human African Trypanosomiasis, also known as sleeping sickness, is a vector-borne parasitic disease. The parasites concerned are protozoa belonging to the *Trypanosoma* Genus. They are transmitted to humans by tsetse fly (*Glossina* Genus) bites which have acquired their infection from human beings or from animals harboring the human pathogenic parasites.

Chagas disease (also called American Trypanosomiasis) is another human parasitic disease that is endemic amongst poor populations on the American continent. The disease is caused by the protozoan parasite *Trypanosoma cruzi*, which is transmitted to humans by blood-sucking insects. The human disease occurs in two stages: the acute stage, which occurs shortly after infection and the chronic stage, which can develop over many years. Chronic infections result in various neurological disorders, including dementia, damage to the heart muscle and sometimes dilation of the digestive tract, as well as weight loss. Untreated, the chronic disease is often fatal.

The drugs currently available for treating Chagas disease are Nifurtimox and benzindazole. However, problems with these current therapies include their diverse side effects, the length of treatment, and the requirement for medical supervision during treatment. Furthermore, treatment is really only effective when given during the acute stage of the disease. Resistance to the two frontline drugs has already occurred. The antifungal agent Amphotericin b has been proposed as a second-line drug, but this drug is costly and relatively toxic.

In view of the foregoing, it is desirable to develop novel compounds as antiparasitic agents.

SUMMARY OF THE INVENTION

The invention therefore provides a compound of the formula (I):

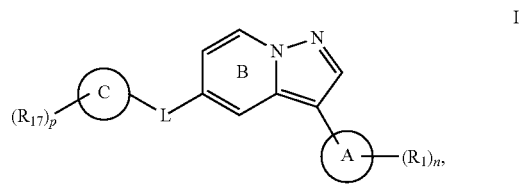

or a pharmaceutical acceptable salt, tautomer or stereoisomer thereof, wherein n is 0, 1, 2 or 3;
p is 0, 1, 2 or 3;
L is selected from the group consisting of *—$(CHR_3)_{1-3}$—, *—$CHR_3N(R_2)$—, *—$CHR_3O$—, *—$CHR_3S$—, *—$CHR_3S(O)$—, *—$CHR_3N(R_2)CHR_3$—, *—$C(O)$—, *—$C(O)N(R_2)$—, *—$C(O)N(R_2)CHR_3$—, *—$N(R_2)$—, *—$N(R_2)CHR_3$—, *—$N(R_2)C(O)$—, *—$N(R_2)C(O)N(R_2)$—, *—$N(R_2)S(O)_2$—, wherein
* represents the point of attachment of L to the pyrazolo [1,5-a]pyridine fused ring depicted in Formula I;
each $R_2$ is independently selected from the group consisting of hydrogen, $C_{1-6}$alkyl, halo$C_{1-6}$alkyl, R—$C_{0-4}$alkylene, and R—$C_{0-4}$alkylene-C(O)—, wherein R is selected from the group consisting of hydroxyl, $C_{1-4}$alkoxy, amino, $C_{1-4}$alkylamino, $C_{3-6}$cycloalkyl, $C_{4-6}$heterocycloalkyl, and $C_{5-6}$heteroaryl, wherein the $C_{3-6}$cycloalkyl, $C_{4-6}$heterocycloalkyl, and $C_{5-6}$heteroaryl of R are each unsubstituted or substituted with 1-2 substituents independently selected from the group consisting of halo, amino, hydroxyl, $C_{1-4}$alkyl, $C_{1-4}$alkoxy, oxo, and $C_{5-6}$heteroaryl; and
each $R_3$ is independently selected from the group consistin of hydrogen and $C_{1-4}$alkyl;
Ring A is selected from the group consistin of $C_{6-10}$aryl and $C_{3-10}$heteroaryl;

Ring C is selected from the group consisting of $C_{8-10}$aryl, $C_{5-10}$heteroaryl, $C_{5-7}$cycloalkyl, $C_{5-7}$heterocycloalkyl, and a fused bicyclyl comprising a $C_{5-6}$heterocycloalky fused to a phenyl;

each $R_1$ is independently selected from the group consisting of halo, cyano, amino, $C_{1-4}$alkyl, $C_{1-4}$alkoxyl, halo-$C_{1-4}$alkyl, —C(O)NR$_7$R$_8$, —NHC(O)R$_{11}$, phenyl, and $C_{5-6}$heteroaryl; wherein the phenyl and $C_{5-6}$heteroaryl of $R_1$ are each unsubstituted or substituted with 1-2 substituents independently selected from the group consisting of $C_{1-4}$alkyl, amino, halo, and $C_{1-4}$alkylamino;

$R_7$ and $R_8$ are each independently selected from the group consisting of hydrogen, $C_{1-4}$alkyl or haloC$_{1-4}$alkyl;

$R_{11}$ is $C_{1-6}$alkyl unsubstituted or substituted with 1-2 substituents independently selected from the group consisting of amino, $C_{3-6}$cycloalkyl and $C_{4-6}$heterocycloalkyl;

$R_{17}$ is selected from the group consisting of cyano, halo, $C_{1-4}$alkyl, halo-$C_{1-4}$alkyl, oxo, $C_{3-6}$cycloalkyl, and —SO$_2$—$C_{1-4}$alkyl.

In a second aspect, the present invention provides a pharmaceutical composition which contains a compound selected from Formula I, IA, or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which a compound of the invention can prevent, inhibit, ameliorate, or eradicate the pathology and/or symptomology of disease caused by a parasite (such as, for example, *Plasmodium falciparum, Plasmodium vivax, Plasmodium ovale, Plasmodium* malaria, *Trypanosoma cruzi* or a parasite of the *Leishmania* genus such as, for example, *Leishmania donovani*) which method comprises administering to the animal a therapeutically effective amount of a compound selected from Formula I, IA, or a N-oxide derivative, individual isomers and mixture of isomers thereof, or a pharmaceutically acceptable salt thereof.

In a fourth aspect, the present invention provides a compound for treating, preventing, inhibiting, ameliorating, or eradicating the pathology and/or symptomology of a disease caused by a parasite (such as, for example, *Plasmodium falciparum, Plasmodium vivax, Plasmodium ovale, Plasmodium* malaria, *Trypanosoma cruzi* or a parasite of the *Leishmania* genus such as, for example, *Leishmania donovani*). Particularly, the parasite is a *Plasmodium* which can be at the blood stages or at the hepatic stages, and the disease is malaria.

In a fifth aspect, the present invention provides the use of a compound selected from Formula I or Formula 1a in the manufacture of a medicament for treating a disease caused by a parasite in an animal. The disease may be malaria, leishmaniasis and/or Chagas disease.

In a sixth aspect, the present invention provides a process for preparing compounds selected from Formula I, Formula 1a and the N-oxide derivatives, prodrug derivatives, individual isomers and mixture of isomers thereof, and the pharmaceutically acceptable salts thereof.

Unless specified otherwise, the term "compounds of the present invention" refers to compounds of Fomula (I) and subformulae thereof, salts of the compound, hydrates or solvates of the compounds, salts, as well as all stereoisomers (including diastereoisomers and enantiomers), tautomers and isotopically labeled compounds (including deuterium substitutions). Compounds of the present invention further comprise polymorphs of compounds of formula I (or subformulae thereof) and salts thereof.

DETAILED DESCRIPTION OF THE INVENTION

Definitions

For purposes of interpreting this specification, the following definitions will apply and whenever appropriate, terms used in the singular will also include the plural and vice versa.

"Acyl" as used herein refers to the radical —C(=O)R$_a$, where R$_a$ is hydrogen or a non-hydrogen substituent on the carbonyl carbon, forming different carbonyl-containing groups including, but are not limited to, acids, acid halides, aldehydes, amides, esters, and ketones.

"Alkoxy" as used herein refers the radical —O-alkyl, wherein the alkyl is as defined herein. $C_X$alkoxy and $C_{X-Y}$alkoxy as used herein describe alkoxy groups where X and Y indicate the number of carbon atoms in the alkyl chain. Representative examples of $C_{1-10}$alkoxy include, but are not limited to, methoxy, ethoxy, propoxy, 2-propoxy, butoxy, tert-butoxy, pentyloxy, hexyloxy, heptyloxy, octyloxy and decyloxy. The alkyl portion of the alkoxy may be optionally substituted, and the substituents include those described for the alkyl group below.

"Alkyl" as used herein refers to a fully saturated branched or unbranched hydrocarbon chain having up to 10 carbon atoms. $C_X$alkyl and $C_{X-Y}$alkyl as used herein describe alkyl groups where X and Y indicate the number of carbon atoms in the alkyl chain. For example, $C_{1-10}$ alkyl refers to an alkyl radical as defined above containing one to ten carbon atoms. $C_{1-10}$ alkyl includes, but are not limited to, methyl, ethyl, n-propyl, isopropyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Alkyl represented along with another radical like arylalkyl, heteroarylalkyl, alkoxyalkyl, alkoxyalkyl, alkylamino, where the alkyl portion shall have the same meaning as described for alkyl and is bonded to the other radical. For example, $(C_{6-10})$aryl$(C_{1-3})$alkyl includes, benzyl, phenylethyl, 1-phenylethyl, 3-phenylpropyl, 2-thienylmethyl, 2-pyridinylmethyl and the like.

Unless stated otherwise specifically in the specification, an alkyl group may be unsubstituted or substituted by one or more substituents to the extent that such substitution makes sense chemically. Typical substituents include, but are not limited to halo, hydroxyl, alkoxy, cyano, amino, acyl, aryl, arylalkyl, and cycloalkyl, or an heteroforms of one of these groups, and each of which can be substituted by the substituents that are appropriate for the particular group.

"Alkenyl" as used herein refers to a straight or branched, hydrocarbon chain having up to 10 carbon atoms and at least one carbon-carbon double bond. $C_X$alkenyl and $C_{X-Y}$alkenyl as used herein describe alkenyl groups where X and Y indicate the number of carbon atoms in the alkenyl chain. Examples of $C_{2-7}$alkenyl include vinyl, allyl, isopropenyl, pentenyl, hexenyl, heptenyl, 1-propenyl, 2-butenyl, 2-methyl-2-butenyl, and the like. The alkenyl may be optionally substituted, and the substituents include those described for the alkyl group descried herein.

"Alkynyl" as used herein refers to a straight or branched, hydrocarbon chain having up to 10 carbon atoms and at least one carbon-carbon triple bond. $C_X$alkenyl and $C_{X-Y}$alkenyl as used herein describe alkynyl groups, where X and Y indicate the number of carbon atoms in the alkynyl chain. For example, $C_{2-7}$alkenyl include, but are not limited to, ethynyl, propargyl, 3-methyl-1-pentynyl, 2-heptynyl and the like. An alkynyl may be optionally substituted, and the substituents include those described for the alkyl group described herein.

"Alkylene" as used herein refers to a divalent alkyl group defined herein. Examples of $C_{1-10}$alkylene includes, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene and n-decylene. An alkylene group may be optionally substituted, and the substituents include those described for the alkyl group described herein.

"Alkenylene" as used herein refers to a divalent alkenyl group defined herein. Examples of $C_{1-3}$alkenylene include, but are not limited to, ethene-1,2-diyl, propene-1,3-diyl, and methylene-1,1-diyl. An alkenylene may be optionally substituted, and the substituents include those described for the alkyl group described herein.

"Alkynylene" as used herein refers to a divalent alkynyl group defined herein. Examples of alkynylene include ethyne-1,2-diylene, propyne-1,3-diylene, and the like. An alkynylene may be optionally substituted, and the substituents include those described for the alkyl group described herein.

"Amino" as used herein refers to the radical —$NH_2$. When an amino is described as "substituted" or "optionally substituted", the term includes NR'R" wherein each R' and R" is independently H, or is an alkyl, alkenyl, alkynyl, acyl, aryl, aryl, cycloalkyl, arylalkyl cycloalkylalkyl group or a heteroform of one of these groups, and each of the alkyl, alkenyl, alkynyl, acyl, aryl, arylalkyl or groups or heteroforms of one of these groups, each of which is optionally substituted with the substituents described herein as suitable for the corresponding group.

The term "amino" also includes forms wherein R' and R" are linked together to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Alkylamino" as used herein refers to the radical —$NR_aR_b$, where at least one of, or both, $R_a$ and $R_b$ are an alkyl group as described herein. An $C_{1-4}$alkylamino group includes —$NHC_{1-4}$alkyl and —$N(C_{1-4}alkyl)_2$; e.g., —$NHCH_3$, —$N(CH_3)_2$, —$NH(CH_2CH_3)$, —$N(CH_2CH_3)_2$, and the like.

"Aromatic" as used herein refers to a moiety wherein the constituent atoms make up an unsaturated ring system, where all atoms in the ring system are $sp^2$ hybridized and the total number of pi electrons is equal to 4n+2. An aromatic ring may be such that the ring atoms are only carbon atoms or may include carbon and non-carbon atoms (see Heteroaryl).

"Aryl" as used herein refers to a 6-14 membered monocyclic or polycyclic aromatic ring assembly where all the ring atoms are carbon atoms. Typically, the aryl is a 6 membered monocyclic, a 10-12 membered bicyclic or a 14-membered fused tricyclic aromatic ring system. $C_X$aryl and $C_{X-Y}$aryl as used herein describe an aryl group where X and Y indicate the number of carbon atoms in the ring system. $C_{6-14}$aryls include, but are not limited to, phenyl, biphenyl, naphthyl, azulenyl, and anthracenyl.

An aryl may be unsubstituted or substituted by 1-5 (such as one, or two, or three) substituents independently selected from the group consisting of hydroxy, thiol, cyano, nitro, $C_{1-4}$alkyl, $C_{1-4}$alkenyl, $C_{1-4}$alkynyl, $C_{1-4}$alkoxy, thio$C_{1-4}$alkyl, $C_{1-4}$alkenyloxy, $C_{1-4}$alkynyloxy, halogen, $C_{1-4}$alkylcarbonyl, carboxy, $C_{1-4}$alkoxycarbonyl, amino, $C_{1-4}$alkylamino, di-$C_{1-4}$alkylamino, $C_{1-4}$alkylaminocarbonyl, di-$C_{1-4}$alkylaminocarbonyl, $C_{1-4}$alkylcarbonylamino, $C_{1-4}$alkylcarbonyl($C_{1-4}$alkyl)amino, sulfonyl, sulfamoyl, alkylsulfamoyl, $C_{1-4}$alkylaminosulfonyl, aryl, heteroaryl, cycloalkyl and heterocycloalkyl, wherein each of the afore-mentioned substitutents may be further substituted by one or more substituents independently selected from halogen, alkyl, hydroxyl or $C_{1-4}$alkoxy groups.

When an "aryl" is represented along with another radical like "arylalkyl", "aryloxyalkyl", "aryloxycarbonyl", "aryloxy-carbonylalkyl", the aryl portion shall have the same meaning as described in the above-mentioned definition of "aryl".

"Aryloxy" as used herein, refers to the radical —O-aryl, wherein aryl is as defined herein.

"Bicyclic" or "bicyclyl" as used here in refers to a ring assembly of two rings where the two rings are fused together, linked by a single bond or linked by two bridging atoms. The rings may be a carbocyclyl, a heterocyclyl, or a mixture thereof.

"Bridging ring" as used herein refers to a polycyclic ring system where two ring atoms that are common to two rings are not directly bound to each other. One or more rings of the ring system may also comprise heteroatoms as ring atoms. Non-exclusive examples of bridging rings include norbornanyl, 7-oxabicyclo[2.2.1]heptanyl, adamantanyl, and the like.

"Carbamoyl" as used herein refers to the radical —C(O)$NR_a$— where $R_a$ is H, or is an alkyl, alkenyl, alkynyl, acyl, aryl, or arylalkyl group or a heteroform of one of these groups, and each of the alkyl, alkenyl, alkynyl, acyl, aryl, arylalkyl or heteroforms of one of these groups is optionally substituted with the substituents described herein as suitable for the corresponding group.

"Cycloalkyl", as used herein, means a radical comprising a non-aromatic, saturated or partially unsaturated, monocyclic, bicyclic, tricyclic, fused, bridged or spiro polycyclic hydrocarbon ring system of 3-20 carbon atoms. $C_X$cycloalkyl and $C_{X-Y}$cycloalkyl are typically used where X and Y indicate the number of carbon atoms in the ring assembly. For example, $C_{3-6}$cycloalkyl includes cyclopropyl, cyclobutyl, cyclopentyl, cyclohexyl, cyclohexenyl, 2,5-cyclohexadienyl.

Exemplary monocyclic cycloalkyl include, but are not limited to, cyclopropyl, cyclobutyl, cyclopentyl, cyclopentenyl, cyclohexyl and cyclohexenyl and the like.

Exemplary bicyclic cycloalkyls include bornyl, norbornanyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl. Exemplary tricyclic cycloalkyl groups include, for example, adamantyl.

A cycloalkyl may be unsubstituted or substituted by one, or two, or three, or more substituents independently selected from the group consisting of hydroxyl, thiol, cyano, nitro, oxo, alkylimino, $C_{1-4}$alkyl, $C_{1-4}$alkenyl, $C_{1-4}$alkynyl, $C_{1-4}$alkoxy, $C_{1-4}$thioalkyl, $C_{1-4}$alkenyloxy, $C_{1-4}$alkynyloxy, halogen, $C_{1-4}$alkylcarbonyl, carboxy, $C_{1-4}$alkoxycarbonyl, amino, $C_{1-4}$alkylamino, di-$C_{1-4}$alkylamino, $C_{1-4}$alkylaminocarbonyl, di-$C_{1-4}$alkylaminocarbonyl, $C_{1-4}$alkylcarbonylamino, $C_{1-4}$alkylcarbonyl($C_{1-4}$alkyl)amino, sulfonyl, sulfamoyl, alkylsulfamoyl, $C_{1-4}$alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_{1-4}$alkoxy groups.

"Cycloalkylene", as used herein, refers to a divalent radical comprising a cycloalkyl ring assembly as defined herein.

"Cycloalkoxy", as used herein, refers to —O-cycloalkyl, wherein the cycloalkyl is defined herein. Representative examples of $C_{3-12}$cycloalklyoxy include, but are not limited to, monocyclic groups such as cyclopropoxy, cyclobutoxy, cyclopentyloxy, cyclopentenyloxy, cyclohexyloxy and cyclohexenyloxy and the like. Exemplary bicyclic hydrocarbon groups include bornyloxy, indyloxy, hexahydroindyloxy, tetrahydronaphthyloxy, decahydronaphthyloxy, bicyclo[2.1.1]hexyloxy, bicyclo[2.2.1]heptyloxy, bicyclo[2.2.1]heptenyloxy, 6,6-dimethylbicyclo[3.1.1]heptyloxy, 2,6,6-trimethylbicyclo[3.1.1]heptyloxy, bicyclo[2.2.2]octyloxy and the like. Exemplary tricyclic hydrocarbon groups include, for example, adamantyloxy.

"Cyano", as used herein, refers to the radical —CN.

"$EC_{50}$", refers to the molar concentration of an inhibitor or modulator that produces 50% efficacy.

"Fused ring", as used herein, refers to a multi-ring assembly wherein the rings comprising the ring assembly are so linked that the ring atoms that are common to two rings are directly bound to each other. The fused ring assemblies may be saturated, partially saturated, aromatics, carbocyclics, heterocyclics, and the like. Non-exclusive examples of common fused rings include decalin, naphthalene, anthracene, phenanthrene, indole, benzofuran, purine, quinoline, and the like.

"Halo" or "halogen" as used herein refers to fluoro, chloro, bromo, and iodo.

"Haloalkyl", or halo-substituted-alkyl" as used herein, refers to an alkyl as defined herein, which is substituted by one or more halo atoms defined herein. The haloalkyl can be mono-haloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. $C_X$haloalkyl and $C_{X-Y}$haloalkyl are typically used where X and Y indicate the number of carbon atoms in the alkyl chain. Non-limiting examples of $C_{1-4}$haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A $C_{1-4}$perhaloalkyl group refers to a $C_{1-4}$alkyl group having all hydrogen atoms replaced with halo atoms.

"Heteroaryl", as used herein, refers to a 5-14 membered ring assembly (e.g., a 5-7 membered monocycle, an 8-10 membered bicycle, or a 13-14 membered tricyclic ring system) having 1 to 8 heteroatoms selected from N, O and S as ring atoms and the remaining ring atoms are carbon atoms. The nitrogen atoms of such heteroaryl rings can be optionally quaternerized and the sulfur atoms of such heteroaryl rings can be optionally oxidized. $C_X$heteroaryl and $C_{X-Y}$heteroaryl as used herein describe heteroaryls where X and Y indicate the number of ring atoms in the heteroaryl ring. Typical $C_{5-7}$heteroaryl groups include thienyl, furanyl, imidazolyl, pyrazolyl, pyrrolyl, pyrrolinyl, thiazolyl, 1,3,4-thiadiazolyl, isothiazolyl, oxazolyl, oxadiazole isoxazolyl, triazolyl, tetrazolyl, pyridyl, pyridazinyl, pyrazinyl, pyrazinyl, pyrimidinyl, and the like. Bicyclic or tricyclic $C_{8-14}$heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, quinazolinyle, pteridinyl, indolizine, imidazo[1,2a]pyridine, quinoline, quinolinyl, isoquinoline, phthalazine, quinoxaline, naphthyridine, naphthyridinyl, quinolizine, indolyl, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, purinyl, carbazole, acridine, phenazine, phenothiazene, phenoxazine, 1,2-dihydropyrrolo[3,2,1-hi]indole, indolizine, pyrido[1,2-a]indole and 2(1H)-pyridinone.

A heteroaryl may be unsubstituted or substituted with one or more substituents independently selected from hydroxyl, thiol, cyano, nitro, $C_{1-4}$alkyl, $C_{1-4}$alkenyl, $C_{1-4}$alkynyl, $C_{1-4}$alkoxy, thio$C_{1-4}$alkyl, $C_{1-4}$alkenyloxy, $C_{1-4}$alkynyloxy, halogen, $C_{1-4}$alkylcarbonyl, carboxy, $C_{1-4}$alkoxycarbonyl, amino, $C_{1-4}$alkylamino, di-$C_{1-4}$alkylamino, $C_{1-4}$alkylaminocarbonyl, di-$C_{1-4}$alkylaminocarbonyl, $C_{1-4}$alkylcarbonylamino, $C_{1-4}$alkylcarbonyl($C_{1-4}$alkyl)amino, sulfonyl, sulfamoyl, alkylsulfamoyl, $C_{1-4}$alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_{1-4}$alkoxy groups.

When a heteroaryl is represented along with another radical like "heteroaryloxy", "heteroaryloxyalkyl", "heteroaryloxycarbonyl", the heteroaryl portion shall have the same meaning as described in the above-mentioned definition of "heteroaryl".

"Heteroaryloxy", as used herein, refers to an —O-heteroaryl group, wherein the heteroaryl is as defined in this Application.

"Heteroatom", as used herein, refers to an atom that is not a carbon atom. Particular examples of heteroatoms include, but are not limited to nitrogen, oxygen, and sulfur.

"Heterocycloalkyl", as used herein, refers to a 4-20 membered, non-aromatic, saturated or partially unsaturated, monocyclic or polycyclic ring system, comprising 1-8 heteroatoms as ring atoms and that the remaining ring atoms are carbon atoms. The heteroatoms are selected from N, O, and S, preferably O and N. The nitrogen atoms of the heterocycloalkyl can be optionally quaternerized and the sulfur atoms of the heterocycloalkyl can be optionally oxidized. The heterocycloalkyl can include fused or bridged rings as well as spirocyclic rings. $C_X$heterocycloalkyl and $C_{X-Y}$heterocycloalkyl are typically used where X and Y indicate the number of ring atoms in the ring. Typically, the heterocycloalkyl is 4-8-membered monocyclic ring containing 1 to 3 heteroatoms, a 7 to 12-membered bicyclic ring system containing 1-5 heteroatoms, or a 10-15-membered tricyclic ring system containing 1 to 7 heteroatoms. Examples of $C_{4-6}$heterocycloalkyl include azetidinyl, tetrahydrofuran (THF), dihydrofuran, 1,4-dioxane, morpholine, 1,4-dithiane, piperazine, piperidine, 1,3-dioxolane, imidazolidine, imidazoline, pyrazolidinyl, pyrroline, pyrrolidine, tetrahydropyran, dihydropyran, oxathiolane, dithiolane, 1,3-dioxane, 1,3-dithiane, oxathiane, thiomorpholine, and the like A heterocycloalkyl may be unsubstituted or substituted with 1-5 substituents (such as one, or two, or three) each independently selected from hydroxyl, thiol, cyano, nitro, oxo, alkylimino, $C_{1-4}$alkyl, $C_{1-4}$alkenyl, $C_{1-4}$alkynyl, $C_{1-4}$alkoxy, $C_{1-4}$thioalkyl, $C_{1-4}$alkenyloxy, $C_{1-4}$alkynyloxy, halogen, $C_{1-4}$alkylcarbonyl, carboxy, $C_{1-4}$alkoxycarbonyl, amino, $C_{1-4}$alkylamino, di-$C_{1-4}$alkylamino, $C_{1-4}$alkylaminocarbonyl, di-$C_{1-4}$alkylaminocarbonyl, $C_{1-4}$alkylcarbonylamino, $C_{1-4}$alkylcarbonyl($C_{1-4}$alkyl)amino, sulfonyl, sulfamoyl, alkylsulfamoyl, $C_{1-4}$alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_{1-4}$alkoxy groups.

When a heterocycloalkyl forms part of other groups like "heterocycloalkyl-alkyl", "heterocycloalkoxy", "heterocycloalkyl-aryl", the heteroaryl portion shall have the same meaning as described in the above-mentioned definition of "heteroaryl"

"Heterocycloalkylene", as used herein, refers to a cycloalkylene, as defined in this Application, provided that one or more of the ring member carbon atoms is replaced by a heteroatom.

"Heterocycloalkyl fused to a phenyl" as used herein, refers to a bicyclic fused ring system that one of the ring is heterocycloalkyl as defined above and the other ring is a phenyl. A heterocycloalkyl fused to a phenyl includes but are not limited to benzo[b][1,4]oxazinyl, oxo-benzo[b][1,4]oxazinyl, tetrahydroquinoxalinyl, tetrahydroquinolinyl, indolinyl, benzo[d]imidazolyl, and the like.

"Heterocyclyl", "heterocycle" or "heterocyclo", as used herein, refers to a 3-20 membered, monocyclic or polycyclic ring system containing at least one heteroatom moiety selected from the group consisting of N, O, SO, $SO_2$, (C=O), and S, and preferably N, O, S, optionally containing one to four additional heteroatoms in each ring. $C_X$heterocyclyl and $C_{X-Y}$heterocyclyl are typically used where X and Y indicate the number of ring atoms in the ring system. Unless otherwise specified, a heterocyclyl may be saturated, partially unsaturated, aromatic or partially aromatic.

Hydroxy, as used herein, refers to the radical —OH.

"Hydroxyalkyl" or "hydroxyl-substituted alkyl" as used herein, refers to an alkyl as defined herein, having one or more of the available hydrogen of the alkyl replaced by a hydroxyl group. For example, a hydroxy$C_{1-4}$alkyl includes, but are not limited to, —$CH_2CH_2OH$, —CH(OH)$CH_2CH_2OH$, —CH(OH)$CH_2CH$(OH)$CH_3$.

"Nitro", as used herein, refers to the radical —$NO_2$.

"Oxo", as used herein, refers to the divalent radical =O

"Protected derivatives" means derivatives of inhibitors in which a reactive site or sites are blocked with protecting groups. Protected derivatives are useful in the preparation of inhibitors or in themselves may be active as inhibitors. Examples of protected group includes, but are not limited to, acetyl, tetrahydropyran, methoxymethyl ether, β-methoxyethoxymethyl ether, p-methoxybenzyl, methylthiomethyl ether, pivaloyl, silyl ether, carbobenzyloxy, benzyl, tert-butoxycarbonyl, p-methoxyphenyl, 9-fluorenylmethyloxycarbonyl, acetals, ketals, acylals, dithianes, methylesters, benzyl esters, tert-butyl esters, and silyl esters. A comprehensive list of suitable protecting groups can be found in T. W. Greene, *Protecting Groups in Organic Synthesis,* 3rd edition, John Wiley & Sons, Inc. 1999.

"Unsubstituted or substituted" or "optionally substituted" as used herein indicate the substituent bound on the available valance of a named group or radical. "Unsubstituted" as used herein indicates that the named group or radical will have no further non-hydrogen substituents. "Substituted" or "optionally substituted" as used herein indicates that at least one of the available hydrogen atoms of named group or radical has been (or may be) replaced by a non-hydrogen substituent.

"Substituted terminally" as used herein referred to a substituent replacing a hydrogen at a terminal position of the parent molecule. For example $C_{1-4}$alkyl substituted terminally by an amino means —$C_{1-4}$alkylene-amino, which includes —($CH_2$)—$NH_2$, —($CH_2$)$_2$—$NH_2$, —($CH_2$)$_3$—$NH_2$, —($CH_2$)$CH_2$($CH_2$—$NH_2$), —($CH_2$)$_4$—$NH_2$, —C($CH_2$)($CH_2CH_2$—$NH_2$)—C($CH_3$)$_2$($CH_2$—$NH_2$), and the like.

Unless otherwise specified, examples of substituents may include, but are not limited to, halo, nitro, cyano, thio, oxy, hydroxy, carbonyloxy, $C_{1-6}$alkoxy, $C_{6-10}$aryloxy, hetero $C_{5-10}$aryloxy, carbonyl, oxycarbonyl, aminocarbonyl, amino, $C_{1-6}$alkylamino, sulfonamido, imino, sulfonyl, sulfinyl, $C_{1-6}$alkyl, $C_{1-6}$haloalkyl, hydroxy$C_{1-6}$alkyl, carbonyl$C_{1-6}$ alkyl, thiocarbonyl$C_{1-10}$alkyl, sulfonyl$C_{1-6}$alkyl, sulfinyl$C_{1-6}$alkyl, $C_{1-10}$azaalkyl, imino$C_{1-6}$alkyl, $C_{3-12}$cycloalkyl$C_{1-6}$alkyl, $C_{4-15}$heterocycloalkyl$C_{1-6}$alkyl, $C_{6-10}$aryl$C_{1-6}$alkyl, $C_{5-10}$heteroaryl$C_{1-6}$alkyl, $C_{10-12}$bicycloaryl$C_{1-6}$alkyl, $C_{9-12}$heterobicycloaryl$C_{1-6}$alkyl, $C_{3-12}$cycloalkyl, $C_{4-12}$heterocycloalkyl, $C_{9-12}$bicycloalkyl, $C_{3-12}$heterobicycloalkyl, $C_{4-12}$aryl, hetero$C_{1-10}$aryl, $C_{9-12}$bicycloaryl and $C_{4-12}$heterobicycloaryl.

"Sulfamoyl" as used herein refers to the radical —S(O)$_2$NR$_a$R$_b$ where R$_a$ and R$_b$ are independently H, or is an alkyl, alkenyl, alkynyl, acyl, aryl, aryl, cycloalkyl, arylalkyl cycloalkylalkyl group or a heteroform of one of these groups, and each of the alkyl, alkenyl, alkynyl, acyl, aryl, arylalkyl groups or heteroforms of one of these groups, is optionally substituted with the substituents described herein as suitable for the corresponding group.

"Sulfanyl" as used herein, means the radical —S—.

"Sulfinyl", as used herein, means the radical —S(O)—. It is noted that the term "sulfinyl" when referring to a monovalent substituent can alternatively refer to a substituted sulfinyl group, —S(=O)R, where R is hydrogen or a non-hydrogen substituent on the sulfur atom forming different sulfinyl groups including sulfinic acids, sulfinamides, sulfinyl esters, and sulfoxides.

"Sulfonyl", as used herein, means the radical —S(O)$_2$—. It is noted that the term "sulfonyl" when referring to a monovalent substituent can alternatively refer to a substituted sulfonyl group, —S(=O)$_2$R, where R is hydrogen or a non-hydrogen substituent on the sulfur atom forming different sulfonyl groups including sulfonic acids, sulfonamides, sulfonate esters, and sulfones.

"Thiocarbonyl", as used herein, refers to the radical —C(=S)—. It is noted that the term thiocarbonyl when referring to a monovalent substituent can alternatively refer to a substituted thiocarbonyl group, —C(=S)R, where R is hydrogen or a non-hydrogen substituent on the carbon atom forming different thiocarbonyl groups including thioacids, thioamides, thioesters, and thioketones.

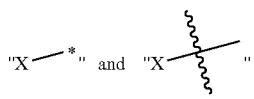

are symbols denoting the point of attachment of X, to other part of the molecule.

Any definition herein may be used in combination with any other definition to describe a composite structural group. By convention, the trailing element of any such definition is that which attaches to the parent moiety. For example, the composite group alkoxyalkyl would represent an alkoxy group attached to the parent molecule through an alkyl group.

It is noted in regard to all of the definitions provided herein that the definitions should be interpreted as being open ended in the sense that further substituents beyond those specified may be included. Hence, a $C_1$alkyl indicates that there is one carbon atom but does not indicate what are the substituents on the carbon atom. Hence, a $C_1$alkyl comprises methyl (i.e., —CH$_3$) as well as —CR$_a$R$_b$R$_c$ where R$_a$, R$_b$, and R$_c$ may each independently be hydrogen or any other substituent where the atom attached to the carbon is not a hydrogen atom. Hence, —CF$_3$, —CH$_2$OH and —CH$_2$CN, for example, are all $C_1$alkyls.

Any definition herein may be used in combination with any other definition to describe a composite structural group. By convention, the trailing element of any such definition is that which attaches to the parent moiety. For example, the composite group alkoxyalkyl would represent an alkoxy group attached to the parent molecule through an alkyl group.

It is noted in regard to all of the definitions provided herein that the definitions should be interpreted as being open ended in the sense that further substituents beyond those specified may be included. Hence, a $C_1$alkyl indicates that there is one carbon atom but does not indicate what are the substituents on the carbon atom. Hence, a $C_1$alkyl comprises methyl (i.e., —CH$_3$) as well as —CR$_a$R$_b$R$_c$ where R$_a$, R$_b$, and R$_c$ may each independently be hydrogen or any other substituent where the atom attached to the carbon is not a hydrogen atom. Hence, —CF$_3$, —CH$_2$OH and —CH$_2$CN, for example, are all $C_1$alkyls.

DESCRIPTION OF THE PREFERRED EMBODIMENTS

The invention provides a novel class of compounds, pharmaceutical compositions comprising such compounds and methods of using such compounds to treat or prevent diseases or disorders associated with a parasite. In particular, the compounds can be used to treat malaria, leishmaniasis and/or Chagas disease. The compounds of the invention are effective in inhibiting, ameliorating, or eradicating the pathology and/or symptomology of the parasite at both the blood stage and hepatic stage.

In one embodiment, the compounds of the invention are of Formula I:

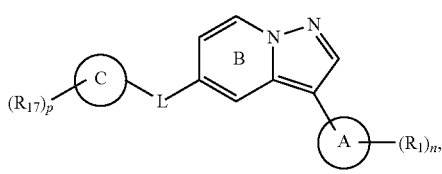

or a pharmaceutical acceptable salt, enantiomer or tautomer or stereoisomer thereof, wherein n is 0, 1, 2 or 3;

p is 0, 1, 2 or 3;

L is selected from the group consisting of *—(CHR$_3$)$_{1-3}$—, *—CHR$_3$N(R$_2$)—, *—CHR$_3$O—, *—CHR$_3$S—, *—CHR$_3$S(O)$_2$—, *—S(O)$_2$N(R$_2$)—, *—CHR$_3$N(R$_2$)CHR$_3$—, *—C(O)—, *—C(O)N(R$_2$)—, *—C(O)N(R$_2$)CHR$_3$—, *—N(R$_2$)—, *—N(R$_2$)CHR$_3$—, *—N(R$_2$)C(O)—, *—N(R$_2$)C(O)N(R$_2$)—, *—N(R$_2$)S(O)$_2$—, wherein

* represents the point of attachment of L to the pyrazolo[1,5-a]pyridine fused ring depicted in Formula I;

each R$_2$ is independently selected from the group consisting of hydrogen, $C_{1-6}$alkyl, halo$C_{1-6}$alkyl, R—$C_{0-4}$alkylene, and R—$C_{0-4}$alkylene-C(O)—, wherein R is selected from the group consisting of hydroxyl, $C_{1-4}$alkoxy, amino, $C_{1-4}$alkylamino, $C_{3-6}$cycloalkyl, $C_{4-6}$heterocycloalkyl, and $C_{5-6}$heteroaryl, wherein the $C_{3-6}$cycloalkyl, $C_{4-6}$heterocycloalkyl, and $C_{5-6}$heteroaryl of R are each unsubstituted or substituted with 1-2 substituents independently selected from the group consisting of halo, amino, hydroxyl, $C_{1-4}$alkyl, $C_{1-4}$alkoxy, oxo, and $C_{5-6}$heteroaryl; and.

each R$_3$ is independently selected from the group consisting of hydrogen and $C_{1-4}$alkyl, Ring A is selected from the group consisting of $C_{6-10}$aryl and $C_{3-10}$heteroaryl;

Ring C is selected from the group consisting of $C_{6-10}$aryl, $C_{5-10}$heteroaryl, $C_{5-7}$cycloalkyl, $C_{5-7}$heterocycloalkyl, and a fused bicyclyl comprising a $C_{5-6}$heterocycloalky fused to a phenyl;

each R$_1$ is independently selected from the group consisting of halo, cyano, amino, $C_{1-4}$alkyl, $C_{1-4}$alkoxyl, halo-$C_{1-4}$alkyl, $C_{1-4}$alkylsulfonyl, —C(O)OR$_7$, —NR$_7$R$_8$, —S(O)$_2$NR$_7$R$_8$, —C(O)NR$_7$R$_8$, —NHC(O)R$_{11}$, phenyl, and $C_{5-6}$heteroaryl; wherein the phenyl and $C_{5-6}$heteroaryl of R$_1$ are each unsubstituted or substituted with 1-2 substituents independently selected from the group consisting of $C_{1-4}$alkyl, amino, halo, and $C_{1-4}$alkylamino;

R$_7$ and R$_8$ are each independently selected from the group consisting of hydrogen, $C_{1-4}$alkyl, amino $C_{1-4}$alkyl, $C_{1-4}$alkylamino$C_{1-4}$alkyl, hydroxy$C_{1-4}$alkyl, $C_{1-4}$alkylsulfonyl, hetero$C_{4-6}$cycloalkyl, $C_{3-6}$cycloalkyl, and halo$C_{1-4}$alkyl;

R$_{11}$ is $C_{1-6}$alkyl unsubstituted or substituted with 1-2 substituents independently selected from the group consisting of amino, $C_{3-6}$cycloalkyl and $C_{4-6}$heterocycloalkyl;

R$_{17}$ is selected from the group consisting of cyano, halo, $C_{1-4}$alkyl, halo-$C_{1-4}$alkyl, oxo, $C_{3-6}$cycloalkyl, $C_{1-4}$alkoxy, amino$C_{1-4}$alkoxy, hydroxy$C_{1-4}$alkoxy, —C(O)OH, —C(O)NH$_2$, and —SO$_2$—$C_{1-4}$alkyl.

In one embodiment of the compounds of the invention, with reference to Formula I, L is selected from the group consisting of *—(CHR$_3$)$_{1-3}$—, *—CHR$_3$N(R$_2$)—, *—CHR$_3$O—, *—CHR$_3$S—, *—CHR$_3$S(O)—, *—C(O)—, *—C(O)N(R$_2$)—, *—N(R$_2$)—, *—N(R$_2$)CHR$_3$—, *—N(R$_2$)C(O)—, *—N(R$_2$)C(O)N(R$_2$)—, *—N(R$_2$)S(O)$_2$—, wherein each R$_2$ is independently selected from the group consisting of hydrogen, $C_{1-6}$alkyl, halo$C_{1-6}$alkyl, R—$C_{0-4}$alkylene, and R—$C_{0-4}$alkylene-C(O)—, wherein each R is independently selected from the group consisting of hydroxyl, $C_{1-4}$alkoxy, amino, $C_{1-4}$alkylamino, di-$C_{1-4}$alkylamino, $C_{3-6}$cycloalkyl, $C_{4-6}$heterocycloalkyl, and $C_{5-6}$heteroaryl, wherein said $C_{3-6}$cycloalkyl, $C_{4-6}$heterocycloalkyl and $C_{5-6}$heteroaryl are each unsubstituted or substituted with 1-2 substituents independently selected from the group consisting of $C_{1-4}$alkyl, halo, amino, hydroxyl, $C_{1-4}$alkoxy, oxo, and $C_{5-6}$heteroaryl.

In another variation, L is selected from the group consisting of *—(CHR$_3$)$_{1-3}$—, *—CHR$_3$N(R$_2$)—, *—CHR$_3$O—, *—CHR$_3$S—, *—CHR$_3$S(O)—, *—C(O)—, *—C(O)N(R$_2$)—, *—N(R$_2$)—, *—N(R$_2$)CHR$_3$—, *—N(R$_2$)C(O)—, *—N(R$_2$)C(O)N(R$_2$)—, *—N(R$_2$)S(O)$_2$—, wherein each R$_2$ is independently selected from the group consisting of hydrogen, $C_{1-6}$alkyl, R—$C_{0-4}$alkylene, wherein R is selected from the group consisting of $C_{1-4}$alkoxy, $C_{1-4}$alkylamino, di-$C_{1-4}$alkylamino, $C_{3-6}$cycloalkyl, $C_{4-6}$heterocycloalkyl and $C_{5-6}$heteroaryl, wherein the $C_{3-6}$cycloalkyl, $C_{4-6}$heterocycloalkyl and $C_{5-6}$heteroaryl of R are each unsubstituted or substituted with 1-2 substituents independently selected from the group consisting of halo, amino, hydroxyl, $C_{1-4}$alkyl, $C_{1-4}$alkoxy, oxo, and $C_{5-6}$heteroaryl.

In another variation, L is selected from the group consisting of *—C(O)N(R$_2$)—, and *—N(R$_2$)C(O)—, wherein each R$_2$ is independently selected from hydrogen, $C_{1-6}$alkyl, and R—$C_{0-4}$alkylene, and wherein R is selected from the group consisting of $C_{1-4}$alkylamino, $C_{3-6}$cycloalkyl, $C_{4-6}$heterocycloalkyl and $C_{5-6}$heteroaryl, each of which is unsubstituted or substituted with 1-2 substituents independently selected from the group consisting of halo, amino, hydroxyl, $C_{1-4}$alkyl, $C_{1-4}$alkoxy, oxo, and $C_{5-6}$heteroaryl In still another variation, L is selected from the group consisting of *—CH(CH$_3$)—, *—CH$_2$CH$_2$—, —*—CH$_2$N(CH$_3$)—, *—CH$_2$N(C(O)(CH$_2$)$_{1-2}$NH(CH$_3$))—, *—CH$_2$N(C(O)—(CH$_2$)$_{1-2}$NH$_2$)—, *—CH$_2$N((C(O)—(CH$_2$)$_{1-2}$N(CH$_3$)$_2$)—, *—CH$_2$N(C(O)(CH$_2$)$_{1-2}$OH)—, *—CH(CH$_3$)N(CH$_3$)—, *—CH$_2$O—, *—CH$_2$S—, *—CH$_2$S(O)—, *—C(O)—, *—C(O)N(CH$_3$)—, *—C(O)N(CH$_2$CH$_3$)—, *—C(O)N(CH(CH$_3$)$_2$)—, *—C(O)N(C(CH$_3$)$_3$)—, *—C(O)N(CH$_2$CH(CH$_3$)$_2$)—, *—C(O)N(CH(CH$_3$)CH$_2$CH$_3$)—, *—C(O)N(CH$_2$CH$_2$OCH$_3$)—, *—C(O)N(NH(CH$_3$))—, *—C(O)N(CH$_2$CH$_2$N(CH$_3$)$_2$)—, *—C(O)N(CH$_3$)CH$_2$—, *—NHCH$_2$—, *—N(CH$_3$)CH$_2$—, *—N(CH$_2$-tetrahydropyran-4-yl)-C(O)—,*—N(CH$_3$)C(O)—, *—N(CH$_3$)C(O)NH—, *—N(CH$_3$)S(O)$_2$—, *—C(O)N((CH$_2$)$_{0-1}$-cyclopropyl)-, *—C(O)N((CH$_2$)$_{0-1}$-cyclobutyl)-, *—C(O)N((CH$_2$)$_{0-1}$-cyclopentyl)-, *—C(O)N((CH$_2$)$_{0-1}$-cyclohexyl)-, *—C(O)N(CH$_2$-tetrahydropyran-4-yl)-, *—C(O)N((CH$_2$)$_2$-(1,1-dioxidothiomorpholino-4-yl))-, *—C(O)N(CH$_2$-1,1-dioxidothiomorpholino-4-yl)-, *—C(O)N((CH$_2$)$_2$-tetrahydropyran-4-yl))-, *—C(O)N((CH$_2$)$_{1-2}$-morpholin-4-yl)-, *—C(O)N(oxetan-3-yl)-, *—C(O)N(CH$_2$-oxetan-3-yl)-, *—C(O)N(CH(CH$_3$)—CH$_2$-1-H-pyrazoly-1-yl)-, *—CH$_2$N(C(O)—(CH$_2$)$_{1-2}$-morpholinyl))-, *—CH$_2$N(C(O)—(CH$_2$)$_{1-2}$-4-methylpiperizin-1-yl)), *—CH$_2$N(C(O)—(CH$_2$)$_{1-2}$-tetrahydropyran-4-yl)-, and *—CH$_2$N(C(O)(CH$_2$)$_{1-2}$-oxetan-3-yl)-.

In still another variation, L is selected from the group consisting of *—CH(CH$_3$)—, *—CH$_2$CH$_2$—, —*—CH$_2$N(CH$_3$)—, *—CH(CH$_3$)N(CH$_3$)—, *—CH$_2$O—, —*—CH$_2$S—, —*—CH$_2$S(O)—, *—C(O)—, *—C(O)N(CH$_3$)—, *—C(O)N(CH$_2$CH$_3$)—, *—C(O)N(CH(CH$_3$)$_2$)—, *—C(O)N(CH$_3$)CH$_2$—, *—C(O)N(CH$_2$CH$_2$OCH$_3$)—, *—C(O)N(NH(CH$_3$))—, *—C(O)N(CH$_2$CH$_2$N(CH$_3$)$_2$)—, *—NHCH$_2$—, *—N(CH$_3$)CH$_2$—, *—N(CH$_2$-tetrahydropyran-4-yl)-C(O)—,*—N(CH$_3$)C(O)—, *—N(CH$_3$)C(O)NH—, *—N(CH$_3$)S(O)$_2$—, *—C(O)N((CH$_2$)$_{0-1}$-cyclopropyl)-, *—C(O)N(CH$_2$-tetrahydropyran-4-yl)-, *—C(O)N(oxetan-3-yl)-, and *—C(O)N(CH(CH$_3$)CH$_2$-(1-H-pyrazoly-1-yl))-.

In a further variation, L is selected from the group consisting of *—C(O)N(CH$_3$)—, *—C(O)N(CH$_2$CH$_3$)—, *—C(O)N(CH(CH$_3$)$_2$)—, *—C(O)N(C(CH$_3$)$_3$)—, *—C(O)N(CH$_2$CH(CH$_3$)$_2$)—, *—C(O)N(CH(CH$_3$)CH$_2$CH$_3$)—, *—C(O)N((CH$_2$)$_{0-1}$-cyclopropyl)-, *—C(O)N((CH$_2$)$_{0-1}$-cyclobutyl)-, *—C(O)N((CH$_2$)$_{0-1}$-cyclopentyl)-, and *—C(O)N((CH$_2$)$_{0-1}$-cyclohexyl)-.

In still another further variation, L is selected from the group consisting of *—C(O)N(CH$_3$)—*—C(O)N(CH$_2$CH$_3$)—, *—C(O)N(CH(CH$_3$)$_2$)—, *—C(O)N(NH(CH$_3$))—, and *—N(CH$_3$)C(O)—.

In a particular variation, L is *—C(O)N(CH$_3$)— or *—N(CH$_3$)C(O)—. In a particular variation, L is *—C(O)N(CH$_3$)—. In another particular variation, L is *—N(CH$_3$)C(O)—. In another particular variation, L is *—C(O)N(CH$_2$CH$_3$)—. In another particular variation, L is *—C(O)N(CH(CH$_3$)$_2$)—. In another particular variation, L is *—C(O)N(NH(CH$_3$))—. In another particular variation, L is *—N((CH$_2$)$_{0-2}$)-tetrahydropyran-4-yl)-C(O)—. In still another particular variation, L is *—C(O)—. In still another particular variation, L is —CH(CH$_3$)—. In yet still another particular variation, L is *—C(O)N(CH$_2$-cyclopropyl)-. In yet still another particular variation, L is *—C(O)N(CH$_2$-cyclopropyl)-.

In still another embodiment of the compounds of the invention, with reference to any one of the above embodiments and variations, Ring A is selected from the group consisting of phenyl, pyridinyl, pyrimidinyl, pyrazinyl, pyridazinyl, pyrrolopyridinyl, indazolyl, each of which is unsubstituted or substituted by (R$_1$)$_n$.

In one variation, Ring A is selected from the group consisting of

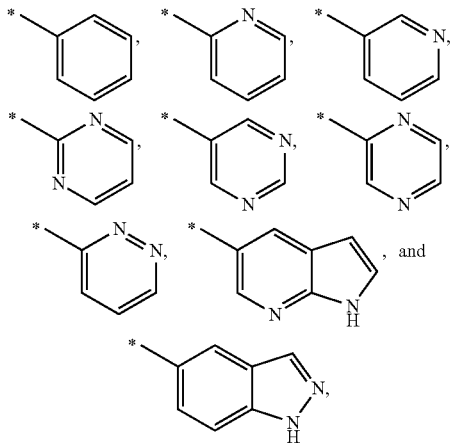

each of which is unsubstituted or substituted by (R$_1$)$_n$. In another particular variation, Ring A is selected from the group consisting of

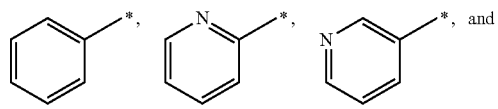

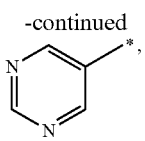

each unsubstituted or substituted by 1 to 2 R₁ groups.

In a particular variation, -Ring A-R₁ is of the formula

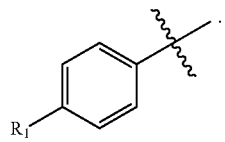

In another particular variation, Ring A is of the formula

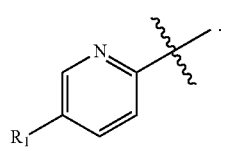

In yet another particular variation, -Ring A-R₁ is of the formula

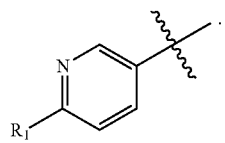

In yet still another particular variation, Ring A is of the formula

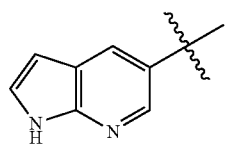

In another embodiment of the compounds of the invention, with reference to any one of the above embodiments and variations, Ring C is selected from the group consisting of

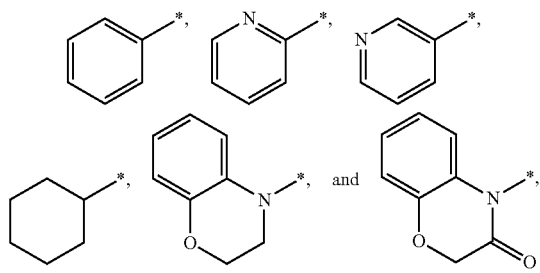

each of which is unsubstituted or substituted by (R₁₇)$_p$.

In one variation, Ring C is selected from the group consisting of phenyl and pyridinyl, each unsubstituted or substituted by (R₁₇)$_p$.

In another variation, -Ring C—R₁₇ is of the formula

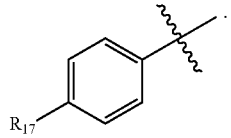

In still another variation, -Ring C—R₁₇ is of the formula

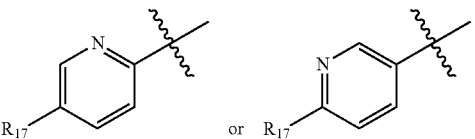

In yet another variation, -Ring C—R₁₇ is of the formula

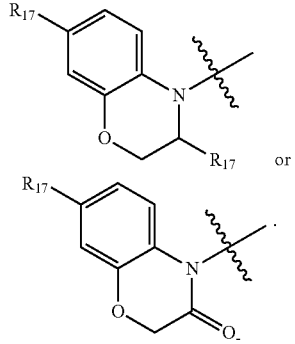

In still another embodiment of the compounds of the invention, with reference to any one of the above embodiments and variations, each R₁ is independently selected from the group consisting of fluoro, chloro, cyano, methyl, trifluoromethyl, methoxy, —NH₂, —C(O)NH₂, —C(O)NH(CH₃), —C(O)N(CH₃)₂, —NHC(O)CH₃, —NHC(O)CH₂NH₂, —NHC(O)CH(NH₂)(CH₃), —NHC(O)CH(NH₂)(cyclohexyl), —NHC(O)CH(NH₂)CH(CH₃)₂, —NHC(O)CH(CH₃)₂,

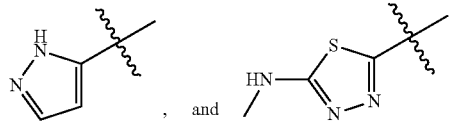

In one variation, each R₁ is independently selected from the group consisting of trifluoromethyl, cyano, —NH₂—, —C(O)NH₂, —C(O)NHCH₃, —C(O)N(CH₃)₂, and —NHC (O)CH(NH$_2$)(CH$_3$). In another variation, R$_1$ is trifluoromethyl. In another variation, R$_1$ is —NH$_2$. In still another variation, R$_1$ is —C(O)NH$_2$. In yet another variation, R$_1$ is —C(O)NHCH$_3$. In yet another variation, R$_1$ is —C(O)N (CH$_3$)$_2$. In still yet another variation R$_1$ is NH$_2$.

In another embodiment of the compound of the invention, with reference to any one of the above embodiments and variations, each R$_{17}$ is independently selected from the group consisting of cyano, halo, C$_{1-4}$alkyl, haloC$_{1-4}$alkyl, —SO$_2$—C$_{1-4}$alkyl, and C$_{3-6}$cycloalkyl.

In one variation, each R$_{17}$ is independently selected from the group consisting of cyano, fluoro, chloro, methyl, trifluoromethyl, 1,1-difluoroethyl, methylsulfonyl, and cyclopropyl.

In another variation, each R$_{17}$ is independently selected from the group consisting of cyano, chloro, fluoro, methylsulfonyl, and trifluoromethyl.

In one particular variation, at least one of R$_{17}$ is cyano. In another particular variation, at least one of R$_{17}$ is trifluoromethyl. In another particular variation, R$_{17}$ is chloro or fluoro. In still another variation, R$_{17}$ is methylsulfonyl. In still another variation, R$_{17}$ is methyl or fluoro. In yet still another variation, R$_{17}$ is cyano.

In another embodiment of the compound of the invention according to any one of the above embodiments and variations, n is 1 or 2. In another variation, n is 1. In another variation, n is 2.

In another embodiment of the compounds of the present invention, with reference to any one of the above embodiments and variations, p is 1, 2 or 3. In another variation, p is 1. In still another variation, p is 1. In yet still another variation, p is 3.

In a particular embodiment of the compounds of the invention, or a pharmaceutical acceptable salt, tautomer or stereoisomer thereof, the compound is of Formula Ia:

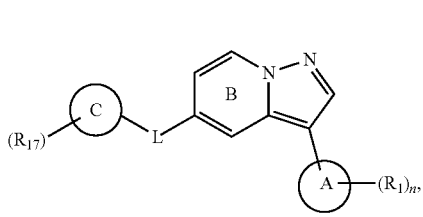

wherein
n is 1 or 2;
Ring A is phenyl, pyridinyl, or pyrimidinyl;
Ring C is phenyl or pyridinyl;
L is *—C(O)NR$_2$— or *—NR$_2$C(O)—, wherein R$_2$ is selected from hydrogen, C$_{1-4}$alkyl, C$_{1-4}$alkylamino-(C$_{0-4}$)alkylene, C$_{3-6}$cycloalkyl-(C$_{0-4}$)alkylene, C$_{4-6}$heterocycloalkyl-(C$_{0-4}$)alkylene, wherein the C$_{4-6}$heterocycloalkyl is selected from the group consisting of piperazinyl, morpholinyl, thiomorpholinyl, tetrahydropyranyl, and oxetanyl, and wherein the C$_{3-6}$cycloalkyl is selected from cyclopropyl, cyclobutyl, cyclopentyl and cyclohexyl;
each R$_1$ is independently *—C(O)NR$_7$R$_8$ or —NH$_2$—, wherein R$_7$ and R$_8$ are each independently hydrogen or C$_{1-4}$alkyl; and
R$_{17}$ is selected from the group consisting of cyano, halo, —NH$_2$—, —C(O)NH$_2$, —C(O)NH(CH$_3$), and —C(O)N(CH$_3$)$_2$.

In one variation of the compounds of the present invention, with reference to the particular embodiment above, -Ring A-R$_1$ is of the formula

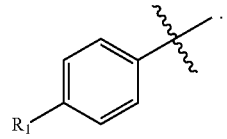

In another variation, -Ring A-R$_1$ is of the formula

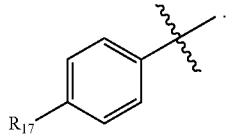

In another variation of the compounds of the present invention, with reference to the particular embodiment and any one of the variations above, -Ring C—R$_{17}$ is of the formula

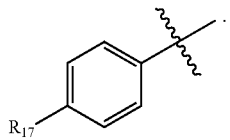

In another variation, -Ring C—R$_{17}$ is of the formula

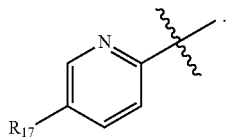

In still another variation of the compounds of the present invention, with reference to the particular embodiment or any one of the variations above, L is *—C(O)N(CH$_3$)— or *—N(CH$_3$)C(O)—. In another variation, L is *—C(O)NH (CH$_3$)—, *—C(O)N(CH$_2$CH$_3$)—, *—C(O)N(CH (CH$_3$)$_2$)—, *—C(O)N(NH(CH$_3$))—, or *—NH(CH$_3$)C (O)—. In another variation, L is *—C(O)N(CH$_3$)— In another variation, L is *—N(CH$_3$)C(O)—. In another variation, L is *—C(O)N(CH$_2$CH$_3$)—. In another variation, L is *—C(O)N(CH(CH$_3$)$_2$)—. In another variation, L is *—C (O)N(NH(CH$_3$))—, In still another variation, L is *—C(O) N(CH$_2$-cyclopropyl)-. In still another variation, L is *—C (O)N(cyclopropyl)-.

In still another variation of the compounds of the present invention, with reference to the particular embodiment or any one of the variations above, R$_1$ is —NH$_2$—. In another variation, R$_1$ is *—C(O)NH$_2$. In another variation, R$_1$ is —C(O)NH$_2$. In still another variation, R$_1$ is —C(O)NCH$_3$.

In still another variation of the compounds of the present invention, with reference to the particular embodiment or any one of the variations above, R$_{17}$ is cyano. In another variation R$_{17}$ is halo.

Particular examples of compounds or a pharmaceutically acceptable salt, tautomer or stereoisomer thereof, according to the present invention include, but are not limited to: N-(4-cyanophenyl)-N-methyl-3-(4-(trifluoromethyl)phenyl) pyrazolo[1,5-a]pyridine-5-carboxamide; 4-fluoro-N-methyl-N-((3-(4-(trifluoromethyl)phenyl)pyrazolo[1,5-a] yridine-5-yl)methyl)aniline; N-(4-chlorophenyl)-N-methyl-3-(4-(trifluoromethyl)phenyl)pyrazolo[1,5-a]pyridine-5-carboxamide; N-(4-fluorophenyl)-N-methyl-3-(4-(trifluoromethyl)phenyl)pyrazolo[1,5-a]pyridine-5-carboxamide; N-methyl-N-(5-methylpyridin-2-yl)-3-(4-(trifluoromethyl)phenyl)pyrazolo[1,5-a]pyridine-5-carboxamide; 4-chloro-N-methyl-N-((3-(4-(trifluoromethyl)phenyl)pyrazolo[1,5-a]yridine-5-yl) methyl)aniline; N,5-dimethyl-N-((3-(4-(trifluoromethyl) phenyl)pyrazolo[1,5-a]yridine-5-yl)methyl)yridine-2-amine; 5-((4-fluorophenoxy)methyl)-3-(4-(trifluoromethyl) phenyl)pyrazolo[1,5-a]pyridine; N-(4-cyanophenyl)-N-(2-methoxyethyl)-3-(4-(trifluoromethyl)phenyl)pyrazolo[1,5-a]pyridine-5-carboxamide; N-(4-cyanophenyl)-N-(2-(dimethylamino)ethyl)-3-(4-(trifluoromethyl)phenyl) pyrazolo[1,5-a]pyridine-5-carboxamide; N-(4-cyanophenyl)-N-((tetrahydro-2H-pyran-4-yl)methyl)-3-(4-(trifluoromethyl)phenyl)pyrazolo[1,5-a]pyridine-5-carboxamide; N-(4-(methylsulfonyl)phenyl)-N-((tetrahydro-2H-pyran-4-yl)methyl)-3-(4-(trifluoromethyl) phenyl)pyrazolo[1,5-a]pyridine-5-carboxamide; N-(5-cyanopyridin-2-yl)-N-methyl-3-(4-(trifluoromethyl)phenyl) pyrazolo[1,5-a]pyridine-5-carboxamide; N-methyl-N-(5-methylpyridin-3-yl)-3-(4-(trifluoromethyl)phenyl)pyrazolo [1,5-a]pyridine-5-carboxamide; 5-(((5-methylpyridin-2-yl) oxy)methyl)-3-(4-(trifluoromethyl)phenyl)pyrazolo[1,5-a] pyridine; 5-(4-fluorophenethyl)-3-(4-(trifluoromethyl) phenyl)pyrazolo[1,5-a]pyridine; N-(4-cyanophenyl)-N-methyl-3-(1-methyl-1H-indazol-5-yl)pyrazolo[1,5-a] pyridine-5-carboxamide; 3-(6-acetamidopyridin-3-yl)-N-(4-cyanophenyl)-N-methylpyrazolo[1,5-a]pyridine-5-carboxamide; 3-(4-carbamoylphenyl)-N-(4-cyanophenyl)-N-methylpyrazolo[1,5-a]pyridine-5-carboxamide; 3-(4-carbamoylphenyl)-N-(4-fluorophenyl)-N-methylpyrazolo [1,5-a]pyridine-5-carboxamide; 5-(((4-fluorophenyl)thio) methyl)-3-(4-(trifluoromethyl)phenyl)pyrazolo[1,5-a] pyridine; 5-(((4-fluorophenyl)sulfinyl)methyl)-3-(4-(trifluoromethyl)phenyl)pyrazolo[1,5-a]pyridine; 3-(4-(1H-pyrazol-5-yl)phenyl)-N-(4-cyanophenyl)-N-methylpyrazolo [1,5-a]pyridine-5-carboxamide; N-(4-cyanophenyl)-N-methyl-3-(5-(trifluoromethyl)pyridine-2-yl)pyrazolo[1,5-a] pyridine-5-carboxamide; N-(5-cyanopyridin-2-yl)-N-methyl-3-(5-(trifluoromethyl)pyridine-2-yl)pyrazolo[1,5-a] pyridine-5-carboxamide; (S)-3-(4-(2-aminopropanamido) phenyl)-N-(4-cyanophenyl)-N-methylpyrazolo[1,5-a] pyridine-5-carboxamide; 3-(5-carbamoylpyridin-2-yl)-N-(4-cyanophenyl)-N-methylpyrazolo[1,5-a]pyridine-5-carboxamide; 4-cyano-N-methyl-N-(3-(4-(trifluoromethyl) phenyl)pyrazolo[1,5-a]yridine-5-yl)benzamide; 4-fluoro-N-methyl-N-(3-(4-(trifluoromethyl)phenyl)pyrazolo[1,5-a] yridine-5-yl)benzamide; 4-cyano-N-methyl-N-(3-(4-(trifluoromethyl)phenyl)pyrazolo[1,5-a]pyridine-5-yl) benzenesulfonamide; 4-fluoro-N-methyl-N-(3-(4-(trifluoromethyl)phenyl)pyrazolo[1,5-a]pyridine-5-yl) benzenesulfonamide; 3-(4-carbamoylphenyl)-N-(5-cyanopyridin-2-yl)-N-methylpyrazolo[1,5-a]pyridine-5-carboxamide; N-methyl-3-(4-(trifluoromethyl)phenyl)-N-(5-(trifluoromethyl)pyridine-2-yl)pyrazolo[1,5-a]pyridine-5-carboxamide; N-methyl-N-(5-(methylsulfonyl)pyridine-2-yl)-3-(4-(trifluoromethyl)phenyl)pyrazolo[1,5-a]pyridine-5-carboxamide; N-(4-fluorobenzyl)-3-(4-(trifluoromethyl) phenyl)pyrazolo[1,5-a]yridine-5-amine; N-(4-fluorobenzyl)-3-(4-(trifluoromethyl)phenyl)pyrazolo[1,5-a]yridine-5-amine; N-methyl-6-(trifluoromethyl)-N-(3-(4-(trifluoromethyl)phenyl)pyrazolo[1,5-a]yridine-5-yl)nicotinamide; N-methyl-5-(trifluoromethyl)-N-(3-(4-(trifluoromethyl) phenyl)pyrazolo[1,5-a]yridine-5-yl)picolinamide; 4-cyano-N-((tetrahydro-2H-pyran-4-yl)methyl)-N-(3-(4-(trifluoromethyl)phenyl)pyrazolo[1,5-a]pyridin-5-yl)benzamide; N-(4-cyanophenyl)-N-methyl-3-(1H-pyrrolo[2,3-b]pyridin-5-yl) pyrazolo[1,5-a]pyridine-5-carboxamide; 3-(6-aminopyridin-3-yl)-N-(4-cyanophenyl)-N-methylpyrazolo [1,5-a]pyridine-5-carboxamide; 3-(4-aminophenyl)-N-(4-cyanophenyl)-N-methylpyrazolo[1,5-a]pyridine-5-carboxamide; 3-(4-(2-aminoacetamido)phenyl)-N-(4-cyanophenyl)-N-methylpyrazolo[1,5-a]pyridine-5-carboxamide; (R)-3-(4-(2-aminopropanamido)phenyl)-N-(4-cyanophenyl)-N-methylpyrazolo[1,5-a]pyridine-5-carboxamide; (S)-3-(4-(2-amino-3-methylbutanamido) phenyl)-N-(4-cyanophenyl)-N-methylpyrazolo[1,5-a] pyridine-5-carboxamide; (S)-3-(4-(2-amino-2-cyclohexylacetamido)phenyl)-N-(4-cyanophenyl)-N-methylpyrazolo[1,5-a]pyridine-5-carboxamide; 3-(4-fluorophenyl)-1-methyl-1-(3-(4-(trifluoromethyl)phenyl) pyrazolo[1,5-a]pyridin-5-yl)urea; 6-(1,1-difluoroethyl)-N-methyl-N-(3-(4-(trifluoromethyl)phenyl)pyrazolo[1,5-a] pyridin-5-yl)nicotinamide; 6-cyclopropyl-N-methyl-N-(3-(4-(trifluoromethyl)phenyl)pyrazolo[1,5-a]pyridin-5-yl) nicotinamide; 4-cyclopropyl-N-methyl-N-(3-(4-(trifluoromethyl)phenyl)pyrazolo[1,5-a]pyridin-5-yl) benzamide; 5-fluoro-N-methyl-N-(3-(4-(trifluoromethyl) phenyl)pyrazolo[1,5-a]pyridin-5-yl)picolinamide; N-methyl-4-(methylsulfonyl)-N-(3-(4-(trifluoromethyl)phenyl)pyrazolo[1,5-a]pyridin-5-yl)benzamide; N-(5-cyanopyridin-2-yl)-N-methyl-3-(1H-pyrrolo[2,3-b]pyridin-5-yl) pyrazolo[1,5-a]pyridine-5-carboxamide; 3-(6-aminopyridin-3-yl)-N-(5-cyanopyridin-2-yl)-N-methylpyrazolo[1,5-a]pyridine-5-carboxamide; 4-chloro-N-methyl-N-(3-(4-(trifluoromethyl)phenyl)pyrazolo[1,5-a] pyridin-5-yl)benzamide; N-(3-(4-carbamoylphenyl) pyrazolo[1,5-a]pyridin-5-yl)-4-fluoro-N-methylbenzamide; 4-fluoro-N-methyl-N-(3-(4-(5-(methylamino)-1,3,4-thiadiazol-2-yl)phenyl)pyrazolo[1,5-a]pyridin-5-yl)benzamide; N-methyl-N-(5-(methylsulfonyl)pyridin-2-yl)-3-(1H-pyrrolo[2,3-b]pyridin-5-yl)pyrazolo[1,5-a]pyridine-5-carboxamide; N-(5-cyanopyridin-2-yl)-N-methyl-3-5-methylpyridin-2-yl)pyrazolo[1,5-a]pyridine-5-carboxamide; N-(5-cyanopyridin-2-yl)-3-(5-methoxypyridin-2-yl)-N-methylpyrazolo[1,5-a]pyridine-5-carboxamide; 3-(5-carbamoylpyridin-2-yl)-N-(5-cyanopyridin-2-yl)-N-methylpyrazolo[1,5-a]pyridine-5-carboxamide; 3-(4-carbamoylphenyl)-N-methyl-N-(5-(trifluoromethyl)pyridin-2-yl)pyrazolo[1,5-a]pyridine-5-carboxamide; 3-(4-carbamoylphenyl)-N-methyl-N-(5-methylpyridin-2-yl) pyrazolo[1,5-a]pyridine-5-carboxamide; N-(4-fluorophenyl)-N-methyl-3-(4-(methylcarbamoyl)phenyl) pyrazolo[1,5-a]pyridine-5-carboxamide; 4-(5-(1-(methyl(5-methylpyridin-2-yl)amino)ethyl)pyrazolo[1,5-a]pyridin-3-yl)benzamide; 4-(5-(1-(7-fluoro-3-oxo-2H-benzo[b][1,4] oxazin-4(3H)-yl)ethyl)pyrazolo[1,5-a]pyridin-3-yl) benzamide; N-(4-cyanophenyl)-N-methyl-3-(4-(methylcarbamoyl)phenyl)pyrazolo[1,5-a]pyridine-5-carboxamide; N-(4-(5-(1-(methyl(5-methylpyridin-2-yl) amino)ethyl)pyrazolo[1,5-a]pyridin-3-yl)phenyl)acetamide; 3-(4-acetamidophenyl)-N-(5-cyanopyridin-2-yl)-N-methyl-pyrazolo[1,5-a]pyridine-5-carboxamide; 4-(5-(7-fluoro-3,4-dihydro-2H-benzo[b][1,4]oxazine-4-carbonyl)pyrazolo[1,5-a]pyridin-3-yl)benzamide; 4-(5-(7-fluoro-3-methyl-3,4- dihydro-2H-benzo[b][1,4]oxazine-4-carbonyl)pyrazolo[1,5-a]pyridin-3-yl)benzamide; 4-(5-(7-fluoro-3,4-dihydro-2H-benzo[b][1,4]oxazine-4-carbonyl)pyrazolo[1,5-a]pyridin-3-yl)-N-methylbenzamide; 4-(5-(7-fluoro-3-methyl-3,4-dihydro-2H-benzo[b][1,4]oxazine-4-carbonyl)pyrazolo[1,5-a]pyridin-3-yl)-N-methylbenzamide; N-(5-cyanopyridin-2-yl)-N-methyl-3-(4-(methylcarbamoyl)phenyl)pyrazolo[1,5-a]pyridine-5-carboxamide; N-(5-cyanopyridin-2-yl)-3-(4-(methylcarbamoyl)phenyl)-N-(oxetan-3-yl)pyrazolo[1,5-a]pyridine-5-carboxamide; N-(1-(1H-pyrazol-1-yl)propan-2-yl)-3-(4-carbamoylphenyl)-N-(5-cyanopyridin-2-yl)pyrazolo[1,5-a]pyridine-5-carboxamide; 3-(6-amino-5-fluoropyridin-3-yl)-N-(4-cyanophenyl)-N-methylpyrazolo[1,5-a]pyridine-5-carboxamide; 3-(4-amino-3,5-dimethylphenyl)-N-(4-cyanophenyl)-N-methylpyrazolo[1,5-a]pyridine-5-carboxamide; 3-(6-amino-5-methylpyridin-3-yl)-N-(4-cyanophenyl)-N-methylpyrazolo[1,5-a]pyridine-5-carboxamide; 3-(4-carbamoylphenyl)-N-(4-cyanocyclohexyl)-N-methylpyrazolo[1,5-a]pyridine-5-carboxamide; 3-(2-aminopyrimidin-5-yl)-N-(4-cyanophenyl)-N-methylpyrazolo[1,5-a]pyridine-5-carboxamide; 3-(6-amino-5-(trifluoromethyl)pyridin-3-yl)-N-(5-cyanopyridin-2-yl)-N-methylpyrazolo[1,5-a]pyridine-5-carboxamide; 3-(6-amino-5-cyanopyridin-3-yl)-N-(5-cyanopyridin-2-yl)-N-methylpyrazolo[1,5-a]pyridine-5-carboxamide; 3-(6-amino-5-chloropyridin-3-yl)-N-(5-cyanopyridin-2-yl)-N-methylpyrazolo[1,5-a]pyridine-5-carboxamide; 3-(6-amino-5-(dimethylcarbamoyl)pyridin-3-yl)-N-(5-cyanopyridin-2-yl)-N-methylpyrazolo[1,5-a]pyridine-5-carboxamide; 3-(6-amino-5-methoxypyridin-3-yl)-N-(5-cyanopyridin-2-yl)-N-methylpyrazolo[1,5-a]pyridine-5-carboxamide; 3-(4-carbamoylphenyl)-N-(4-chloro-2-formylphenyl)-N-methylpyrazolo[1,5-a]pyridine-5-carboxamide; N-(5-Cyanopyridin-2-yl)-N-ethyl-3-(4-(methylcarbamoyl)phenyl)pyrazolo[1,5-a]pyridine-5-carboxamide; N-(5-cyanopyridin-2-yl)-N-isopropyl-3-(4-(methylcarbamoyl)phenyl)pyrazolo[1,5-a]pyridine-5-carboxamide; 5-(5-(1-(4-cyanophenyl)-2-methylhydrazinecarbonyl)pyrazolo[1,5-a]pyridin-3-yl)-N-methyl picolinamide; N-(5-cyanopyridin-2-yl)-N-cyclopropyl-3-(4-(methylcarbamoyl)phenyl)pyrazolo[1,5-a]pyridine-5-carboxamide; N-(5-cyanopyridin-2-yl)-N-methyl-3-(4-(methylcarbamoyl)phenyl)pyrazolo[1,5-a]pyridine-5-carboxamide; N-ethyl-N-(5-fluoropyridin-2-yl)-3-(4-(methylcarbamoyl)phenyl)pyrazolo[1,5-a]pyridine-5-carboxamide; N-ethyl-3-(4-(methylcarbamoyl)phenyl)-N-(5-(trifluoromethyl)pyridin-2-yl)pyrazolo[1,5-a]pyridine-5-carboxamide; N-(4-Cyanophenyl)-N-methyl-3-(6-(methylcarbamoyl)pyridin-3-yl)pyrazolo[1,5-a]pyridine-5-carboxamide; 3-(5-Amino-6-chloropyridin-3-yl)-N-(5-cyanopyridin-2-yl)-N-methylpyrazolo[1,5-a]pyridine-5-carboxamide; N-(4-Chlorophenyl)-N-methyl-3-(4-(methylcarbamoyl)phenyl)pyrazolo[1,5-a]pyridine-5-carboxamide; 3-(4-Carbamoylphenyl)-N-(4-chlorophenyl)-N-methylpyrazolo[1,5-a]pyridine-5-carboxamide; 4-(5-((5-Cyanopyridin-2-yl)(methyl)carbamoyl)pyrazolo[1,5-a]pyridin-3-yl)benzoic acid; N-(5-Cyanopyridin-2-yl)-3-(4-((2-hydroxyethyl)carbamoyl)phenyl)-N-methylpyrazolo[1,5-a]pyridine-5-carboxamide; N-Methyl-3-(4-(methylcarbamoyl)phenyl)-N-(4-(trifluoromethyl)phenyl)pyrazolo[1,5-a]pyridine-5-carboxamide; 3-(4-((2-Aminoethyl)carbamoyl)phenyl)-N-(5-cyanopyridin-2-yl)-N-methylpyrazolo[1,5-a]pyridine-5-carboxamide; 3-(4-Carbamoylphenyl)-N-(4-cyanophenyl)-N-(2-hydroxyethyl)pyrazolo[1,5-a]pyridine-5-carboxamide; N-(5-Cyanopyridin-2-yl)-3-(4-(methylcarbamoyl)phenyl)pyrazolo[1,5-a]pyridine-5-carboxamide; 3-(6-Chloro-5-(methylsulfonamido)pyridin-3-yl)-N-(5-cyanopyridin-2-yl)-N-methylpyrazolo[1,5-a]pyridine-5-carboxamide; 3-(2-Aminopyridin-4-yl)-N-(5-cyanopyridin-2-yl)-N-methylpyrazolo[1,5-a]pyridine-5-carboxamide; N-(4-Chlorophenyl)-N-methyl-3-(6-(methylcarbamoyl)pyridin-3-yl)pyrazolo[1,5-a]pyridine-5-carboxamide; N-(4-Cyanophenyl)-N-(2-hydroxyethyl)-3-(4-(methylcarbamoyl)phenyl)pyrazolo[1,5-a]pyridine-5-carboxamide; N-(5-(2-Aminoethoxy)pyridin-2-yl)-N-methyl-3-(4-(methylcarbamoyl)phenyl)pyrazolo[1,5-a]pyridine-5-carboxamide; N-(5-Cyanopyridin-2-yl)-N-cyclobutyl-3-(4-(methylcarbamoyl)phenyl)pyrazolo[1,5-a]pyridine-5-carboxamide; N-(5-Cyanopyridin-2-yl)-N-methyl-3-(4-(piperidin-4-ylcarbamoyl)phenyl)pyrazolo[1,5-a]pyridine-5-carboxamide; N-(5-Cyanopyridin-2-yl)-N-methyl-3-(4-((2-(methylamino)ethyl)carbamoyl)phenyl)pyrazolo[1,5-a]pyridine-5-carboxamide; N-(5-cyanopyridin-2-yl)-3-(4-((2-(dimethylamino)ethyl)carbamoyl)phenyl)-N-methylpyrazolo[1,5-a]pyridine-5-carboxamide; N-(4-Chlorophenyl)-N-cyclopropyl-3-(4-(methylcarbamoyl)phenyl)pyrazolo[1,5-a]pyridine-5-carboxamide; N-(5-Cyanopyridin-2-yl)-N-(cyclopropylmethyl)-3-(4-(methylcarbamoyl)phenyl)pyrazolo[1,5-a]pyridine-5-carboxamide; N-(4-Cyanophenyl)-N-cyclopropyl-3-(4-(methylcarbamoyl)phenyl)pyrazolo[1,5-a]pyridine-5-carboxamide; N-(tert-Butyl)-N-(5-cyanopyridin-2-yl)-3-(4-(methylcarbamoyl)phenyl)pyrazolo[1,5-a]pyridine-5-carboxamide; 3-(4-Carbamoylphenyl)-N-(5-cyanopyridin-2-yl)-N-cyclopropylpyrazolo[1,5-a]pyridine-5-carboxamide; N-(5-Cyanopyridin-2-yl)-N-cyclopropyl-3-(4-(isopropylcarbamoyl)phenyl)pyrazolo[1,5-a]pyridine-5-carboxamide; N-(6-Methoxypyridin-3-yl)-N-methyl-3-(4-(methylcarbamoyl)phenyl)pyrazolo[1,5-a]pyridine-5-carboxamide; N-(5-Cyanopyridin-2-yl)-N-cyclopropyl-3-(4-(cyclopropylcarbamoyl)phenyl)pyrazolo[1,5a]pyridine-5-carboxamide; N-(5-Chloropyridin-2-yl)-N-cyclopropyl-3-(4-(methylcarbamoyl)phenyl)pyrazolo[1,5-a]pyridine-5-carboxamide; N-Cyclopropyl-N-(5-fluoropyridin-2-yl)-3-(4-(methylcarbamoyl)phenyl)pyrazolo[1,5a]pyridine-5-carboxamide; N-(5-Cyanopyridin-2-yl)-N-cyclopentyl-3-(4-(methylcarbamoyl)phenyl)pyrazolo[1,5-a]pyridine-5-carboxamide; N-(5-Cyanopyridin-2-yl)-N-cyclopropyl-3-(4-(ethylcarbamoyl)phenyl)pyrazolo[1,5-a]pyridine-5-carboxamide; 6-(N-Cyclopropyl-3-(4-(methylcarbamoyl)phenyl)pyrazolo[1,5-a]pyridine-5-carboxamido) nicotinic acid; N-(5-Carbamoylpyridin-2-yl)-N-cyclopropyl-3-(4-(methylcarbamoyl)phenyl)pyrazolo[1,5-a]pyridine-5-carboxamide; N-Cyclopropyl-N-(3,4-difluorophenyl)-3-(4-(methylcarbamoyl)phenyl)pyrazolo[1,5-a]pyridine-5-carboxamide; N-(5-Cyanopyridin-2-yl)-N-cyclopropyl-3-(4-(oxetan-3-ylcarbamoyl)phenyl)pyrazolo[1,5-a]pyridine-5-carboxamide; N-Cyclopropyl-3-(4-(methylcarbamoyl)phenyl)-N-(5-(trifluoromethyl)pyridin-2-yl)pyrazolo[1,5-a]pyridine-5-carboxamide; N-(5-Cyanopyridin-2-yl)-N-cyclopropyl-3-(5-(methylcarbamoyl)pyridin-2-yl)pyrazolo[1,5-a]pyridine-5-carboxamide; 3-(4-carbamoylphenyl)-N-(4-cyanophenyl)-N-cyclopropylpyrazolo[1,5-a]pyridine-5-carboxamide; 3-(4-Carbamoylphenyl)-N-cyclopropyl-N-(3,4-difluorophenyl)pyrazolo[1,5-a]pyridine-5-carboxamide; N-Cyclopropyl-3-(4-(methylcarbamoyl)phenyl)-N-(5-methylpyridin-2-yl)pyrazolo[1,5-a]pyridine-5-carboxamide; N-(4-Cyanophenyl)-N-cyclopropyl-3-(6-(methylcarbamoyl)pyridin-3-yl)pyrazolo[1,5-a]pyridine-5-carboxamide; 3-(6-Carbamoylpyridin-3-yl)-N-(4-cyanophenyl)-N-cyclopropylpyrazolo[1,5-a]pyridine-5-carboxamide; 3-(5-Carbamoylpyridin-2-yl)-N-(5-cyanopyridin-2-yl)-N-cyclopropylpyrazolo[1,5-a]pyridine-5-carboxamide; N-(5- cyanopyridin-2-yl)-N-ethyl-3-(4-[N-methylsulfamoyl] phenyl)pyrazolo[1,5-a]pyridine-5-carboxamide; N-(4-Cyanophenyl)-N-cyclopropyl-3-(5-(methylcarbamoyl) pyridin-2-yl)pyrazolo[1,5-a]pyridine-5-carboxamide; 3-(5-Carbamoylpyridin-2-yl)-N-(4-cyanophenyl)-N-cyclopropylpyrazolo[1,5-a]pyridine-5-carboxamide; N-(4-Chlorophenyl)-N-cyclopropyl-3-(6-(methylcarbamoyl) pyridin-3-yl)pyrazolo[1,5-a]pyridine-5-carboxamide; N-(5-Cyanopyridin-2-yl)-N-cyclobutyl-3-(6-(methylcarbamoyl) pyridin-3-yl)pyrazolo[1,5-a]pyridine-5-carboxamide; N-(4-Cyanophenyl)-N-cyclobutyl-3-(6-(methylcarbamoyl) pyridin-3-yl)pyrazolo[1,5-a]pyridine-5-carboxamide; N-(4-Cyanophenyl)-N-isopropyl-3-(6-(methylcarbamoyl) pyridin-3-yl)pyrazolo[1,5-a]pyridine-5-carboxamide; 5-Cyano-N-cyclopropyl-N-(3-(4-(methylcarbamoyl)phenyl)pyrazolo[1,5-a]pyridin-5-yl) picolinamide; N-(5-Cyanopyridin-2-yl)-N-isopropyl-3-(6-(methylcarbamoyl)pyridin-3-yl)pyrazolo[1,5-a]pyridine-5-carboxamide; N-(5-Cyano-6-methoxypyridin-2-yl)-N-cyclopropyl-3-(4-(methylcarbamoyl)phenyl)pyrazolo[1,5-a]pyridine-5-carboxamide; N-(5-cyanopyridin-2-yl)-N-ethyl-3-(6-[methylcarbamoyl]pyridin-3-yl)pyrazolo[1,5-a]pyridine-5-carboxamide; N-(5-fluoropyridin-2-yl)-N-isopropyl-3-(4-(methylcarbamoyl)phenyl)pyrazolo[1,5-a]pyridine-5-carboxamide; N-Isopropyl-3-(6-(methylcarbamoyl)pyridin-3-yl)-N-(5-(trifluoromethyl)pyridin-2-yl)pyrazolo[1,5-a]pyridine-5-carboxamide; N-Isopropyl-3-(4-(methylcarbamoyl)phenyl)-N-(5-(trifluoromethyl)pyridin-2-yl)pyrazolo[1,5-a]pyridine-5-carboxamide; N-(5-cyanopyridin-2-yl)-N-isopropyl-3-(5-(methylcarbamoyl) pyridin-2-yl)pyrazolo[1,5-a]pyridine-5-carboxamide; N-(5-Cyanopyridin-2-yl)-N-cyclobutyl-3-(5-(methylcarbamoyl) pyridin-2-yl)pyrazolo[1,5-a]pyridine-5-carboxamide; N-(5-fluoropyridin-2-yl)-N-isopropyl-3-(6-(methylcarbamoyl) pyridin-3-yl)pyrazolo[1,5-a]pyridine-5-carboxamide; N-ethyl-3-(6-(methylcarbamoyl)pyridin-3-yl)-N-(5-(trifluoromethyl)pyridin-2-yl)pyrazolo[1,5-a]pyridine-5-carboxamide; N-(5-cyanopyridin-2-yl)-N-ethyl-3-(4-(methylsulfonyl)phenyl)pyrazolo[1,5-a]pyridine-5-carboxamide; N-ethyl-N-(5-fluoropyridin-2-yl)-3-(6-(methylcarbamoyl) pyridin-3-yl)pyrazolo[1,5-a]pyridine-5-carboxamide; N-cyclobutyl-3-(4-(methylcarbamoyl)phenyl)-N-(5-(trifluoromethyl)pyridin-2-yl)pyrazolo[1,5-a]pyridine-5-carboxamide; N N-cyclobutyl-3-(6-(methylcarbamoyl)pyridin-3-yl)-N-(5-(trifluoromethyl)pyridin-2-yl)pyrazolo[1,5-a]pyridine-5-carboxamide; N-(5-cyano-6-(2-hydroxyethoxy)pyridin-2-yl)-N-ethyl-3-(4-(methylcarbamoyl)phenyl)pyrazolo[1,5-a] pyridine-5-carboxamide; 4-(5-(N-(5-Cyanopyridin-2-yl)-N-methylsulfamoyl)pyrazolo[1,5-a]pyridin-3-yl)-N-methyl benzamide; 4-(5-(N-(5-Cyanopyridin-2-yl)-N-cyclopropylsulfamoyl)pyrazolo[1,5-a]pyridin-3-yl)-N-methylbenzamide; 4-(5-(N-(5-cyanopyridin-2-yl)-N-cyclopropylsulfamoyl)pyrazolo[1,5-a]pyridin-3-yl)benzamide.

Particular examples of the compounds or a pharmaceutically acceptable salt, tautomer or stereoisomer thereof, according to the present invention include, but are not limited to: 3-(4-carbamoylphenyl)-N-(5-cyanopyridin-2-yl)-N-methylpyrazolo[1,5-a]pyridine-5-carboxamide; N-(4-cyanophenyl)-N-methyl-3-(1H-pyrrolo[2,3-b]pyridin-5-yl) pyrazolo[1,5-a]pyridine-5-carboxamide; 3-(6-aminopyridin-3-yl)-N-(4-cyanophenyl)-N-methylpyrazolo[1,5-a]pyridine-5-carboxamide; (R)-3-(4-(2-aminopropanamido)phenyl)-N-(4-cyanophenyl)-N-methylpyrazolo[1,5-a]pyridine-5-carboxamide; N-(5-cyanopyridin-2-yl)-N-methyl-3-(1H-pyrrolo[2,3-b]pyridin-5-yl)pyrazolo[1,5-a]pyridine-5-carboxamide; N-(5-cyanopyridin-2-yl)-N-methyl-3-(4-(methylcarbamoyl) phenyl)pyrazolo[1,5-a]pyridine-5-carboxamide; 3-(2-aminopyrimidin-5-yl)-N-(4-cyanophenyl)-N-methylpyrazolo[1,5-a]pyridine-5-carboxamide; and 3-(6-amino-5-(dimethylcarbamoyl)pyridin-3-yl)-N-(5-cyanopyridin-2-yl)-N-methylpyrazolo[1,5-a]pyridine-5-carboxamide.

Another particular examples of the compounds or a pharmaceutically acceptable salt, tautomer or stereoisomer thereof, according to the present invention include, but are not limited to: N-(5-Cyanopyridin-2-yl)-N-ethyl-3-(4-(methylcarbamoyl)phenyl)pyrazolo[1,5-a]pyridine-5-carboxamide; N-(5-cyanopyridin-2-yl)-N-isopropyl-3-(4-(methylcarbamoyl)phenyl)pyrazolo[1,5-a]pyridine-5-carboxamide; 5-(5-(1-(4-cyanophenyl)-2-methylhydrazinecarbonyl)pyrazolo[1,5-a]pyridin-3-yl)-N-methyl picolinamide; N-(5-cyanopyridin-2-yl)-N-cyclopropyl-3-(4-(methylcarbamoyl)phenyl)pyrazolo[1,5-a]pyridine-5-carboxamide; N-(5-cyanopyridin-2-yl)-N-methyl-3-(4-(methylcarbamoyl)phenyl)pyrazolo[1,5-a] pyridine-5-carboxamide; N-ethyl-N-(5-fluoropyridin-2-yl)-3-(4-(methylcarbamoyl)phenyl)pyrazolo[1,5-a]pyridine-5-carboxamide; and N-ethyl-3-(4-(methylcarbamoyl)phenyl)-N-(5-(trifluoromethyl)pyridin-2-yl)pyrazolo[1,5-a] pyridine-5-carboxamide.

It is noted that the compounds of the present invention may be in the form of a pharmaceutically acceptable salt. It is further note that the compounds of the present invention may be a mixture of stereoisomers, or the compound may comprise a single stereoisomer.

Further compounds of the invention are detailed in the Examples, infra.

In another aspect, the present invention is directed to a pharmaceutical composition which includes as an active ingredient a compound according to any one of the above embodiments and variations in combination with a pharmaceutically acceptable carrier, diluent or excipient.

In one embodiment, the pharmaceutical composition further includes a second agent which can be a kinase inhibitor, an anti-malarial drug or an anti-inflammatory agent.

In another embodiment, the pharmaceutical composition includes an antimalarial drug as a second agent. The selections for the antimalarial drug may includes, but are not limited to, artemisinin, artemether, artesunate, arteflene, dihydroartemisinin, chlorproguanil, trimethoprim, chloroquine, quinine, mefloquine, amodiaquine, atovaquone, proguanil, lumefantrine, piperaquine, pyronaridine, halofantrine, pyrimethamine-sulfadoxine, quinacrine, pyrimethamine-dapsone, quinidine, amopyroquine, sulphonamides, primaquine, ferroquine, tafenoquine, arterolane, and pyronaridine.

In another embodiment, the pharmaceutical composition is a solid formulation adapted for oral administration. In another embodiment, the composition is a liquid formulation adapted for oral administration. In yet another embodiment, the composition is a tablet. In still another embodiment, the composition is a liquid formulation adapted for parenteral administration.

In yet another embodiment, the pharmaceutical composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

In another aspect, the present application is directed to a compound or a pharmaceutical composition according to any one of the above embodiments and variations for use in a therapeutic application.

In another aspect, the present application is directed to a compound or a pharmaceutical composition according to any one of the above embodiments and variations for use as a medicament.

In yet another aspect, the present invention is directed to a method for treating, preventing, inhibiting, ameliorating, or eradicating the pathology and/or symptomology of a disease caused by a *Plasmodium* parasite. The method involves administering to a subject a therapeutically effective amount of a compound or a pharmaceutical composition according to the above embodiments and variations. In addition, the administering may be in combination with a second agent.

In one embodiment of the method of the invention, the method is directed to treatment of malaria; particularly malaria caused by the parasites *Plasmodium falciparum, Plasmodium vivax, Plasmodium ovale*, and *Plasmodium malaria*; more particularly, the parasite *Plasmodium falciparum*. Further, the *Plasmodium* parasite can be at the blood stages or at the hepatic stages.

In the treatment method of the invention, the compounds or pharmaceutical compositions may be administered with prior to, simultaneously with, or after a second agent. The second agent can be a kinase inhibitor, an anti-malarial drug or an anti-inflammatory agent. In one particular variation of the method, the second agent is an anti-malarial drug. The selection of the antimalarial drug, includes, but is not limited to, artemisinin, artemether, artesunate, arteflene, dihydroartemisinin, chlorproguanil, trimethoprim, chloroquine, quinine, mefloquine, amodiaquine, atovaquone, proguanil, lumefantrine, piperaquine, pyronaridine, halofantrine, pyrimethamine-sulfadoxine, quinacrine, pyrimethamine-dapsone, quinidine, amopyroquine, sulphonamides, primaquine, ferroquine, tafenoquine, arterolane, and pyronaridine.

In another aspect, the invention is directed to a compound, salt, steroisomer, or pharmaceutical composition thereof, according to any one of the above embodiments or variation, for treating, preventing, inhibiting, ameliorating, or eradicating the pathology and/or symptomology of a disease caused by a *Plasmodium* parasite. In one embodiment, the disease is malaria caused by the *Plasmodium* parasite *Plasmodium falciparum, Plasmodium vivax, Plasmodium ovale*, or *Plasmodium* malaria; particularly, the parasite *Plasmodium falciparum*. Further, the *Plasmodium* parasite can be at the blood stages, or the *Plasmodium* parasite can be at the hepatic stages.

In still another aspect, the present invention is directed to the use of the compound, or a salt, a stereoisomer, or a pharmaceutical composition thereof, according to the any one of the above embodiments or variations in the manufacture of a medicament for treating, preventing, inhibiting, ameliorating, or eradicating the pathology and/or symptomology of a disease caused by a *Plasmodium* parasite. In one embodiment, the medicament is for treating malaria causes by the parasite *Plasmodium falciparum, Plasmodium vivax, Plasmodium ovale*, or *Plasmodium* malaria; in particular, the parasite *Plasmodium falciparum*. Further, the *Plasmodium* parasite can be at the blood stages or at the hepatic stages.

The medicament, in addition to the compound of the invention, may further include a second agent. The second agent may be a kinase inhibitor, an anti-malarial drug or an anti-inflammatory agent. In one particular embodiment, the second agent is an anti-malarial drug selected from artemisinin, artemether, artesunate, arteflene, dihydroartemisinin, chlorproguanil, trimethoprim, chloroquine, quinine, mefloquine, amodiaquine, atovaquone, proguanil, lumefantrine, piperaquine, pyronaridine, halofantrine, pyrimethamine-sulfadoxine, quinacrine, pyrimethamine-dapsone, quinidine, amopyroquine, sulphonamides, primaquine, ferroquine, tafenoquine, arterolane, and pyronaridine.

In another aspect, the invention is related to a kit which comprises a compound of any one of the above embodiments and variations, and optionally a second therapeutic agent. In one particular variation, the kit comprises the compound in a multiple dose form.

Enumerated Embodiments

Various enumerated embodiments of the invention are described herein. It will be recognized that features specified in each embodiment may be combined with other specified features to provide further embodiments of the present invention.

In a first embodiment, the invention provides a compound of the formula (I), or a pharmaceutical acceptable salt, tautomer or stereoisomer thereof,

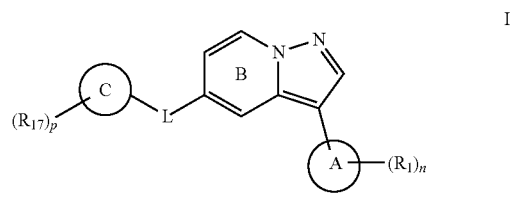

wherein:
n is 0, 1, 2 or 3;
p is 0, 1, 2 or 3;
L is selected from the group consisting of
*—(CHR$_3$)$_{1-3}$—, *—CHR$_3$N(R$_2$)—, *—CHR$_3$O—, *—CHR$_3$S—, *—CHR$_3$S(O)—, *—CHR$_3$N(R$_2$)CHR$_3$—, *—C(O)—, *—C(O)N(R$_2$)—, *—C(O)N(R$_2$)CHR$_3$—, *—N(R$_2$)—, *—N(R$_2$)CHR$_3$—, *—N(R$_2$)C(O)—, *—N(R$_2$)C(O)N(R$_2$)—, and *—N(R$_2$)S(O)$_2$—, wherein
* represents the point of attachment of L to the pyrazolo[1,5-a]pyridine fused ring depicted in Formula I;
each R$_2$ is independently selected from the group consisting of hydrogen, C$_{1-6}$alkyl, haloC$_{1-6}$alkyl, R—C$_{0-4}$alkylene, and R—C$_{0-4}$alkylene-C(O)—, wherein R is selected from the group consisting of hydroxyl, C$_{1-4}$alkoxy, amino, C$_{1-4}$alkylamino, C$_{3-6}$cycloalkyl, C$_{4-6}$heterocycloalkyl, and C$_{5-6}$heteroaryl, wherein the C$_{3-6}$cycloalkyl, C$_{4-6}$heterocycloalkyl, and C$_{5-6}$heteroaryl of R are each unsubstituted or substituted with 1-2 substituents independently selected from the group consisting of halo, amino, hydroxyl, C$_{1-4}$alkyl, C$_{1-4}$alkoxy, oxo, and C$_{5-6}$heteroaryl; and
each R$_3$ is independently selected from the group consisting of hydrogen and C$_{1-4}$alkyl,
Ring A is selected from the group consisting of C$_{6-10}$aryl and C$_{3-10}$heteroaryl;
Ring C is selected from the group consisting of C$_{6-10}$aryl, C$_{5-10}$heteroaryl, C$_{5-7}$cycloalkyl, C$_{5-7}$heterocycloalkyl, and a fused bicyclyl comprising a $C_{5-6}$heterocycloalky fused to a phenyl;

each $R_1$ is independently selected from the group consisting of halo, cyano, amino, $C_{1-4}$alkyl, $C_{1-4}$alkoxyl, halo-$C_{1-4}$alkyl, —C(O)NR$_7$R$_8$, —NHC(O)R$_{11}$, phenyl, and $C_{5-6}$heteroaryl; wherein
the phenyl and $C_{5-6}$heteroaryl are each unsubstituted or substituted with 1-2 substituents independently selected from the group consisting of $C_{1-4}$alkyl, amino, halo, and $C_{1-4}$alkylamino;

$R_7$ and $R_8$ are each independently selected from hydrogen, $C_{1-4}$alkyl and haloC$_{1-4}$alkyl;

$R_{11}$ is $C_{1-6}$alkyl unsubstituted or substituted with 1-2 substituents independently selected from the group consisting of amino, $C_{3-6}$cycloalkyl and $C_{4-6}$heterocycloalkyl; and $R_{17}$ is selected from the group consisting of cyano, halo, $C_{1-4}$alkyl, halo-$C_{1-4}$alkyl, oxo, $C_{3-6}$cycloalkyl, and —SO$_2$—C$_{1-4}$alkyl.

Embodiment 2

A compound of the formula (I), or a salt, tautomer or stereoisomer thereof, according to embodiment 1, wherein L is selected from the group consisting of *—(CHR$_3$)$_{1-3}$—, *—CHR$_3$N(R$_2$)—, *—CHR$_3$O—, *—CHR$_3$S—, *—CHR$_3$S(O)—, *—C(O)—, *—C(O)N(R$_2$)—, *—N(R$_2$)—, *—N(R$_2$)CHR$_3$—, *—N(R$_2$)C(O)—, *—N(R$_2$)C(O)N(R$_2$)—, *—N(R$_2$)S(O)$_2$—, wherein
each $R_2$ is independently selected from the group consisting of hydrogen, $C_{1-6}$alkyl, R—C$_{0-4}$alkylene, wherein R is selected from the group consisting of $C_{1-4}$alkoxy, $C_{1-4}$alkylamino, di-$C_{1-4}$alkylamino, $C_{3-6}$cycloalkyl, $C_{4-6}$heterocycloalkyl and $C_{5-6}$heteroaryl, wherein the $C_{3-6}$cycloalkyl, $C_{4-6}$heterocycloalkyl and $C_{5-6}$heteroaryl of R are each unsubstituted or substituted with 1-2 substituents independently selected from the group consisting of halo, amino, hydroxyl, $C_{1-4}$alkyl, $C_{1-4}$alkoxy, oxo, and $C_{5-6}$heteroaryl.

Embodiment 3

A compound of the formula (I), or a salt, tautomer or stereoisomer thereof, according to embodiment 1, wherein L is selected from the group consisting of *—C(O)N(R$_2$)—, and *—N(R$_2$)C(O)—, wherein each $R_2$ is independently selected from hydrogen, $C_{1-4}$alkyl, and R—C$_{0-4}$alkylene, wherein R is selected from the group consisting of $C_{1-4}$alkylamino, $C_{3-6}$cycloalkyl, $C_{4-6}$heterocycloalkyl and $C_{5-6}$heteroaryl, each unsubstituted or substituted with 1-2 substituents independently selected from the group consisting of halo, amino, hydroxyl, $C_{1-4}$alkyl, $C_{1-4}$alkoxy, oxo, and $C_{5-6}$heteroaryl.

Embodiment 4

A compound of the formula (I), or a salt, tautomer or stereoisomer thereof, according to embodiment 1, wherein L is selected from the group consisting of *—CH(CH$_3$)—, *—CH$_2$CH$_2$—, —*—CH$_2$N(CH$_3$)—, *—CH$_2$N(C(O)(CH$_2$)$_{1-2}$NH(CH$_3$))—, *—CH$_2$N(C(O)—(CH$_2$)$_{1-2}$NH$_2$)—, *—CH$_2$N((C(O)—(CH$_2$)$_{1-2}$N(CH$_3$)$_2$)—, *—CH$_2$N(C(O)(CH$_2$)$_{1-2}$OH)—, *—CH(CH$_3$)N(CH$_3$)—, *—CH$_2$O—, *—CH$_2$S—, *—CH$_2$S(O)—, *—C(O)—, *—C(O)N(CH$_3$)—, *—C(O)N(CH$_2$CH$_3$)—, *—C(O)N(CH(CH$_3$)$_2$)—, *—C(O)N(C(CH$_3$)$_3$)—, *—C(O)N(CH$_2$CH(CH$_3$)$_2$)—, *—C(O)N(CH(CH$_3$)CH$_2$CH$_3$)—, *—C(O)N(CH$_2$CH$_2$OCH$_3$)—, *—C(O)N(NH(CH$_3$))—, *—C(O)N(CH$_2$CH$_2$N(CH$_3$)$_2$)—, *—C(O)N(CH$_3$)CH$_2$—, *—NHCH$_2$—, *—N(CH$_3$)CH$_2$—, *—N(CH$_2$-tetrahydropyran-4-yl)-C(O)—, *—N(CH$_3$)C(O)—, *—N(CH$_3$)C(O)NH—, *—N(CH$_3$)S(O)$_2$—, *—C(O)N((CH$_2$)$_{0-1}$-cyclopropyl)-, *—C(O)N(CH$_2$)$_{0-1}$-cyclobutyl)-, *—C(O)N((CH$_2$)$_{0-1}$-cyclopentyl)-, *—C(O)N((CH$_2$)$_{0-1}$-cyclohexyl)-, *—C(O)N(CH$_2$-tetrahydropyran-4-yl)-, *—C(O)N((CH$_2$)$_2$-(1,1-dioxidothiomorpholino-4-yl))-, *—C(O)N(CH$_2$-1,1-dioxidothiomorpholino-4-yl)-, *—C(O)N((CH$_2$)$_2$-tetrahydropyran-4-yl))-, *—C(O)N((CH$_2$)$_{1-2}$-morpholin-4-yl)-, *—C(O)N(oxetan-3-yl)-, *—C(O)N(CH$_2$-oxetan-3-yl)-, *—C(O)N(CH(CH$_3$)—CH$_2$-1-H-pyrazoly-1-yl)-, *—CH$_2$N(C(O)—(CH$_2$)$_{1-2}$-morpholinyl))-, *—CH$_2$N(C(O)—(CH$_2$)$_{1-2}$-4-methylpiperizin-1-yl), *—CH$_2$N(C(O)—(CH$_2$)$_{1-2}$-tetrahydropyran-4-yl)-, and *—CH$_2$N(C(O)(CH$_2$)$_{1-2}$-oxetan-3-yl)-.

Embodiment 5

A compound of the formula (I), or a salt, tautomer or stereoisomer thereof, according to embodiment 1, wherein L is selected from the group consisting of *—CH(CH$_3$)—, *—CH$_2$CH$_2$—, —*—CH$_2$N(CH$_3$)—, *—C(O)N(CH$_2$CH$_3$)—, *—C(O)N(CH(CH$_3$)$_2$)—, *—CH(CH$_3$)N(CH$_3$)—, *—CH$_2$O—, *—CH$_2$S—, —*—CH$_2$S(O)—, *—C(O)—, *—C(O)N(CH$_3$)—, *—C(O)N(CH$_3$)CH$_2$—, *—C(O)N(CH$_2$CH$_2$OCH$_3$)—, *—C(O)N(NH(CH$_3$))—, *—C(O)N(CH$_2$CH$_2$N(CH$_3$)$_2$)—, *—NHCH$_2$—, *—N(CH$_3$)CH$_2$—, *—N(CH$_2$-tetrahydropyran-4-yl)-C(O)—, *—N(CH$_3$)C(O)—, *—N(CH$_3$)C(O)NH—, *—N(CH$_3$)S(O)$_2$—, *—C(O)N((CH$_2$)$_{0-1}$-cyclopropyl)-, *—C(O)N(CH$_2$-tetrahydropyran-4-yl)-, *—C(O)N(oxetan-3-yl)-, and *—C(O)N(CH(CH$_3$)CH$_2$-(1-H-pyrazoly-1-yl))-.

Embodiment 6

A compound of the formula (I), or a salt, tautomer or stereoisomer thereof, according to embodiment 1, wherein L is *—C(O)N(CH$_3$)—, *—C(O)N(CH$_2$CH$_3$)—, *—C(O)N(CH(CH$_3$)$_2$)—, *—C(O)N(NH(CH$_3$))—, or *—N(CH$_3$)C(O)—.

Embodiment 7

A compound of the formula (I), or a salt, tautomer or stereoisomer thereof, according to embodiment 1, wherein L is *—C(O)N(cyclopropyl)-.

Embodiment 8

A compound of the formula (I), or a salt, tautomer or stereoisomer thereof, according to embodiment 1, wherein L is *—C(O)— or —CH(CH$_3$)—.

Embodiment 9

A compound of the formula (I), or a salt, tautomer or stereoisomer thereof, according to embodiments 1 to 8, wherein Ring A is selected from the group consisting of phenyl, pyridinyl, pyrimidinyl, pyrazinyl, pyridazinyl, pyrrolopyridinyl, and indazolyl, each of which is unsubstituted or substituted by $(R_1)_n$.

Embodiment 10

A compound of the formula (I), or a salt, tautomer or stereoisomer thereof, according to any one of embodiments 1 to 8, wherein Ring A is selected from the group consisting of

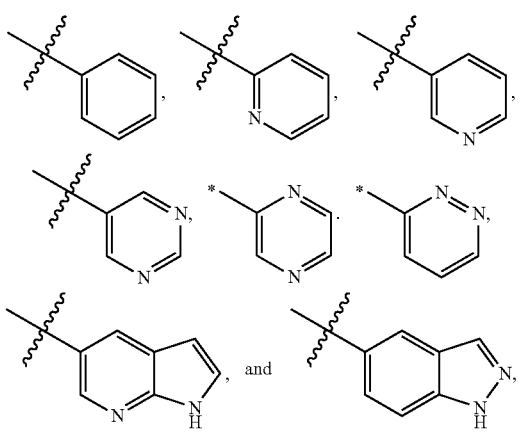

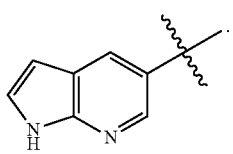 [SMILES: *c1cnc2[nH]ccc2c1]

each of which is unsubstituted or substituted by $(R_1)_n$.

Embodiment 11

A compound of the formula (I), or a salt, tautomer or stereoisomer thereof, according to any one of embodiments 1 to 8, wherein -Ring A-R$_1$ is of the formula

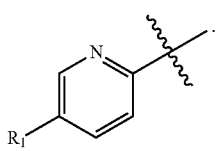

Embodiment 12

A compound of the formula (I), or a salt, tautomer or stereoisomer thereof, according to any one of embodiments 1 to 8, wherein -Ring A-R$_1$ is of the formula

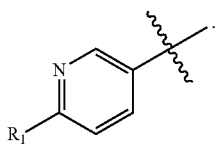

Embodiment 13

A compound of the formula (I), or a salt, tautomer or stereoisomer thereof, according to any one of embodiments 1 to 8, wherein -Ring A-R$_1$ is of the formula

Embodiment 14

A compound of the formula (I), or a salt, tautomer or stereoisomer thereof, according to any one of embodiments 1 to 8, wherein Ring A is of the formula

Embodiment 15

A compound of the formula (I), or a salt, tautomer or stereoisomer thereof, according to any one of embodiments 1 to 14, wherein Ring C is selected from the group consisting of

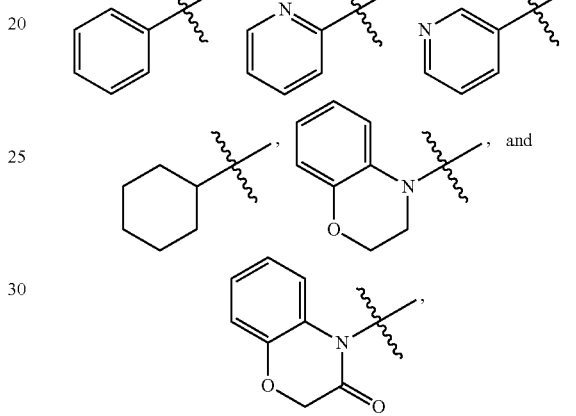

each of which is unsubstituted or substituted by $(R_{17})_p$.

Embodiment 16

A compound of the formula (I), or a salt, tautomer or stereoisomer thereof, according to any one of embodiments 1 to 7 and 9-14, wherein Ring C is selected from the group consisting of phenyl and pyridinyl, each of which is unsubstituted or substituted by $(R_{17})_p$.

Embodiment 17

A compound of the formula (I), or a salt, tautomer or stereoisomer thereof, according to any one of embodiments 1 to 7 and 9-14, wherein -Ring C—R$_{17}$ is of the formula

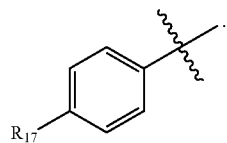

Embodiment 18

A compound of the formula (I), or a salt, tautomer or stereoisomer thereof, according to any one of embodiments 1 to 7 and 9-14, wherein -Ring C—R$_{17}$ is of the formula

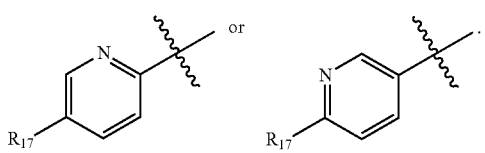

Embodiment 19

A compound of the formula (I), or a salt, tautomer or stereoisomer thereof, according to any one of embodiments 1-2, 4-5 and 8-14, wherein -Ring C—$R_{17}$ is of the formula

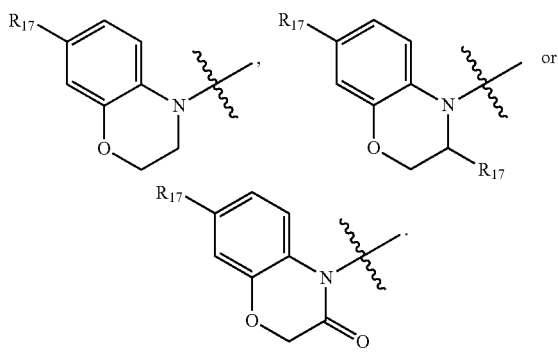

Embodiment 20

A compound of the formula (I), or a salt, tautomer or stereoisomer thereof, according to any one of embodiments 1 to 19, wherein each $R_1$ is independently selected from the group consisting of fluoro, chloro, cyano, methyl, trifluoromethyl, methoxy, —$NH_2$, —$C(O)NH_2$, —$C(O)NH(CH_3)$, —$C(O)N(CH_3)_2$, —$NHC(O)CH_3$, —$NHC(O)CH_2NH_2$, —$NHC(O)CH(NH_2)(CH_3)$, —$NHC(O)CH(NH_2)$(cyclohexyl), —$NHC(O)CH(NH_2)CH(CH_3)_2$, —$NHC(O)CH(CH_3)_2$,

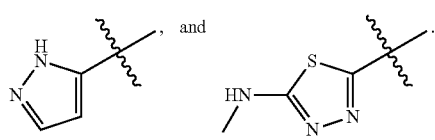

Embodiment 21

A compound of the formula (I), or a salt, tautomer or stereoisomer thereof, according to any one of embodiments 1 to 19, wherein each $R_1$ is independently selected from the group consisting of trifluoromethyl, cyano, —$NH_2$—, —$C(O)NH_2$, —$C(O)NHCH_3$, and —$C(O)N(CH_3)_2$,

Embodiment 22

A compound of the formula (I), or a salt, tautomer or stereoisomer thereof, according to any one of embodiments 1 to 19, wherein $R_1$ is trifluoromethyl.

Embodiment 23

A compound of the formula (I), or a salt, tautomer or stereoisomer thereof, according to any one of embodiments 1 to 19, wherein $R_1$ is —$NH_2$.

Embodiment 24

A compound of the formula (I), or a salt, tautomer or stereoisomer thereof, according to any one of embodiments 1 to 19, wherein $R_1$ is —$C(O)NH_2$.

Embodiment 25

A compound of the formula (I), or a salt, tautomer or stereoisomer thereof, according to any one of embodiments 1 to 19, wherein $R_1$ is —$C(O)NHCH_3$.

Embodiment 26

A compound of the formula (I), or a salt, tautomer or stereoisomer thereof, according to any one of embodiments 1 to 19, wherein $R_1$ is —$NHC(O)CH(NH_2)(CH_3)$.

Embodiment 27

A compound of the formula (I), or a salt, tautomer or stereoisomer thereof, according to any one of embodiments 1 to 26, wherein each $R_{17}$ is independently selected from the group consisting of cyano, halo, $C_{1-4}$alkyl, halo$C_{1-4}$alkyl, —$SO_2$—$C_{1-4}$alkyl, and $C_{3-6}$cycloalkyl.

Embodiment 28

A compound of the formula (I), or a salt, tautomer or stereoisomer thereof, according to any one of embodiments 1 to 26, wherein each $R_{17}$ is independently selected from the group consisting of cyano, fluoro, chloro, methyl, trifluoromethyl, 1,1-difluoroethyl, methylsulfonyl, and cyclopropyl.

Embodiment 29

A compound of the formula (I), or a salt, tautomer or stereoisomer thereof, according to any one of embodiments 1-7, 9-18 and 20-26, $R_{17}$ is cyano.

Embodiment 30

A compound of the formula (I), or a salt, tautomer or stereoisomer thereof, according to any one of embodiments 1-7, 9-18 and 20-26, $R_{17}$ is trifluoromethyl

Embodiment 31

A compound of the formula (I), or a salt, tautomer or stereoisomer thereof, according to any one of embodiments 1-7, 9-18 and 20-26, wherein $R_{17}$ is fluoro or chloro.

Embodiment 32

A compound of the formula (I), or a salt, tautomer or stereoisomer thereof, according to any one of embodiments 1-7, 9-18 and 20-26, wherein $R_{17}$ is methylsulfonyl.

Embodiment 33

A compound of the formula (I), or a salt, tautomer or stereoisomer thereof, according to any one of embodiments 1-2, 4-5, 8-15 and 19, where each $R_{17}$ is methyl.

Embodiment 34

A compound of the formula (I), or a salt, tautomer or stereoisomer thereof, according to embodiment 1, wherein the compound is of Formula Ia

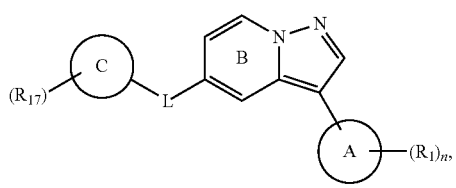

wherein
n is 1 or 2;
Ring A is phenyl, pyridinyl, or pyrimidinyl;
Ring C is phenyl or pyridinyl;
L is *—C(O)NR$_2$— or *—NR$_2$C(O)—, wherein R$_2$ is selected from hydrogen, C$_{1-4}$alkyl, C$_{1-4}$alkylamino-(C$_{0-4}$)alkylene, C$_{3-6}$cycloalkyl-(C$_{0-4}$)alkylene, C$_{4-6}$heterocycloalkyl-(C$_{0-4}$)alkylene, wherein the C$_{4-6}$heterocycloalkyl is selected from the group consisting of piperazinyl, morpholinyl, thiomorpholinyl, tetrahydropyranyl, and oxetanyl, and wherein the C$_{3-6}$cycloalkyl is selected from cyclopropyl, cyclobutyl, cyclopentyl and cyclohexyl;
each R$_1$ is independently *—C(O)NR$_7$R$_8$ or —NH$_2$—, wherein R$_7$ and R$_8$ are each independently hydrogen or C$_{1-4}$alkyl; and
R$_{17}$ is selected from the group consisting of cyano, halo, —NH$_2$—, —C(O)NH$_2$, —C(O)NH(CH$_3$), and —C(O)N(CH$_3$)$_2$.

Embodiment 35

A compound of the formula (I), or a salt, tautomer or stereoisomer thereof, according to embodiment 34, wherein -Ring A-R$_1$ is of the formula

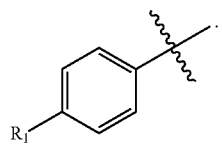

Embodiment 36

A compound of the formula (I), or a salt, tautomer or stereoisomer thereof, according to embodiment 34, wherein -Ring A-R$_1$ is of the formula

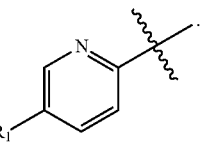

Embodiment 37

A compound of the formula (I), or a salt, tautomer or stereoisomer thereof, according to embodiments 34-36, wherein -Ring C—R$_{17}$ is of the formula

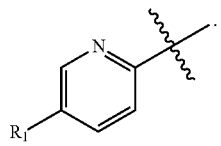

Embodiment 38

A compound of the formula (I), or a salt, tautomer or stereoisomer thereof, according to embodiments 34-36, wherein -Ring C—R$_{17}$ is of the formula

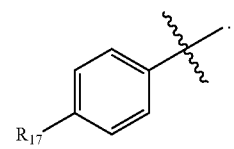

Embodiment 39

A compound of the formula (I), or a salt, tautomer or stereoisomer thereof, according to embodiments 36-38, wherein L is *—C(O)NH(CH$_3$)—, *—C(O)N(CH$_2$CH$_3$)—, *—C(O)N(CH(CH$_3$)$_2$)—, *—C(O)N(NH(CH$_3$))—, or *—NH(CH$_3$)C(O)—.

Embodiment 40

A compound of the formula (I), or a salt, tautomer or stereoisomer thereof, according to embodiments 36-38, wherein L is *—C(O)N(cyclopropyl)-Embodiment 41. A compound of the formula (I), or a salt, tautomer or stereoisomer thereof, according to embodiments 36-40, wherein R$_1$ is —NH$_2$—.

Embodiment 42

A compound of the formula (I), or a salt, tautomer or stereoisomer thereof, according to embodiments 36-40, wherein R$_1$ is —C(O)NH$_2$ or —C(O)NCH$_3$.

Embodiment 43

A compound of the formula (I), or a salt, tautomer or stereoisomer thereof, according to embodiments 36-42, wherein R$_{17}$ is cyano.

Embodiment 44

A compound of the formula (I), or a salt, tautomer or stereoisomer thereof, according to embodiments 36-42, wherein $R_{17}$ is halo.

Embodiment 45

A compound of the formula (I), or a salt, tautomer or stereoisomer thereof, according to embodiment 1, wherein the compound is selected from the group consisting of: N-(4-cyanophenyl)-N-methyl-3-(4-(trifluoromethyl)phenyl) pyrazolo[1,5-a]pyridine-5-carboxamide; 4-fluoro-N-methyl-N-((3-(4-(trifluoromethyl)phenyl)pyrazolo[1,5-a] yridine-5-yl)methyl)aniline; N-(4-chlorophenyl)-N-methyl-3-(4-(trifluoromethyl)phenyl)pyrazolo[1,5-a]pyridine-5-carboxamide; N-(4-fluorophenyl)-N-methyl-3-(4-(trifluoromethyl)phenyl)pyrazolo[1,5-a]pyridine-5-carboxamide; N-methyl-N-(5-methylpyridin-2-yl)-3-(4-(trifluoromethyl)phenyl)pyrazolo[1,5-a]pyridine-5-carboxamide; 4-chloro-N-methyl-N-((3-(4-(trifluoromethyl)phenyl)pyrazolo[1,5-a]yridine-5-yl) methyl)aniline; N,5-dimethyl-N-((3-(4-(trifluoromethyl) phenyl)pyrazolo[1,5-a]yridine-5-yl)methyl)yridine-2-amine; 5-((4-fluorophenoxy)methyl)-3-(4-(trifluoromethyl) phenyl)pyrazolo[1,5-a]pyridine; N-(4-cyanophenyl)-N-(2-methoxyethyl)-3-(4-(trifluoromethyl)phenyl)pyrazolo[1,5-a]pyridine-5-carboxamide; N-(4-cyanophenyl)-N-(2-(dimethylamino)ethyl)-3-(4-(trifluoromethyl)phenyl) pyrazolo[1,5-a]pyridine-5-carboxamide; N-(4-cyanophenyl)-N-((tetrahydro-2H-pyran-4-yl)methyl)-3-(4-(trifluoromethyl)phenyl)pyrazolo[1,5-a]pyridine-5-carboxamide; N-(4-(methylsulfonyl)phenyl)-N-((tetrahydro-2H-pyran-4-yl)methyl)-3-(4-(trifluoromethyl) phenyl)pyrazolo[1,5-a]pyridine-5-carboxamide; N-(5-cyanopyridin-2-yl)-N-methyl-3-(4-(trifluoromethyl)phenyl) pyrazolo[1,5-a]pyridine-5-carboxamide; N-methyl-N-(5-methylpyridin-3-yl)-3-(4-(trifluoromethyl)phenyl)pyrazolo [1,5-a]pyridine-5-carboxamide; 5-(((5-methylpyridin-2-yl) oxy)methyl)-3-(4-(trifluoromethyl)phenyl)pyrazolo[1,5-a] pyridine; 5-(4-fluorophenethyl)-3-(4-(trifluoromethyl) phenyl)pyrazolo[1,5-a]pyridine; N-(4-cyanophenyl)-N-methyl-3-(1-methyl-1H-indazol-5-yl)pyrazolo[1,5-a] pyridine-5-carboxamide; 3-(6-acetamidopyridin-3-yl)-N-(4-cyanophenyl)-N-methylpyrazolo[1,5-a]pyridine-5-carboxamide; 3-(4-carbamoylphenyl)-N-(4-cyanophenyl)-N-methylpyrazolo[1,5-a]pyridine-5-carboxamide; 3-(4-carbamoylphenyl)-N-(4-fluorophenyl)-N-methylpyrazolo [1,5-a]pyridine-5-carboxamide; 5-(((4-fluorophenyl)thio) methyl)-3-(4-(trifluoromethyl)phenyl)pyrazolo[1,5-a] pyridine; 5-(((4-fluorophenyl)sulfinyl)methyl)-3-(4-(trifluoromethyl)phenyl)pyrazolo[1,5-a]pyridine; 3-(4-(1H-pyrazol-5-yl)phenyl)-N-(4-cyanophenyl)-N-methylpyrazolo [1,5-a]pyridine-5-carboxamide; N-(4-cyanophenyl)-N-methyl-3-(5-(trifluoromethyl)pyridine-2-yl)pyrazolo[1,5-a] pyridine-5-carboxamide; N-(5-cyanopyridin-2-yl)-N-methyl-3-(5-(trifluoromethyl)pyridine-2-yl)pyrazolo[1,5-a] pyridine-5-carboxamide; (S)-3-(4-(2-aminopropanamido) phenyl)-N-(4-cyanophenyl)-N-methylpyrazolo[1,5-a] pyridine-5-carboxamide; 3-(5-carbamoylpyridin-2-yl)-N-(4-cyanophenyl)-N-methylpyrazolo[1,5-a]pyridine-5-carboxamide; 4-cyano-N-methyl-N-(3-(4-(trifluoromethyl) phenyl)pyrazolo[1,5-a]yridine-5-yl)benzamide; 4-fluoro-N-methyl-N-(3-(4-(trifluoromethyl)phenyl)pyrazolo[1,5-a] yridine-5-yl)benzamide; 4-cyano-N-methyl-N-(3-(4-(trifluoromethyl)phenyl)pyrazolo[1,5-a]pyridine-5-yl) benzenesulfonamide; 4-fluoro-N-methyl-N-(3-(4-(trifluoromethyl)phenyl)pyrazolo[1,5-a]pyridine-5-yl)benzenesulfonamide; 3-(4-carbamoylphenyl)-N-(5-cyanopyridin-2-yl)-N-methylpyrazolo[1,5-a]pyridine-5-carboxamide; N-methyl-3-(4-(trifluoromethyl)phenyl)-N-(5-(trifluoromethyl)yridine-2-yl)pyrazolo[1,5-a]pyridine-5-carboxamide; N-methyl-N-(5-(methylsulfonyl)pyridine-2-yl)-3-(4-(trifluoromethyl)phenyl)pyrazolo[1,5-a]pyridine-5-carboxamide; N-(4-fluorobenzyl)-3-(4-(trifluoromethyl)phenyl)pyrazolo[1,5-a]yridine-5-amine; N-(4-fluorobenzyl)-3-(4-(trifluoromethyl)phenyl)pyrazolo[1,5-a]yridine-5-amine; N-methyl-6-(trifluoromethyl)-N-(3-(4-(trifluoromethyl) phenyl)pyrazolo[1,5-a]yridine-5-yl)nicotinamide; N-methyl-5-(trifluoromethyl)-N-(3-(4-(trifluoromethyl) phenyl)pyrazolo[1,5-a]yridine-5-yl)picolinamide; 4-cyano-N-((tetrahydro-2H-pyran-4-yl)methyl)-N-(3-(4-(trifluoromethyl)phenyl)pyrazolo[1,5-a]pyridin-5-yl)benzamide; N-(4-cyanophenyl)-N-methyl-3-(1H-pyrrolo[2,3-b]pyridin-5-yl) pyrazolo[1,5-a]pyridine-5-carboxamide; 3-(6-aminopyridin-3-yl)-N-(4-cyanophenyl)-N-methylpyrazolo [1,5-a]pyridine-5-carboxamide; 3-(4-aminophenyl)-N-(4-cyanophenyl)-N-methylpyrazolo[1,5-a]pyridine-5-carboxamide; 3-(4-(2-aminoacetamido)phenyl)-N-(4-cyanophenyl)-N-methylpyrazolo[1,5-a]pyridine-5-carboxamide; (R)-3-(4-(2-aminopropanamido)phenyl)-N-(4-cyanophenyl)-N-methylpyrazolo[1,5-a]pyridine-5-carboxamide; (S)-3-(4-(2-amino-3-methylbutanamido) phenyl)-N-(4-cyanophenyl)-N-methylpyrazolo[1,5-a] pyridine-5-carboxamide; (S)-3-(4-(2-amino-2-cyclohexylacetamido)phenyl)-N-(4-cyanophenyl)-N-methylpyrazolo[1,5-a]pyridine-5-carboxamide; 3-(4-fluorophenyl)-1-methyl-1-(3-(4-(trifluoromethyl)phenyl) pyrazolo[1,5-a]pyridin-5-yl)urea; 6-(1,1-difluoroethyl)-N-methyl-N-(3-(4-(trifluoromethyl)phenyl)pyrazolo[1,5-a] pyridin-5-yl)nicotinamide; 6-cyclopropyl-N-methyl-N-(3-(4-(trifluoromethyl)phenyl)pyrazolo[1,5-a]pyridin-5-yl) nicotinamide; 4-cyclopropyl-N-methyl-N-(3-(4-(trifluoromethyl)phenyl)pyrazolo[1,5-a]pyridin-5-yl) benzamide; 5-fluoro-N-methyl-N-(3-(4-(trifluoromethyl) phenyl)pyrazolo[1,5-a]pyridin-5-yl)picolinamide; N-methyl-4-(methylsulfonyl)-N-(3-(4-(trifluoromethyl)phenyl)pyrazolo[1,5-a]pyridin-5-yl)benzamide; N-(5-cyanopyridin-2-yl)-N-methyl-3-(1H-pyrrolo[2,3-b]pyridin-5-yl) pyrazolo[1,5-a]pyridine-5-carboxamide; 3-(6-aminopyridin-3-yl)-N-(5-cyanopyridin-2-yl)-N-methylpyrazolo[1,5-a]pyridine-5-carboxamide; 4-chloro-N-methyl-N-(3-(4-(trifluoromethyl)phenyl)pyrazolo[1,5-a] pyridin-5-yl)benzamide; N-(3-(4-carbamoylphenyl) pyrazolo[1,5-a]pyridin-5-yl)-4-fluoro-N-methylbenzamide; 4-fluoro-N-methyl-N-(3-(4-(5-(methylamino)-1,3,4-thiadiazol-2-yl)phenyl)pyrazolo[1,5-a]pyridin-5-yl)benzamide; N-methyl-N-(5-(methylsulfonyl)pyridin-2-yl)-3-(1H-pyrrolo[2,3-b]pyridin-5-yl)pyrazolo[1,5-a]pyridine-5-carboxamide; N-(5-cyanopyridin-2-yl)-N-methyl-3-(5-methylpyridin-2-yl)pyrazolo[1,5-a]pyridine-5-carboxamide; N-(5-cyanopyridin-2-yl)-3-(5-methoxypyridin-2-yl)-N-methylpyrazolo[1,5-a]pyridine-5-carboxamide; 3-(5-carbamoylpyridin-2-yl)-N-(5-cyanopyridin-2-yl)-N-methylpyrazolo[1,5-a]pyridine-5-carboxamide; 3-(4-carbamoylphenyl)-N-methyl-N-(5-(trifluoromethyl)pyridin-2-yl)pyrazolo[1,5-a]pyridine-5-carboxamide; 3-(4-carbamoylphenyl)-N-methyl-N-(5-methylpyridin-2-yl) pyrazolo[1,5-a]pyridine-5-carboxamide; N-(4-fluorophenyl)-N-methyl-3-(4-(methylcarbamoyl)phenyl) pyrazolo[1,5-a]pyridine-5-carboxamide; 4-(5-(1-(methyl(5-methylpyridin-2-yl)amino)ethyl)pyrazolo[1,5-a]pyridin-3-yl)benzamide; 4-(5-(1-(7-fluoro-3-oxo-2H-benzo[b][1,4] oxazin-4(3H)-yl)ethyl)pyrazolo[1,5-a]pyridin-3-yl)

benzamide; N-(4-cyanophenyl)-N-methyl-3-(4-(methylcarbamoyl)phenyl)pyrazolo[1,5-a]pyridine-5-carboxamide; N-(4-(5-(1-(methyl(5-methylpyridin-2-yl)amino)ethyl)pyrazolo[1,5-a]pyridin-3-yl)phenyl)acetamide; 3-(4-acetamidophenyl)-N-(5-cyanopyridin-2-yl)-N-methylpyrazolo[1,5-a]pyridine-5-carboxamide; 4-(5-(7-fluoro-3,4-dihydro-2H-benzo[b][1,4]oxazine-4-carbonyl)pyrazolo[1,5-a]pyridin-3-yl)benzamide; 4-(5-(7-fluoro-3-methyl-3,4-dihydro-2H-benzo[b][1,4]oxazine-4-carbonyl)pyrazolo[1,5-a]pyridin-3-yl)benzamide; 4-(5-(7-fluoro-3,4-dihydro-2H-benzo[b][1,4]oxazine-4-carbonyl)pyrazolo[1,5-a]pyridin-3-yl)-N-methylbenzamide; 4-(5-(7-fluoro-3-methyl-3,4-dihydro-2H-benzo[b][1,4]oxazine-4-carbonyl)pyrazolo[1,5-a]pyridin-3-yl)-N-methylbenzamide; N-(5-cyanopyridin-2-yl)-N-methyl-3-(4-(methylcarbamoyl)phenyl)pyrazolo[1,5-a]pyridine-5-carboxamide; N-(5-cyanopyridin-2-yl)-3-(4-(methylcarbamoyl)phenyl)-N-(oxetan-3-yl)pyrazolo[1,5-a]pyridine-5-carboxamide; N-(1-(1H-pyrazol-1-yl)propan-2-yl)-3-(4-carbamoylphenyl)-N-(5-cyanopyridin-2-yl)pyrazolo[1,5-a]pyridine-5-carboxamide; 3-(6-amino-5-fluoropyridin-3-yl)-N-(4-cyanophenyl)-N-methylpyrazolo[1,5-a]pyridine-5-carboxamide; 3-(4-amino-3,5-dimethylphenyl)-N-(4-cyanophenyl)-N-methylpyrazolo[1,5-a]pyridine-5-carboxamide; 3-(6-amino-5-methylpyridin-3-yl)-N-(4-cyanophenyl)-N-methylpyrazolo[1,5-a]pyridine-5-carboxamide; 3-(4-carbamoylphenyl)-N-(4-cyanocyclohexyl)-N-methylpyrazolo[1,5-a]pyridine-5-carboxamide; 3-(2-aminopyrimidin-5-yl)-N-(4-cyanophenyl)-N-methylpyrazolo[1,5-a]pyridine-5-carboxamide; 3-(6-amino-5-(trifluoromethyl)pyridin-3-yl)-N-(5-cyanopyridin-2-yl)-N-methylpyrazolo[1,5-a]pyridine-5-carboxamide; 3-(6-amino-5-cyanopyridin-3-yl)-N-(5-cyanopyridin-2-yl)-N-methylpyrazolo[1,5-a]pyridine-5-carboxamide; 3-(6-amino-5-chloropyridin-3-yl)-N-(5-cyanopyridin-2-yl)-N-methylpyrazolo[1,5-a]pyridine-5-carboxamide; 3-(6-amino-5-(dimethylcarbamoyl)pyridin-3-yl)-N-(5-cyanopyridin-2-yl)-N-methylpyrazolo[1,5-a]pyridine-5-carboxamide; 3-(6-amino-5-methoxypyridin-3-yl)-N-(5-cyanopyridin-2-yl)-N-methylpyrazolo[1,5-a]pyridine-5-carboxamide; 3-(4-carbamoylphenyl)-N-(4-chloro-2-formylphenyl)-N-methylpyrazolo[1,5-a]pyridine-5-carboxamide; N-(5-Cyanopyridin-2-yl)-N-ethyl-3-(4-(methylcarbamoyl)phenyl)pyrazolo[1,5-a]pyridine-5-carboxamide; N-(5-cyanopyridin-2-yl)-N-isopropyl-3-(4-(methylcarbamoyl)phenyl)pyrazolo[1,5-a]pyridine-5-carboxamide; 5-(5-(1-(4-cyanophenyl)-2-methylhydrazinecarbonyl)pyrazolo[1,5-a]pyridin-3-yl)-N-methyl picolinamide; N-(5-cyanopyridin-2-yl)-N-cyclopropyl-3-(4-(methylcarbamoyl)phenyl)pyrazolo[1,5-a]pyridine-5-carboxamide; N-(5-cyanopyridin-2-yl)-N-methyl-3-(4-(methylcarbamoyl)phenyl)pyrazolo[1,5-a]pyridine-5-carboxamide; N-ethyl-N-(5-fluoropyridin-2-yl)-3-(4-(methylcarbamoyl)phenyl)pyrazolo[1,5-a]pyridine-5-carboxamide; and N-ethyl-3-(4-(methylcarbamoyl)phenyl)-N-(5-(trifluoromethyl)pyridin-2-yl)pyrazolo[1,5-a]pyridine-5-carboxamide.

Embodiment 46

A compound of the formula (I), or a salt, tautomer or stereoisomer thereof, according to embodiment 1, wherein the compound is selected from the group consisting of: 3-(4-carbamoylphenyl)-N-(5-cyanopyridin-2-yl)-N-methylpyrazolo[1,5-a]pyridine-5-carboxamide; N-(4-cyanophenyl)-N-methyl-3-(1H-pyrrolo[2,3-b]pyridin-5-yl)pyrazolo[1,5-a]pyridine-5-carboxamide; 3-(6-aminopyridin-3-yl)-N-(4-cyanophenyl)-N-methylpyrazolo[1,5-a]pyridine-5-carboxamide; (R)-3-(4-(2-aminopropanamido)phenyl)-N-(4-cyanophenyl)-N-methylpyrazolo[1,5-a]pyridine-5-carboxamide; N-(5-cyanopyridin-2-yl)-N-methyl-3-(1H-pyrrolo[2,3-b]pyridin-5-yl)pyrazolo[1,5-a]pyridine-5-carboxamide; N-(5-cyanopyridin-2-yl)-N-methyl-3-(4-(methylcarbamoyl)phenyl)pyrazolo[1,5-a]pyridine-5-carboxamide; 3-(2-aminopyrimidin-5-yl)-N-(4-cyanophenyl)-N-methylpyrazolo[1,5-a]pyridine-5-carboxamide; 3-(6-amino-5-(dimethylcarbamoyl)pyridin-3-yl)-N-(5-cyanopyridin-2-yl)-N-methylpyrazolo[1,5-a]pyridine-5-carboxamide.

Embodiment 47

A compound of the formula (I), or a salt, tautomer or stereoisomer thereof, according to embodiment 1, wherein the compound is selected from the group consisting of: N-(5-Cyanopyridin-2-yl)-N-ethyl-3-(4-(methylcarbamoyl)phenyl)pyrazolo[1,5-a]pyridine-5-carboxamide; N-(5-cyanopyridin-2-yl)-N-isopropyl-3-(4-(methylcarbamoyl)phenyl)pyrazolo[1,5-a]pyridine-5-carboxamide; 5-(5-(1-(4-cyanophenyl)-2-methylhydrazinecarbonyl)pyrazolo[1,5-a]pyridin-3-yl)-N-methyl picolinamide; N-(5-cyanopyridin-2-yl)-N-cyclopropyl-3-(4-(methylcarbamoyl)phenyl)pyrazolo[1,5-a]pyridine-5-carboxamide; N-(5-cyanopyridin-2-yl)-N-methyl-3-(4-(methylcarbamoyl)phenyl)pyrazolo[1,5-a]pyridine-5-carboxamide; N-ethyl-N-(5-fluoropyridin-2-yl)-3-(4-(methylcarbamoyl)phenyl)pyrazolo[1,5-a]pyridine-5-carboxamide; and N-ethyl-3-(4-(methylcarbamoyl)phenyl)-N-(5-(trifluoromethyl)pyridin-2-yl)pyrazolo[1,5-a]pyridine-5-carboxamide.

Embodiment 48

A pharmaceutical composition comprising at least one compound of any one of embodiments 1 to 47 or a pharmaceutically acceptable salt thereof, and a pharmaceutically acceptable carrier, diluent or excipient.

Embodiment 49

A pharmaceutical composition according to embodiment 48 further comprising a second agent.

Embodiment 50

A pharmaceutical composition according to embodiment 49, wherein the second agent is an antimalarial drug selected from the group consisting of artemisinin, artemether, artesunate, arteflene, dihydroartemisinin, chlorproguanil, trimethoprim, chloroquine, quinine, mefloquine, amodiaquine, atovaquone, proguanil, lumefantrine, piperaquine, pyronaridine, halofantrine, pyrimethamine-sulfadoxine, quinacrine, pyrimethamine-dapsone, quinidine, amopyroquine, sulphonamides, primaquine, ferroquine, tafenoquine, arterolane, and pyronaridine.

Embodiment 51

A compound according to any one of embodiments 1 to 47 or a pharmaceutical composition according to any one of embodiments 48-50 for use as a medicament.

Embodiment 52

A method for treating, preventing, inhibiting, ameliorating, or eradicating the pathology and/or symptomology of a disease caused by a *Plasmodium* parasite, comprising administering to a subject a therapeutically effective amount of a compound according to any one of embodiments 1 to 47 or a composition according to any one of embodiments 48 to 50, wherein the administering may be in combination with a second agent.

Embodiment 53

A method for treating, preventing, inhibiting, ameliorating, or eradicating the pathology and/or symptomology of a disease caused by a *Plasmodium* parasite, according to embodiment 52, wherein the disease is malaria.

Embodiment 54

A method for treating, preventing, inhibiting, ameliorating, or eradicating the pathology and/or symptomology of a disease caused by a *Plasmodium* parasite according to embodiments 52-53, wherein the *Plasmodium* parasite is at the blood stages.

Embodiment 55

A method for treating, preventing, inhibiting, ameliorating, or eradicating the pathology and/or symptomology of a *Plasmodium* related disease caused by a *Plasmodium* parasite according to embodiments 52-53, wherein the *Plasmodium* parasite is at the hepatic stages.

Embodiment 56

A method for treating, preventing, inhibiting, ameliorating, or eradicating the pathology and/or symptomology of a *Plasmodium* related disease caused by a *Plasmodium* parasite according to embodiments 52-55, wherein the *Plasmodium* parasite is selected from group consisting of *Plasmodium falciparum, Plasmodium vivax, Plasmodium ovale*, and *Plasmodium* malaria.

Embodiment 57

A method for treating, preventing, inhibiting, ameliorating, or eradicating the pathology and/or symptomology of a *Plasmodium* related disease caused by a *Plasmodium* parasite according to embodiments 52-55, wherein the *Plasmodium* parasite is *Plasmodium falciparum*.

Embodiment 58

A method for treating, preventing, inhibiting, ameliorating, or eradicating the pathology and/or symptomology of a *Plasmodium* related disease caused by a *Plasmodium* parasite according to embodiments 52-57, wherein the second agent is selected from a kinase inhibitor, an anti-malarial drug and an anti-inflammatory agent.

Embodiment 59

A method for treating, preventing, inhibiting, ameliorating, or eradicating the pathology and/or symptomology of a disease caused by *Plasmodium* parasite according to embodiment 58, wherein the anti-malarial drug is selected from the group consisting of artemisinin, artemether, artesunate, arteflene, dihydroartemisinin, chlorproguanil, trimethoprim, chloroquine, quinine, mefloquine, amodiaquine, atovaquone, proguanil, lumefantrine, piperaquine, pyronaridine, halofantrine, pyrimethamine-sulfadoxine, quinacrine, pyrimethamine-dapsone, quinidine, amopyroquine, sulphonamides, primaquine, ferroquine, tafenoquine, arterolane, and pyronaridine.

Embodiment 60

A method for treating, preventing, inhibiting, ameliorating, or eradicating the pathology and/or symptomology of a disease caused by *Plasmodium* parasite according to embodiments 52-59, wherein the compound is administered prior to, simultaneously with, or after the second agent.

Embodiment 61

A compound according to any one of embodiments 1-46 or a composition according to any one of embodiments 48 to 50 for treating, preventing, inhibiting, ameliorating, or eradicating the pathology and/or symptomology of a disease caused by a *Plasmodium* parasite.

Embodiment 62

Use of a compound according to any one of embodiments 1-47 or a pharmaceutical composition according to embodiments 48-50 in the manufacture of a medicament for treating, preventing, inhibiting, or ameliorating the pathology and/or symptomology of a disease caused by a *Plasmodium* parasite, wherein the medicament may further include a second agent.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by Plasdmodium or (ii) associated with Plasdmodium activity, or (iii) characterized by activity (normal or abnormal) of Plasdmodium or (2) reduce or inhibit the activity of Plasdmodium; or (3) reduce or inhibit the growth of Plasdmodium. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of Plasdmodium; or at least partially reducing or inhibiting the growth of Plasdmodium.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95 enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

Pharmacology and Administration

Compounds of the invention are useful in the treatment and/or prevention of infections such as those caused by *Plasmodium falciparum; Plasmodium vivax; Plasmodium ovale*; and *Plasmodium* malaria, *Trypanosoma cruzi* and parasites of the *Leishmania* genus, such as, for example, *Leishmania donovani*.

Plasmodia spp. which causes malaria belongs to the phylum, Apicomplexa, which is a large and diverse group of protists that are human or animal parasites. These parasites are unicellular, spore-forming, and possess motile structures such as flagella or pseudopods at certain gamete stages. Most of these parasites possess a unique organelle called apicoplast and an apical complex structure involved in penetrating a host's cell. The pathogenesis associated the diseases caused by these parasites is due to repeated cycles of host-cell invasion, intracellular replication and host-cell lysis. Therefore, understanding parasite proliferation is essential for development of novel drugs and vaccines, for example, to treat malaria.

In vertebrate hosts, the parasite undergoes two main phases of development, the hepathocytic and erythrocytic phases, but it is the erythrocytic phase of its life cycle that causes severe pathology. During the erythrocytic phase, the parasite goes through a complex but well synchronized series of stages, suggesting the existence of tightly regulated signaling pathways.

Calcium serves as an intracellular messenger to control synchronization and development in the erythrocytic life phase. The *Plasmodium* spp. genomes reveal many sequence identities with calcium binding/sensing protein motifs that include Pf39, calmodulin, and calcium dependent protein kinases (CDPKs). *Plasmodium* CDPKs, *Plasmodium* CDPK3 and 4, have been shown to be involved in mosquito infection. CDPK4 has been demonstrated to be essential for the sexual reproduction in the midgut of mosquito by translating the calcium signal into a cellular response and regulating cell cycle progression in the male gametocyte. CDPK3 regulates ookinete gliding motility and penetration of the layer covering the midgut epithelium. *P. falciparum* CDPK1 (PfCDPK1) is expressed during late schizogony of blood stage and in the infectious sporozoite stage and is secreted to the parasitophorous vacuole by an acylation-dependent mechanism. It can be myristoylated and is abundantly found in detergent-resistant membrane fractions isolated from schizogony-phase parasites. Ontology based pattern identification analysis reveals that PfCDPK1 is clustered with genes associated with either parasite egress or erythrocyte invasion. Direct inhibition of PfCDPK1 can arrest the parasite erythrocytic life cycle progression in the late schizogony phase.

Therefore, kinase activity is distributed in all the stages of *P. falciparum* parasite maturation and kinase inhibitors of the present invention can be used for treating *Plasmodium* related diseases.

The in vitro cellular assay, infra, can be used to assess the activity of compounds of the invention against a variety of malarial parasite strains.

In accordance with the foregoing, the present invention further provides a method for preventing or treating malaria in a subject in need of such treatment, which method comprises administering to the subject a therapeutically effective amount of a compound selected from Formula I and Ia or a pharmaceutically acceptable salt, tautomer or stereoisomer, thereof. The required dosage will vary depending on the mode of administration, the particular condition to be treated and the effect desired.

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). Non-limiting examples of compounds which can be used in combination with compounds of the invention are known anti-malarial drugs, for example, artemisinin, artemether, artesunate, arteflene, dihydroartemisinin, chlorproguanil, trimethoprim, chloroquine, quinine, mefloquine, amodiaquine, atovaquone, proguanil, lumefantrine, piperaquine, pyronaridine, halofantrine, pyrimethamine-sulfadoxine, quinacrine, pyrimethamine-dapsone, quinidine, amopyroquine, sulphonamides, primaquine, ferroquine, tafenoquine, arterolane, and pyronaridine, etc.

Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Biological Assays

The activity of a compound according to the present invention for inhibition of parasitemai in infected blood cells and liver cells can be assessed by the following assays. It is understood that the assays illustrate the invention without in any way limiting the scope of the invention.

Assay for *P. falciparum* Proliferation in Infected Human Blood Cells

Compounds of the invention can be assayed to measure their capacity to inhibit proliferation of *P. falciparum* parasitemia in infected red blood cells. This parasite proliferation assay measures the increase in parasite DNA content using a DNA intercalating dye, SYBR Green® (INVITROGEN®) which has a high affinity for double stranded DNA.

NF54 or 3D7 *P. falciparum* strain is grown in complete culturing media until parasitemia reaches 3% to 8% with O+ human erythrocytes. The selection of either strain is of convenience (3D7 is a clone of NF54) and does not make a difference to the assay. 20 µl of screening media is dispensed into 384 well assay plates. 50 nl of compounds of the invention (in DMSO), including antimalarial controls (mefloquine, pyrimethamine and artemisinin), are then transferred into the assay plates, as well as DMSO alone to serve as a negative control for inhibition. Then 30 µl of a suspension of a NF54 or 3D7 *P. falciparum* infected erythrocytes in screening media is dispensed into the assay plates such that the final hematocrit is 2.5% with a final parasitemia of 0.3%. The plates are placed in a 37° C. incubator for 72 hours in a low oxygen environment containing 93% $N_2$, 4% $CO_2$, and 3% $O_2$ gas mixture. 10 µl of lysis buffer (saponin, triton-X, EDTA) containing a 10× solution of SYBR Green I® in RPMI media is dispensed into the plates. The plates are lidded and kept at room temperature overnight for the lysis of the infected red blood cells. The fluorescence intensity is measured (excitation 425 nm, emission 530 nm) using the Envision™ system (Perkin Elmer). The percentage inhibition of 50%, $EC_{50}$, is calculated for each compound.

Using the *P. falciparum* Proliferation Assay above, compounds of the invention exhibit inhibitory efficacy ($EC_{50}$) of typically 10 µM or less, more typically less than 1 µM, most typically less than 200 nM. Compounds of the invention can significantly delay the increase in *P. falciparum* parasitemia. For example, 3-(4-carbamoylphenyl)-N-(5-cyanopyridin-2-yl)-N-methylpyrazolo[1,5-a]pyridine-5-carboxamide (Example 32), N-(4-cyanophenyl)-N-methyl-3-(1H-pyrrolo[2,3-b]pyridin-5-yl)pyrazolo[1,5-a]pyridine-5-carboxamide (Example 40), 3-(6-aminopyridin-3-yl)-N-(4-cyanophenyl)-N-methylpyrazolo[1,5-a]pyridine-5-carboxamide (Example 41), (R)-3-(4-(2-aminopropanamido)phenyl)-N-(4-cyanophenyl)-N-methylpyrazolo[1,5-a]pyridine-5-carboxamide (Example 44), N-(5-cyanopyridin-2-yl)-N-methyl-3-(1H-pyrrolo[2,3-b]pyridin-5-yl)pyrazolo[1,5-a]pyridine-5-carboxamide (Example 53), N-(5-cyanopyridin-2-yl)-N-methyl-3-(4-(methylcarbamoyl)phenyl)pyrazolo[1,5-a]pyridine-5-carboxamide (Example 75), and 3-(2-aminopyrimidin-5-yl)-N-(4-cyanophenyl)-N-methylpyrazolo[1,5-a]pyridine-5-carboxamide (Example 83) all have $EC_{50}$ values of less than 5 nM.

The inhibitory efficacy of the compounds of the invention in delaying the increase in *P. falciparum* parasitemia in infected human blood cells is provided in Table 1.

TABLE 1

Inhibitory Efficacy of Compounds of the Invention in delaying
*P. falciparum* Proliferation in Infected Human Blood Cells

| Example No. | EC50 (nM) |
|---|---|
| 1 | 8 |
| 2 | 342 |
| 3 | 94 |
| 4 | 46 |
| 5 | 88 |
| 6 | 284 |
| 7 | 975 |
| 8 | 532 |
| 9 | 6 |
| 10 | 7 |
| 11 | 6 |
| 12 | 9 |
| 13 | 8 |
| 14 | 134 |
| 15 | 2318 |
| 16 | 477 |

TABLE 1-continued

Inhibitory Efficacy of Compounds of the Invention in delaying *P. falciparum* Proliferation in Infected Human Blood Cells

| Example No. | EC50 (nM) |
|---|---|
| 17 | 3 |
| 18 | 3 |
| 19 | 1 |
| 20 | 9 |
| 21 | 472 |
| 22 | 25 |
| 23 | 2 |
| 24 | 10 |
| 25 | 7 |
| 26 | 22 |
| 27 | 10 |
| 28 | 7 |
| 29 | 150 |
| 30 | 62 |
| 31 | 143 |
| 32 | 1 |
| 33 | 59 |
| 34 | 22 |
| 35 | 2044 |
| 36 | 390 |
| 37 | 121 |
| 38 | 179 |
| 39 | 831 |
| 40 | 1 |
| 41 | 2 |
| 42 | 18 |
| 43 | 9 |
| 44 | 1 |
| 45 | 16 |
| 46 | 18 |
| 47 | >9000 |
| 48 | 288 |
| 49 | 2290 |
| 50 | 3850 |
| 51 | 60 |
| 52 | 13 |
| 53 | 1 |
| 54 | 9 |
| 55 | 32 |
| 56 | 8 |
| 57 | 4 |
| 58 | 30 |
| 59 | 228 |
| 60 | 683 |
| 61 | 20 |
| 63 | 6 |
| 64 | 20 |
| 65 | 504 |
| 66 | 49 |
| 67 | 5 |
| 68 | 6750 |
| 69 | 13 |
| 70 | 4190 |
| 71 | 3 |
| 72 | 5 |
| 73 | >10,000 |
| 74 | 52 |
| 75 | 4 |
| 76 | 82 |
| 77 | 146 |
| 79 | 7 |
| 80 | 824 |
| 81 | 36 |
| 82 | 1160 |
| 83 | 4 |
| 84 | 6 |
| 85 | 16 |
| 86 | 10 |
| 87 | 41 |
| 88 | 83 |
| 89 | 6 |
| 90 | 8 |
| 91 | 13 |
| 92 | 24 |
| 93 | 6 |
| 94 | 17 |
| 95 | 23 |
| 96 | 12 |
| 97 | 13 |
| 98 | 19 |
| 99 | 1 |
| 100 | 9 |
| 101 | 6164 |
| 102 | 10 |
| 103 | 3 |
| 104 | 125 |
| 105 | 935 |
| 106 | 521 |
| 107 | 10 |
| 108 | 2466 |
| 109 | 19 |
| 110 | 54 |
| 111 | 6296 |
| 112 | 4 |
| 113 | 311 |
| 114 | 52 |
| 115 | 155 |
| 116 | 1 |
| 117 | 4 |
| 118 | 3 |
| 119 | 95 |
| 120 | 9 |
| 121 | 1157 |
| 122 | >10,000 |
| 123 | 393 |
| 124 | 19 |
| 125 | 80 |
| 126 | 67 |
| 127 | 49 |
| 128 | 4268 |
| 129 | 2439 |
| 130 | 12 |
| 131 | 324 |
| 132 | 29 |
| 133 | 58 |
| 134 | 4 |
| 135 | 1 |
| 137 | 12 |
| 138 | 10 |
| 139 | 30 |
| 140 | 199 |
| 141 | 65 |
| 142 | 48 |
| 143 | 12 |
| 144 | 27 |
| 145 | 12 |
| 146 | 45 |
| 147 | 814 |
| 148 | 67 |
| 149 | 4 |
| 150 | 51 |
| 151 | 67 |
| 152 | 228 |
| 153 | 88 |
| 154 | 200 |
| 155 | 82 |
| 156 | 210 |
| 157 | 91 |
| 158 | 111 |
| 159 | 56 |
| 160 | 4 |
| 161 | 68 |
| 162 | 9 |
| 163 | 4 |
| 164 | 2 |
| 165 | 3 |

Assay for Proliferation of Parasite in Infected Liver Cells

Compounds of the invention can be assayed to measure their capacity to inhibit proliferation of parasites in liver cells. The proliferation is quantified by determine the number of infected cells by immunofluorescence.

Parasites

Due to the difficulty of successfully infecting immortalized human liver cell lines with the human malaria sporozoites (liver-stage parasite), rodent malaria sporozoites from *Plasmodium yoelii* (17XNL) and *P. berghei* (ANKA) are the preferred surrogate. Sporozoites are obtained from *Anopheles stephensi* mosquitoes supplied by the New York University Insectary, which ships the malaria-infected mosquitoes 10-13 days following the ingestion of an infective blood meal.

Cell Line

A transgenic HepG2 cell line expressing the tetraspanin CD81 receptor (HepG2-A16-CD81$^{EGFP}$) is used to increase the infectivity rate of rodent-malaria sporozoites into human cells. HepG2-A16-CD81$^{EGFP}$ cells are stably transformed to express a GFP-CD81 fusion protein. A continuous in vitro culture of this line was maintained at 37° C. in 4% $CO_2$ in complete media (CM) which contains: DMEM (Invitrogen, Carlsbad, USA) supplemented with 10% FCS, 0.29 mg/ml glutamine, 100 units penicillin and 100 µg/ml streptomycin (SigmaAldrich, USA).

Liver Stage *P. yoelii* Sporozoite Invasion Assay

Twenty to twenty-six hours prior to sporozoite infection, $7.5 \times 10^3$ HepG2-A16-CD81$^{EGFP}$ cells are seeded into 384-well plates (Aurora 384 IQ-EB black plates with clear bottoms; 50 µl of $1.5 \times 10^5$ cells/ml in CM). These plates are incubated at 37° C. with 4% $CO_2$ overnight. Two hours prior to infection, 50 nl of compound dissolved in DMSO (0.1% final DMSO concentration per well) were transferred with a PinTool (GNF Systems) into the assay plates (10 µM final concentration). A 1:3 serial dilution of atovaquone (10 µM at the highest final concentration) and wells treated only with DMSO were used as positive and negative controls, respectively.

Freshly dissected salivary glands from infected mosquitoes were homogenized in a glass tissue grinder, filtered twice through Nylon cell strainers (40 µm pore size, BD Falcon) and counted using a hemocytometer. The assay plate with HepG2-A16-CD81$^{EGFP}$ cells and compound were then infected with $8 \times 10^3$ sporozoitesper well and the plates are subjected to a centrifugal force of 650×g to pellet the sporozoites onto the liver cell monolayer. The assay plate is incubated at 37° C. for 2 hours to permit sporozoite invasion, then the media is aspirated from the media plate, and replaced with 50 µl CM (containing a 5× concentration of penicillin/streptomycin; 500 units penicillin and 0.5 mg streptomycin per ml) per well. 50 nl of compound is re-introduced by PinTool and the assay plate incubated for 48 hours at 37° C. before quantification of infected cells by immunofluorescence. The increased antibiotic concentration does not interfere with the parasite or HepG2-A16-CD81$^{EGFP}$ growth.

Atovaquone and uninfected wells were used as controls on each plate. Two replicate plates are tested for each assay.

After fixing the cells by addition of 12.5 µl of 20% solution of paraformaldehyde (EMS, Hatfield, USA) to each assay well (4% final formaldehyde concentration), membranes were permeabilized with 0.5% Triton-X-100 (Thermo Fisher Scientific) and EEFs were stained using a mouse polyclonal serum raised against the *Plasmodium yoelii* heat shock protein 70 (PyHSP70), a DyLight 649 goat anti-mouse IgG, Fc(gamma) fragment specific secondary antibody (Jackson Immuno Research, Cat#115-495-071) and the Hoechst 33342 nucleic acid dye (Invitrogen, Carlsbad, USA). Stained EEFs were then quantified using the Opera Confocal High Content Screening System (Perkin Elmer, Waltham, USA). Images were collected using a 20× objective lens (20×/0.45 NA, LWD Plan Fluor, Olympus) at a binning of 2, using a 365 nm Xeon arc lamp illumination to detect the Hoechst-labeled nuclei and 635 nm laser line to excite DyLight649-labeled parasites. The image resolution yielded was approximately 0.66 µm/pixel (~0.43 µm 2/pixel). All images were analyzed using a custom Acapella™ (PerkinElmer) script parametrized for this assay. In brief, images from fields inside the well were first discarded as out-of focus when the intensity in the nuclear channel was too low. Then, HepG2-A16-CD81$^{EGFP}$ cells were counted by detecting the nuclei labeled with Hoechst using the nuclei detection libraries available with Acapella™. Parasites were later segmented using the αPyHSP70 immuno-labeling signal, using a custom script library. Once the objects were segmented from the picture, morphological-based (e.g. size, roundness, etc) and intensity-based features were measured for each object detected in the image (i.e. nuclei and parasites). Infection ratio was set as the ratio between parasite number and number of nuclei counted in images considered as "in-focus". $EC_{50}$ values were obtained using parasite area and a custom curve fitting model, and a standard logistic regression model was applied for curve fitting.

Using the *P. yoelii* Sporozoite Invasion Assay, compounds of the invention exhibit inhibitory efficacy ($EC_{50}$) of typically 500 nM or less, more typically less than 200 nM, most typically less than 10 nM. Compounds of the invention show significantly delay of the proliferation of *P. yoelii* in liver cells. For example N-(4-cyanophenyl)-N-methyl-3-(4-(trifluoromethyl)phenyl)pyrazolo[1,5-a]pyridine-5-carboxamide (Example 1), 3-(4-carbamoylphenyl)-N-(4-cyanophenyl)-N-methylpyrazolo[1,5-a]pyridine-5-carboxamide (Example 19), 3-(4-carbamoylphenyl)-N-(5-cyanopyridin-2-yl)-N-methylpyrazolo[1,5-a]pyridine-5-carboxamide (Example 32), 3-(4-carbamoylphenyl)-N-(5-cyanopyridin-2-yl)-N-methylpyrazolo[1,5-a]pyridine-5-carboxamide (Example 67), and N-(5-cyanopyridin-2-yl)-N-methyl-3-(4-(methylcarbamoyl)phenyl)pyrazolo[1,5-a]pyridine-5-carboxamide (Example 75) all have $EC_{50}$ of less than 10 nM.

Inhibitory efficacy of selected compounds in delaying the proliferation of *P. yoelii* Sporozoite in liver cells is listed in Table 2.

Liver Stage *P. berghei* Luciferase Proliferation Assay

CD81-GFP-HepG2 cells (obtained from the lab of Dominique Mazier) were seeded into GNF custom Greiner plates (1536-well, white, TC-treated, solid bottom). A final density of 3000 cells/well was achieved by dispensing 5 ul per well of a 600,000 cells/mL resuspended in Assay Media (AM; phenol-red free DMEM, 2% FBS, 5×PSG) via a MicroFlo (Biotek; 5 ul dispense cassette). The seeded assay plates were incubated overnight at 37° C. in an incubator with 5% $CO_2$. The following day, a 10 nL volume of compound was transferred acoustically (ECHO 525, Labcyte Inc.) to each well in the assay plate. Sporozoite forms of a *Plasmodium berghei* line expressing luciferase (Pb-luc) were dissected and purified from infected *Anopheles stephensi* mosquitoes (provided by the NYU insectary) as previously described by Meister et al. (Science, 2011). Purified sporozoites (spz) were stored at 250 spz/uL in chilled PBS supplemented with 3% BSA. 3 uL of Pb-luc spz solution was dispensed to each assay well using a Bottlevalve equipped with a custom, single-tip dispense head (GNF Systems). Assay plates were centrifuged at 330×g for 3 minutes to pellet the spz, then the assay plates were returned to the 37° C. incubator for 48 h. Luciferase signal, which corresponds with parasite proliferation, was detected by adding 2 uL of BrightGlo (Promega) to each well using the MicroFlo (Biotek; 1 ul cassette). Luminescence was immediately measured on an Envision MultiLabel Plate Reader (PerkinElmer). Wells treated with only DMSO or atovaquone (potent inhibitor of liver-stage parasites) were used for normalization of these data.

Using the P. berghei luciferase Proliferation Assay, four compounds, 5-(5-(1-(4-cyanophenyl)-2-methylhydrazinecarbonyl)pyrazolo[1,5-a]pyridin-3-yl)-N-methyl picolinamide (Example 92), 5-cyano-N-methyl-N-(3-(4-(methylcarbamoyl)phenyl)pyrazolo[1,5-a]pyridin-5-yl)picolinamide (Example 94), N-ethyl-N-(5-fluoropyridin-2-yl)-3-(4-(methylcarbamoyl)phenyl)pyrazolo[1,5-a]pyridine-5-carboxamide (Example 95), and N-ethyl-3-(4-(methylcarbamoyl)phenyl)-N-(5-(trifluoromethyl)pyridin-2-yl)pyrazolo[1,5-a]pyridine-5-carboxamide (Example 96) all exhibit inhibitory efficacy ($EC_{50}$) of 20 nM or less. The inhibitory efficacy of the four compounds in delaying the proliferation of P. berghei Sporozoite in liver cells is listed in Table 2 (identified by "*").

TABLE 2

Inhibitory Efficacy of Compounds of the Invention by the P. yoelii Sporozoite Invasion Assay or the P. berghei luciferase Proliferation Assay

| Example No. | $EC_{50}$ (nM) |
|---|---|
| 1 | 7.3 |
| 13 | 17.9 |
| 19 | 4.3 |
| 20 | 13.5 |
| 25 | 229 |
| 27 | 201 |
| 28 | 23.2 |
| 32 | 8.0 |
| 34 | 53.2 |
| 40 | 63.1 |
| 41 | 14.3 |
| 54 | 79 |
| 67 | 4.6 |
| 75 | 2.25 |
| 90 | 39 |
| 91 | 23 |
| 92 | 15* |
| 93 | 10 |
| 94 | 13* |
| 95 | 5* |
| 96 | 4* |
| 97 | 92 |
| 98 | 2063 |
| 99 | 15 |
| 100 | 20 |
| 102 | 660 |
| 103 | 62 |
| 104 | 1200 |
| 107 | 180 |
| 108 | 472 |
| 109 | 62 |
| 110 | 253 |
| 111 | >10,000 |
| 112 | 9 |
| 113 | 1649 |
| 114 | 950 |
| 115 | 79 |
| 116 | 3 |
| 117 | 7 |
| 118 | 1 |
| 119 | 56 |
| 133 | 34* |
| 136 | 10* |
| 137 | 10* |
| 140 | 84 |
| 141 | 17* |
| 143 | 7* |
| 144 | 22* |
| 145 | 8* |
| 146 | 20* |
| 147 | 151* |
| 148 | 18* |
| 149 | 1* |
| 150 | 19* |
| 151 | 7* |
| 152 | 182* |
| 153 | 16* |
| 154 | 36* |
| 155 | 21* |
| 156 | 54* |
| 157 | 60* |
| 158 | 11* |
| 159 | 43* |
| 160 | 4* |
| 161 | 41* |
| 162 | 8* |
| 163 | 2* |

*analyzed by the P. berghei luciferase Proliferation Assay

Preparation of the Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Synthesis", John Wiley and Sons, 1991.

Typically, the compounds of formula (I) can be prepared according to synthetic routes 1-6 provided infra., where Ring A, Ring C, $R_1$, $R_2$, $R_{17}$, n and p are as defined in the Summary of the Invention. The following reaction schemes are given to be illustrative, not limiting, descriptions of the synthesis of compounds of the invention. Detailed descriptions of the synthesis of compounds of the invention are given in the Examples, infra.

General Synthetic Route I

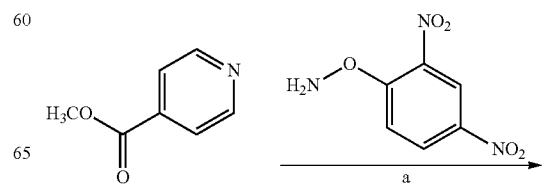

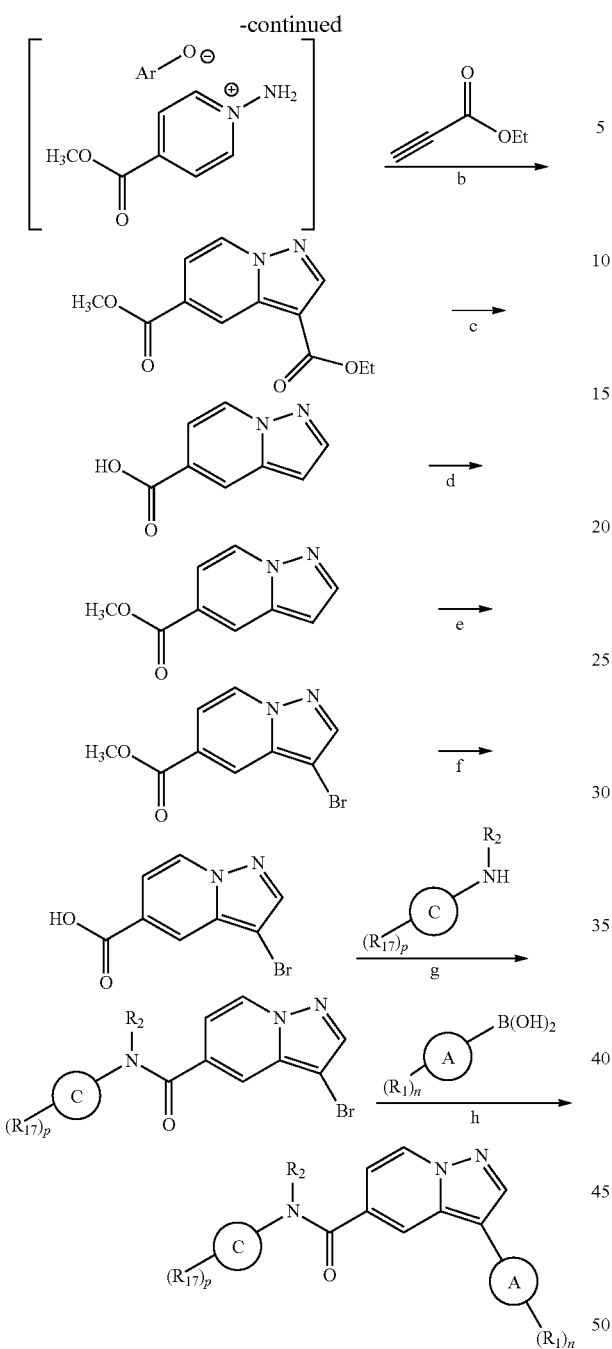

f. conventional base-catalyzed hydrolysis in aqueous alcohol solvent;

g. the carboxylic acid can be activated by various known methods, e.g., forming an acid chloride using oxalyl chloride or thionyl chloride and DMF followed by acylation of an amine of formula

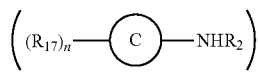

in a non-reactive solvent using an amine base such as $Et_3N$, DIEA (Hunig's base) or DMAP (dimethylaminopyridine). Various amide coupling reagents such as dicyclohexyl carbodiimide can also be used; and h. Pd-catalyzed Suzuki coupling.

General Synthetic Route 2

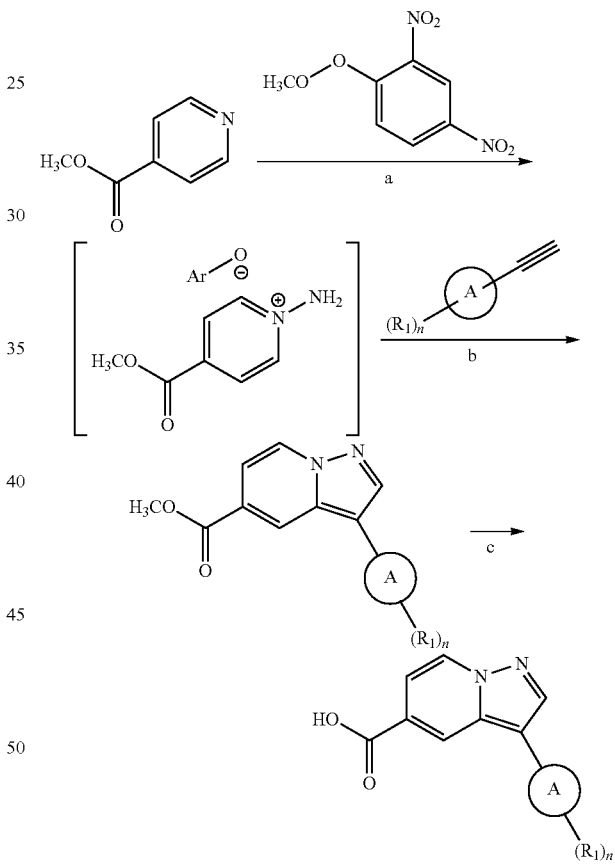

Reaction Conditions:
a. mild heating in a polar, aprotic solvent such as DMF, NMP, DMA or DMSO;
b. base such as $K_2CO_3$ or $Na_2CO_3$ in a polar organic solvent such as DMF, NMP or DMSO;
c. esters can be hydrolyzed under conventional acidic or basic conditions; decarboxylation occurs when the diacid is heated at 50-100° C.;
d. esterification can be done in alcohol (MeOH, EtOH) using acid catalysis (AcCl or TMSCl to generate HCl, or catalytic $H_2SO_4$ or toluene sulfonic acid, for example);
e. N-bromosuccinimide (NBS) or similar brominating agent in $CH_2Cl_2$, $CHCl_3$ or $CCl_4$ at −78° C. to room temperature;

Reaction Conditions:
a. mild heating in a polar, aprotic solvent such as DMF, NMP, DMA or DMSO;
b. base such as $K_2CO_3$ or $Na_2CO_3$ in a polar organic solvent such as DMF, NMP or DMSO;
c. conventional base-catalyzed hydrolysis in aqueous alcohol solvent.

Ring C can then be added using known methods, such as amide formation to link the carboxylic acid with an amine of formula

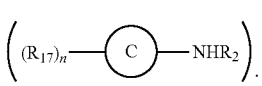

General Synthetic Route 3

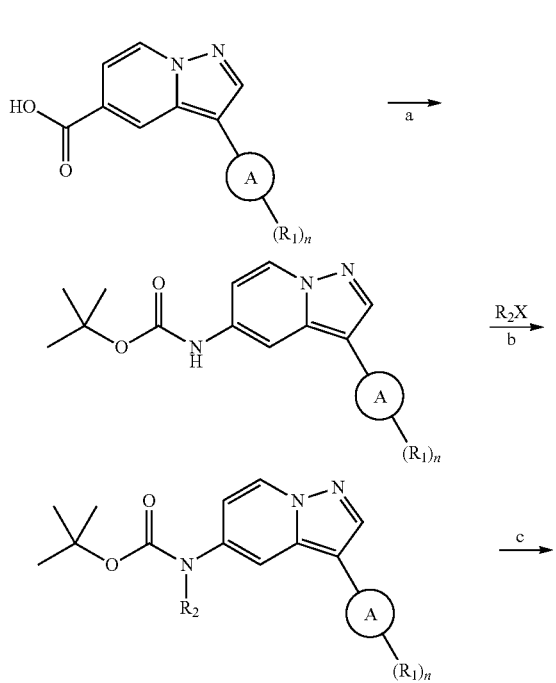

General Synthetic Route 4

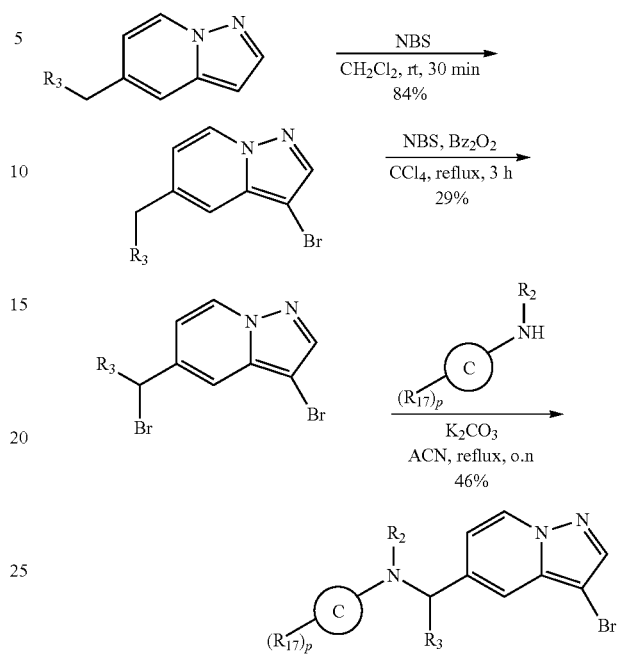

Ring A may be added by known methods such as the Suzuki coupling illustrated in Synthetic Route 1.

General Synthetic Route 5

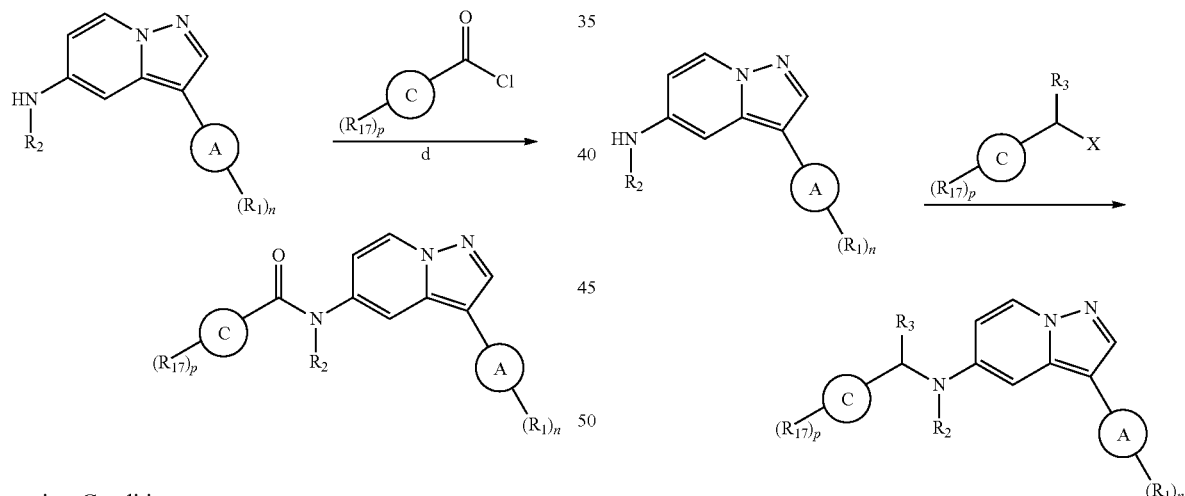

Reaction Conditions:
a. Curtius rearrangement of carboxylic acid using diphenyl phosphoryl azide, t-butyl alcohol and an appropriate base.
b. optionally exchanged hydrogen on the carbamate with an $R_2$ group by reacting with and $R_2X$ group where X is a leaving group (such as Cl), in basic DMF at room temperature or lightly elevated temperature for a few hours;
c. Acidic cleavage of t-butyl carbamate
d. acylation with acid chlorides in dichloromethane/triethylamine at room temperature.

The amine intermediate (Step c of Synthetic Route 3) may be alkylated with the Ring C moiety (where X is a leaving group, such as Cl, Br or I, or a sulfonate ester such as $MeSO_3$-TsO—, and the like) in an organic solvent, with a catalytic amount of DMAP and a non-nucleophilic base, at 0° C. to mild heating. Typical organic solvent includes halogenated solvents like DCM or $CHCl_3$; ether solvents such as THF, dioxane, MTBE, diethyl ether. Typical non-nucleophilic base includes triethylamine, diisopropyl ethylamine, potassium t-butoxide, potassium carbonate, and the like.

General Synthetic Route 6

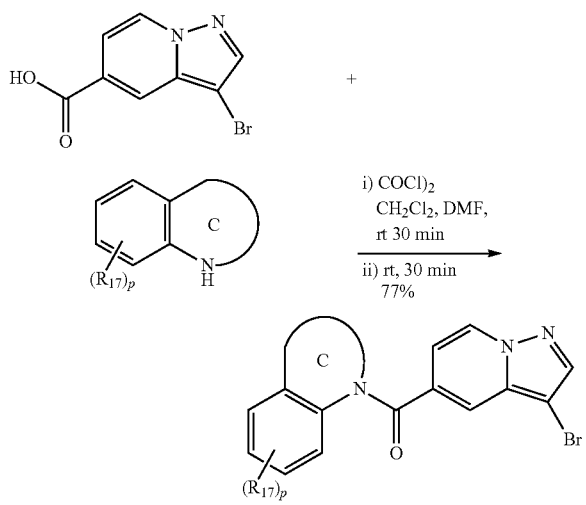

Ring A may be then added by known methods such as the Suzuki coupling illustrated in Synthetic Route I.

General Procedures for Boronic Ester Synthesis

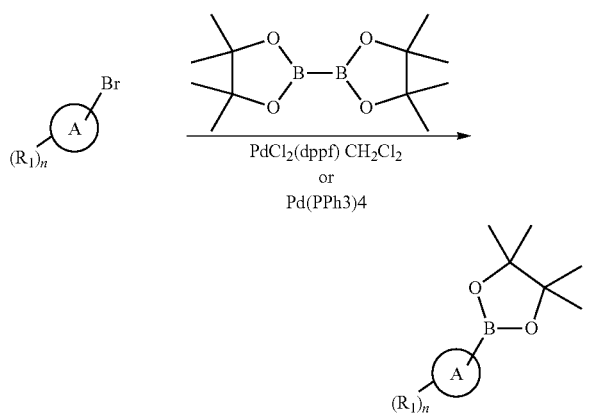

Boronic Ester Synthesis Procedure A: $PdCl_2(dppf)$-$CH_2Cl_2$;

A mixture of bromo compound (1.0 eq.) and bis(pinacolato)diboron (1.1 eq.) and potassium acetate (2.0 eq.) dissolved in 1,4-dioxane (10 vol) was degassed with argon gas for 15 min. Subsequently, $PdCl_2(dppf) \cdot CH_2Cl_2$ (0.05 eq.) was added and the reaction mixture was stirred at 85-100° C. for 16 h. The reaction mixture (generally black color) was filtered and concentrated under reduced pressure. The resulting black mixture was used further without any purification.

Boronic Ester Synthesis Procedure B: $Pd(PPh_3)_4$;

A mixture of bromo compound (1.0 eq.) and bis(pinacolato)diboron (1.1 eq.), and potassium acetate (2.0 eq.) dissolved in 1,4-dioxane (10 vol) was degassed with argon gas for 15 min. Subsequently, $Pd_2(dba)_3$ (0.05 eq.) and tricyclohexyl phosphine (0.05 eq.) were added and the reaction mixture was stirred at 90-110° C. for 16 h. The reaction mixture (generally black color) was filtered and concentrated under reduced pressure. The crude product was used further without any purification.

General Procedures for Suzuki Couplings

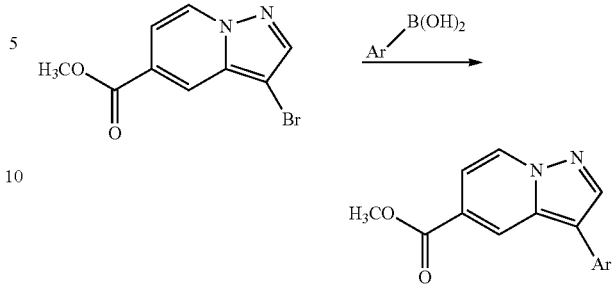

Suzuki Procedure A: SiliaCat® DPP-Pd and $K_2CO_3$:

A mixture of bromo compound (51 mg, 0.2 mmol, 1.0 equiv.), boronic acid (0.22 mmol, 1.1 equiv.), and SiliaCat® DPP-Pd (0.25 mmol/g loading, 34 mg, 0.01 mmol, 0.05 equiv.) was treated with 660 μL dioxane and 220 μL 1 M aq. $K_2CO_3$ and the resulting mixture was allowed to heat overnight at 100° C. in a capped vial. The resulting black mixture was dry-loaded onto silica gel and was purified by silica gel chromatography, eluting with hexanes/EtOAc to give the desired product.

Suzuki Procedure B: Pd(Dppf)Cl2 and $K_2CO_3$ in the Microwave:

A mixture of aryl bromide (1.0 equiv.), aryl boronic acid (1.5 equiv.), $K_2CO_3$ (2.5 equiv.), and $Pd(dppf)Cl_2$ (0.05-0.15 equiv.) in THF/water was allowed to heat at 140° C. in a microwave reactor for 40 minutes. Purified by mass-triggered HPLC or silica gel chromatography to provide the desired product.

Suzuki Procedure C: SiliaCat® DPP-Pd/Pd(Dppf)Cl$_2$ and $K_2HPO_4$ in the Microwave:

A mixture of aryl bromide (1.0 equiv.), aryl boronic acid (1.5 equiv.), $KH_2PO_4$ (3.5 equiv.), and SiliaCat® DPP-Pd or $Pd(dppf)Cl_2$ (0.05-0.15 equiv.) in THF/water was allowed to heat at 150° C. in a microwave reactor for 40-60 minutes. Purified by mass-triggered HPLC or silica gel chromatography to provide the desired product.

Suzuki Procedure D: $Pd(Dppf)Cl_2$, $K_2CO_3$, DME-WATER:

A mixture of aryl bromide (1.0 equiv.), aryl boronic acid (1.5 equiv.), $K_2CO_3$ (3.0 equiv.), and $Pd(dppf)Cl_2$ (0.05-0.15 equiv.) in DME/water was allowed to heat at 110° C. for two hours. Following extraction of the reaction mixture with $CH_2Cl_2$, the combined organic extracts were concentrated and the residue was purified by silica gel chromatography, eluting with hexanes/EtOAc to give the desired product.

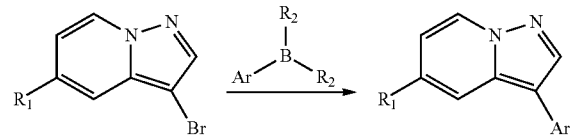

Suzuki Procedure E: $Pd_2(Dba)_3$, P(O-Tolyl)$_3$, 2M KF Solution in Toluene/Ethanol:

A mixture of aryl bromide (1.0 equiv.), aryl boronic acid (1.2-2.0 equiv.), 2 M aq KF (3 equiv.), and $Pd_2(dba)_3$ (0.1 equiv.), P(o-tolyl)$_3$ (0.1 equiv.) in toluene:ethanol (7:3) was degassed and heated to 100° C. for 1-5 h. The crude products were purified by preparative TLC or silica gel chromatography to provide the desired product.

Suzuki Procedure F: Pd(PPh$_3$)$_4$, 1N Na$_2$CO$_3$, Dioxane:

A mixture of aryl bromide (1.0 equiv.), aryl boronic acid (1.2-2.0 equiv.), 1 N Na$_2$CO$_3$ (2.0 equiv.), and Pd(PPh$_3$)$_4$ (0.2 equiv.) in 1,4-dioxane was degassed and heated in a sealed tube to 100° C. (microwave or conventional heating) for 2-6 h. The crude products were purified by preparative TLC or silica gel chromatography to provide the desired product.

Suzuki Procedure G:

A solution mixture of bromo compound (1.0 equivalent), boronic acid (1.3 equiv) and aq. 1N Na$_2$CO$_3$ (2.0 equivalent) in 1,4-dioxane (0.1 M) taken in a sealed tube was degassed with argon for about 20 min. Pd(PPh$_3$)$_4$ (0.1 equivalent) was added under argon atmosphere. The resulting reaction mixture was stirred at 90-100° C. for 2-16 h. The reaction mixture cooled to room temperature and filtered through celite. The filtrate was taken in to water and ethyl acetate. The ethyl acetate layer was washed with water, brine, dried over anhydrous Na$_2$SO$_4$ and concentrated. The crude compound was purified by silica (100-200 mesh) column chromatography using a solvent gradient of 1-2% methanol in chloroform as eluant. Some instances compounds were further purified by prep-TLC or prep-HPLC to obtain as yellow solids.

Suzuki Procedure H:

A solution mixture of bromo compound (1.0 equivalent), boronic acid (1.3 equivalent) and aq. 2M KF solution (3.0 equivalent) in toluene:ethanol (7:3) (0.1 M) was degassed with argon for about 15 min. Pd$_2$(dba)$_3$ (0.1 equivalent) and P(o-tolyl)$_3$ (0.1 equivalent) were added under argon atmosphere. The resulting reaction mixture was maintained at 100° C. for 2-16 h. The reaction mixture was allowed to room temperature and filtered through celite. The filtrate was partitioned between water and ethyl acetate. The ethyl acetate layer was washed with brine, dried over anhydrous Na$_2$SO$_4$ and evaporated under reduced pressure. The crude compound was purified by column chromatography over silica gel (100-200 mesh) using a solvent gradient of 1-2% methanol in chloroform as eluant to obtain product.

Suzuki Procedure I:

A solution mixture of bromo compound (1.0 equivalent), boronic acid (1.5 equivalent) and NaHCO$_3$ (2.5 equivalent) in acetonitrile:water (9:1) (0.1 M) was degassed with argon for about 30 min. Pd$_2$(dba)$_3$.CHCl$_3$ adduct (0.1 equivalent) and X-phos (0.1 equivalent) were added under argon atmosphere. The resulting reaction mixture was maintained at 100° C. for 2 h and allowed it to room temperature and filtered through celite. The filtrate was partitioned between water and ethyl acetate. The ethyl acetate layer was washed with brine, dried over anhydrous Na$_2$SO$_4$ and concentrated. The crude compound was purified by column chromatography over silica gel (100-200 mesh) using a solvent gradient of 80-100% of EA in cyclohexane or 1-2% methanol in dichloromethane as eluant to obtain products as yellow solids. This solids on re-precipitation from dichloromethane-pentane mixture afforded pure compounds.

General Procedures of Amide Coupling
Amide Coupling Method 1:

To a solution of carboxylic acid (1.0 equivalent) in dichloromethane (0.2 M) was added oxalyl chloride (2.8 equivalent) followed by catalytic amount of N,N-dimethylformamide at room temperature and stirred for 0.5-2 h. The resultant volatiles were distilled-off under reduced pressure to afford crude acid chloride. The acid chloride in dichloromethane (0.2 M) was added to corresponding amine (1.0 equivalent) and DIPEA (2.8 equivalent) in dichloromethane (1 M) at 0° C. The resulting reaction mixture was stirred at room temperature for 1 h-16 h. The reaction mixture was diluted with dichloromethane (50 mL). The organic layer was washed with 1N HCl, sat. NaHCO$_3$, water, brine, dried over anhydrous Na$_2$SO$_4$ and evaporated under reduced pressure. The crude product was purified by column chromatography over silica gel (100-200 mesh) using a solvent gradient of 25%-100% of ethyl acetate in pet-ether.

Amide Coupling Method 2:

A solution mixture of acid (1.0 equivalent), amine (3.0 equivalent), HATU (1.0 equivalent), and DIPEA (3.0 equivalent) in dry THF (0.1 M) was stirred at room temperature for 16 h. The volatiles were distilled off under reduced pressure, the residue was dilute with water and extracted with ethyl acetate. The combined extracts were washed with brine, dried over anhydrous Na$_2$SO$_4$ and concentrated. The crude compound was purified by column chromatography over silica-gel (100-200 mesh) using a solvent gradient of ethyl acetate in chloroform as eluant.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

The present invention is further exemplified, but not to be limited, by the following examples and intermediates that illustrate the preparation of compounds of the invention. It is understood that if there appears to be a discrepancy between the name and structure of a particular compound, the structure is to be considered correct as the compound names were generated from the structures.

Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

LC-MS Methods
Method 1:

Waters Acquity Binary Gradient Pump; Waters Acquity PDA Detector. Waters Auto sampler; Waters Quattro micro API Mass Spectrometer with ESI and APCI ion source; UPLC Column: Waters Acquity; BEH; C18 1.7 um 50×2.1 mm; Mobile Phase: (A) H$_2$O+0.025% TFA and (B) Acetonitrile+0.025% TFA. Gradient: 0.4 mL/minute, initial 15% B ramp to 95% B over 3.0 minutes, then hold until 4.0 minutes, return to 15% B at 4.1 minutes until end of run, then equilibrated the column for 2.0 minutes; MS Scan: 100 to 1000 amu in 0.5 seconds per channel; Diode Array Detector: 200 nm and 400 nm.

Method 2:

Waters Acquity Binary Gradient Pump; Waters Acquity PDA Detector. Waters Auto sampler; Waters Quattro micro API Mass Spectrometer with ESI and APCI ion source; UPLC Column: Waters Acquity; BEH; C18 1.7 um 50×2.1 mm; Mobile Phase: (A) $H_2O$+0.025% TFA and (B) Acetonitrile+0.025% TFA. Gradient: 0.4 mL/minute, initial 20% B ramp to 90% B over 2.0 minutes, then hold until 4.0 minutes, return to 20% B at 4.1 minutes until end of run, then equilibrated the column for 2.0 minutes; MS Scan: 100 to 1000 amu in 0.5 seconds per channel; Diode Array Detector: 200 nm and 400 nm.

Method 3:

Waters Acquity Binary Gradient Pump; Waters Acquity PDA Detector. Waters Auto sampler; Waters Acquity Evaporative Light Scattering Detector; Waters Quattro micro API Mass Spectrometer with ESI and APCI ion source; UPLC Column: Waters Acquity; BEH; C18 1.7 um 100×2.1 mm; Mobile Phase: (A) $H_2O$+0.025% TFA and (B) Acetonitrile+0.025% TFA. Gradient: 0.3 mL/minute, initial 10% B ramp to 80% B over 4.0 minutes, then hold until 6.0 minutes, return to 10% B at 6.1 minutes until end of run, then equilibrated the column for 2.5 minutes; MS Scan: 100 to 1000 amu in 0.5 seconds per channel; Diode Array Detector: 200 nm and 400 nm; Drift tube temperature: 50° C. and N2 gas flow: 40 Psi for ELSD Detector.

Method 4:

Waters Acquity Binary Gradient Pump; Waters Acquity PDA Detector. Waters Auto sampler; Waters Quattro micro API Mass Spectrometer with ESI and APCI ion source; UPLC Column: Waters Acquity; BEH; C18 1.7 um 50×2.1 mm; Mobile Phase: (A) $H_2O$+0.025% TFA and (B) Acetonitrile+0.025% TFA. Gradient: 0.4 mL/minute, initial 20% B ramp to 80% B over 2.0 minutes, then hold until 4.0 minutes, return to 20% B at 4.1 minutes until end of run, then equilibrated the column for 2.0 minutes; MS Scan: 100 to 1000 amu in 0.5 seconds per channel; Diode Array Detector: 200 nm and 400 nm Method 5:

Waters Acquity Binary Gradient Pump; Waters Acquity PDA Detector. Waters Auto sampler; Waters Quattro micro API Mass Spectrometer with ESI and APCI ion source; UPLC Column: Waters Acquity; BEH; C18 1.7 um 50×2.1 mm; Mobile Phase: (A) $H_2O$+0.025% TFA and (B) Acetonitrile+0.025% TFA. Gradient: 0.4 mL/minute, initial 10% B ramp to 80% B over 3.0 minutes, then hold until 4.0 minutes, return to 20% B at 4.1 minutes until end of run, then equilibrated the column for 2.0 minutes; MS Scan: 100 to 1000 amu in 0.5 seconds per channel; Diode Array Detector: 200 nm and 400 nm Method 6:

Agilent G1379A Degasser; Agilent G1312A Binary Pump; Agilent G1315C Diode Array Detector; Agilent G1367A Auto sampler; Agilent Ion Trap Mass Spectrometer with ESI source; HPLC Column: Waters X-Terra; MS; C18; 2.5 um 50×4.6 mm; Mobile Phase: (A) 0.01 M Ammonium Bicarbonate in Water and (B) Acetonitrile; Gradient: 1 mL/minute, initial 50% B, ramp to 80% B over 4.0 minutes, and hold until 6.0 minutes, return to 50% B at 6.1 minutes until end of run. The column is re-equilibrated for 3 minutes. MS Scan: 100 to 1200 amu; Diode Array Detector: 200 nm-400 nm.

Method 7:

Agilent G1379A Degasser; Agilent G1312A Binary Pump; Agilent G1315C Diode Array Detector; Agilent G1367A Auto sampler; Agilent Ion Trap Mass Spectrometer with ESI source; HPLC Column: Waters X-Bridge; C18; 3.5 um 150×4.6 mm; Mobile Phase: (A) 0.01 M Ammonium Bicarbonate in Water and (B) Acetonitrile; Gradient: 1 mL/minute, initial 20% B, ramp to 80% B over 4.0 minutes, and hold until 8.0 minutes, return to 20% B at 8.1 minutes until end of run. The column is re-equilibrated for 3 minutes. MS Scan: 100 to 1200 amu; Diode Array Detector: 200 nm-400 nm.

Method 8:

Agilent G1379A Degasser; Agilent G1312A Binary Pump; Agilent G1315C Diode Array Detector; Agilent G1367A Auto sampler; Agilent Ion Trap Mass Spectrometer with ESI source; HPLC Column: Waters Symmetry; C18; 3.5 um 75×4.6 mm; Mobile Phase: (A) $H_2O$+0.1% Formic acid and (B) Acetonitrile+0.1% Formic acid; Gradient: 1 mL/minute, initial 20% B, ramp to 80% B over 4.0 minutes, and hold until 7.0 minutes, return to 20% B at 7.1 minutes until end of run. The column is re-equilibrated for 3 minutes. MS Scan: 100 to 1200 amu; Diode Array Detector: 200 nm-400 nm.

EXAMPLES

Intermediate I-1

Methyl 3-(4-(trifluoromethyl)phenyl)pyrazolo[1,5-a]pyridine-5-carboxylate

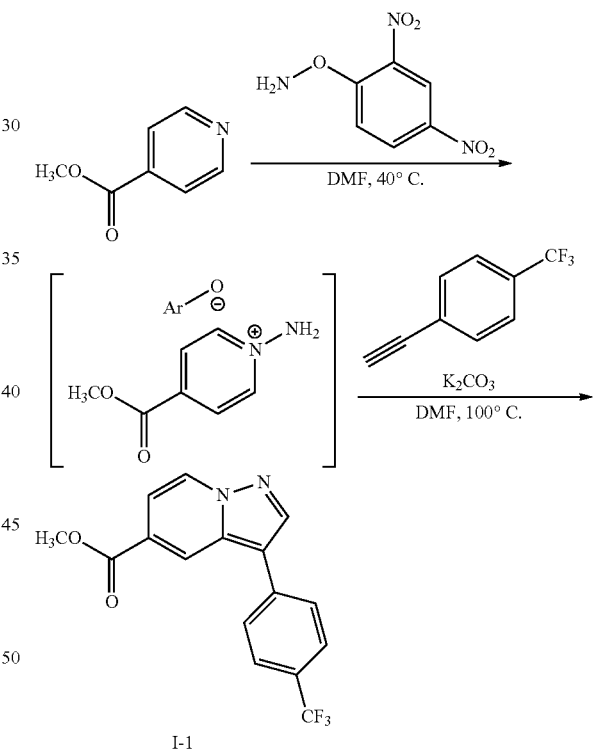

To a solution of methyl isonicotinate (500 μL, 4.23 mmol, 1.0 equiv.) in 2 mL DMF was added O-(2,4-dinitrophenyl)hydroxylamine (1 g, 5.02 mmol, 1.2 equiv.) and the resulting solution was allowed to stir overnight at 40° C., during which time the reaction became heterogeneous. The mixture was allowed to cool to rt before being diluted with 10 mL DMF, then treated with 4-ethynyl-α,α,α-trifluorotoluene (863 μL, 5.29 mmol, 1.25 equiv.) and potassium carbonate (877 mg, 6.35 mmol, 1.5 equiv.). The mixture was allowed to stir overnight at 100° C. The resulting mixture was allowed to cool to rt, and then the solvent was removed under reduced pressure. The residue was diluted with water and the aqueous layer was extracted with EtOAc five times.

The combined EtOAc extracts were washed once with water, once with brine, and then dried with MgSO$_4$, filtered, and the solvent removed under reduced pressure. The material was purified by silica gel chromatography, eluting with hexanes/EtOAc (Rf=0.26 in 5:1 hexanes/EtOAc) to give 335 mg (25% yield) I-1. $^1$H NMR (400 MHz, CDCl$_3$, δ): 8.52 (m, 2H), 8.23 (s, 1H), 7.72 (s, 4H), 7.40 (dd, J=1.59, 7.50 Hz, 1H), 3.96 (s, 3H).

Intermediate I-2

3-(4-(trifluoromethyl)phenyl)pyrazolo[1,5-a]pyridine-5-carboxylic acid

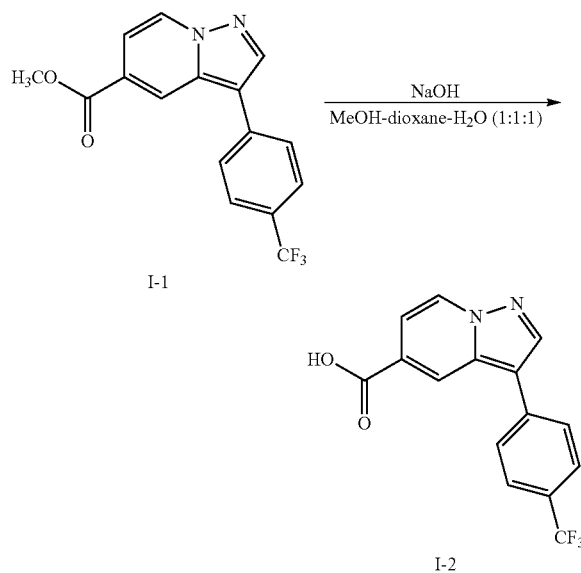

A solution of ester (320 mg, 1 mmol, 1.0 equiv.) in 3 mL 1:1 MeOH-dioxane was treated with 1 N aq. NaOH (1.5 mL, 1.5 mmol, 1.5 equiv.) dropwise over a few minutes, during which time the reaction became heterogeneous. The thick mixture was allowed to stir well at room temperature until complete (approximately three hours). As the reaction progressed, it became homogeneous. The resulting solution was diluted with 6 mL water, then was treated with 1 N aq. HCl (1.5 mL, 1.5 mmol, 1.5 equiv.) dropwise over a few minutes and allowed to stir well several minutes more to break up any clumps. The mixture was filtered and the filter cake was rinsed with water, followed by hexanes. The solid was dried under high vacuum overnight to provide I-2 (quant.).

Intermediate I-3

3-ethyl 5-methyl pyrazolo[1,5-a]pyridine-3,5-dicarboxylate

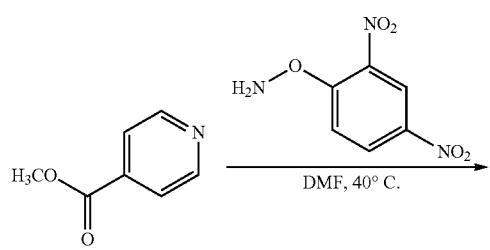

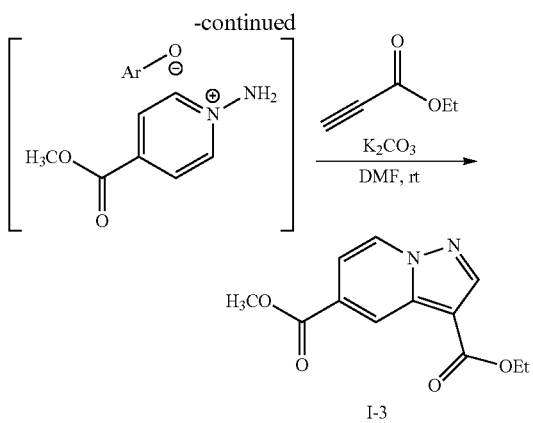

To a solution of methyl isonicotinate (500 μL, 4.23 mmol, 1.0 equiv.) in 2 mL DMF was added O-(2,4-dinitrophenyl)hydroxylamine (1 g, 5.02 mmol, 1.2 equiv.) and the solution was allowed to stir overnight at 40° C., during which time the reaction became heterogeneous. The mixture was allowed to cool to room temperature before being diluted with 10 mL DMF, then treated with ethyl propiolate (536 μL, 5.29 mmol, 1.25 equiv.) and potassium carbonate (877 mg, 6.35 mmol, 1.5 equiv.). The mixture was allowed to stir overnight at rt. After the solvent was removed under reduced pressure, the residue was diluted with water and the aqueous layer was extracted with EtOAc five times. The combined EtOAc extracts were washed once with water and once with brine, then dried with MgSO$_4$, filtered, and the solvent was removed under reduced pressure. The material was purified by silica gel chromatography, eluting with hexanes/EtOAc to give 778 mg (74% yield) of I-3. $^1$H NMR (400 MHz, CDCl$_3$) δ 8.86 (dd, J=0.9, 1.8, 1H), 8.55 (dd, J=0.9, 7.2, 1H), 8.47 (s, 1H), 7.52 (dd, J=1.8, 7.2, 1H), 4.42 (q, J=7.1, 2H), 3.99 (s, 3H), 1.44 (t, J=7.1, 3H).

Intermediate I-4

Pyrazolo[1,5-a]pyridine-5-carboxylic acid

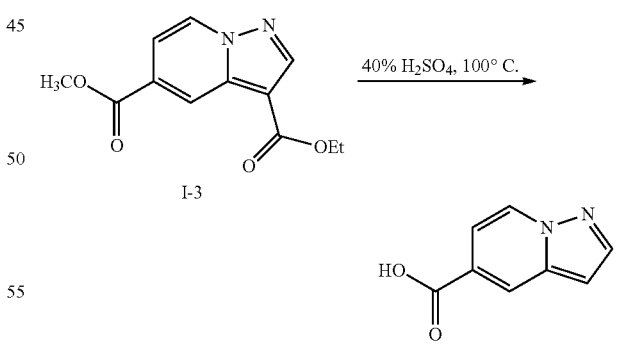

A suspension of diester (8.5 g, 34.2 mmol, 1.0 equiv.) in 150 mL 40% H$_2$SO$_4$ was allowed to heat at 100° C. overnight in a septum-capped vial fitted with a needle outlet to an empty balloon to accommodate the gas evolution. The resulting solution was allowed to cool to rt, then placed in a cold water bath before bringing to approx. pH=2 with NaOH. During this pH adjustment, the acid precipitated and was isolated by filtration. The solid was washed with water, and then dried under high vacuum overnight to provide acid I-4. $^1$H NMR (400 MHz, DMSO) δ 12.5 (br s, 1H), 8.74 (d, J=7.3, 1H), 8.34 (m, 1H), 8.11 (d, J=2.3, 1H), 7.25 (dd, J=1.9, 7.3, 1H), 6.89 (dd, J=0.8, 2.3, 1H).

Intermediate I-5

Methyl pyrazolo[1,5-a]pyridine-5-carboxylate

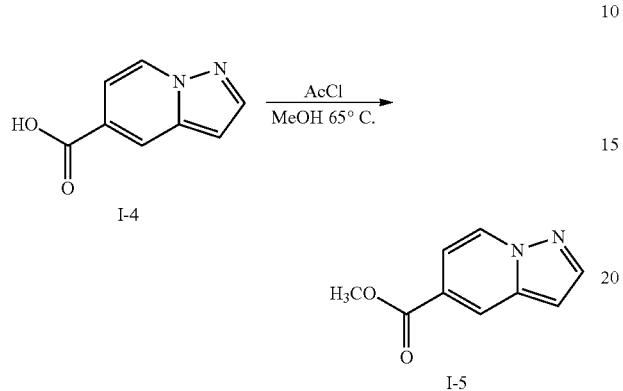

A solution of acid (200 mg, 1.23 mmol, 1.0 equiv.) in 3.7 mL MeOH was allowed to cool to 0° C., then AcCl (370 µL) was added dropwise with efficient stirring. The resulting solution was allowed to warm to rt, then allowed to heat at 65° C. overnight in a sealed vial. The resulting solution was allowed to cool to rt before the solvent was evaporated. The residue was diluted with EtOAc, and then washed with saturated aq. NaHCO$_3$ and brine, dried with MgSO$_4$, filtered, and the solvent was removed under reduced pressure to give 110 mg of the desired ester I-5, which was taken on without further purification.

Intermediate I-6

Methyl 3-bromopyrazolo[1,5-a]pyridine-5-carboxylate

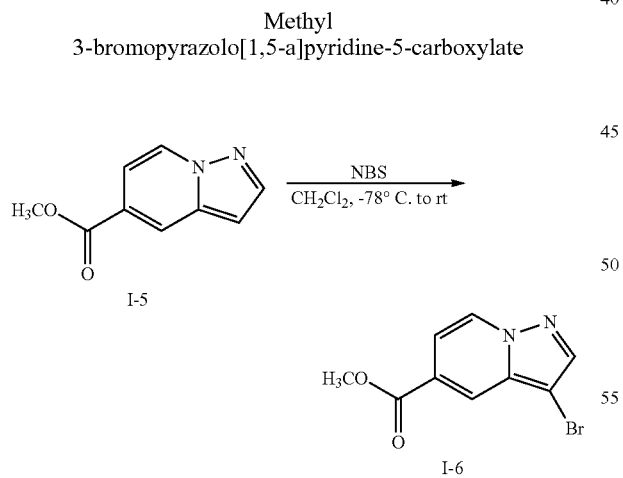

A solution ester (110 mg, 0.62 mmol, 1.0 equiv.) in 6.3 mL CH$_2$Cl$_2$ was allowed to cool to −78° C., then NBS (110 mg, 0.62 mmol, 1.0 equiv.) was added in one portion. The resulting mixture was allowed to warm to rt and then stir at that temperature for one hour. The solvent was removed under reduced pressure and the resulting material was purified by silica gel chromatography, eluting with hexanes/EtOAc to give I-6. $^1$H NMR (400 MHz, CDCl$_3$, δ): 8.43 (dd, J=0.80, 7.28, 1H), 8.27 (m, 1H), 7.99 (s, 1H), 7.36 (dd, J=1.83, 7.30 Hz, 1H), 3.96 (s, 3H).

Intermediate I-7

3-bromopyrazolo[1,5-a]pyridine-5-carboxylic acid

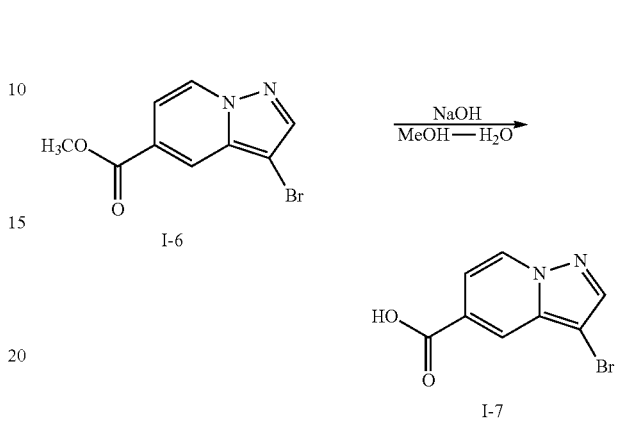

A solution of ester (195 mg, 0.764 mmol, 1.0 equiv.) in 4 mL MeOH was treated with 1 N aq. NaOH (2 mL, 2.0 mmol, 2.6 equiv.) at rt, and then allowed to stir at rt for one hour. Concentrated under reduced pressure, then diluted with water and acidified with 4 N aq. HCl. Extracted 3×10 mL EtOAc, dried the combined organic extracts with Na$_2$SO$_4$, filtered and the solvent removed under reduced pressure to give the desired acid I-7, which was taken on without further purification.

Intermediate I-8

3-bromo-N-(4-cyanophenyl)-N-methylpyrazolo[1,5-a]pyridine-5-carboxamide

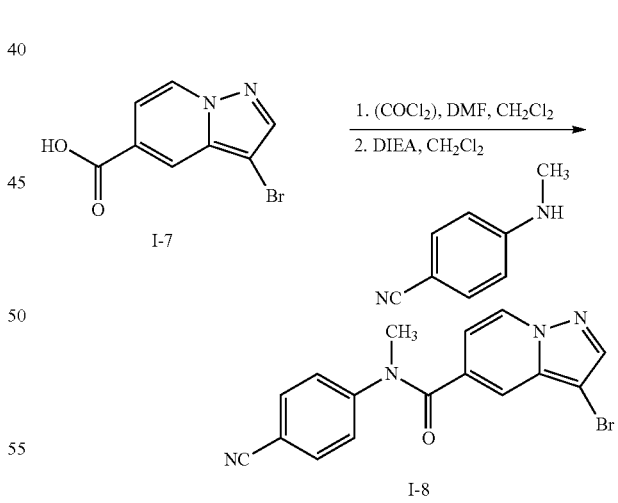

A solution of acid (1.0 equiv.) in CH$_2$Cl$_2$ (~0.05-0.1 M) was treated with oxalyl chloride (2.0-3.0 equiv.) and a catalytic amount of DMF. The resulting solution was allowed to stir at rt for between five minutes and one hour, then was concentrated and dried briefly under high vacuum. The resulting acid chloride was diluted with CH$_2$Cl$_2$ (~0.05-0.1 M), and to this solution was added 4-cyano-N-methyl-aniline (1.1-3.0 equiv.) and either DIEA or Et3N (3.0 equiv.). The resulting mixture was allowed to stir at room temperature until complete conversion (generally less than three hours). The solvent was removed under reduced pressure, and the residue was purified by silica gel chromatography.

Intermediate I-9

3-bromo-N-(5-cyanopyridin-2-yl)-N-methylpyrazolo[1,5-a]pyridine-5-carboxamide

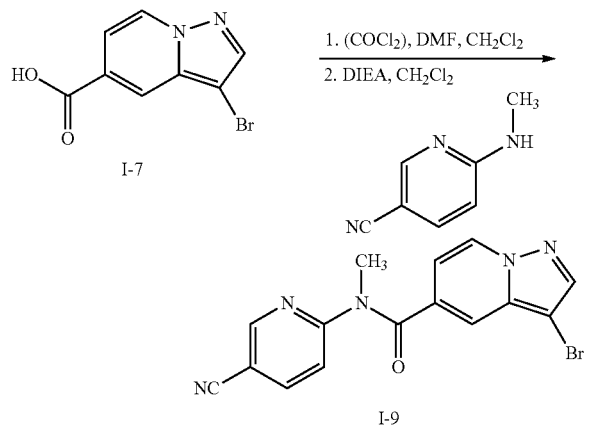

Intermediate I-9 was prepared according to the procedure described for the synthesis of intermediate I-8 by replacing 4-(methylamino)benzonitrile with 6-(methylamino)nicotinonitrile.

Alternatively, I-9 was prepared using the general procedure of amide coupling-Method 1. Yield 45%. White solid. $^1$H NMR (400 MHz, CDCl$_3$): δ 8.68 (s, 1H), 8.35 (d, J=6.83 Hz, 1H), 7.99 (s, 1H), 7.82 (dd, J=1.9, 7.7 Hz, 1H), 7.68 (s, 1H), 7.37 (d, J=8.8 Hz, 1H), 6.73-6.75 (m, 1H), 3.64 (s, 3H).

Intermediate I-10

3-bromo-N-methyl-N-(5-(methylsulfonyl)pyridin-2-yl)pyrazolo[1,5-a]pyridine-5-carboxamide

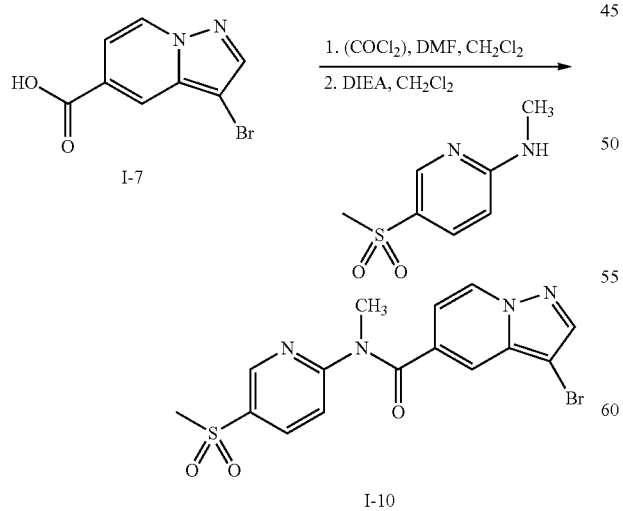

Intermediate I-10 was prepared according to the procedure described for the synthesis of intermediate I-8 by replacing 4-(methylamino)benzonitrile with N-methyl-5-(methylsulfonyl)pyridin-2-amine.

Intermediate I-11

3-bromo-N-methyl-N-(5-(trifluoromethyl)pyridin-2-yl)pyrazolo[1,5-a]pyridine-5-carboxamide

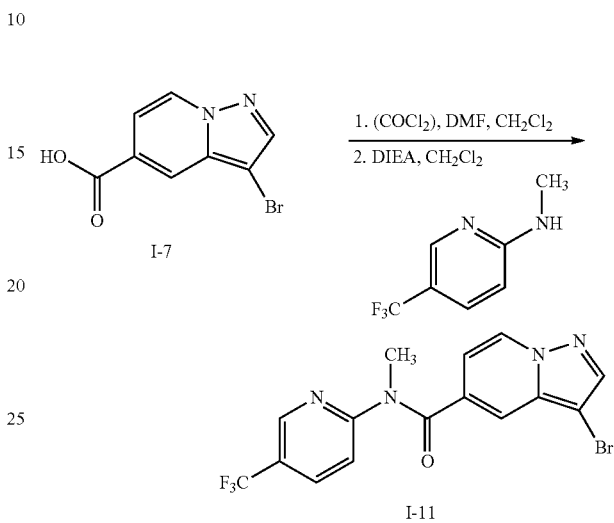

Intermediate I-11 was prepared according to the procedure described for the synthesis of intermediate I-8 by replacing 4-(methylamino)benzonitrile with N-methyl-5-(trifluoromethyl)pyridin-2-amine.

Intermediate I-12

3-bromo-N-methyl-N-(5-methylpyridin-2-yl)pyrazolo[1,5-a]pyridine-5-carboxamide

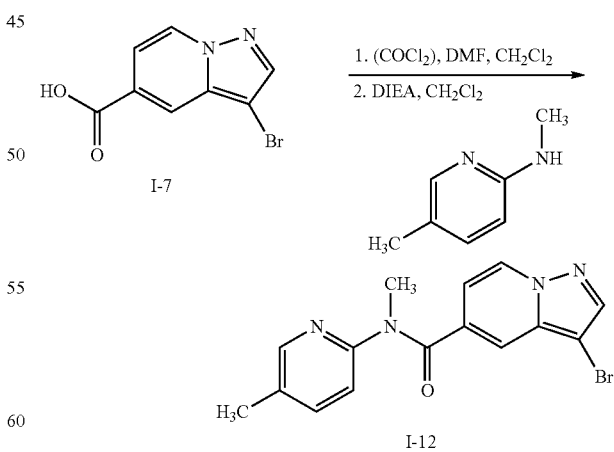

Intermediate I-12 was prepared according to the procedure described for the synthesis of intermediate I-8 by replacing 4-(methylamino)benzonitrile with N,5-dimethylpyridin-2-amine.

Intermediate I-13

3-bromo-N-(4-fluorophenyl)-N-methylpyrazolo[1,5-a]pyridine-5-carboxamide (Example 64)

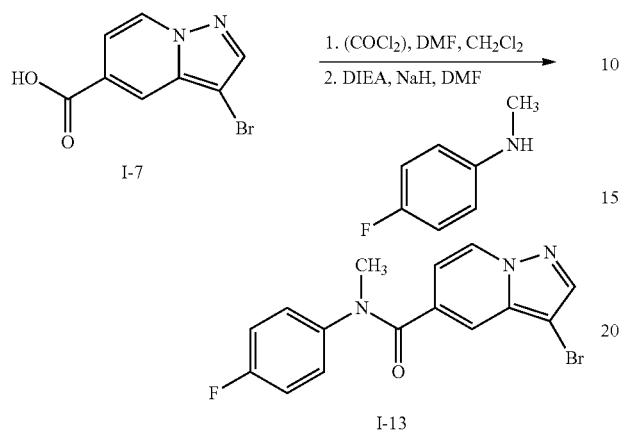

Intermediate I-13 was prepared according to the procedure described for the synthesis of intermediate I-8 by replacing 4-(methylamino)benzonitrile with 4-fluoro-N-methylaniline. $^1$H NMR (400 MHz, METHANOL-d$_4$) δ 3.49 (s, 3H) 6.80 (d, J=7.53 Hz, 1H) 7.00-7.14 (m, 2H) 7.24-7.37 (m, 2H) 7.50 (s, 1H) 7.97 (s, 1H) 8.38 (d, J=7.28 Hz, 1H); ESI-LC/MS (m/z): [M–H]$^+$ 349.

Intermediate I-14

3-bromo-N-(4-chloro-2-formylphenyl)-N-methylimidazo[1,2-a]pyrazine-6-carboxamide

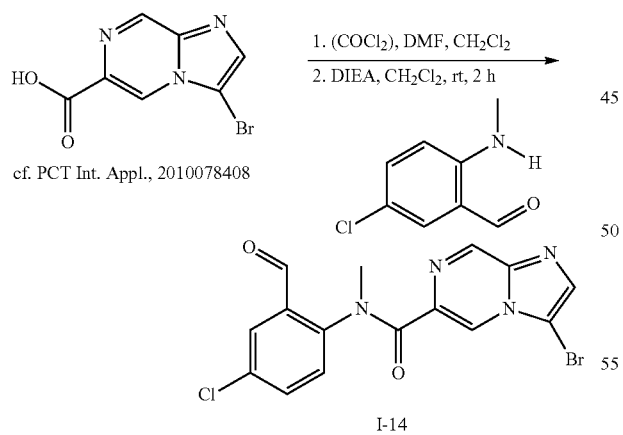

Intermediate I-14 was prepared according to the procedure described for the synthesis of intermediate I-8 by replacing 4-(methylamino)benzonitrile with 5-chloro-2-(methylamino)benz-aldehyde. $^1$H NMR (400 MHz, CDCL$_3$) δ 10.21 (s, 1H), 8.77 (s, 1H), 8.45-8.48 (m, 1H), 7.77-7.84 (m, 2H), 7.44-7.46 (m, 2H), 7.09-7.11 (m, 1H), 5.25 (s, 3H); ESI-LC/MS (Method 1) (m/z): [M+H]$^+$ 392.89 [M+2H]$^+$ 394.90 & [M+4H]$^+$ 396.92.

Intermediate I-15

3-bromo-N-(4-chloro-2-formylphenyl)-N-methyl-pyrazolo[1,5-a]pyridine-5-carboxamide

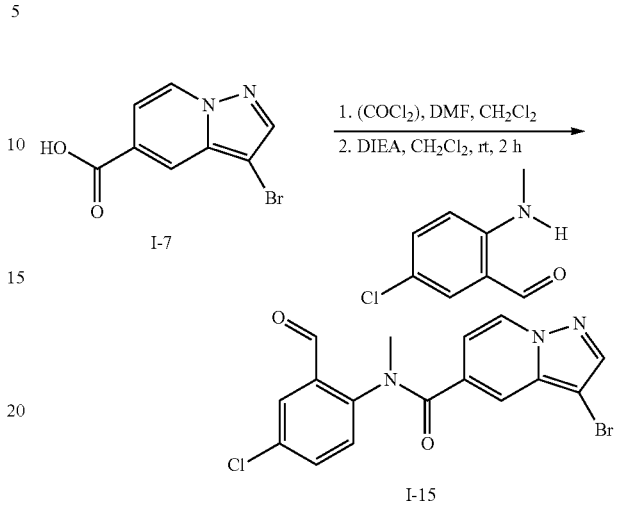

Intermediate I-15 was prepared according to the procedure described for the synthesis of intermediate I-8 by replacing 4-(methylamino)benzonitrile with 5-chloro-2-(methylamino)benz-aldehyde. $^1$H NMR (400 MHz, CDCL$_3$) δ 10.04 (s, 1H), 8.18-8.28 (m, 1H) 7.90-7.95 (m, 1H) 7.77 (s, 1H) 7.57-7.61 (m, 1H) 7.40 (s, 1H) 6.61 (br. s, 1H) 3.49 (s, 3H); ESI-LC/MS (Method 1) (m/z): [M+H]$^+$ 391.94 & [M+2H]$^+$ 393.89 & [M+4H]$^+$ 395.91.

Intermediate I-16

3-(4-aminophenyl)-N-(4-cyanophenyl)-N-methyl-pyrazolo[1,5-a]pyridine-5-carboxamide

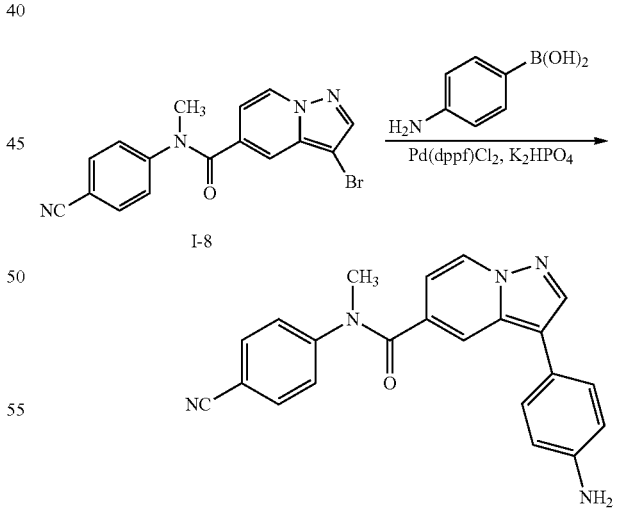

A mixture of aryl bromide (1.0 equiv.), aryl boronic acid (1.5 equiv.), K$_2$CO$_3$ (2.5 equiv.), and Pd(dppf)Cl$_2$ (0.05-0.15 equiv.) in THF/water was allowed to heat at 140° C. in a microwave reactor for 40 minutes. The resulting mixture was concentrated under reduced pressure and purified by silica gel chromatography to give I-16.

Intermediate I-17

3-bromo-5-ethylpyrazolo[1,5-a]pyridine

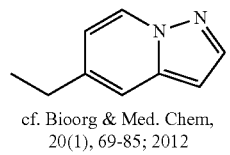

cf. Bioorg & Med. Chem, 20(1), 69-85; 2012

NBS
CH₂Cl₂, rt, 30 min
84%

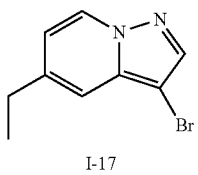

I-17

To a stirred solution of 5-ethylpyrazolo[1,5-a]pyridine (1.1 g, 0.008 mmol) in dichloromethane (10 mL) at 0° C. was added NBS (1.75 g, 0.009 mmol) and reaction mixture was stirred at room temperature for 5 min. Subsequently, water was added and the reaction mixture was extracted with dichloromethane (2×10 mL). The organic layer was washed with water (1×30 mL), sat. NaHCO₃ solution (1×10 mL), brine (1×10 mL), dried over Na₂SO₄ and concentrated to afford 2.1 g (84%) of 3-bromo-5-ethylpyrazolo[1,5-a]pyridine (I-17) as a brownish highly viscous liquid. The crude was progressed to next step without any further purification. ESI-LC/MS (m/z): [M+H]⁺ 225.0, [(M+2)+H]⁺ 227.0, RT 2.50 min.

Intermediate I-18

3-bromo-5-(1-bromoethyl)pyrazolo[1,5-a]pyridine

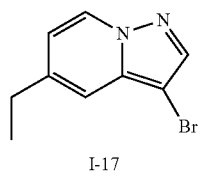

I-17

NBS, Bz₂O₂
CCl₄, reflux, 3 h
29%

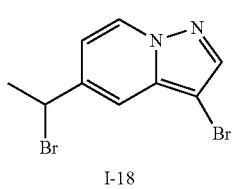

I-18

To a stirred solution of 3-bromo-5-ethylpyrazolo[1,5-a]pyridine (I-17, 2.1 g, 0.0094 mmol) in CCl₄ (20 mL) at rt was added NBS (2 g, 0.01 mmol) followed by benzoyl peroxide (1.1 g, 0.004 mmol). The resulting reaction mixture was heated to 77° C. After 2 h, the reaction mixture was allowed to cool to rt and subsequently water (20 mL) was added followed by extraction with dichloromethane (2×20 mL). The combined organic layers were washed with water (1×20 mL), sat NaHCO₃ solution (1×10 mL), brine (1×10 mL), dried over Na₂SO₄ and the solvent was removed under reduced pressure. The resulting crude product was purified by column chromatography over silica gel (petroleum ether/EtOAc, 0-5% EtOAc) to afford 820 mg (29%) of 3-bromo-5-(1-bromoethyl)pyrazolo[1,5-a]pyridine (I-18) as a brown solid. ¹H NMR (400 MHz, CDCl₃) δ 8.45 (d, J=7.91 Hz, 1H), 7.93 (s, 1H), 7.46 (d, J=1.32 Hz, 1H), 6.90-6.92 (dd, J=1.76, 5.71 Hz, 1H), 5.19-5.24 (m, 2H), 2.08 (d, J=7.04 Hz, 3H); ESI-LC/MS (m/z): [M+H]⁺ 302.9, [(M+2)+H]⁺ 304.9, [(M+4)+H]⁺ 306.9, RT 2.65 min

Intermediate I-19

N-(1-(3-bromopyrazolo[1,5-a]pyridin-5-yl)ethyl)-N, 5-dimethylpyridin-2-amine

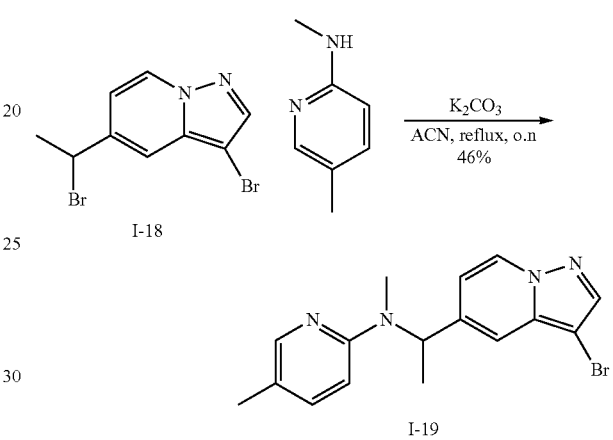

A suspension of 3-bromo-5-(1-bromoethyl)pyrazolo[1,5-a]pyridine (I-18, 400 mg, 1.32 mmol), N,5-dimethylpyridin-2-amine (230 mg, 1.98 mmol) and K₂CO₃ (546 mg, 3.96 mmol) in acetonitrile was heated to 90° C. in a sealed tube for overnight. The reaction mixture was cooled to room temperature and water (10 mL) was added. The aqueous phase was extracted with ethyl acetate (2×10 mL). The combined organic layers were dried over Na₂SO₄ and solvents were removed under reduced pressure. The resulting crude product was purified by column chromatography over silica gel (petroleum ether/EtOAc, 0-4% EtOAc) to afford 210 mg (46%) of N-(1-(3-bromopyrazolo[1,5-a]pyridin-5-yl)ethyl)-N,5-dimethylpyridin-2-amine (I-19) as a yellow solid. ESI-LC/MS (m/z): [M+H]⁺ 345.2, [(M+2)+H]⁺ 347, RT 3.31 min.

Intermediate I-20

(3-bromopyrazolo[1,5-a]pyridin-5-yl)(7-fluoro-2H-benzo[b][1,4]oxazin-4(3H)-yl)methanone

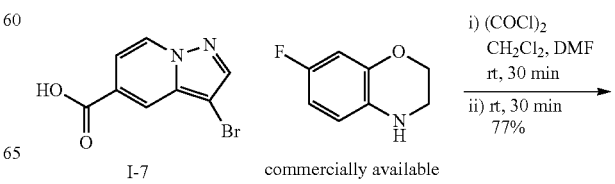

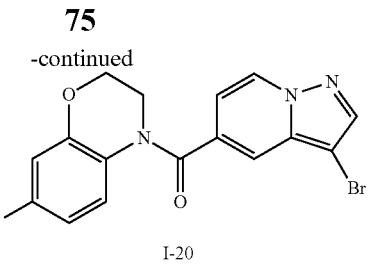

I-20

To a solution of 3-bromopyrazolo[1,5-a]pyridine-5-carboxylic acid (I-7, 250 mg, 1.040 mmol) in dichloromethane (10 mL) was added oxalyl chloride (0.25 mL), followed by catalytic amount DMF (0.1 M) at rt and the mixture was stirred for 30 min. The resultant volatiles were removed under reduced pressure to afford a residue of acid chloride. To this residue was added 7-fluoro-3,4-dihydro-2H-benzo[b][1,4]oxazine (191 mg, 1.25 mmol) in dichloromethane (10.0 mL), followed by DIPEA (0.5 mL) and the mixture was stirred at rt for 30 min. The reaction mixture was diluted with dichloromethane (50 mL).

The reaction mixture was washed with 1N HCl, sat. NaHCO$_3$ solution, water, brine, dried over Na$_2$SO$_4$, and the solvent was removed under reduced pressure to afford 300 mg (77%) of (3-bromopyrazolo[1,5-a]pyridin-5-yl)(7-fluoro-2H-benzo[b][1,4]oxazin-4(3H)-yl)methanone (I-20) as a brown solid. $^1$H NMR (400 MHz, DMSO-d$_6$) δ 8.87 (d, J=7.68 Hz, 1H), 8.27 (s, 1H), 7.80 (s, 1H), 7.06 (d, J=6.7 Hz, 1H), 6.84 (d, J=10.3 Hz, 1H), 6.65-6.68 (m, 1H), 6.50-6.52 (m, 1H), 4.36 (m, 2H), 3.92 (m, 2H); ESI-LC/MS (m/z): [M+H]$^+$ 376.0, [(M+2)+H]$^+$ 378.0, RT 2.37 min.

Intermediate I-21

2-chloro-N-(4-fluoro-2-hydroxyphenyl)acetamide

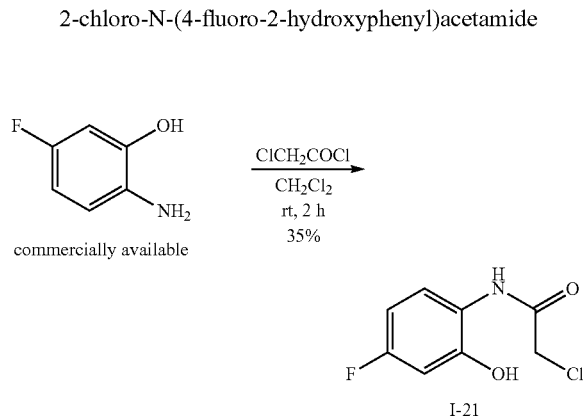

To a solution of 2-amino-5-fluorophenol (1.0 g, 7.87 mmol) in dichloromethane (50 mL) at 0° C. was added 2-Chloroacetyl chloride (978 mg, 8.66 mmol). The reaction mixture was stirred at rt for 2 h, followed by addition of aqueous saturated NaOH solution. The organic layer was washed with brine, dried over Na$_2$SO$_4$ and solvent was removed under reduced pressure to afford 550 mg (35%) of 2-chloro-N-(4-fluoro-2-hydroxyphenyl)acetamide (I-21) as a brown solid. ESI-LC/MS (m/z): (M−H)$^-$ 201.6, RT 2.65 min.

Intermediate I-22

7-fluoro-4a,5-dihydro-2H-benzo[b][1,4]oxazin-3(4H)-one

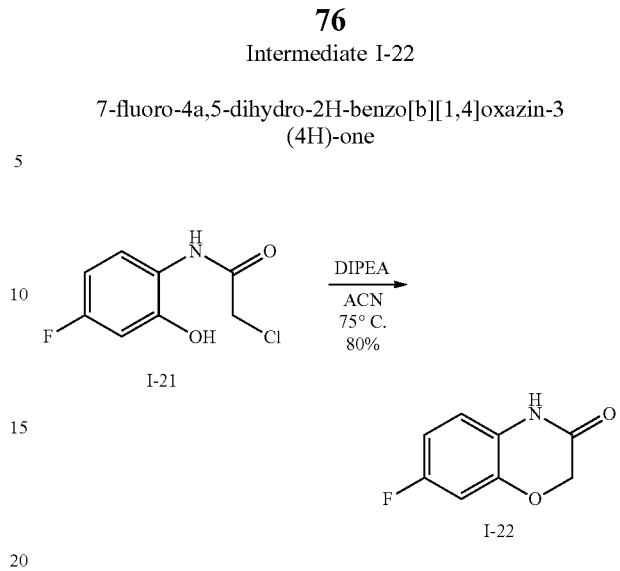

To a solution of 2-chloro-N-(4-fluoro-2-hydroxyphenyl)acetamide (5.5 g, 27 mmol) in acetonitrile (40 mL) was added DIPEA (7 g, 54 mmol) and the reaction solution was stirred at 80° C. for 2 h. The solvent was removed under reduced pressure and the residue was partitioned between dichloromethane (50 mL) and water (50 mL). The organic layer was washed with brine, dried over Na$_2$SO$_4$ and concentrated under reduced pressure to afford 3.5 g (78%) of 7-fluoro-2H-benzo[b][1,4]oxazin-3(4H)-one as a brown solid. $^1$H NMR (400 MHz, CDCl$_3$) δ 8.35 (br. s, 1H) 6.67-6.77 (m, 3H) 4.62 (s, 2H).

Intermediate I-23

7-fluoro-3-methyl-3,4-dihydro-2H-benzo[b][1,4]oxazine

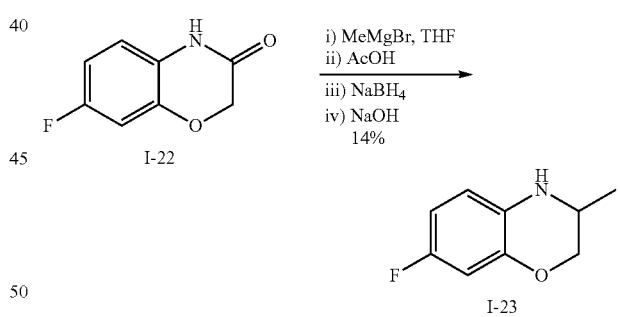

To a stirred solution of 7-fluoro-2H-benzo[b][1,4]oxazin-3(4H)-one (I-22, 1 g, 5.98 mmol) in THF (25 mL) at 0° C. was added 3M CH$_3$MgBr (8 mL, 24 mmol). After addition, the cooling bath was removed and the mixture was heated to 65° C. for 4 h. The reaction mixture was quenched with acetic acid (10 mL) at 0° C. and NaBH$_4$ (568 mg, 15 mmol) was added to the solution. The resulting solution was stirred at rt for overnight. Subsequently, 3N aqueous NaOH solution was cautiously added until pH value of the mixture was adjusted to 10.0. The basic solution was extracted with ethyl acetate (2×30 mL). The combined organic layers were washed with water, brine, dried over Na$_2$SO$_4$ and the solvent was removed under reduced pressure. The resulting crude product was purified by column chromatography over neutral alumina (petroleum ether/EtOAc, 0-15% EtOAc) to afford 135 mg (14%) of 7-fluoro-3-methyl-3,4-dihydro-2H-benzo[b][1,4]oxazine (I-23) as a brown oil. $^1$H NMR (400 MHz, DMSO) δ 6.45-6.55 (m, 3H), 4.16-4.19 (m, 1H), 3.73-3.77 (m, 1H), 3.44-3.51 (m, 2H), 1.17 (d, J=6.34 Hz, 3H).

Intermediate I-24

(3-bromopyrazolo[1,5-a]pyridin-5-yl)(7-fluoro-3-methyl-2H-benzo[b][1,4]oxazin-4(3H)-yl)methanone

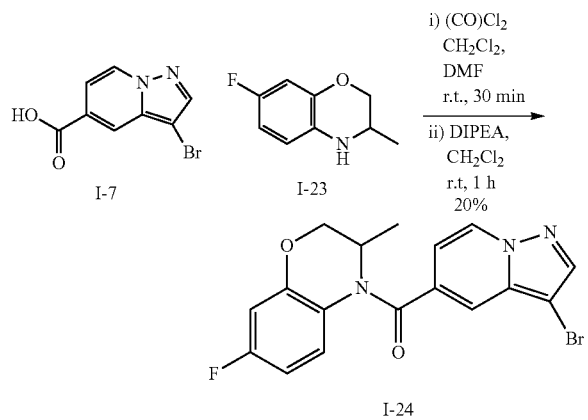

Intermediate I-24 was prepared according to the procedure described for the synthesis of intermediate I-8 by replacing 4-(methylamino)benzonitrile with 7-fluoro-3-methyl-3,4-dihydro-2H-benzo[b][1,4]oxazine (I-23, 350 mg, 2.1 mmol). The resulting crude product was purified by column chromatography over silica gel (chloroform/EtOAc, 0-30% EtOAc) to afford 150 mg (20%) of (3-bromopyrazolo[1,5-a]pyridin-5-yl)(7-fluoro-3-methyl-2H-benzo[b][1,4]oxazin-4(3H)-yl)-methanone (I-24) as an off-white solid. $^1$H NMR (400 MHz, DMSO) δ $^1$H NMR (400 MHz, CDCl$_3$) δ 8.36 (d, J=7.0 Hz, 1H), 7.99 (s, 1H), 7.81 (s, 1H), 6.88 (br. s, 1H), 6.67-6.78 (m, 3H), 6.42-6.46 (m, 1H), 4.82 (br. s, 1H), 4.28-4.35 (m, 2H), 1.33 (d, J=7.0 Hz, 3H).

Intermediate I-25

6-(oxetan-3-ylamino)nicotinonitrile

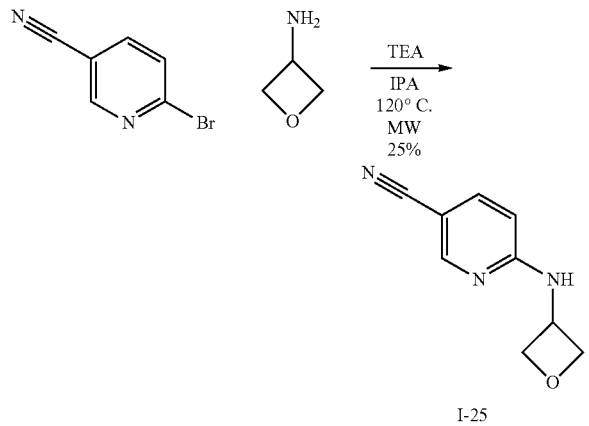

In a microwave vial, oxetan-3-amine (125 mg, 1.736 mmol), triethylamine (526 mg, 5.21 mmol) were added to a solution of 2-bromo-5-cyanopyridine (317 mg, 1.736 mmol) in isopropanol (3 mL). The vial was capped and irradiated in a microwave oven at 120° C. for 5 h. The reaction mixture was partitioned between ethyl acetate (10 mL) and water (10 mL). The organic layer was washed with brine, dried over Na$_2$SO$_4$ and the solvent was removed under reduced pressure. The resulting crude product was purified by column chromatography over silica gel (chloroform/MeOH, 0-5% EtOAc) to afford 75 mg (25%) of 6-(oxetan-3-ylamino) nicotinonitrile (I-25) as an off-white solid. $^1$H NMR (400 MHz, DMSO) δ 8.36 (s, 1H), 7.58-7.61 (dd, J=1.9, 6.9 Hz, 1H), 6.39 (d, J=8.7 Hz, 2H), 5.37 (br. s, 1H), 4.91-5.06 (m, 3H), 4.54-4.57 (m, 2H); ESI-LC/MS (m/z): [M+H]$^+$ 176.2, RT 1.65 min.

Intermediate I-26

3-bromo-N-(5-cyanopyridin-2-yl)-N-(oxetan-3-yl) pyrazolo[1,5-a]pyridine-5-carboxamide

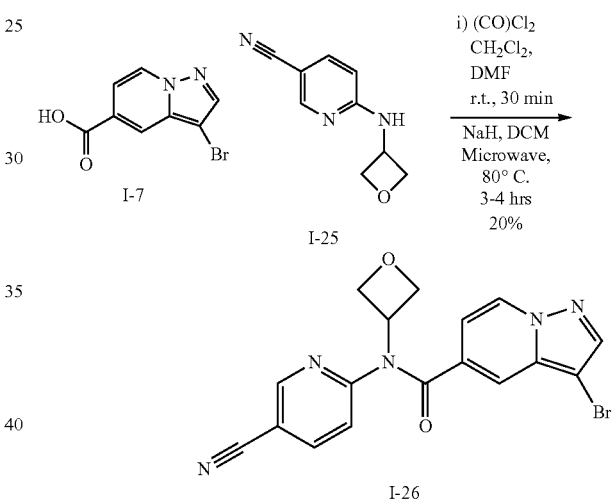

To a solution of 3-bromopyrazolo[1,5-a]pyridine-5-carboxylic acid (I-7, 240 mg, 1 mmol) in dichloromethane (10 mL) was added oxalyl chloride (0.25 mL) and catalytic amounts of anhydrous dimethylformamide at rt. The reaction mixture was stirred for 30 minutes and subsequently the solvent was removed under reduced pressure. To the residual acid chloride was added a solution of 6-(oxetan-3-ylamino) nicotinonitrile (I-25, 175 mg, 1 mmol) in dichloromethane (10 mL). The resulting reaction mixture was quickly transferred to a microwave vial and NaH (60% in mineral oil) (191 mg, 5 mmol) was added. The vial was heated in a microwave oven at 80° C. for 3 h. The reaction mixture was diluted with dichloromethane (15 mL) and subsequently washed with water, sat. NaHCO$_3$ solution and brine. The organic layer was dried over Na$_2$SO$_4$ and the solvent was removed under reduced pressure. The resulting crude product was purified by column chromatography over silica gel (chloroform/MeOH, 0-10% EtOAc) to afford 75 mg (20%) of 3-bromo-N-(5-cyanopyridin-2-yl)-N-(oxetan-3-yl)pyrazolo[1,5-a]pyridine-5-carboxamide (I-26) as a brown solid. $^1$H NMR (400 MHz, CDCl$_3$) δ 8.45 (d, J=7.0 Hz, 1H), 8.16 (s, 1H), 8.02 (t, J=7.90 Hz, 1H), 7.53 (d, J=0.8 Hz, 1H), 7.33-7.31 (m, 1H), 6.90-6.87 (m, 1H), 6.43 (d, J=10.1 Hz, 1H), 4.67-4.62 (m, 1H), 4.52-4.43 (m, 2H), 4.25-4.19 (m, 1H), 4.03-3.98 (m, 1H); ESI-LC/MS (m/z): [M+H]+ 398.13, [(M+2)+H]+ 400.08, RT 1.25 min.

Intermediate I-27

N-(1-(1H-pyrazol-1-yl)propan-2-yl)-3-bromo-N-(5-cyanopyridin-2-yl)pyrazolo[1,5-a]pyridine-5-carboxamide

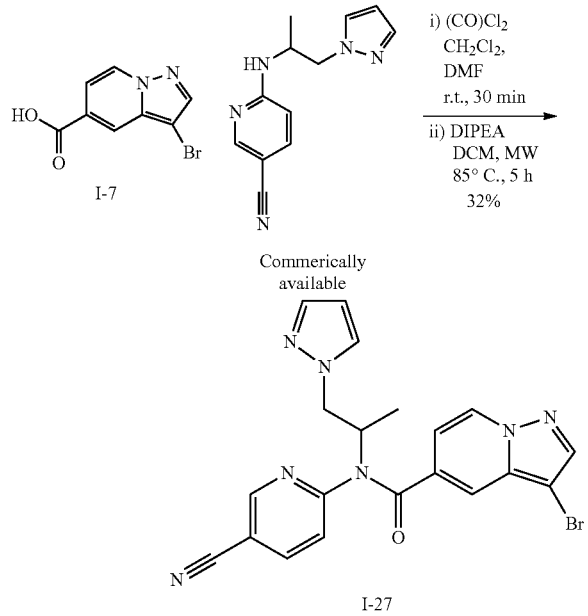

Intermediate I-27 was prepared according to the procedure described for the synthesis of intermediate I-7 by replacing 6-(oxetan-3-ylamino)nicotinonitrile with 6-(1-(1H-pyrazol-1-yl)propan-2-ylamino)nicotinonitrile (283 mg, 1.25 mmol). Microwave irradiation at 85° C. for 5 h. The resulting crude product was purified by preparative TLC to afford 180 mg (32%) of N-(1-(1H-pyrazol-1-yl)propan-2-yl)-3-bromo-N-(5-cyanopyridin-2-yl)pyrazolo[1,5-a]pyridine-5-carboxamide (I-27) as a pale brown highly viscous oil. $^1$H NMR (400 MHz, DMSO-$d_6$) δ 8.84 (d, J=2.2 Hz, 1H), 8.60 (d, J=7.1 Hz, 1H), 8.19 (s, 1H), 8.13 (d, J=2.2 Hz, 1H), 7.75 (d, J=1.8 Hz, 1H), 7.38 (d, J=1.3 Hz, 1H), 7.27 (s, 1H), 7.12 (d, J=8.3 Hz, 1H), 6.62 (d, J=1.7 Hz, 1H), 6.19 (t, J=1.7 Hz, 1H), 5.06-5.10 (m, 1H), 4.82-4.87 (m, 1H), 4.43-4.47 (m, 1H), 1.36 (d, J=7.0 Hz, 3H); ESI-LC/MS (m/z): [M+H]+ 450.2, RT 3.73 min.

Intermediate I-28

(5-cyanopyridin-2-yl)(methyl)carbamic chloride

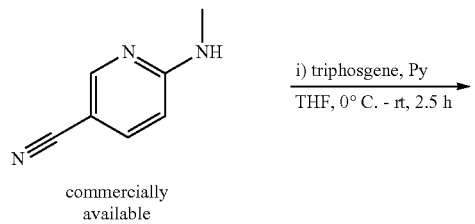

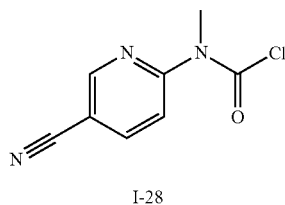

To a solution of bis (trichloromethyl) carbonate (50 mg, 0.17 mmol) in tetrahydrofuran (2.0 mL) was added pyridine (0.04 mL, 0.510 mmol) dropwise under ice-cooling. After stirring under ice-cooling for 30 min, 6-(methylamino)nicotinonitrile (68 mg, 0.510 mmol) was added and the mixture was stirred at room temperature for 2.5 hours. The precipitated solid was filtered off. The filtrate containing (5-cyanopyridin-2-yl)(methyl)carbamic chloride (I-28) was directly used for next step.

Intermediate I-29

3-bromo-N-(5-cyanopyridin-2-yl)-6,7-dihydropyrazolo[1,5-a]pyrazine-5(4H)-carboxamide

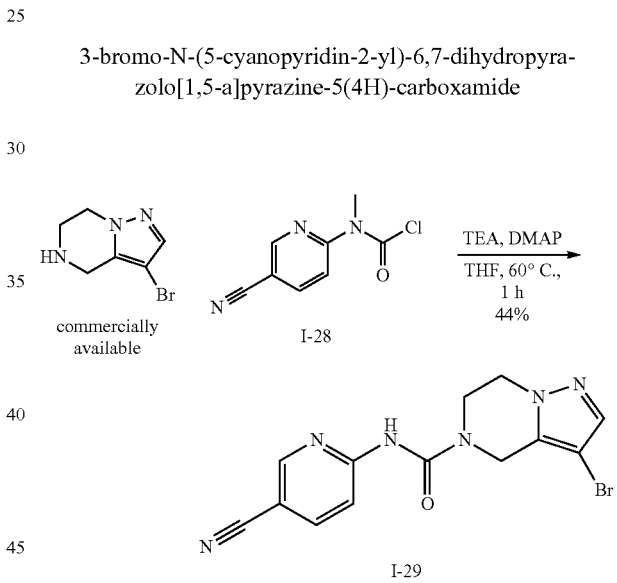

To a solution of (5-cyanopyridin-2-yl)(methyl)carbamic chloride (I-28) in THF (2.0 mL) were added 3-bromo-4,5,6,7-tetrahydropyrazolo[1,5-a]pyrazine (137 mg, 0.680 mmol), triethylamine (0.14 mL, 1.021 mmol) and 4-dimethylaminopyridine (2.0 mg, 0.017 mmol). The mixture was stirred at 60° C. for 1 h. Subsequently, water (25 mL) was added and the mixture was extracted with ethyl acetate. The organic layer was washed with brine, dried over Na$_2$SO$_4$ and the solvent was removed under reduced pressure. The resulting crude product was purified by preparative TLC to afford 60 mg (44%) of 3-bromo-N-(5-cyanopyridin-2-yl)-N-methyl-6,7-dihydropyrazolo-[1,5-a]pyrazine-5(4H)-carboxamide (I-29) as a off white solid. $^1$H NMR (400 MHz, DMSO) δ 8.64 (s, 1H), 8.07 (d, J=8.8 Hz, 1H), 7.60 (s, 1H), 7.18 (d, J=8.4 Hz, 1H), 4.53 (s, 2H), 4.16 (t, J=4.9 Hz, 2H), 3.84 (t, J=4.9 Hz, 2H), 3.26 (s, 3H); ESI-LC/MS (m/z): [M+H]+ 360.91, [(M+2)+H]+ 362.93, RT 1.63 min.

Intermediate I-30

4-(chloromethyl)-N-methylbenzamide

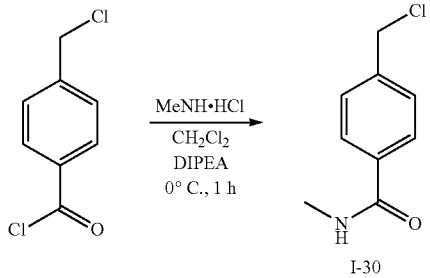

To a solution 4-(chloromethyl)benzoyl chloride (1.0 g, 5.29 mmol) and methylamine.HCl (1.0 g, 5.80 mmol) in dichloromethane (40 mL) was added DIPEA (2.01 g, 15.6 mmol) at 0° C. and stirred for 1 h. The reaction mixture was extracted with water (1×50 mL). The organic layer was extracted with brine (1×50 mL), dried over $Na_2SO_4$ and the solvent was removed under reduced pressure to afford 1.0 g (quantitative) of 4-(chloromethyl)-N-methylbenzamide (I-30) as an off white solid. $^1$H NMR (400 MHz, DMSO) δ 8.46 (d, J=3.5 Hz, 1H), 7.82 (d, J=8.4 Hz, 2H), 7.51 (d, J=8.3 Hz, 2H), 4.80 (s, 2H), 2.78 (d, J=4.4 Hz, 3H); ESI-LC/MS (m/z): [M+H]$^+$ 184.2, RT 2.46 min.

Intermediate I-31

N-methyl-4-((trimethylstannyl)methyl)benzamide

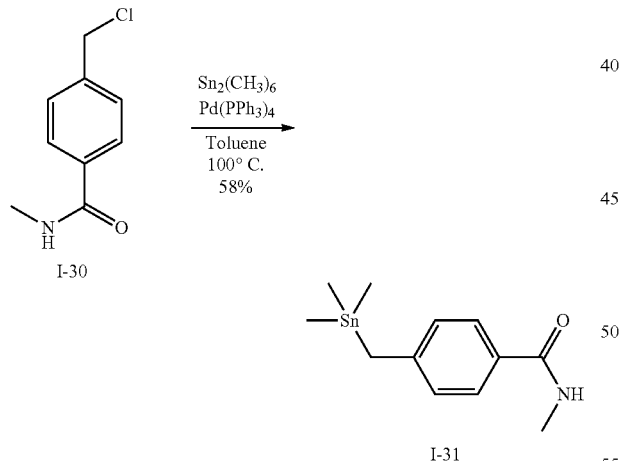

A solution of 4-(chloromethyl)-N-methylbenzamide (I-30, 200 mg, 1.092 mmol) and hexamethylditin (0.26 mL, 1.20 mmol) in toluene (5 mL) was degassed with argon gas for 15 min, followed by addition of Pd(PPh$_3$)$_4$ (63.05 mg, 0.054 mmol). The mixture was heated to reflux for 8 h. The reaction mixture was filtered and the solvent was removed under reduced pressure to afford 200 mg (58%) of N-methyl-4-((trimethylstannyl)methyl)benzamide (I-31) as a brown semi-solid. $^1$H NMR (400 MHz, DMSO-d$_6$) δ 7.58 (d, J=8.0 Hz, 2H), 7.00 (d, J=7.9 Hz, 2H), 2.99 (d, J=5.8 Hz, 2H), 2.35 (s, 2H), 0.04 (s, 9H); MS (m/z): [M+H]$^+$ 314.0.

Intermediate I-32

4-(methylamino)cyclohexanecarbonitrile

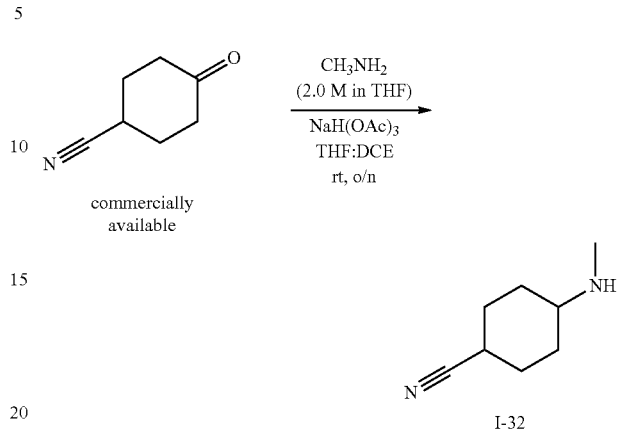

To a solution of 4-cyanocyclohexanone (200 mg, 1.626 mmol) and CH$_3$NH$_2$ (2M in THF) (0.8 mL, 1.626 mmol) in THF:CH$_2$Cl$_2$ (1:1) (4.0 mL) at 0° C. was added NaBH(OAc)$_3$ (689 mg, 3.252 mmol) and the resulting mixture was stirred at rt for 48 h. Subsequently, the solvent was removed under reduced pressure and the residue was dissolved in ethyl acetate, washed with water, brine, dried over Na$_2$SO$_4$ and concentrated to afford 200 mg (89%) of 4-(methylamino)cyclohexanecarbonitrile as a white solid. $^1$H NMR (400 MHz, DMSO-d$_6$) 2.91 & 2.61 (two signals, 1H) 2.23-2.24 (m, 3H) 1.02-1.99 (m, 9H); ELSD/MS (Method 3) (m/z): [M+H]$^+$ 139.06.

Intermediate I-33

3-bromo-N-(4-cyanocyclohexyl)-N-methylpyrazolo[1,5-a]pyridine-5-carboxamide (Example 84)

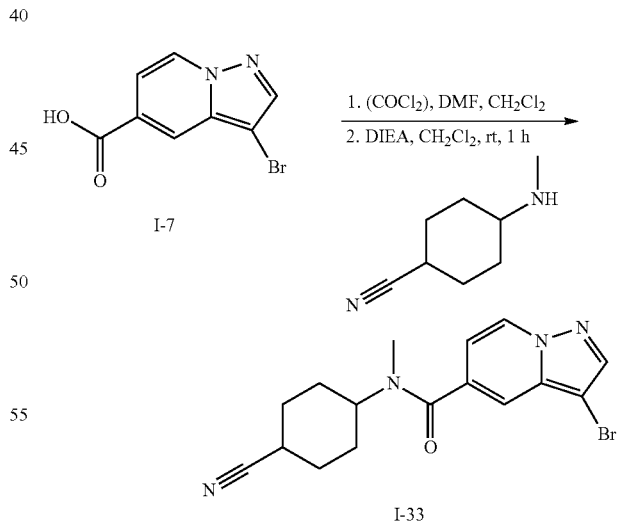

Intermediate I-33 was prepared according to the procedure described for the synthesis of intermediate I-8 by replacing 4-(methylamino)benzonitrile with 4-(methylamino)cyclohexane-carbonitrile. $^1$H NMR (400 MHz, DMSO-d$_6$) 8.77-8.79 (m, 1H) 8.23 (s, 1H) 7.58 (br.s, 1H) 6.95-6.97 (m, 1H) 4.30 & 3.50 (two signals, 1H) 2.76-3.19 (m, 4H) 1.48-1.98 (m, 8H); ESI-LC/MS (Method 1) (m/z): [M+H]$^+$ 361 & [M+2H]$^+$ 363.

Intermediate I-34

2-amino-5-bromonicotinonitrile

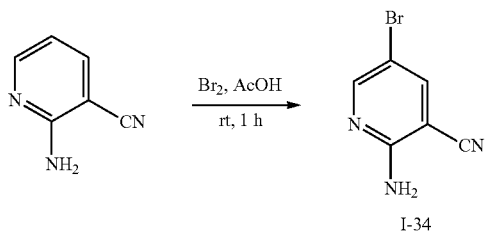

To a solution of 2-aminonicotinonitrile (1.5 g, 12.5 mmol, 1.0 eq.) in AcOH (30 mL) was added $Na_2CO_3$ (1.3 g, 12.5 mmol). Bromine (0.7 ml, 13.8 mmol) was added drop wise to the resulting suspension and reaction mixture was stirred at rt for 1 h. The orange precipitate formed was collected by filtration, washed with water and dried to afford 2.0 g (80%) of I-34 as a yellow solid. $^1$H NMR (400 MHz, DMSO) δ 8.27 (s, 1H), 8.15 (s, 1H), 7.12 (brs, 2H).

Intermediate I-35

2-amino-5-bromonicotinonitrile

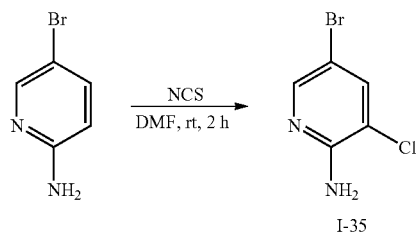

To a solution of 2-amino-5-bromopyridine (3 g, 17.3 mmol, 1.0 eq.) dissolved in DMF (10 ml) was added NCS (2.54 g, 19.07 mmol, 1.1 eq.) and the resulting mixture was stirred at rt for 2 h. Subsequently, 5N NaOH was used to adjust the pH of the reaction mixture to 7-8 followed by extraction with ethyl acetate (2×40 mL). The combined organic layers were washed with water, brine, dried over anhydrous $Na_2SO_4$ solution and concentrated under reduced pressure to afford 2.0 g (55%) of I-35 as a yellow solid. $^1$H NMR (400 MHz, DMSO) δ 7.98 (s, 1H), 7.84 (s, 1H), 6.52 (brs, 2H); ESI-LC/MS (m/z): [M+H]$^+$ 206.96, [(M+2)+H]$^+$ 208.91, RT 1.59 min.

Intermediate I-36

2-amino-5-bromo-N,N-dimethylnicotinamide

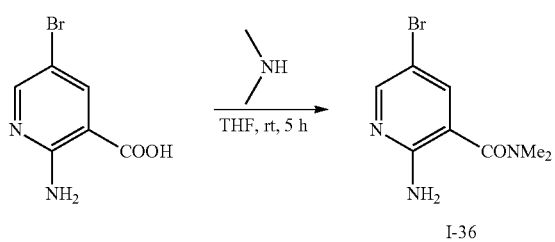

To a stirred solution of 2-amino-5-bromo-3-carboxypyridine (1.0 g, 4.60 mmol, 1.0 eq.), dimethylamine (0.227 g, 5.06 mmol, 1.1 eq.) and TEA (1.2 ml, 9.20 mmol, 2.0 eq.) dissolved in THF (20 mL) was added diethyl cyanophosphate (0.8 ml, 5.06 mmol, 1.1 eq.) drop wise. Stirring at rt was continued for 4 h. The reaction mixture was partitioned between water and ethyl acetate (2×30 mL). The combined organic layers were washed with water, brine, dried over anhydrous $Na_2SO_4$ solution and concentrated under reduced pressure. The crude compound was purified by column chromatography over silica gel (100-200 mesh) using a solvent gradient of 4% MeOH in DCM as eluant to afford 500 mg (44%) of I-36 as a off-white solid. $^1$H NMR (400 MHz, DMSO) δ 8.05 (s, 1H), 7.54 (s, 1H), 6.20 (brs, 2H), 2.90 (brs, 6H); ESI-LC/MS (m/z): [M+H]$^+$ 244.01, [(M+2)+H]$^+$ 246.01, RT 0.84 min.

Intermediate I-37

3-fluoro-5-(4,4,5,5-tetramethyl-1,3,2-dioxaborolan-2-yl)pyridin-2-amine

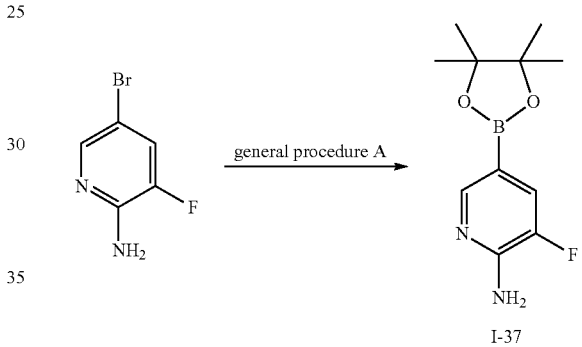

Intermediate I-37 was prepared according to the general boronic ester synthesis procedure A by utilizing 5-bromo-3-fluoropyridin-2-amine (reaction time: 16 h, temperature: 85° C.). ESI-LC/MS (m/z): [M+H]$^+$ 239.1, RT 5.60 min.

Intermediate I-38

2,6-dimethyl-4-(4,4,5,5-tetramethyl-1,3,2-dioxaborolan-2-yl)aniline

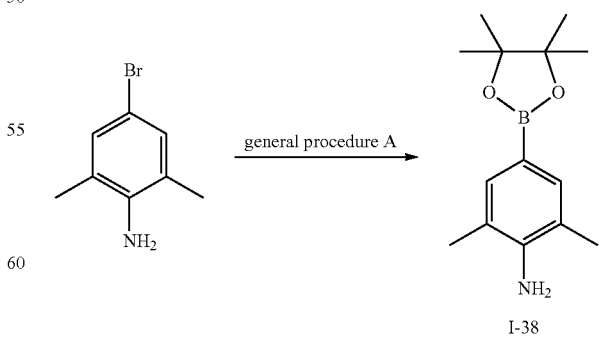

Intermediate I-38 was prepared according to the general boronic ester synthesis procedure A by utilizing 4-bromo-2,6-dimethylaniline (reaction time: 16 h, temperature: 85° C.). ESI-LC/MS (m/z): [M+H]$^+$ 248.1, RT 6.67 min.

Intermediate I-39

3-methyl-5-(4,4,5,5-tetramethyl-1,3,2-dioxaborolan-2-yl)pyridin-2-amine

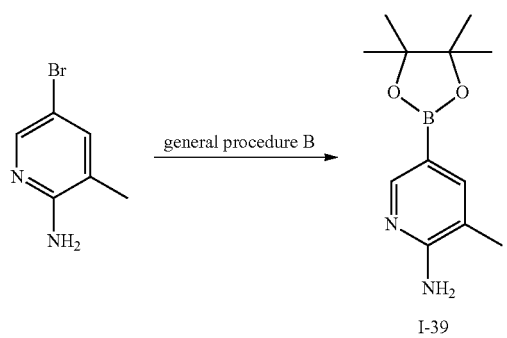

Intermediate I-39 was prepared according to the general boronic ester synthesis procedure B by utilizing 2-amino-3-methyl-5-bromopyridine (reaction time: 16 h, temperature: 90° C.). ESI-LC/MS (m/z): [M+H]$^+$ 235.1, RT 1.26 min.

Intermediate I-40

5-(4,4,5,5-tetramethyl-1,3,2-dioxaborolan-2-yl)pyrimidin-2-amine

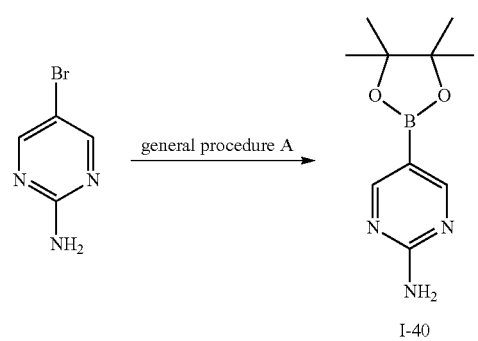

Intermediate I-40 was prepared according to the general boronic ester synthesis procedure A by utilizing 5-bromopyrimidin-2-amine (reaction time: 5 h, temperature: 100° C.). $^1$H NMR (400 MHz, DMSO) δ 8.59 (s, 2H), 5.43 (brs, 2H), 1.32 (s, 12H);

Intermediate I-41

5-(4,4,5,5-tetramethyl-1,3,2-dioxaborolan-2-yl)-3-(trifluoromethyl)pyridin-2-amine

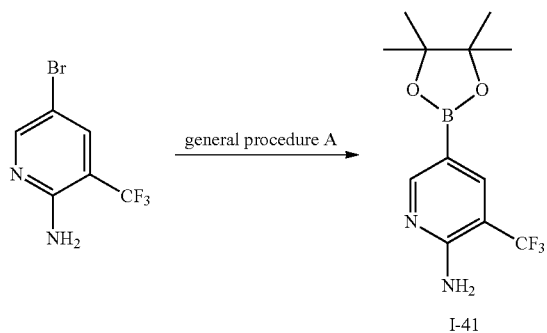

Intermediate I-41 was prepared according to the general boronic ester synthesis procedure A by utilizing 5-bromo-3-(trifluoromethyl)pyridin-2-amine (reaction time: 5 h, temperature: 100° C.). $^1$H NMR (400 MHz, DMSO) δ 8.37 (s, 1H), 7.80 (s, 1H), 6.89 (s, 2H), 1.27 (s, 12H); ESI-LC/MS (m/z): [M+H]$^+$ 289.1, RT 4.83 min.

Intermediate I-42

2-amino-5-(4,4,5,5-tetramethyl-1,3,2-dioxaborolan-2-yl)nicotinonitrile

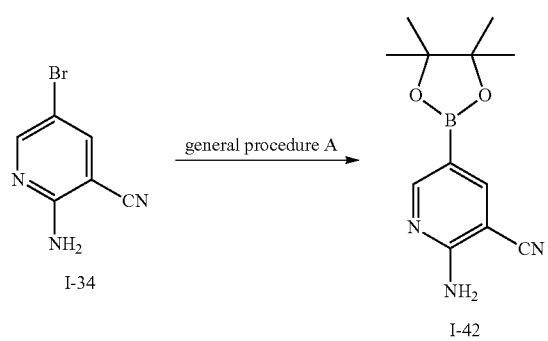

Intermediate I-42 was prepared according to the general boronic ester synthesis procedure A by utilizing 2-amino-5-bromonicotinonitrile (I-34) (reaction time: 5 h, temperature: 100° C.). $^1$H NMR (400 MHz, DMSO) δ 8.57 (s, 1H), 8.08 (s, 1H), 5.42 (s, 2H), 1.27 (s, 12H); ESI-LC/MS (m/z): [M+H]$^+$ 246.1, RT 5.05 min.

Intermediate I-43

3-chloro-5-(4,4,5,5-tetramethyl-1,3,2-dioxaborolan-2-yl)pyridin-2-amine

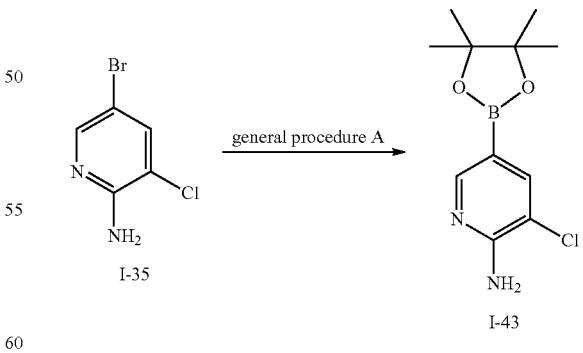

Intermediate I-43 was prepared according to the general boronic ester synthesis procedure A by utilizing 5-bromo-3-chloropyridin-2-amine (I-35) (reaction time: 16 h, temperature: 100° C.). $^1$H NMR (400 MHz, DMSO) δ 8.32 (s, 1H), 7.84 (s, 1H), 5.12 (s, 2H), 1.37 (s, 12H); ESI-LC/MS (m/z): [M+H]$^+$ 256.5, RT 1.67 min.

Intermediate I-44

2-amino-N,N-dimethyl-5-(4,4,5,5-tetramethyl-1,3,2-dioxaborolan-2-yl)nicotinamide

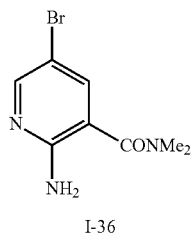

I-36

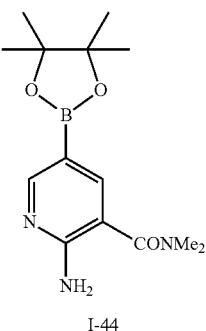

I-44

Intermediate I-44 was prepared according to the general boronic ester synthesis procedure A by utilizing 2-amino-5-bromo-N,N-dimethylnicotinamide (I-36) (reaction time: 16 h, temperature: 100° C.). ESI-LC/MS (m/z): [M-boronicacid]$^+$ 210.1, RT 0.42 min.

Intermediate I-45

3-methoxy-5-(4,4,5,5-tetramethyl-1,3,2-dioxaborolan-2-yl)pyridin-2-amine

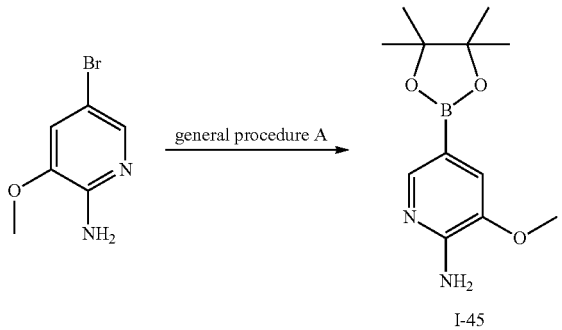

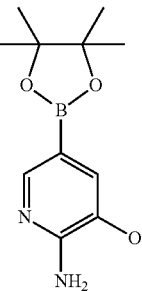

I-45

Intermediate I-45 was prepared according to the general boronic ester synthesis procedure A by utilizing 2-amino-3-methoxy-5-bromopyridine (reaction time: 5 h, temperature: 100° C.). $^1$H NMR (400 MHz, DMSO) δ 8.03 (s, 1H), 7.19 (s, 1H), 5.17 (s, 2H), 3.84 (s, 3H), 1.27 (s, 12H).

Intermediate I-46

Methyl 3-(4,4,5,5-tetramethyl-1,3,2-dioxaborolan-2-yl)pyrazolo[1,5-a]pyridine-5-carboxylate

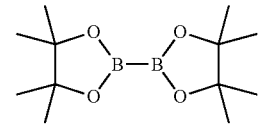

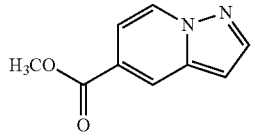

I-5

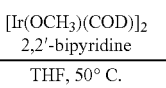

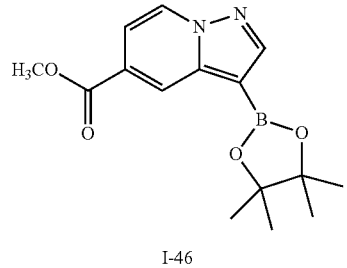

I-46

A solution of pyrazolopyridine (100 mg, 0.568 mmol, 1.0 equiv.) and bis(pinacolato)diboron (158.75 mg, 0.625 mmol, 1.1 equiv.) in 1 mL THF was treated with 2,2'-bipyridine (0.6 mg, 0.00224 mmol, 0.04 equiv.) and (1,5-cyclooctadiene)(methoxy)iridium(I) dimer (0.75 mg, 0.00113 mmol, 0.02 equiv.) at rt. The flask was charged with nitrogen gas, and the resulting mixture was allowed to stir at 50° C. for three hours. The reaction was concentrated and the residue was purified by silica gel chromatography, eluting with CH$_2$Cl$_2$/EtOAc to give I-46. $^1$H NMR (400 MHz, MeOD) δ 8.68 (dd, J=0.6, 7.2, 1H), 8.60-8.57 (m, 1H), 8.24 (s, 1H), 7.46 (dd, J=1.9, 7.3, 1H), 3.98 (s, 3H), 1.39 (s, 12H).

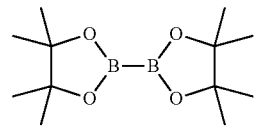

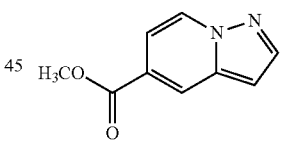

I-5

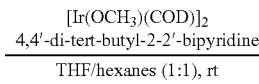

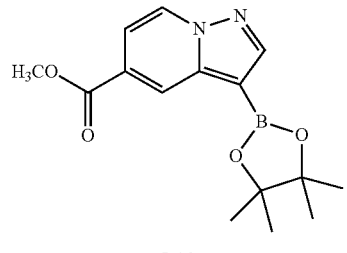

I-46

Alternatively, a solution of pyrazolopyridine (750 mg, 4.26 mmol, 1.0 equiv.) and bis(pinacolato)diboron (1.19 g, 4.69 mmol, 1.1 equiv.) in 10 mL 1:1 THF/hexanes was treated with (1,5-cyclooctadiene)(methoxy)iridium(I) dimer (84 mg, 0.128 mmol, 0.03 equiv.) and 4,4'-di-tert-butyl-2,2'-bipyridine (68 mg, 0.256 mmol, 0.06 equiv.) at rt. The flask was charged with nitrogen gas, and the resulting mixture was allowed to stir at rt overnight. The reaction was concentrated and the residue was purified by silica gel chromatography, eluting with hexanes/EtOAc to give intermediate I-46.

Intermediate I-47

3-(4,4,5,5-tetramethyl-1,3,2-dioxaborolan-2-yl)pyrazolo[1,5-a]pyridine-5-carboxylic acid

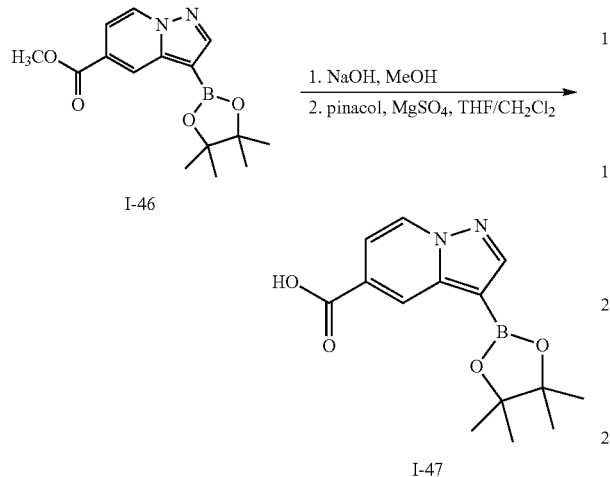

A solution of ester (400 mg, 1.32 mmol, 1.0 equiv.) in 3 mL MeOH was treated with 1 N aq. NaOH (3 mL, 3.0 mmol, 2.26 equiv.) at rt, and then allowed to stir at rt for 30 minutes. The reaction mixture was then neutralized with 3 mL 1 N aq. HCl, and the resulting white solid was isolated by filtration. The filtrate was extracted with EtOAc and the organic extracts were concentrated. The solid products were combined, and then diluted with 22 mL 10:1 CH$_2$Cl$_2$/THF before pinacol (157 mg, 1.32 mmol, 1.0 equiv.) and 1 g MgSO4 were added. The resulting mixture was allowed to stir at rt for 20 minutes, filtered, and concentrated under reduced pressure. The resulting white solid was triturated with hexanes to give the acid I-47, which was taken on without further purification.

Intermediate I-48

Methyl 3-(5-(trifluoromethyl)pyridin-2-yl)pyrazolo[1,5-a]pyridine-5-carboxylate

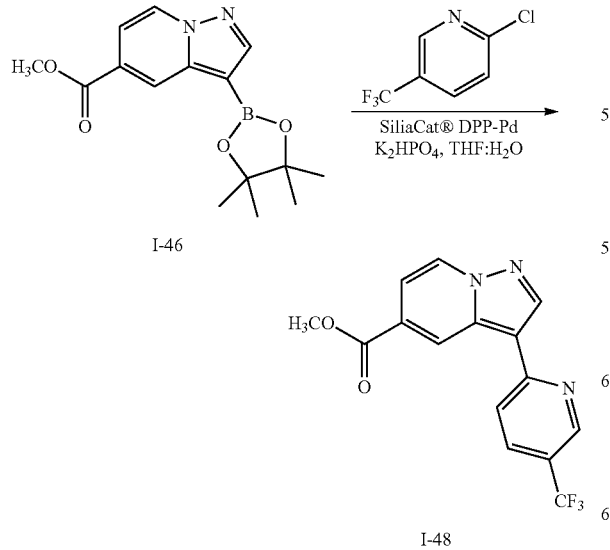

A mixture of 2-chloro-5-(trifluoromethyl)pyridine (1.5 equiv.), aryl boronic ester (1.0 equiv.), K2HPO4 (3.5 equiv.), and SiliaCat® DPP-Pd or Pd(dppf)Cl2 (0.05-0.15 equiv.) in THF/water was allowed to heat at 150° C. in a microwave reactor for 40-60 minutes. After cooling to room temperature, the solvent was removed under reduced pressure. The crude residue was purified by mass-triggered HPLC or silica gel chromatography to provide intermediate I-48.

Intermediate I-49

3-(5-(trifluoromethyl)pyridin-2-yl)pyrazolo[1,5-a]pyridine-5-carboxylic acid

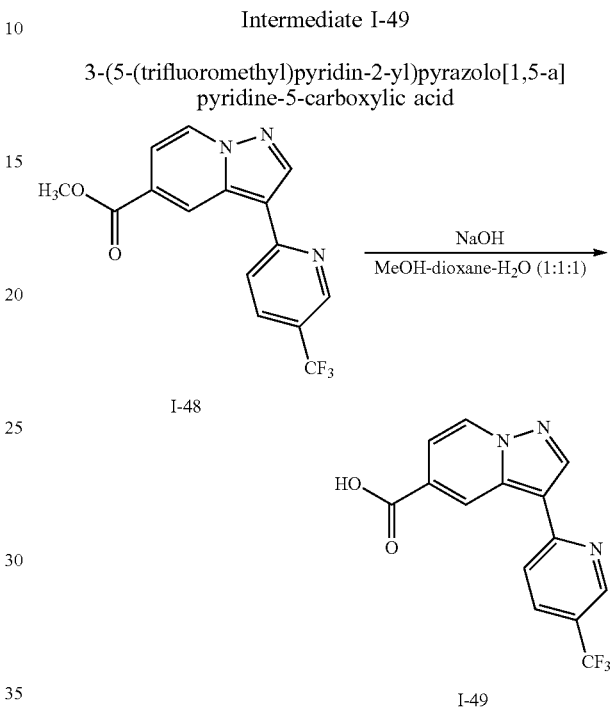

Intermediate I-49 was prepared according to the procedure described for the synthesis of intermediate I-7.

Intermediate I-50

N-(4-cyanophenyl)-N-methyl-3-(4,4,5,5-tetramethyl-1,3,2-dioxaborolan-2-yl)pyrazolo[1,5-a]pyridine-5-carboxamide

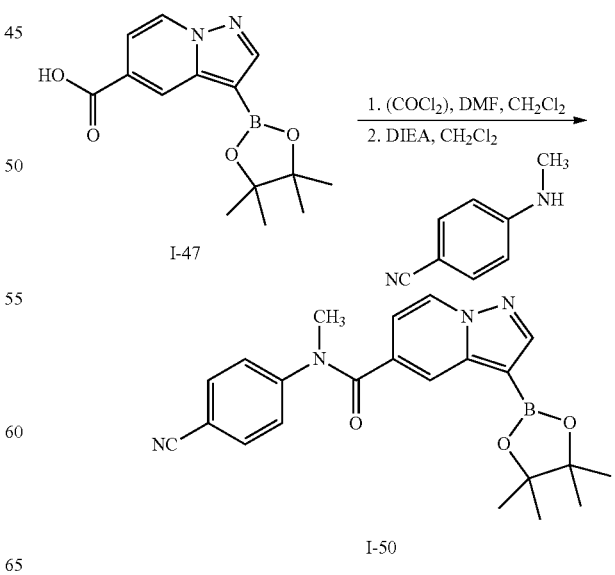

Intermediate I-50 was prepared according to the procedure described for the synthesis of intermediate I-8.

Intermediate I-51 & I-52

(3-(4-(trifluoromethyl)phenyl)pyrazolo[1,5-a]pyridin-5-yl)methanol

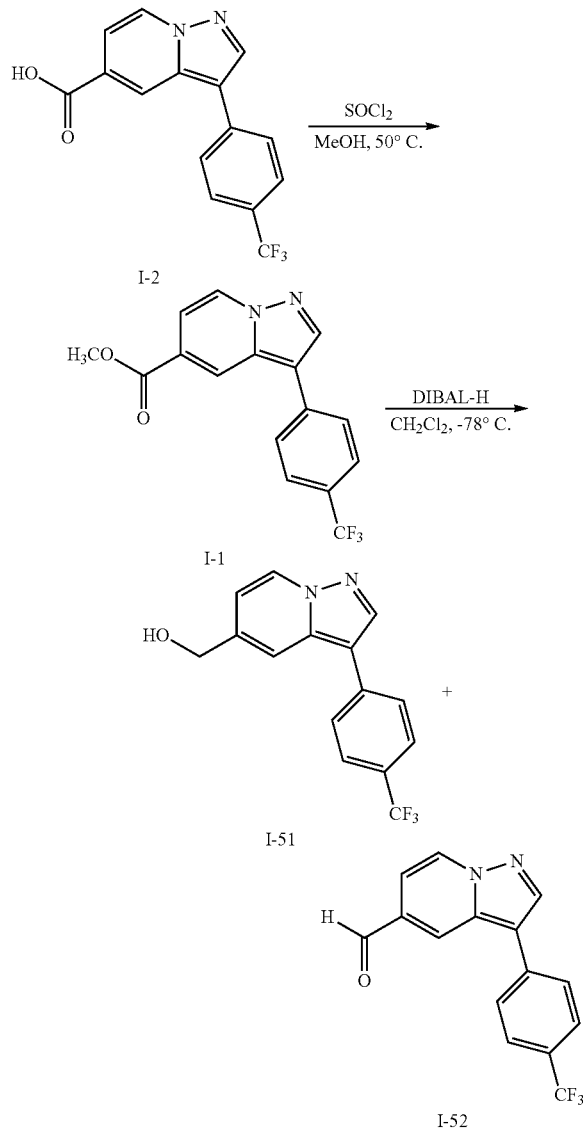

A solution of acid (450 mg, 1.47 mmol, 1.0 equiv.) in 8 mL MeOH was treated with SOCl₂ (300 μL, 4.14 mmol, 2.8 equiv.) dropwise and the resulting solution was allowed to heat at 50° C. overnight. The solution was diluted with 10 mL CH₂Cl₂, then washed with saturated aq. NaHCO₃, dried with Na₂SO₄, filtered, and concentrated under reduced pressure to give the desired ester (I-1), which was taken on without further purification. $^1$H NMR (400 MHz, CDCl₃,): 8.52 (m, 2H), 8.23 (s, 1H), 7.72 (s, 4H), 7.40 (dd, J=1.59, 7.50 Hz, 1H), 3.96 (s, 3H).

A solution of the ester (100 mg, 0.31 mmol, 1.0 equiv.) in 3 mL CH₂Cl₂ was allowed to cool to −78° C., and then a solution of DIBAL-H (1.0 M in toluene, 1.24 mL, 1.24 mmol, 4.0 equiv.) was added dropwise. The resulting solution was allowed to stir at −78° C. for 90-120 minutes and then was quenched with Na₂SO₄.10H₂O. The resulting mixture was allowed to stir at rt for 30 minutes, then was filtered and concentrated. The residue was purified by silica gel chromatography, eluting with hexanes/EtOAc to give the desired alcohol (I-51), as well as a small amount of the corresponding aldehyde (I-52).

Intermediate I-53

5-(bromomethyl)-3-(4-(trifluoromethyl)phenyl)pyrazolo[1,5-a]pyridine

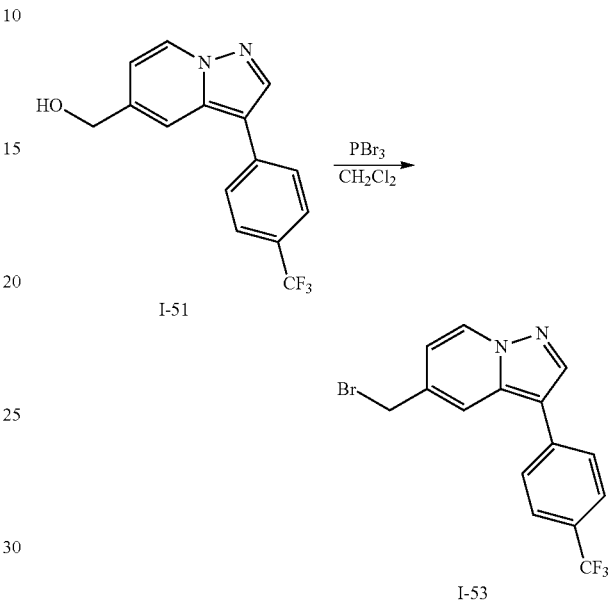

A solution of alcohol (160 mg, 0.546 mmol, 1.0 equiv.) in 3 mL CH₂Cl₂ was treated with PBr₃ (27 μL, 0.273 mmol, 0.5 equiv.) dropwise at rt, then was allowed to stir at rt for two hours. The solution was diluted with 20 mL CH₂Cl₂, then washed with saturated aq. NaHCO₃, dried with Na₂SO₄, filtered, and concentrated under reduced pressure to give the desired bromide (I-53), which was taken on without further purification.

Intermediate I-54

3-bromo-N-(4-fluorophenyl)-N-methylpyrazolo[1,5-a]pyridine-5-carboxamide

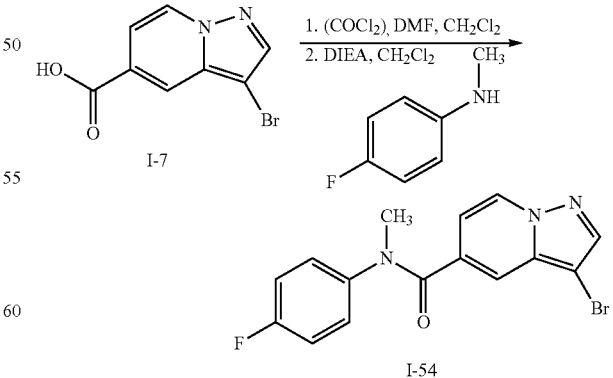

Intermediate I-54 was prepared according to the procedure described for the synthesis of intermediate I-8 by replacing 4-(methylamino)benzonitrile with 4-fluoro-N-methylaniline.

Intermediate I-55

N-(5-cyanopyridin-2-yl)-N-methyl-3-(4,4,5,5-tetramethyl-1,3,2-dioxaborolan-2-yl)pyrazolo[1,5-a]pyridine-5-carboxamide

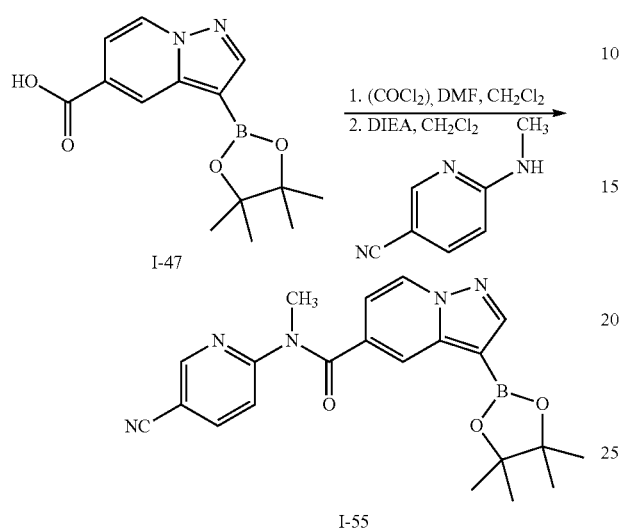

Intermediate I-55 was prepared according to the procedure described for the synthesis of intermediate I-8 by replacing 4-(methylamino)benzonitrile with 6-(methylamino)nicotinonitrile.

Intermediate I-56 tert-butyl(3-(4-(trifluoromethyl)phenyl)pyrazolo[1,5-a]pyridin-5-yl)carbamate

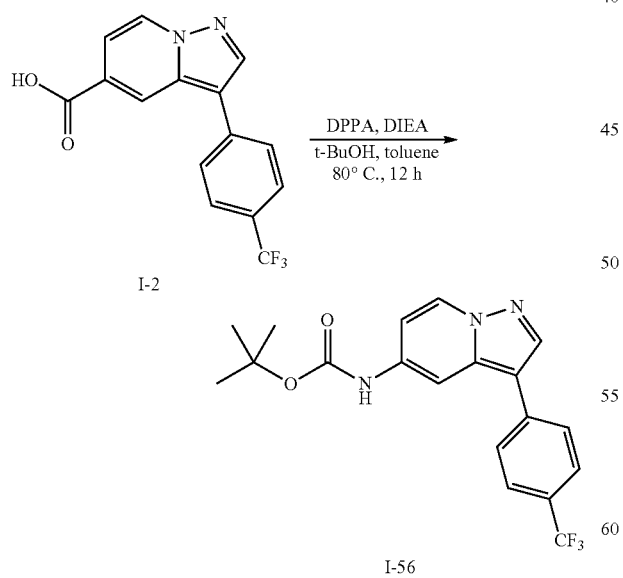

A mixture of pyrazolopyridine (153 mg, 0.50 mmol), DPPA (0.129 mL, 0.60 mmol), t-BuOH (0.5 mL) and toluene (2.0 mL) was heated to 80° C. overnight. After cooling to room temperature, water was added to the reaction mixture and extracted with dichloromethane. The combined organic layers were washed with brine and dried over anhydrous $Na_2SO_4$. The solvent was removed and the product was purified by silica gel chromatography, eluting with ethyl acetate and hexanes. $^1H$ NMR (400 MHz, DMSO) δ 9.88 (s, 1H), 8.67 (d, J=7.6, 1 H), 8.40 (d, J=7.8, 1 H), 8.30-8.07 (m, 1H), 7.91-7.64 (m, 4H), 7.00 (dd, J=2.1, 7.5, 1 H), 1.59-1.41 (m, 9H).

Intermediate I-57 tert-butyl methyl(3-(4-(trifluoromethyl)phenyl)pyrazolo[1,5-a]pyridin-5-yl)carbamate

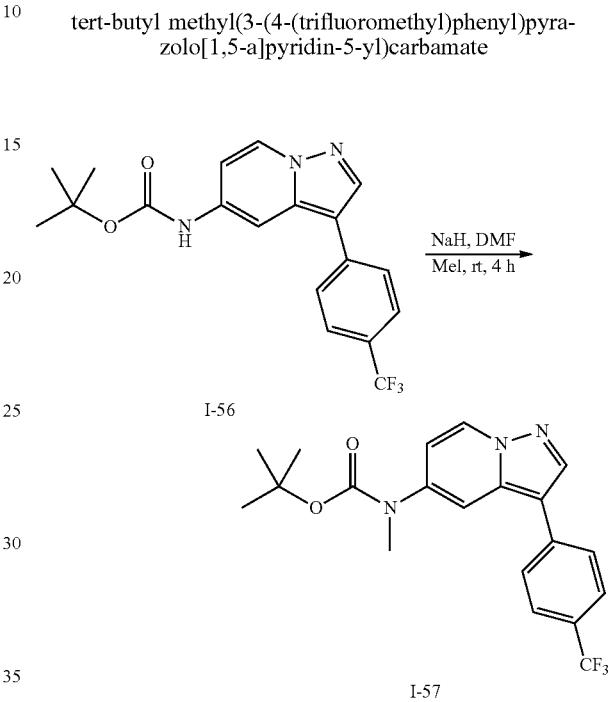

NaH (7 mg, 0.15 mmol) was added to a solution of pyrazolopyridine in DMF (2.0 mL). The reaction stirred at room temperature for 15 minutes. Methyl iodide was added (0.018 mL, 0.12 mmol) and the reaction stirred for 4 hours at room temperature. The reaction was quenched with water and extracted with ethyl acetate. The combined organic layers were washed with brine and dried over anhydrous $Na_2SO_4$. The solvent was removed and the material was purified by silica gel chromatography, eluting with ethyl acetate and hexanes. $^1H$ NMR (400 MHz, MeOD) δ 8.44 (d, J=7.5, 1 H), 8.20 (s, 1H), 7.77-7.59 (m, 5H), 6.94 (d, J=5.3, 1H), 3.26 (s, 3H), 1.41 (s, 9H).

Intermediate I-58

N-methyl-3-(4-(trifluoromethyl)phenyl)pyrazolo[1,5-a]pyridin-5-amine

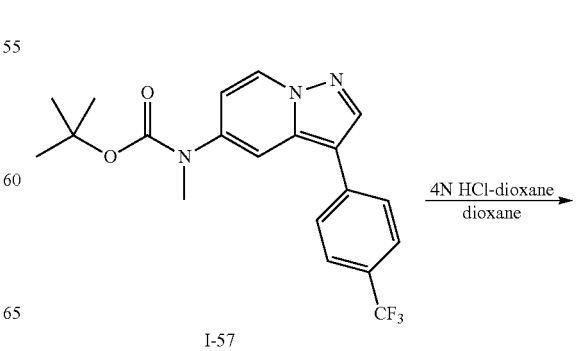

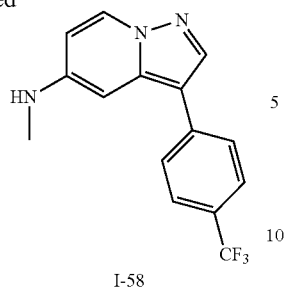

I-58

To a solution of pyrazolopyridine (30 mg, 0.80 mmol) in dioxane (1.0 mL) was added 4N HCl in dioxane and the reaction stirred at room temperature for 2 hours. The resultant HCl salt was filtered and dried to give the desired product. No further purification was necessary.

Intermediate I-59 tert-butyl 4-fluorobenzyl(3-(4-(trifluoromethyl)phenyl)pyrazolo[1,5-a]pyridin-5-yl)carbamate

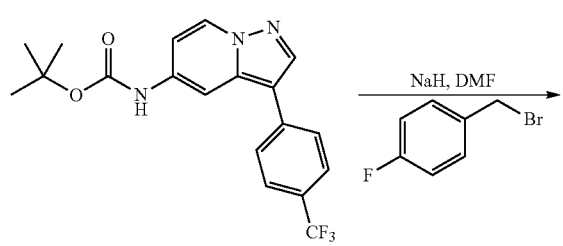

Intermediate I-59 was prepared according to the procedure described for the synthesis of intermediate I-57 by replacing methyl iodide with 4-fluorobenzyl bromide.

Intermediate I-60 tert-butyl((tetrahydro-2H-pyran-4-yl)methyl)(3-(4-(trifluoromethyl)phenyl)pyrazolo[1,5-a]pyridin-5-yl)carbamate

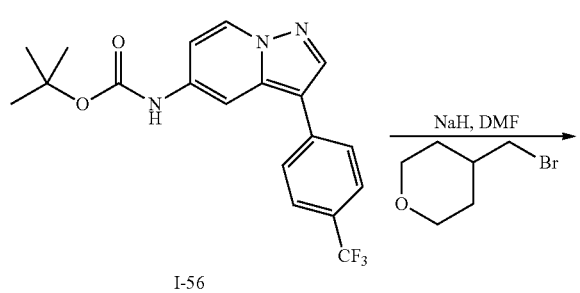

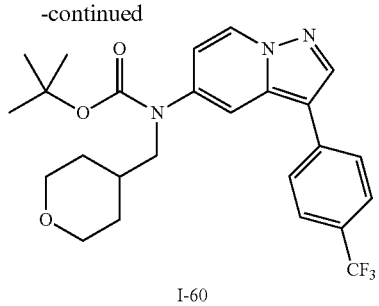

I-60

Intermediate I-60 was prepared according to the procedure described for the synthesis of intermediate I-25 by replacing methyl iodide with 4-(bromomethyl)tetrahydro-2H-pyran.

Intermediate I-61

N-((tetrahydro-2H-pyran-4-yl)methyl)-3-(4-(trifluoromethyl)phenyl)pyrazolo[1,5-a]pyridin-5-amine

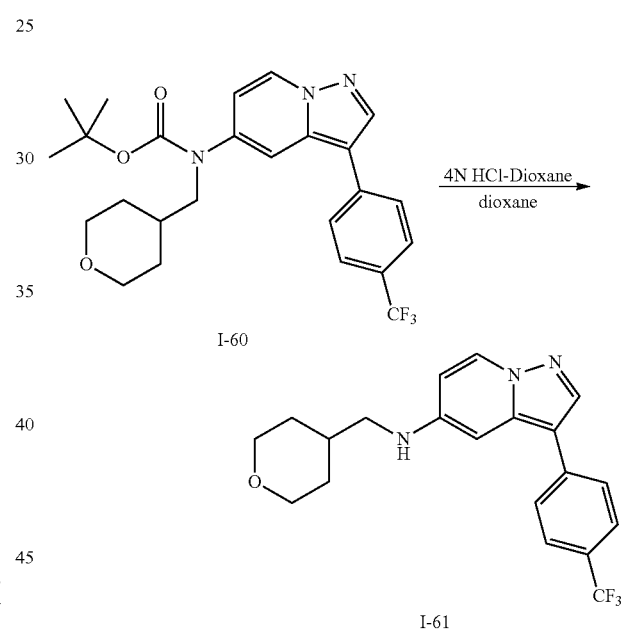

Intermediate I-29 was prepared according to the procedure described for the synthesis of intermediate I-57.

Intermediate I-62 tert-butyl(3-bromopyrazolo[1,5-a]pyridin-5-yl)carbamate

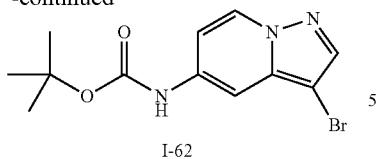

I-62

To a mixture of pyrazolopyridine (240 mg, 1.00 mmol), diisopropylethylamine (0.160 mL, 1.00 mmol), t-BuOH (1.00 mL) and toluene (4.00 mL) was added dry 4 angstrom molecular sieves. The reaction stirred at room temperature for 30 minutes. DPPA (0.260 mL, 1.20 mmol) was added and the reaction was heated to 80° C. overnight. After cooling to room temperature, the material was purified by silica gel chromatography, eluting with ethyl acetate and hexanes.

Intermediate I-63 tert-butyl(3-bromopyrazolo[1,5-a]pyridin-5-yl)(methyl)carbamate

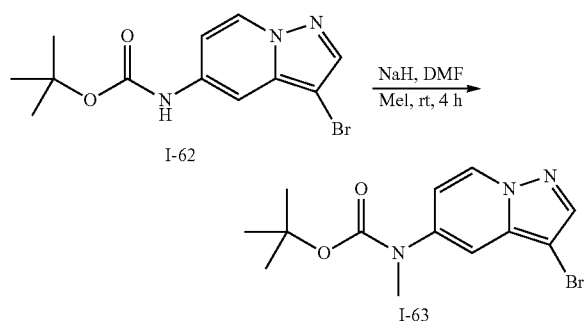

Intermediate I-63 was prepared according to the procedure described for the synthesis of intermediate I-57.

Intermediate I-64

3-bromo-N-methylpyrazolo[1,5-a]pyridin-5-amine

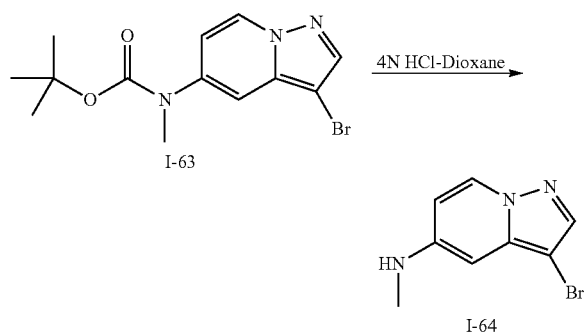

Intermediate I-64 was prepared according to the procedure described for the synthesis of intermediate I-58.

Intermediate I-65

N-(3-bromopyrazolo[1,5-a]pyridin-5-yl)-4-fluoro-N-methylbenzamide

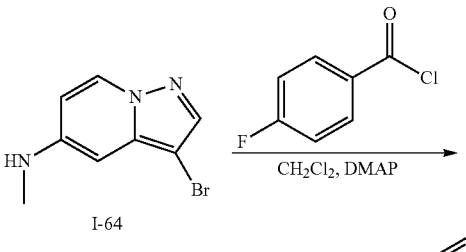

To a solution of pyrazolopyridine (22.6 mg, 0.10 mmol) in dichloromethane (2.0 mL) was added triethylamine (0.042 mL, 0.30 mmol) and a catalytic amount of DMAP. The reaction was cooled to 0° C. and 4-fluorobenzoyl chloride was added. The reaction warmed to room temperature and stirred for 2 hours. The reaction was diluted with water and extracted with dichloromethane. The organic extracts were washed with brine and dried over anhydrous Na₂SO₄. The solvent was removed and the material was purified by silica gel chromatography, eluting with ethyl acetate and hexanes.

Intermediate I-66

3-bromo-N-methyl-N-(5-(methylsulfonyl)pyridin-2-yl)pyrazolo[1,5-a]pyridine-5-carboxamide

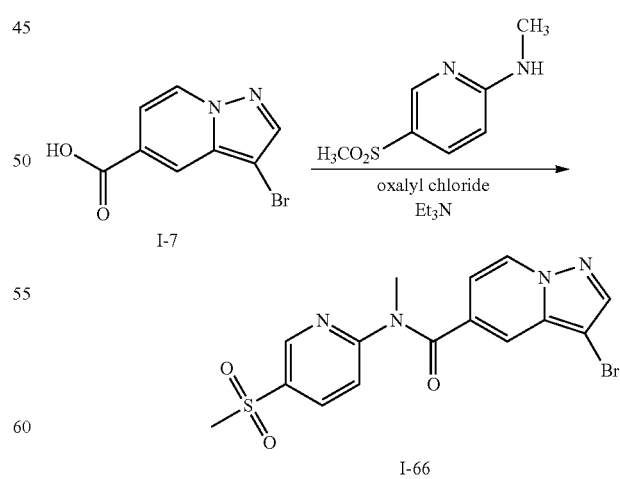

Intermediate I-66 was prepared according to the procedure described for the synthesis of intermediate I-8 by replacing 4-(methylamino)benzonitrile with N-methyl-5-(methylsulfonyl)pyridin-2-amine.

Intermediate I-67

4-(1-(3-Bromopyrazolo[1,5-a]pyridin-5-yl)ethyl)-7-fluoro-2H-benzo[b][1,4]oxazin-3(4H)-one

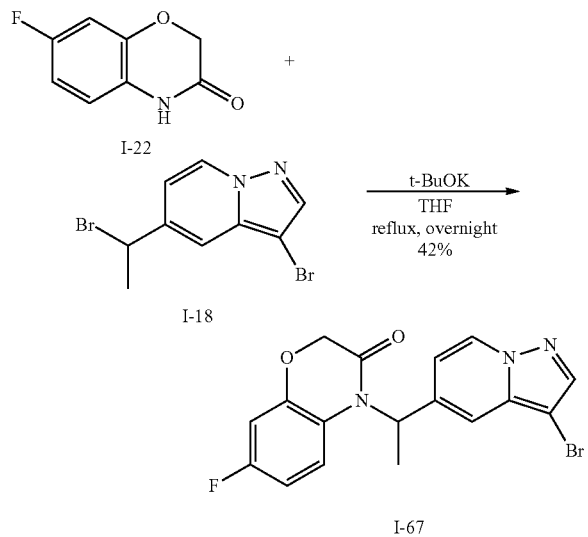

Potassium tert-butoxide (75 mg, 0.666 mmol) was added to a stirred solution of 7-fluoro-2H-benzo[b][1,4]oxazin-3(4H)-one (I-22, 100 mg, 0.606 mmol) in dry THF at rt. After 5 min, a solution of 3-bromo-5-(1-bromoethyl) pyrazolo[1,5-a]pyridine (I-18, 202 mg, 0.666 mmol) in dry THF was added drop wise to reaction mixture at rt. The resulting reaction mixture was heated to reflux for overnight and subsequently cooled to room temperature. The reaction mixture was diluted with water (10 mL) and extracted with ethyl acetate (2×10 mL). The combined organic layers were dried over $Na_2SO_4$ and concentrated under reduced pressure. The crude compound was purified by column chromatography over silica gel (chloroform/EtOAc, 0-4% EtOAc) to afford 110 mg (42%) of 4-(1-(3-bromopyrazolo[1,5-a]pyridin-5-yl)ethyl)-7-fluoro-2H-benzo[b][1,4]oxazin-3(4H)-one I-67 as a yellow solid. ESI-LC/MS (Method 1) (m/z): [M+H]+ 389.9, [(M+2)+H]+ 391.9.

Intermediate I-68

6-(Ethylamino)nicotinonitrile

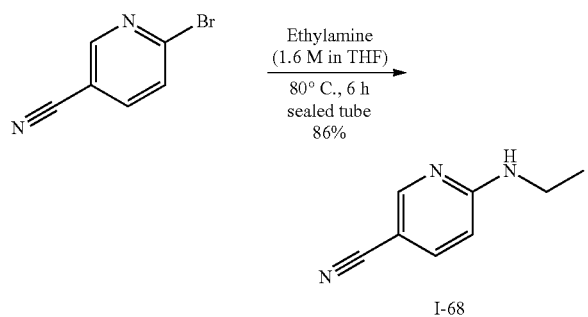

A solution of 2-bromo-5-cyanopyridine (75.0 g, 409.8 mmol), ethylamine solution (2 M in THF) (300 mL) was stirred at 100° C. for 6 h in sealed tube. Then the solvent was distilled off and the residue was partitioned between dichloromethane (1000 mL) and water (2×500 mL). The separated organic layer was washed with brine, dried over anhyd. $Na_2SO_4$ and concentrated in vacuo. The crude compound was passed through silica (100-200 mesh) column using a solvent gradient of 15% ethyl acetate in pet-ether as eluant to afford 52.0 g (86%) of 6-(ethylamino)nicotinonitrile I-68 as a off white crystalline solid. $^1$H NMR (DMSO-$d_6$) δ 8.37 (s, 1H), 7.64 (d, J=8.04 Hz, 1H), 7.54 (brs, 1H), 6.51 (d, J=8.8 Hz, 1H), 3.30-3.25 (m, 2H), 1.13 (t, J=6.8 Hz, 3H). ESI/LC-MS: m/z 148.14 (M+H), r.t.=0.85 [Waters Acquity UPLC with 3100 SQD; Waters Acquity BEH C18, 1.7 μm, 2.1×50 mm column; gradient of 97:3 $H_2O$ (0.05% TFA):$CH_3CN$ (0.05% TFA) to 2:98 $H_2O$ (0.05% TFA):$CH_3CN$ (0.05% TFA) for 4 minutes with 0.6 mL/min flow rate].

Intermediate I-69

3-Bromo-N-(5-cyanopyridin-2-yl)-N-ethylpyrazolo[1,5-a]pyridine-5-carboxamide

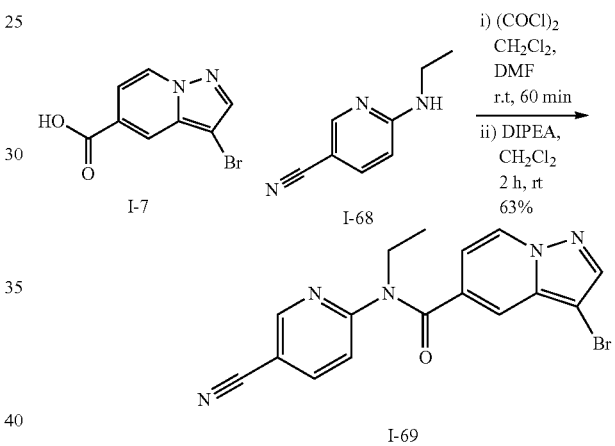

To a solution of 3-bromopyrazolo[1,5-a]pyridine-5-carboxylic acid I-7 (25.0 g, 103.71 mmol) in dichloromethane (500 mL) was added oxalyl chloride (25 mL, 290 mmol) followed by catalytic amount dimethylformamide (0.1 mL) at rt and stirred for 60 min. The resultant volatiles were distilled-off under reduced pressure. The resulting crude acid chloride was dissolved in dichloromethane (500 mL), and to the resulting solution were added a solution of 6-(ethylamino)nicotinonitrile I-68 (15.3 g, 103.71 mmol) in dichloromethane (100 mL) followed by DIPEA (50 mL, 286.4 mmol). The reaction mixture was stirred for 2 h at rt and diluted with dichloromethane (500 mL). The organic layer was washed with water, brine, dried over anhydrous $Na_2SO_4$ and concentrated. The crude compound was purified by column chromatography over silica-gel (100-200 mesh) using a solvent gradient of 20-30% ethyl acetate and pet-ether as eluant to afford solid product. This solid was washed with 20% ethyl acetate in pet-ether and dried to obtain 24.0 g (63%) of 3-bromo-N-(5-cyanopyridin-2-yl)-N-ethylpyrazolo[1,5-a]pyridine-5-carboxamide I-69 as a white solid. $^1$H NMR (400 MHz, DMSO) δ 8.81 (d, J=2.0 Hz, 1H), 8.65 (d, J=7.2 Hz, 1H), 8.20-8.22 (m, 2H), 7.54 (s, 1H), 7.49 (d, J=8.4 Hz, 1H), 6.75 (dd, J=1.6, 6.8 Hz, 1H), 4.09 (q, J=7.2, 6.0 Hz, 2H), 1.20 (t, J=6.8 Hz, 3H); ESI-LC/MS: m/z 372.12 [(M+2)+H]; r.t.=1.85 [Waters Acquity UPLC with 3100

SQD; Waters Acquity BEH C18, 1.7 μm, 2.1×50 mm column; gradient of 90:10 H₂O (0.1% formic acid):CH₃CN (0.1% formic acid) to 10:90 H₂O (0.1% formic acid):CH₃CN (0.1% formic acid) for 5 minutes with 0.4 mL/min flow rate].

Intermediate I-70

6-(isopropylamino)nicotinonitrile

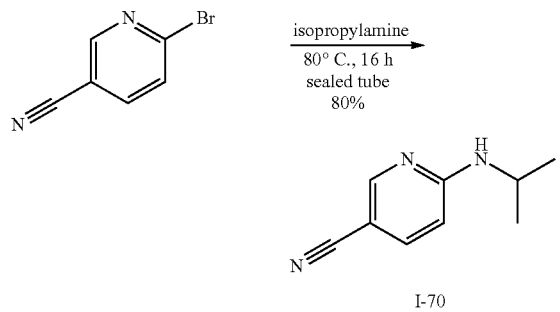

I-70 similar to Tetrahedron 57 (2001) 2953-2956

A solution of 2-bromo-5-cyanopyridine (20 g, 109.29 mmol) and isopropylamine (12.9 mL, 150.15 mmol) was maintained at 80° C. for 16 h in a sealed tube. The reaction mixture was diluted with water and extracted with ethyl acetate (2×500 mL). The combined organic layer was washed with water, brine solution, dried over anhydrous Na₂SO₄ and concentrated. The crude product was purified by column chromatography over silica-gel (100-200 mesh) using a solvent gradient of 20% ethyl acetate and pet-ether to afford 14 g (79%) of 6-(isopropylamino)nicotinonitrile 1 as a white solid. ¹H NMR (400 MHz, CDCl₃) δ 8.34 (d, J=1.8 Hz, 1H), 7.55 (dd, J=2.1, 8.7 Hz, 1H), 6.33 (d, J=8.7 Hz, 1H), 4.87 (br. s, 1H), 3.96-3.99 (m, 1H), 1.26 (d, J=6.6 Hz, 6H).

Intermediate I-71

3-Bromo-N-(5-cyanopyridin-2-yl)-N-isopropylpyrazolo[1,5-a]pyridine-5-carboxamide

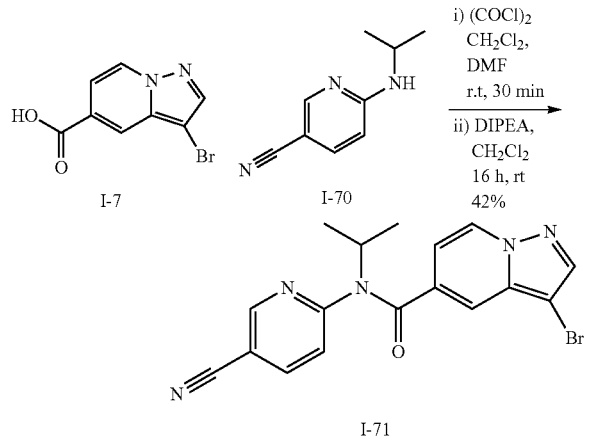

To a solution of 3-bromopyrazolo[1,5-a]pyridine-5-carboxylic acid I-7 (6 g, 25.0 mmol) in dichloromethane (20 mL) were added oxalyl chloride (6.0 mL, 69.5 mmol) followed by catalytic amount dimethylformamide (0.01 mL) at rt and stirred for 30 min. The resultant volatiles were distilled-off under reduced pressure to afford residue of acid chloride. The acid chloride was dissolved in dichloromethane (20 mL), and to the solution was added DIPEA (12 mL, 68.73 mmol) and 6-(isopropylamino)nicotinonitrile I-70 (4 g, 24.8 mmol). The resulting reaction mixture was stirred for 16 h at rt and diluted with dichloromethane (100 mL). The organic layer was washed with water, brine, dried over anhydrous Na₂SO₄ and concentrated. The crude compound was purified by column chromatography over silica (100-200 mesh) using a solvent gradient of 30% ethyl acetate in pet-ether as eluant to afford 4 g (42%) of 3-bromo-N-(5-cyanopyridin-2-yl)-N-isopropylpyrazolo[1,5-a]pyridine-5-carboxamide I-71 as a yellow solid ¹H NMR (400 MHz, DMSO) δ 8.92 (m, 1H), 8.61 (d, J=7.6 Hz, 1H), 8.19-8.23 (m, 2H), 7.50 (d, J=8.4 Hz, 1H), 7.36 (s, 1H), 6.71 (dd, J=1.6, 6.8 Hz, 1H), 4.88-4.90 (m, 1H), 1.31 (d, J=6.4 Hz, 6H); ESI-LC/MS: m/z 386.09 [(M+2)+H]; r.t.=1.71. [Waters Acquity UPLC with QuattroMicro; Waters Acquity BEH C18, 1.7 μm, 2.1×50 mm column; gradient of 80:20 H₂O (0.025% TFA):CH₃CN (0.025% TFA) to 10:90 H₂O (0.025% TFA):CH₃CN (0.025% TFA) for 3 minutes with 0.4 mL/min flow rate].

Intermediate I-72 tert-Butyl 2-(4-cyanophenyl)-1-methylhydrazinecarboxylate

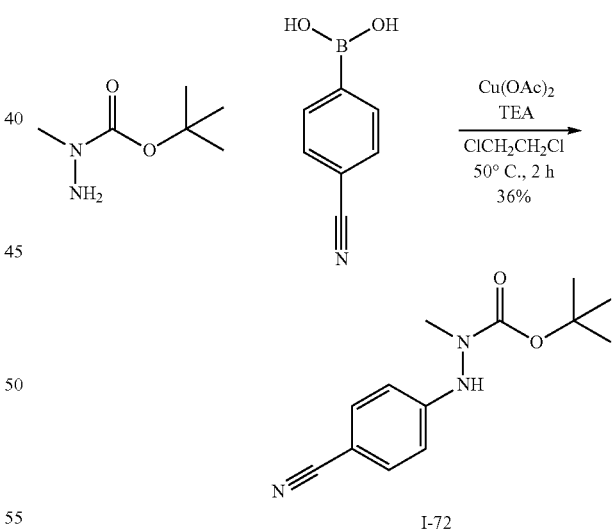

I-72 similar to US 2007/49632

To a solution of 4-cyanophenylboronic acid (2.0 g, 13.62 mmol), tert-butyl 1-methyl hydrazinecarboxylate (2.0 g, 13.48 mmol) in 1,2-dichloroethane (10 mL), copper acetate (2.71 g, 13.6 mmol) and TEA (1.85 mL, 13.3 mmol) were added and stirred at 50° C. for 2 h. The reaction mixture was partitioned between water (50 mL) and ethyl acetate (2×50 mL). The ethyl acetate layer was washed with brine (100 mL), dried over anhydrous Na₂SO₄ and concentrated under vacuum. The crude compound was purified by column chromatography over silica (100-200 mesh) using a solvent gradient of 20% ethyl acetate in chloroform as eluant to afford 1.2 g (36%) of tert-butyl 2-(4-cyanophenyl)-1-methylhydrazinecarboxylate I-72 as an off white solid. $^1$H NMR (400 MHz, DMSO-d$_6$). ESI/LC-MS: m/z: 248.08, (M+H), 97.78% $^1$H NMR (400 MHz, CDCl$_3$) δ 8.78 (s, 1H), 7.58 (d, J=8.8 Hz, 2H), 6.65 (d, J=8.8 Hz, 2H), 3.06 (s, 3H), 1.36 (s, 9H); ESI-LC/MS m/z 248.08 (M+H); r.t.=2.76 [Waters Acquity UPLC with QuattroMicro; Waters Acquity BEH C18, 1.7 μm, 2.1×50 mm column; gradient of 98:2 H$_2$O (0.025% TFA):CH$_3$CN (0.025% TFA) to 0:100 H$_2$O (0.025% TFA):CH$_3$CN (0.025% TFA) for 5 minutes with 0.4 mL/min flow rate].

Intermediate I-73 tert-Butyl 2-(3-bromopyrazolo[1,5-a]pyridine-5-carbonyl)-2-(4-cyanophenyl)-1-methyl hydrazinecarboxylate

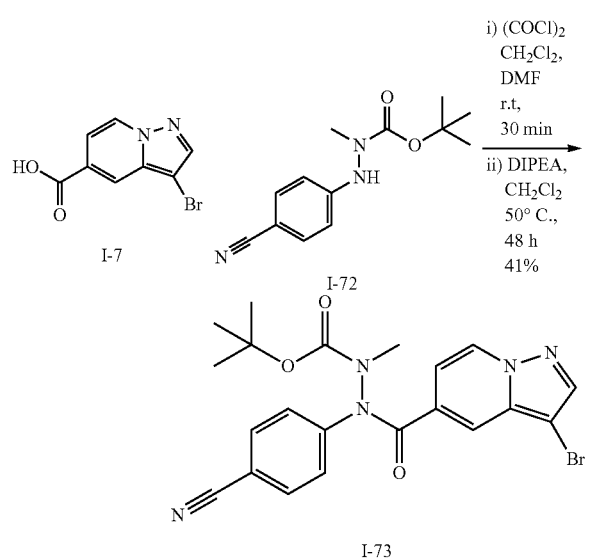

To a solution of 3-bromopyrazolo[1,5-a]pyridine-5-carboxylic acid I-7 (1.0 g, 4.16 mmol) in dichloromethane (30 mL) were added oxalyl chloride (1.5 mL, 17.37 mmol) followed by catalytic amount of N,N-dimethylformamide (0.01 mL) at rt and stirred for 30 min. The resultant volatiles were distilled-off under reduced pressure. The crude acid chloride was dissolved in dichloromethane (20 mL), and to the resulting solution were added DIPEA (3.0 mL, 17.18 mmol), tert-butyl 2-(4-cyanophenyl)-1-methylhydrazinecarboxylate I-72 (800 mg, 3.24 mmol). The reaction mixture was stirred for 48 h at 50° C. and diluted with dichloromethane (150 mL). The organic layer was washed with water, brine, dried over anhydrous Na$_2$SO$_4$ and the solvent was distilled off under reduced pressure. The crude compound was purified by column chromatography over silica gel (100-200 mesh) using a solvent gradient of 40% ethyl acetate in pet-ether as eluant to afford 700 mg (36%) of tert-butyl2-(3-bromopyrazolo[1,5-a]pyridine-5-carbonyl)-2-(4-cyanophenyl)-1-methyl hydrazine carboxylate I-73 as a yellow solid. $^1$H NMR (400 MHz, DMSO-d$_6$) δ 8.81 (d, J=7.2 Hz, 1H), 8.28 (s, 1H), 7.89-7.91 (m, 2H), 7.71 (s, 1H), 7.45-7.51 (m, 2H), 6.99-7.03 (m, 1H), 3.12 (s, 3H), 1.34 (s, 9H).

Intermediate I-74

6-(cyclopropylamino)nicotinonitrile

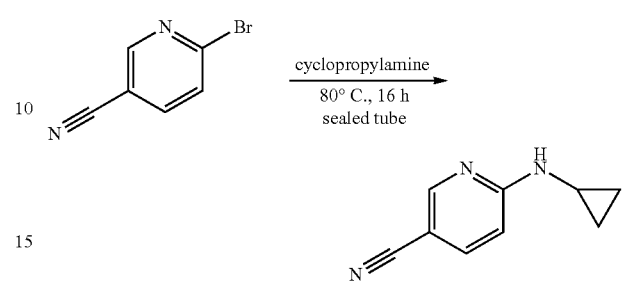

similar to Tetrahedron 57 (2001) 2953-2956

Intermediate I-74 may be prepared by reacting 2-bromo-5-cyanopyridine with cyclopropylamine following the procedure for the synthesis of Intermediate I-70.

Intermediate I-75

3-Bromo-N-(5-cyanopyridin-2-yl)-N-cyclopropylpyrazolo[1,5-a]pyridine-5-carboxamide

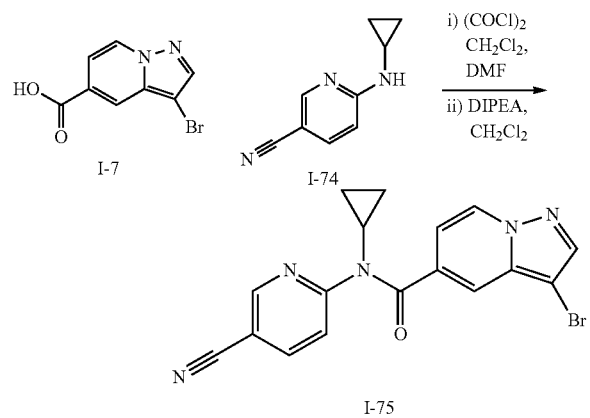

Intermediate I-75 may be prepared by reacting Intermediate I-7 with Intermediate I-74 according the procedure described for the synthesis of Intermediate I-71.

Intermediate I-76

N-ethyl-5-fluoropyridin-2-amine

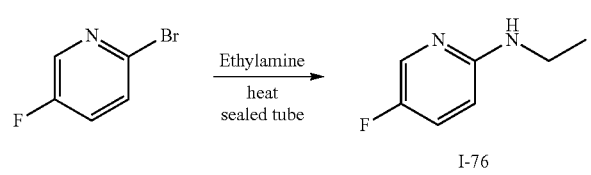

Intermediate I-76 may be prepared by reacting 2-bromo-5-fluoropyridine with ethylamine according to the procedure described for the synthesis of Intermediate I-68.

Intermediate I-77

3-bromo-N-ethyl-N-(5-fluoropyridin-2-yl)pyrazolo[1,5-a]pyridine-5-carboxamide

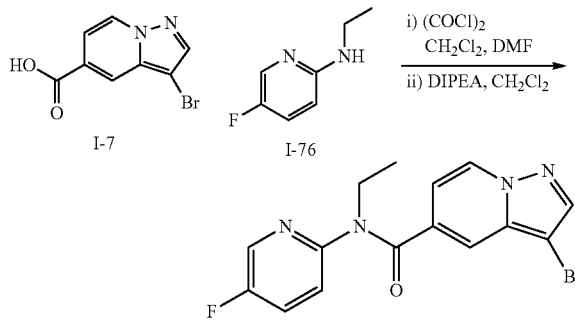

Intermediate I-77 may be prepared by reacting Intermediate I-7 with Intermediate I-76 according to the procedure described for the synthesis of Intermediate I-69.

Intermediate I-78

N-ethyl-5-(trifluoromethyl)pyridin-2-amine

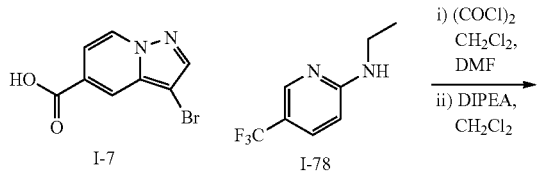

Intermediate I-78 may be prepared by reacting 2-bromo-5-(trifluoromethyl)pyridine with ethylamine according to the procedure described for the synthesis of Intermediate I-68.

Intermediate I-79

3-bromo-N-ethyl-N-(5-(trifluoromethyl)pyridin-2-yl)pyrazolo[1,5-a]pyridine-5-carboxamide

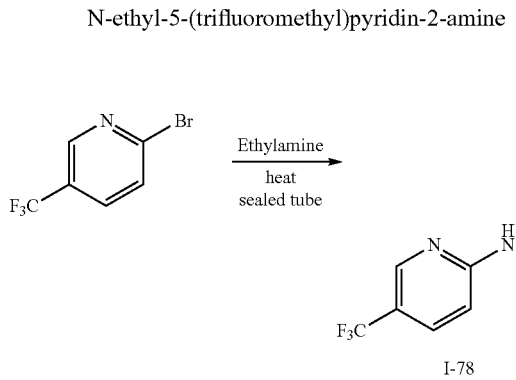

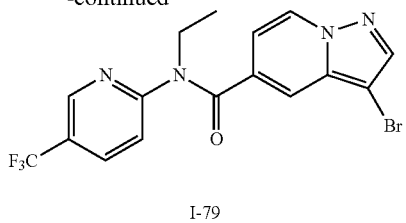

Intermediate I-79 may be prepared by reacting Intermediate I-7 with Intermediate I-78 according to the procedure described for the synthesis of Intermediate I-69.

Intermediate I-80

N-(3-bromopyrazolo[1,5-a]pyridin-5-yl)-5-cyano-N-methylpicolinamide

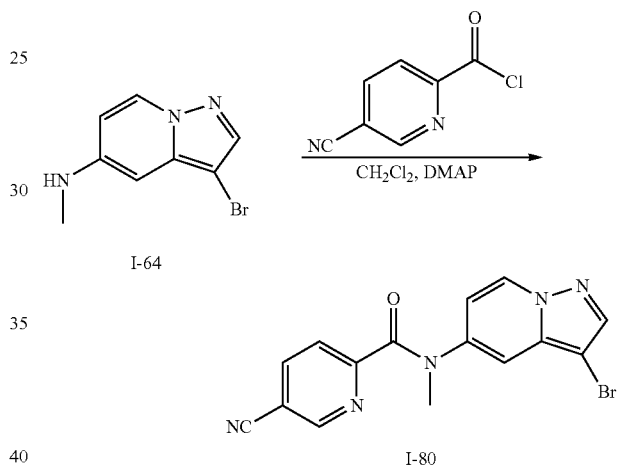

Intermediate I-80 may be prepared by reacting Intermediate I-64 with 5-cyanopicolinoyl chloride according to the procedure described for the synthesis of Intermediate I-65.

Example 1

N-(4-cyanophenyl)-N-methyl-3-(4-(trifluoromethyl)phenyl)pyrazolo[1,5-a]pyridine-5-carboxamide

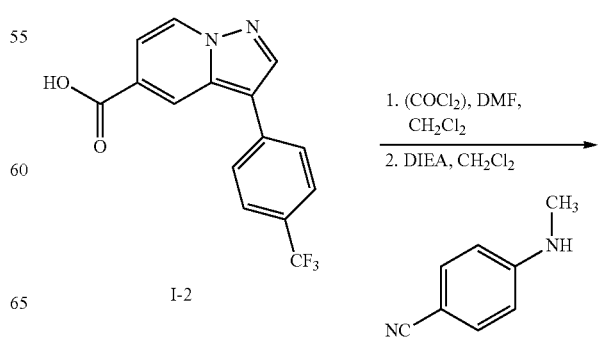

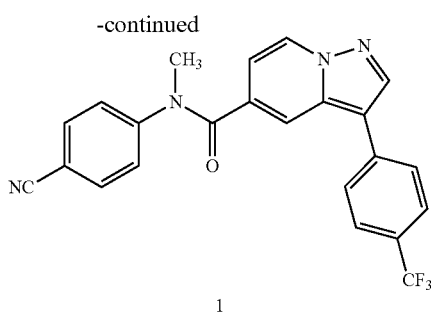

1

A solution of acid (1.0 equiv.) in CH$_2$Cl$_2$ (~0.05-0.1 M) was treated with oxalyl chloride (2.0-3.0 equiv.) and a catalytic amount of DMF. The resulting solution was allowed to stir at rt for between five minutes and one hour, then was concentrated and dried briefly under high vacuum. The resulting acid chloride was diluted with CH$_2$Cl$_2$ (~0.05-0.1 M), and to this solution was added 4-(methylamino) benzonitrile (1.1-3.0 equiv.) and either DIEA or Et3N (3.0 equiv.). The resulting mixture was allowed to stir at rt until complete conversion (generally less than three hours). The solvent was removed under reduced pressure, and the residue was purified by silica gel chromatography, eluting with hexanes/ethyl acetate to provide 1. $^1$H NMR (400 MHz, CDCl3) δ 8.30 (dd, J=0.7, 7.3, 1H), 8.16 (s, 1H), 7.82 (m, 1H), 7.66 (d, J=8.2, 2H), 7.60 (d, J=8.6, 2H), 7.47 (d, J=8.1, 2H), 7.23 (obscured by CDCl$_3$ peak, 2H), 6.64 (dd, J=1.8, 7.3, 1H), 3.54 (s, 3H). ESI-LC/MS m/z 421.1 (M+H)+; r.t.=1.871.

Example 2

4-fluoro-N-methyl-N-((3-(4-(trifluoromethyl)phenyl) pyrazolo[1,5-a]pyridine-5-yl)methyl)aniline

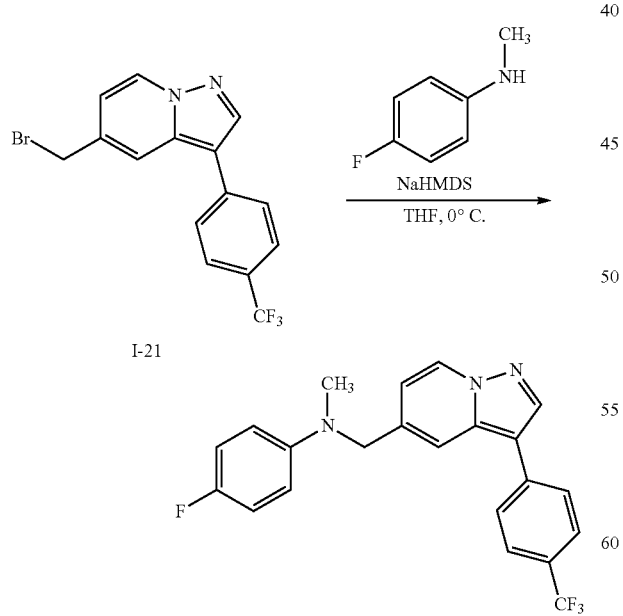

A solution of N-methyl aniline (18.8 mg, 0.15 mmol, 1.5 equiv.) in 0.5 mL THF was allowed to cool to 0° C., then a solution of NaHMDS (1.0 M in THF, 150 μL, 0.15 mmol, 1.5 equiv.) was added dropwise. After allowing the resulting solution to stir at 0° C. for 10 minutes, a solution of bromide (35.4 mg, 0.10 mmol, 1.0 equiv.) in 0.5 mL THF was added dropwise. The reaction mixture was allowed to stir at 0° C. for another 10-20 minutes, and then the reaction was quenched with water and concentrated under reduced pressure. The residue was diluted with MeOH-DMSO and the resulting solution was purified by mass-triggered HPLC to provide 2 as the TFA salt. $^1$H NMR (400 MHz, CDCl$_3$) δ 8.44 (d, J=7.2, 1H), 8.14 (s, 1H), 7.65 (d, J=8.3, 2H), 7.59 (m, 3H), 6.94 (m, 2H), 6.72 (m, 3H), 4.48 (s, 2H), 2.99 (s, 3H). ESI-MS (m/z): [M+H]$^+$ 400.2, RT 2.409 min.

Example 3

N-(4-chlorophenyl)-N-methyl-3-(4-(trifluoromethyl) phenyl)pyrazolo[1,5-a]pyridine-5-carboxamide

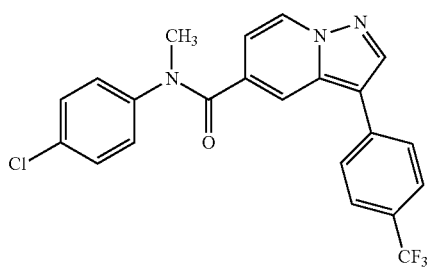

3

Example 3 was prepared according to the procedure described for the synthesis of Example 1 by replacing 4-(methylamino)benzonitrile with 4-chloro-N-methylaniline. ESI-LC/MS m/z 430.1 (M+H)+; r.t.=2.275.

Example 4

N-(4-fluorophenyl)-N-methyl-3-(4-(trifluoromethyl) phenyl)pyrazolo[1,5-a]pyridine-5-carboxamide

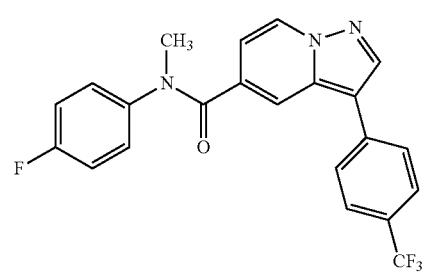

4

Example 4 was prepared according to the procedure described for the synthesis of Example 1 by replacing 4-(methylamino)benzonitrile with 4-fluoro-N-methylaniline. ESI-LC/MS m/z 414.1 (M+H)+; r.t.=2.165.

Example 5

N-methyl-N-(5-methylpyridin-2-yl)-3-(4-(trifluoromethyl)phenyl)pyrazolo[1,5-a]pyridine-5-carboxamide

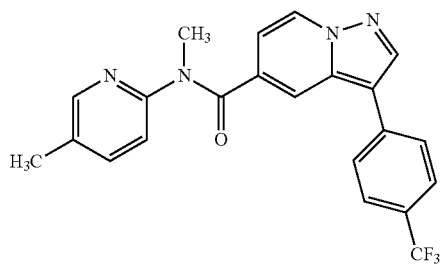

5

Example 5 was prepared according to the procedure described for the synthesis of Example 1 by replacing 4-(methylamino)benzonitrile with N,5-dimethylpyridin-2-amine. ESI-LC/MS m/z 411.2 (M+H)+; r.t.=2.005.

Example 6

4-chloro-N-methyl-N-((3-(4-(trifluoromethyl)phenyl)pyrazolo[1,5-a]pyridine-5-yl)methyl)aniline

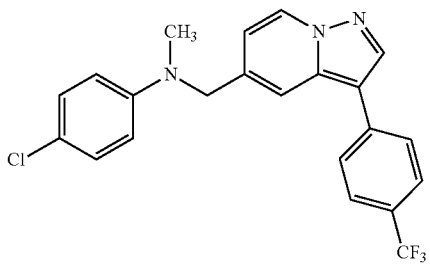

6

Example 6 was prepared according to the procedure described for the synthesis of Example 2 by replacing 4-fluoro-N-methylaniline with 4-chloro-N-methylaniline. $^1$H NMR (400 MHz, CDCl3) δ 8.48 (d, J=7.2, 1 H), 8.15 (s, 1H), 7.66 (d, J=8.3, 2H), 7.62-7.55 (m, 3H), 7.18 (d, J=9.1, 2H), 6.74-6.65 (m, 3H), 4.53 (s, 2H), 3.03 (s, 3H). ESI-MS (m/z): [M+H]$^+$ 416.1, RT 2.5357 min.

Example 7

N,5-dimethyl-N-((3-(4-(trifluoromethyl)phenyl)pyrazolo[1,5-a]114yridine-5-yl)methyl)pyridine-2-amine

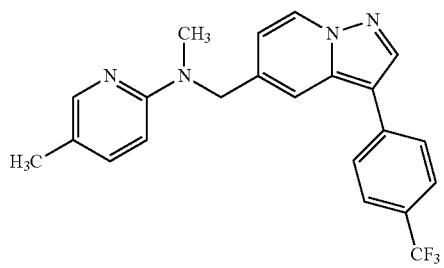

7

Example 7 was prepared according to the procedure described for the synthesis of Example 2 by replacing 4-fluoro-N-methylaniline with N,5-dimethylpyridin-2-amine (2.0 equiv) and using 2.0 equiv of NaHMDS. $^1$H NMR (400 MHz, CDCl3) δ 8.50 (d, J=7.2, 1 H), 8.18 (s, 1H), 8.03 (s, 1H), 7.73-7.65 (m, 3H), 7.62 (d, J=8.2, 3H), 6.82 (d, J=9.2, 1H), 6.66 (dd, J=1.8, 7.2, 1H), 4.88 (s, 2H), 3.37 (s, 3H), 2.27 (s, 3H). ESI-MS (m/z): [M+H]$^+$ 397.2, RT 1.5837 min.

Example 8

5-((4-fluorophenoxy)methyl)-3-(4-(trifluoromethyl)phenyl)pyrazolo[1,5-a]pyridine

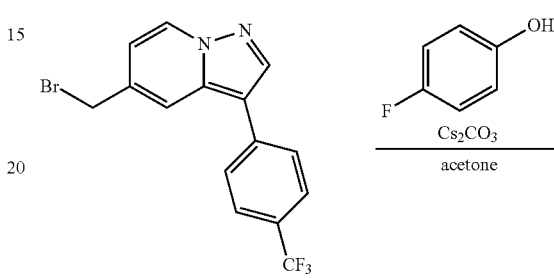

I-53

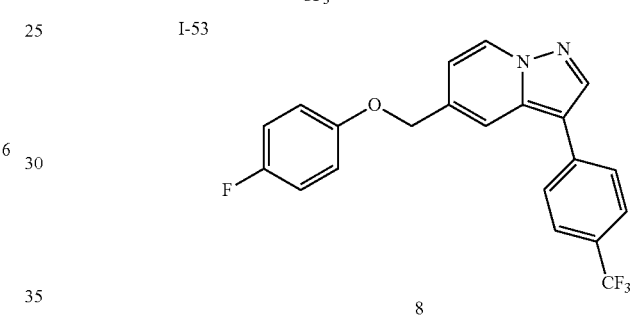

8

A mixture of pyrazolopyridine alkyl bromide (I-53) (17.7 mg, 0.05 mmol, 1.0 equiv.), 4-fluorophenol (11.2 mg, 0.1 mmol, 2.0 equiv.), and Cs$_2$CO$_3$ (48 mg, 0.15 mmol, 3.0 equiv.) in acetone was allowed to stir at rt for one hour. The mixture was filtered and purified by mass-triggered HPLC to provide 8. $^1$H NMR (400 MHz, CDCl3) δ 8.51 (d, J=7.2, 1 H), 8.17 (s, 1H), 7.83 (s, 1H), 7.68 (d, J=1.6, 4H), 7.05-6.82 (m, 5H), 5.07 (s, 2H). ESI-MS (m/z): [M+H]$^+$ 387.1, RT 2.5104 min.

Example 9

N-(4-cyanophenyl)-N-(2-methoxyethyl)-3-(4-(trifluoromethyl)phenyl)pyrazolo[1,5-a]pyridine-5-carboxamide

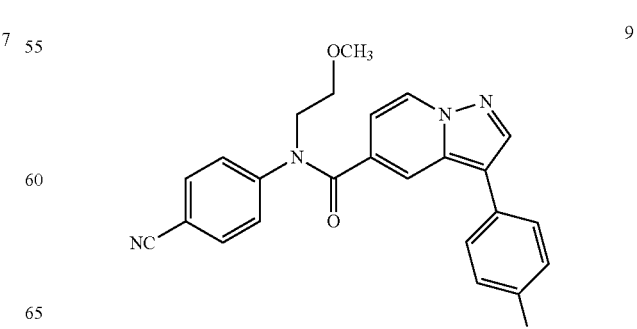

9

Example 9 was prepared according to the procedure described for the synthesis of Example 1 by replacing 4-(methylamino)benzonitrile with 4-((2-methoxyethyl)amino)benzonitrile. ESI-LC/MS m/z 465.2 (M+H)+; r.t.=2.098.

Example 10

N-(4-cyanophenyl)-N-(2-(dimethylamino)ethyl)-3-(4-(trifluoromethyl)phenyl)pyrazolo[1,5-a]pyridine-5-carboxamide

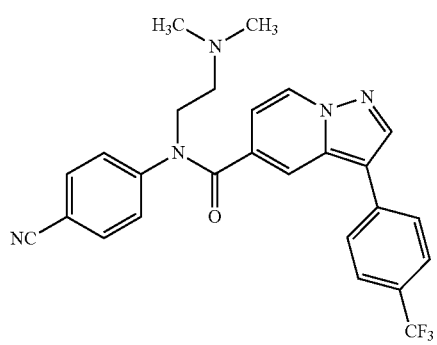

Example 10 was prepared according to the procedure described for the synthesis of Example 1 by replacing 4-(methylamino)benzonitrile with 4-((2-(dimethylamino)ethyl)amino)benzonitrile. ESI-LC/MS m/z 478.2 (M+H)+; r.t.=1.550.

Example 11

N-(4-cyanophenyl)-N-((tetrahydro-2H-pyran-4-yl)methyl)-3-(4-(trifluoromethyl)phenyl)pyrazolo[1,5-a]pyridine-5-carboxamide

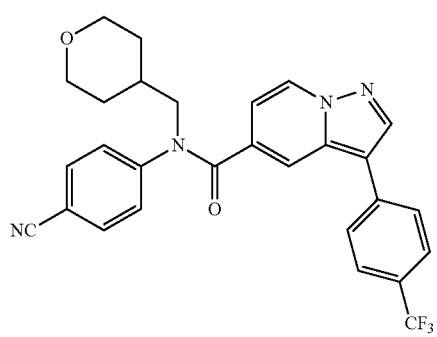

Example 11 was prepared according to the procedure described for the synthesis of Example 1 by replacing 4-(methylamino)benzonitrile with 4-(((tetrahydro-2H-pyran-4-yl)methyl)amino)benzonitrile. ESI-LC/MS m/z 505.2 (M+H)+; r.t.=1.997.

Example 12

N-(4-(methylsulfonyl)phenyl)-N-((tetrahydro-2H-pyran-4-yl)methyl)-3-(4-(trifluoromethyl)phenyl)pyrazolo[1,5-a]pyridine-5-carboxamide

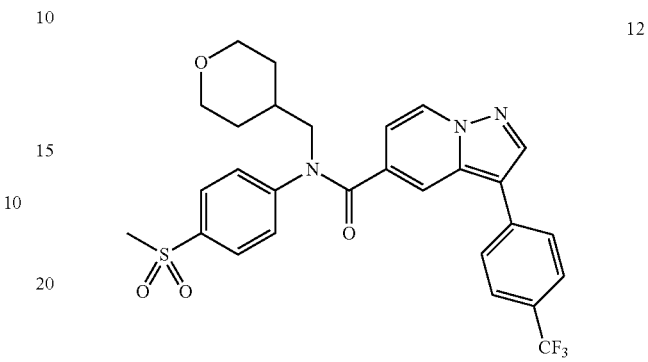

Example 12 was prepared according to the procedure described for the synthesis of Example 1 by replacing 4-(methylamino)benzonitrile with 4-(methylsulfonyl)-N-((tetrahydro-2H-pyran-4-yl)methyl)aniline. ESI-LC/MS m/z 558.2 (M+H)+; r.t.=1.828.

Example 13

N-(5-cyanopyridin-2-yl)-N-methyl-3-(4-(trifluoromethyl)phenyl)pyrazolo[1,5-a]pyridine-5-carboxamide

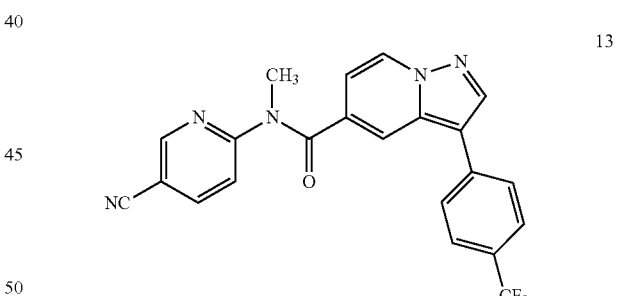

Example 13 was prepared according to the procedure described for the synthesis of Example 1 by replacing 4-(methylamino)benzonitrile with 6-(methylamino)nicotinonitrile. Purification by silica gel chromatography, eluting with hexane/ethyl acetate provided the desired product (13). $^1$H NMR (400 MHz, CDCl3) δ 8.67 (dd, J=0.8, 2.3, 1H), 8.41 (dd, J=0.7, 7.2, 1H), 8.21 (s, 1H), 7.98 (m, 1H), 7.80 (dd, J=2.3, 8.6, 1H), 7.69 (d, J=8.2, 2H), 7.59 (d, J=8.1, 2H), 7.35 (dd, J=0.8, 8.7, 1H), 6.73 (dd, J=1.9, 7.2, 1H), 3.62 (s, 3H). ESI-MS (m/z): [M+H]$^+$ 422.1, RT 1.9712 min. Anal. Calcd for $C_{22}H_{14}F_3N_5O+0.2H_2O$: C, 62.18; H, 3.42; N, 16.48. Found: C, 62.26, 62.26; H, 3.39, 3.38; N, 16.40, 16.38.

Example 14

N-methyl-N-(5-methylpyridin-3-yl)-3-(4-(trifluoromethyl)phenyl)pyrazolo[1,5-a]pyridine-5-carboxamide

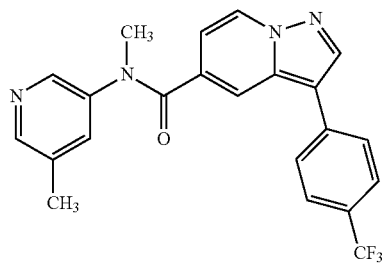

14

Example 14 was prepared according to the procedure described for the synthesis of Example 1 by replacing 4-(methylamino)benzonitrile with N,5-dimethylpyridin-3-amine. The reaction was purified by mass-triggered HPLC to provide the desired product, 14. ESI-MS (m/z): [M+H]⁺ 411.2, RT 1.5164 min.

Example 15

5-(((5-methylpyridin-2-yl)oxy)methyl)-3-(4-(trifluoromethyl)phenyl)pyrazolo[1,5-a]pyridine

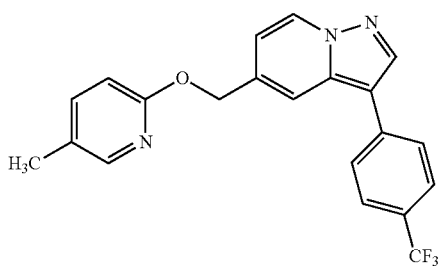

15

Example 15 was prepared according to the procedure described for the synthesis of Example 8 by replacing 4-fluorophenol with 1.5 equiv. of 5-methylpyridin-2-ol and using 2.0 equiv. Cs₂CO₃ in acetonitrile (to replace acetone). The reaction was purified by mass-triggered HPLC to provide the desired product. $^1$H NMR (400 MHz, MeOD) δ 8.57 (d, J=7.2, 1H), 8.32 (s, 1H), 7.91 (s, 1H), 7.84 (d, J=8.2, 2H), 7.74 (d, J=8.3, 2H), 7.61 (s, 1H), 7.47 (dd, J=2.5, 9.2, 1H), 6.94 (dd, J=1.8, 7.2, 1H), 6.57 (d, J=9.2, 1H), 5.26 (s, 2H), 2.12 (s, 3H). ESI-MS (m/z): [M+H]⁺ 384.1, RT 1.8029 min.

Example 16

5-(4-fluorophenethyl)-3-(4-(trifluoromethyl)phenyl)pyrazolo[1,5-a]pyridine

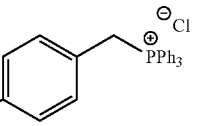

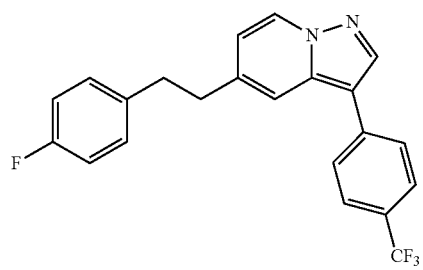

I-52

1. DBU, acetonitrile, 50° C.
2. Pd/C, H₂ (1 atm), EtOH

16

A mixture of pyrazolopyridine aldehyde (I-52) (48 mg, 0.165 mmol, 1.0 equiv.) and Wittig salt (74 mg, 0.18 mmol, 1.1 equiv.) in acetonitrile was treated with DBU (28 mg, 0.18 mmol, 1.1 equiv.). The resulting mixture was allowed to stir at 50° C. for two hours, and then the reaction mixture was concentrated. The residue was purified by silica gel chromatography, eluting with hexanes/EtOAc to give the desired olefin. A solution of olefin (22 mg, 0.0575 mmol, 1.0 equiv.) in 5 mL EtOH was purged with nitrogen gas, then 10% Pd/C (5 mg) was added. The resulting mixture was purged with hydrogen gas and allowed to stir at room temperature overnight under an atmosphere of hydrogen gas. The mixture was then filtered through Celite® and purified by mass-triggered HPLC to provide the desired product. $^1$H NMR (400 MHz, CDCl3) δ 8.40 (d, J=7.6, 1H), 8.12 (s, 1H), 7.66 (d, J=8.3, 2H), 7.59 (d, J=8.2, 2H), 7.42 (s, 1H), 7.10 (dd, J=5.4, 8.6, 2H), 6.96 (t, J=8.7, 2H), 6.63 (dd, J=1.8, 7.1, 1H), 2.95 (s, 4H). ESI-MS (m/z): [M+H]⁺ 385.2, RT 2.5863 min.

Example 17

N-(4-cyanophenyl)-N-methyl-3-(1-methyl-1H-indazol-5-yl)pyrazolo[1,5-a]pyridine-5-carboxamide

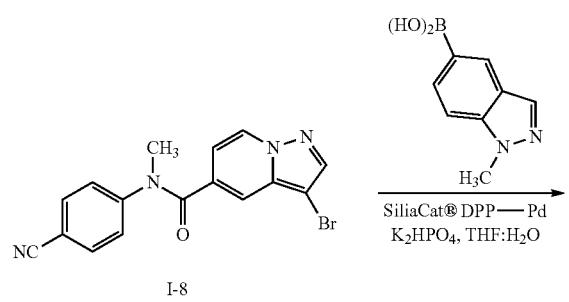

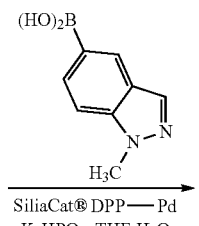

SiliaCat® DPP—Pd
K₂HPO₄, THF:H₂O

I-8

-continued

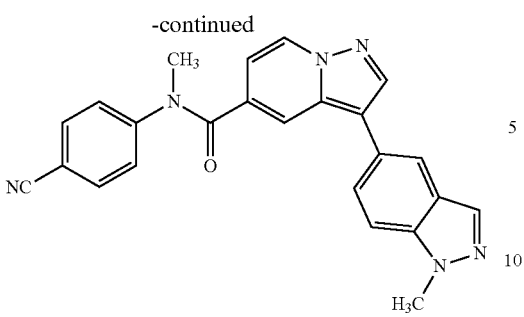

17

A mixture of aryl bromide (I-8) (1.0 equiv.), (1-methyl-1H-indazol-5-yl)boronic acid (1.5 equiv.), KH₂PO₄ (3.5 equiv.), and SiliaCat® DPP-Pd or Pd(dppf)Cl₂ (0.05-0.15 equiv.) in THF/water was allowed to heat at 150° C. in a microwave reactor for 40-60 minutes. The solvent was removed under reduced pressure and the crude material was purified by silica gel chromatography eluting with ethyl acetate and hexanes. ¹H NMR (400 MHz, CDCl3) δ 8.28 (dd, J=0.8, 7.4, 1H), 8.12 (s, 1H), 8.01 (d, J=0.8, 1H), 7.80 (m, 1H), 7.65 (s, 1H), 7.60 (d, J=8.6, 2H), 7.44 (d, J=8.6, 1H), 7.36 (dd, J=1.5, 8.6, 1H), 7.22 (obscured by CDCl₃ peak, 2H), 6.62 (dd, J=1.9, 7.3, 1 H), 4.11 (s, 3H), 3.53 (s, 3H). ESI-MS (m/z): [M+H]⁺ 407.1, RT 1.6596 min. Anal. Calcd for C₂₄H₁₈N₆O+0.1H₂O: C, 70.61; H, 4.49; N, 20.59. Found: C, 70.59, 70.57; H, 4.43, 4.43; N, 20.57, 20.57.

Example 18

3-(6-acetamidopyridin-3-yl)-N-(4-cyanophenyl)-N-methylpyrazolo[1,5-a]pyridine-5-carboxamide

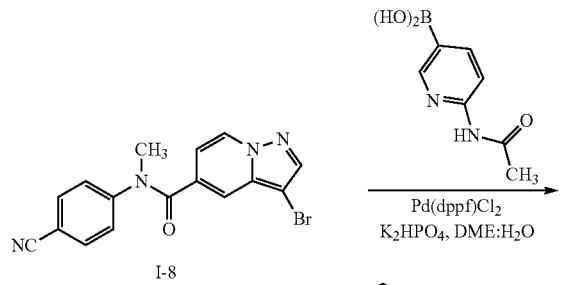

A mixture of aryl bromide (I-8) (1.0 equiv.), (6-acetamidopyridin-3-yl)boronic acid (1.5 equiv.), K₂CO₃ (3.0 equiv.), and Pd(dppf)Cl₂ (0.05-0.15 equiv.) in DME/water was allowed to heat at 110° C. for two hours. Following extraction of the reaction mixture with CH₂Cl₂, the combined organic extracts were concentrated and the residue was purified by silica gel chromatography, eluting with hexanes/EtOAc to give the desired product. ¹H NMR (400 MHz, MeOD) δ 8.48 (dd, J=0.8, 7.0, 1 H), 8.35 (d, J=2.4, 1 H), 8.26 (s, 1H), 8.18 (d, J=8.4, 1 H), 7.81 (dd, J=2.4, 8.6, 1 H), 7.78 (s, 1H), 7.71 (d, J=8.6, 2H), 7.48 (d, J=8.6, 2H), 6.87 (dd, J=1.8, 7.3, 1 H), 3.55 (s, 3H), 2.21 (s, 3H). ESI-MS (m/z): [M+H]⁺ 411.2, RT 1.2806 min.

Example 19

3-(4-carbamoylphenyl)-N-(4-cyanophenyl)-N-methylpyrazolo[1,5-a]pyridine-5-carboxamide

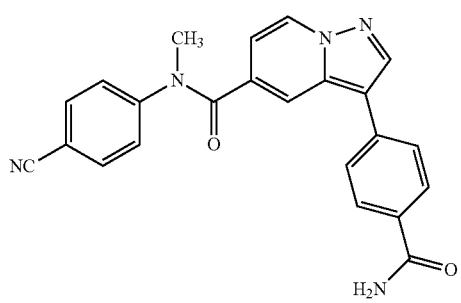

Example 19 was prepared according to the procedure described for the synthesis of Example 17 by replacing (1-methyl-1H-indazol-5-yl)boronic acid with (4-carbamoylphenyl)boronic acid. The reaction was purified by silica gel chromatography, eluting with hexanes/EtOAc to give 19 as the desired product. ¹H NMR (400 MHz, MeOD) δ 8.49 (dd, J=0.8, 7.2, 1 H), 8.31 (s, 1H), 7.97 (d, J=8.4, 2H), 7.84 (s, 1H), 7.74 (d, J=8.6, 2H), 7.53-7.46 (2d, J=8.6, 4H), 6.91 (dd, J=1.6, 7.2, 1 H), 3.56 (s, 3H). ESI-MS (m/z): [M+H]⁺ 397.2, RT 1.3648 min. Anal. Calcd for C₂₃H₁₇N₅O₂+0.5H₂O: C, 68.31; H, 4.49; N, 17.32. Found: C, 68.61, 68.54; H, 4.46, 4.40; N, 17.07, 16.99.

Example 20

3-(4-carbamoylphenyl)-N-(4-fluorophenyl)-N-methylpyrazolo[1,5-a]pyridine-5-carboxamide

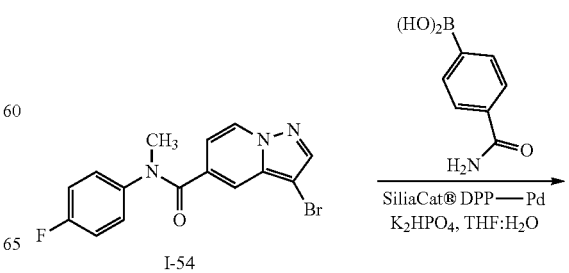

-continued

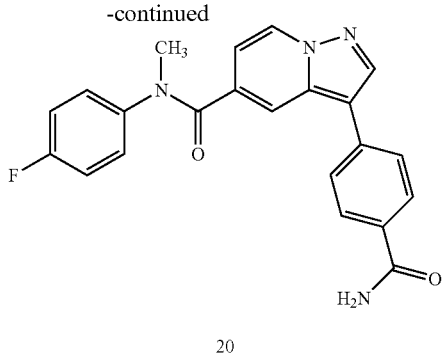

20

A mixture of aryl bromide (I-54) (1.0 equiv.), (4-carbamoylphenyl)boronic acid (1.5 equiv.), KH$_2$PO$_4$ (3.5 equiv.), and SiliaCat® DPP-Pd or Pd(dppf)Cl2 (0.05-0.15 equiv.) in THF/water was allowed to heat at 150° C. in a microwave reactor for 40-60 minutes. The solvent was removed under reduced pressure and the crude material was purified by silica gel chromatography, eluting with hexanes/EtOAc to give 20 as the desired product. $^1$H NMR (400 MHz, CDCl3) δ 8.28 (dd, J=0.8, 7.2, 1H), 8.14 (s, 1H), 7.84 (dt, J=2.0, 8.4, 2H), 7.74 (s, 1H), 7.42 (d, J=8.4, 2H), 7.14-7.08 (m, 2H), 7.06-6.99 (m, 2H), 6.75 (dd, J=1.8, 7.4, 1H), 6.07 (br s, 1H), 5.56 (br s, 1H), 3.49 (s, 3H). ESI-MS (m/z): [M+H]$^+$ 389.1, RT 1.4322 min. Anal. Calcd for C$_{22}$H$_{17}$FN$_4$O$_2$+0.4H$_2$O: C, 66.79; H, 4.54; N, 14.16. Found: C, 66.97, 66.74; H, 4.49, 4.43; N, 14.20, 14.16.

Example 21

5-(((4-fluorophenyl)thio)methyl)-3-(4-(trifluoromethyl)phenyl)pyrazolo[1,5-a]pyridine

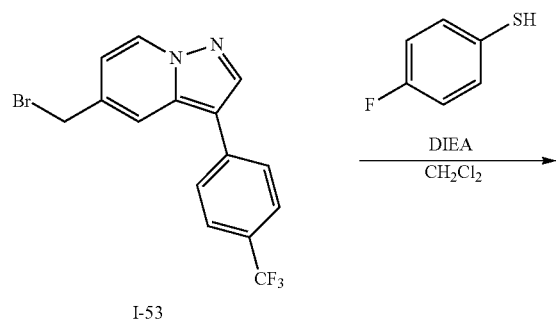

21

A solution of pyrazolopyridine alkyl bromide (I-53) (45 mg, 0.127 mmol, 1.0 equiv.) and 4-fluorobenzenethiol (24 mg, 0.19 mmol, 1.5 equiv.) in CH$_2$Cl$_2$ was treated with DIEA (33 mg, 0.254 mmol, 2.0 equiv.) and the resulting solution was allowed to stir at rt for 20 minutes. The reaction was concentrated and the residue was purified by silica gel chromatography, eluting with hexanes/EtOAc to give 21 as the desired product. $^1$H NMR (400 MHz, CDCl3) δ 8.41 (d, J=7.2, 1H), 8.11 (s, 1H), 7.64 (d, J=8.1, 2H), 7.50 (d, J=8.1, 2H), 7.36-7.27 (m, 3H), 6.96 (t, J=8.7, 2H), 6.78 (dd, J=1.9, 7.2, 1 H), 4.00 (s, 2H). ESI-MS (m/z): [M+H]$^+$ 403.1, RT 2.5275 min.

Example 22

5-(((4-fluorophenyl)sulfinyl)methyl)-3-(4-(trifluoromethyl)phenyl)pyrazolo[1,5-a]pyridine

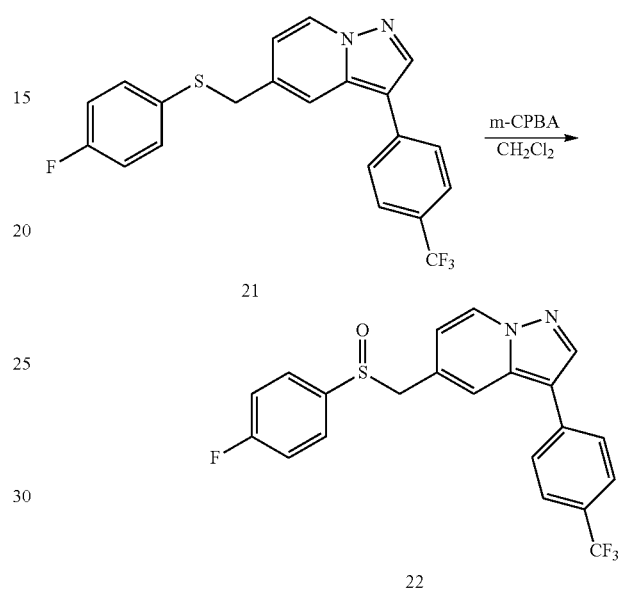

A solution of sulfide (21) (30 mg, 0.75 mmol, 1.0 equiv.) in 1 mL of CH$_2$Cl$_2$ was treated with m-CPBA (77% purity, 16.6 mg, 0.75 mmol, 1.0 equiv.) and the resulting mixture was allowed to stir at rt for 20 minutes. The reaction was concentrated and the residue was purified by silica gel chromatography, eluting with hexanes/EtOAc to give 22 as the desired product. $^1$H NMR (400 MHz, CDCl3) δ 8.38 (d, J=7.2, 1H), 8.15 (s, 1H), 7.66 (d, J=8.2, 2H), 7.53 (d, J=8.0, 2H), 7.49-7.43 (m, 2H), 7.32 (d, J=0.7, 1 H), 7.20-7.13 (m, 2H), 6.46 (dd, J=1.8, 7.1, 1H), 4.12 (d, J=12.9, 1H), 3.95 (d, J=12.9, 1H). ESI-MS (m/z): [M+H]$^+$ 419.1, RT 2.0051 min.

Example 23

3-(4-(1H-pyrazol-5-yl)phenyl)-N-(4-cyanophenyl)-N-methylpyrazolo[1,5-a]pyridine-5-carboxamide

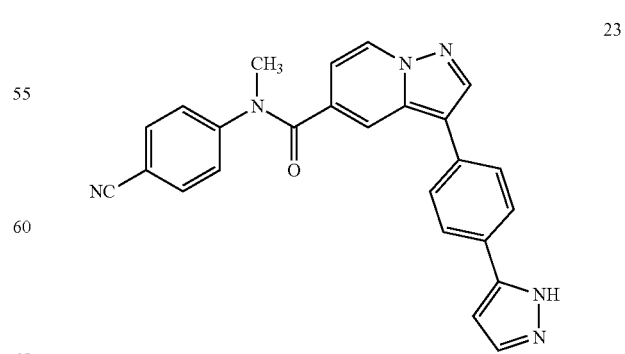

Example 23 was prepared according to the procedure described for the synthesis of Example 17 by replacing (1-methyl-1H-indazol-5-yl)boronic acid with ((4-(1H-pyrazol-5-yl)phenyl)boronic acid. The reaction was purified by mass-triggered HPLC to provide 23 as the desired product. ¹H NMR (400 MHz, CDCl3) δ 8.30 (dd, J=0.9, 7.3, 1 H), 8.15 (s, 1H), 7.83-7.78 (m, 3H), 7.65 (d, J=2.3, 1 H), 7.64-7.59 (m, 2H), 7.41-7.34 (m, 2H), 7.25-7.21 (m, 2H), 6.70-6.65 (m, 2H), 3.54 (s, 3H). ESI-MS (m/z): [M+H]⁺ 419.2, RT 1.5585 min.

Example 24

N-(4-cyanophenyl)-N-methyl-3-(5-(trifluoromethyl)122yridine-2-yl)pyrazolo[1,5-a]pyridine-5-carboxamide

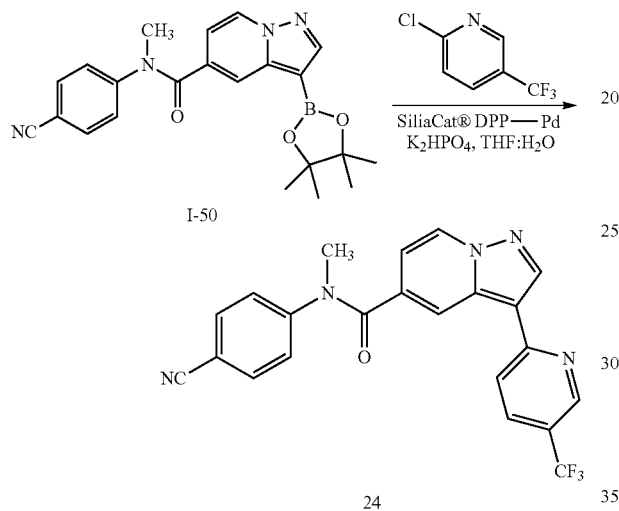

I-50

24

A mixture of 2-chloro-5-(trifluoromethyl)pyridine (1.0 equiv.), I-50 (1.5 equiv.), KH₂PO₄ (3.5 equiv.), and SiliaCat® DPP-Pd or Pd(dppf)Cl2 (0.05-0.15 equiv.) in THF/water was allowed to heat at 150° C. in a microwave reactor for 40-60 minutes. The solvent was removed under reduced pressure and the crude material was purified by silica gel chromatography eluting with ethyl acetate and hexanes. ¹H NMR (400 MHz, CDCl3) δ 8.77 (s, 1H), 8.63 (dd, J=0.8, 2.0, 1H), 8.40 (s, 1H), 8.33 (dd, J=0.8, 7.2, 1H), 7.88 (dd, J=2.4, 8.4, 1H), 7.66 (d, J=8.4, 1H), 7.56 (dt, J=2.1, 8.7, 2H), 7.25 (app dt, obscured by CDCl3 peak, 2H), 6.79 (dd, J=1.9, 7.2, 1 H), 3.56 (s, 3H). ESI-MS (m/z): [M+H]⁺ 422.1, RT 1.8535 min.

Example 25

N-(5-cyanopyridin-2-yl)-N-methyl-3-(5-(trifluoromethyl)122yridine-2-yl)pyrazolo[1,5-a]pyridine-5-carboxamide

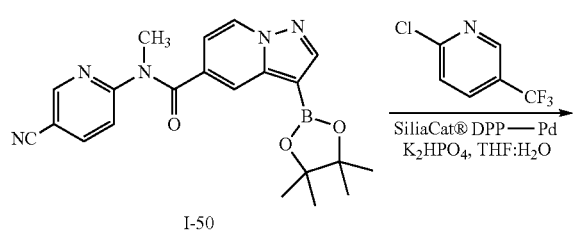

I-50

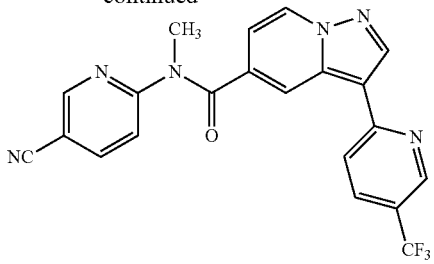

25

A mixture of 2-chloro-5-(trifluoromethyl)pyridine (1.0 equiv.), I-50 (1.5 equiv.), KH₂PO₄ (3.5 equiv.), and SiliaCat® DPP-Pd or Pd(dppf)Cl2 (0.05-0.15 equiv.) in THF/water was allowed to heat at 150° C. in a microwave reactor for 40-60 minutes. The solvent was removed under reduced pressure and the crude material was purified by silica gel chromatography eluting with ethyl acetate and hexanes. ¹H NMR (400 MHz, MeOD) δ 8.88-8.84 (m, 1H), 8.73 (dd, J=0.8, 2.4, 1 H), 8.69 (s, 1H), 8.65 (dd, J=1.2, 2.4, 1 H), 8.61 (dd, J=0.8, 7.2, 1 H), 8.09-8.02 (m, 2H), 7.99 (d, J=8.5, 1 H), 7.53 (dd, J=0.8, 8.5, 1 H), 7.02 (dd, J=2.0, 7.2, 1 H), 3.65 (s, 3H). ESI-MS (m/z): [M+H]⁺ 423.0, RT 1.8535 min.

Example 26

(S)-3-(4-(2-aminopropanamido)phenyl)-N-(4-cyanophenyl)-N-methylpyrazolo[1,5-a]pyridine-5-carboxamide

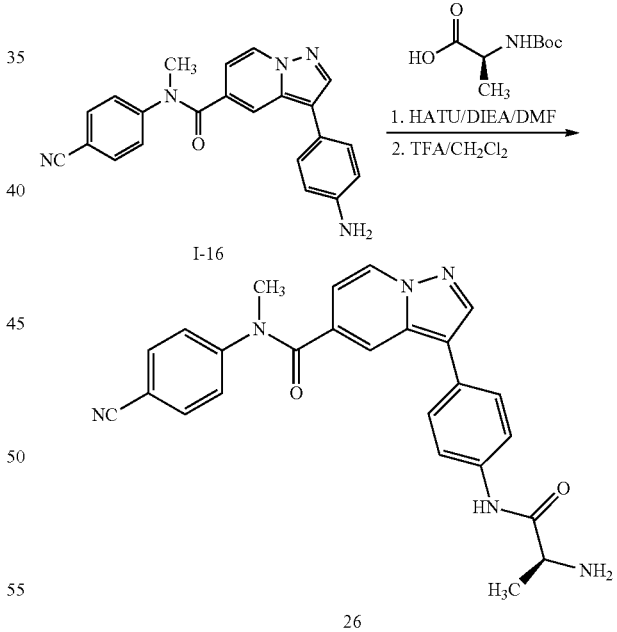

26

A solution of the aniline (30 mg, 0.082 mmol, 1.0 equiv.) in CH₂Cl₂ was treated with N-Boc-L-Ala-OH (18.5 mg, 0.098 mmol, 1.2 equiv.), followed by HATU (34.3 mg, 0.0902 mmol, 1.1 equiv.) and DIEA (21 mg, 0.16 mmol, 2.0 equiv.). The resulting mixture was allowed to stir at rt for two hours, and then was purified by silica gel chromatography, eluting with CH₂Cl₂/EtOAc to give the desired N-Boc coupled product. The N-Boc alanine amide (35 mg) was dissolved in 1 mL CH₂Cl₂ and 1 mL TFA was added. The resulting solution was allowed to stir at rt for 30 minutes, and the solvents were removed under reduced pressure. The residue was taken up in 2 mL EtOAc and 3 mL hexanes was added to precipitate the product TFA salt, which was isolated by filtration and dried under high vacuum. A solution of the TFA salt (16 mg) in 20% MeOH/CH$_2$Cl$_2$ was run through a 100 mg cartridge of Varian Stratospheres™ PL-HCO3 MP resin. The solvents were removed under reduced pressure, and the residue was dissolved in 10% MeOH/CH$_2$Cl$_2$ and run through a 200 mg cartridge of Varian Stratospheres™ PL-HCO3 MP resin. The solvents were removed under reduced pressure to provide 26 as the free base. $^1$H NMR (400 MHz, MeOD) δ 8.45 (dd, J=0.8, 7.2, 1 H), 8.18 (s, 1H), 7.75-7.71 (m, 3H), 7.68 (d, J=8.6, 2H), 7.47 (d, J=8.6, 2H), 7.32 (d, J=8.6, 2H), 6.87 (dd, J=1.8, 7.3, 1H), 3.61 (q, J=6.9, 1H), 3.55 (s, 3H), 1.40 (d, J=6.9, 3H). ESI-MS (m/z): [M+H]$^+$ 439.1, RT 1.1711 min.

Example 27

3-(5-carbamoylpyridin-2-yl)-N-(4-cyanophenyl)-N-methylpyrazolo[1,5-a]pyridine-5-carboxamide

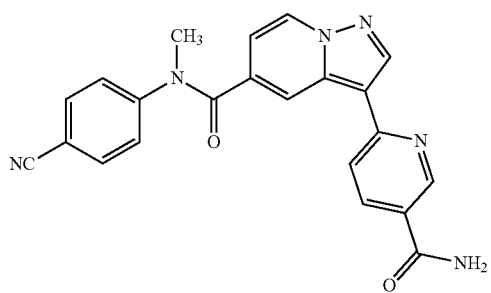

27

Example 27 was prepared according to the procedure described for the synthesis of Example 25 by replacing 2-chloro-5-(trifluoromethyl)pyridine with 6-chloronicotinamide. Purification by silica gel chromatography, eluting with hexanes/EtOAc, then 5% MeOH/CH$_2$Cl$_2$ gave the desired product. $^1$H NMR (400 MHz, DMSO) δ 9.04 (dd, J=0.8, 2.3, 1H), 8.81 (s, 1H), 8.68 (dd, J=0.8, 7.2, 1H), 8.56 (s, 1H), 8.22 (dd, J=2.3, 8.4, 1H), 8.14 (s, 1H), 7.94 (d, J=8.3, 1H), 7.81 (d, J=8.7, 2H), 7.58 (s, 1H), 7.54 (d, J=8.6, 2H), 6.85 (dd, J=1.9, 7.2, 1 H), 3.47 (s, 3H). ESI-MS (m/z): [M+H]$^+$ 397.1, RT 1.2047 min.

Example 28

4-cyano-N-methyl-N-(3-(4-(trifluoromethyl)phenyl) pyrazolo[1,5-a]pyridine-5-yl)benzamide

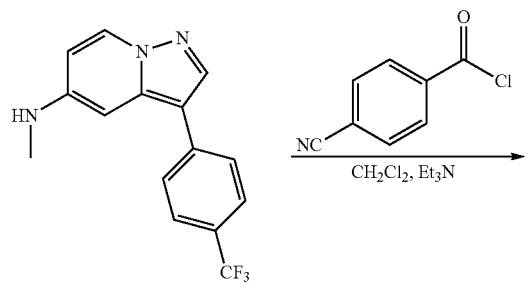

I-58

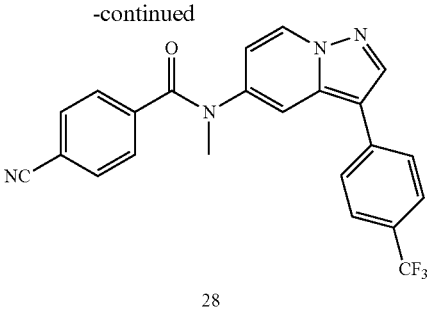

28

To a solution of pyrazolopyridine (15 mg, 0.05 mmol) in CH$_2$Cl$_2$ containing triethylamine (0.020 mL, 3.00 mmol) at 0° C. was added 4-cyanobenzoyl chloride (14 mg, 1.50 mmol). The reaction was allowed to warm to room temperature and stir for 1 hour. The reaction was diluted with water and extracted with dichloromethane. The organic extracts were washed with brine and dried over anhydrous Na$_2$SO$_4$. The solvent was removed and the residue was purified by mass-trigger HPLC. $^1$H NMR (400 MHz, MeOD) δ 8.54 (d, J=7.4, 1H), 8.29 (s, 1H), 7.66 (ddd, J=8.1, 12.9, 29.8, 9H), 6.92 (dd, J=2.2, 7.4, 1H), 3.56 (s, 3H); MS m/z 421.0 (M+H)$^+$.

Example 29

4-fluoro-N-methyl-N-(3-(4-(trifluoromethyl)phenyl) pyrazolo[1,5-a]pyridine-5-yl)benzamide

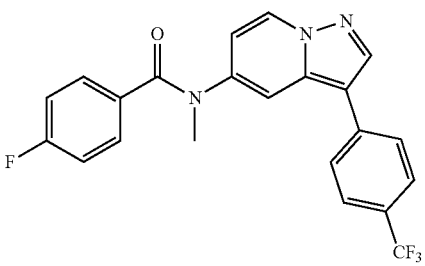

29

Example 29 was prepared according to the procedure described for the synthesis of Example 28 by replacing 4-cyanobenzoyl chloride with 4-fluorobenzoyl chloride. $^1$H NMR (400 MHz, MeOD) δ 8.43 (d, J=7.4, 1H), 8.18 (s, 1H), 8.06-7.84 (m, 1H), 7.60 (d, J=8.3, 2H), 7.50 (d, J=8.5, 3H), 7.40 (dd, J=5.3, 8.8, 2H), 7.08 (t, J=8.8, 1H), 6.96 (t, J=8.8, 2H), 6.78 (d, J=7.4, 1H), 3.45 (s, 3H); MS m/z 414.1 (M+H)$^+$.

Example 30

4-cyano-N-methyl-N-(3-(4-(trifluoromethyl)phenyl) pyrazolo[1,5-a]pyridine-5-yl)benzenesulfonamide

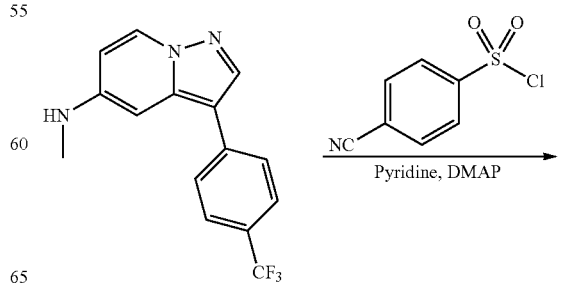

I-58

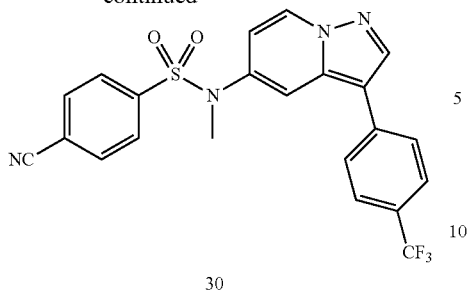

30

To a solution of pyrazolopyridine (15 mg, 0.05 mmol) and a catalytic amount of DMAP in pyridine (1.0 mL) at 0° C. was added 4-cyanobenzene-1-sulfonyl chloride (18 mg, 0.08 mmol). The reaction was allowed to warm to room temperature and stir overnight. The reaction was diluted with water and extracted with dichloromethane. The organic extracts were washed with saturated $CuSO_4$ solution and brine, dried over anhydrous $Na_2SO_4$. The solvent was removed and the crude material was purified by mass-triggered HPLC. $^1$H NMR (400 MHz, MeOD) δ 8.57 (d, J=7.6, 1 H), 8.34 (s, 1H), 7.95 (d, J=8.3, 2H), 7.83 (d, J=8.4, 2H), 7.73 (s, 4H), 7.61 (s, 1H), 6.85 (d, J=7.5, 1 H), 3.32 (s, 3H, obscured by MeOD peak); MS m/z 457.0 (M+H)$^+$.

Example 31

4-fluoro-N-methyl-N-(3-(4-(trifluoromethyl)phenyl) pyrazolo[1,5-a]pyridine-5-yl)benzenesulfonamide

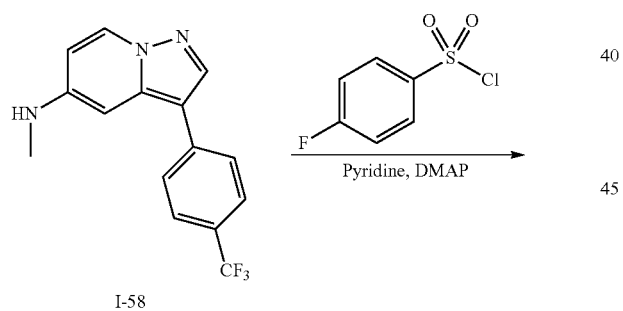

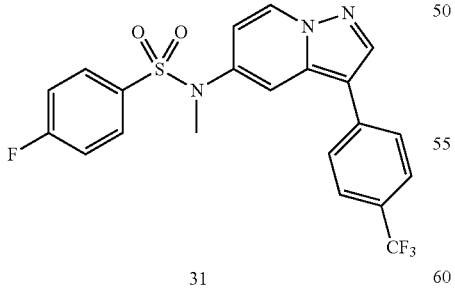

31

Example 31 was prepared according to the procedure described for the synthesis of Example 30 by replacing 4-cyanobenzene-1-sulfonyl chloride with 4-fluorobenzene-1-sulfonyl chloride. ESI-LC/MS m/z 450.0 (M+H)+; r.t.=1.954.

Example 32

3-(4-carbamoylphenyl)-N-(5-cyanopyridin-2-yl)-N-methylpyrazolo[1,5-a]pyridine-5-carboxamide

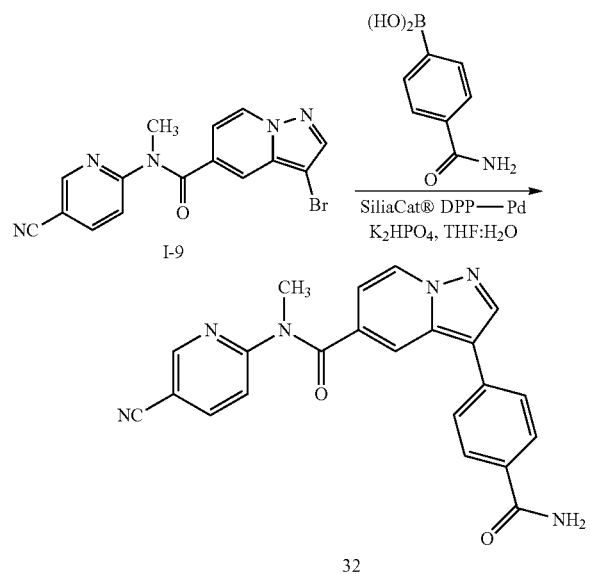

32

Example 32 was prepared from intermediate I-9 according to the procedure described for the synthesis of Example 17 by replacing (1-methyl-1H-indazol-5-yl)boronic acid with (4-carbamoylphenyl)boronic acid. The reaction was purified by silica gel chromatography, eluting with dichloromethane/ethyl acetate then 5% methanol/dichloromethane to give 32 as the desired product. $^1$H NMR (400 MHz, DMSO) δ 8.87 (dd, J=0.6, 2.2, 1H), 8.72 (dd, J=0.7, 7.2, 1 H), 8.53 (s, 1H), 8.26 (dd, J=2.3, 8.6, 1 H), 8.03 (s, 1H), 8.00-7.91 (m, 3H), 7.67-7.57 (m, 3H), 7.40 (s, 1H), 6.85 (dd, J=1.8, 7.2, 1 H), 3.53 (s, 3H). ESI-MS (m/z): [M+H]$^+$ 398.1, RT 1.2637 min.

Example 33

N-methyl-3-(4-(trifluoromethyl)phenyl)-N-(5-(trifluoromethyl)pyridine-2-yl)pyrazolo[1,5-a]pyridine-5-carboxamide

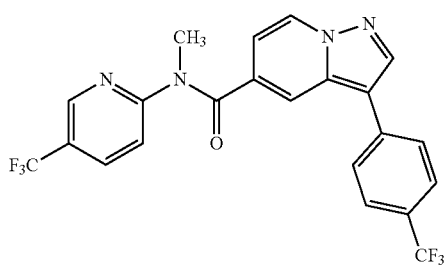

Example 33 was prepared according to the procedure described for the synthesis of Example 1 by replacing 4-(methylamino)benzonitrile with N-methyl-5-(trifluoromethyl)pyridine-2-amine. The reaction was purified by mass-triggered HPLC to provide 33 as the desired product. ESI-MS (m/z): [M+H]⁺ 465.1, RT 2.0724 min.

Example 34

N-methyl-N-(5-(methylsulfonyl)127yridine-2-yl)-3-(4-(trifluoromethyl)phenyl)pyrazolo[1,5-a]pyridine-5-carboxamide

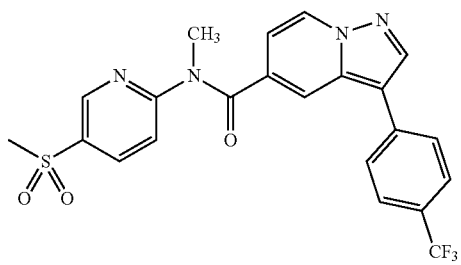 [SMILES: CN(C(=O)c1ccn2ncc(-c3ccc(C(F)(F)F)cc3)c2c1)c1ccc(S(C)(=O)=O)cn1]

Example 33 was prepared according to the procedure described for the synthesis of Example 1 by replacing 4-(methylamino)benzonitrile with N-methyl-5-(methylsulfonyl)pyridine-2-amine. The reaction was purified by silica gel chromatography, eluting with hexanes/EtOAc, followed by purification by mass-triggered HPLC to provide 34 as the desired product. ¹H NMR (400 MHz, MeOD) δ 8.89 (d, J=2.4, 1 H), 8.56 (d, J=7.2, 1 H), 8.35 (s, 1H), 8.23 (dd, J=2.5, 8.6, 1 H), 7.91 (s, 1H), 7.75 (d, J=8.3, 2H), 7.66 (d, J=8.2, 2H), 7.56 (d, J=8.6, 1H), 6.94 (dd, J=1.8, 7.3, 1H), 3.65 (s, 3H), 3.12 (s, 3H). ESI-MS (m/z): [M+H]⁺ 475.1, RT 1.7860 min.

Example 35

N-(4-fluorobenzyl)-3-(4-(trifluoromethyl)phenyl)pyrazolo[1,5-a]pyridine-5-amine

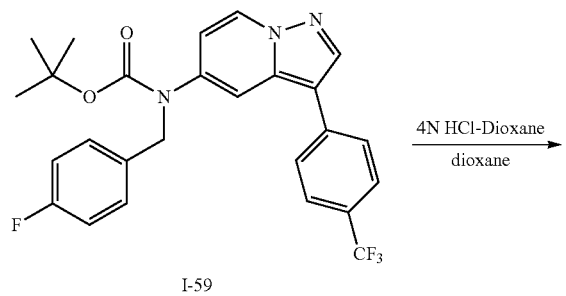

I-59

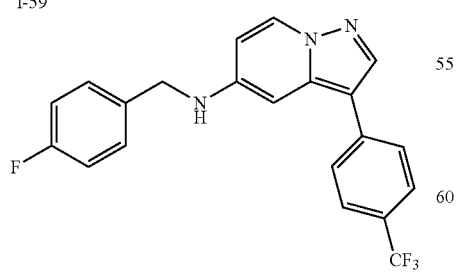

35

To a stirred solution of pyrazolopyridine (25 mg, 0.05 mmol) in dioxane (1.0 mL) was added 4N HCl in dioxane (1.0 mL). The reaction was monitored by LCMS and when the reaction was complete, the resultant HCl salt was filtered and dried to give 35. ESI-LC/MS m/z 386.1 (M+H)+; r.t.=2.167.

Example 36

N-(4-fluorobenzyl)-N-methyl-3-(4-(trifluoromethyl)phenyl)pyrazolo[1,5-a]pyridine-5-amine

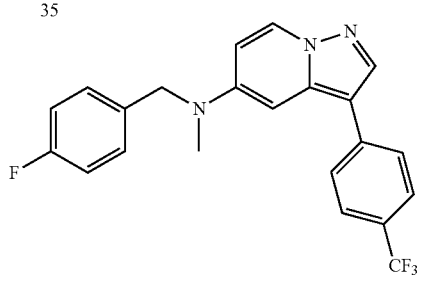

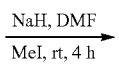

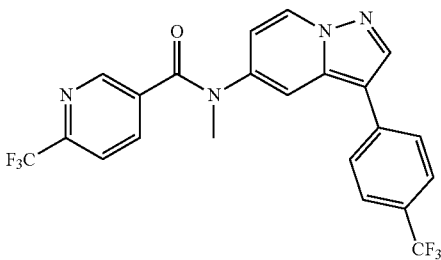

36

NaH (5 mg, 0.08 mmol) was added to a solution of pyrazolopyridine (19 mg, 0.05 mmol) and DMF (1.0 mL). MeI (0.020 mL, 0.06 mmol) was added and the reaction was stirred for 4 h at room temperature. The reaction was quenched by addition of H₂O. The solution was extracted with ethyl acetate. The combined extracts were washed with brine, dried over anhydrous Na₂SO₄ and concentrated. The crude material was purified by silica gel chromatography, eluting with ethyl acetate and hexanes. ¹H NMR (400 MHz, MeOD) δ 8.21 (d, J=8.7, 1H), 8.02 (s, 1H), 7.57 (q, J=8.7, 4H), 7.19 (dd, J=5.4, 8.5, 2H), 6.98 (t, J=8.8, 2H), 6.78-6.63 (m, 2H), 4.60 (s, 2H), 3.09 (s, 3H); MS m/z 400.2 (M+H)⁺.

Example 37

N-methyl-6-(trifluoromethyl)-N-(3-(4-(trifluoromethyl)phenyl)pyrazolo[1,5-a]pyridine-5-yl)nicotinamide

37

Example 37 was prepared according to the procedure described for the synthesis of Example 28 by replacing 4-cyanobenzoyl chloride with 6-(trifluoromethyl)nicotinoyl chloride. ¹H NMR (400 MHz, MeOD) δ 8.69 (s, 1H), 8.48 (d, J=7.5, 1H), 8.20 (s, 1H), 7.97 (d, J=8.1, 1H), 7.63 (dd, J=8.2, 24.5, 5H), 7.48 (d, J=8.1, 2H), 6.86 (dd, J=2.2, 7.4, 1H), 3.48 (s, 3H). ESI-LC/MS m/z 465.1 (M+H)+; r.t.=1.696.

Example 38

N-methyl-5-(trifluoromethyl)-N-(3-(4-(trifluoromethyl)phenyl)pyrazolo[1,5-a]pyridin-5-yl)picolinamide

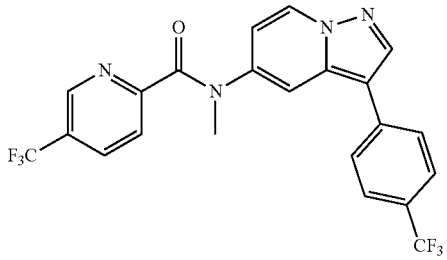

38

Example 38 was prepared according to the procedure described for the synthesis of Example 28 by replacing 4-cyanobenzoyl chloride with 5-(trifluoromethyl)picolinoyl chloride. ¹H NMR (400 MHz, CDCl3) δ 8.56 (s, 1H), 8.35 (d, J=7.4, 1 H), 8.08 (s, 1H), 7.94 (d, J=6.9, 1H), 7.81 (d, J=8.2, 1H), 7.59 (d, J=8.2, 2H), 7.40 (d, J=7.8, 2H), 7.32 (s, 1H), 6.63 (s, 1H), 3.51 (s, 3H). ESI-LC/MS m/z 465.1 (M+H)+; r.t.=1.740.

Example 39

4-cyano-N-((tetrahydro-2H-pyran-4-yl)methyl)-N-(3-(4-(trifluoromethyl)phenyl)pyrazolo[1,5-a]pyridin-5-yl)benzamide

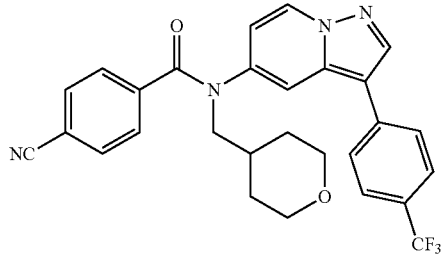

39

Example 39 was prepared according to the procedure described for the synthesis of Example 28. ¹H NMR (400 MHz, CDCl3) δ 8.35 (d, J=7.4, 1H), 8.09 (s, 1H), 7.61 (d, J=8.1, 2H), 7.52 (d, J=8.4, 2H), 7.43 (d, J=8.5, 2H), 7.29 (d, J=8.1, 2H), 7.17 (s, 1H), 6.50 (dd, J=2.3, 7.4, 1 H), 3.97-3.81 (m, 4H), 3.25 (dd, J=9.8, 11.7, 2H), 1.96 (d, J=13.1, 1H), 1.55 (d, J=18.6, 2H), 1.45-1.29 (m, 2H). ESI-LC/MS m/z 505.1 (M+H)+; r.t.=1.689.

Example 40

N-(4-cyanophenyl)-N-methyl-3-(1H-pyrrolo[2,3-b]pyridin-5-yl)pyrazolo[1,5-a]pyridine-5-carboxamide

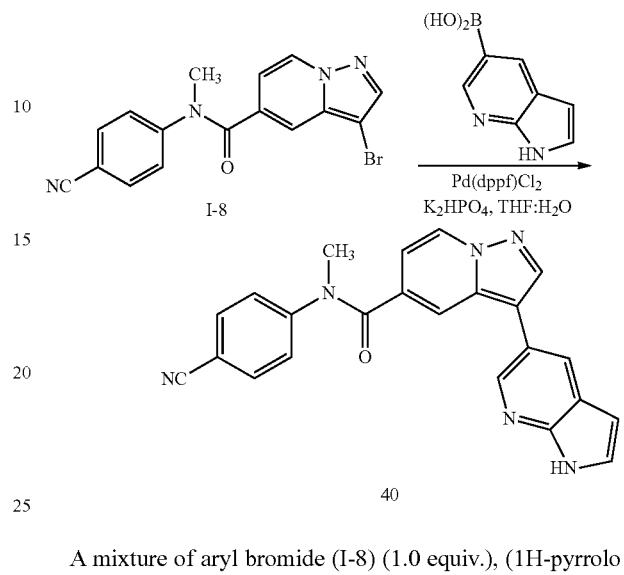

A mixture of aryl bromide (I-8) (1.0 equiv.), (1H-pyrrolo[2,3-b]pyridin-5-yl)boronic acid (1.5 equiv.), K₂HPO₄ (2.5 equiv.), and Pd(dppf)Cl2 (0.05-0.15 equiv.) in THF/water was allowed to heat at 80° C. overnight. The solvent was removed and the crude residue was purified by silica gel chromatography, eluting with hexanes/EtOAc, then 5% MeOH/CH₂Cl₂ gave the desired product. ¹H NMR (400 MHz, DMSO) δ 11.76 (s, 1H), 8.64 (dd, J=0.7, 7.2, 1H), 8.39 (s, 1H), 8.33 (d, J=2.1, 1H), 7.88 (d, J=2.0, 1H), 7.84 (d, J=8.6, 2H), 7.79 (s, 1H), 7.59-7.50 (m, 3H), 6.79 (dd, J=1.8, 7.2, 1H), 6.53 (dd, J=1.8, 3.4, 1 H), 3.46 (s, 3H). ESI-MS (m/z): [M+H]⁺ 393.1, RT 1.1533 min.

Example 41

3-(6-aminopyridin-3-yl)-N-(4-cyanophenyl)-N-methylpyrazolo[1,5-a]pyridine-5-carboxamide

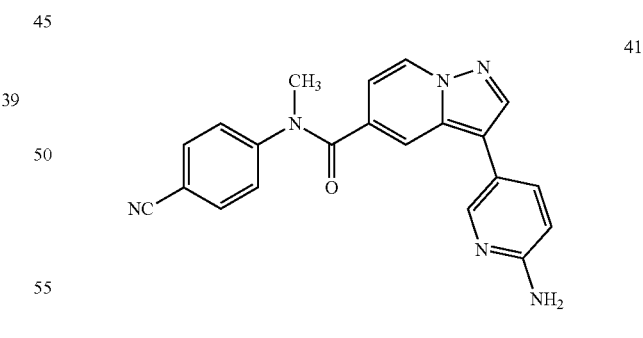

Example 41 was prepared according to the procedure described for the synthesis of Example 40 by replacing (1H-pyrrolo[2,3-b]pyridin-5-yl)boronic acid with (6-aminopyridin-3-yl)boronic acid. The reaction was purified by silica gel chromatography, eluting with hexanes/EtOAc, then 5% MeOH/CH₂Cl₂, followed by purification by mass-triggered HPLC and a NaHCO₃/EtOAc workup gave the desired product. ¹H NMR (400 MHz, MeOD) δ 8.43 (dd, J=0.7, 7.3, 1H), 8.12 (s, 1H), 7.93 (d, J=1.6, 1H), 7.72 (d, J=8.6, 2H), 7.68 (s, 1H), 7.50 (dd, J=2.4, 8.6, 1 H), 7.46 (d, J=8.6, 2H), 6.83 (dd, J=1.8, 7.3, 1 H), 6.69 (d, J=8.6, 1 H), 3.54 (s, 3H). ESI-MS (m/z): [M+H]+ 369.1, RT 0.8592 min.

Example 42

3-(4-aminophenyl)-N-(4-cyanophenyl)-N-methyl-pyrazolo[1,5-a]pyridine-5-carboxamide

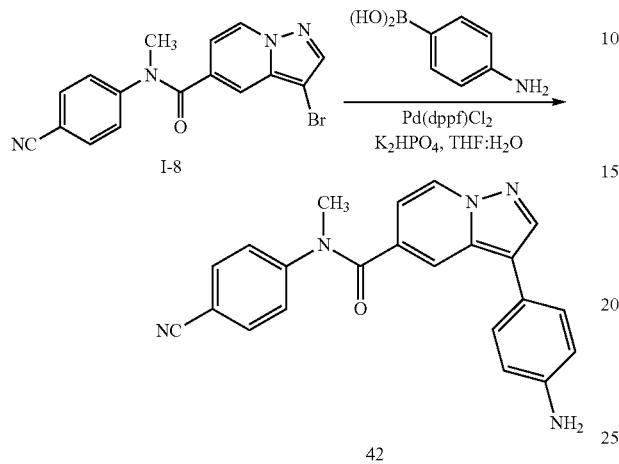

A mixture of aryl bromide (I-8) (1.0 equiv.), (4-aminophenyl)boronic acid (1.5 equiv.), K₂HPO₄ (2.5 equiv.), and Pd(dppf)Cl2 (0.05-0.15 equiv.) in THF/water was allowed to heat at 110° C. overnight. The solvent was removed and the crude residue was by silica gel chromatography, eluting with hexanes/EtOAc gave the desired product. ESI-MS (m/z): [M+H]+ 368.1, RT 1.0446 min.

Example 43

3-(4-(2-aminoacetamido)phenyl)-N-(4-cyanophenyl)-N-methylpyrazolo[1,5-a]pyridine-5-carboxamide

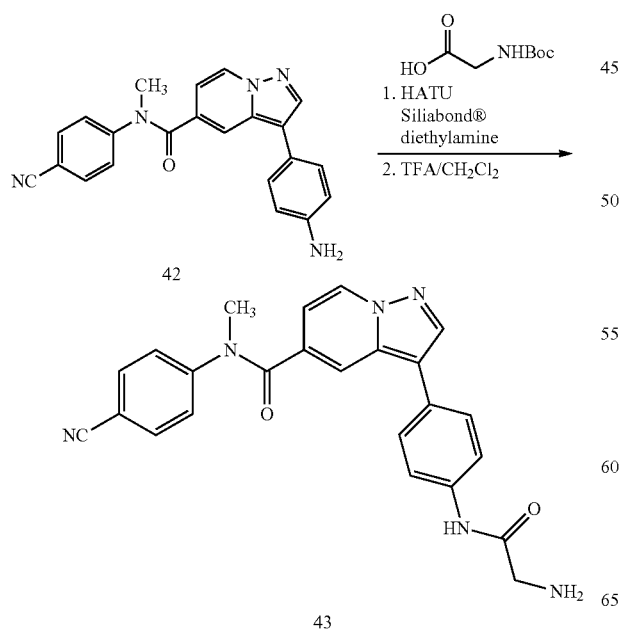

A solution of Example 42 (1.0 equiv.) in CH₂Cl₂ (~0.1 M) was treated with 2-((tert-butoxycarbonyl)amino)acetic acid (1.2 equiv.), followed by HATU (1.1 equiv (2.5 equiv.). The resulting mixture was allowed to stir at rt for two hours, and then was filtered and treated with one volume of TFA. The resulting solution was allowed to stir at rt for 30 minutes, and the solvents were removed under reduced pressure. The residue was purified by mass-triggered HPLC to provide the desired product. ESI-MS (m/z): [M+H]+ 425.1, RT 1.1033 min.

Example 44

(R)-3-(4-(2-aminopropanamido)phenyl)-N-(4-cyanophenyl)-N-methylpyrazolo[1,5-a]pyridine-5-carboxamide

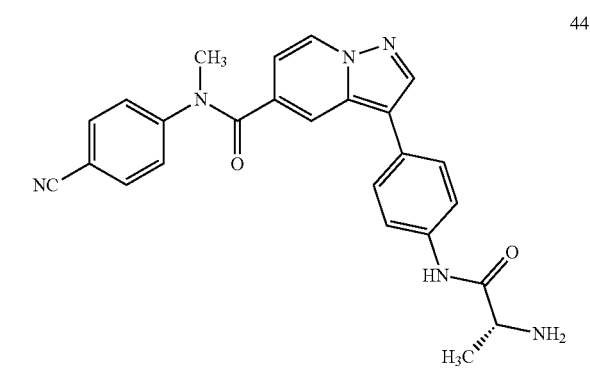 [SMILES: C[C@@H](N)C(=O)Nc1ccc(-c2cnn3ccc(C(=O)N(C)c4ccc(C#N)cc4)cc23)cc1]

44

Example 44 was prepared according to the procedure described for the synthesis of Example 43 by replacing 2-((tert-butoxycarbonyl)amino)acetic acid with (R)-2-((tert-butoxycarbonyl)amino)propanoic acid. ESI-MS (m/z): [M+H]+ 439.2, RT 1.0950 min.

Example 45

(S)-3-(4-(2-amino-3-methylbutanamido)phenyl)-N-(4-cyanophenyl)-N-methylpyrazolo[1,5-a]pyridine-5-carboxamide

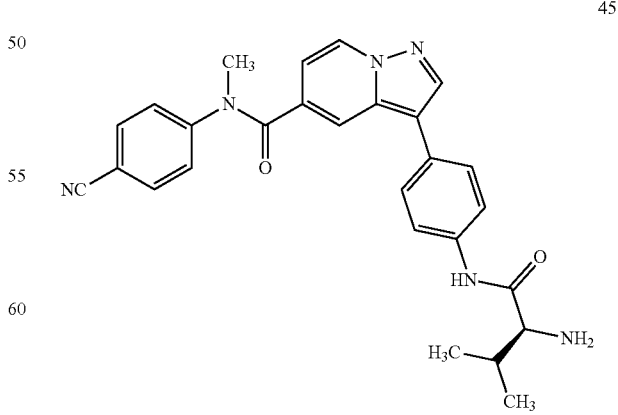

45

Example 45 was prepared according to the procedure described for the synthesis of Example 43 by replacing 2-((tert-butoxycarbonyl)amino)acetic acid with (S)-2-((tert-butoxycarbonyl)amino)-3-methylbutanoic acid. ESI-LC/MS m/z 467.2 (M+H)+; RT=1.230.

Example 46

(S)-3-(4-(2-amino-2-cyclohexylacetamido)phenyl)-N-(4-cyanophenyl)-N-methylpyrazolo[1,5-a]pyridine-5-carboxamide

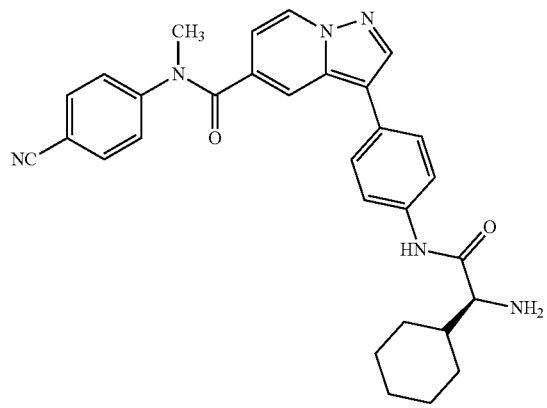

46

Example 46 was prepared according to the procedure described for the synthesis of Example 43 by replacing 2-((tert-butoxycarbonyl)amino)acetic acid with (S)-2-((tert-butoxycarbonyl)amino)-2-cyclohexylacetic acid. ESI-MS (m/z): [M+H]⁺ 507.2, RT 1.4154 min.

Example 47

3-(4-fluorophenyl)-1-methyl-1-(3-(4-(trifluoromethyl)phenyl)pyrazolo[1,5-a]pyridin-5-yl)urea

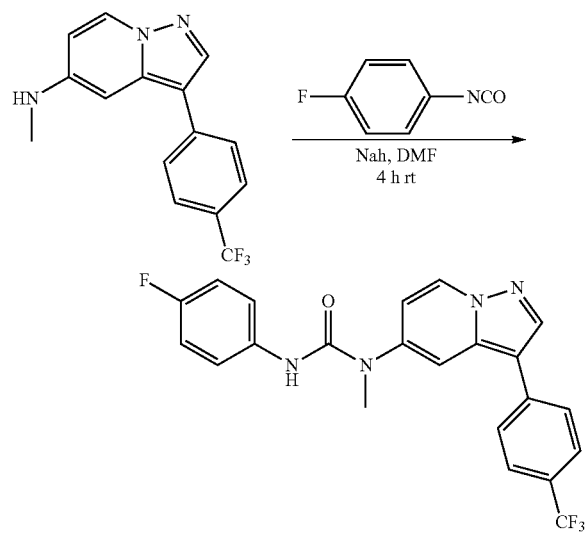

47

NaH (8 mg, 0.15 mmol) was added to a solution of pyrazolopyridine (30 mg, 0.10 mmol) and DMF (2.0 mL). The reaction was stirred at room temperature for 15 minutes. The isocyanate was added and the reaction stirred at room temperature for an additional 4 hours. The reaction was quenched with water and extracted with ethyl acetate. The combined organic extracts were washed with brine and dried over anhydrous Na₂SO₄. The solvent was removed and the material was purified by silica gel chromatography eluting with ethyl acetate and hexanes. ¹H NMR (400 MHz, CDCl3) δ 8.49 (d, J=7.3, 1H), 8.16 (s, 1H), 7.61 (dd, J=8.5, 25.1, 5H), 7.19 (s, 3H), 6.89 (t, J=7.5, 2H), 6.76 (d, J=7.3, 1 H), 6.31 (s, 1H), 3.33 (s, 3H).

Example 48

6-(1,1-difluoroethyl)-N-methyl-N-(3-(4-(trifluoromethyl)phenyl)pyrazolo[1,5-a]pyridin-5-yl)nicotinamide

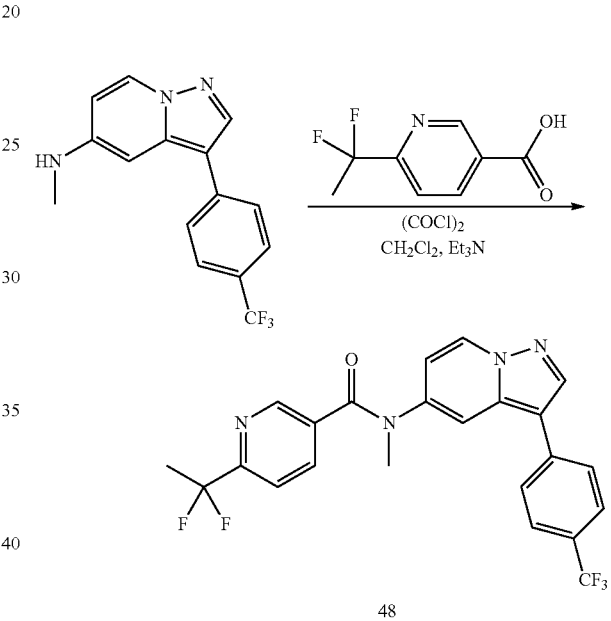

48

To a solution of 6-(1,1-difluoroethyl)nicotinic acid (28 mg, 0.15 mmol) in dichloromethane (1.00 mL) was added triethyl amine (0.042 mL, 0.30 mmml) and a catalytic amount of DMF. The reaction was cooled to 0° C. Oxallyl chloride was added dropwise and the reaction mixture was stirred for 30 minutes. The solvent was removed and the solid was dried under vacuum for 15 minutes. To the crude acid chloride was added dichloromethane (1.00 mL) and triethylamine (0.042 mL, 0.30 mmol) followed by the amine (29 mg, 0.10 mmol) at 0° C. The reaction was allowed to warm to room temperature and stir for two hours. The reaction was quenched with water, extracted with dichloromethane, washed with brine, dried over Na₂SO₄ and concentrated. The reaction was purified by silica gel chromatography, eluting with ethyl acetate and hexanes. ¹H NMR (400 MHz, CDCl₃) δ 8.67 (s, 1H), 8.46 (d, J=7.4, 1H), 8.17 (s, 1H), 7.92 (d, J=8.1, 1H), 7.69 (d, J=8.1, 2H), 7.63 (d, J=8.1, 1H), 7.41 (d, J=7.9, 2H), 7.35 (s, 1H), 6.64 (d, J=7.3, 1H), 3.60 (s, 3H). ESI-LC/MS m/z 461.1 (M+H)+; r.t.=1.993.

Example 49

6-cyclopropyl-N-methyl-N-(3-(4-(trifluoromethyl)phenyl)pyrazolo[1,5-a]pyridin-5-yl)nicotinamide

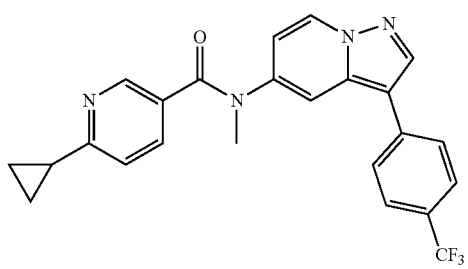

49

Example 49 was prepared according to the procedure described for the synthesis of Example 48 by replacing 6-(1,1-difluoroethyl)nicotinic acid with 6-cyclopropylnicotinic acid. ESI-LC/MS m/z 437.1 (M+H)+; RT=1.640.

Example 50

4-cyclopropyl-N-methyl-N-(3-(4-(trifluoromethyl)phenyl)pyrazolo[1,5-a]pyridin-5-yl)benzamide

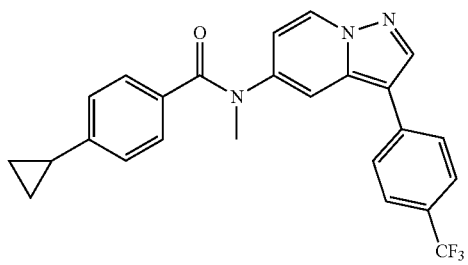

50

Example 50 was prepared according to the procedure described for the synthesis of Example 48 by replacing 6-(1,1-difluoroethyl)nicotinic acid with 4-cyclopropylbenzoic acid. ESI-LC/MS m/z 436.0 (M+H)+; RT=2.408.

Example 51

5-fluoro-N-methyl-N-(3-(4-(trifluoromethyl)phenyl)pyrazolo[1,5-a]pyridin-5-yl)picolinamide

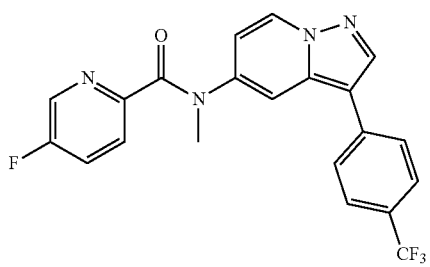

51

Example 51 was prepared according to the procedure described for the synthesis of Example 48 by replacing 6-(1,1-difluoroethyl)nicotinic acid with 5-fluoropicolinic acid. $^1$H NMR (400 MHz, CDCl3) δ 7.71 (d, J=7.4, 1 H), 7.48 (s, 1H), 7.46 (s, 1H), 7.00 (s, 1H), 6.95-6.78 (m, 6H), 6.08 (d, J=7.4, 1H), 2.80 (d, J=38.0, 3H). ESI-LC/MS m/z 415.0 (M+H)+; r.t.=2.158.

Example 52

N-methyl-4-(methylsulfonyl)-N-(3-(4-(trifluoromethyl)phenyl)pyrazolo[1,5-a]pyridin-5-yl)benzamide

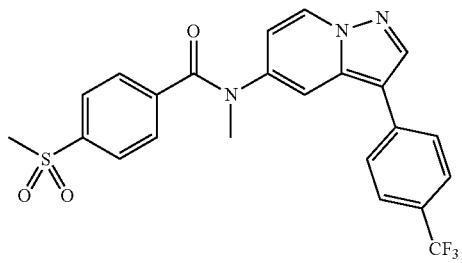

52

Example 52 was prepared according to the procedure described for the synthesis of Example 48 by replacing 6-(1,1-difluoroethyl)nicotinic acid with 4-(methylsulfonyl)benzoic acid. ESI-LC/MS m/z 474.1 (M+H)+; RT=2.071

Example 53

N-(5-cyanopyridin-2-yl)-N-methyl-3-(1H-pyrrolo[2,3-b]pyridin-5-yl)pyrazolo[1,5-a]pyridine-5-carboxamide

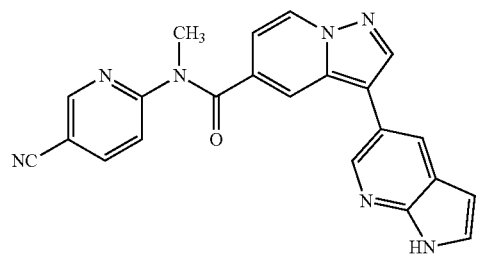

53

Example 53 was prepared from intermediate I-9 according to the procedure described for the synthesis of Example 32 by replacing (4-carbamoylphenyl)boronic acid with (1H-pyrrolo[2,3-b]pyridin-5-yl)boronic acid. Purification by silica gel chromatography, eluting with hexanes/EtOAc, and then 5% EtOH/EtOAc gave the desired product. $^1$H NMR (400 MHz, DMSO) δ 11.76 (s, 1H), 8.88 (dd, J=0.6, 2.3, 1 H), 8.70 (dd, J=0.8, 7.2, 1 H), 8.44 (s, 1H), 8.38 (d, J=2.1, 1 H), 8.26 (dd, J=2.3, 8.6, 1 H), 7.99 (d, J=2.0, 1 H), 7.91 (s, 1H), 7.60 (dd, J=0.5, 8.6, 1H), 7.57-7.50 (m, 1H), 6.82

(dd, J=1.8, 7.2, 1H), 6.51 (dd, J=1.8, 3.4, 1 H), 3.53 (s, 3H). ESI-MS (m/z): [M+H]⁺ 394.0, RT 1.4237 min.

Example 54

3-(6-aminopyridin-3-yl)-N-(5-cyanopyridin-2-yl)-N-methylpyrazolo[1,5-a]pyridine-5-carboxamide

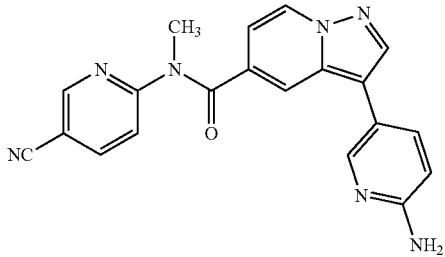

Example 54 was prepared from intermediate I-9 according to the procedure described for the synthesis of Example 32 by replacing (4-carbamoylphenyl)boronic acid with (6-aminopyridin-3-yl)boronic acid. Purification by silica gel chromatography, eluting with hexanes/EtOAc, and then 10% EtOH/EtOAc gave the desired product. ¹H NMR (400 MHz, DMSO) δ 8.84 (d, J=2.3, 1 H), 8.63 (dd, J=0.7, 7.3, 1 H), 8.29 (s, 1H), 8.23 (dd, J=2.3, 8.6, 1 H), 8.09 (d, J=2.2, 1 H), 7.86-7.80 (m, 1H), 7.58 (d, J=8.6, 1 H), 7.54 (dd, J=2.5, 8.5, 1 H), 6.75 (dd, J=1.8, 7.2, 1 H), 6.54 (d, J=8.6, 1 H), 6.05 (s, 2H), 3.52 (s, 3H). ESI-MS (m/z): [M+H]⁺ 370.0, RT 1.2469 min.

Example 55

4-chloro-N-methyl-N-(3-(4-(trifluoromethyl)phenyl)pyrazolo[1,5-a]pyridin-5-yl)benzamide

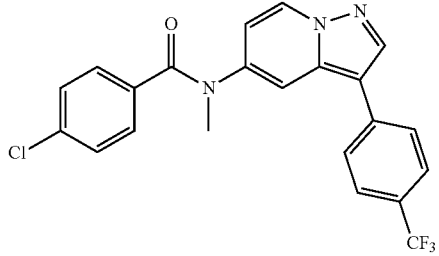

Example 25 was prepared according to the procedure described for the synthesis of Example 28 by replacing 4-cyanobenzoyl chloride with 4-fluorobenzoyl chloride. ¹H NMR (400 MHz, CDCl3) δ 8.33 (d, J=7.5, 1 H), 8.07 (s, 1H), 7.58 (d, J=8.2, 2H), 7.42-7.26 (m, 4H), 7.26-7.12 (m, 3H), 6.53 (dd, J=2.3, 7.4, 1 H), 3.47 (s, 3H). ESI-LC/MS m/z 430.0 (M+H)+; r.t.=2.376.

Example 56

N-(3-(4-carbamoylphenyl)pyrazolo[1,5-a]pyridin-5-yl)-4-fluoro-N-methylbenzamide

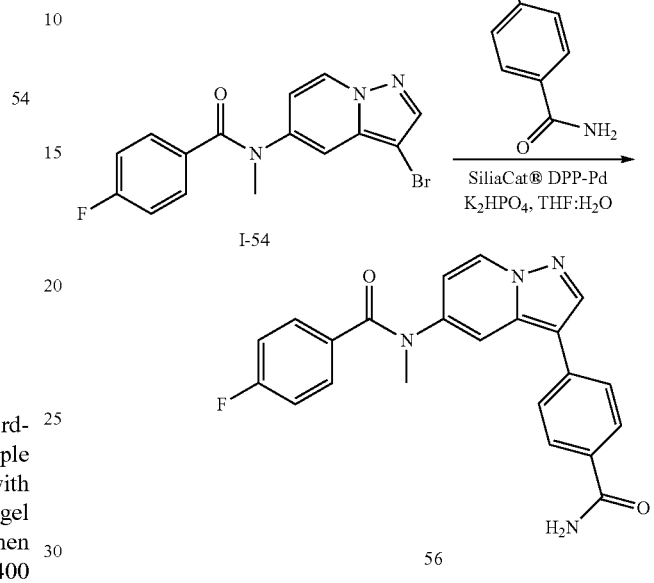

Example 56 was prepared from intermediate I-54 according to the procedure described for the synthesis of Example 17 by replacing (1-methyl-1H-indazol-5-yl)boronic acid with (4-carbamoylphenyl)boronic acid. ESI-LC/MS m/z 389.1 (M+H)+; r.t.=1.603.

Example 57

4-fluoro-N-methyl-N-(3-(4-(5-(methylamino)-1,3,4-thiadiazol-2-yl)phenyl)pyrazolo[1,5-a]pyridin-5-yl)benzamide

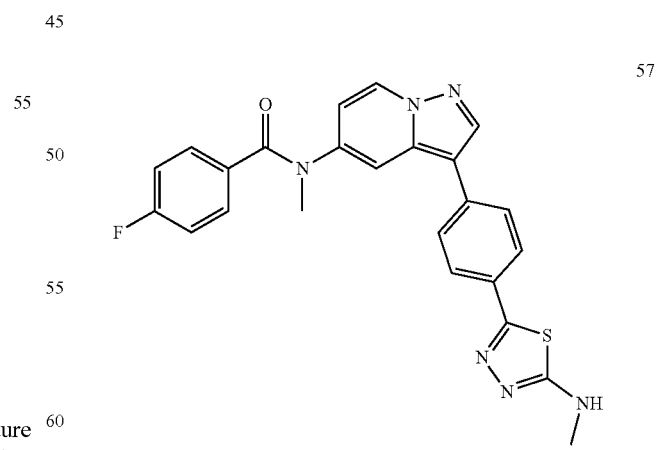

Example 57 was prepared from intermediate I-54 according to the procedure described for the synthesis of Example 17 by replacing (1-methyl-1H-indazol-5-yl)boronic acid with (4-(5-(methylamino)-1,3,4-thiadiazol-2-yl)phenyl)boronic acid. ¹H NMR (400 MHz, MeOD) δ 8.53 (d, J=7.4, 1

H), 8.29 (s, 1H), 7.85 (d, J=8.4, 2H), 7.66-7.45 (m, 5H), 7.07 (t, J=8.8, 2H), 6.90 (dd, J=2.3, 7.5, 1H), 3.56 (s, 3H), 3.12 (s, 3H). ESI-LC/MS m/z 459.0 (M+H)+; r.t.=1.708.

Example 58

N-methyl-N-(5-(methylsulfonyl)pyridin-2-yl)-3-(1H-pyrrolo[2,3-b]pyridin-5-yl)pyrazolo[1,5-a]pyridine-5-carboxamide

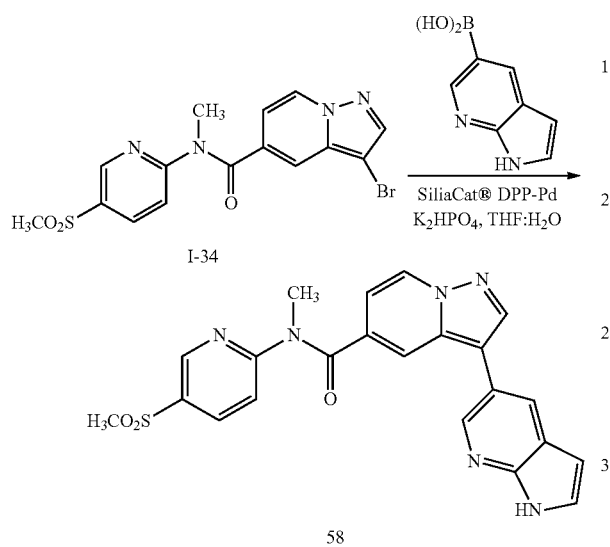

Example 58 was prepared from intermediate I-66 according to the procedure described for the synthesis of Example 17 by replacing (1-methyl-1H-indazol-5-yl)boronic acid with (1H-pyrrolo[2,3-b]pyridin-5-yl)boronic acid. ESI-MS (m/z): [M+H]$^+$ 447.0, RT 1.3983 min. ESI-LC/MS m/z 447.0 (M+H)+; r.t.=1.398.

Example 59

N-(5-cyanopyridin-2-yl)-N-methyl-3-(5-methylpyridin-2-yl)pyrazolo[1,5-a]pyridine-5-carboxamide

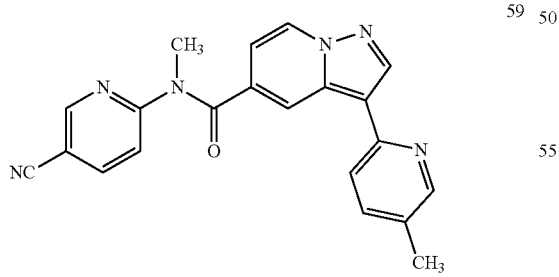

Example 29 was prepared according to the procedure described for the synthesis of Example 25 by replacing 2-chloro-5-(trifluoromethyl)pyridine with 2-chloro-5-methylpyridine. The reaction was purified by mass-triggered HPLC to provide the desired product. ESI-MS (m/z): [M+H]$^+$ 369.1, RT 1.3394 min.

Example 60

N-(5-cyanopyridin-2-yl)-3-(5-methoxypyridin-2-yl)-N-methylpyrazolo[1,5-a]pyridine-5-carboxamide

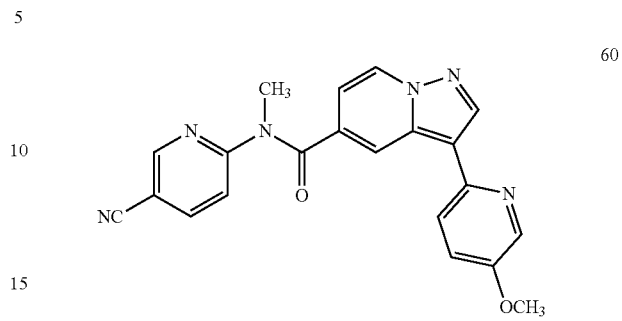

Example 60 was prepared according to the procedure described for the synthesis of Example 25 by replacing 2-chloro-5-(trifluoromethyl)pyridine with 2-chloro-5-methoxypyridine. The reaction was purified by mass-triggered HPLC to provide the desired product. ESI-MS (m/z): [M+H]$^+$ 385.1, RT 1.5073 min.

Example 61

3-(5-carbamoylpyridin-2-yl)-N-(5-cyanopyridin-2-yl)-N-methylpyrazolo[1,5-a]pyridine-5-carboxamide

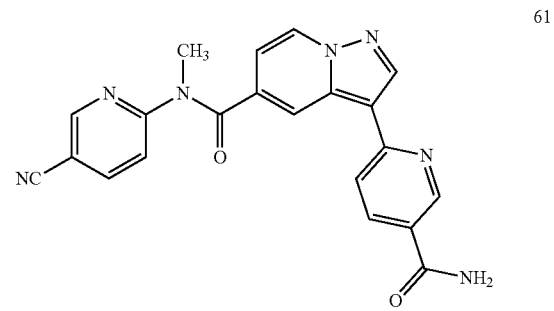 [SMILES: CN(C(=O)c1ccn2ncc(-c3ccc(C(N)=O)cn3)c2c1)c1ccc(C#N)cn1]

Example 61 was prepared according to the procedure described for the synthesis of Example 25 by replacing 2-chloro-5-(trifluoromethyl)pyridine with 6-chloronicotinamide. The reaction was purified by mass-triggered HPLC to provide the desired product. ESI-MS (m/z): [M+H]$^+$ 398.1, RT 1.4232 min.

Example 62

3-(4-carbamoylphenyl)-N-methyl-N-(5-(trifluoromethyl)pyridin-2-yl)pyrazolo[1,5-a]pyridine-5-carboxamide

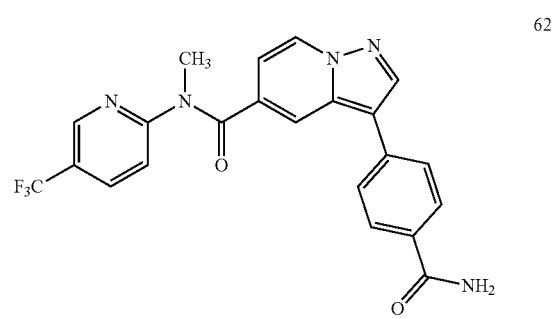 [SMILES: CN(C(=O)c1ccn2ncc(-c3ccc(C(N)=O)cc3)c2c1)c1ccc(C(F)(F)F)cn1]

Example 62 was prepared according to the procedure described for the synthesis of Example 32. The reaction was purified by mass-triggered HPLC to provide the desired product. ESI-MS (m/z): [M+H]+ 440.0, RT 1.7179 min.

Example 63

3-(4-carbamoylphenyl)-N-methyl-N-(5-methylpyridin-2-yl)pyrazolo[1,5-a]pyridine-5-carboxamide

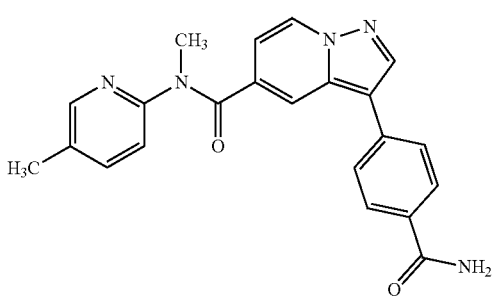

Example 63 was prepared according to the procedure described for the synthesis of Example 32. The reaction was purified by mass-triggered HPLC to provide the desired product. ESI-MS (m/z): [M+H]+ 386.1, RT 1.4742 min.

Example 64

N-(4-fluorophenyl)-N-methyl-3-(4-(methylcarbamoyl)phenyl)pyrazolo[1,5-a]pyridine-5-carboxamide

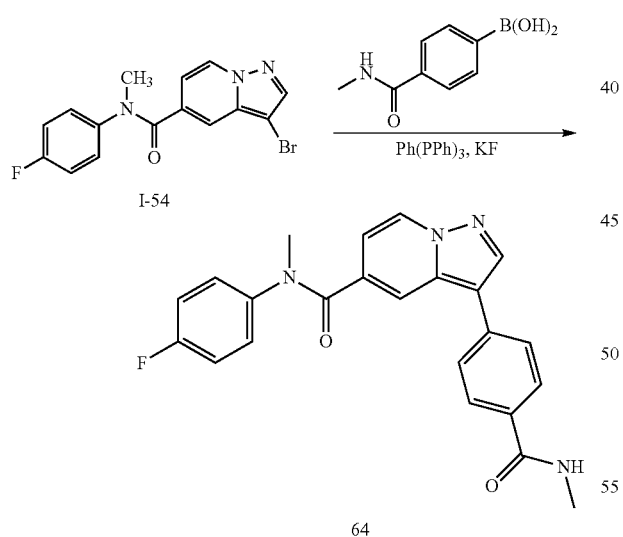

A mixture of aryl bromide (I-54, 1.0 equiv.), (4-(methylcarbamoyl)phenyl)boronic acid (2.0 equiv.), KF (2.0 equiv.), and Pd(PPh)$_3$ (0.05 equiv.) in 1,4-dioxane/DME/water was allowed to heat at 100° C. in a microwave reactor for 5 minutes. Following extraction of the reaction mixture with ethyl acetate, the solvent was removed under reduced pressure and the residue was purified by silica gel chromatography, eluting with ethyl acetate and hexanes to give 64 as the desired product. $^1$H NMR (400 MHz, Methanol-d$_4$) δδ ppm 8.46 (d, J=8.00 Hz, 1H) 8.26 (s, 1H), 7.89 (d, J=8.00 Hz, 2H) 7.76 (s, 1H), 7.49 (d, J=8.00 Hz, 2H) 7.32-7.35 (m, 2H) 7.12 (t, J=8.00 Hz, 2H) 6.91 (d, J=8.00 Hz, 1H) 3.50 (s, 3H) 2.96 (s, 3H); ESI-MS (m/z): [M+H]+ 403.

Example 65

4-(5-(1-(methyl(5-methylpyridin-2-yl)amino)ethyl)pyrazolo[1,5-a]pyridin-3-yl)benzamide

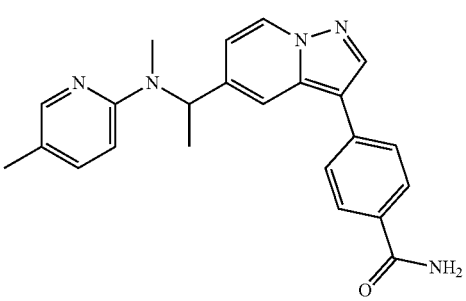

Example 65 was prepared from intermediate I-19 according to general Suzuki procedure E. A mixture of aryl bromide (I-19, 1.0 equiv.), (4-carbamoylphenyl)boronic acid (1.5 equiv.), 2 M aq KF (3 equiv.), and Pd$_2$(dba)$_3$ (0.1 equiv.), P(o-tolyl)$_3$(0.1 equiv.) in toluene:ethanol (7:3) was degassed and heated to 90° C. for 4 h. The crude product was purified by silica gel chromatography, eluting with ethyl acetate and hexanes to give 65 as the desired product. $^1$H NMR (400 MHz, DMSO-d$_6$): δ 8.65 (d, J=7.50 Hz, 1H), 8.43 (s, 1H), 7.97 (d, J=8.3 Hz, 4H), 7.75 (d, J=7.9 Hz, 3H), 7.42-7.40 (m, 1H), 7.38 (d, J=5.0 Hz, 1H), 6.75 (d, J=7.10 Hz, 1H), 6.60 (d, J=8.8 Hz, 1H), 6.14-6.11 (m, 1H), 2.70 (s, 3H), 2.15 (s, 3H), 1.57 (d, J=7.9 Hz, 3H); ESI-MS (m/z): [M+H]+ 386.1.

Example 66

4-(5-(1-(7-fluoro-3-oxo-2H-benzo[b][1,4]oxazin-4(3H)-yl)ethyl)pyrazolo[1,5-a]pyridin-3-yl)benzamide

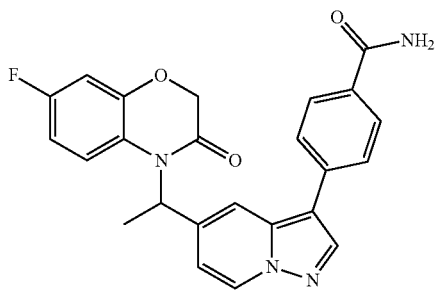

Example 66 was prepared from intermediate I-67 according to general Suzuki procedure E. A mixture of aryl bromide (I-67, 1.0 equiv.), (4-carbamoylphenyl)boronic acid (1.5 equiv.), 2 M aq KF (3 equiv.), and Pd$_2$(dba)$_3$ (0.1 equiv.), P(o-tolyl)$_3$(0.1 equiv.) in toluene:ethanol (7:3) was degassed and heated to 90° C. for 7 h. The crude compound was purified by silica gel chromatography, eluting with 2% MeOH/DCM to give 4-(5-(1-(7-fluoro-3-oxo-2H-benzo[b][1,4]oxazin-4(3H)-yl)ethyl)pyrazolo[1,5-a]pyridin-3-yl)benzamide 66 as the desired product (37%). $^1$H NMR (400 MHz, DMSO-d$_6$). δ 8.69 (d, J=7.50 Hz, 1H), 8.47 (s, 1H), 8.01 (s, 1H), 7.98 (d, J=8.4 Hz, 1H), 7.90 (s, 1H), 7.80 (d, J=8.4 Hz, 2H), 7.37 (br. s, 1H), 7.02 (dd, J=3.1, 9.4 Hz, 1H), 6.96-6.92 (m, 1H), 6.82 (dd, J=1.8, 7.3 Hz, 1H), 6.73 (dt, J=3.0, 8.6, Hz, 1H), 6.16-6.21 (m, 1H), 4.80 (m, 2H), 1.85 (d, J=7.0 Hz, 3H); ESI-LC/MS (Method 1) (m/z): [M+H]$^+$ 431.

Example 67

N-(4-cyanophenyl)-N-methyl-3-(4-(methylcarbamoyl)phenyl)pyrazolo[1,5-a]pyridine-5-carboxamide

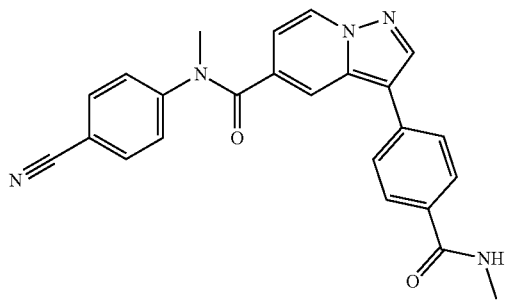

67

Example 67 was prepared from intermediate I-8 according to general Suzuki procedure F. A mixture of aryl bromide (I-8) (1.0 equiv.), (4-(methylcarbamoyl)phenyl)boronic acid (1.2 equiv.), Na$_2$CO$_3$ (2.0 equiv.), and Pd(PPh$_3$)$_4$ (0.1 equiv.) in dioxane was allowed to heat at 100° C. in microwave reactor for 40 minutes. The reaction was filtered over celite and the filtrate was concentrated under reduced pressure. The residue was purified by silica gel chromatography, eluting with hexanes/EtOAc to give 67 as the desired product. $^1$H NMR (400 MHz, DMSO-d$_6$) δ ppm 8.66 (d, J=7.28 Hz, 1H) 8.48 (s, 2H) 7.91 (d, J=8.03 Hz, 2H) 7.81-7.88 (m, 3H) 7.54 (t, J=7.78 Hz, 4H) 6.83 (d, J=7.53 Hz, 1H) 3.46 (s, 3H) 2.82 (d, J=4.02 Hz, 3H). ESI-MS (m/z): [M+H]$^+$ 410.

Example 68

N-(4-(5-(1-(methyl(5-methylpyridin-2-yl)amino)ethyl)pyrazolo[1,5-a]pyridin-3-yl)phenyl)acetamide

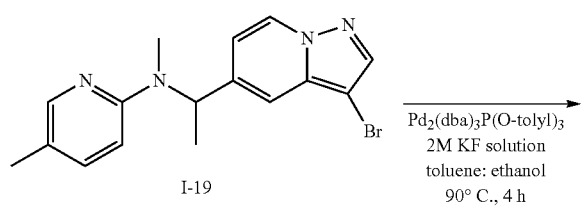

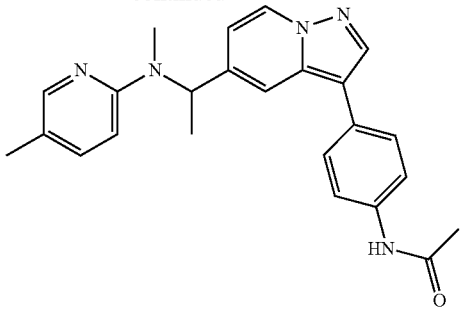

68

Example 68 was prepared from intermediate I-19 according to the procedure described for the synthesis of Example 65 (general Suzuki procedure E) by replacing (4-carbamoylphenyl)boronic acid with (4-acetamidophenyl)boronic acid. The crude product was purified by silica gel chromatography, eluting with ethyl acetate and hexanes to give 68 as the desired product. $^1$H NMR (400 MHz, DMSO-d$_6$) δ 10.01 (s, 1H), 8.60 (d, J=7.5 Hz, 1H), 8.27 (s, 1H), 7.97 (s, 1H), 7.66-7.68 (m, 3H), 7.58 (d, J=8.6 Hz, 2H), 7.40 (d, J=7.0 Hz, 1H), 6.68 (d, J=7.5 Hz, 1H), 6.63 (d, J=8.6 Hz, 1H), 6.11 (d, J=6.5 Hz, 1H), 2.7 (s, 3H), 2.1 (s, 3H), 2.0 (s, 3H), 1.55 (d, J=7.0 Hz, 3H); ESI-LC/MS (Method 2) (m/z): [M+H]$^+$ 400.

Example 69

3-(4-acetamidophenyl)-N-(5-cyanopyridin-2-yl)-N-methylpyrazolo[1,5-a]pyridine-5-carboxamide

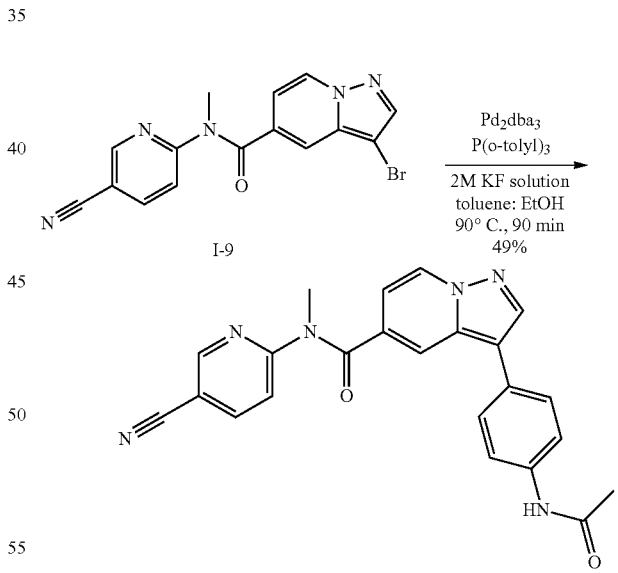

Example 69 was prepared from intermediate I-9 according to the procedure described for the synthesis of Example 65 (general Suzuki procedure E) by replacing (4-carbamoylphenyl)boronic acid with (4-acetamidophenyl)boronic acid. The crude product was purified by column chromatography over silica gel (MeOH/CH$_2$Cl$_2$, 0-2% MeOH) to give 68 as the desired product. $^1$H NMR (400 MHz, DMSO-d$_6$): δ 10.0 (s, 1H), 8.85 (m, 1H), 8.66 (d, J=7.3 Hz, 1H), 8.38 (s, 1H), 8.24 (dd, J=2.1, 8.5 Hz, 1H), 7.93 (s, 1H), 7.66

(d, J=8.6 Hz), 7.61 (d, J=8.6 Hz, 3H), 7.47 (d, J=8.6 Hz, 2H), 6.78 (dd, J=1.6, 7.3 Hz, 1H), 3.5 (s, 3H), 2.06 (s, 3H); ESI-MS (method 2) (m/z): [M+H]⁺ 411.21.

Example 71

4-(5-(7-fluoro-3,4-dihydro-2H-benzo[b][1,4]ox-azine-4-carbonyl)pyrazolo[1,5-a]pyridin-3-yl)benzamide

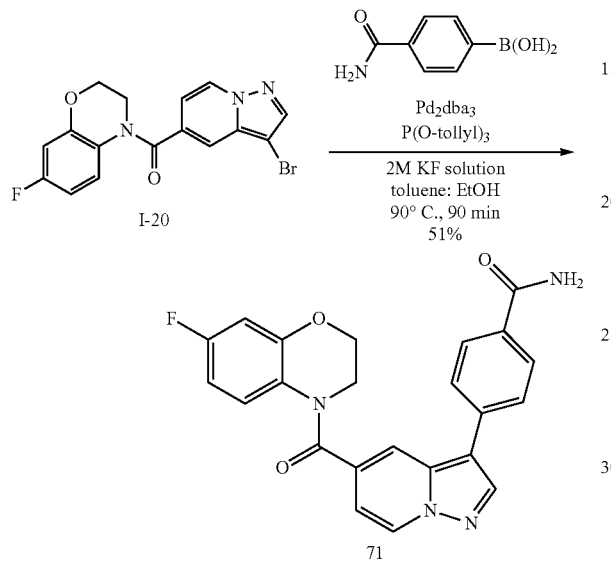

Example 71 was prepared from intermediate I-20 according to the procedure described for the synthesis of Example 65 (general Suzuki procedure E). The crude product was purified by column chromatography over silica gel (MeOH/Chloroform, 0-5% MeOH). to give 71 as the desired product. ¹H NMR (400 MHz, DMSO-d₆ at 80° C.): δ 9.75 (s, 1H), 8.76 (d, J=7.0 Hz, 1H), 8.40 (s, 1H), 8.11 (s, 1H), 7.57-7.68 (m, 4H), 7.28-7.32 (m, 1H), 6.97-6.99 (m, 1H), 6.84-6.87 (m, 1H), 6.68-6.72 (m, 1H), 4.6 (bs, 1H), 4.22-4.4 (m, 2H), 2.06 (s, 3H), 1.195 (d, J=6.6 Hz, 3H); ESI-MS (method 2) (m/z): [M+H]⁺ 445.

Example 72

4-(5-(7-fluoro-3-methyl-3,4-dihydro-2H-benzo[b][1,4]oxazine-4-carbonyl)pyrazolo[1,5-a]pyridin-3-yl)benzamide

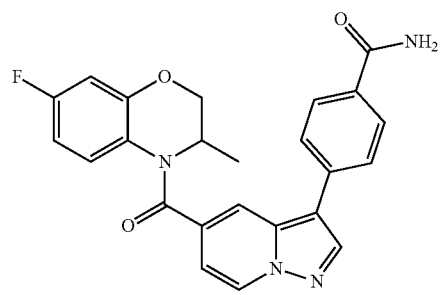

Example 72 was prepared from intermediate I-24 according to the procedure described for the synthesis of Example 65 (general Suzuki procedure E). The crude product was purified by silica gel chromatography (MeOH/Chloroform, 0-5% MeOH) to give 72 as the desired product. ¹H NMR (400 MHz, DMSO-d6 at 80° C.): δ 8.73 (d, J=7.0 Hz, 1H), 8.47 (s, 1H), 8.10 (s, 1H), 7.94 (d, J=8.4 Hz, 2H), 7.69 (d, J=8.3 Hz, 2H), 7.35-7.31 (m, 3H), 6.99-7.02 (m, 1H), 6.78-6.82 (m, 1H), 6.59-6.65 (m, 1H), 4.63 (d, J=6.2 Hz, 1H), 4.36-4.39 (m, 1H), 4.21-4.24 (m, 1H), 1.22 (d, J=7.0 Hz, 3H); ESI-MS (method 2) (m/z): [M+H]⁺ 431.

Example 73

4-(5-(7-fluoro-3,4-dihydro-2H-benzo[b][1,4]oxazine-4-carbonyl)pyrazolo[1,5-a]pyridin-3-yl)-N-methylbenzamide

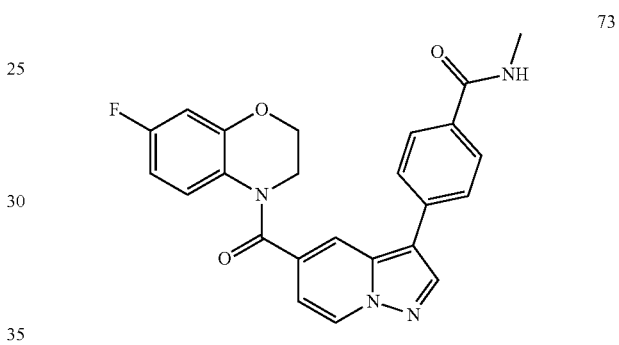

Example 73 was prepared from intermediate I-20 according to the procedure described for the synthesis of Example 65 (general Suzuki procedure E) by replacing (4-carbamoylphenyl)boronic acid with (4-(methylcarbamoyl)phenyl)boronic acid. The residue was purified column chromatography over silica gel (MeOH/Chloroform, 0-2% MeOH) to give 73 as the desired product. ¹H NMR (400 MHz, CDCl₃): δ 9.99 (s, 1H), 8.77 (d, J=7.03 Hz, 1H), 8.40 (d, J=1.31 Hz, 1H), 8.10 (s, 1H), 7.57-7.67 (m, 5H), 6.99-7.01 (m, 1H), 6.83-6.85 (m, 1H), 6.69 (m, 1H), 4.36 (m, 2H), 3.94 (m, 2H), 2.05 (s, 3H); ESI-MS (method 1) (m/z): [M+H]⁺ 431.15.

Example 74

4-(5-(7-fluoro-3-methyl-3,4-dihydro-2H-benzo[b][1,4]oxazine-4-carbonyl)pyrazolo[1,5-a]pyridin-3-yl)-N-methylbenzamide

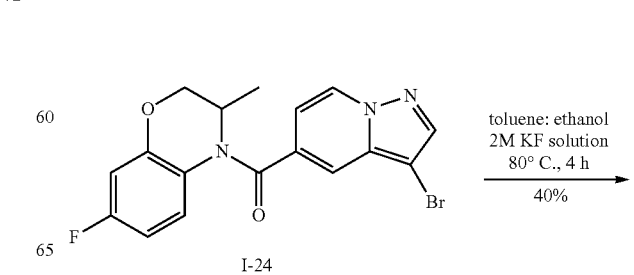

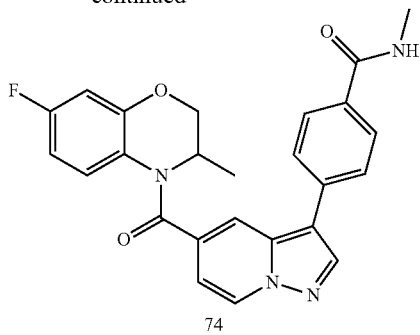

74

Example 74 was prepared from intermediate I-24 according to the procedure described for the synthesis of Example 65 (general Suzuki procedure E) by replacing (4-carbamoylphenyl)boronic acid with (4-(methylcarbamoyl)phenyl)boronic acid. The crude product was purified by column chromatography over silica gel (MeOH/Chloroform, 0-5% MeOH) to give 74 as the desired product. $^1$H NMR (400 MHz, DMSO-d6 at 80° C.): δ 9.75 (s, 1H), 8.76 (d, J=7.0 Hz, 1H), 8.40 (s, 1H), 8.11 (s, 1H), 7.57-7.68 (m, 4H), 7.28-7.32 (m, 1H), 6.97-6.99 (m, 1H), 6.84-6.87 (m, 1H), 6.68-6.72 (m, 1H), 4.6 (bs, 1H), 4.22-4.4 (m, 2H), 2.06 (s, 3H), 1.195 (d, J=6.6 Hz, 3H); ESI-MS (m/z): [M+H]$^+$ 445.

Example 75

N-(5-cyanopyridin-2-yl)-N-methyl-3-(4-(methylcarbamoyl)phenyl)pyrazolo[1,5-a]pyridine-5-carboxamide

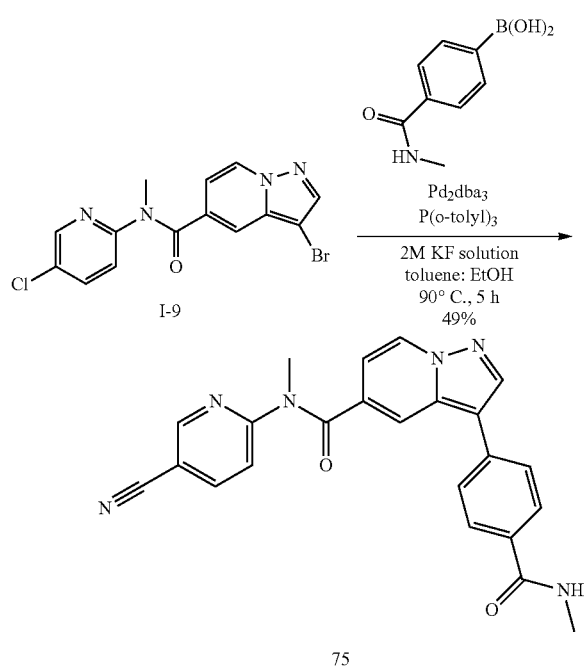

75

Example 75 was prepared from intermediate I-9 according to the procedure described for the synthesis of Example 65 (general Suzuki procedure E) by replacing (4-carbamoylphenyl)boronic acid with (4-(methylcarbamoyl)phenyl) boronic acid. The crude product was purified by column chromatography over silica gel (MeOH/Chloroform, 0-2% MeOH) to give 74 as the desired product. $^1$H NMR (400 MHz, DMSO-d$_6$): δ 8.86 (d, J=1.6 Hz, 1H), 8.71 (dd, J=0.7, 7.3 Hz, 1H), [8.53 (s), 8.49 (d, J=4.6 Hz) 2H], 8.26 (dd, J=2.3, 8.7 Hz, 1H), [7.99 (d, J=0.7 Hz), 7.92 (d, J=8.5 Hz) 3H], 7.65 (m, 3H), 6.84 (dd, J=1.9, 7.3 Hz, 1H), 3.53 (s, 3H), 2.81 (d, J=4.6 Hz, 3H) ESI-MS (Method 2) (m/z): [M+H]$^+$ 411.2.

The difference with Method 2 used here is Gradient: 0.4 mL/minute, initial 20% B ramp to 80% B over 2.0 minutes, (instead of ramp to 90% over 2.0 minutes in Method 2), then hold until 4.0 minutes, return to 20% B at 4.1 minutes until end of run.

Example 76

N-(5-cyanopyridin-2-yl)-3-(4-(methylcarbamoyl)phenyl)-N-(oxetan-3-yl)pyrazolo[1,5-a]pyridine-5-carboxamide

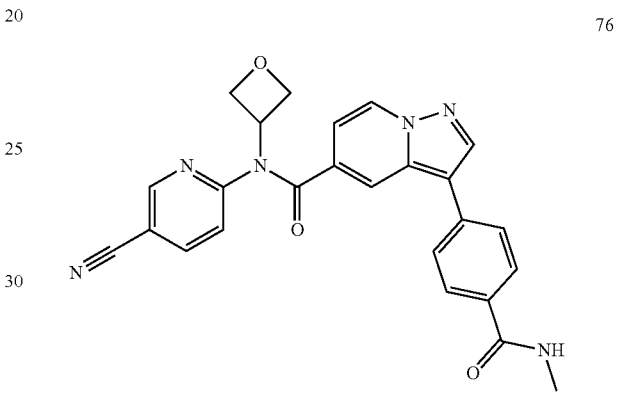

76

Example 76 was prepared from intermediate I-26 according to the procedure described for the synthesis of Example 64 by replacing (4-carbamoylphenyl)boronic acid with (4-(methylcarbamoyl)phenyl)boronic acid. The residue was purified by silica gel chromatography, eluting with ethyl acetate and hexanes to give 76 as the desired product. $^1$H NMR (400 MHz, METHANOL-d$_4$) 8.66 (d, J=7.28 Hz, 1H) 8.52 (s, 1H) 8.38 (s, 1H) 7.93-8.00 (m, 3H) 7.75 (d, J=8.78 Hz, 2H) 7.40 (dd, J=7.28, 1.76 Hz, 1H) 7.00 (dd, J=9.91, 1.88 Hz, 1H) 6.38 (d, J=10.29 Hz, 1H) 4.52-4.62 (m, 1H) 4.46 (d, J=1.00 Hz, 2H) 4.32 (t, J=11.42 Hz, 1H) 4.14 (dd, J=11.92, 7.15 Hz, 1H) 2.96 (s, 3H); ESI-MS (m/z): [M+H]$^+$ 443.

Example 77

N-(1-(1H-pyrazol-1-yl)propan-2-yl)-3-(4-carbamoylphenyl)-N-(5-cyanopyridin-2-yl)pyrazolo[1,5-a]pyridine-5-carboxamide

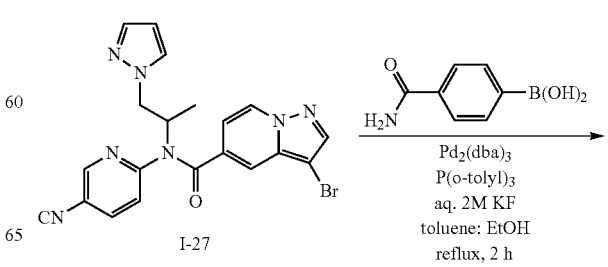

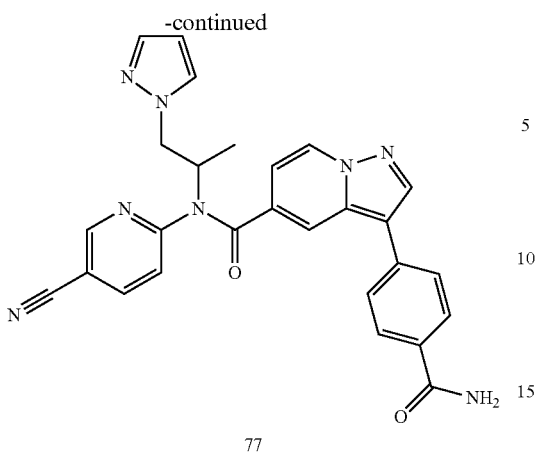

77

Example 77 was prepared from intermediate I-27 according to the procedure described for the synthesis of Example 65 (general Suzuki procedure E). The residue was purified by preparative TLC (silica gel GF 254) using 3% methanol in chloroform as eluant to give 77 as the desired product. ¹H NMR (400 MHz, DMSO) δ 8.90 (s, 1H), 8.63 (d, J=7.5 Hz, 1H), 8.47 (s, 1H), 8.15 (d, J=8.3 Hz, 1H), 8.03 (s, 1H), 7.99 (d, J=8.3 Hz, 2H), 7.75 (s, 1H), 7.61 (s, 1H), 7.51 (d, J=7.9 Hz, 2H), 7.39 (s, 1H), 7.34 (s, 1H), 7.17 (d, J=8.3 Hz, 1H), 6.68 (d, J=7.0 Hz, 1H), 6.14 (s, 1H), 5.75 (m, 1H), 4.85-4.86 (m, 1H), 4.47-4.48 (m, 1H), 1.35 (d, J=7.0 Hz, 3H); ESI-LC/MS (Method 2) (m/z): [M+H]⁺ 491.3, RT 1.32 min.

The difference with Method-2 used here is Gradient: 0.4 mL/minute, initial 20% B ramp to 80% B over 2.0 minutes, (instead of ramp to 90% over 2.0 minutes in Method 2) then hold until 4.0 minutes, return to 20% B at 4.1 minutes until end of run.

Example 79

3-(6-amino-5-fluoropyridin-3-yl)-N-(4-cyanophenyl)-N-methylpyrazolo[1,5-a]pyridine-5-carboxamide

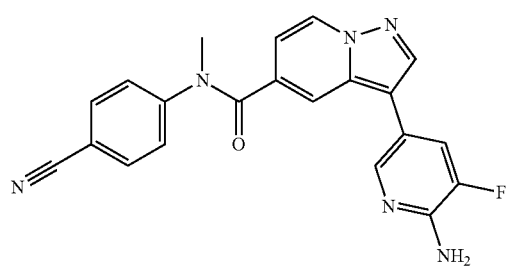

79

A mixture of 3-bromo-N-(4-cyanophenyl)-N-methylpyrazolo[1,5-a]pyridine-5-carboxamide (I-8; 400 mg, 1.10 mmol 1.0 eq), 3-fluoro-5-(4,4,5,5-tetramethyl-1,3,2-dioxaborolan-2-yl)pyridin-2-amine (I-37, 550 mg, 2.20 mmol 2.0 eq) and 1N Na₂CO₃ solution (4.0 mL) in 1,4-dioxane (10 mL) was degassed with argon gas for 10 min. Subsequently, tetrakis (triphenyl phosphine)-palladium(0) (250 mg, 0.22 mmol 0.2 eq) was added and the reaction mixture was stirred in a sealed tube at 100° C. for 2.5 h (cf. general Suzuki Procedure F). The solvent was removed under reduced pressure. Purification by silica gel chromatography, eluting with 5% MeOH/CH₂Cl₂ provided 79 as the desired product (37%). ¹H NMR (400 MHz, DMSO) δ 8.58 (d, J=7.0 Hz, 1H), 8.31 (s, 1H), 7.91 (s, 1H), 7.78 (d, J=8.8 Hz, 3H), 7.53 (d, J=8.30 Hz, 2H), 7.46 (d, J=12.3 Hz, 1H), 6.74 (d, J=7.0 Hz, 1H), 6.30 (s, 2H), 3.45 (s, 3H); ESI-LC/MS (m/z): [M+H]⁺ 387.10, RT 1.71 min.

Example 80

3-(4-amino-3,5-dimethylphenyl)-N-(4-cyanophenyl)-N-methylpyrazolo[1,5-a]pyridine-5-carboxamide

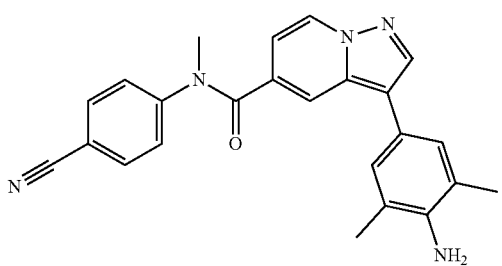

80

Example 80 was prepared from intermediate I-8 according to the procedure described for the synthesis of Example 79 by replacing 3-fluoro-5-(4,4,5,5-tetramethyl-1,3,2-dioxaborolan-2-yl)pyridin-2-amine (I-37) with 2,6-dimethyl-4-(4,4,5,5-tetramethyl-1,3,2-dioxaborolan-2-yl)aniline (I-38). Purification by silica gel chromatography, eluting with 5% MeOH/CH₂Cl₂ provided 80 as the desired product (34%) ¹H NMR (400 MHz, DMSO) δ 8.54 (d, J=7.10 Hz, 1H), 8.15 (s, 1H) I-37, 7.81 (d, J=8.40 Hz, 2H), 7.65 (s, 1H), 7.52 (d, J=8.3 Hz, 2H), 6.87 (s, 2H), 6.72 (d, J=7.40 Hz, 1H), 4.65 (s, 2H), 3.45 (s, 3H), 2.14 (s, 6H); ESI-LC/MS (m/z): [M+H]⁺ 396.16, RT 1.51 min.

Example 81

3-(6-amino-5-methylpyridin-3-yl)-N-(4-cyanophenyl)-N-methylpyrazolo[1,5-a]pyridine-5-carboxamide

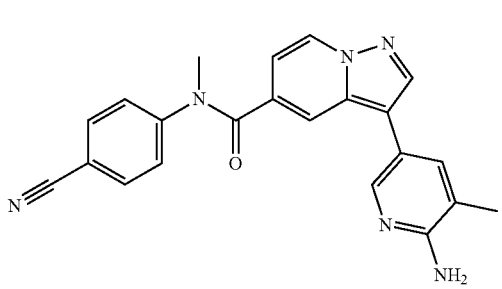

81

Example 81 was prepared from intermediate I-8 according to the procedure described for the synthesis of Example 79 by replacing 3-fluoro-5-(4,4,5,5-tetramethyl-1,3,2-dioxaborolan-2-yl)pyridin-2-amine (I-37) with 3-methyl-5-(4,4,5,5-tetramethyl-1,3,2-dioxaborolan-2-yl)pyridin-2-amine (I-39). Purification by silica gel chromatography, eluting with 5% MeOH/CH$_2$Cl$_2$ provided 81 as the desired product (44%). $^1$H NMR (400 MHz, DMSO) δ 8.56 (d, J=7.50 Hz, 1H), 8.23 (s, 1H), 7.91 (s, 1H), 7.79 (d, J=8.30 Hz, 1H), 7.71 (s, 1H), 7.52 (d, J=8.30 Hz, 1H), 7.31 (s, 1H), 6.72 (d, J=7.50 Hz, 1H), 5.80 (s, 2H), 3.44 (s, 3H), 2.11 (s, 3H); ESI-LC/MS (m/z): [M+H]$^+$ 383.07, RT 1.66 min.

Example 82

3-(4-carbamoylphenyl)-N-(4-cyanocyclohexyl)-N-methylpyrazolo[1,5-a]pyridine-5-carboxamide

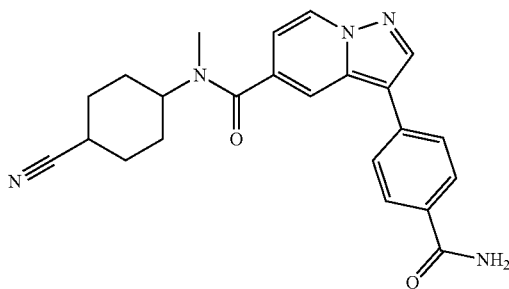

Example 82 was prepared from intermediate I-33 according to the procedure described for the synthesis of Example 65 (general Suzuki procedure E). The residue was purified by silica gel chromatography, eluting with 3% MeOH/CHCl$_3$ to give 82 as the desired product (30%). $^1$H NMR (400 MHz, DMSO) δ 8.68 (d, J=6.6 Hz, 1H), 8.38 (s, 1H), 7.97-8.01 (m, 3H), 7.76-7.78 (m, 2H), 6.97 (m, 1H), 4.42 & 3.62 (two broad signals, 1H), 3.30 (m, 3H), 1.50-2.59 (m, 8H); ESI-LC/MS (m/z): [M+H]$^+$ 402.14, RT 1.02 min.

Example 83

3-(2-aminopyrimidin-5-yl)-N-(4-cyanophenyl)-N-methylpyrazolo[1,5-a]pyridine-5-carboxamide

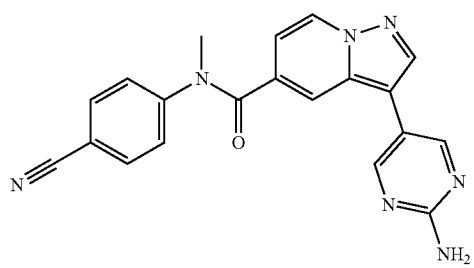

Example 83 was prepared from intermediate I-8 according to the procedure described for the synthesis of Example 79 by replacing 3-fluoro-5-(4,4,5,5-tetramethyl-1,3,2-dioxaborolan-2-yl)pyridin-2-amine (I-37) with 5-(4,4,5,5-tetramethyl-1,3,2-dioxaborolan-2-yl)pyrimidin-2-amine (I-40). Purification by silica gel chromatography, eluting with 5% MeOH/CH$_2$Cl$_2$ provided 83 as the desired product (27%). $^1$H NMR (400 MHz, DMSO) δ 8.59 (d, J=7.50 Hz, 1H), 8.37 (s, 1H), 8.31 (s, 1H), 7.77 (s, 3H), 7.52 (d, J=7.90 Hz, 2H), 6.73 (s, 3H), 3.30 (s, 3H); ESI-LC/MS (m/z): [M+H]$^+$ 370.10, RT 0.93 min.

Example 84

3-(6-amino-5-(trifluoromethyl)pyridin-3-yl)-N-(5-cyanopyridin-2-yl)-N-methylpyrazolo[1,5-a]pyridine-5-carboxamide

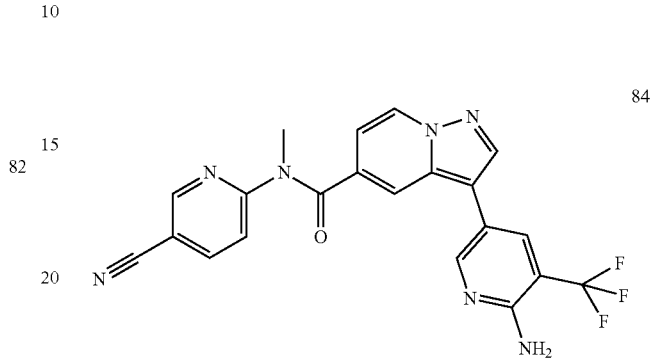

Example 84 was prepared from intermediate I-9 according to the procedure described for the synthesis of Example 79 by replacing 3-fluoro-5-(4,4,5,5-tetramethyl-1,3,2-dioxaborolan-2-yl)pyridin-2-amine (I-37) with 5-(4,4,5,5-tetramethyl-1,3,2-dioxaborolan-2-yl)-3-(trifluoro-methyl)pyridin-2-amine (I-41). Purification by silica gel chromatography, eluting with 1% MeOH/CHCl$_3$ gave the desired product (41%). $^1$H NMR (400 MHz, DMSO) δ 8.82 (d, J=1.2 Hz, 1H), 8.64 (d, J=7.1 Hz, 1H), 8.39-8.41 (m, 2H), 8.21 (dd, J=2.2, 6.1 Hz, 1H), 7.80-7.86 (m, 2H), 7.58 (d, J=8.7 Hz, 1H), 6.78-6.81 (m, 1H), 6.52-6.56 (m, 2H), 3.52 (s, 1H); ESI-LC/MS (m/z): [M+H]$^+$ 438.08, RT 1.37 min.

Example 85

3-(6-amino-5-cyanopyridin-3-yl)-N-(5-cyanopyridin-2-yl)-N-methylpyrazolo[1,5-a]pyridine-5-carboxamide

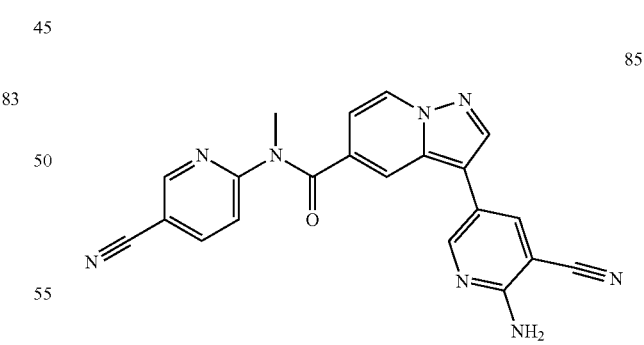

Example 85 was prepared from intermediate I-9 according to the procedure described for the synthesis of Example 79 by replacing 3-fluoro-5-(4,4,5,5-tetramethyl-1,3,2-dioxaborolan-2-yl)pyridin-2-amine (I-37) with 2-amino-5-(4,4,5,5-tetramethyl-1,3,2-dioxaborolan-2-yl)nicotino-nitrile (I-42). Purification by silica gel chromatography, eluting with 5% MeOH/CH$_2$Cl$_2$ provided 85 the desired product (23%). $^1$H NMR (400 MHz, DMSO) δ 8.83 (d, J=1.70 Hz, 1H), 8.66 (d, J=7.10 Hz, 1H), 8.45 (d, J=2.60 Hz, 1H), 8.40

(s, 1H), 8.21 (dd, J=2.2, 6.6 Hz, 1H), 8.06 (d, J=2.10 Hz, 1H), 7.98 (s, 1H), 7.60 (d, J=8.70 Hz, 1H), 7.00 (s, 2H), 6.78 (d, J=8.8 Hz, 1H), 3.52 (s, 3H); ESI-LC/MS (m/z): [M+H]⁺ 395.09, RT 1.45 min.

Example 86

3-(6-amino-5-chloropyridin-3-yl)-N-(5-cyanopyridin-2-yl)-N-methylpyrazolo[1,5-a]pyridine-5-carboxamide

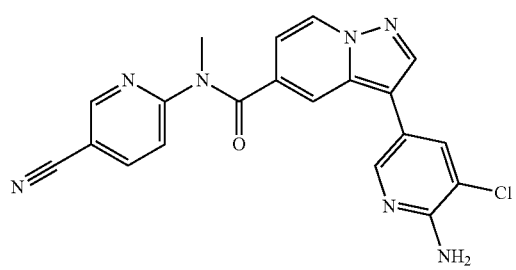

Example 86 was prepared from intermediate I-9 according to the procedure described for the synthesis of Example 79 by replacing 3-fluoro-5-(4,4,5,5-tetramethyl-1,3,2-dioxaborolan-2-yl)pyridin-2-amine (I-37) with 3-chloro-5-(4,4,5,5-tetramethyl-1,3,2-dioxaborolan-2-yl)pyridin-2-amine (I-43). Purification by preparative TLC provided 86 the desired product (41%). ¹H NMR (400 MHz, DMSO) δ 8.85 (s, 1H), 8.65 (d, J=7.50 Hz, 1H), 8.36 (s, 1H), 8.22 (d, J=8.8 Hz, 1H), 8.11 (s, 1H), 7.79 (s, 1H), 7.65 (s, 1H), 7.58 (d, J=8.8 Hz, 1H), 6.79 (d, J=7.0 Hz, 1H), 6.40 (s, 2H), 3.52 (s, 3H); ESI-LC/MS (m/z): [M+H]⁺ 404.09, RT 1.27 min.

Example 87

3-(6-amino-5-(dimethylcarbamoyl)pyridin-3-yl)-N-(5-cyanopyridin-2-yl)-N-methylpyrazolo[1,5-a]pyridine-5-carboxamide

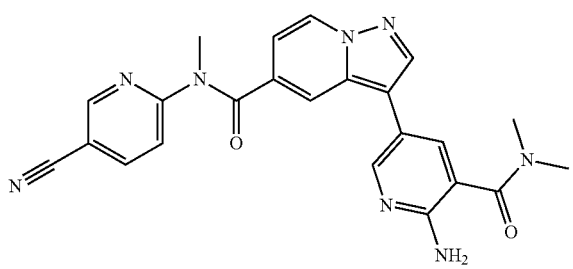

Example 87 was prepared from intermediate I-9 according to the procedure described for the synthesis of Example 79 by replacing 3-fluoro-5-(4,4,5,5-tetramethyl-1,3,2-dioxaborolan-2-yl)pyridin-2-amine (I-37) with 2-amino-N,N-dimethyl-5-(4,4,5,5-tetramethyl-1,3,2-dioxaborolan-2-yl)nicotinamide (I-44). Purification by preparative TLC provided 87 as the desired product (10%). ¹H NMR (400 MHz, DMSO) δ 8.81 (d, J=2.2 Hz, 1H), 8.64 (d, J=7.0 Hz, 1H), 8.35 (s, 1H), 8.20 (d, J=2.2 Hz, 2H), 8.17 (d, J=2.20 Hz, 1H), 7.80 (s, 1H), 7.55 (d, J=8.8 Hz, 1H), 7.48 (d, J=2.2 Hz, 1H), 6.76 (dd, J=1.7, 7.0 Hz, 1H), 3.52 (s, 3H), 2.97 (s, 6H); ESI-LC/MS (m/z): [M+H]⁺ 441.11, RT 1.54 min.

Example 88

3-(6-amino-5-methoxypyridin-3-yl)-N-(5-cyanopyridin-2-yl)-N-methylpyrazolo[1,5-a]pyridine-5-carboxamide

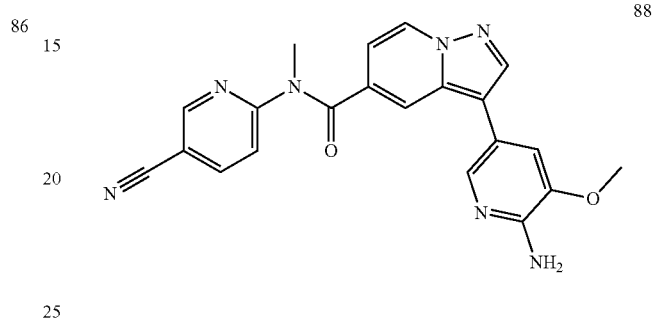

Example 88 was prepared from intermediate I-9 according to the procedure described for the synthesis of Example 79 by replacing 3-fluoro-5-(4,4,5,5-tetramethyl-1,3,2-dioxaborolan-2-yl)pyridin-2-amine (I-37) with 3-methoxy-5-(4,4,5,5-tetramethyl-1,3,2-dioxaborolan-2-yl)-pyridin-2-amine (I-45). Purification by silica gel chromatography, eluting with 5% MeOH/CH₂Cl₂ provided 88 as the desired product (36%). ¹H NMR (400 MHz, DMSO) δ 8.78 (s, 1H), 8.62 (d, J=7.40 Hz, 1H), 8.33 (s, 1H), 8.28-8.20 (dd, J=2.2, 6.60 Hz, 1H), 7.86 (s, 1H), 7.66 (s, 1H), 7.58 (d, J=8.8 Hz, 1H), 7.16 (s, 1H), 6.77 (d, J=5.70 Hz, 1H), 5.79 (s, 2H), 3.84 (s, 3H), 3.52 (s, 3H); ESI-LC/MS (m/z): [M+H]⁺ 400.06, RT 1.11 min.

Example 89

3-(4-carbamoylphenyl)-N-(4-chloro-2-formylphenyl)-N-methylpyrazolo[1,5-a]pyridine-5-carboxamide

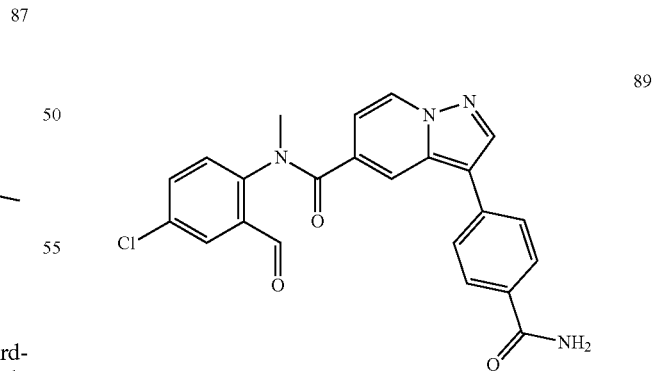

Example 89 was prepared from intermediate I-15 according to the procedure described for the synthesis of Example 65 (general Suzuki procedure E). The crude product was purified by preparative TLC to give 89 as the desired product. ¹H NMR (400 MHz, DMSO) δ 10.02 (s, 1H), 8.62 (d, J=7.0 Hz, 1H), 8.44 (s, 1H), 8.02-7.86 (m, 3H), 7.86 (s, 2H), 7.74 (d, J=5.2 Hz, 1H), 7.63 (s, 1H), 7.43-7.35 (m, 3H), 6.81 (d, J=7.0 Hz, 1H), 3.80 (s, 3H); ESI-LC/MS (m/z): [M+H]+ 433.2, RT 4.75 min.

Example 90

N-(5-Cyanopyridin-2-yl)-N-ethyl-3-(4-(methylcarbamoyl)phenyl)pyrazolo[1,5-a]pyridine-5-carboxamide

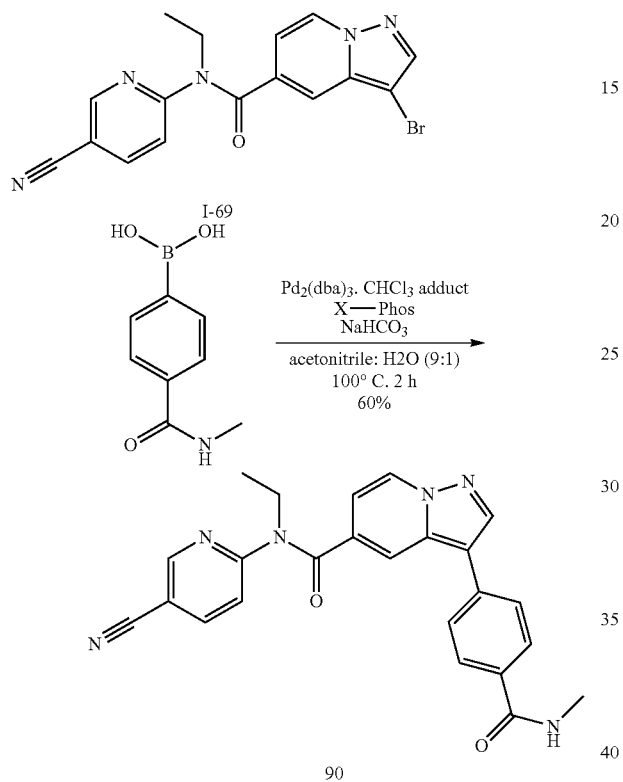

A solution of 3-bromo-N-(5-cyanopyridin-2-yl)-N-ethyl-pyrazolo[1,5-a]pyridine-5-carboxamide I-69 (25.0 g, 67.53 mmol), 4-(N-methylaminocarbonyl)phenylboronic acid (18.19 g, 101.62 mmol) and NaHCO$_3$ (11.24 g, 135.5 mmol) in acetonitrile:water (9:1) (500 mL) was degassed with argon for about 30 min. To this mixture were added Pd$_2$(dba)$_3$.CHCl$_3$ adduct (7.0 g, 6.77 mmol), X-phos (9.69 g, 20.32 mmol) under argon atmosphere. The resulting reaction mixture was maintained at 100° C. for 2 h then allowed to rt and filtered through celite. The filtrate was partitioned between water (2.5 L) and ethyl acetate (2.5 L). The ethyl acetate layer was washed with brine, dried over anhydrous Na$_2$SO$_4$ and concentrated. This crude compound was purified by column chromatography over silica gel (100-200 mesh) using a solvent gradient of 1% methanol in dichloromethane to obtained title compound. This compound was re-precipitation by using a mixture of dichloromethane and n-pentane to give 17.2 g (60%) of N-(5-cyanopyridin-2-yl)-N-ethyl-3-(4-(methylcarbamoyl)phenyl)pyrazolo[1,5-a]pyridine-5-carboxamide 90 as a yellow color solid. H-NMR (DMSO-d$_6$): δ 8.87 (d, J=2.0 Hz, 1H), 8.67 (d, J=7.6 Hz, 1H), 8.50 (s, 1H), 8.44-8.45 (m, 1H), 8.23 (dd, J=2.0, 8.0 Hz, 1H), 7.91-7.93 (m, 3H), 7.60 (d, J=8.8 Hz, 2H), 7.52 (d, J=8.4 Hz, 1H), 6.77 (dd, J=1.6, 7.2 Hz, 1H), 4.11 (q, J=6.8, 6.8 Hz, 2H), 2.81 (d, J=4.4 Hz, 3H), 1.20 (t, J=7.2 Hz, 3H). ESI-LC/MS: m/z 425 (M+H); r.t.=3.17 [Agilent LC1200 with SQD; XBridge C18, 2.5 μm, 4.6×50 mm column; gradient of 95:5 H$_2$O (5 mM ammonium bicarbonate):CH$_3$CN to 2:98 H$_2$O (5 mM ammonium aicarbonate):CH$_3$CN for 6 minutes with 1.3 mL/min flow rate. HPLC purity: 97.52% at 254 nm r.t.=4.68. [Waters HPLC; Waters XBridge C18, 3.5 μm, 4.6×100 mm column; gradient of 90:10 H$_2$O (10 mM ammonium acetate):CH$_3$CN to 5:95 H$_2$O (10 mM ammonium acetate):CH$_3$CN for 15 minutes with 1.0 mL/min flow rate].

Example 91

N-(5-cyanopyridin-2-yl)-N-isopropyl-3-(4-(methylcarbamoyl)phenyl)pyrazolo[1,5-a]pyridine-5-carboxamide

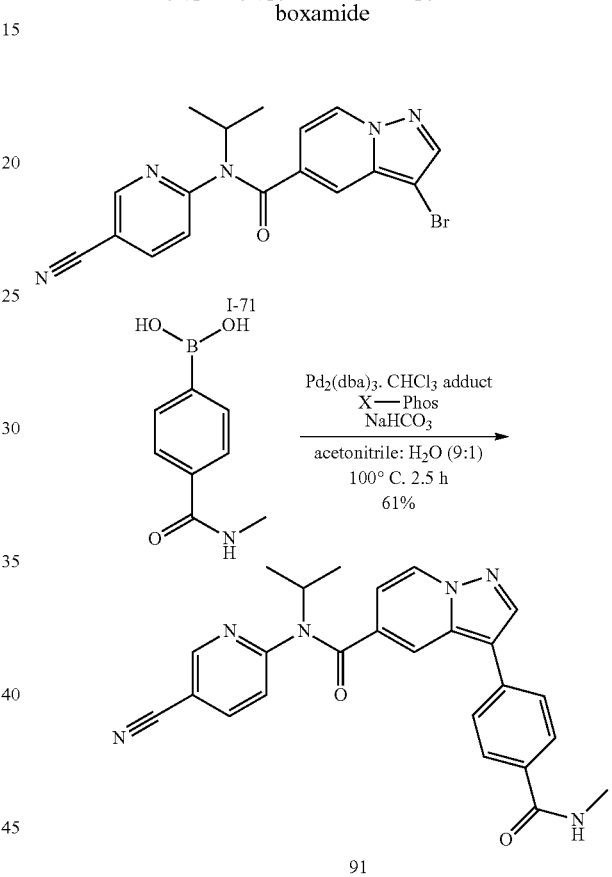

To a stirred solution of 3-bromo-N-(5-cyanopyridin-2-yl)-N-isopropylpyrazolo[1,5-a]pyridine-5-carboxamide I-71 (2 g, 5.22 mmol) in acetonitrile:H$_2$O (9:1) (40 mL), 4-(N-methylaminocarbonyl)phenylboronic acid (1.4 g, 7.8 mmol) and NaHCO$_3$ (860 mg, 10.23 mmol) were added and the mixture was degassed with argon for about 15 min. To this mixture were added Pd$_2$(dba)$_3$ chloroform adduct (540 mg, 0.52 mmol), X-Phos (740 mg, 1.55 mmol) under argon atmosphere. The resulting reaction mixture was maintained at 100° C. for 2.5 h then allowed to rt and diluted with dichloromethane, filtered through celite. The filtrate was extracted with water (100 mL) and dichloromethane (2×100 mL). The crude compound was purified by column chromatography over silica-gel (100-200 mesh) using a solvent gradient of 80% ethyl acetate and pet-ether as eluant to afford 1.4 g (61%) of N-(5-cyanopyridin-2-yl)-N-isopropyl-3-(4-(methylcarbamoyl)phenyl)pyrazolo[1,5-a]pyridine-5-carboxamide 91 as a yellow solid. $^1$H NMR (400 MHz, DMSO-d$_6$): δ 8.98 (s, 1H), 8.63 (d, J=7.4 Hz, 1H), 8.47 (s, 2H), 8.27-8.23 (dd, J=5.8, 2.6 Hz, 1H), 7.94 (d, J=8.4 Hz, 2H), 7.75 (s, 1H), 7.50-7.58 (m, 3H), 6.75-6.72 (dd, J=5.4, 1.9 Hz, 1H), 4.96-4.91 (m, 1H), 2.82 (d, J=4.4 Hz, 3H), 1.33 (d, J=6.8 Hz, 6H). ESI-LC/MS: m/z 439 (M+H); r.t.=3.61 [Shimadzu Nexera with LCMS 2020; Pheonomenex Kinetex C18, 5 µm, 100×4.6 mm column; gradient of 90:10 $H_2O$ (10 mM ammonium bicarbonate):$CH_3CN$ to 0:100 $H_2O$ (10 mM ammonium bicarbonate):$CH_3CN$ for 8 minutes with 0.8 mL/min flow rate]. HPLC purity: 97.31% at 254 nm; r.t.=7.34 [Waters HPLC; Waters XBridge C18 5 µm, 4.6× 250 mm column; gradient of 90:10 $H_2O$ (10 mM ammonium acetate):$CH_3CN$ to 10:90 $H_2O$ (10 mM ammonium acetate):$CH_3CN$ for 20 minutes with 1.0 mL/min flow rate].

Example 92

5-(5-(1-(4-cyanophenyl)-2-methylhydrazinecarbonyl)pyrazolo[1,5-a]pyridin-3-yl)-N-methyl picolinamide

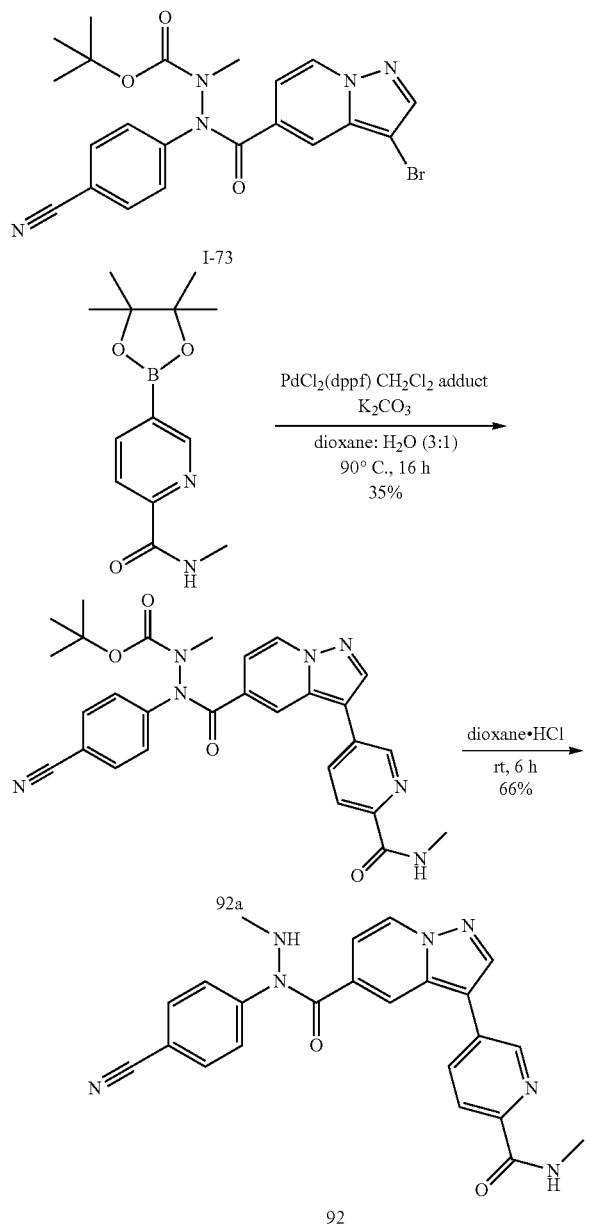

A mixture of tert-butyl 2-(3-bromopyrazolo[1,5-a]pyridine-5-carbonyl)-2-(4-cyanophenyl)-1-methylhydrazinecarboxylate (500 mg, 1.06 mmol), N-methyl-5-(4,4,5,5-tetramethyl-1,3,2-dioxaborolan-2-yl)picolinamide (558 mg, 2.13 mmol) and $K_2CO_3$ (323 mg, 2.34 mmol) in dioxane:water (3:1) (10 mL) was degassed with argon for about 10 min. To the resulting solution were added $PdCl_2$(dppf).$CH_2Cl_2$ (174 mg, 0.213 mmol) and the reaction mixture was maintained at 90° C. for 16 h. The reaction mixture was filtered through celite and the celite pad was washed with ethyl acetate (50 mL). The filtrate was concentrated and the residue was purified by column chromatography over silica (100-200 mesh) using a solvent gradient of 1% methanol in chloroform as eluant to afford 200 mg (36%) of tert-butyl 2-(4-cyanophenyl)-1-methyl-2-(3-(6-(methylcarbamoyl)pyridin-3-yl)pyrazolo[1,5-a]pyridine-5-carbonyl)hydrazinecarboxylate 92a as an yellow color solid. $^1$H NMR (300 MHz, DMSO-$d_6$): δ 8.90 (s, 1H), 8.84-8.86 (m, 1H), 8.71-8.73 (m, 1H), 8.69 (s, 1H), 8.18 (m, 2H), 8.08-8.11 (m, 1H), 7.92 (d, J=6.9 Hz, 2H), 7.47-7.56 (m, 2H), 6.94-7.06 (m, 1H), 3.14 (s, 3H), 2.85 (d, J=4.8 Hz, 3H), 1.32 (s, 9H); ESI-LC/MS m/z 526.03 (M+H); r.t.=2.81 [Waters Acquity UPLC with QuattroMicro; Waters Acquity BEH C18, 1.7 µm, 2.1×50 mm column; gradient of 98:2 $H_2O$ (0.025% TFA):$CH_3CN$ (0.025% TFA) to 0:100 $H_2O$ (0.025% TFA):$CH_3CN$ (0.025% TFA) for 5 minutes with 0.4 mL/min flow rate].

4.0 M HCl in dioxane (3.0 mL) was added to tert-butyl 2-(4-cyanophenyl)-1-methyl-2-(3-(6-(methylcarbamoyl)pyridin-3-yl)pyrazolo[1,5-a]pyridine-5-carbonyl)hydrazinecarboxylate (3)_(150 mg, 0.28 mmol) and the resulting reaction mixture was stirred for 6 h at rt. The reaction mixture was partitioned between water (20 mL) and ethyl acetate (2×20 mL). The ethyl acetate layer was washed with water, brine and dried over anhyd. $Na_2SO_4$ and concentrated in vacuo. The crude compound was purified by Preparative Thin-Layer Chromatography (Prep TLC) using 4% of methanol in dichloromethane to afford 80 mg (66%) of 5-(5-(1-(4-cyanophenyl)-2-methylhydrazinecarbonyl) pyrazolo[1,5-a]pyridin-3-yl)-N-methylpicolinamide 92 as a yellow solid. $^1$H NMR (300 MHz, DMSO-$d_6$): δ 8.94 (d, J=2.0 Hz, 1H), 8.80 (d, J=7.6 Hz, 1H), 8.71 (m, 1H), 8.65 (s, 1H), 8.20-8.25 (m, 2H), 8.09 (d, J=8.1 Hz, 1H), 7.91 (d, J=8.6 Hz, 2H), 7.71 (d, J=8.9 Hz, 2H), 7.07-7.09 (m, 1H), 6.17 (q, J=5.6, 5.3 Hz, 1H), 2.85 (d, J=5.8 Hz, 3H), 2.50 (d, J=3.6 Hz, 3H); ESI-LC/MS m/z 424.3 (M–H); r.t.=3.29 [Agilent 1200 HPLC; XBridge C18, 3.5 µm, 4.6×75 mm column; gradient of 80:20 $H_2O$ (5 mM ammonium bicarbonate):$CH_3CN$ to 20:80 $H_2O$ (5 mM ammonium bicarbonate):$CH_3CN$ for 7 minutes with 1.0 mL/min flow rate]. HPLC purity: 98.94% at 254 nm; r.t.=2.74 [Waters Acquity UPLC; Waters Acquity BEH C18, 1.7 µm, 2.1×100 mm column; gradient of 90:10 $H_2O$ (0.025% TFA):$CH_3CN$ (0.025% TFA) to 10:90 $H_2O$ (0.05% TFA):$CH_3CN$ (0.05% TFA) for 6 minutes with 0.3 mL/min flow rate].

Example 93

N-(5-Cyanopyridin-2-yl)-N-cyclopropyl-3-(4-(methylcarbamoyl)phenyl)pyrazolo[1,5-a]pyridine-5-carboxamide Step 1

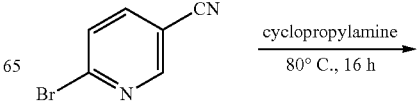

-continued

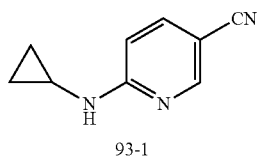

93-1

A solution mixture of 2-bromo-5-cyanopyridine (5.0 g, 27.32 mmol) and cyclopropylamine (40 mL) in a sealed tube was stirred at 80° C. for 16 h. The reaction mixture was partitioned between water (100 mL) and ethyl acetate (150 mL). The separated organic layer was washed with brine (50 ml), dried over anhydrous Na$_2$SO$_4$ and concentrated. The crude compound was purified by column chromatography over silica-gel (100-200 mesh) using a solvent gradient of 5% ethyl acetate in pet-ether and then 5% ethyl acetate in chloroform as eluant to afford 3.5 g (81%) of 6-(cyclopropylamino)nicotinonitrile 93-1 as an off-white solid. $^1$H NMR (400 MHz, DMSO-d$_6$): δ 8.40 (d, J=1.8 Hz, 1H), 7.76-7.81 (m, 2H), 6.63 (br.s, 1H), 2.55-2.69 (m, 1H), 0.72-0.76 (m, 2H), 0.44-0.48 (m, 2H).

Step 2

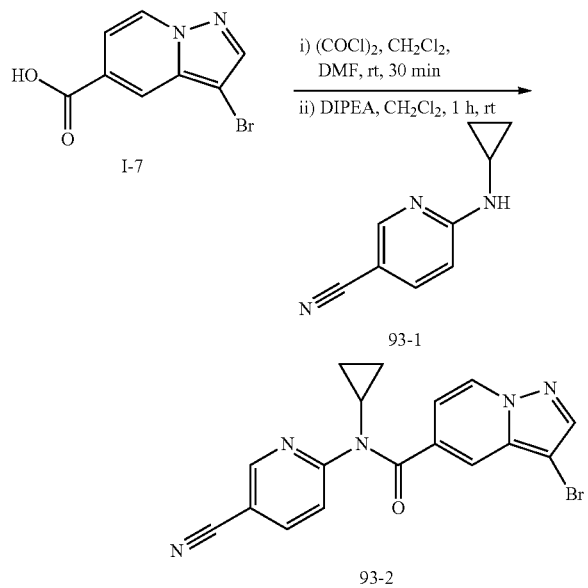

Compound 93-2 was prepared using the general procedure described in Amide Coupling-Method 1 with the appropriate starting materials. Yield 41%. Off-white solid. $^1$H NMR (400 MHz, DMSO-d$_6$): δ 8.77 (d, J=1.7 Hz, 1H), 8.70 (d, J=7.0 Hz, 1H), 8.33 (dd, J=2.2, 8.3 Hz, 1H), 8.23 (s, 1H), 7.78 (d, J=8.8 Hz, 1H), 7.65 (s, 1H), 6.96 (d, J=7.0 Hz, 1H), 3.23-3.27 (m, 1H), 0.89-0.91 (m, 2H), 0.60-0.65 (m, 2H). ESI-LC/MS: m/z 381.95 (M+H) & 383.95 [(M+2)+H]; R$_t$=2.72 min [Waters Acquity UPLC with Quattro micro TQD; Waters Acquity BEH C18, 1.7 µm, 2.1×50 mm column; gradient of 90:10 H$_2$O (0.025% TFA):CH$_3$CN (0.025% TFA) hold for 0.5 min to 10:90 H$_2$O (0.025% TFA):CH$_3$CN (0.025% TFA) in 2.5 min and hold for 2 min with flow rate of 0.4 mL/min].

Step 3

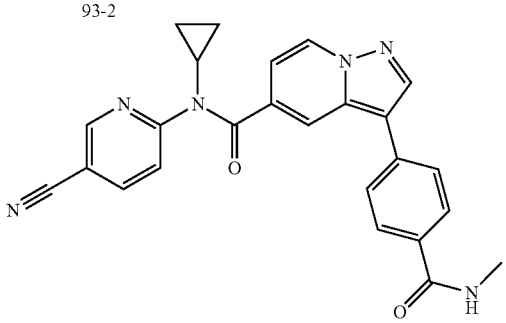

93

Compound 93 was prepared using the general procedure described in Suzuki Procedure G with the appropriate starting materials. Yield 41%. Yellow solid. $^1$H NMR (400 MHz, DMSO-d$_6$): δ 8.83 (d, J=1.7 Hz, 1H), 8.73 (d, J=7.5 Hz, 1H), 8.52 (s, 1H), 8.44-8.50 (m, 1H), 8.36 (dd, J=2.6, 8.7 Hz, 1H), 8.03 (s, 1H), 7.93 (d, J=8.4 Hz, 2H), 7.81 (d, J=8.8 Hz, 1H), 7.66 (d, J=8.4 Hz, 2H), 7.00 (dd, J=1.8, 7.1 Hz, 1H), 3.26-3.30 (m, 1H), 2.81 (d, J=4.4 Hz, 3H), 0.87-0.92 (m, 2H), 0.63-0.67 (m, 2H). ESI-LC/MS: m/z 437.14 (M+H); R$_t$=2.28 min [Waters Acquity UPLC with Quattro micro TQD; Waters Acquity BEH C18, 1.7 µm, 2.1×50 mm column; gradient of 90:10 H$_2$O (0.025% TFA):CH$_3$CN (0.025% TFA) hold for 0.5 min to 10:90 H$_2$O (0.025% TFA):CH$_3$CN (0.025% TFA) in 2.5 min and hold for 2 min with flow rate of 0.4 mL/min]. HPLC purity=>99% at 254 nm; R$_t$=2.15 min [Waters Acquity UPLC with PDA detector; Waters Acquity BEH C18, 1.7 µm, 2.1×100 mm column; gradient of 70:30 H$_2$O (0.025% TFA):CH$_3$CN (0.025% TFA) to 20:80 H$_2$O (0.025% TFA):CH$_3$CN (0.025% TFA) in 4 min and hold for 2 min with flow rate of 0.3 mL/min].

Example 94

5-Cyano-N-methyl-N-(3-(4-(methylcarbamoyl)phenyl)pyrazolo[1,5-a]pyridin-5-yl)picolinamide Step 1

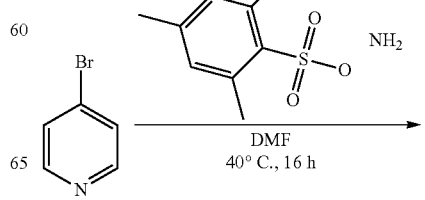

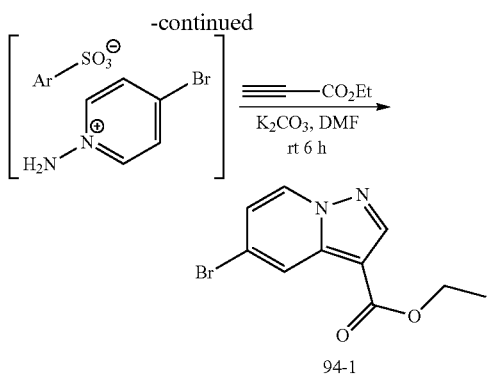

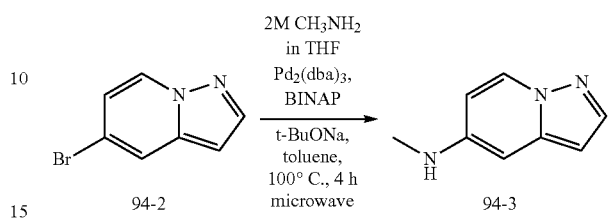

To a stirred solution of 4-bromopyridine (64.0 g, 40.5 mmol) in DMF (200 mL) at 0° C. was added O-(mesitylsulfonyl)hydroxylamine (80.0 g, 37.1 mmol) portion wise over a period of 20 min. The resultant reaction mixture was allowed to warm to room temperature and maintained at 40° C. for 16 h. The reaction mixture was cooled to 0° C., diluted with DMF (200 mL), $K_2CO_3$ (128 g, 92.7 mmol) followed by ethyl propiolate (43.07 mL, 42.5 mmol) were added and the resulting reaction mixture was stirred at rt for 6 h. The reaction mixture was poured on to ice-cold water, extracted with ethyl acetate (2×1000 mL). The ethyl acetate layer was washed with water, brine, dried over anhyd. $Na_2SO_4$ and concentrated. The crude compound was purified by column chromatography over silica gel (100-200 mesh) using a solvent gradient mixture of 7% ethyl acetate in pet-ether to afford 3.5 g (3%) of ethyl 5-bromopyrazolo[1,5-a]pyridine-3-carboxylate 94-1 as a light brown solid. ESI-LC/MS: m/z 269.2 (M+H) & 271.2 [(M+2)+H]; $R_t$=3.46 min [Agilent LC with Ion trap Detector; Symmetry C18, 3.5 µm, 4.6×75 mm column; gradient of 50:50 $H_2O$ (0.1% HCOOH):$CH_3CN$ (0.1% HCOOH) to 10:90 $H_2O$ (0.1% HCOOH):$CH_3CN$ (0.1% HCOOH) in 4.0 min and hold for 3.0 min with flow rate of 1.0 mL/min].

Step 2

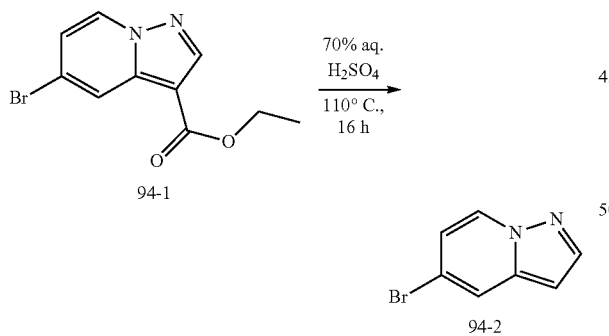

A suspension of ethyl 5-bromopyrazolo[1,5-a]pyridine-3-carboxylate 94-1 (1.6 g, 5.94 mmol) in 70% aq. $H_2SO_4$ (15 mL) was maintained at 110° C. for 16 h. The reaction mixture was cooled to room temperature and poured into ice-cold water. The pH was adjusted to 7.0 using aq. 1N NaOH solution, filtered the precipitated solid, washed with water, pet-ether and dried under vacuum to afford 700 mg (60%) of 5-bromopyrazolo[1,5-a]pyridine 94-2 as an off white solid. ESI-LC/MS: m/z 196.74 (M+H) & 198.71 & [(M+2)+H]; $R_t$=2.39 min [Waters Acquity UPLC with Quattro-micro detector; Waters Acquity BEH C18, 1.7 µm, 2.1×50 mm column; gradient of 90:10 $H_2O$ (0.025% TFA):$CH_3CN$ (0.025% TFA) hold for 0.5 min and to 10:90 $H_2O$ (0.025% TFA):$CH_3CN$ (0.025% TFA) in 3.5 min and hold for 1.5 min with flow rate of 0.4 mL/min].

Step 3

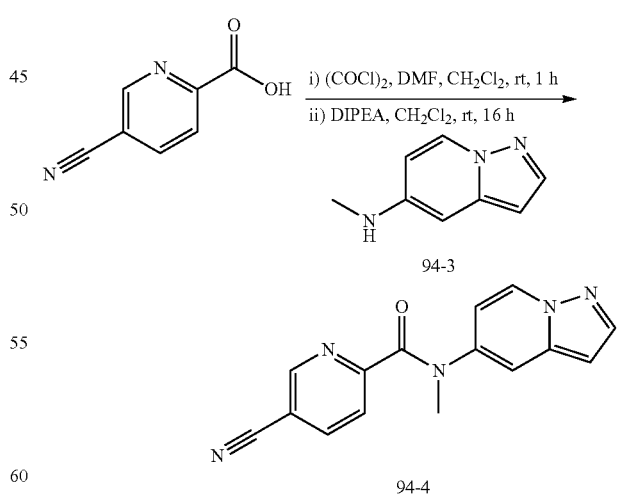

A solution mixture of 5-bromopyrazolo[1,5-a]pyridine 94-2 (500 mg, 2.537 mmol) and t-BuONa (367 mg, 3.822 mmol) in toluene (10 mL) was degassed with argon for about 10 min. To this mixture were added $Pd_2(dba)_3$ (46.7 mg, 0.051 mmol), BINAP (63.4 mg, 0.102 mmol) and 2.0 M methylamine in THF (2 mL, 4.081 mmol) under argon atmosphere. The resulting reaction mixture was maintained at 100° C. for 4 h under microwave irradiation. The reaction mixture was diluted with water (30 mL) and extracted with ethyl acetate (2×50 mL). The combined organic layer was washed with water (20 mL), brine (20 mL), dried over anhydrous $Na_2SO_4$ and concentrated. The residue was passed through a column silica-gel (100-200 mesh) using a solvent gradient of 25% ethyl acetate in pet-ether to afford 110 mg (crude) of N-methylpyrazolo[1,5-a]pyridin-5-amine 94-3 as an off white solid. The crude product was used as such for next step without further purification. ESI-LC/MS: m/z 147.48 (M+H); $R_t$=1.53 min [Waters Acquity UPLC with Quattro-micro detector; Waters Acquity BEH C18, 1.7 µm, 2.1×50 mm column; gradient of 90:10 $H_2O$ (0.025% TFA):$CH_3CN$ (0.025% TFA) hold for 0.5 min and to 10:90 $H_2O$ (0.025% TFA):$CH_3CN$ (0.025% TFA) in 3.5 min and hold for 1.5 min with flow rate of 0.4 mL/min].

Step 4

Compound 94-4 was prepared using the general procedure described in Amide Coupling-Method 1 with the appropriate starting materials. Yield 13% (over two steps). Off-white solid. ESI-LC/MS: m/z 278.3 (M+H); $R_t$=2.88 min [Agilent LC with Ion trap Detector; Symmetry C18, 3.5 µm, 4.6×75 mm column; gradient of 80:20 H$_2$O (0.1% HCOOH):CH$_3$CN (0.1% HCOOH) to 10:90 H$_2$O (0.1% HCOOH):CH$_3$CN (0.1% HCOOH) in 4.0 min and hold for 3.0 min with flow rate of 1.0 mL/min].

Step 5

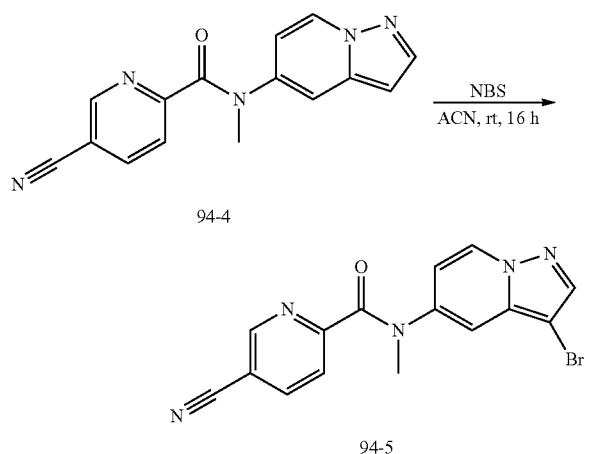

94-4

94-5

To a stirred solution of 5-cyano-N-methyl-N-(pyrazolo[1,5-a]pyridin-5-yl)picolinamide 94-4 (70 mg, 0.252 mmol) in aceotnitrile (6 mL) was added NBS (49.4 mg, 0.277 mmol) at room temperature and stirred for 16 h. Ethyl acetate (30 mL) was added to reaction mixture, washed with water (20 mL), brine (20 ml), dried over anhyd. Na$_2$SO$_4$ and concentrated to afford 90 mg (crude) of N-(3-bromopyrazolo[1,5-a]pyridin-5-yl)-5-cyano-N-methylpicolinamide 94-5 as a brown solid. The crude product was used as such for next step without further purification. $^1$H-NMR (400 MHz, DMSO-d$_6$): δ 8.82 (s, 1H), 8.64 (d, J=7.6 Hz, 1H), 8.41 (dd, J=1.2, 8.4 Hz, 1H), 8.13 (s, 1H), 7.91 (d, J=8.4 Hz, 1H), 7.36 (s, 1H), 6.68-6.88 (m, 1H), 3.46 (s, 3H). ESI-LC/MS: m/z 356.26 (M+H)+ & 358.24 [(M+2)+H] R$_t$=2.32 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.5 min and hold for 1.5 min with flow rate of 0.4 mL/min].

Step 6

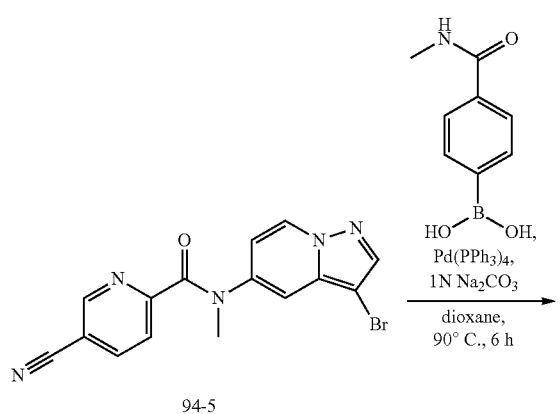

94-5

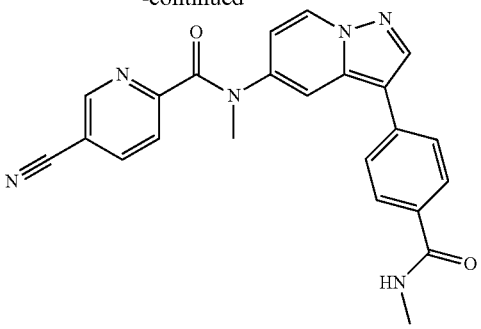

94

Compound 94 was prepared using the general procedure described in Suzuki Procedure G with the appropriate starting materials. Yield 29% (over two steps). Light yellow solid. $^1$H NMR (400 MHz, DMSO-d$_6$): δ 8.83 (s, 1H), 8.69 (d, J=7.5 Hz, 1H), 8.40-8.46 (m, 3H), 7.87-7.94 (m, 3H), 7.74 (s, 1H), 7.55-7.60 (m, 2H), 6.94 (s, 1H), 3.48 (s, 3H), 2.80 (d, J=4.3 Hz, 3H). ESI-LC/MS: m/z 411.42 (M+H); R$_t$=1.97 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.5 min and hold for 1.5 min with flow rate of 0.4 mL/min]. HPLC purity=91.9% at 227 nm; R$_t$=1.64 min [Waters Acquity UPLC with PDA; Waters Acquity UPLC BEH C18, 1.7 μm, 2.1×100 mm column; gradient of 70:30 H$_2$O (0.025% TFA):CH$_3$CN (0.025% TFA) to 20:80 H$_2$O (0.025% TFA):CH$_3$CN (0.025% TFA) in 4.0 min and hold for 2.0 min with flow rate of 0.3 mL/min].

Example 95

N-ethyl-N-(5-fluoropyridin-2-yl)-3-(4-(methylcarbamoyl)phenyl)pyrazolo[1,5-a]pyridine-5-carboxamide Step 1

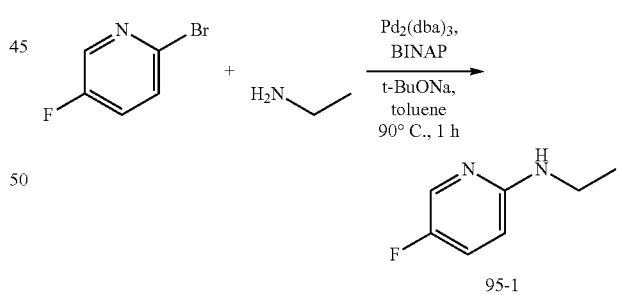

95-1

A solution of 2-bromo-5-fluoropyridine (3.0 g, 17.04 mmol) and t-BuONa (2.4 g, 25.00 mmol) in toluene (60 mL) was degassed with argon for about 10 min. Pd$_2$(dba)$_3$ (155 mg, 0.169 mmol), BINAP (318 mg, 0.510 mmol) and ethylamine (2M in THF) (30 mL) were added under argon atmosphere. The resulting reaction mixture was maintained at 90° C. for 1 h in sealed tube. The reaction mixture was partitioned between water (50 mL) and ethyl acetate (100 mL). The organic layer was washed with water, brine solution, dried over anhydrous Na$_2$SO$_4$ and concentrated. The crude product was purified by column chromatography over silica-gel (100-200 mesh) using a solvent gradient mixture of 5% ethyl acetate in pet-ether to afford 1.5 g (63%) of N-ethyl-5-fluoropyridin-2-amine 95-1 as an off-white solid. ¹H NMR (400 MHz, DMSO-d₆): δ 7.90 (d, J=3.2 Hz, 1H), 7.31 (td, J=2.8, 8.4 Hz, 1H), 6.44 (dd, J=3.6, 9.2 Hz, 1H), 6.39 (br.s, 1H), 3.19 (q, J=7.2 Hz, 2H), 1.10 (t, J=7.2 Hz, 3H). ESI-LC/MS: m/z 141.4 (M+H); R$_t$=3.10 min [Agilent LC with Ion trap Detector; XBridge-C18, 3.5 μm, 4.6×75 mm column; gradient of 80:20 H₂O (0.005 M ammonium bicarbonate):CH₃CN to 10:90 H₂O (0.01 M ammonium bicarbonate):CH₃CN in 4.0 min and hold for 3.0 min with flow rate of 1.0 mL/min].

Step 2

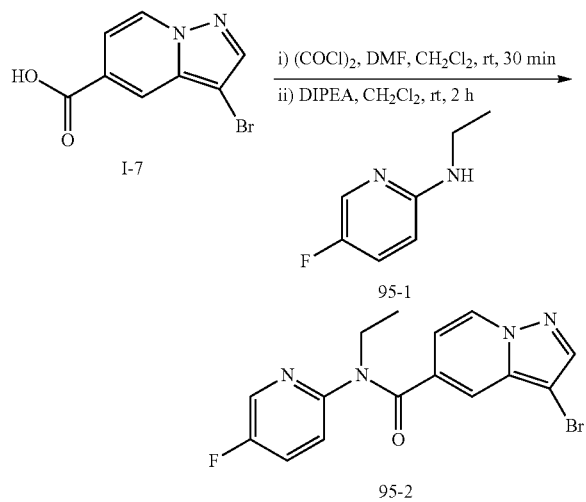

Compound 95-2 was prepared using the general procedure described in Amide Coupling Method 1 with the appropriate starting materials. Yield 83%. Pale yellow solid. ¹H NMR (400 MHz, DMSO-d₆): δ 8.62 (d, J=10.0 Hz, 1H), 8.42 (d, J=4.0 Hz, 1H), 8.19 (s, 1H), 7.71 (td, J=4.0, 11.6 Hz, 1H), 7.39-7.42 (m, 2H), 6.71 (dd, J=2.8, 10.0 Hz, 1H), 3.99 (q, J=9.6 Hz, 2H), 1.16 (t, J=9.6 Hz, 3H). ESI-LC/MS: m/z 369.92 (M+H) & 364.92 [(M+2)+H]; R$_t$=2.75 min [Waters Acquity UPLC with SQD; Waters Acquity UPLC BEH C18, 1.7 μm, 2.1×50 mm column; gradient of 98:02 H₂O (0.025% TFA):CH₃CN (0.025% TFA) hold for 0.8 min and to 45:55 H₂O (0.025% TFA):CH₃CN (0.025% TFA) in 2.0 min and hold for 1.0 min and to 0:100 H₂O (0.025% TFA):CH₃CN (0.025% TFA) in 0.5 minute and hold for 1.5 min with flow rate of 0.4 mL/min].

Step 3

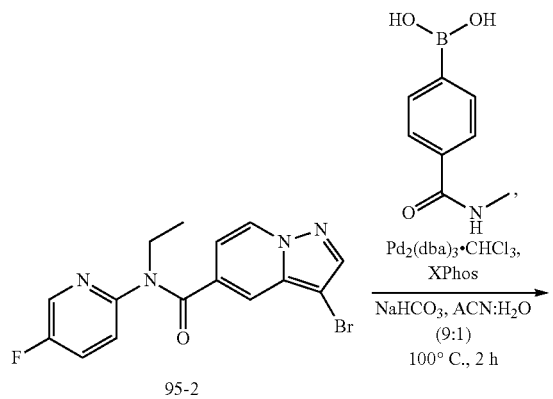

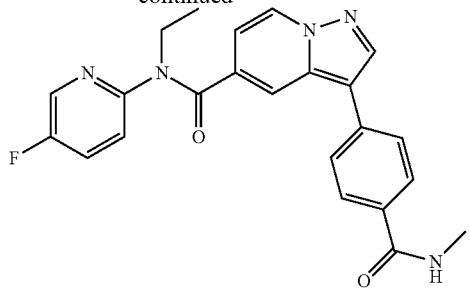

Compound 95 was prepared using the general procedure described in Suzuki Procedure I with the appropriate starting materials. Yield 52%. Pale yellow solid. ¹H-NMR (400 MHz, DMSO-d₆): δ 8.64 (d, J=7.4 Hz, 1H), 8.45-8.48 (m, 3H), 7.92 (d, J=8.3 Hz, 2H), 7.71-7.77 (m, 2H), 7.56 (d, J=8.3 Hz, 2H), 7.42 (dd, J=4.0, 8.9 Hz, 1H), 6.76 (d, J=1.4, 7.3 Hz, 1H), 4.01 (q, J=7.4 Hz, 2H), 2.82 (d, J=4.4 Hz, 3H), 1.17 (t, J=7.3 Hz, 3H). ESI-LC/MS: m/z 418.1 (M+H); R$_t$=3.22 min [Agilent LC with Ion trap Detector; XBridge-C18, 3.5 μm, 4.6×75 mm column; gradient of 80:20 H₂O (0.005 M ammonium bicarbonate):CH₃CN to 20:80 H₂O (0.01 M ammonium bicarbonate):CH₃CN in 4.0 min and hold for 3.0 min with flow rate of 1.0 mL/min]. HPLC purity: 98.9% at 254 nm; R$_t$=2.75 min [Waters Acquity UPLC with PDA; Waters Acquity UPLC BEH C18, 1.7 μm, 2.1×100 mm column; gradient of 90:10 H₂O (0.025% TFA):CH₃CN (0.025% TFA) to 10:90 H₂O (0.025% TFA):CH₃CN (0.025% TFA) in 4.0 min and hold for 2.0 min with flow rate of 0.3 mL/min].

Example 96

N-ethyl-3-(4-(methylcarbamoyl)phenyl)-N-(5-(trifluoromethyl)pyridin-2-yl)pyrazolo[1,5-a]pyridine-5-carboxamide Step 1

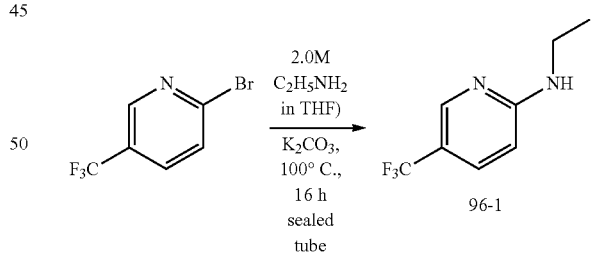

A solution mixture of 2-bromo-5-trifluoromethylpyridine (3.0 g, 13.274 mmol), 2.0 M ethylamine in THF (10 mL) and K₂CO₃ (3.6 g, 26.05 mmol) were stirred in sealed tube at 100° C. for 16 h. The reaction mixture was partitioned between water (100 mL) and ethyl acetate (200 mL). The ethyl acetate layer was washed with brine (100 mL), dried over anhydrous Na₂SO₄ and concentrated to afford 1.6 g (63%) of N-ethyl-5-(trifluoromethyl)pyridin-2-amine 1 as an off-white solid. ¹H-NMR (400 MHz, DMSO-d₆): 8.37 (d, J=2.1 Hz, 1H), 7.57-7.66 (m, 2H), 6.51 (d, J=8.4 Hz, 1H), 3.26-3.30 (m, 2H), 1.13 (t, J=6.9 Hz, 3H).

Step 2

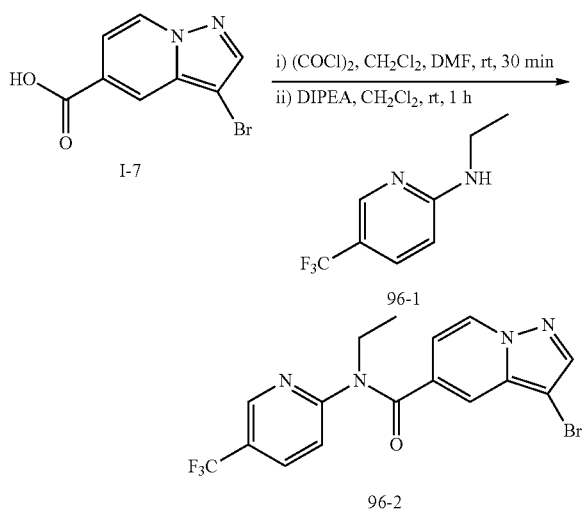

Compound 96-2 was prepared using the general procedure described in Amide Coupling-Method 1 with the appropriate starting materials. Yield 64%. Off-white solid. ¹H NMR (400 MHz, DMSO-d₆): δ 8.78 (s, 1H), 8.66 (d, J=7.6 Hz, 1H), 8.22 (s, 1H), 8.15 (dd, J=2.4, 8.8 Hz, 1H), 7.49-7.53 (m, 2H), 6.77 (dd, J=1.2, 7.2 Hz, 1H), 4.10 (q, J=6.8, 7.2 Hz, 2H), 1.20 (t, J=6.8 Hz, 3H). ESI-LC/MS: m/z 412.95 (M+H) & 414.95 [(M+2)+H]; R$_t$=3.34 min [Waters Acquity UPLC with Quattro-micro detector; Waters Acquity UPLC BEH C18, 1.7 μm, 2.1×50 mm column; gradient of 90:10 H₂O (0.025% TFA):CH₃CN (0.025% TFA) hold for 0.8 min and to 20:80 H₂O (0.025% TFA):CH₃CN (0.025% TFA) in 3.5 min and hold for 1.5 min with flow rate of 0.4 mL/min].

Step 2

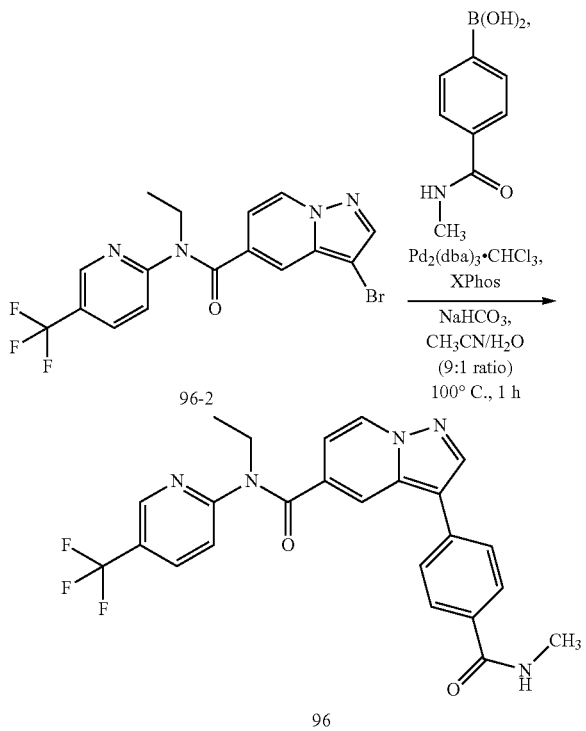

Compound 96 was prepared using the general procedure described in Suzuki Procedure I with the appropriate starting materials. Yield 60%. yellow solid. ¹H NMR (400 MHz, DMSO-d₆): δ 8.89-8.82 (m, 1H), 8.70 (dd, J=0.69, 7.22 Hz, 1H), 8.50 (s, 1H), 8.40-8.48 (m, 1H), 8.19 (dd, J=2.32, 8.60 Hz, 1H), 7.91 (d, J=8.28 Hz, 2H), 7.84 (d, J=0.72 Hz, 1H), 7.51-7.59 (m, 3H), 6.83 (dd, J=1.82, 7.22 Hz, 1H), 4.13 (q, J=7.03 Hz, 2H), 2.82 (d, J=4.52 Hz, 3H), 1.22 (t, J=7.09 Hz, 3H). ESI-LC/MS: m/z 467.5 (M+H); R$_t$=0.95 min [Agilent UHPLC 1290 coupled with API 3200; Acquity UPLC BEH C18 column, 1.7 μm, 2.1×50 mm; gradient of 98:2 H₂O (0.1% HCOOH):CH₃CN to 2:98 H₂O (0.1% HCOOH):CH₃CN for 2 min run time with 1.0 mL/min flow rate]. HPLC purity=>99% at 254 nm; R$_t$=1.64 min [Waters Acquity UPLC equipped with a Acquity UPLC HSS T3 column, 1.8 μm, 2.1×50 mm; gradient of 95:5 H₂O (0.1% HCOOH):CH₃CN to 2:98 H₂O (0.1% HCOOH):CH₃CN for 2 min run time with 1.0 mL/min flow rate].

Example 97

N-(4-Cyanophenyl)-N-methyl-3-(6-(methylcarbamoyl)pyridin-3-yl)pyrazolo[1,5-a]pyridine-5-carboxamide Step 1

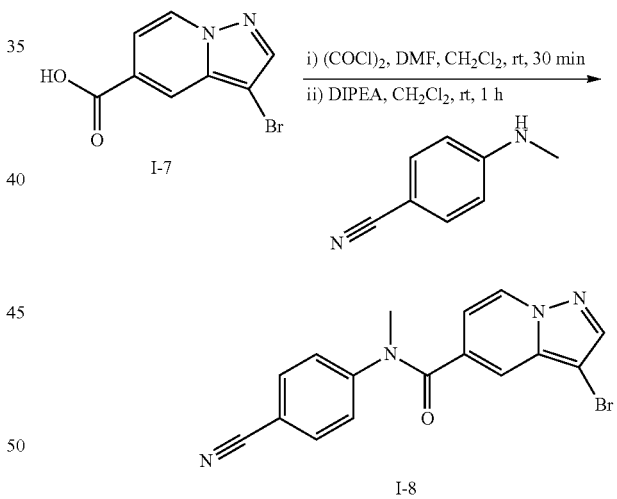

Compound I-8 was prepared using the general procedure described in Amide Coupling-Method 1 with the appropriate starting materials. Yield 51%. White solid. ¹H NMR (400 MHz, DMSO-d₆): δ 8.63 (d, J=7.0 Hz, 1H), 8.20 (s, 1H), 7.80 (d, J=8.8 Hz, 2H), 7.50-7.52 (m, 3H), 6.78 (dd, J=1.7, 7.4 Hz, 1H), 3.44 (s, 3H). ESI-LC/MS: m/z 355.05 (M+H) & 357.03 [(M+2)+H]; R$_t$=2.64 min [Waters Acquity UPLC with Quattro-micro detector; Waters Acquity BEH C18, 1.7 μm, 2.1×50 mm column; gradient of 90:10 H₂O (0.025% TFA):CH₃CN (0.025% TFA) hold for 0.5 min and to 10:90 H₂O (0.025% TFA):CH₃CN (0.025% TFA) in 3.0 min and hold for 2.0 min with flow rate of 0.4 mL/min].

Step 2

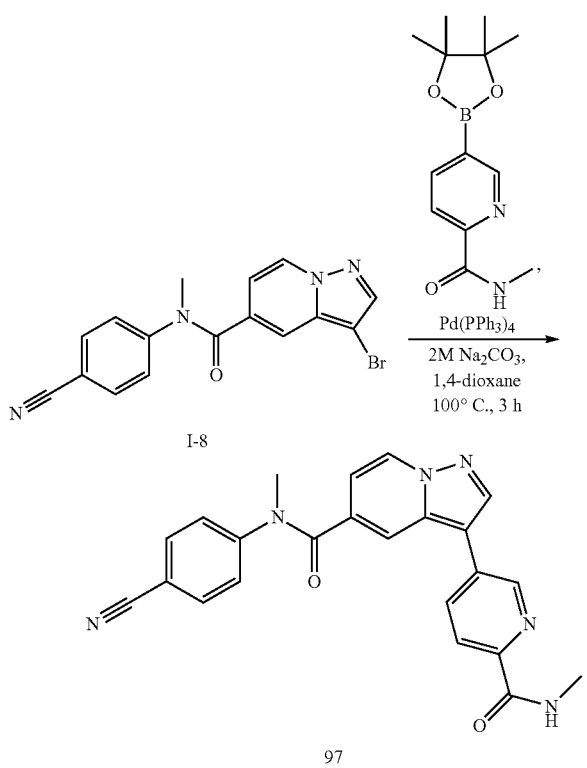

Compound 97 was prepared using the general procedure described in Suzuki Procedure G with the appropriate starting materials. Yield 13%. Yellow solid. $^1$H-NMR (400 MHz, DMSO-$d_6$): δ 8.82 (d, J=1.3 Hz, 1H), 8.69-8.74 (m, 2H), 8.63 (s, 1H), 8.06-8.10 (m, 2H), 7.96 (s, 1H), 7.83 (d, J=8.8 Hz, 2H), 7.55 (d, J=8.8 Hz, 2H), 6.85 (dd, J=1.8, 7.5 Hz, 1H), 3.46 (s, 3H), 2.86 (d, J=4.9 Hz, 3H). ESI-LC/MS: m/z 411.20 (M+H); $R_t$=2.41 min [Waters Acquity UPLC with Quattro micro TQD; Waters Acquity BEH C18, 1.7 μm, 2.1×50 mm column; gradient of 90:10 $H_2O$ (0.025% TFA): $CH_3CN$ (0.025% TFA) hold for 0.5 min to 10:90 $H_2O$ (0.025% TFA):$CH_3CN$ (0.025% TFA) in 2.5 min and hold for 2 min with flow rate of 0.4 mL/min]. HPLC purity: 98.3% at 254 nm; $R_t$=3.05 min [Waters Acquity UPLC with PDA detector; Waters Acquity BEH C18, 1.7 μm, 2.1×100 mm column; gradient of 90:10 $H_2O$ (0.025% TFA):$CH_3CN$ (0.025% TFA) to 20:80 $H_2O$ (0.025% TFA):$CH_3CN$ (0.025% TFA) in 4 min and hold for 2 min with flow rate of 0.3 mL/min].

Example 98

3-(5-Amino-6-chloropyridin-3-yl)-N-(5-cyanopyridin-2-yl)-N-methylpyrazolo[1,5-a]pyridine-5-carboxamide Step 1

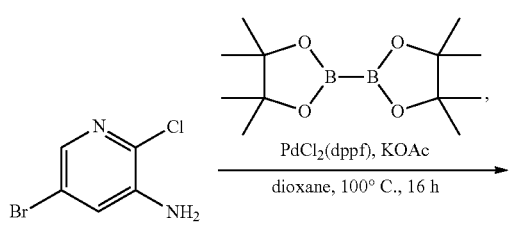

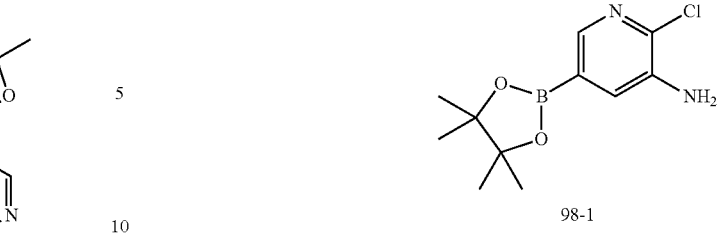

5-Bromo-2-chloropyridin-3-amine (500 mg, 2.410 mmol), bis(pinacolato)diboron (672.9 mg, 2.649 mmol) and potassium acetate (467 mg, 4.765 mmol) in 1,4-dioxane (15 mL) were degassed with argon gas for 15 min. PdCl$_2$(dppf) dichloromethane complex (98 mg, 0.120 mmol) was added and the reaction mixture was stirred at 100° C. for 4 h. The reaction mixture was diluted with ethyl acetate, filtered through celite and the filtrate was concentrated to afford 800 mg (crude) of 2-chloro-5-(4,4,5,5-tetramethyl-1,3,2-dioxaborolan-2-yl)pyridin-3-amine 98-1 as a deep brown solid. The crude product was used as such for the next step without further purification. ESI-LC/MS: m/z 254.9 (M+H) & 256.9 [(M+H)+2]; $R_t$=3.14 min [Agilent LC with Ion trap Detector; Xterra MS-C18, 2.5 μm, 4.6×50 mm column; gradient of 80:20 $H_2O$ (0.01 M ammonium bicarbonate):$CH_3CN$ to 10:90 $H_2O$ (0.01 M ammonium bicarbonate):$CH_3CN$ in 4.0 min and hold for 3.0 min with flow rate of 1.0 mL/min].

Step 2

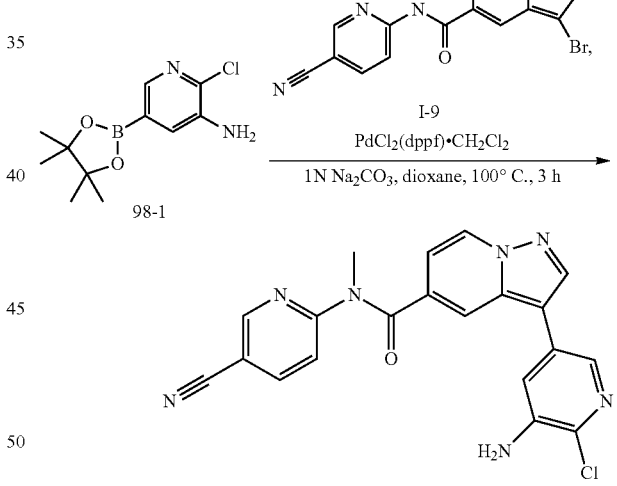

A solution mixture of 3-bromo-N-(5-cyanopyridin-2-yl)-N-methylpyrazolo[1,5-a]pyridine-5-carboxamide 1 (150 mg, 0.42 mmol), 2-chloro-5-(4,4,5,5-tetramethyl-1,3,2-dioxaborolan-2-yl)pyridin-3-amine 98-1 (106.9 mg, crude) and 1N Na$_2$CO$_3$ solution (0.42 mL, 0.84 mmol) in 1,4-dioxane (15 mL) was degassed with argon gas for 10 min. PdCl$_2$(dppf)dichloromethane complex (34.4 mg, 0.042 mmol) was added and stirred at 100° C. for 3 h in sealed tube. The reaction mixture was cooled to room temperature and partitioned between water and ethyl acetate. The organic layer was washed with water, brine, dried over anhydrous Na$_2$SO$_4$ solution and concentrated under reduced pressure.

The crude compound was purified by column chromatography over silica gel (100-200 mesh) using a solvent gradient of 2% methanol in chloroform as an eluant to afford 25 mg (20% over two steps) of 3-(5-amino-6-chloropyridin-3-yl)-N-(5-cyanopyridin-2-yl)-N-methylpyrazolo[1,5-a]pyridine-5-carboxamide 98 as a yellow solid. $^1$H NMR (400 MHz, DMSO-d$_6$): δ 8.82 (d, J=2.2 Hz, 1H), 8.69 (d, J=7.5 Hz, 1H), 8.44 (s, 1H), 8.24 (dd, J=2.2, 8.7 Hz, 1H), 8.02 (s, 1H), 7.82 (d, J=2.3 Hz, 1H), 7.64 (d, J=8.8 Hz, 1H), 7.41 (d, J=1.8 Hz, 1H), 6.78 (dd, J=2.8, 7.5 Hz, 1H), 5.67 (s, 2H), 3.53 (s, 3H). ESI-LC/MS: m/z 404.09 (M+H) & 406.04 [(M+2)H+]; R$_t$=1.65 min [Waters Acquity UPLC with Quattro-micro detector; Waters Acquity BEH C18, 1.7 μm, 2.1×50 mm column; gradient of 85:15 H$_2$O (0.025% TFA):CH$_3$CN (0.025% TFA) to 5:95 H$_2$O (0.025% TFA):CH$_3$CN (0.025% TFA) in 3.0 min and hold for 1.0 min with flow rate of 0.4 mL/min]. HPLC purity: 97.1% at 254 nm; R$_t$=2.452 min [Waters Acquity UPLC with PDA; Waters Acquity BEH C18, 1.7 μm, 2.1×100 mm column; gradient of 70:30 H$_2$O (0.025% TFA):CH$_3$CN (0.025% TFA) to 20:80 H$_2$O (0.025% TFA):CH$_3$CN (0.025% TFA) in 4.0 min and hold for 2.0 min with flow rate of 0.3 mL/min].

Example 99

N-(4-Chlorophenyl)-N-methyl-3-(4-(methylcarbamoyl)phenyl)pyrazolo[1,5-a]pyridine-5-carboxamide Step 1

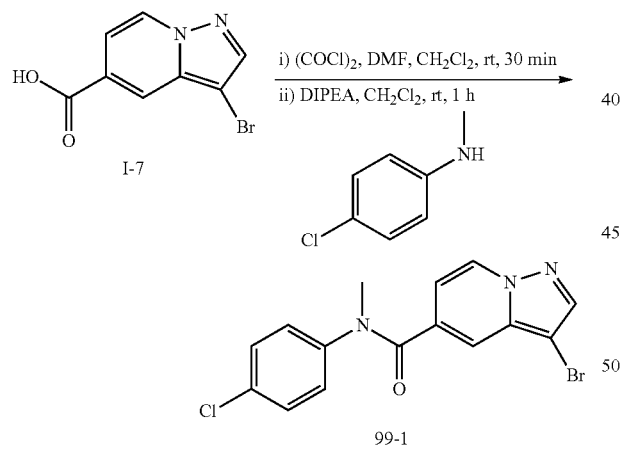

Compound 99-1 was prepared using the general procedure described in Amide Coupling-Method 1 with the appropriate starting materials. Yield 50%. White solid. $^1$H NMR (400 MHz, DMSO-d$_6$): δ 8.62 (d, J=7.0 Hz, 1H), 8.19 (s, 1H), 7.48 (s, 1H), 7.33-7.39 (m, 4H), 6.77 (d, J=6.6 Hz, 1H), 3.35 (s, 3H). ESI-LC/MS: m/z 363.94 (M+H) & 365.92 [(M+2)+H]; R$_t$=3.01 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.0 min and hold for 2.0 min with flow rate of 0.4 mL/min].

Step 2

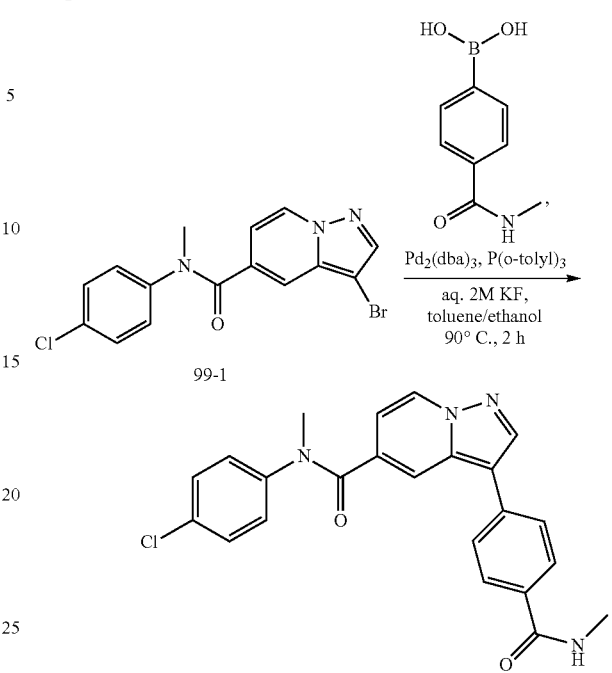

Compound 99 was prepared using the general procedure described in Suzuki Procedure H with the appropriate starting materials. Yield 32%). Light yellow solid. $^1$H-NMR (400 MHz, DMSO-d$_6$): δ 8.66 (d, J=7.0 Hz, 1H), 8.45-8.52 (m, 2H), 7.91 (d, J=8.30 Hz, 2H), 7.79 (s, 1H), 7.52 (d, J=8.30 Hz, 2H), 7.36-7.46 (m, 4H), 6.85 (d, J=7.0 Hz, 1H), 3.41 (s, 3H), 2.81 (d, J=4.40 Hz, 3H). ESI-LC/MS: m/z 419.13 (M+H) & 421.11 [(M+2)+H]; R$_t$=2.52 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.0 min and hold for 2.0 min with flow rate of 0.4 mL/min]. HPLC purity: 98.6% at 278 nm; R$_t$=3.42 min [Waters Acquity UPLC with PDA; Waters Acquity BEH C18, 1.7 μm, 2.1×100 mm column; gradient of 90:10 H$_2$O (0.025% TFA):CH$_3$CN (0.025% TFA) to 20:80 H$_2$O (0.025% TFA):CH$_3$CN (0.025% TFA) in 4.0 min and hold for 2.0 min with flow rate of 0.3 mL/min].

Example 100

3-(4-Carbamoylphenyl)-N-(4-chlorophenyl)-N-methylpyrazolo[1,5-a]pyridine-5-carboxamide

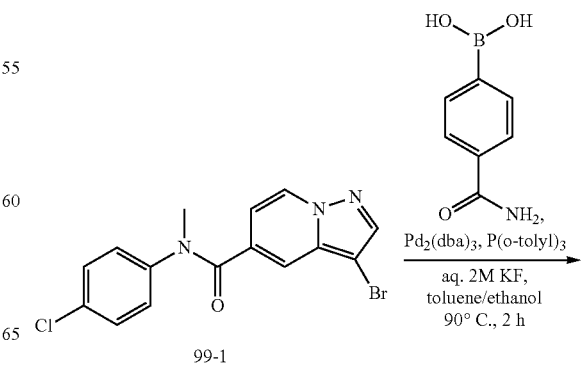

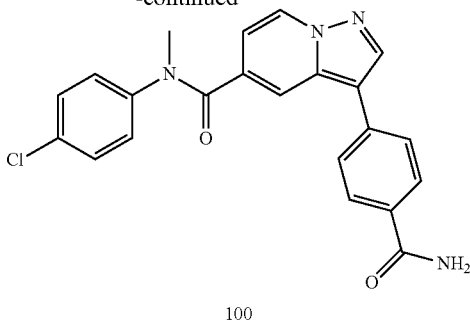

100

Compound 100 was prepared using the general procedure described in Suzuki Procedure H with the appropriate starting materials. Yield 15%. Light yellow solid. $^1$H-NMR (400 MHz, DMSO-d$_6$): δ 8.66 (d, J=7.0 Hz, 1H), 8.47 (s, 1H), 8.04 (s, 1H), 7.95 (d, J=8.30 Hz, 2H), 7.78 (s, 1H), 7.51 (d, J=8.40 Hz, 2H), 7.38-7.47 (m, 5H), 6.85-6.87 (m, 1H), 3.41 (s, 3H). ESI-LC/MS: m/z 405.12 (M+H) & 407.04 [(M+2) H+]; R$_t$=2.41 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.0 min and hold for 2.0 min with flow rate of 0.4 mL/min]. HPLC purity: 99.4% at 254 nm; R$_t$=3.25 min [Waters Acquity UPLC with PDA; Waters Acquity BEH C18, 1.7 μm, 2.1×100 mm column; gradient of 90:10 H$_2$O (0.025% TFA):CH$_3$CN (0.025% TFA) to 20:80 H$_2$O (0.025% TFA):CH$_3$CN (0.025% TFA) in 4.0 min and hold for 2.0 min with flow rate of 0.3 mL/min].

Example 101

4-(5-((5-Cyanopyridin-2-yl)(methyl)carbamoyl) pyrazolo[1,5-a]pyridin-3-yl)benzoic acid

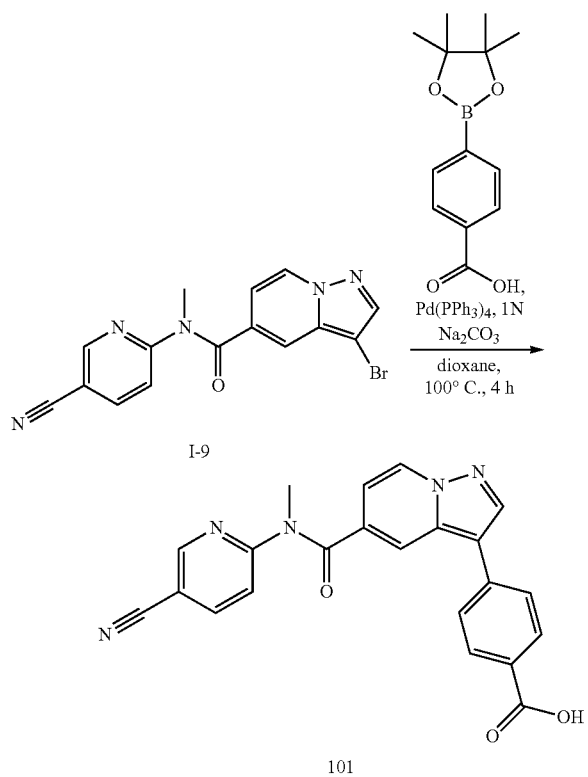

Compound 101 was prepared using the general procedure described in Suzuki Procedure G with the appropriate starting materials. Yield 72%. Yellow solid. $^1$H NMR (400 MHz, DMSO-d$_6$): δ 8.87 (d, J=2.4 Hz, 1H), 8.72 (d, J=7.2 Hz, 1H), 8.51 (s, 1H), 8.27 (dd, J=2.2, 8.4 Hz, 1H), 7.95-8.02 (m, 3H), 7.57-7.66 (m, 3H), 6.85 (d, J=8.8 Hz, 1H), 3.53 (s, 3H). ESI-LC/MS: m/z 398.15 (M+H) & 399.05 [(M+2)+H]; R$_t$=2.36 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.0 min and hold for 2.0 min with flow rate of 0.4 mL/min. HPLC Purity: >99% at 297 nm; R$_t$=2.30 min. Waters Acquity UPLC with PDA; Waters Acquity BEH C18, 1.7 μm, 2.1×100 mm column; gradient of 90:10 H$_2$O (0.025% TFA):CH$_3$CN (0.025% TFA) to 20:80 H$_2$O (0.025% TFA):CH$_3$CN (0.025% TFA) in 4.0 min and hold for 2.0 min with flow rate of 0.3 mL/min].

Example 102

N-(5-Cyanopyridin-2-yl)-3-(4-((2-hydroxyethyl) carbamoyl)phenyl)-N-methylpyrazolo[1,5-a]pyridine-5-carboxamide Step 1

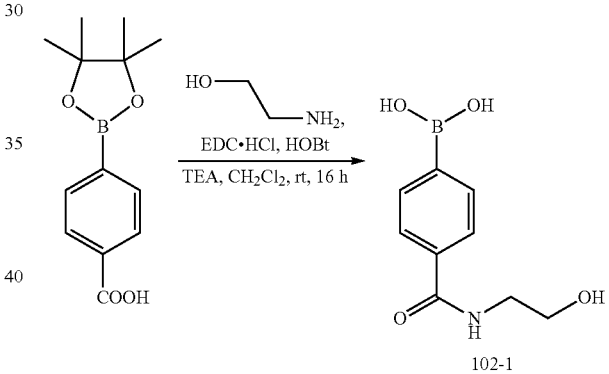

102-1

To a solution mixture of 4-(4,4,5,5-tetramethyl-1,3,2-dioxaborolan-2-yl)benzoic acid (1.0 g, 4.03 mmol), HOBT (925.3 mg, 6.85 mmol) and EDC.HCl (1.15 g, 5.98 mmol) in dichloromethane (20 mL) was stirred at room temperature for 5 min and were added ethanolamine (270.5 mg, 4.42 mmol) and TEA (1.15 mL, 8.19 mmol). The resulting reaction mixture was stirred at temperature for 16 h. The reaction mixture was partitioned between water and ethyl acetate. The organic layer was washed with water, brine, dried over anhydrous Na$_2$SO$_4$ and the solvent was distilled off under reduced pressure to afford 1.0 g (crude) of (4-((2-hydroxyethyl)carbamoyl)phenyl)boronic acid 102-1 as an off white solid. The crude product was used as such for the next step without further purification. ESI-LC/MS: m/z 209.95 (M+H); R$_t$=0.72 min [Waters Acquity UPLC with Quattro-micro detector; Waters Acquity BEH C18, 1.7 μm, 2.1×50 mm column; gradient of 90:10 H$_2$O (0.025% TFA): CH$_3$CN (0.025% TFA) hold for 0.5 min and to 10:90 H$_2$O (0.025% TFA):CH$_3$CN (0.025% TFA) in 3.0 min and hold for 2.0 min with flow rate of 0.4 mL/min].

Step 2

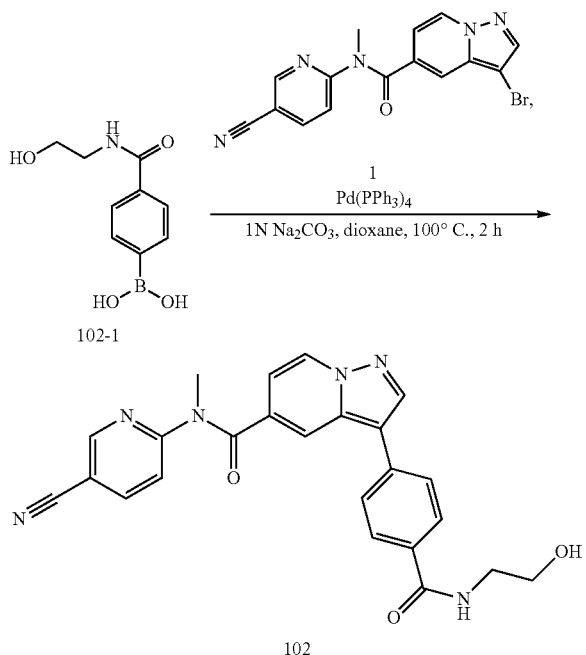

The compound 102 was prepared using the general procedure described in Suzuki Procedure G with the appropriate starting materials. Yield 10% (over two steps). Light yellow solid. $^1$H-NMR (400 MHz, DMSO-d$_6$): δ 8.86 (s, 1H), 8.71 (d, J=7.0 Hz, 1H), 8.54 (s, 1H), 8.47-8.52 (m, 1H), 8.27 (dd, J=2.2, 8.8 Hz, 1H), 8.06 (s, 1H), 7.93 (d, J=5.7 Hz, 1H), 7.61-7.66 (m, 3H), 6.84 (d, J=7.0 Hz, 1H), 4.77 (t, J=5.7 Hz, 1H), 3.50-3.53 (s, 5H), 3.37-3.39 (m, 2H). ESI-LC/MS: m/z 441.19 (M+H); R$_t$=2.09 min [Waters Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.0 min and hold for 2.0 min with flow rate of 0.4 mL/min]. HPLC Purity: 98.1% at 254 nm; R$_t$=1.63 min [Waters Acquity UPLC with PDA; Waters Acquity BEH C18, 1.7 μm, 2.1×100 mm column; gradient of 90:10 H$_2$O (0.025% TFA):CH$_3$CN (0.025% TFA) to 20:80 H$_2$O (0.025% TFA):CH$_3$CN (0.025% TFA) in 4.0 min and hold for 2.0 min with flow rate of 0.3 mL/min].

Example 103

N-Methyl-3-(4-(methylcarbamoyl)phenyl)-N-(4-(trifluoromethyl)phenyl)pyrazolo[1,5-a]pyridine-5-carboxamide

Step 1

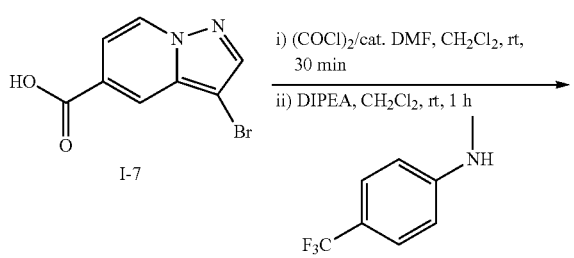

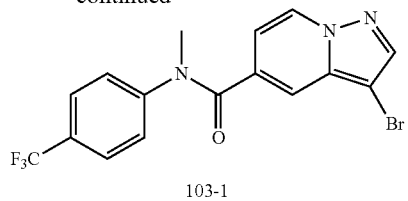

Compound 103-1 was prepared using the general procedure described in Amide Coupling Method 1 with the appropriate starting materials. Yield 27%. Off-white solid. $^1$H NMR (400 MHz, DMSO-d$_6$): δ 8.64 (d, J=7.1 Hz, 1H), 8.19 (s, 1H), 7.68-7.70 (m, 2H), 7.49-7.54 (m, 3H), 6.80 (dd, J=1.7, 7.0 Hz, 1H), 3.45 (s, 3H). ESI-LC/MS: m/z 397.96 (M+H) & 400.01 [(M+2)+H]; R$_t$=2.77 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.0 min and hold for 2.0 min with flow rate of 0.4 mL/min].

Step 2

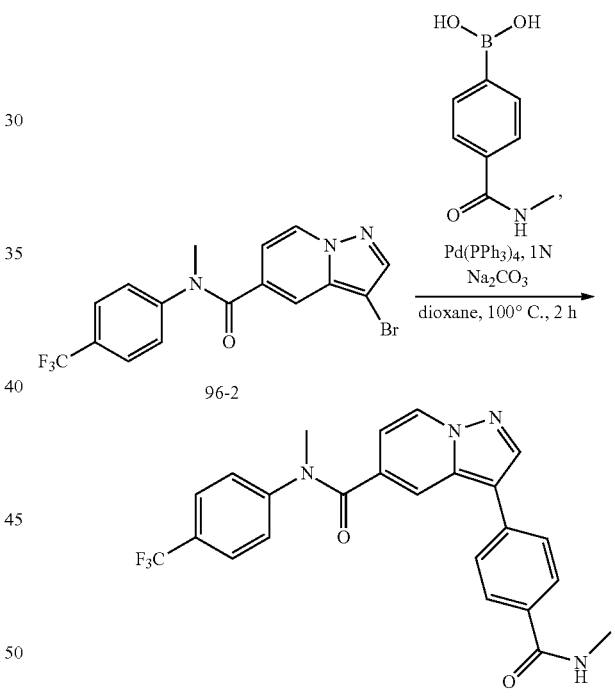

Compound 103 was prepared using the general procedure described in Suzuki Procedure G with the appropriate starting materials. Yield 22%. Light yellow solid. $^1$H-NMR (400 MHz, DMSO-d$_6$): δ 8.68 (d, J=7.0 Hz, 1H), 8.44-8.52 (m, 2H), 7.89 (d, J=8.30 Hz, 2H), 7.79 (s, 1H), 7.74 (d, J=8.7 Hz, 2H), 7.58 (d, J=8.3 Hz, 2H), 7.47 (d, J=8.3 Hz, 2H), 6.88 (dd, J=1.3, 7.0 Hz, 1H), 3.47 (s, 3H), 2.81 (d, J=4.4 Hz, 3H). ESI-LC/MS: m/z 453.16 (M+H); R$_t$=2.60 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.0 min and hold for 2.0 min with flow rate of 0.4 mL/min].

HPLC purity: 98.7% at 281 nm; R$_t$=2.74 min [Waters Acquity UPLC with PDA; Waters Acquity BEH C18, 1.7 µm, 2.1×100 mm column; gradient of 70:30 H$_2$O (0.025% TFA):CH$_3$CN (0.025% TFA) to 20:80 H$_2$O (0.025% TFA): CH$_3$CN (0.025% TFA) in 4.0 min and hold for 2.0 min with flow rate of 0.3 mL/min].

Example 104

3-(4-((2-Aminoethyl)carbamoyl)phenyl)-N-(5-cyanopyridin-2-yl)-N-methylpyrazolo[1,5-a]pyridine-5-carboxamide Step 1

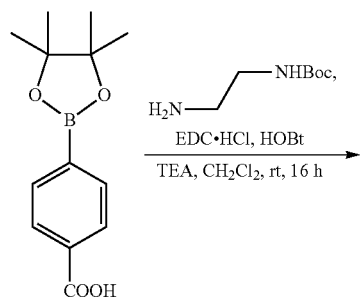

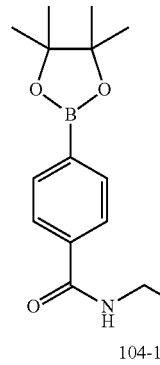

104-1

To a solution mixture of 4-(4,4,5,5-tetramethyl-1,3,2-dioxaborolan-2-yl)benzoic acid (1.0 g, 4.03 mmol), HOBT (925.3 mg, 6.85 mmol) and EDC.HCl (1.15 g, 5.98 mmol) in dichloromethane (20 mL) was stirred at room temperature for 5 min and were added tert-butyl(2-aminoethyl)carbamate (645 mg, 4.03 mmol) and TEA (1.15 mL, 8.19 mmol). The resulting reaction mixture was stirred at temperature for 16 h. The reaction mixture was partitioned between water and ethyl acetate. The organic layer was washed with water, brine, dried over anhydrous Na$_2$SO$_4$ and the solvent was distilled off under reduced pressure to afford 1.0 g (crude) of tert-Butyl(2-(4-(4,4,5,5-tetramethyl-1,3,2-dioxaborolan-2-yl)benzamido)ethyl) carbamate 104-1 as white solid. The crude product was used as such for the next step without further purification.

Step 2

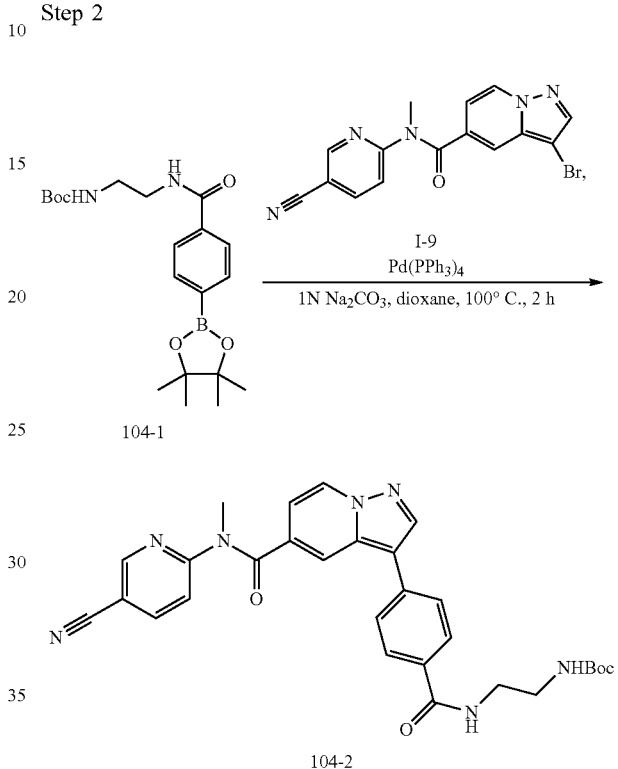

104-1

104-2

The compound 104-2 was prepared using the general procedure described in Suzuki Procedure G with the appropriate starting materials. The yellow color gum crude product was used as such for the next step without further purification. ESI-LC/MS: m/z 540.13 (M+H); R$_t$=2.67 min [Waters Acquity UPLC with Quattro-micro detector; Waters Acquity BEH C18, 1.7 µm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.0 min and hold for 2.0 min with flow rate of 0.4 mL/min].

Step 3

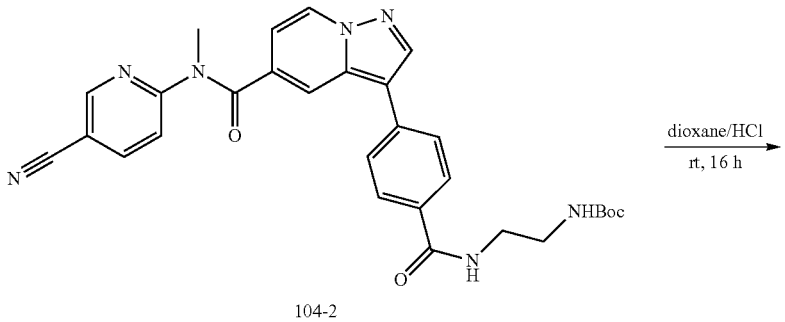

104-2

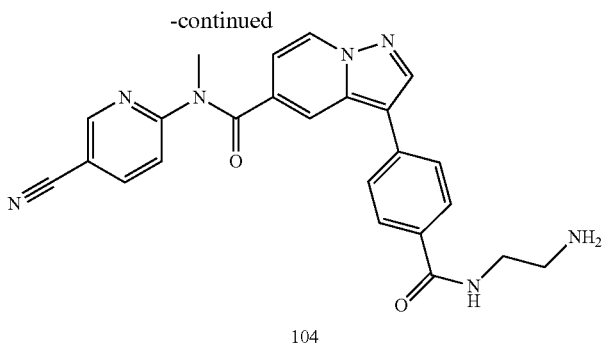

104

A solution mixture of tert-butyl 2-(4-(5-((5-cyanopyridin-2-yl)(methyl)carbamoyl)pyrazolo[1,5-a]pyridin-3-yl)benzamido)ethylcarbamate 104-2 (400 mg, crude) in dioxane-.HCl (4 mL) was stirred at room temperature for 16 h. The volatiles were distilled off under reduced pressure. The crude compound was purified by prep-TLC to afford 19 mg (4% over three steps) of 3-(4-(2-aminoethyl)carbamoyl) phenyl)-N-(5-cyanopyridin-2-yl)-N-methylpyrazolo[1,5-a] pyridine-5-carboxamide 104 as light yellow solid. $^1$H-NMR (400 MHz, DMSO-$d_6$, $D_2O$ Exchange): δ 8.53-8.85 (m, 3H), 8.22 (d, J=7.0 Hz, 1H), 7.84-8.00 (m, 3H), 7.39-7.77 (m, 3H), 6.88 (d, J=6.6 Hz, 1H), 3.54-3.59 (m, 5H), 3.02 (s, 2H). ESI-LC/MS: m/z 440.17 (M+H); $R_f$=1.85 min [Waters Acquity UPLC with Quattro-micro detector; Waters Acquity BEH C18, 1.7 μm, 2.1×50 mm column; gradient of 90:10 $H_2O$ (0.025% TFA):$CH_3CN$ (0.025% TFA) hold for 0.5 min and to 10:90 $H_2O$ (0.025% TFA):$CH_3CN$ (0.025% TFA) in 3.0 min and hold for 2.0 min with flow rate of 0.4 mL/min]. HPLC purity: 94.9% at 294 nm; $R_f$=2.36 min [Waters Acquity UPLC with PDA; Waters Acquity BEH C18, 1.7 μm, 2.1×100 mm column; gradient of 90:10 $H_2O$ (0.025% TFA):$CH_3CN$ (0.025% TFA) to 20:80 $H_2O$ (0.025% TFA):$CH_3CN$ (0.025% TFA) in 4.0 min and hold for 2.0 min with flow rate of 0.3 mL/min].

Example 105

3-(4-Carbamoylphenyl)-N-(4-cyanophenyl)-N-(2-hydroxyethyl)pyrazolo[1,5-a]pyridine-5-carboxamide

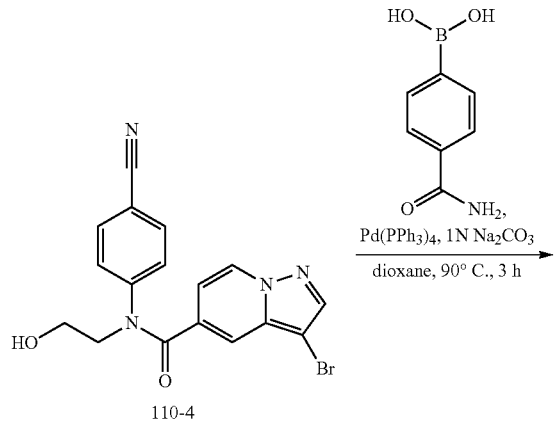

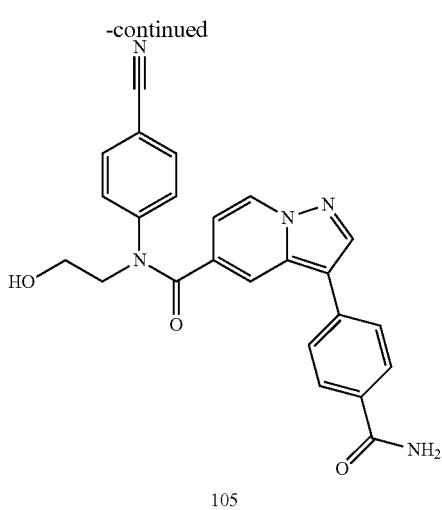

105

Compound 105 was prepared using the general procedure described in Suzuki Procedure G with the appropriate starting materials. Yield 14%. Light green solid. $^1$H-NMR (400 MHz, DMSO-$d_6$): δ 8.89 (d, J=7.50 Hz, 1H), 8.60 (s, 1H), 8.50 (s, 1H), 7.98-8.06 (m, 3H), 7.80 (d, J=8.30 Hz, 2H), 7.42 (d, J=8.8 Hz, 2H), 7.39 (dd, J=1.8, 7.5 Hz, 2H), 6.98 (t, J=5.7 Hz, 1H), 6.74 (d, J=8.70 Hz, 2H), 4.46 (t, J=5.7 Hz, 2H), 3.55-3.60 (m, 2H). ESI-LC/MS: m/z 426.16 (M+H); $R_f$=2.51 min [Waters Acquity UPLC with Quattro micro TQD; Waters Acquity BEH C18, 1.7 μm, 2.1×50 mm column; gradient of 90:10 $H_2O$ (0.025% TFA):$CH_3CN$ (0.025% TFA) hold for 0.5 min to 10:90 $H_2O$ (0.025% TFA):$CH_3CN$ (0.025% TFA) in 2.5 min and hold for 2 min with flow rate of 0.4 mL/min]. HPLC purity: 97.0% at 285 nm; $R_f$=2.542 min [Waters Acquity UPLC with PDA detector; Waters Acquity BEH C18, 1.7 μm, 2.1×100 mm column; gradient of 70:30 $H_2O$ (0.025% TFA):$CH_3CN$ (0.025% TFA) to 20:80 $H_2O$ (0.025% TFA):$CH_3CN$ (0.025% TFA) in 4 min and hold for 2 min with flow rate of 0.3 mL/min].

Example 106

N-(5-Cyanopyridin-2-yl)-3-(4-(methylcarbamoyl) phenyl)pyrazolo[1,5-a]pyridine-5-carboxamide Step 1

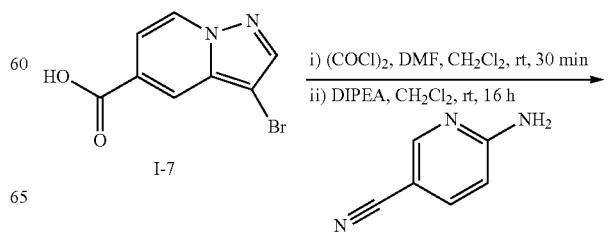

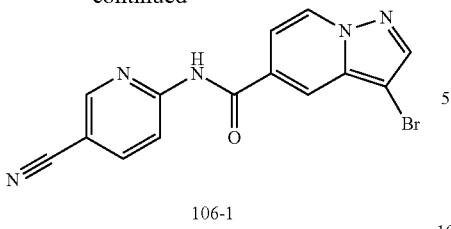

106-1

Compound 106-1 was prepared using the general procedure described in Amide Coupling-Method 1 with the appropriate starting materials. The pale brown solid crude product (900 mg) was used as such for the next step without further purification. ESI-LC/MS: m/z 343.41 [(M+2)H+]; $R_t$=2.60 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.0 min and hold for 2.0 min with flow rate of 0.4 mL/min].

Step 2

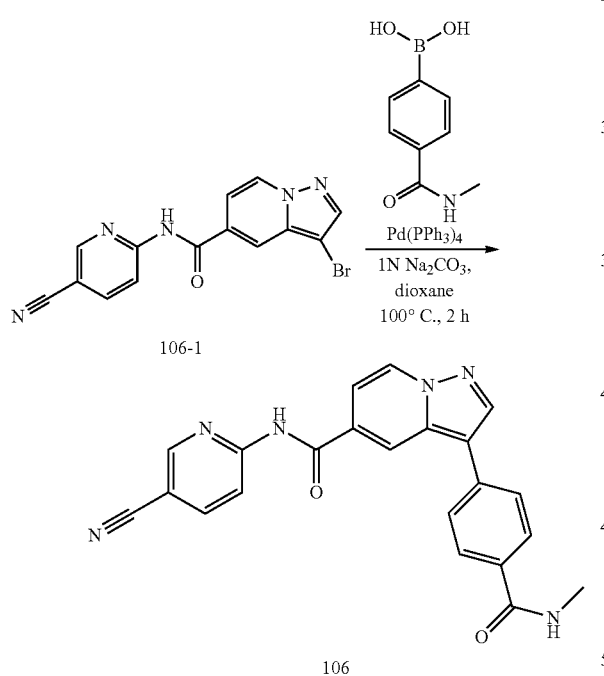

Compound 106 was prepared using the general procedure described in Suzuki Procedure G with the appropriate starting materials. Yield 9% (over two steps). Yellow solid. $^1$H-NMR (400 MHz, DMSO-d$_6$): δ 11.81 (s, 1H), 8.91 (s, 1H), 8.86 (d, J=7.0 Hz, 1H), 8.73 (s, 1H), 8.59 (s, 1H), 8.46-8.52 (m, 1H), 8.33-8.40 (m, 2H), 7.93-7.99 (m, 4H), 7.41 (d, J=7.0 Hz, 1H), 2.81 (d, J=4.4 Hz, 3H). ESI-LC/MS: m/z 397.13 (M+H); $R_t$=2.39 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.0 min and hold for 2.0 min with flow rate of 0.4 mL/min]. HPLC purity: 98.3% at 294 nm; $R_t$=2.28 min [Waters HPLC with PDA; Xterra RP18, 5.0 μm, 4.6×150 mm column; gradient of 70:30 H$_2$O (0.025% TFA):CH$_3$CN (0.025% TFA) to 20:80 H$_2$O (0.025% TFA):CH$_3$CN (0.025% TFA) in 4.0 min and hold for 2.0 min with flow rate of 0.3 mL/min.

Example 107

3-(6-Chloro-5-(methylsulfonamido)pyridin-3-yl)-N-(5-cyanopyridin-2-yl)-N-methylpyrazolo[1,5-a]pyridine-5-carboxamide (NVP-LMX045)

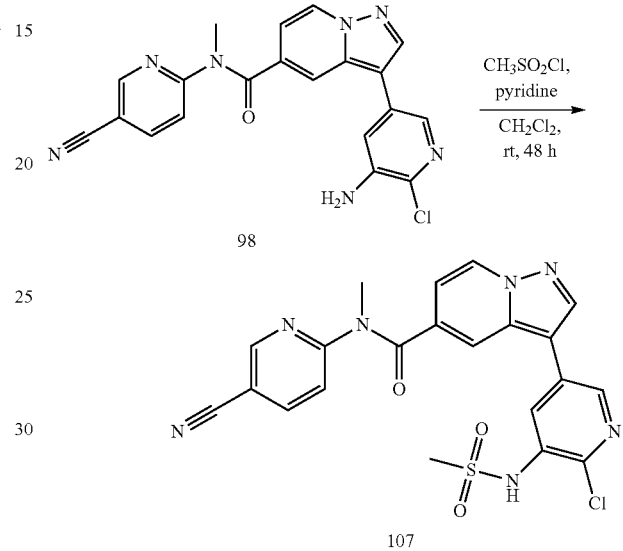

To a stirred solution of 3-(5-amino-6-chloropyridin-3-yl)-N-(5-cyanopyridin-2-yl)-N-methyl pyrazolo[1,5-a]pyridine-5-carboxamide 98 (50 mg, 0.123 mmol) in dichloromethane was added pyridine (0.019 mL, 0.236 mmol), methanesulfonyl chloride (0.01 mL, 0.129 mmol) and maintained at room temperature for 48 h. The reaction mixture was partitioned between water and dichloromethane. The organic layer was washed with water, brine, dried over anhydrous Na$_2$SO$_4$ solution and concentrated under reduced pressure. The crude compound was purified by prep-TLC to afford 7 mg (12%) of 3-(6-chloro-5-(methylsulfonamido)pyridin-3-yl)-N-(5-cyanopyridin-2-yl)-N-methylpyrazolo[1,5-a]pyridine-5-carboxamide 107 as a pale yellow solid. $^1$H NMR (400 MHz, DMSO-d$_6$): 9.87 (s, 1H), 8.80 (d, J=1.70 Hz, 1H), 8.75 (d, J=7.10 Hz, 1H), 8.60 (s, 1H), 8.52 (s, 1H), 8.23 (dd, J=2.2, 8.8 Hz, 1H), 8.03 (s, 1H), 8.02 (s, 1H), 7.62 (d, J=8.8 Hz, 1H), 6.86 (dd, J=1.8, 7.0 Hz, 1H), 3.53 (s, 3H), 3.16 (s, 3H). ESI-LC/MS: m/z 482.13 (M+H) & 483.99 [(M+2)+H]; $R_t$=2.30 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.0 min and hold for 2.0 min with flow rate of 0.4 mL/min]. HPLC purity: 96.1% at 254 nm; $R_t$=2.19 min [Waters Acquity UPLC with PDA; Waters Acquity BEH C18, 1.7 μm, 2.1× 100 mm column; gradient of 70:30 H$_2$O (0.025% TFA):CH$_3$CN (0.025% TFA) to 20:80 H$_2$O (0.025% TFA):CH$_3$CN (0.025% TFA) in 4.0 min and hold for 2.0 min with flow rate of 0.3 mL/min].

Example 108

3-(2-Aminopyridin-4-yl)-N-(5-cyanopyridin-2-yl)-N-methylpyrazolo[1,5-a]pyridine-5-carboxamide Step 1

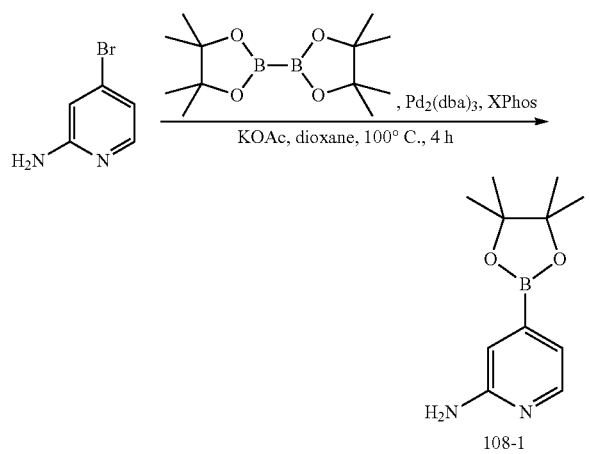

A solution mixture of 4-bromopyridin-2-amine (1.0 g, 5.78 mmol), bis(pinacolato)diboron (1.6 g, 6.299 mmol) and potassium acetate (1.12 g, 11.42 mmol) in 1,4-dioxane (15 mL) was degassed with argon gas for 15 min. Pd$_2$(dba)$_3$ (265.9 mg, 0.290 mmol) and X-phos (277 mg, 0.580 mmol) were added. The resulting reaction mixture was stirred at 110° C. for 4 h, cooled to room temperature and filtered through celite. The filtrate was concentrated under reduced pressure to obtain 500 mg of 4-(4,4,5,5-tetramethyl-1,3,2-dioxaborolan-2-yl)pyridin-2-amine 108-1 as a brown color solid. The crude product was used as such in next step without further purification Step 2

To a stirred solution of 3-bromo-N-(5-cyanopyridin-2-yl)-N-methylpyrazolo[1,5-a]pyridine-5-carboxamide I-9 (300 mg, 0.84 mmol), 4-(4,4,5,5-tetramethyl-1,3,2-dioxaborolan-2-yl)pyridin-2-amine 108-1 (223 mg, crude), K$_3$PO$_4$ (1.12 g, 5.28 mmol) in dioxane/water (9:1) (10 mL) was degassed with argon for about 10 min. Pd$_2$(dba)$_3$ (38.65 mg, 0.042 mmol) was added under argon atmosphere. The resulting reaction mixture was maintained at 90-100° C. for 16 h. The reaction mass was cooled to room temperature and filtered through celite. The filtrate was partitioned between water (10 mL) and ethyl acetate (20 mL). The organic layer was washed water, brine, dried over anhyd. Na$_2$SO$_4$ and concentrated. The crude compound was purified by column chromatography over silica gel (100-200 mesh) using a solvent gradient of 1-2% methanol in chloroform to afford 120 mg (9% over two steps) of 3-(2-aminopyridin-4-yl)-N-(5-cyanopyridin-2-yl)-N-methylpyrazolo[1,5-a]pyridine-5-carboxamide 108 as a yellow solid. $^1$H-NMR (400 MHz, DMSO-d$_6$): δ 8.83 (s, 1H), 8.71 (d, J=7.0 Hz, 1H), 8.52 (s, 1H), 8.27 (d, J=2.2, 8.8 Hz, 1H), 8.06 (s, 1H), 7.93 (d, J=5.7 Hz, 1H), 7.65 (d, J=8.4 Hz, 1H), 6.74-6.82 (m, 3H), 6.18 (brs, 2H), 3.53 (s, 3H). ESI-LC/MS: m/z 370.14 (M+H); R$_t$=1.97 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.0 min and hold for 2.0 min with flow rate of 0.4 mL/min]. HPLC purity: 98.0% at 298 nm; R$_t$=1.93 min [Waters Acquity UPLC with PDA; Waters Acquity BEH C18, 1.7 μm, 2.1×100 mm column; gradient of 70:30 H$_2$O (0.025% TFA):CH$_3$CN (0.025% TFA) to 20:80 H$_2$O (0.025% TFA):CH$_3$CN (0.025% TFA) in 4.0 min and hold for 2.0 min with flow rate of 0.3 mL/min].

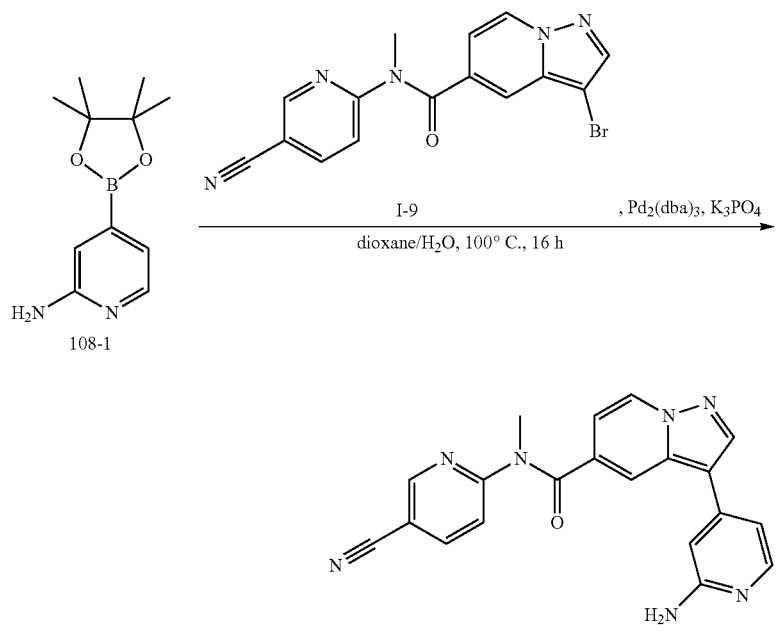

Example 109

N-(4-Chlorophenyl)-N-methyl-3-(6-(methylcarbamoyl)pyridin-3-yl)pyrazolo[1,5-a]pyridine-5-carboxamide

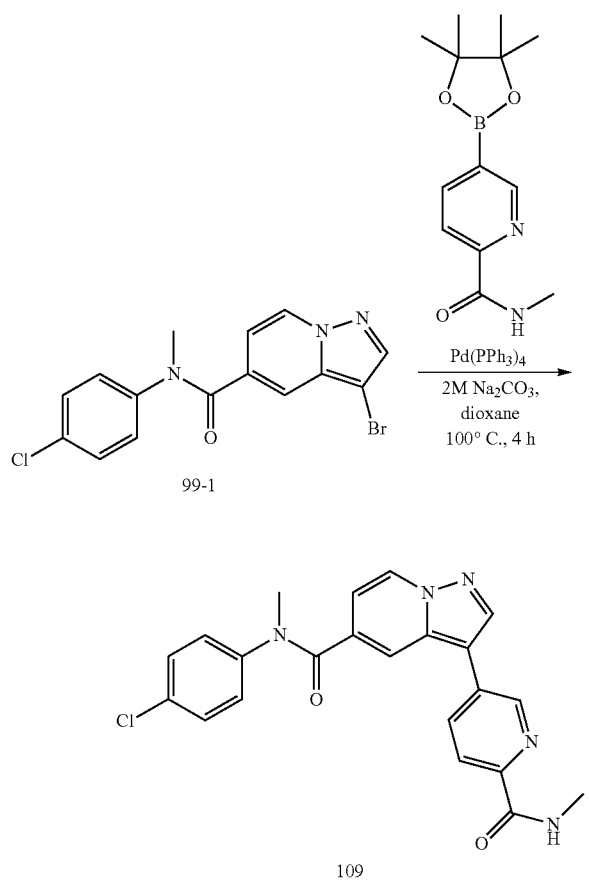

Compound 109 was prepared using the general procedure described in Suzuki Procedure G with the appropriate starting materials. Yield 15%. Yellow solid. $^1$H-NMR (400 MHz, DMSO-$d_6$): δ 8.84 (s, 1H), 8.68-8.74 (m, 2H), 8.61 (s, 1H), 8.02-8.09 (m, 2H), 7.91 (s, 1H) 7.37-7.44 (m, 4H), 6.86 (d, J=7.1 Hz, 1H), 3.41 (s, 3H), 2.86 (d, J=4.4 Hz, 3H). ESI-LC/MS: m/z 420.15 (M+H) & 422.13 [(M+2)+H]; $R_t$=2.76 min [Waters Acquity UPLC with Quattro micro TQD; Waters Acquity BEH C18, 1.7 μm, 2.1×100 mm column; gradient of 80:20 H$_2$O (0.025% TFA):CH$_3$CN (0.025% TFA) to 20:80 H$_2$O (0.025% TFA):CH$_3$CN (0.025% TFA) in 3 min and hold for 2 min with flow rate of 0.4 mL/min]. HPLC purity: 98.4% at 254 nm; $R_t$=2.68 min [Waters Acquity UPLC with PDA detector; Waters Acquity BEH C18, 1.7 μm, 2.1×100 mm column; gradient of 70:30 H$_2$O (0.025% TFA):CH$_3$CN (0.025% TFA) to 20:80 H$_2$O (0.025% TFA):CH$_3$CN (0.025% TFA) in 4 min and hold for 2 min with flow rate of 0.3 mL/min].

Example 110

N-(4-Cyanophenyl)-N-(2-hydroxyethyl)-3-(4-(methylcarbamoyl)phenyl)pyrazolo[1,5-a]pyridine-5-carboxamide Step 1

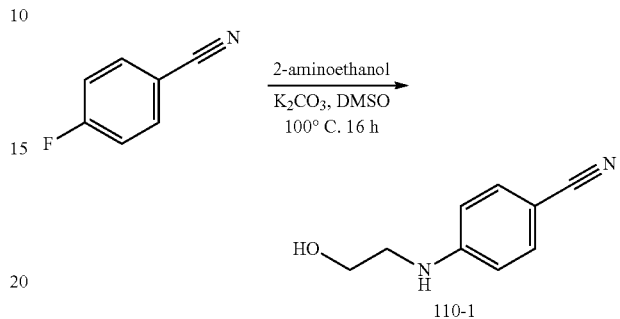

A mixture of 4-fluorobenzonitrile (2.0 g, 16.52 mmol), 2-aminoethanol (1.21 mL, 20.16 mmol) and potassium carbonate (2.76 g, 20.00 mmol) in DMSO (16 mL) was stirred at 100° C. for 16 h. The reaction mixture was diluted with water and extracted with ethyl acetate (4×200 mL). The combined organic layer was washed with water, brine solution, dried over Na$_2$SO$_4$ and concentrated. The crude product was passed through a column of silica gel (100-200 mesh) using a solvent gradient of 30% ethyl acetate in pet-ether as eluant and obtained 1.2 g (44%) of 4-((2-hydroxyethyl)amino)benzonitrile 110-1 as a yellow solid. $^1$H NMR (400 MHz, CDCl$_3$): δ 7.42 (d, J=8.8 Hz, 2H), 6.60 (d, J=8.8 Hz, 2H), 4.55-4.65 (m, 1H), 3.85-3.90 (m, 2H), 3.33 (d, J=5.9 Hz, 2H). ESI-LC/MS: m/z 163.4 (M+H); $R_t$=2.71 min [Agilent LC with Ion trap Detector; Waters Symmetry C18, 3.5 μm, 4.6×75 mm column; gradient of 80:20 H$_2$O (0.1% HCOOH):CH$_3$CN (0.1% HCOOH) to 10:90 H$_2$O (0.1% HCOOH):CH$_3$CN (0.1% HCOOH) in 3 min and hold for 4 min with flow rate of 1.0 mL/min].

Step 2

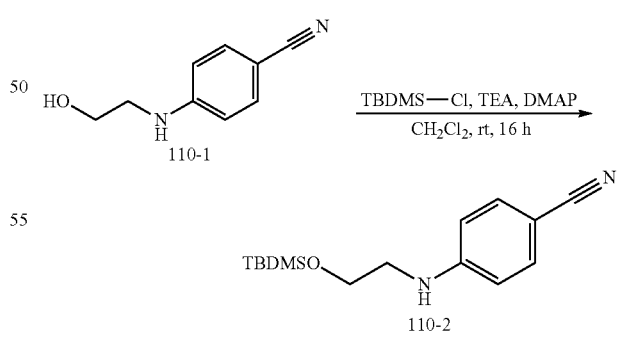

To a solution of 4-(2-hydroxyethylamino)benzonitrile 110-1 (1.0 g, 6.17 mmol) in dichloromethane (20 mL) was added TBDMS-Cl (930 mg, 6.17 mmol), TEA (1.78 mL, 12.76 mmol) and DMAP (6 mg, 0.049 mmol) and the resulting reaction mixture was stirred at rt for 16 h. The reaction mixture was diluted with water and extracted with dichloromethane (3×200 mL). The organic layer was separated and washed with water, brine solution, dried over Na₂SO₄ and concentrated. The crude product was passed through a column of silica gel (100-200 mesh) using a solvent gradient of 3% methanol in chloroform as eluant and obtained 900 mg (53%) of 4-(2-(tert-butyldimethylsilyloxy)ethylamino)benzonitrile 110-2 as a colorless liquid. ¹H NMR (400 MHz, CDCl₃): δ 7.42 (d, J=8.8 Hz, 2H), 6.57 (d, J=8.8 Hz, 2H), 4.60-4.50 (m, 1H), 3.82 (t, J=5.3 Hz, 2H), 3.25 (q, J=4.3, 10.6 Hz, 2H), 0.90 (s, 9H), 0.06 (s, 6H).

Step 3

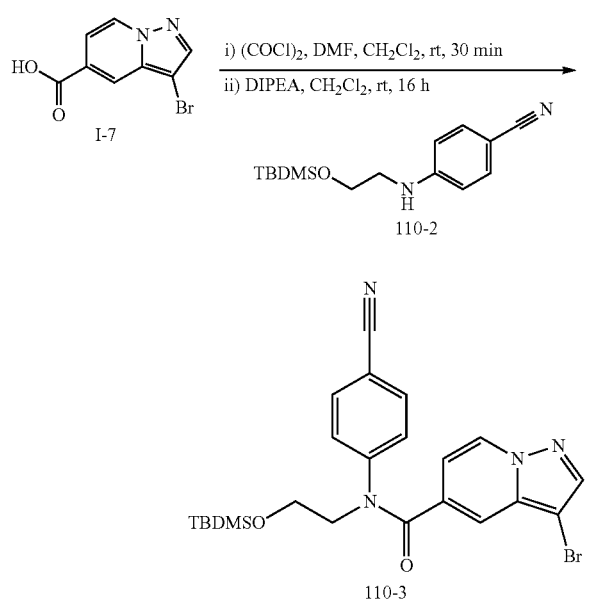

Compound 110-3 was prepared using the general procedure described in Amide Coupling-Method 1 with the appropriate starting materials. Yield 64%. Off-white solid. ESI-LC/MS: m/z 499.08 (M+H) & 501.07 [(M+2)+H]; R_f=3.92 min [Waters Acquity UPLC with Quattro micro TQD; Waters Acquity BEH C18, 1.7 µm, 2.1×50 mm column; gradient of 90:10 H₂O (0.025% TFA):CH₃CN (0.025% TFA) hold for 0.5 min to 10:90 H₂O (0.025% TFA):CH₃CN (0.025% TFA) in 2.5 min and hold for 2 min with flow rate of 0.4 mL/min].

Step 4

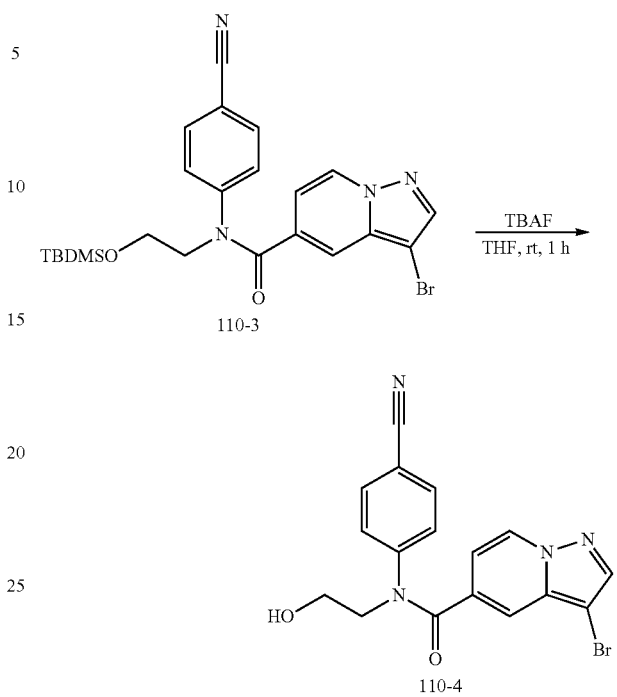

To a solution of 3 (700 mg, 1.40 mmol) in THF (20 mL) was added TBAF (2M solution in THF) (10 mL) and stirred at rt for 1 h. The reaction mixture was diluted with water, concentrated to remove the solvent and the residue was extracted with ethyl acetate twice. The organic layer was washed with water, brine, dried over anhydrous Na₂SO₄ and concentrated. The crude compound was washed with pentane to afford 270 mg (50%) of 3-bromo-N-(4-cyanophenyl)-N-(2-hydroxyethyl)pyrazolo[1,5-a]pyridine-5-carboxamide 110-4 as an off-white solid. ¹H-NMR (400 MHz, DMSO-d₆): δ 8.86 (d, J=7.5 Hz, 1H), 8.34 (s, 1H), 8.10 (s, 1H), 7.47 (d, J=8.4 Hz, 2H), 7.36 (dd, J=1.8, 7.5 Hz, 1H), 6.96-7.00 (m, 1H), 6.76 (d, J=8.8 Hz, 2H), 4.44 (t, J=5.3 Hz, 2H), 3.57 (q, J=5.3, 11.0 Hz, 2H). ESI-LC/MS: m/z 385.04 (M+H) & 387.02 [(M+2)H+]; R_f=3.00 min [Waters Acquity UPLC with Quattro micro TQD; Waters Acquity BEH C18, 1.7 µm, 2.1×50 mm column; gradient of 90:10 H₂O (0.025% TFA):CH₃CN (0.025% TFA) hold for 0.5 min to 10:90 H₂O (0.025% TFA):CH₃CN (0.025% TFA) in 2.5 min and hold for 2 min with flow rate of 0.4 mL/min].

Step 5

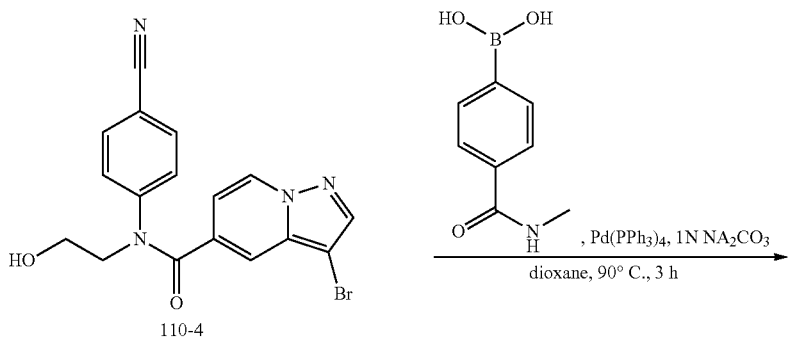

-continued

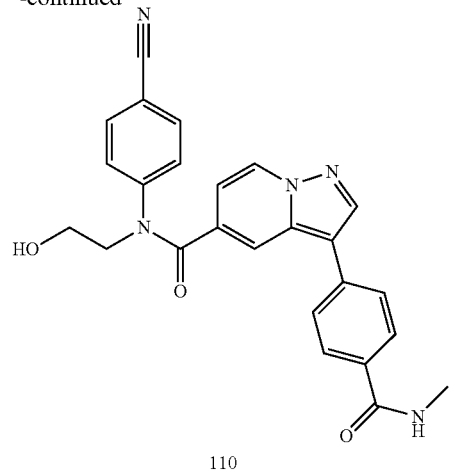

110

Compound 110 was prepared using the general procedure described in Suzuki Procedure G with the appropriate starting materials. Yield 15%. Light green solid. ¹H-NMR (400 MHz, DMSO-$d_6$): δ 8.89 (d, J=7.5 Hz, 1H), 8.50-8.61 (m, 3H), 7.97 (d, J=7.9 Hz, 2H), 7.80 (d, J=8.30 Hz, 2H), 7.43 (d, J=8.30 Hz, 2H), 7.36 (d, J=7.0 Hz, 1H), 6.95-7.05 (m, 1H), 6.74 (d, J=8.30 Hz, 2H), 4.40-4.50 (m, 2H), 3.54 (d, J=4.9 Hz, 2H), 2.81 (d, J=4.0 Hz, 3H). ESI-LC/MS: m/z 440.17 (M+H); $R_t$=2.73 min [Waters Acquity UPLC with Quattro micro TQD; Waters Acquity BEH C18, 1.7 µm, 2.1×50 mm column; gradient of 90:10 H₂O (0.025% TFA):CH₃CN (0.025% TFA) hold for 0.5 min to 10:90 H₂O (0.025% TFA):CH₃CN (0.025% TFA) in 2.5 min and hold for 2 min with flow rate of 0.4 mL/min]. HPLC purity: 96.8% at 284 nm; $R_t$=2.775 min [Waters Acquity UPLC with PDA detector; Waters Acquity BEH C18, 1.7 µm, 2.1×100 mm column; gradient of 70:30 H₂O (0.025% TFA):CH₃CN (0.025% TFA) to 20:80 H₂O (0.025% TFA):CH₃CN (0.025% TFA) in 4 min and hold for 2 min with flow rate of 0.3 mL/min].

Example 111

N-(5-(2-Aminoethoxyl)pyridin-2-yl)-N-methyl-3-(4-(methylcarbamoyl)phenyl)pyrazolo[1,5-a]pyridine-5-carboxamide Step 1

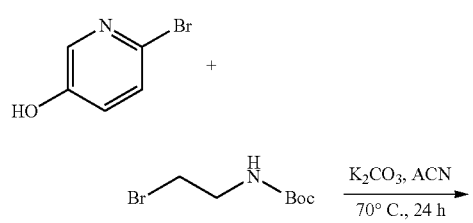

K₂CO₃, ACN
70° C., 24 h

-continued

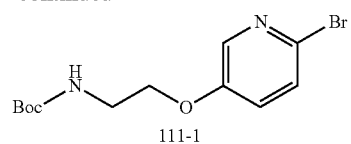

111-1

A suspension of 2-bromo-5-hydroxypyridine (250 mg g, 1.43 mmol), tert-butyl(2-bromoethyl)carbamate (321.8 g, 1.43 mmol) and potassium carbonate (592 mg, 4.31 mmol) in acetonitrile (5 mL) was stirred at 70° C. for 24 h. The reaction mixture was diluted with water and extracted with ethyl acetate. The organic layer was washed with water, brine, dried over anhydrous Na₂SO₄ and concentrated. The crude compound was purified by column chromatography over silica gel (100-200 mesh) using a solvent gradient mixture of 25% of ethyl acetate in pet-ether as eluant to afford 90 mg (20%) of tert-butyl 2-(6-bromopyridin-3-yloxy)ethylcarbamate 111-1 as a pale yellow solid. ¹H NMR (400 MHz, CDCl₃): δ 8.06 (d, J=3.0 Hz, 1H), 7.37 (d, J=8.8 Hz, 1H), 7.10 (dd, J=3.1, 8.4 Hz, 1H), 4.95-5.05 (m, 1H), 4.04 (t, J=5.2 Hz, 2H), 3.54 (d, J=5.3 Hz, 2H), 1.45 (s, 9H). ESI-LC/MS: m/z 319.2 [(M+2)+H]; $R_t$=2.72 min [Agilent LC with Ion trap Detector; Waters Symmetry C18, 3.5 µm, 4.6×75 mm column; gradient of 50:50 H₂O (0.1% HCOOH):CH₃CN (0.1% HCOOH) to 10:90 H₂O (0.1% HCOOH):CH₃CN (0.1% HCOOH) in 3 min and hold for 4 min with flow rate of 1.0 mL/min].

Step 2

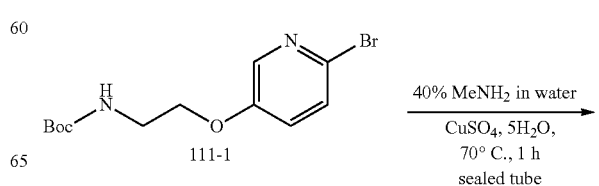

40% MeNH₂ in water
CuSO₄, 5H₂O,
70° C., 1 h
sealed tube

-continued

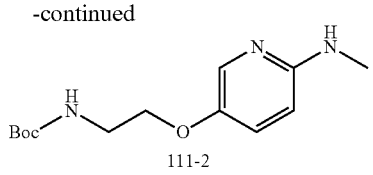
111-2

Step 3

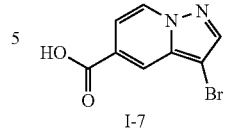
I-7 i) (COCl)₂, DMF, CH₂Cl₂, rt, 30 min
ii) DIPEA, CH₂Cl₂, rt, 16 h

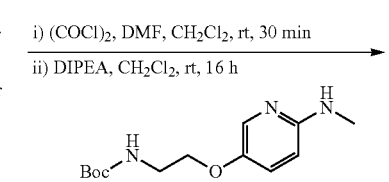
111-2

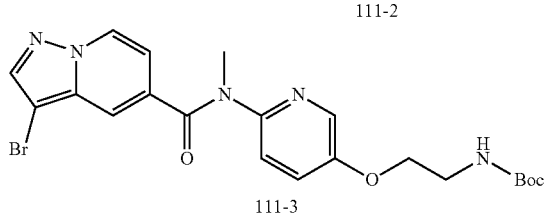
111-3

A solution mixture of tert-butyl 2-(6-bromopyridin-3-yloxy)ethylcarbamate 111-1 (1.0 g, 3.16 mmol), 40% methylamine in water (10 mL) and CuSO₄.5H₂O (236 mg, 0.94 mmol) in sealed tube was stirred at 70° C. for 1 h then allowed to rt and filtered. The filtrate was concentrated to afford 700 mg (83%) of tert-butyl 2-(6-(methylamino)pyridin-3-yloxy)ethylcarbamate 111-2 as an off-white solid. ¹H NMR (400 MHz, CDCl₃): δ 7.82 (s, 1H), 7.12 (dd, J=2.6, 8.7 Hz, 1H), 6.36 (d, J=9.2 Hz, 1H), 4.98 (br s, 1H), 4.28 (br s, 1H), 3.96 (t, J=5.3 Hz, 2H), 3.49 (d, J=4.9 Hz, 2H), 2.89 (d, J=4.9 Hz, 3H), 1.45 (s, 9H). ESI-LC/MS: m/z 268.16 (M+H); $R_t$=1.76 min [Waters Acquity UPLC with Quattro micro TQD; Waters Acquity BEH C18, 1.7 μm, 2.1×50 mm column; gradient of 90:10 H₂O (0.025% TFA):CH₃CN (0.025% TFA) hold for 0.5 min to 10:90 H₂O (0.025% TFA):CH₃CN (0.025% TFA) in 2.5 min and hold for 2 min with flow rate of 0.4 mL/min].

Compound 111-3 was prepared using the general procedure described in Amide Coupling-Method 1 with the appropriate starting materials. The crude product (100 mg) was used as such for the next step without further purification. ESI-LC/MS: m/z 490.5 (M+H); $R_t$=4.08 [Agilent LC with Ion trap Detector; Xterra MS-C18, 2.5 μm, 4.6×50 mm column; gradient of 80:20 H₂O (0.01 M ammonium bicarbonate):CH₃CN to 10:90 H₂O (0.01 M ammonium bicarbonate):CH₃CN in 4.0 min and hold for 3.0 min with flow rate of 1.0 mL/min].

Step 4

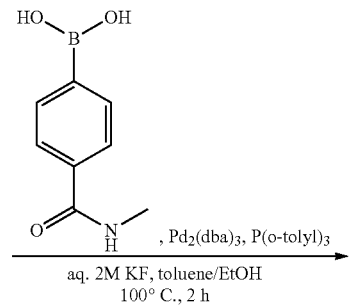

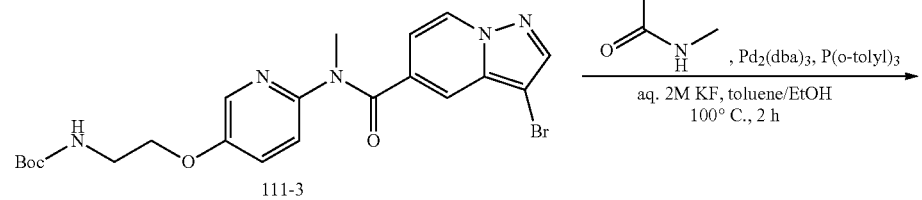
111-3

, Pd₂(dba)₃, P(o-tolyl)₃
aq. 2M KF, toluene/EtOH
100° C., 2 h

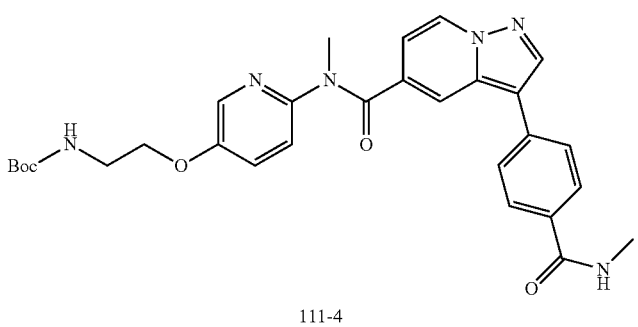
111-4

Compound 111-4 was prepared using the general procedure described in Suzuki Procedure H with the appropriate starting materials. The crude product (200 mg) was used as such for next step without further purification. ESI-LC/MS: m/z 545.31 (M+H); $R_t$=2.33 min [Waters Acquity UPLC with Quattro micro TQD; Waters Acquity BEH C18, 1.7 μm, 2.1×50 mm column; gradient of 90:10 H₂O (0.025% TFA): CH₃CN (0.025% TFA) hold for 0.5 min to 10:90 H₂O (0.025% TFA):CH₃CN (0.025% TFA) in 2.5 min and hold for 2 min with flow rate of 0.4 mL/min].

Step 5

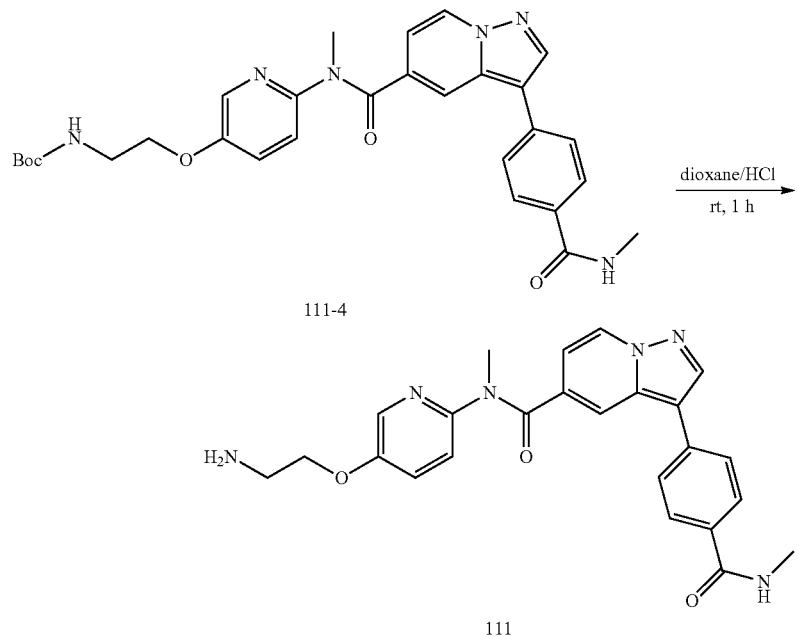

A solution mixture of tert-butyl 2-(6-(N-methyl-3-(4-(methylcarbamoyl)phenyl)pyrazolo[1,5-a]pyridine-5-carboxamido)pyridin-3-yloxy)ethylcarbamate 111-4 (200 mg, 0.36 mmol) in 1,4-dioxane HCl (4.0 M, 5 mL) was stirred at rt for 1 h. The reaction mixture was diluted with ice-water and basified (pH: 8.0) with saturated NaHCO₃ solution and then extracted with ethyl acetate. The organic layer was washed with water, brine solution, dried over Na₂SO₄ and concentrated. The crude compound was purified by prep-HPLC to afford 80 mg (4% over three steps) of N-(5-(2-aminoethoxyl)pyridin-2-yl)-N-methyl-3-(4-(methylcarbamoyl)phenyl)pyrazolo[1,5-a]pyridine-5-carboxamide 111 as a yellow solid. ¹H-NMR (400 MHz, DMSO-d₆): δ 8.65 (d, J=7.0 Hz, 1H), 8.42-8.52 (m, 2H), 8.15 (d, J=2.2 Hz, 1H), 7.91 (d, J=7.9 Hz, 2H), 7.70 (s, 1H), 7.53 (d, J=7.9 Hz, 2H), 7.36-7.42 (m, 1H), 7.28 (d, J=8.8 Hz, 1H), 6.80 (d, J=6.6 Hz, 1H), 3.90 (brs, 2H), 3.40 (s, 3H), 3.20 (brs, 1H), 2.75-2.80 (m, 6H). ESI-LC/MS: m/z 445.20 (M+H); $R_t$=1.58 min [Waters Acquity UPLC with Quattro micro TQD; Waters Acquity BEH C18, 1.7 μm, 2.1×50 mm column; gradient of 90:10 H₂O (0.025% TFA):CH₃CN (0.025% TFA) hold for 0.5 min to 10:90 H₂O (0.025% TFA):CH₃CN (0.025% TFA) in 2.5 min and hold for 2 min with flow rate of 0.4 mL/min]. HPLC purity: 98.5% at 254 nm; $R_t$=2.11 min [Waters Acquity UPLC with PDA detector; Waters Acquity BEH C18, 1.7 μm, 2.1×100 mm column; gradient of 90:10 H₂O (0.025% TFA):CH₃CN (0.025% TFA) to 20:80 H₂O (0.025% TFA):CH₃CN (0.025% TFA) in 4 min and hold for 2 min with flow rate of 0.3 mL/min].

Example 112

N-(5-Cyanopyridin-2-yl)-N-cyclobutyl-3-(4-(methylcarbamoyl)phenyl)pyrazolo[1,5-a]pyridine-5-carboxamide Step 1

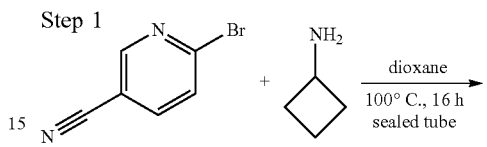

-continued

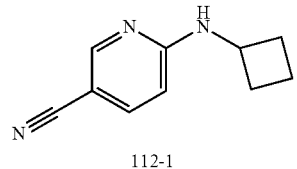

A solution mixture of 2-bromo-5-cyanopyridine (10.0 g, 54.64 mmol), cyclobutylamine (9.36 mL, 109.6 mmol) in dioxane (100 mL) was stirred at 100° C. for 16 h in sealed tube. The reaction mixture was partitioned between water (200 mL) and ethyl acetate (100 mL). The ethyl acetate layer was washed with brine (100 mL), dried over anhydrous Na₂SO₄ and concentrated. The crude compound was purified by column chromatography over silica gel (100-200 mesh) using a solvent gradient of 20% ethyl acetate in pet-ether as eluant to give 7.0 g (74%) of 6-(cyclobutylamino)nicotinonitrile 112-1 as an off-white solid. ¹H NMR (300 MHz, DMSO-d₆): δ 8.36 (d, J=2.1 Hz, 1H), 7.84 (d, J=6.6 Hz, 1H), 7.67 (d, J=8.4 Hz, 1H), 6.47 (d, J=9.0 Hz, 1H), 4.32 (br. s, 1H), 2.10-2.35 (m, 2H), 1.82-1.96 (m, 2H), 1.61-1.73 (m, 2H). ESI-LC/MS: m/z 172.0 (M–H); $R_t$=4.28 min [Agilent LC with Ion trap Detector; XBridge-C18, 3.5 μm, 4.6×75 mm column; gradient of 80:20 H₂O (0.005 M ammonium bicarbonate):CH₃CN to 20:80 H₂O (0.005 M ammonium bicarbonate):CH₃CN in 4.0 min and hold for 3.0 min with flow rate of 1.0 mL/min].

Step 2

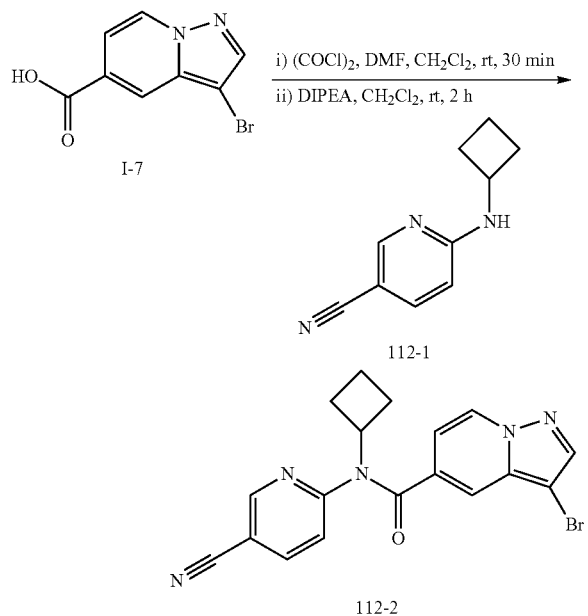

Compound 112-2 was prepared using the general procedure described in Amide Coupling—Method 1 with the appropriate starting materials. Yield 33%. Yellow solid. ¹H NMR (400 MHz, DMSO-d₆): δ 8.92 (d, J=2.2 Hz, 1H), 8.61 (d, J=7.0 Hz, 1H), 8.30 (dd, J=2.2, 7.9 Hz, 1H), 8.19 (s, 1H), 7.58 (d, J=8.4 Hz, 1H), 7.39 (s, 1H), 6.72 (dd, J=1.7, 8.5 Hz, 1H), 4.85-4.90 (m, 1H), 2.07-2.24 (m, 4H), 1.60-1.66 (m, 2H). ESI-LC/MS m/z 396.10 (M+H) & 397.99 [(M+2)+H]; R$_t$=2.88 min [Waters Acquity UPLC with Quattro micro TQD; Waters Acquity BEH C18, 1.7 μm, 2.1×50 mm column; gradient of 90:10 H₂O (0.025% TFA):CH₃CN (0.025% TFA) hold for 0.5 min to 10:90 H₂O (0.025% TFA):CH₃CN (0.025% TFA) in 2.5 min and hold for 2 min with flow rate of 0.4 mL/min].

Step 3

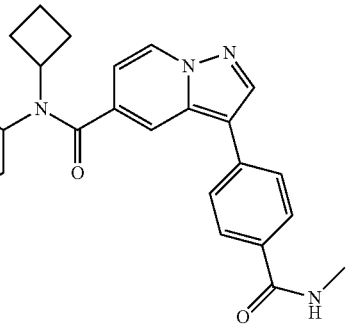

Compound 112 was prepared using the general procedure described in Suzuki Procedure H with the appropriate starting materials. Yield 22%. Yellow solid. ¹H-NMR (400 MHz, DMSO-d₆): δ 8.98 (d, J=2.2 Hz, 1H), 8.64 (d, J=7.40 Hz, 1H), 8.46-8.52 (m, 2H), 8.33 (dd, J=2.2, 8.4 Hz, 1H), 7.94 (d, J=8.30 Hz, 2H), 7.76 (s, 1H), 7.62 (d, J=8.30 Hz, 1H), 7.56 (d, J=8.4 Hz, 2H), 6.77 (dd, J=1.8, 7.1 Hz, 1H), 4.91-4.95 (m, 1H), 2.82 (d, J=4.4 Hz, 3H), 2.20-2.26 (m, 2H), 2.07-2.15 (m, 2H), 1.59-1.69 (m, 2H). ESI-LC/MS: m/z 451.18 (M+H); R$_t$=2.42 min [Waters Acquity UPLC with Quattro micro TQD; Waters Acquity BEH C18, 1.7 μm, 2.1×50 mm column; Gradient of 90:10 H₂O (0.025% TFA):CH₃CN (0.025% TFA) hold for 0.5 min to 10:90 H₂O (0.025% TFA):CH₃CN (0.025% TFA) in 2.5 min and hold for 2 min with flow rate of 0.4 mL/min]. HPLC purity: 97.0% at 282 nm; R$_t$=2.293 min [Waters Acquity UPLC with PDA detector; Waters Acquity HSS T3, 1.7 μm, 2.1×100 mm column; gradient of 70:30 H₂O (0.025% TFA):CH₃CN (0.025% TFA) to 20:80 H₂O (0.025% TFA):CH₃CN (0.025% TFA) in 4 min and hold for 2 min with flow rate of 0.4 mL/min].

Example 113

N-(5-Cyanopyridin-2-yl)-N-methyl-3-(4-(piperidin-4-ylcarbamoyl)phenyl)pyrazolo[1,5-a]pyridine-5-carboxamide Step 1

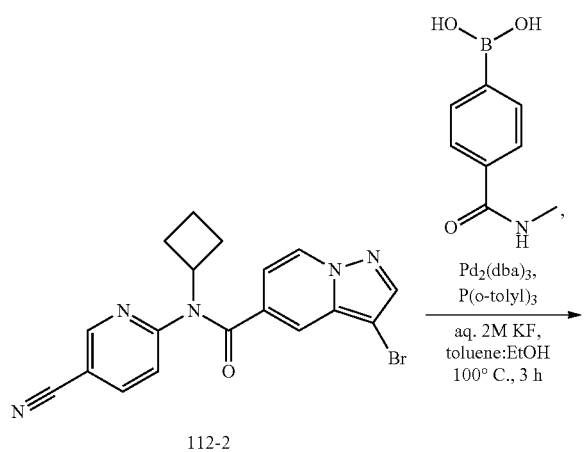

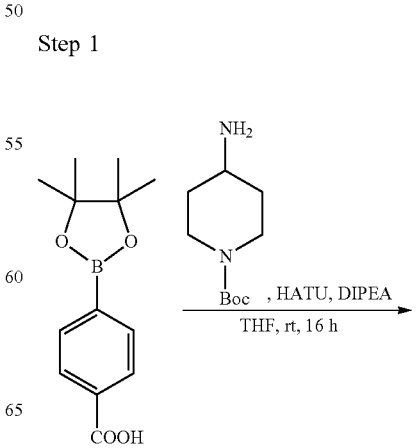

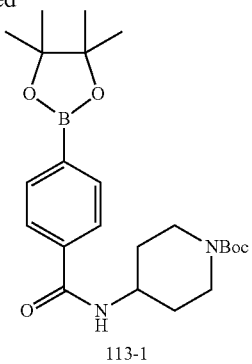

113-1

Compound 113-1 was prepared using the general procedure described in Amide Coupling-Method 2 with the appropriate starting materials. The colorless crude gum product was used as such for the next step without further purification. ESI-LC/MS: m/z 431.29 (M+H); $R_t$=3.27 min [Waters Waters Acquity UPLC with Quattro-micro detector; Waters Acquity BEH C18, 1.7 μm, 2.1×50 mm column; gradient of 90:10 $H_2O$ (0.025% TFA):$CH_3CN$ (0.025% TFA) hold for 0.5 min and to 10:90 $H_2O$ (0.025% TFA):$CH_3CN$ (0.025% TFA) in 3.0 min and hold for 2.0 min with flow rate of 0.4 mL/min].

Step 2

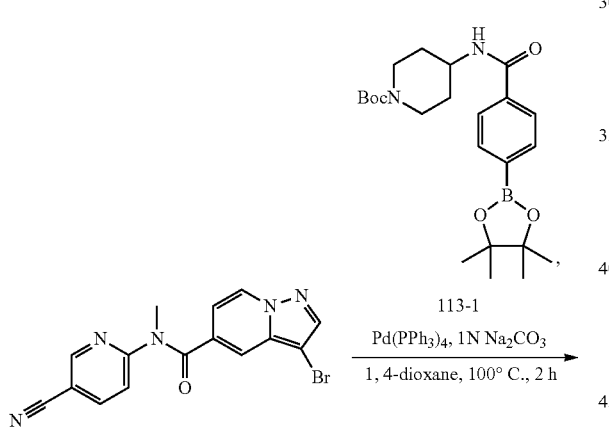

Compound 113-2 was prepared using the general procedure described in Suzuki Procedure G with the appropriate starting materials. The yellow color crude was used as such for the next step without further purification. ESI-LC/MS: m/z 580.19 (M+H); $R_t$=2.85 min [Waters Acquity UPLC with Quattro-micro detector; Waters Acquity BEH C18, 1.7 μm, 2.1×50 mm column; gradient of 90:10 $H_2O$ (0.025% TFA):$CH_3CN$ (0.025% TFA) hold for 0.5 min and to 10:90 $H_2O$ (0.025% TFA):$CH_3CN$ (0.025% TFA) in 3.0 min and hold for 2.0 min with flow rate of 0.4 mL/min].

Step 3

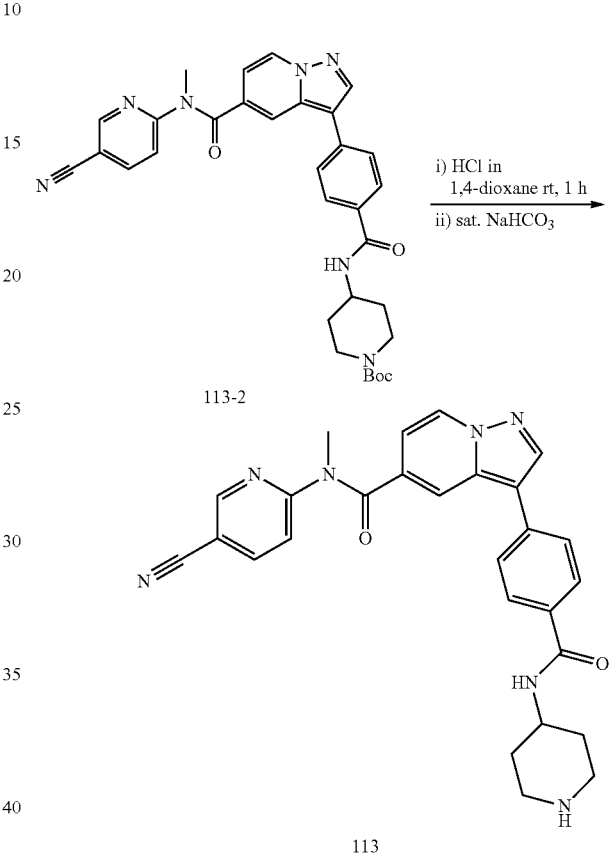

A solution mixture of tert-butyl 4-(4-(5-((5-cyanopyridin-2-yl)(methyl)carbamoyl)pyrazolo[1,5-a]pyridin-3-yl)benzamido)piperidine-1-carboxylate 113-2 (450 mg, crude) and 1,4-dioxane.HCl (4M) (3.0 mL) in 1,4-dioxane (10 mL) was stirred at room temperature for 1 h. Diethyl ether was added to reaction mixture and filtered. The solid collected was dissolved in water, basified with sat. $NaHCO_3$ to pH 10 and extracted with 10% methanol in chloroform. The organic extracts were dried over $Na_2SO_4$ and concentrated. The crude compound was purified by prep-TLC followed by prep-HPLC gave 70 mg (13%) of N-(5-cyanopyridin-2-A-N-methyl-3-(4-(piperidin-4-ylcarbamoyl)phenyl)pyrazolo[1,5-a]pyridine-5-carboxamide 113 as yellow color solid. $^1$H-NMR (400 MHz, DMSO-$d_6$): δ 8.85 (d, J=1.7 Hz, 1H), 8.72 (d, J=7.4 Hz, 1H), 8.53 (s, 1H), 8.35 (d, J=7.9 Hz, 1H), 8.25 (dd, J=2.2, 8.3 Hz, 1H), 7.98 (s, 1H), 7.93 (d, J=8.3 Hz, 2H), 7.61-7.65 (m, 3H), 6.85 (dd, J=1.8, 7.4 Hz, 1H), 3.92-3.94 (m, 1H), 3.53 (s, 3H), 3.01-3.12 (m, 2H), 2.67-2.74 (m, 2H), 1.82-1.85 (m, 2H), 1.54-1.59 (m, 2H). ESI-LC/MS: m/z 480.40 (M+H); $R_t$=2.55 min [Agilent LC with Ion trap Detector; Symmetry C18, 3.5 μm, 4.6×75 mm column; gradient of 80:20 $H_2O$ (0.1% HCOOH):$CH_3CN$ (0.1% HCOOH) to 10:90 H₂O (0.1% HCOOH):CH₃CN (0.1% HCOOH) in 4.0 min and hold for 3.0 min with flow rate of 1.0 mL/min]. HPLC purity: 97.5% at 294 nm; r.t.=3.27 min [Waters HPLC with PDA; Xterra RP18, 5.0 μm, 4.6×150 mm column; gradient of 70:30 H₂O (0.01 M ammonium bicarbonate):CH₃CN to 10:90 H₂O (0.01 M ammonium bicarbonate):CH₃CN in 5.0 min and hold for 10.0 min with flow rate of 1.0 mL/min].

Example 114

N-(5-Cyanopyridin-2-yl)-N-methyl-3-(4-((2-(methylamino)ethyl)carbamoyl)phenyl)pyrazolo[1,5-a]pyridine-5-carboxamide Step 1

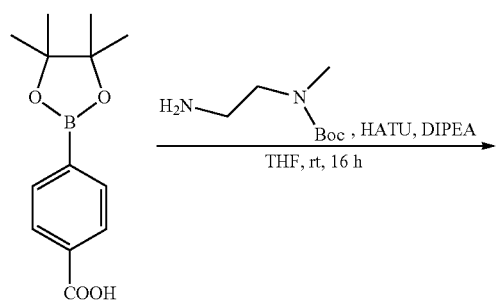

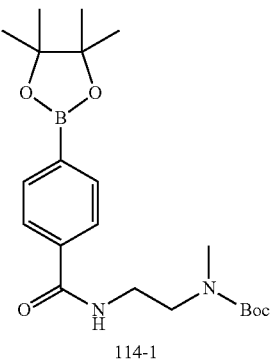

Compound 114-1 was prepared using the general procedure described in Amide Coupling-Method 2 with the appropriate starting materials. The pale red semi solid crude product was used as such for the next step without further purification. ESI-LC/MS: m/z 405.29 (M+H); R$_t$=3.14 min [Waters Acquity UPLC with Quattro-micro detector; Waters Acquity BEH C18, 1.7 μm, 2.1×50 mm column; gradient of 90:10 H₂O (0.025% TFA):CH₃CN (0.025% TFA) hold for 0.5 min and to 10:90 H₂O (0.025% TFA):CH₃CN (0.025% TFA) in 3.0 min and hold for 2.0 min with flow rate of 0.4 mL/min].

Step 2

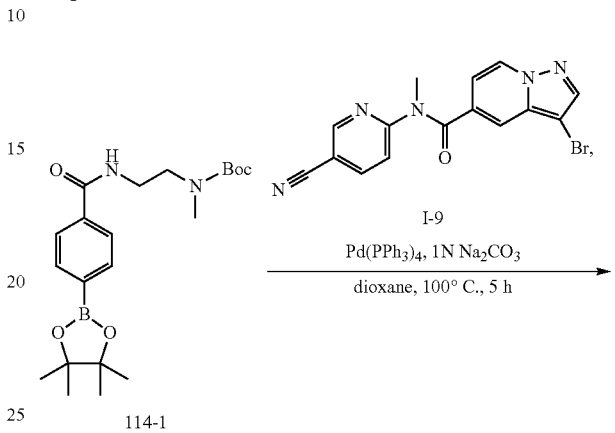

Compound 114-2 was prepared using the general procedure described in Suzuki Procedure G with the appropriate starting materials. The yellow color semi solid crude product was used as such for the next step without further purification. ESI-LC/MS: m/z 554.12 (M+H); R$_t$=2.68 min [Waters Acquity UPLC with Quattro-micro detector; Waters Acquity BEH C18, 1.7 μm, 2.1×50 mm column; gradient of 90:10 H₂O (0.025% TFA):CH₃CN (0.025% TFA) hold for 0.5 min and to 10:90 H₂O (0.025% TFA):CH₃CN (0.025% TFA) in 3.0 min and hold for 2.0 min with flow rate of 0.4 mL/min].

Step 3

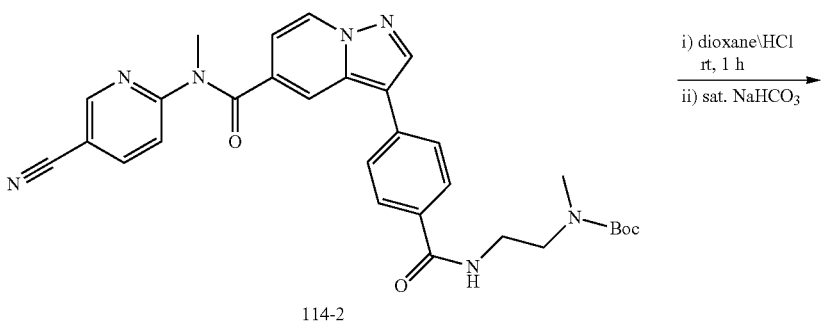

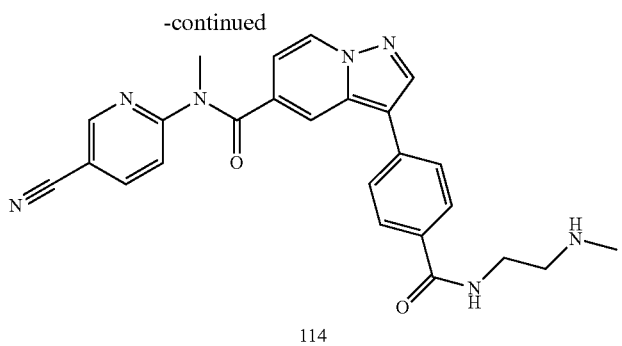

114

A solution mixture of N-(5-cyanopyridin-2-yl)-N-methyl-3-(4-(2-(methylamino)ethylcarbamoyl)phenyl)pyrazolo[1,5-a]pyridine-5-carboxamide 6 (350 mg) and dioxane.HCl (4M) (3.0 mL) in dioxane (10 mL) was stirred at room temperature for 1 h. The reaction mixture was diluted with diethyl ether and filtered. The collected solid was dissolved in water, basified with sat. NaHCO$_3$ to pH 10 and extracted with 10% methanol in chloroform. The combined organic extracts were dried over anhydrous Na$_2$SO$_4$ and concentrated. The crude compound was purified by prep-TLC to afford 60 mg (17% over three steps from SM) of N-(5-cyanopyridin-2-yl)-N-methyl-3-(4-(2-(methylamino)ethylcarbamoyl)phenyl)pyrazolo[1,5-a]pyridine-5-carboxamide 114 as a yellow color solid. $^1$H-NMR (400 MHz, CD$_3$OD): δ 8.71 (d, J=1.8 Hz, 1H), 8.53 (d, J=6.6 Hz, 1H), 8.34 (s, 1H), 8.04 (dd, J=2.2, 8.8 Hz, 1H), 7.93-7.98 (m, 3H), 7.62 (d, J=8.4 Hz, 2H), 7.49 (d, J=7.9 Hz, 1H), 6.87 (dd, J=2.2, 7.4 Hz, 1H), 3.59-3.61 (m, 5H), 2.90-2.91 (m, 2H), 2.54 (s, 3H). ESI-LC/MS: m/z 454.18 (M+H); R$_t$=1.85 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 minute and to 10:90 H$_2$O (0.025% TFA):CH$_3$CN (0.025% TFA) in 3.0 min and hold for 2.0 min with flow rate of 0.4 mL/min]. HPLC purity: 95.2% at 295 nm; R$_t$=2.40 min [Waters Acquity UPLC with PDA; Waters Acquity BEH C18, 1.7 μm, 2.1×100 mm column; gradient of 90:10 H$_2$O (0.025% TFA):CH$_3$CN (0.025% TFA) to 20:80 H$_2$O (0.025% TFA):CH$_3$CN (0.025% TFA) in 4.0 min and hold for 2.0 min with flow rate of 0.3 mL/min].

Example 115

N-(5-cyanopyridin-2-yl)-3-(4-((2-(dimethylamino)ethyl)carbamoyl)phenyl)-N-methylpyrazolo[1,5-a]pyridine-5-carboxamide Step 1

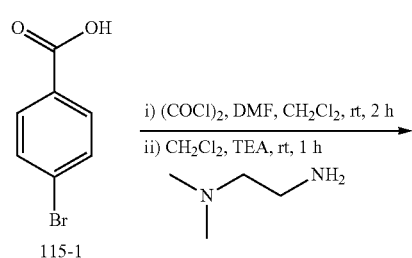
115-1

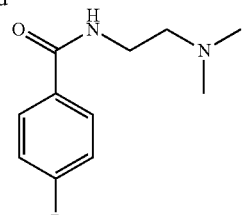
115-2

Compound 115-2 was prepared using the general procedure described in Amide Coupling-Method 1 with the appropriate starting materials. Yield 59%. Off-white solid. $^1$H NMR (DMSO-d$_6$): δ 8.47 (br. s, 1H), 7.77 (d, J=8.4 Hz, 2H), 7.67 (d, J=8.4 Hz, 2H), 3.33-3.35 (m, 2H), 2.41 (t, J=7.0 Hz, 2H), 2.18 (s, 6H). ESI-LC/MS: m/z 270.99 (M+H) & 273.07 [(M+2)+H]; R$_t$=1.64 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.0 min and hold for 2.0 min with flow rate of 0.4 mL/min].

Step 2

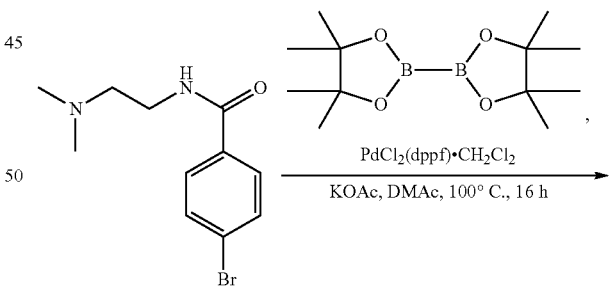

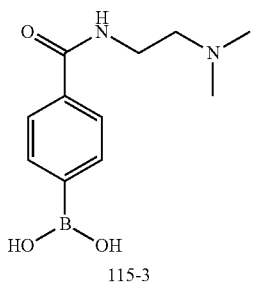
115-3

To a stirred solution of 4-bromo-N-(2-(dimethylamino)ethyl)benzamide 115-1 (1.0 g, 3.703 mmol), bis(pinacolato)diboron (1.12 g, 4.44 mmol), KOAc (1.08 g, 11.109 mmol) in N,N-dimethylacetamide (40 mL) was degassed with argon for about 15 min. PdCl$_2$(dppf)CH$_2$Cl$_2$ (91 mg, 0.111 mmol) was added under argon atmosphere. The resulting reaction mixture was maintained at 100° C. for 16 h. The reaction mixture was cooled to room temperature, water (50 mL) was added to reaction mass and filtered through celite. The filtrate was distilled under reduced pressure to afford 1.8 g (crude) of 4-(2-(dimethylamino)ethylcarbamoyl)phenylboronic acid 115-3 as brown semi solid. The crude product was used as such for next reaction.

Step 3

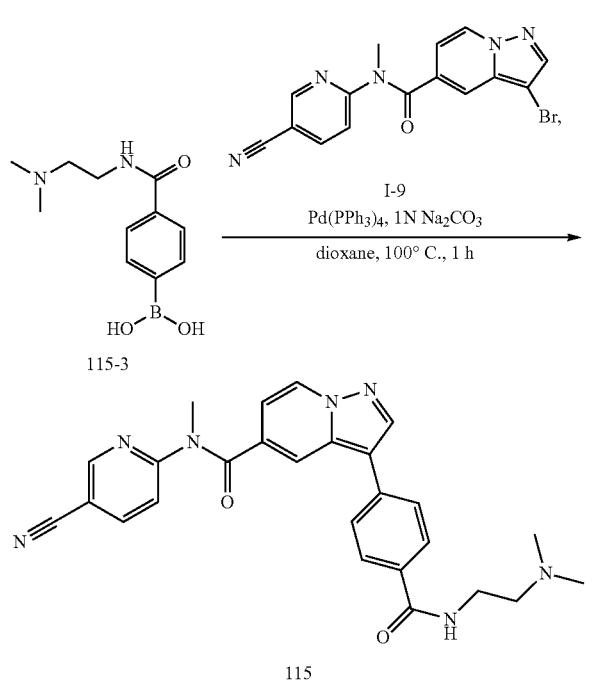

Compound 115 was prepared using the general procedure described in Suzuki procedure G with the appropriate starting materials. Yield 3% (over two steps). Yellow color solid. $^1$H NMR (400 MHz, DMSO-d$_6$): δ 8.85 (d, J=3.2 Hz, 1H), 8.72 (d, J=7.0 Hz, 1H), 8.53 (s, 1H), 8.45 (br. s, 1H), 8.25 (dd, J=2.2, 8.8 Hz, 1H), 7.99 (s, 1H), 7.92 (d, J=8.3 Hz, 2H), 7.61-7.68 (m, 3H), 6.84 (dd, J=1.3, 7.0 Hz, 1H), 3.53 (s, 3H), 3.37-3.41 (m, 2H), 2.44 (m, 2H), 2.32 (br s, 6H). ESI-LC/MS: m/z 468.18 (M+H); R$_f$=1.86 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.0 min and hold for 2.0 min with flow rate of 0.4 mL/min]. HPLC purity: >99% at 254 nm; R$_f$=1.34 min [Waters Acquity UPLC with PDA; Waters Acquity BEH C18, 1.7 μm, 2.1×100 mm column; gradient of 70:30 H$_2$O (0.025% TFA):CH$_3$CN (0.025% TFA) to 20:80 H$_2$O (0.025% TFA):CH$_3$CN (0.025% TFA) in 4.0 min and hold for 2.0 min with flow rate of 0.3 mL/min].

Example 116

N-(4-Chlorophenyl)-N-cyclopropyl-3-(4-(methylcarbamoyl)phenyl)pyrazolo[1,5-a]pyridine-5-carboxamide Step 1

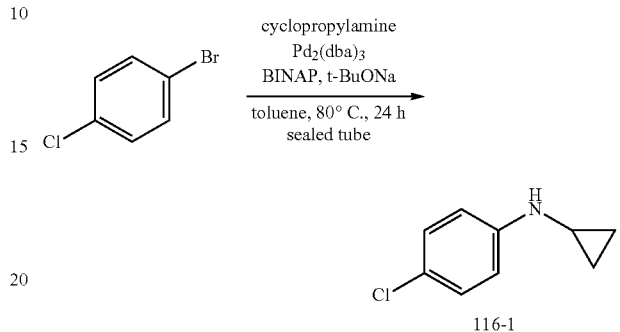

A solution mixture of 1-bromo-4-chlorobenzene (300 mg, 1.57 mmol) and t-BuONa (226 mg, 2.35 mmol) in toluene (3.0 mL) was degassed with argon for about 10 min. Pd$_2$(dba)$_3$ (14 mg, 0.015 mmol), BINAP (29 mg, 0.04 mmol) and cyclopropylamine (0.179 mL, 2.58 mmol) were added under argon atmosphere. The resulting reaction mixture was maintained at 80° C. for 24 h. The reaction mixture was diluted with water and extracted with ethyl acetate (2×50 mL). The combined organic layer was washed with water, brine solution, dried over anhydrous Na$_2$SO$_4$ and concentrated. The crude product was purified by column chromatography over silica-gel (100-200 mesh) using a solvent gradient mixture of 0.5% ethyl acetate in pet-ether to afford 50 mg (19%) of 4-chloro-N-cyclopropylaniline 116-1 as a pale yellow liquid. $^1$H NMR (400 MHz, CDCl$_3$): δ7.12 (d, J=8.8 Hz, 2H), 6.70 (d, J=8.8 Hz, 2H), 4.16 (br. s, 1H), 2.37-2.40 (m, 1H), 0.70-0.75 (m, 2H), 0.48-0.51 (m, 2H).

Step 2

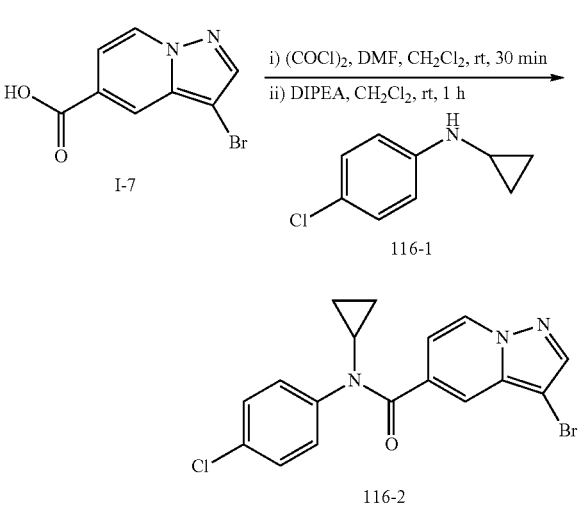

Compound 116-2 was prepared using the general procedure described in Amide Coupling-Method 1 with the appropriate starting materials. Yield 37%. Off white solid. $^1$H NMR (400 MHz, DMSO-$d_6$): b 8.69 (d, J=6.8 Hz, 1H), 8.20 (s, 1H), 7.65 (s, 1H), 7.36-7.42 (m, 4H), 6.98 (d, J=6.8 Hz, 1H), 3.28-3.32 (m, 1H), 0.73-0.74 (m, 2H), 0.52-0.54 (m, 2H). ESI-LC/MS: m/z 391.6 (M+H); $R_f$=3.14 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.5 min and hold for 1.5 min with flow rate of 0.4 mL/min]

Step 3

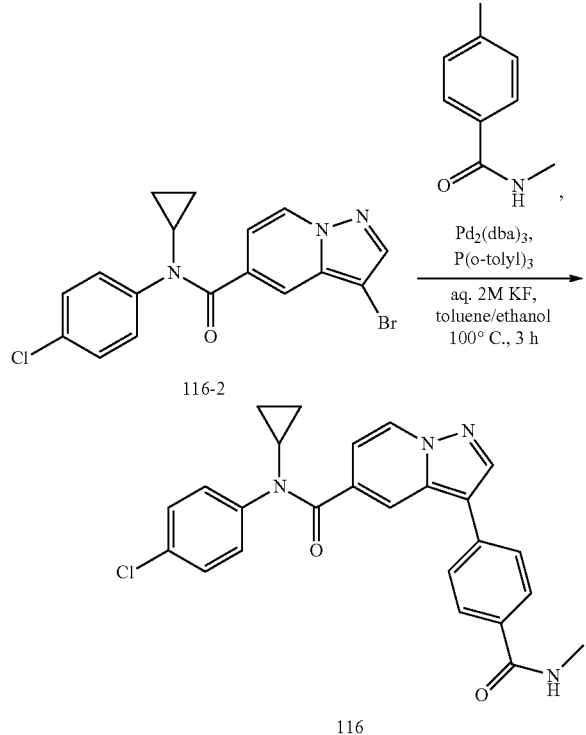

Compound 116 was prepared using the general procedure described in Suzuki Procedure H with the appropriate starting materials. Yield 20%. Yellow solid. $^1$H-NMR (400 MHz, DMSO-$d_6$): b 8.71 (d, J=7.0 Hz, 1H), 8.45-8.48 (m, 2H), 7.92-7.96 (m, 3H), 7.63 (d, J=7.9 Hz, 2H), 7.38-7.45 (m, 4H), 7.00 (d, J=6.6 Hz, 1H), 3.28-3.20 (m, 1H), 2.82 (d, J=4.4 Hz, 3H), 0.75-0.80 (m, 2H), 0.53-0.57 (m, 2H). ESI-LC/MS: m/z 445.14 (M+H) & 446.92 [(M+2)H+]; $R_f$=2.61 min [Waters Acquity UPLC with Quattro micro TQD; Waters Acquity BEH C18, 1.7 μm, 2.1×50 mm column; gradient of 90:10 H$_2$O (0.025% TFA):CH$_3$CN (0.025% TFA) hold for 0.5 min to 10:90 H$_2$O (0.025% TFA):CH$_3$CN (0.025% TFA) in 2.5 min and hold for 2 min with flow rate of 0.4 mL/min]. HPLC Purity: 97.3% at 254 nm; $R_f$=2.87 min [Waters Acquity UPLC with PDA detector; Waters Acquity BEH C18, 1.7 μm, 2.1×100 mm column; gradient of 70:30 H$_2$O (0.025% TFA):CH$_3$CN (0.025% TFA) to 20:80 H$_2$O (0.025% TFA):CH$_3$CN (0.025% TFA) in 4 min and hold for 2 min with flow rate of 0.3 mL/min].

Example 117

N-(5-Cyanopyridin-2-yl)-N-(cyclopropylmethyl)-3-(4-(methylcarbamoyl)phenyl)pyrazolo[1,5-a]pyridine-5-carboxamide Step 1

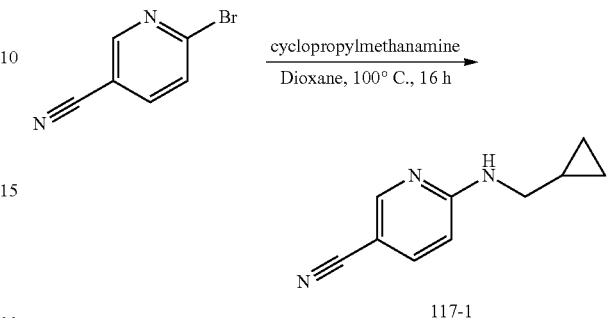

A solution mixture of 2-bromo-5-cyanopyridine (1.0 g, 5.46 mmol), cyclopropylmethylamine (0.939 mL, 10.95 mmol) and in dioxane (20 mL) was stirred at 100° C. for 16 h in sealed tube. Distilled off the volatiles and the crude residue was passed through silica-gel (100-200 mesh) column with 20% ethyl acetate in pet-ether as eluant to gave 900 mg (95%) of 6-(cyclopropylmethylamino)nicotinonitrile 117-1 as an off-white solid. ESI-LC/MS: m/z 174.0 (M+H); $R_f$=3.52 min [Agilent LC with Ion trap Detector; Xterra MS-C18, 2.5 μm, 4.6×50 mm column; gradient of 80:20 H$_2$O (0.01 M ammonium bicarbonate):CH$_3$CN to 10:90 H$_2$O (0.01 M ammonium bicarbonate):CH$_3$CN in 4.0 min and hold for 3.0 min with flow rate of 1.0 mL/min].

Step 2

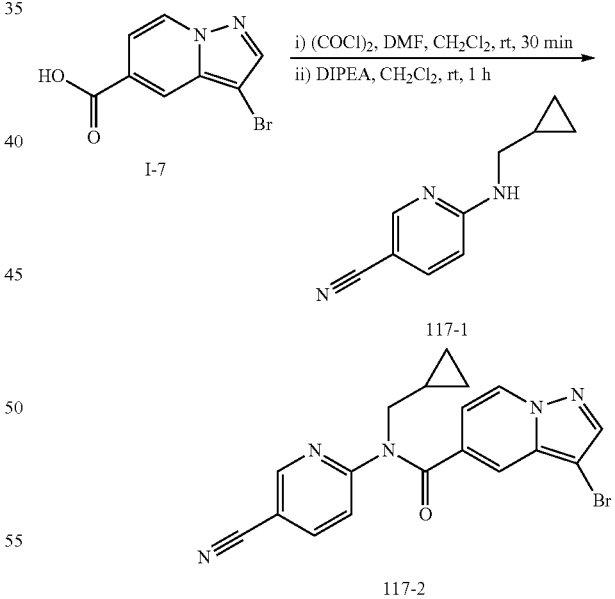

Compound 117-2 was prepared using the general procedure described in Amide Coupling-Method 1 with the appropriate starting materials. The crude (500 mg) compound was used directly for next reaction. ESI-LC/MS: m/z 396.00 (M+H) & 398.00 [(M+2)+H]; $R_f$=2.98 min [Waters Acquity UPLC with Quattro micro TQD; Waters Acquity BEH C18, 1.7 μm, 2.1×50 mm column; gradient of 90:10 H$_2$O (0.025% TFA):CH$_3$CN (0.025% TFA) hold for 0.5 min to 10:90 H$_2$O (0.025% TFA):CH$_3$CN (0.025% TFA) in 2.5 min and hold for 2 min with flow rate of 0.4 mL/min].

Step 3

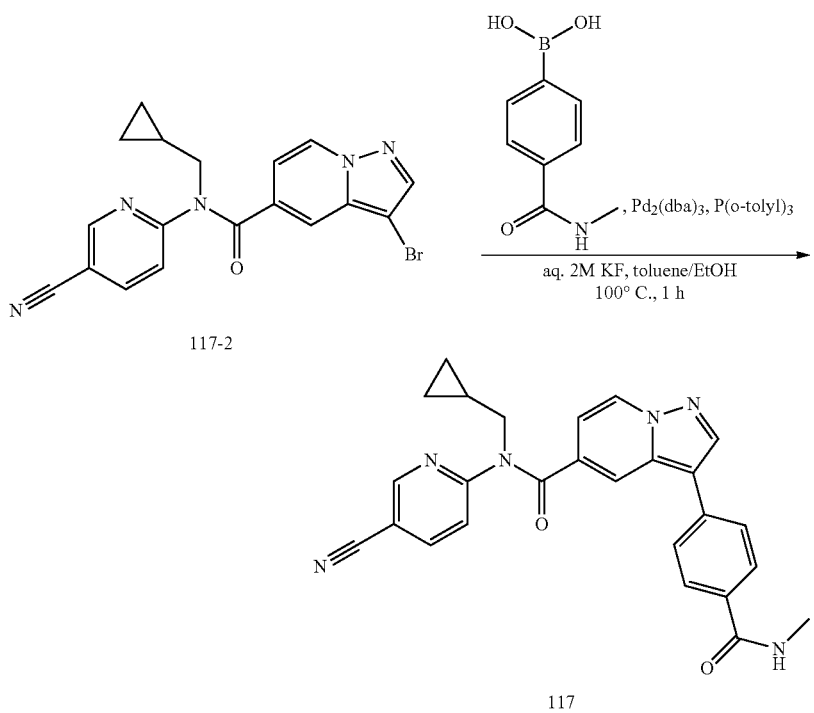

Compound 117 was prepared using the general procedure described in Suzuki Procedure H with the appropriate starting materials. Yield 20% (over two steps yield). Yellow solid. ¹H-NMR (400 MHz, DMSO-$d_6$): δ8.88 (d, J=2.2 Hz, 1H), 8.67 (d, J=7.5 Hz, 1H), 8.51 (s, 1H), 8.45-8.48 (m, 1H), 8.24 (dd, J=2.2, 6.2 Hz, 1H), 7.90-7.94 (m, 3H), 7.51-7.61 (m, 3H), 6.75 (dd, J=1.8, 5.7 Hz, 1H), 3.99 (d, J=6.0 Hz, 2H), 2.82 (d, J=4.4 Hz, 3H), 1.15-1.22 (m, 1H), 0.38-0.42 (m, 2H), 0.17-0.21 (m, 2H). ESI-LC/MS: m/z 451.28 (M+H); $R_t$=2.49 min [Waters Acquity UPLC with Quattro micro TQD; Waters Acquity BEH C18, 1.7 μm, 2.1×50 mm column; gradient of 90:10 $H_2O$ (0.025% TFA):$CH_3CN$ (0.025% TFA) hold for 0.5 min to 10:90 $H_2O$ (0.025% TFA):$CH_3CN$ (0.025% TFA) in 2.5 min and hold for 2 min with flow rate of 0.4 mL/min]. HPLC purity: 97.2% at 254 nm; $R_t$=1.30 min [Waters Acquity UPLC with PDA detector; Waters Acquity BEH C18, 1.7 μm, 2.1×100 mm column; gradient of 70:30 $H_2O$ (0.025% TFA):$CH_3CN$ (0.025% TFA) to 20:80 $H_2O$ (0.025% TFA):$CH_3CN$ (0.025% TFA) in 4 min and hold for 2 min with flow rate of 0.3 mL/min].

Example 118

N-(4-Cyanophenyl)-N-cyclopropyl-3-(4-(methylcarbamoyl)phenyl)pyrazolo[1,5-a]pyridine-5-carboxamide Step 1

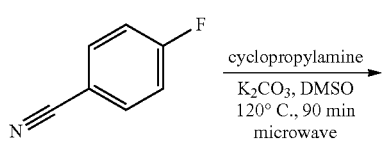

-continued

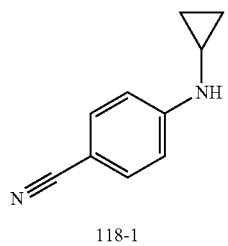

A mixture of 4-fluorobenzonitrilre (1.0 g, 8.264 mmol), cyclopropylamine (20 mL) and $K_2CO_3$ (3.42 g, 24.745 mmol) in DMSO (10 mL) was stirred at 120° C. for 90 min under MW irradiation. The reaction mixture was partitioned between water (50 mL) and ethyl acetate (100 mL). The combined organic layer was washed with brine (100 mL), dried over anhydrous $Na_2SO_4$ and concentrated to afford 650 mg (50%) of 4-(cyclopropylamino)benzonitrile 118-1 as a white solid. ¹H NMR (400 MHz, DMSO-$d_6$): 7.47 (d, J=7.6 Hz, 2H), 7.05 (s, 1H), 6.75 (d, J=7.2 Hz, 2H), 2.28-2.40 (m, 1H), 0.72-0.76 (m, 2H), 0.38-0.44 (m, 2H).

Step 2

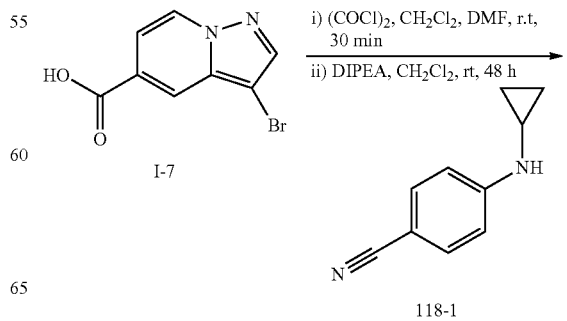

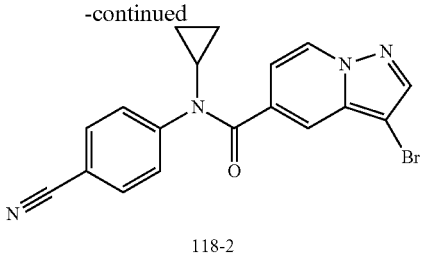

118-2

Compound 118-2 was prepared using the general procedure described in Amide Coupling-Method 1 with the appropriate starting materials. Yield 13%. Yellow solid. ESI-LC/MS: m/z 380.99 (M+H) & 382.97 [(M+2)+H]; $R_t$=2.77 min [Waters Acquity UPLC with Quattro micro TQD; Waters Acquity BEH C18, 1.7 μm, 2.1×50 mm column; gradient of 90:10 H$_2$O (0.025% TFA):CH$_3$CN (0.025% TFA) hold for 0.5 min to 10:90 H$_2$O (0.025% TFA):CH$_3$CN (0.025% TFA) in 2.5 min and hold for 2 min with flow rate of 0.4 mL/min]. Step 3

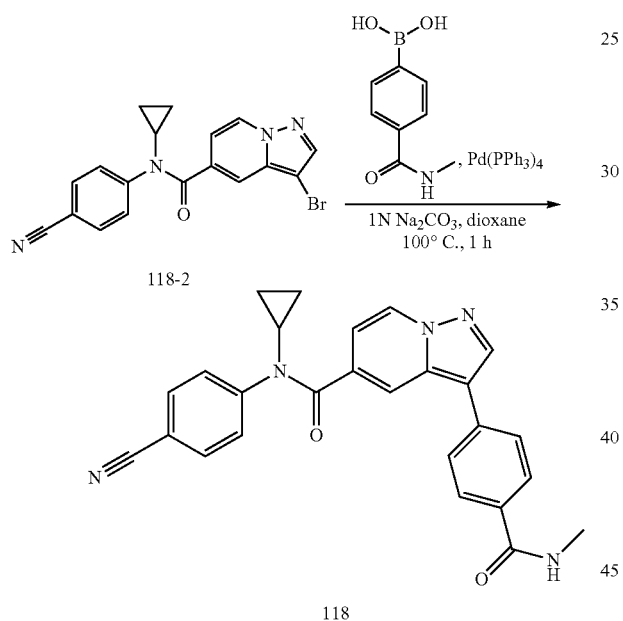

118

Compound 118 was prepared using the general procedure described in Suzuki Procedure G with the appropriate starting materials. Yield 44%. Yellow solid. $^1$H-NMR (400 MHz, DMSO-d$_6$): δ 8.75 (d, J=7.4 Hz, 1H), 8.51 (s, 1H), 8.42-8.50 (br.s, 1H), 8.07 (s, 1H), 7.93 (d, J=8.3 Hz, 2H), 7.88 (d, J=8.8 Hz, 2H), 7.62-7.70 (m, 4H), 7.05 (d, J=7.4 Hz, 1H), 3.30-3.37 (m, 1H), 2.82 (d, J=4.0 Hz, 3H), 0.80-0.83 (m, 2H), 0.77-0.79 (m, 2H). ESI-LC/MS: m/z 436.11 (M+H); $R_t$=2.35 min [Waters Acquity UPLC with Quattro micro TQD; Waters Acquity BEH C18, 1.7 μm, 2.1×50 mm column; gradient of 90:10 H$_2$O (0.025% TFA):CH$_3$CN (0.025% TFA) hold for 0.5 min to 10:90 H$_2$O (0.025% TFA):CH$_3$CN (0.025% TFA) in 2.5 min and hold for 2 min with flow rate of 0.4 mL/min]. HPLC purity: 98.0% at 254 nm; $R_t$=2.15 min [Waters Acquity UPLC with PDA detector; Waters Acquity BEH C18, 1.7 μm, 2.1×100 mm column; gradient of 50:50 H$_2$O (0.025% TFA):CH$_3$CN (0.025% TFA) to 20:80 H$_2$O (0.025% TFA):CH$_3$CN (0.025% TFA) in 4 min and hold for 2 min with flow rate of 0.3 mL/min].

Example 119

N-(tert-Butyl)-N-(5-cyanopyridin-2-yl)-3-(4-(methylcarbamoyl)phenyl)pyrazolo[1,5-a]pyridine-5-carboxamide Step 1

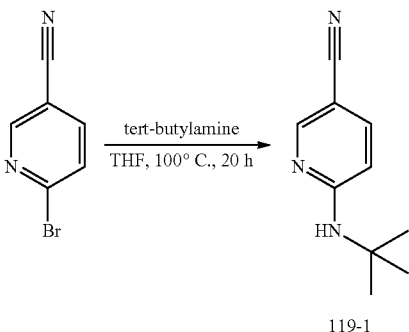

119-1

A solution mixture of 2-bromo-5-cyanopyridine (1.0 g, 5.46 mmol) and t-butylamine (2.0 g, 27.39 mmol) in THF (10 mL) was stirred at 100° C. for 20 h in sealed tube. The reaction mixture was partitioned between water (50 mL) and ethyl acetate (100 mL). The ethyl acetate was washed with brine (50 mL), dried over anhydrous Na$_2$SO$_4$ and concentrated to afford 400 mg of crude 6-(tert-butylamino)nicotinonitrile 119-1 as a white solid. The crude product was used as such for the next step without further purification.

Step 2

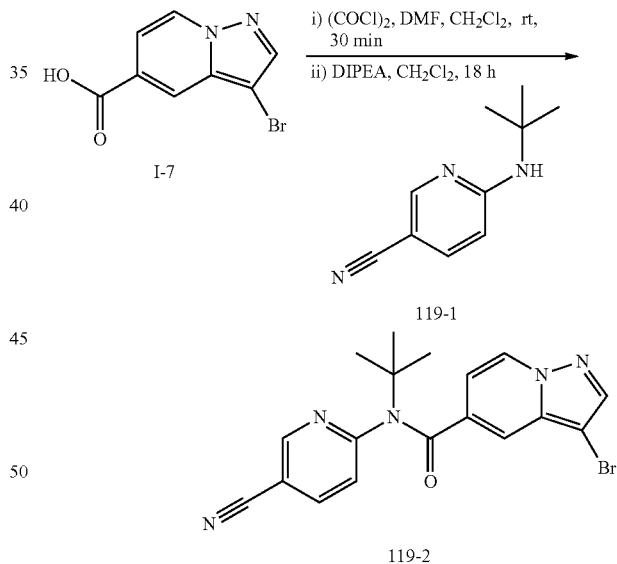

119-2

Compound 119-2 was prepared using the general procedure described in Amide Coupling-Method 1 with the appropriate starting materials. Yield 30% (over two steps). Brown solid. $^1$H NMR (400 MHz, DMSO-d$_6$): δ 8.91 (d, J=1.7 Hz, 1H), 8.54-8.56 (m, 1H), 8.26 (dd, J=2.6, 8.3 Hz, 1H), 8.14 (s, 1H), 7.73 (d, J=8.3 Hz, 1H), 7.28 (s, 1H), 6.73 (dd, J=1.8, 7.0 Hz, 1H), 1.47 (s, 9H). ESI-LC/MS: m/z 398.06 (M+H) & 400.04 [(M+2)+H]; $R_t$=2.94 min. [Waters Acquity UPLC with Quattro micro TQD; Waters Acquity BEH C18, 1.7 μm, 2.1×50 mm column; gradient of 90:10 H$_2$O (0.025% TFA):CH$_3$CN (0.025% TFA) hold for 0.5 minutes to 10:90 H$_2$O (0.025% TFA):CH$_3$CN (0.025% TFA) in 2.5 minutes and hold for 2 minutes with flow rate of 0.4 mL/min].

Step 3

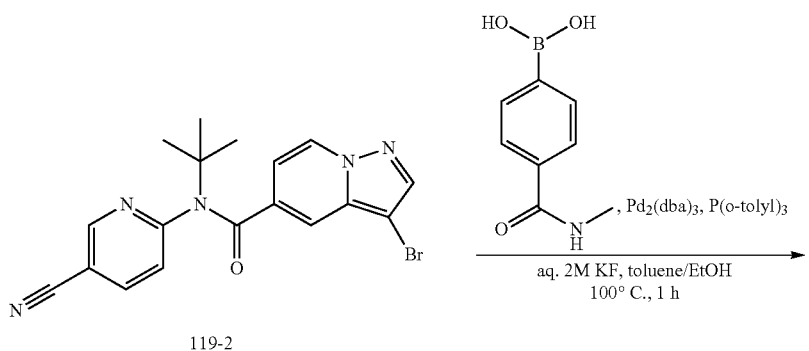

Compound 119 was prepared using the general procedure described in Suzuki Procedure H with the appropriate starting materials. Yield 30%. Yellow solid. $^1$H-NMR (400 MHz, DMSO-$d_6$): δ 8.96 (s, 1H), 8.58 (d, J=6.6 Hz, 1H), 8.48 (s, 1H), 8.42 (s, 1H), 8.29 (d, J=7.9 Hz, 1H), 7.97 (d, J=7.0 Hz, 2H), 7.77 (d, J=7.4 Hz, 1H), 7.66 (s, 1H), 7.58 (d, J=7.5 Hz, 2H), 6.76 (d, J=7.4 Hz, 1H), 2.82 (s, 3H), 1.47 (s, 9H). ESI-LC/MS: m/z 453.19 (M+H); $R_t$=2.43 min. [Waters Acquity UPLC with Quattro micro TQD; Waters Acquity BEH C18, 1.7 μm, 2.1×50 mm column; gradient of 90:10 H$_2$O (0.025% TFA):CH$_3$CN (0.025% TFA) hold for 0.5 min to 10:90 H$_2$O (0.025% TFA):CH$_3$CN (0.025% TFA) in 2.5 min and hold for 2 min with flow rate of 0.4 mL/min]. HPLC purity: 98.4% at 282 nm; $R_t$=2.492 min. [Waters Acquity UPLC with PDA detector; Waters Acquity BEH C18, 1.7 μm, 2.1×100 mm column; gradient of 70:30 H$_2$O (0.025% TFA):CH$_3$CN (0.025% TFA) to 20:80 H$_2$O (0.025% TFA): CH$_3$CN (0.025% TFA) in 4 min and hold for 2 min with flow rate of 0.3 mL/min].

Example 120

3-(4-Carbamoylphenyl)-N-(5-cyanopyridin-2-yl)-N-cyclopropylpyrazolo[1,5-a]pyridine-5-carboxamide -continued

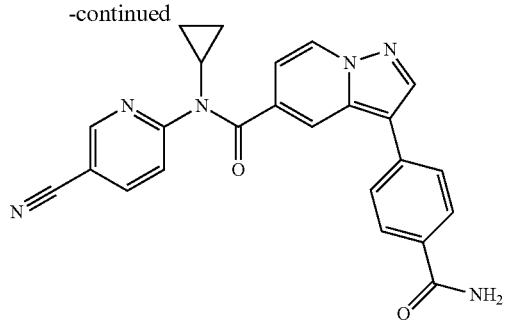

120

Compound 120 was prepared using the general procedure described in Suzuki Procedure H with the appropriate starting materials. Yield 29%. Yellow solid. $^1$H NMR (400 MHz, DMSO-d$_6$): δ 8.84 (d, J=1.8 Hz, 1H), 8.74 (d, J=7.1 Hz, 1H), 8.53 (s, 1H), 8.37 (dd, J=2.2, 8.8 Hz, 1H), 8.02 (br. s, 2H), 7.97 (d, J=8.4 Hz, 2H), 7.82 (d, J=8.3 Hz, 1H), 7.64 (d, J=8.3 Hz, 2H), 7.40 (s, 1H), 7.00 (dd, J=1.8, 7.5 Hz, 1H), 3.24-3.30 (m, 1H), 0.85-90 (m, 2H), 0.65-0.67 (m, 2H). ESI-LC/MS: m/z 423.25 (M+H); R$_t$=2.39 min [Waters Acquity UPLC with Quattro micro TQD; Waters Acquity BEH C18, 1.7 μm, 2.1×50 mm column; gradient of 90:10 H$_2$O (0.025% TFA):CH$_3$CN (0.025% TFA) hold for 0.5 min to 10:90 H$_2$O (0.025% TFA):CH$_3$CN (0.025% TFA) in 2.5 min and hold for 2 min with flow rate of 0.4 mL/min]. HPLC purity=98.4% at 254 nm; R$_t$=1.72 min [Waters Acquity UPLC with PDA detector; Waters Acquity HSS C18, 1.8 μm, 2.1×100 mm column; gradient of 70:30 H$_2$O (0.025% TFA):CH$_3$CN (0.025% TFA) to 20:80 H$_2$O (0.025% TFA):CH$_3$CN (0.025% TFA) in 4 min and hold for 2 min with flow rate of 0.4 mL/min].

Example 121

N-(5-Cyanopyridin-2-yl)-N-cyclopropyl-3-(4-(isopropylcarbamoyl)phenyl)pyrazolo[1,5-a]pyridine-5-carboxamide Step 1

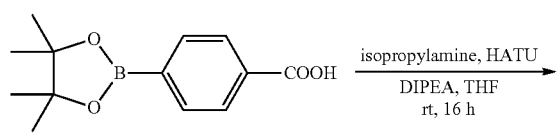

-continued

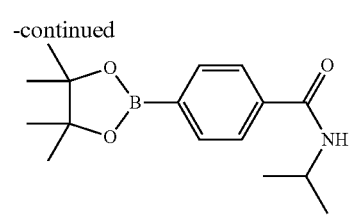

121-1

Compound 121-1 was prepared using the general procedure described in Amide Coupling-Method 2 with the appropriate starting materials. Yield 220 mg (crude). Off-white solid. The crude product was used as such for the next step without further purification. ESI-LC/MS: m/z 290.22 (M+H); R$_t$=2.88 min. [Waters Acquity UPLC with Quattro micro TQD; Waters Acquity BEH C18, 1.7 μm, 2.1×50 mm column; gradient of 90:10 H$_2$O (0.025% TFA):CH$_3$CN (0.025% TFA) hold for 0.5 min to 10:90 H$_2$O (0.025% TFA):CH$_3$CN (0.025% TFA) in 2.5 min and hold for 2 min with flow rate of 0.4 mL/min].

Step 2

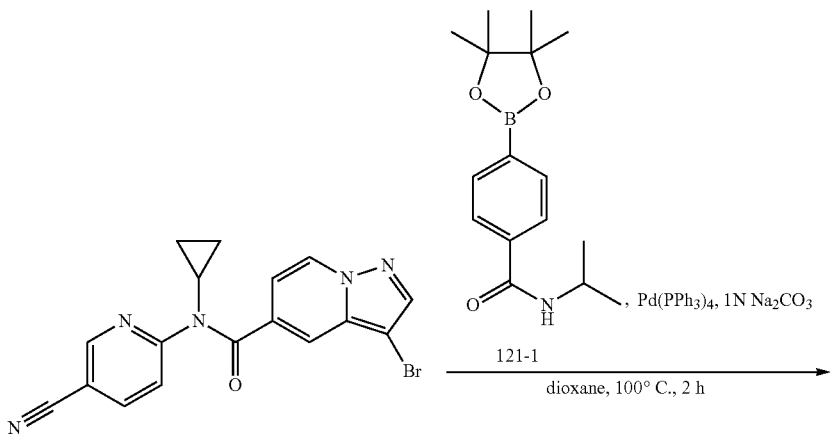

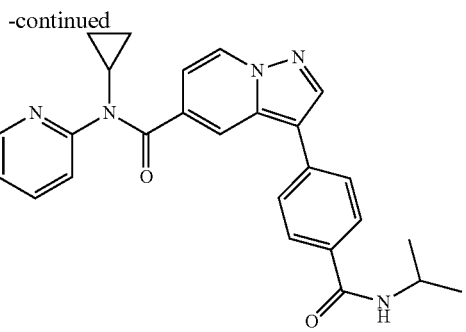

121

Compound 121 was prepared using the general procedure described in Suzuki Procedure G with the appropriate starting materials. Yield 1% (over two steps). yellow solid. $^1$H-NMR (400 MHz, CD$_3$OD): δ 8.67 (d, J=2.2 Hz, 1H), 8.55 (d, J=7.0 Hz, 1H), 8.34 (s, 1H), 8.18 (dd, J=2.2, 8.3 Hz, 1H), 8.00 (s, 1H), 7.92 (d, J=8.3 Hz, 2H), 7.75 (d, J=8.8 Hz, 1H), 7.63 (d, J=8.4 Hz, 2H), 6.98 (dd, J=1.8, 7.1 Hz, 1H), 4.22-4.30 (m, 1H), 2.82 (br. s, 1H), 1.28 (d, J=6.6 Hz, 6H), 0.96-1.00 (m, 2H), 0.69-0.73 (m, 2H). ESI-LC/MS: m/z 465.19 (M+H); R$_t$=2.73 min [Waters Acquity UPLC with Quattro micro TQD; Waters Acquity BEH C18, 1.7 μm, 2.1×50 mm column; gradient of 90:10 H$_2$O (0.025% TFA): CH$_3$CN (0.025% TFA) hold for 0.5 min to 10:90 H$_2$O (0.025% TFA):CH$_3$CN (0.025% TFA) in 2.5 min and hold for 2 min with flow rate of 0.4 mL/min]. HPLC purity=98.4% at 290 nm; R$_t$=1.41 min [Waters Acquity UPLC with PDA detector; Waters Acquity HSS C18, 1.8 μm, 2.1×100 mm column; gradient of 50:50 H$_2$O (0.025% TFA): CH$_3$CN (0.025% TFA) to 20:80 H$_2$O (0.025% TFA):CH$_3$CN (0.025% TFA) in 4 min and hold for 2 min with flow rate of 0.4 mL/min].

Example 122

N-(6-Methoxypyridin-3-yl)-N-methyl-3-(4-(methylcarbamoyl)phenyl)pyrazolo[1,5-a]pyridine-5-carboxamide Step 1

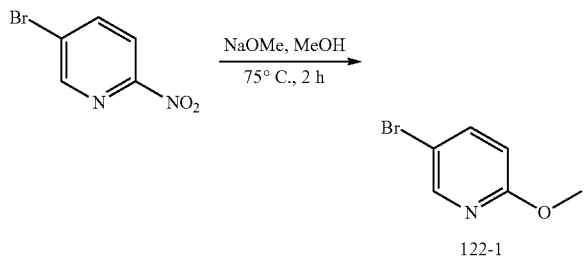

A solution of 5-bromo-2-nitropyridine (5.0 g, 24.63 mmol), in methanol (100 mL) was added sodium methoxide (2.67 g, 49.44 mmol) and stirred at 75° C. for 2 h. The reaction mixture was diluted with water (150 mL) and extracted with ethyl acetate (2×200 mL). The combined extracts were washed with water (200 mL), brine (200 mL), dried over anhydrous Na$_2$SO$_4$ and concentrated. The crude compound was purified by column chromatography over silica gel (100-200 mesh) using a solvent gradient mixture of 5% ethyl acetate in pet-ether as eluant to afford 2.5 g (54%) of 5-bromo-2-methoxypyridine 122-1 as a colorless liquid. $^1$H NMR (400 MHz, CDCl$_3$): b 8.19 (d, J=2.2 Hz, 1H), 7.63 (dd, J=1.8, 8.8 Hz, 1H), 6.66 (d, J=8.7 Hz, 1H), 3.90 (s, 3H). ESI-LC/MS: m/z 190.13 [(M+2)H+]; R$_t$=3.13 min [Agilent LC with Ion trap Detector; Waters Symmetry C18, 3.5 μm, 4.6×75 mm column; gradient of 50:50 H$_2$O (0.1% HCOOH):CH$_3$CN (0.1% HCOOH) to 10:90 H$_2$O (0.1% HCOOH):CH$_3$CN (0.1% HCOOH) in 4 min and hold for 3 min with flow rate of 1.0 mL/min].

Step 2

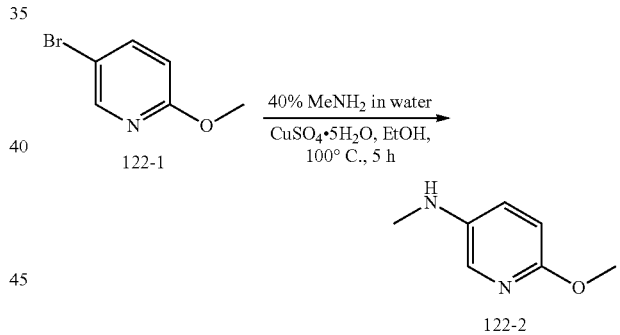

A solution mixture of 5-bromo-2-methoxypyridine (1.2 g, 6.38 mmol), 40% methylamine in water (20 mL) and CuSO$_4$. 5H$_2$O (320 mg, 1.28 mmol) in ethanol (10 mL) was stirred at 100° C. for 5 h. The reaction mixture was partitioned between water (50 mL) and ethyl acetate (3×50 mL). The combined ethyl acetate layer was washed with brine (100 mL), dried over anhydrous Na$_2$SO$_4$ and concentrated to afford 800 mg (91%) of 6-methoxy-N-methylpyridin-3-amine 122-2 as a pale brown solid. $^1$H NMR (400 MHz, CDCl$_3$): b 7.56 (d, J=3.1 Hz, 1H), 6.98 (dd, J=2.6, 8.8 Hz, 1H), 6.63 (d, J=8.8 Hz, 1H), 3.87 (s, 3H), 3.37 (br.s, 1H), 2.87 (s, 3H). ESI-LC/MS: m/z 139.06 (M+H); R$_t$=0.59 min [Waters Acquity UPLC with Quattro micro TQD; Waters Acquity BEH C18, 1.7 μm, 2.1×50 mm column; gradient of 90:10 H$_2$O (0.025% TFA):CH$_3$CN (0.025% TFA) hold for 0.5 min to 10:90 H$_2$O (0.025% TFA):CH$_3$CN (0.025% TFA) in 2.5 min and hold for 2 min with flow rate of 0.4 mL/min].

Step 3

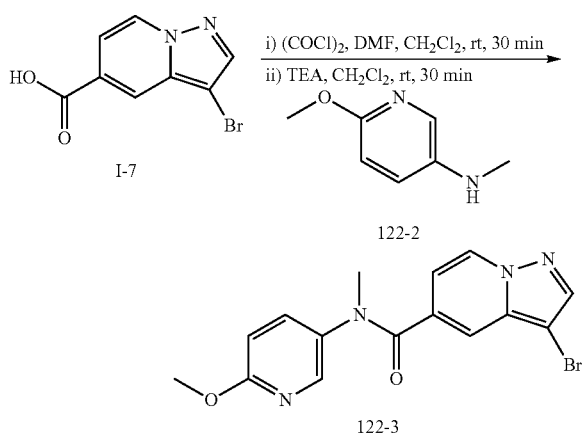

Compound 122-3 was prepared using the general procedure described in Amide Coupling-Method 1 with the appropriate starting materials. Yield 87%. Pale brown solid. $^1$H NMR (400 MHz, DMSO-d$_6$): δ 8.61 (s, 1H), 8.18 (s, 1H), 8.07 (s, 1H), 7.79 (dd, J=2.2, 8.7 Hz, 1H), 7.50 (s, 1H), 6.79-6.81 (m, 2H), 3.75 (m, 3H), 3.36 (s, 3H). ESI-LC/MS: m/z 360.98 (M+H) & 363.05 [(M+2)+H]; R$_t$=2.47 min [Waters Acquity UPLC with Quattro micro TQD; Waters Acquity BEH C18, 1.7 μm, 2.1×50 mm column; gradient of 90:10 H$_2$O (0.025% TFA):CH$_3$CN (0.025% TFA) hold for 0.5 min to 10:90 H$_2$O (0.025% TFA):CH$_3$CN (0.025% TFA) in 2.5 min and hold for 2 min with flow rate of 0.4 mL/min.

Step 4

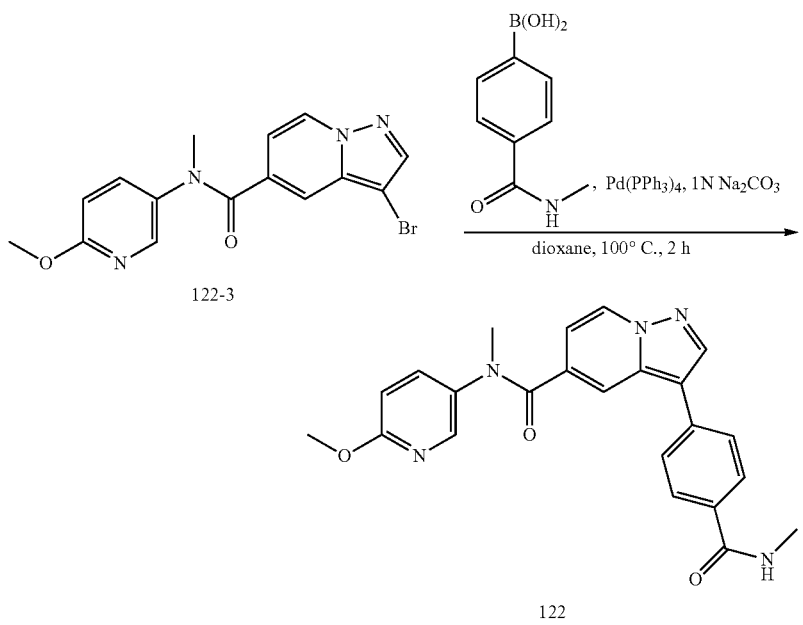

Compound 122 was prepared using the general procedure described in Suzuki Procedure G with the appropriate starting materials. Yield 13%. Yellow solid. $^1$H-NMR (400 MHz, DMSO-d$_6$): δ 8.63-8.65 (m, 1H), 8.44-8.52 (m, 2H), 8.11 (s, 1H), 7.82-7.93 (m, 4H), 7.56-7.64 (m, 2H), 6.83-6.85 (d, J=8.8 Hz, 2H), 3.75 (s, 3H), 3.38 (s, 3H), 2.81 (d, J=4.4 Hz, 3H). ESI-LC/MS: m/z 416.20 (M+H); R$_t$=2.28 min [Waters Acquity UPLC with Quattro micro TQD; Waters Acquity BEH C18, 1.7 μm, 2.1×50 mm column; gradient of 90:10 H$_2$O (0.025% TFA):CH$_3$CN (0.025% TFA) hold for 0.5 min to 10:90 H$_2$O (0.025% TFA):CH$_3$CN (0.025% TFA) in 2.5 min and hold for 2 min with flow rate of 0.4 mL/min]. HPLC purity: 98.9% at 290 nm; R$_t$=1.81 min [Waters Acquity UPLC with PDA detector; Waters Acquity BEH C18, 1.7 μm, 2.1×100 mm column; gradient of 70:30 H$_2$O (0.025% TFA):CH$_3$CN (0.025% TFA) to 20:80 H$_2$O (0.025% TFA):CH$_3$CN (0.025% TFA) in 4 min and hold for 2 min with flow rate of 0.3 mL/min].

Example 123

N-(5-Cyanopyridin-2-yl)-N-cyclopropyl-3-(4-(cyclopropylcarbamoyl)phenyl)pyrazolo[1,5a]pyridine-5-carboxamide Step 1

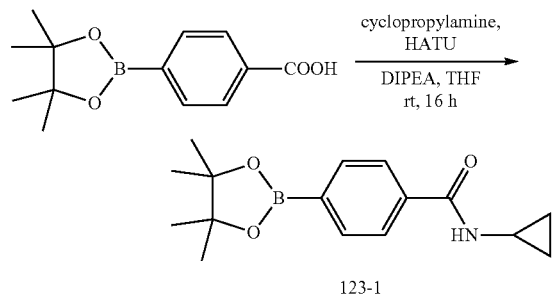

Compound 123-1 was prepared using the general procedure described in Amide Coupling-Method 2 with the appropriate starting materials. The crude colorless gum product was used as such for next step without further purification. ESI-LC/MS: m/z 288.4 (M+H); R$_t$=4.47 min [Agilent LC with Ion trap Detector; Waters Symmetry C18, 3.5 μm, 4.6×75 mm column; gradient of 80:20 H$_2$O (0.1%

HCOOH):CH₃CN (0.1% HCOOH) hold for 1 minutes to 10:90 H₂O (0.1% HCOOH):CH₃CN (0.1% HCOOH) in 4 min and hold for 3 min with flow rate of 1.0 mL/min].

Step 2

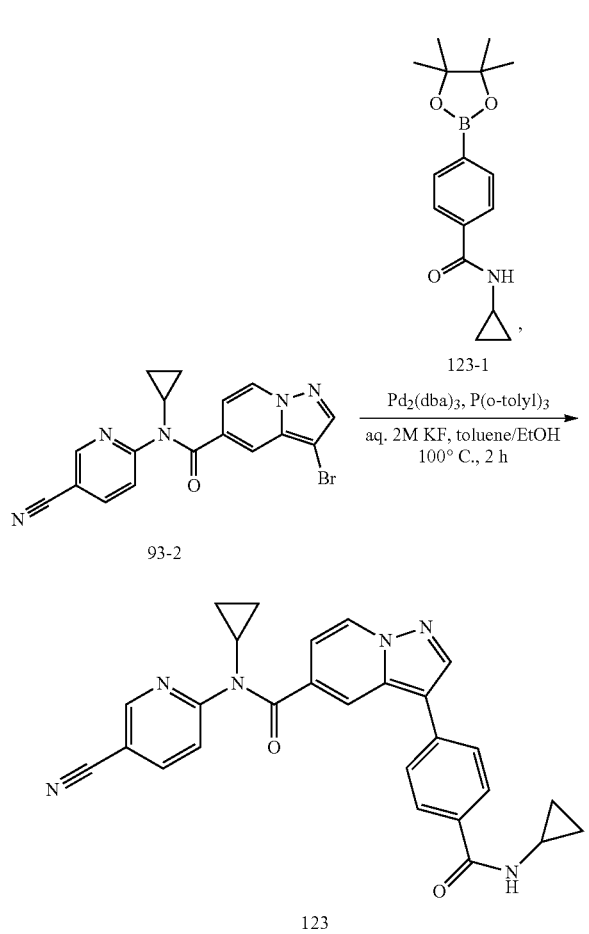

Compound 123 was prepared using the general procedure described in Suzuki Procedure H with the appropriate starting materials. Yield 6.5% (over two steps). Yellow solid. ¹H NMR (400 MHz, DMSO-d₆): δ 8.83 (d, J=1.8 Hz, 1H), 8.74 (d, J=7.5 Hz, 1H), 8.52 (s, 1H), 8.49 (d, J=4.0 Hz, 1H), 8.36 (dd, J=2.2, 8.3 Hz, 1H), 8.03 (brs, 1H), 7.91 (d, J=8.3 Hz, 2H), 7.82 (d, J=8.8 Hz, 1H), 7.66 (d, J=8.4 Hz, 2H), 7.00 (d, J=5.8 Hz, 1H), 3.20-3.26 (m, 1H), 2.84-2.90 (m, 1H), 0.89-0.90 (m, 2H), 0.55-0.74 (m, 6H). ESI-LC/MS: m/z 463.21 (M+H); R$_t$=2.40 min [Waters Acquity UPLC with Quattro micro TQD; Waters Acquity BEH C18, 1.7 μm, 2.1×50 mm column; gradient of 90:10 H₂O (0.025% TFA): CH₃CN (0.025% TFA) hold for 0.5 min to 10:90 H₂O (0.025% TFA):CH₃CN (0.025% TFA) in 2.5 min and hold for 2 min with flow rate of 0.4 mL/min]. HPLC purity=97.1% at 234 nm; R$_t$=2.46 min [Waters Acquity UPLC with PDA detector; Waters Acquity BEH C18, 1.7 μm, 2.1×100 mm column; gradient of 70:30 H₂O (0.025% TFA):CH₃CN (0.025% TFA) to 20:80 H₂O (0.025% TFA): CH₃CN (0.025% TFA) in 4 min and hold for 2 min with flow rate of 0.3 mL/min].

Example 124

N-(5-Chloropyridin-2-yl)-N-cyclopropyl-3-(4-(methylcarbamoyl)phenyl)pyrazolo[1,5-a]pyridine-5-carboxamide Step 1

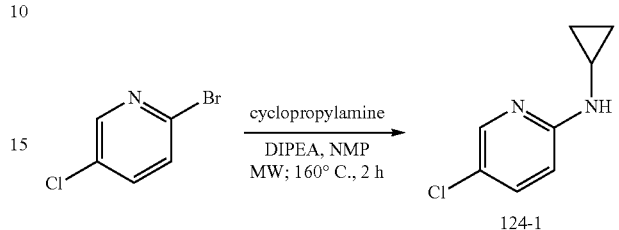

A mixture of 2-bromo-5-chloropyridine (2.0 g, 10.392 mmol), cyclopropylamine (3.62 mL, 52.249 mmol) and DIPEA (9.12 mL, 52.36 mmol) in NMP (20 mL) was stirred at 160° C. for 2 h under MW irradiation. The reaction mixture was partitioned between water (2×100 mL) and ethyl acetate (100 mL). The ethyl acetate was washed with brine (100 mL), dried over anhydrous Na₂SO₄ and concentrated. The crude compound was purified by column chromatography over silica-gel (100-200 mesh) using a solvent gradient of 4% ethyl acetate in chloroform as eluant to afford 400 mg (23%) of 5-chloro-N-cyclopropylpyridin-2-amine 124-1 as an off-white solid. ¹H NMR (400 MHz, DMSO-d₆): δ7.98 (d, J=2.2 Hz, 1H), 7.50 (dd, J=2.6, 8.8 Hz, 1H), 7.00 (s, 1H), 6.58 (d, J=8.8 Hz, 1H), 2.45-2.48 (m, 1H), 0.66-0.69 (m, 2H), 0.38-0.41 (m, 2H). ESI-LC/MS: m/z 169.0 (M+H) & 171.0 [(M+2)+H]; R$_t$=3.73 min [Agilent LC with Ion trap Detector; Waters Xterra MS-C18, 2.5 μm, 4.6×50 mm column; gradient of 95:5 H₂O (0.01 M ammonium bicarbonate):CH₃CN to 20:80 H₂O (0.01 M ammonium bicarbonate):CH₃CN in 4 min and hold for 3 min with flow rate of 1.0 mL/min].

Step 2

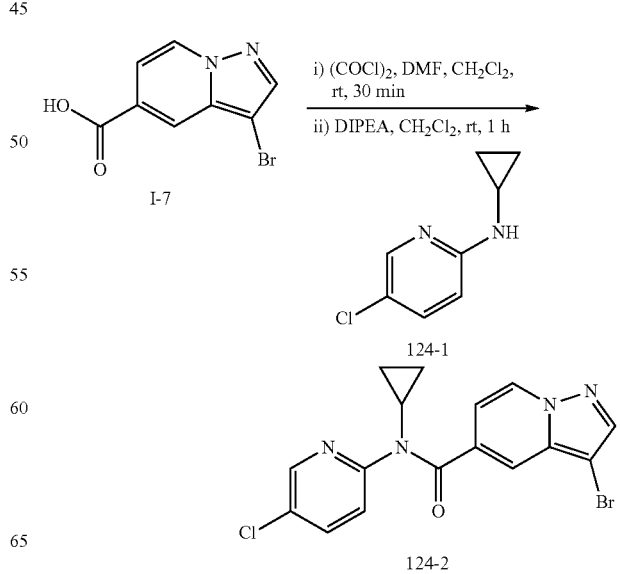

Compound 124-2 was prepared using the general procedure described in Amide Coupling-Method 1 with the appropriate starting materials. Yield 61%. Pale brown solid. $^1$H NMR (400 MHz, DMSO-d$_6$): b 8.68 (d, J=7.5 Hz, 1H), 8.43 (d, J=2.6 Hz, 1H), 8.21 (s, 1H), 7.99 (dd, J=2.6, 8.3 Hz, 1H), 7.55-7.57 (m, 2H), 6.90 (dd, J=1.7, 7.0 Hz, 1H), 3.20-3.22 (m, 1H), 0.83-0.84 (m, 2H), 0.63-0.66 (m, 2H). ESI-LC/MS: m/z 393.2 [(M+2)+H]; R$_t$=5.02 min [Agilent LC with Ion trap Detector; Waters Symmetry C18, 3.5 μm, 4.6×75 mm column; gradient of 80:20 H$_2$O (0.1% HCOOH):CH$_3$CN (0.1% HCOOH) to 10:90 H$_2$O (0.1% HCOOH):CH$_3$CN (0.1% HCOOH) in 4 min and hold for 3 min with flow rate of 1.0 mL/min.

Step 3

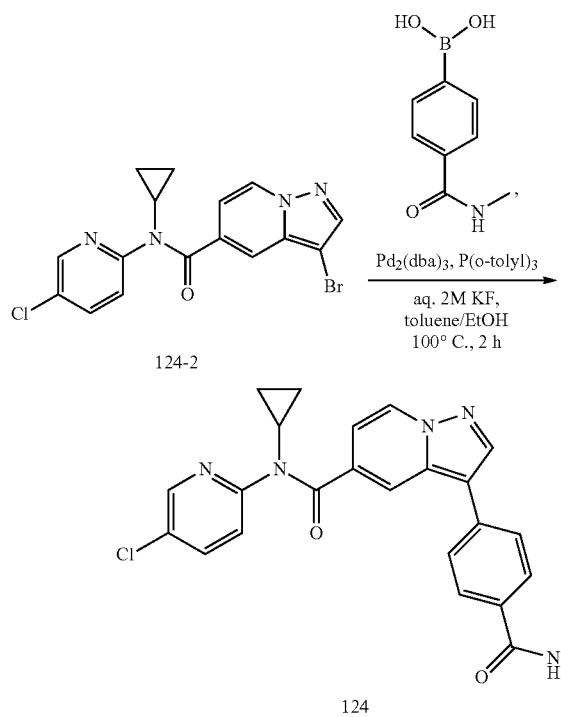

Compound 124 was prepared using the general procedure described in Suzuki Procedure H with the appropriate starting materials. Yield 18%. Yellow solid. $^1$H-NMR (400 MHz, DMSO-d$_6$): b 8.71 (d, J=7.0 Hz, 1H), 8.48-8.52 (m, 3H), 8.02 (dd, J=2.6, 8.3 Hz, 1H), 7.93 (d, J=8.3 Hz, 2H), 7.88 (s, 1H), 7.57-7.64 (m, 3H), 6.95 (dd, J=1.8, 7.5 Hz, 1H), 3.21-3.25 (m, 1H), 2.81 (d, J=4.4 Hz, 3H), 0.81-0.86 (m, 2H), 0.62-0.66 (m, 2H). ESI-LC/MS: m/z 446.13 (M+H); R$_t$=2.35 min [Waters Acquity UPLC with Quattro micro TQD; Waters Acquity BEH C18, 1.7 μm, 2.1×50 mm column; gradient of 90:10 H$_2$O (0.025% TFA):CH$_3$CN (0.025% TFA) hold for 0.5 min to 10:90 H$_2$O (0.025% TFA):CH$_3$CN (0.025% TFA) in 2.5 min and hold for 2 min with flow rate of 0.4 mL/min. HPLC purity: 98.7% at 284 nm; R$_t$=1.153 min [Waters Acquity UPLC with PDA detector; Waters Acquity HSS C18, 1.8 μm, 2.1×100 mm column; gradient of 50:50 H$_2$O (0.025% TFA):CH$_3$CN (0.025% TFA) to 20:80 H$_2$O (0.025% TFA):CH$_3$CN (0.025% TFA) in 4 min and hold for 2 min with flow rate of 0.4 mL/min].

Example 125

N-Cyclopropyl-N-(5-fluoropyridin-2-yl)-3-(4-(methylcarbamoyl)phenyl)pyrazolo[1,5a]pyridine-5-carboxamide Step 1

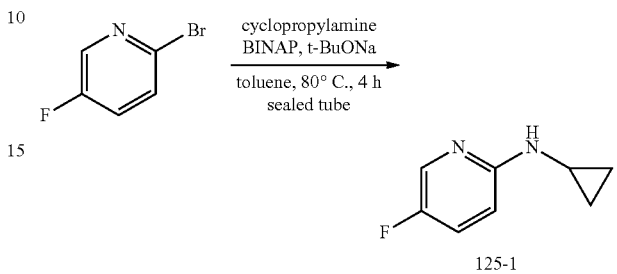

A solution mixture of 2-bromo-5-fluoropyridine (2.0 g, 11.36 mmol), t-BuONa (1.65 g, 17.17 mmol) and toluene (20.0 mL) in sealed tube was degassed with argon for 15 min. Then were added Pd$_2$(dba)$_3$ (105 mg, 0.114 mmol), BINAP (214 mg, 0.343 mmol) and finally cyclopropylamine (1.59 mL, 22.98 mmol). The reaction mixture was maintained at 80° C. for 4 h. The reaction mixture was filtered through celite and washed with ethyl acetate (50 mL). The filtrate was concentrated in-vacuo. The resulting crude compound was passed through column silica-gel (100-200 mesh) using a solvent gradient of 10% ethyl acetate in pet-ether as eluant to give 1.4 g of crude N-cyclopropyl-5-fluoropyridin-2-amine 125-1 as a red color oil. The crude product was used as such for the next step without further purification. ESI-LC/MS: m/z 153.4 (M+H); R$_t$=4.00 min [Agilent LC with Ion trap Detector; Waters Symmetry C18, 3.5 μm, 4.6×75 mm column; gradient of 80:20 H$_2$O (0.1% HCOOH):CH$_3$CN (0.1% HCOOH) to 10:90 H$_2$O (0.1% HCOOH):CH$_3$CN (0.1% HCOOH) in 4 min and hold for 3 min with flow rate of 1.0 mL/min].

Step 2

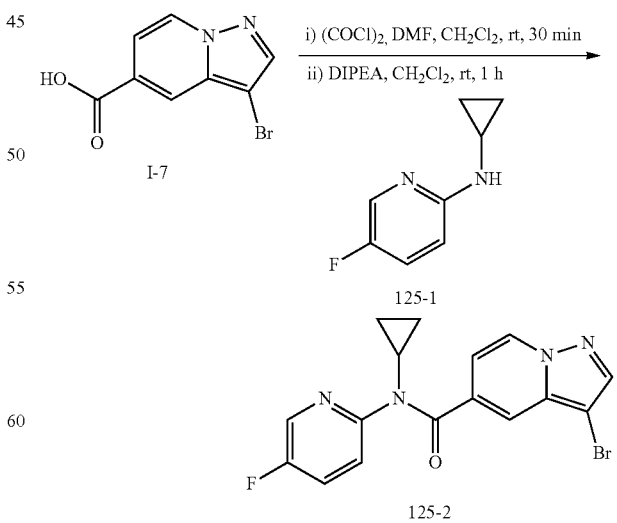

Compound 125-2 was prepared using the general procedure described in Amide Coupling-Method 1 with the appropriate starting materials. Yield 19% (over two steps). Off white solid. $^1$H NMR (400 MHz, DMSO-$d_6$): δ 8.66 (d, J=7.6 Hz, 1H), 8.39 (d, J=3.2 Hz, 1H), 8.19 (s, 1H), 7.79 (td, J=3.6, 8.8 Hz, 1H), 7.56 (dd, J=4.4, 8.8 Hz, 1H), 7.50 (s, 1H), 6.88 (dd, J=1.6, 7.6 Hz, 1H), 3.18-3.31 (m, 1H), 0.79-0.85 (m, 2H), 0.62-0.66 (m, 2H). ESI-LC/MS: m/z 377.2 [(M+2)+H]; $R_t$=2.44 min [Agilent LC with Ion trap Detector; Waters Symmetry C18, 3.5 µm, 4.6×75 mm column; gradient of 90:10 $H_2O$ (0.1% HCOOH):$CH_3CN$ (0.1% HCOOH) to 10:90 $H_2O$ (0.1% HCOOH):$CH_3CN$ (0.1% HCOOH) in 4 min and hold for 3 min with flow rate of 1.0 mL/min].

Step 3

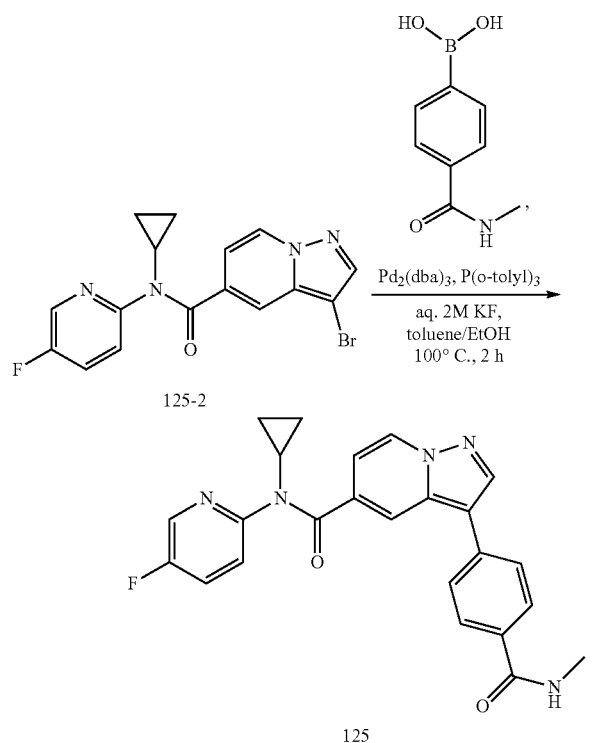

125

Compound 125 was prepared using the general procedure described in Suzuki Procedure H with the appropriate starting materials. Yield 35%. Yellow solid. $^1$H-NMR (400 MHz, DMSO-$d_6$): δ 8.70 (d, J=7.1 Hz, 1H), 8.44-8.49 (m, 3H), 7.94 (d, J=8.4 Hz, 2H), 7.80-7.87 (m, 2H), 7.57-7.64 (m, 3H), 6.93 (d, J=7.4 Hz, 1H), 3.21-3.24 (m, 1H), 2.82 (d, J=3.9 Hz, 3H), 0.80-0.85 (m, 2H), 0.63-0.67 (m, 2H). ESI-LC/MS: m/z 430.24 (M+H); $R_t$=2.21 min [Waters Acquity UPLC with Quattro micro TQD; Waters Acquity BEH C18, 1.7 µm, 2.1×50 mm column; gradient of 90:10 $H_2O$ (0.025% TFA):$CH_3CN$ (0.025% TFA) hold for 0.5 min to 10:90 $H_2O$ (0.025% TFA):$CH_3CN$ (0.025% TFA) in 2.5 min and hold for 2 min with flow rate of 0.4 mL/min]. HPLC purity: 96.4% at 254 nm; $R_t$=2.00 min [Waters Acquity UPLC with PDA detector; Waters Acquity BEH C18, 1.7 µm, 2.1×100 mm column; gradient of 70:30 $H_2O$ (0.025% TFA):$CH_3CN$ (0.025% TFA) to 20:80 $H_2O$ (0.025% TFA):$CH_3CN$ (0.025% TFA) in 4 min and hold for 2 min with flow rate of 0.3 mL/min].

Example 126

N-(5-Cyanopyridin-2-yl)-N-cyclopentyl-3-(4-(methylcarbamoyl)phenyl)pyrazolo[1,5-a]pyridine-5-carboxamide Step 1

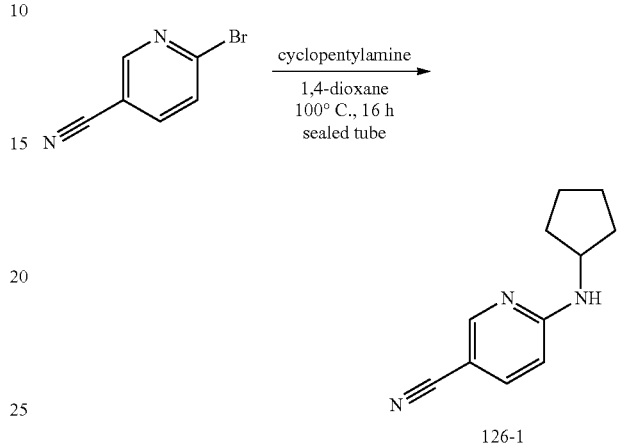

A solution mixture of 2-bromo-5-cyanopyridine (2.0 g, 10.92 mmol), cyclopentylamine (2.17 mL, 21.99 mmol) in dioxane (20 mL) was stirred at 100° C. for 16 h. The reaction mixture was partitioned between water (100 mL) and ethyl acetate (100 mL). The ethyl acetate was washed with brine (100 mL), dried over anhydrous $Na_2SO_4$ and concentrated. The crude compound was passed through silica-gel (100-200 mesh) to afford 1.9 g (93%) of 6-(cyclopentylamino) nicotinonitrile 126-1 as an off-white solid. $^1$H NMR (400 MHz, DMSO-$d_6$): δ 8.37 (d, J=1.8 Hz, 1H), 7.59-7.61 (m, 2H), 6.51 (d, J=8.8 Hz, 1H), 4.17 (br.s, 1H), 1.87-1.93 (m, 2H), 1.60-1.69 (m, 2H), 1.53-1.59 (m, 2H), 1.40-1.45 (m, 2H). ESI-LC/MS: m/z 188.18 (M+H); $R_t$=2.11 min [Waters Acquity UPLC with Quattro micro TQD; Waters Acquity BEH C18, 1.7 µm, 2.1×50 mm column; gradient of 90:10 $H_2O$ (0.025% TFA):$CH_3CN$ (0.025% TFA) hold for 0.5 min to 10:90 $H_2O$ (0.025% TFA):$CH_3CN$ (0.025% TFA) in 2.5 min and hold for 2 min with flow rate of 0.4 mL/min].

Step 2

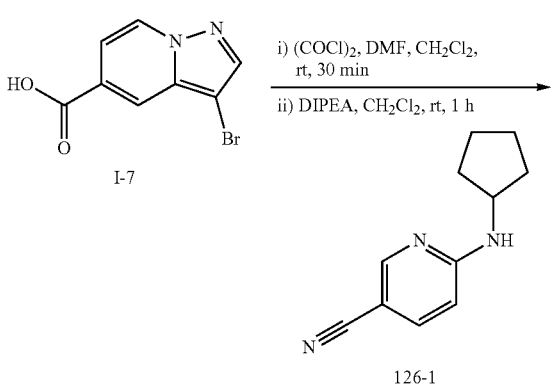

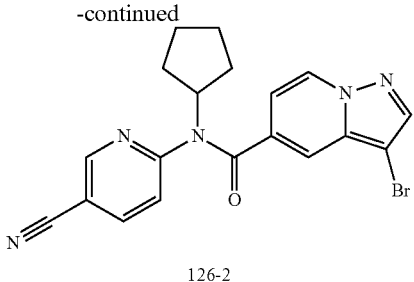

126-2

Compound 126-2 was prepared using the general procedure described in Amide Coupling-Method 1 with the appropriate starting materials. Yield 59%). Pale brown solid. $^1$H NMR (400 MHz, DMSO-$d_6$): δ 8.92 (d, J=1.8 Hz, 1H), 8.61 (d, J=7.5 Hz, 1H), 8.24 (dd, J=2.2, 8.4 Hz, 1H), 8.20 (s, 1H), 7.55 (d, J=8.3 Hz, 1H), 7.38 (s, 1H), 6.71 (dd, J=1.8, 7.5 Hz, 1H), 4.87-4.91 (m, 1H), 1.84-1.95 (m, 2H), 1.77-1.81 (m, 2H), 1.52-1.75 (m, 4H). ESI-LC/MS: m/z 410.06 (M+H) & 412.11 [(M+2)+H]; $R_t$=2.44 min [Waters Acquity UPLC with Quattro micro TQD; Waters Acquity BEH C18, 1.7 μm, 2.1×50 mm column; gradient of 90:10 H$_2$O (0.025% TFA):CH$_3$CN (0.025% TFA) hold for 0.5 min to 10:90 H$_2$O (0.025% TFA):CH$_3$CN (0.025% TFA) in 2.5 min and hold for 2 min with flow rate of 0.4 mL/min].

Step 3

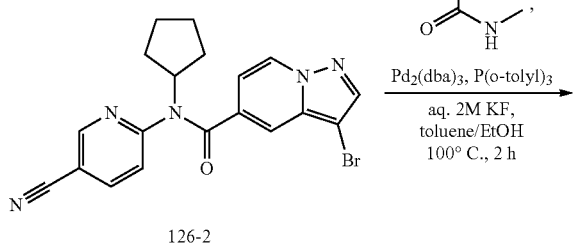

126

Compound 126 was prepared using the general procedure described in Suzuki Procedure H with the appropriate starting materials. Yield 21%. Yellow solid. $^1$H-NMR (400 MHz, DMSO-$d_6$): δ 8.98 (d, J=2.2 Hz, 1H), 8.64 (d, J=7.0 Hz, 1H), 8.48-8.50 (m, 2H), 8.27 (dd, J=2.2, 8.3 Hz, 1H), 7.94 (d, J=8.3 Hz, 2H), 7.77 (s, 1H), 7.54-7.60 (m, 3H), 6.73 (dd, J=1.8, 7.5 Hz, 1H), 4.90-4.96 (m, 1H), 2.83 (d, J=4.4 Hz, 3H), 1.95-1.97 (m, 2H), 1.79-1.83 (m, 2H), 1.53-1.77 (m, 4H). ESI-LC/MS: m/z 465.26 (M+H); $R_t$=2.58 min [Waters Acquity UPLC with Quattro micro TQD; Waters Acquity BEH C18, 1.7 μm, 2.1×50 mm column; gradient of 90:10 H$_2$O (0.025% TFA):CH$_3$CN (0.025% TFA) hold for 0.5 min to 10:90 H$_2$O (0.025% TFA):CH$_3$CN (0.025% TFA) in 2.5 min and hold for 2 min with flow rate of 0.4 mL/min]. HPLC purity: 99.3% at 292 nm; $R_t$=1.57 min [Waters Acquity UPLC with PDA detector; Waters Acquity BEH C18, 1.7 μm, 2.1×100 mm column; gradient of 70:30 H$_2$O (0.025% TFA):CH$_3$CN (0.025% TFA) to 20:80 H$_2$O (0.025% TFA): CH$_3$CN (0.025% TFA) in 4 min and hold for 2 min with flow rate of 0.3 mL/min].

Example 127

N-(5-Cyanopyridin-2-yl)-N-cyclopropyl-3-(4-(ethylcarbamoyl)phenyl)pyrazolo[1,5-a]pyridine-5-carboxamide Step 1

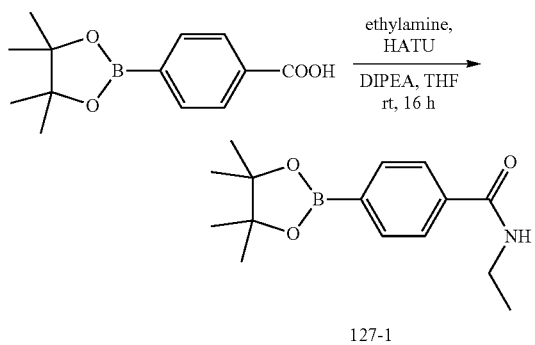

127-1

Compound 127-1 was prepared using the general procedure described in Amide Coupling-Method 2 with the appropriate starting materials. The crude product was used as such for next step without further purification. ESI-LC/MS: m/z 276.1 (M+H); $R_t$=3.86 min [Agilent LC with Ion trap Detector; Waters Xterra C18, 2.5 μm, 4.6×150 mm column; gradient of 80:20 H$_2$O (0.01 M Ammonium bicarbonate): CH$_3$CN to 10:90 H$_2$O (0.01 M Ammonium bicarbonate): CH$_3$CN in 4 min and hold for 3 min with flow rate of 1.0 mL/min].

Step 2

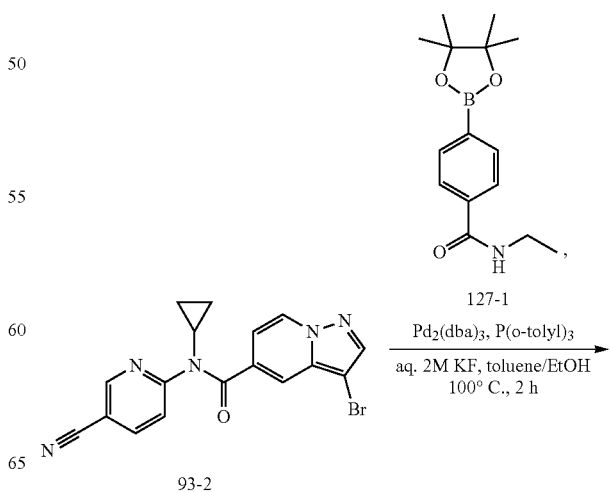

93-2

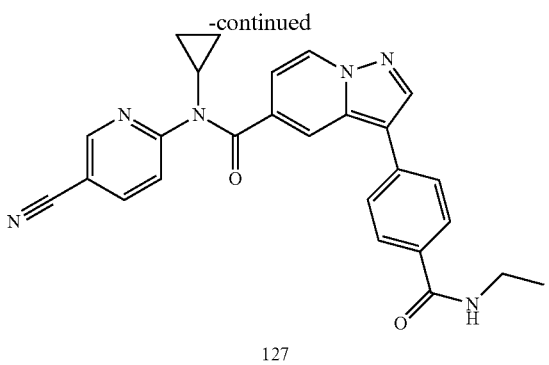

127

Compound 127 was prepared using the general procedure described in Suzuki Procedure H with the appropriate starting materials. Yield 1.3% (over two steps). Yellow solid. $^1$H NMR (400 MHz, DMSO-$d_6$): δ 8.83 (d, J=2.2 Hz, 1H), 8.73 (d, J=7.0 Hz, 1H), 8.48-8.54 (m, 2H), 8.36 (dd, J=2.2, 8.8 Hz, 1H), 8.03 (brs, 1H), 7.93 (d, J=8.3 Hz, 2H), 7.81 (d, J=8.3 Hz, 1H), 7.66 (d, J=8.4 Hz, 2H), 6.99 (dd, J=1.8, 7.5 Hz, 1H), 3.24-3.30 (m, 1H) 3.32 (m, 2H), 1.14 (t, J=1.7 Hz, 3H), 0.88-0.92 (m, 2H), 0.63-0.67 (m, 2H). ESI-LC/MS: m/z 451.29 (M+H); $R_t$=2.38 min [Waters Acquity UPLC with Quattro micro TQD; Waters Acquity BEH C18, 1.7 μm, 2.1×50 mm column; gradient of 90:10 H$_2$O (0.025% TFA):CH$_3$CN (0.025% TFA) hold for 0.5 min to 10:90 H$_2$O (0.025% TFA):CH$_3$CN (0.025% TFA) in 2.5 min and hold for 2 min with flow rate of 0.4 mL/min]. HPLC purity=97% at 214 nm; $R_t$=1.27 min [Waters Acquity UPLC with PDA detector; Waters Acquity BEH C18, 1.7 μm, 2.1×100 mm column; gradient of 50:50 H$_2$O (0.025% TFA):CH$_3$CN (0.025% TFA) to 20:80 H$_2$O (0.025% TFA):CH$_3$CN (0.025% TFA) in 4 min and hold for 2 min with flow rate of 0.3 mL/min].

Example 128

6-(N-Cyclopropyl-3-(4-(methylcarbamoyl)phenyl) pyrazolo[1,5-a]pyridine-5-carboxamido) nicotinic acid Step 1

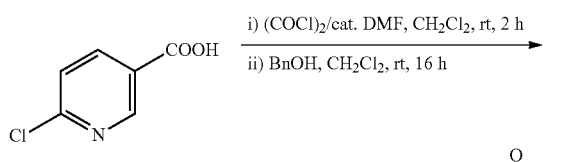

To a solution of 6-chloronicotinic acid (2.0 g, 12.69 mmol) in dichloromethane (20 mL) was added oxalyl chloride (2.0 mL, 23.27 mmol) followed by catalytic amount N,N-dimethylformamide at rt and stirred for 2 h. The resultant volatiles were distilled-off under reduced pressure to afford residue of acid chloride. The acid chloride was dissolved in dichloromethane (20 mL), and was added benzyl alcohol (1.44 mL, 13.92 mmol). The resulting reaction mixture was stirred for overnight at rt. The reaction mixture was diluted with dichloromethane (100 mL), washed with water (50 mL), brine (25 mL), dried over anhydrous Na$_2$SO$_4$ and concentrated. The crude compound was purified by column chromatography over silica-gel (100-200 mesh) with a gradient mixture of 10% ethyl acetate in pet-ether to afford 1.2 g (crude) of benzyl 6-chloronicotinate 128-1 as an off-white solid. The crude product was used as such for next step without further purification. ESI-LC/MS: m/z 248.4 (M+H); $R_t$=5.12 min [Agilent LC with Ion trap Detector; Symmetry C18, 3.5 μm, 4.6×75 mm column; gradient of 80:20 H$_2$O (1% HCOOH):CH$_3$CN (0.1% HCOOH) to 10:90 H$_2$O (0.1% HCOOH):CH$_3$CN (0.1% HCOOH) in 4.0 min and hold for 3.0 min with flow rate of 1.0 mL/min].

Step 2

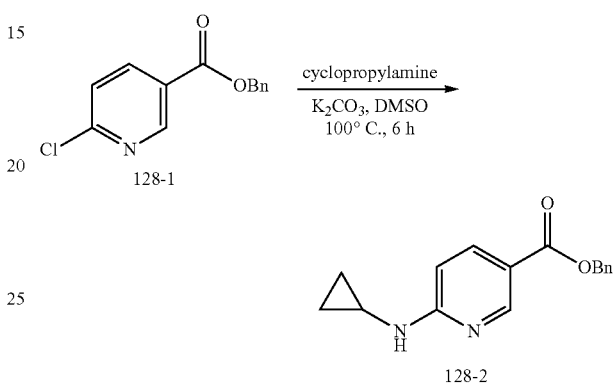

A solution mixture of benzyl 6-chloronicotinate 128-1 (1.20 g, 4.84 mmol), cyclopropylamine (0.68 mL, 9.83 mmol) and K$_2$CO$_3$ (1.34 g, 9.71 mmol) in DMSO (12 mL) was stirred at 100° C. for 6 h. The reaction mixture was partitioned between water (150 mL) and ethyl acetate (100 mL). The ethyl acetate layer was washed with brine (100 mL), dried over anhydrous Na$_2$SO$_4$ and concentrated. The crude compound was purified by column chromatography over silica-gel (100-200 mesh) using a solvent gradient mixture of 10% ethyl acetate in chloroform as eluant to afford (700 mg, 20% over two steps) benzyl 6-(cyclopropylamino)nicotinate 128-2 as an off-white solid. $^1$H NMR (400 MHz, DMSO-$d_6$): δ 8.62 (s, 1H), 7.93 (d, J=7.9 Hz, 1H), 7.69 (s, 1H), 7.25-7.50 (m, 5H), 6.62 (d, J=7.9 Hz, 1H), 5.28 (s, 2H), 2.60 (br.s, 1H), 0.66-0.80 (m, 2H), 0.40-0.51 (m, 2H). ESI-LC/MS: m/z 269.14 (M+H); $R_t$=2.07 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.0 min and hold for 2.0 min with flow rate of 0.4 mL/min].

Step 3

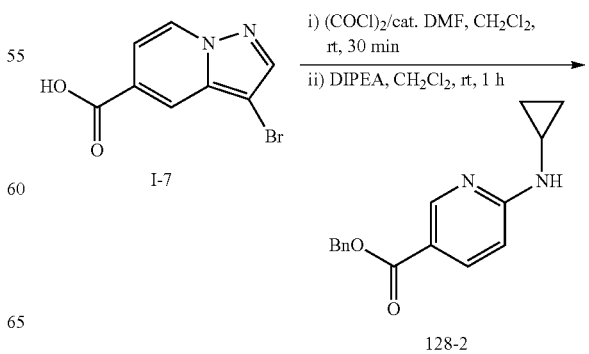

-continued

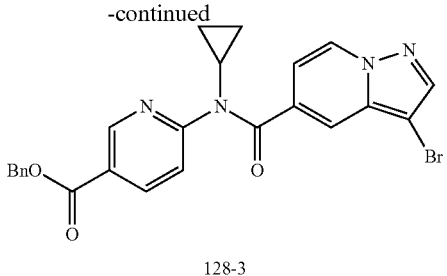

128-3

Compound 128-3 was prepared using the general procedure described in Amide Coupling-Method 1 with the appropriate starting materials. Yield 36%. Off-white solid. ESI-LC/MS: m/z 493.02 [(M+2)+H]; $R_t$=3.32 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.0 min and hold for 2.0 min with flow rate of 0.4 mL/min].

Step 4

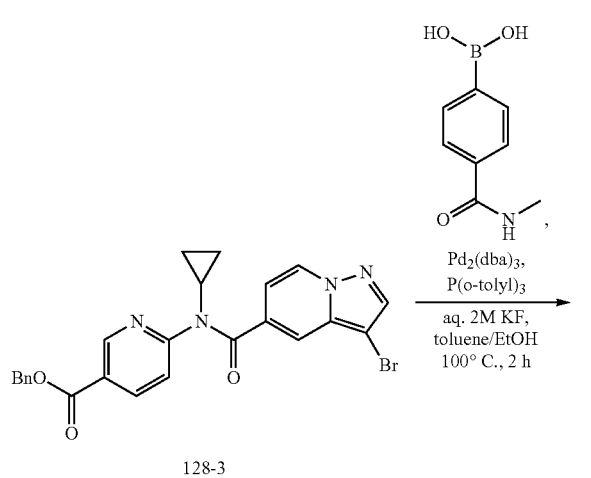

128-3

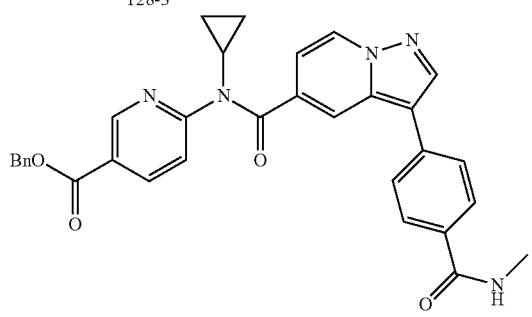

128-4

Compound 128-4 was prepared using the general procedure described in Suzuki Procedure H with the appropriate starting materials. Yield 45%. Yellow solid. $^1$H NMR (400 MHz, DMSO-d$_6$): δ 8.90 (d, J=2.2 Hz, 1H), 8.71 (d, J=7.4 Hz, 1H), 8.42-8.55 (m, 2H), 8.37 (dd, J=2.2, 8.4 Hz, 1H), 7.86-8.00 (m, 3H), 7.72 (d, J=8.4 Hz, 1H), 7.62 (d, J=7.9 Hz, 2H), 7.34-7.50 (m, 5H), 6.97 (dd, J=1.3, 7.4 Hz, 1H), 5.33 (s, 2H), 3.20-3.25 (m, 1H), 2.81 (d, J=4.4 Hz, 3H), 0.82-0.92 (m, 2H), 0.63-0.67 (m, 2H). ESI-LC/MS: m/z 546.18 (M+H); $R_t$=2.88 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.0 min and hold for 2.0 min with flow rate of 0.4 mL/min].

Step 5

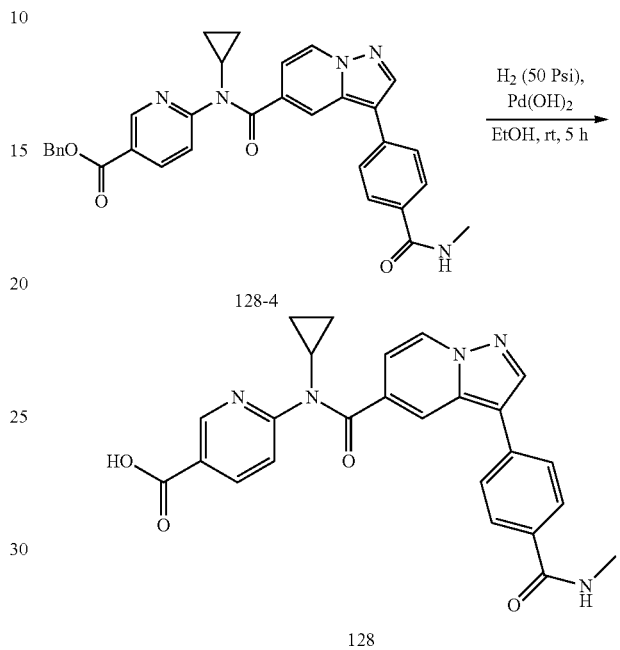

A suspension of benzyl6-(N-cyclopropyl-3-(4-(methylcarbamoyl)phenyl)pyrazolo[1,5-a]pyridine-5-carboxamido)nicotinate 128-4 (200 mg, 0.366 mmol) and Pd(OH)$_2$ (40 mg, 20% w/w) in ethanol (4.0 mL) was hydrogenated in Parr hydrogenation at 50 psi of H$_2$ gas pressure for 5 h at rt. The reaction mixture was filtered through celite, washed the bed with ethanol, and then distilled off the solvent under reduced pressure. The crude compound was purified by column chromatography over silica gel (100-200 mesh) using a solvent gradient of 5-10% methanol in chloroform as eluant to afford 50 mg (30%) of 6-(N-cyclopropyl-3-(4-(methylcarbamoyl)phenyl)pyrazolo[1,5-a]pyridine-5-carboxamido)nicotinic acid 128 as a yellow solid. $^1$H NMR (400 MHz, DMSO-d$_6$): δ 8.81 (s, 1H), 8.69 (d, J=7.7 Hz, 1H), 8.50-8.56 (m, 1H), 8.48 (s, 1H), 8.24 (d, J=7.9 Hz, 1H), 7.91 (d, J=7.9 Hz, 2H), 7.83 (br.s, 1H), 7.52-7.58 (m, 3H), 6.95 (d, J=7.0 Hz, 1H), 3.20-3.27 (m, 1H), 2.81 (d, J=4.4 Hz, 3H), 0.83-0.88 (m, 2H), 0.62-0.68 (m, 2H). ESI-LC/MS: m/z 456.16 (M+H); $R_t$=1.94 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.0 min and hold for 2.0 min with flow rate of 0.4 mL/min]. HPLC purity=97.9% at 285 nm; $R_t$=1.57 min [Waters Acquity UPLC with PDA; Waters Acquity BEH C18, 1.7 μm, 2.1×100 mm column; gradient of 70:30 H$_2$O (0.025% TFA):CH$_3$CN (0.025% TFA) to 20:80 H$_2$O (0.025% TFA):CH$_3$CN (0.025% TFA) in 4.0 min and hold for 2.0 min with flow rate of 0.3 mL/min].

Example 129

N-(5-Carbamoylpyridin-2-yl)-N-cyclopropyl-3-(4-(methylcarbamoyl)phenyl)pyrazolo[1,5-a]pyridine-5-carboxamide

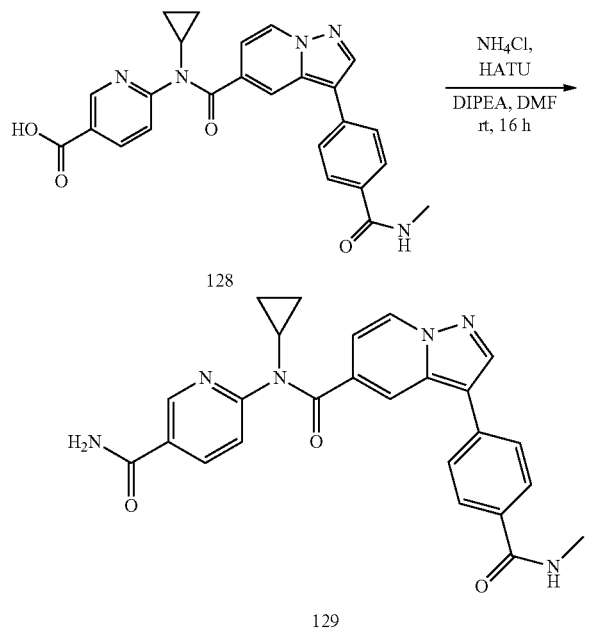

A suspension of 6-(N-cyclopropyl-3-(4-(methylcarbamoyl)phenyl)pyrazolo[1,5-a]pyridine-5-carboxamido)nicotinic acid 128 (200 mg, 0.439 mmol), NH$_4$Cl (200 mg 3.739 mmol), HATU (183 mg, 0.481 mmol) and DIPEA (0.337 mL, 1.938 mmol) in DMF (6.0 mL) was stirred at rt for 16 h. The reaction mixture was diluted with water (75 mL) and extracted with ethyl acetate (3×30 mL). The combined organic layer was washed with brine (25 mL), dried over anhydrous Na$_2$SO$_4$ and concentrated. The crude compound was purified by pre-TLC and then prep-HPLC to afford (70 mg, 35%) of N-(5-carbamoylpyridin-2-A-N-cyclopropyl-3-(4-(methylcarbamoyl)phenyl)pyrazolo[1,5-a]pyridine-5-carboxamide 129 as a yellow solid. $^1$H NMR (400 MHz, DMSO-d$_6$): δ 8.81 (d, J=2.2 Hz, 1H), 8.70 (d, J=7.4 Hz, 1H), 8.45-8.54 (m, 2H), 8.26 (dd, J=2.2, 8.4 Hz, 1H), 8.11 (s, 1H), 7.89-7.96 (m, 3H), 7.56-7.65 (m, 4H), 6.94 (dd, J=1.7 Hz, 7.5 Hz, 1H), 3.22-3.29 (m, 1H), 2.81 (d, J=4.4 Hz, 3H), 0.85-0.90 (m, 2H), 0.64-0.68 (m, 2H). ESI-LC/MS: m/z 455.23 (M+H); R$_t$=1.82 min [Waters Acquity UPLC with Quattro-micro detector; Waters Acquity BEH C18, 1.7 µm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.0 min and hold for 2.0 min with flow rate of 0.4 mL/min]. HPLC purity=>99% at 254 nm; R$_t$=2.30 min [Waters Acquity UPLC with PDA; Waters Acquity BEH C18, 1.7 µm, 2.1×100 mm column; gradient of 90:10 H$_2$O (0.025% TFA):CH$_3$CN (0.025% TFA) to 20:80 H$_2$O (0.025% TFA):CH$_3$CN (0.025% TFA) in 4.0 min and hold for 2.0 min with flow rate of 0.3 mL/min].

Example 130

N-Cyclopropyl-N-(3,4-difluorophenyl)-3-(4-(methylcarbamoyl)phenyl)pyrazolo[1,5-a]pyridine-5-carboxamide Step 1

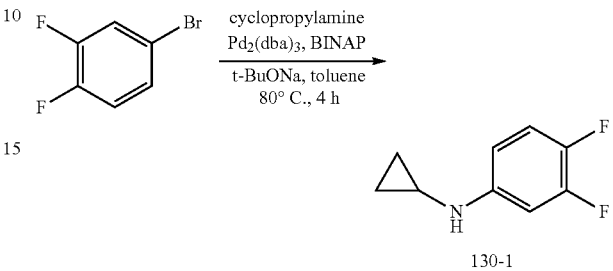

A solution mixture of 1-bromo-3,4-difluorobenzene (2 g, 10.362 mmol) and t-BuONa (1.5 g, 15.62 mmol) in toluene (20 mL) was degassed with argon for about 10 min. Pd$_2$(dba)$_3$ (95 mg, 0.103 mmol), BINAP (194 mg, 0.311 mmol), cyclopropylamine (1.18 mL, 17.05 mmol) were added under argon atmosphere and sealed the reaction vessel. The resulting reaction mixture was maintained at 80° C. for 4 h. The reaction mixture was coiled to room temperature and partitioned between ethyl acetate (2×100 mL) and water (100 mL). The combined organic layer was washed with water, brine solution, dried over anhydrous Na$_2$SO$_4$ and concentrated to afford 2 g (quantitative) of N-cyclopropyl-3,4-difluoroaniline 130-1 as a thick brown liquid. The crude material was used further without purification. ESI-LC/MS: m/z 170.13 (M+H); R$_t$=2.99 min [Waters Acquity UPLC with Quattro-micro detector; Waters Acquity BEH C18, 1.7 µm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.0 min and hold for 2.0 min with flow rate of 0.4 mL/min].

Step 2

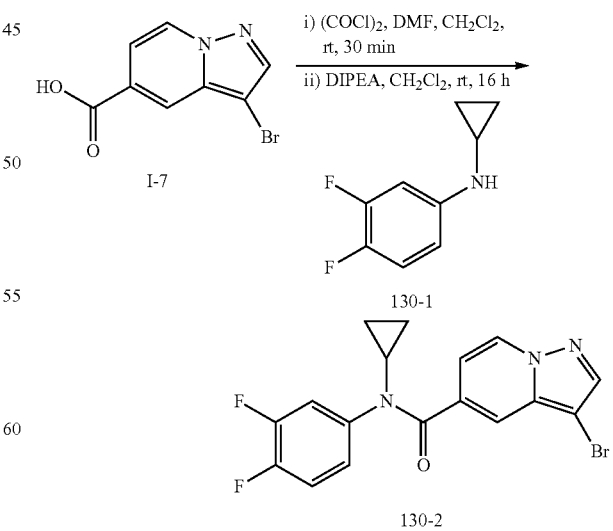

Compound 130-2 was prepared using the general procedure described in Amide Coupling-Method 1 with the appropriate starting materials. Yield 7.4% (over two steps). Pale yellow solid. $^1$H NMR (400 MHz, CDCl$_3$): δ 8.29 (d, J=7.4 Hz, 1H), 7.99 (s, 1H), 7.60 (s, 1H), 7.04-7.14 (m, 2H), 6.87-6.89 (m, 1H) 6.75 (d, J=7.4 Hz, 1H), 3.22-3.25 (m, 1H), 0.92-0.95 (m, 2H), 0.61-0.63 (m, 2H). ESI-LC/MS: m/z 392.06 (M+H) & 394.04 [(M+2)H+]; R$_t$=3.06 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.0 min and hold for 2.0 min with flow rate of 0.4 mL/min].

Step 3

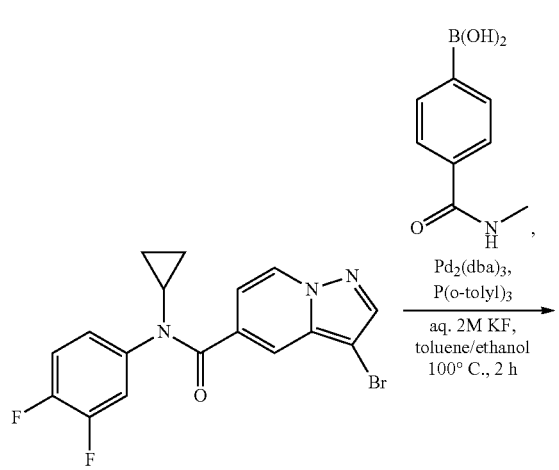

Compound 130 was prepared using the general procedure described in Suzuki Procedure H with the appropriate starting materials. Yield 15%. Yellow solid. $^1$H-NMR (400 MHz, DMSO-d$_6$): δ 8.74 (d, J=7.0 Hz, 1H), 8.45-8.51 (m, 2H), 8.06 (s, 1H), 7.94 (d, J=7.9 Hz, 2H), 7.70 (d, J=8.30 Hz, 2H), 7.63-7.67 (m, 1H), 7.41-7.48 (m, 1H), 7.25 (d, J=8.80 Hz, 1H), 7.02 (d, J=6.60 Hz, 1H), 3.26-3.30 (m, 1H), 2.81 (d, J=4.40 Hz, 3H), 0.73-0.78 (m, 2H), 0.55-0.60 (m, 2H). ESI-LC/MS: m/z 447.19 (M+H); R$_t$=2.55 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.0 min and hold for 2.0 min with flow rate of 0.4 mL/min. HPLC purity: 95.4% at 254 nm; R$_t$=2.60 min [Waters Acquity UPLC with PDA; Waters Acquity; UPLC; HSS-T3, 1.7 μm, 2.1×100 mm column; gradient of 70:30 H$_2$O (0.025% TFA):CH$_3$CN (0.025% TFA) to 20:80 H$_2$O (0.025% TFA):CH$_3$CN (0.025% TFA) in 4.0 min and hold for 2.0 min with flow rate of 0.4 mL/min].

Example 131

N-(5-Cyanopyridin-2-yl)-N-cyclopropyl-3-(4-(oxetan-3-ylcarbamoyl)phenyl)pyrazolo[1,5-a]pyridine-5-carboxamide Step 1

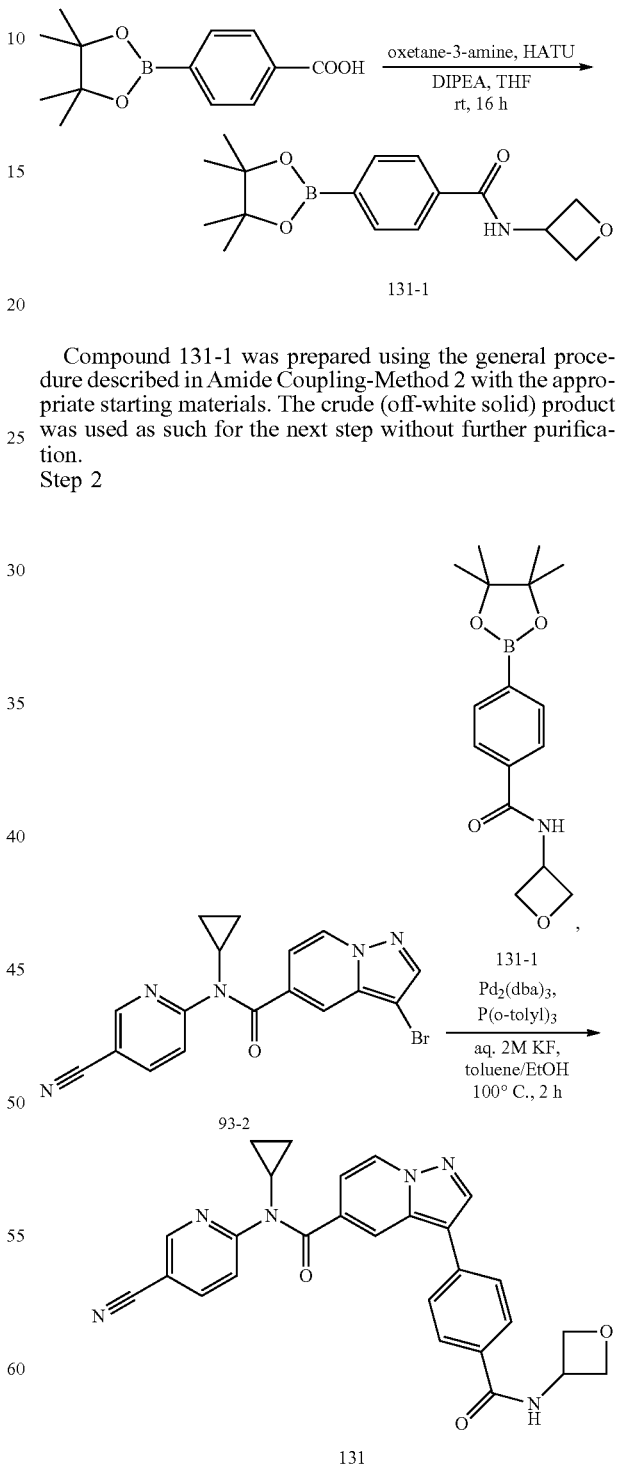

Compound 131-1 was prepared using the general procedure described in Amide Coupling-Method 2 with the appropriate starting materials. The crude (off-white solid) product was used as such for the next step without further purification.

Step 2

Compound 131 was prepared using the general procedure described in Suzuki Procedure H with the appropriate starting materials. Yield 4% (over two steps). Yellow solid. $^1$H NMR (400 MHz, DMSO-d$_6$): δ9.14 (d, J=6.2 Hz, 1H), 8.83 (d, J=2.2 Hz, 1H), 8.75 (d, J=7.4 Hz, 1H), 8.55 (brs, 1H), 8.36 (dd, J=2.2, 8.8 Hz, 1H), 8.05 (brs, 1H), 7.98 (d, J=7.9 Hz, 2H), 7.82 (d, J=8.3 Hz, 1H), 7.70 (d, J=8.3 Hz, 2H), 7.01 (d, J=7.0 Hz, 1H), 5.01-5.06 (m, 1H), 4.79 (t, J=6.6 Hz, 2H), 4.62 (t, J=6.2 Hz, 2H), 3.23-3.29 (m, 1H), 0.88-0.92 (m, 2H), 0.62-0.65 (m, 2H). ESI-LC/MS: m/z 479.24 (M+H); R$_t$=2.22 min [Waters Acquity UPLC with Quattro micro TQD; Waters Acquity BEH C18, 1.7 µm, 2.1×50 mm column; gradient of 90:10 H$_2$O (0.025% TFA):CH$_3$CN (0.025% TFA) hold for 0.5 min to 10:90 H$_2$O (0.025% TFA):CH$_3$CN (0.025% TFA) in 2.5 min and hold for 2 min with flow rate of 0.4 mL/min]. HPLC purity=98.9% at 214 nm; R$_t$=1.90 min [Waters Acquity UPLC with PDA detector; Waters Acquity HSS T3, 1.7 µm, 2.1×100 mm column; gradient of 70:30 H$_2$O (0.025% TFA):CH$_3$CN (0.025% TFA) to 20:80 H$_2$O (0.025% TFA):CH$_3$CN (0.025% TFA) in 4 min and hold for 2 min with flow rate of 0.4 mL/min].

Example 132

N-Cyclopropyl-3-(4-(methylcarbamoyl)phenyl)-N-(5-(trifluoromethyl)pyridin-2-yl)pyrazolo[1,5-a]pyridine-5-carboxamide Step 1

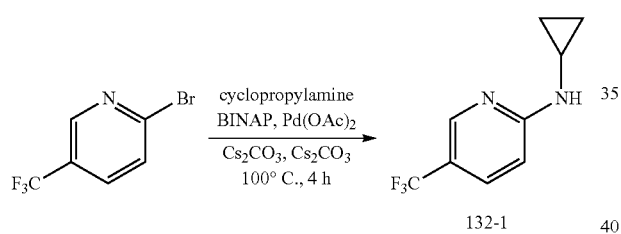

A solution of 2-bromo-5-trifluoromethylpyridine (500 mg, 2.21 mmol) and Cs$_2$CO$_3$ (216 mg, 0.662 mmol) in 1,4-dioxane (5 mL) was degassed with argon for about 10 min. Pd(OAc)$_2$ (29 mg, 0.129 mmol), BINAP (55 mg, 0.883 mmol) and cyclopropylamine (0.18 mL, 2.60 mmol) were added under argon atmosphere. The resulting reaction mixture was maintained at 100° C. for 4 h. The reaction mixture was diluted with water (1×50 mL) and extracted with ethyl acetate (2×100 mL). The combined organic layer was washed with water, brine solution, dried over Na$_2$SO$_4$ and concentrated. The crude product was passed through a column of silica-gel (100-200 mesh) using a solvent gradient mixture of 15% ethyl acetate in pet-ether to afford 200 mg (11%) of N-cyclopropyl-5-(trifluoromethyl)pyridin-2-amine 132-1 as a yellow solid. $^1$H NMR (400 MHz, CDCl$_3$): 8.37 (s, 1H), 7.66-7.68 (m, 1H), 6.77 (d, J=8.8 Hz, 1H), 5.33 (brs, 1H), 2.55-2.60 (m, 1H), 0.83-0.87 (m, 2H), 0.58-0.65 (m, 2H); ESI-LC/MS: m/z 203.3 (M+H); R$_t$=2.87 min [Agilent LC with Ion trap Detector; Waters Symmetry C18, 3.5 µm, 4.6×75 mm column; gradient of 80:20 H$_2$O (0.1% HCOOH):CH$_3$CN (0.1% HCOOH) hold for 1 min to 10:90 H$_2$O (0.1% HCOOH):CH$_3$CN (0.1% HCOOH) in 4 min and hold for 3 min with flow rate of 1.0 mL/min]

Step 2

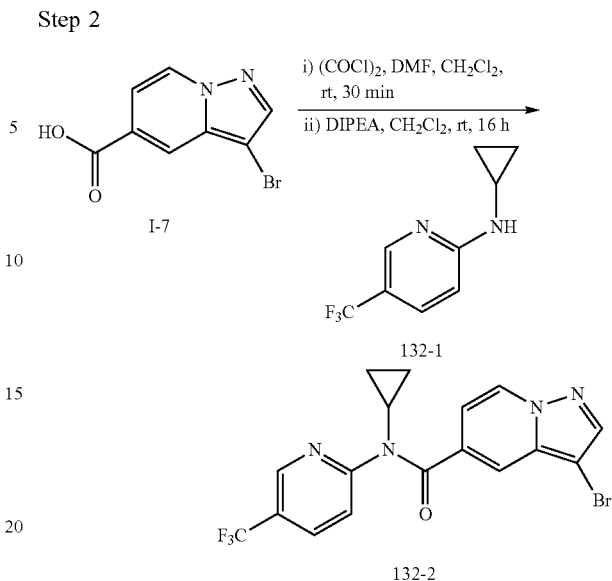

Compound 132-2 was prepared using the general procedure described in Amide Coupling-Method 1 with the appropriate starting materials. The crude product (250 mg) was used as such for the next step without further purification. ESI-LC/MS: m/z 425.03 (M+H) & 427.01 [(M+2)+H]; R$_t$=3.09 min [Waters Acquity UPLC with Quattro micro TQD; Waters Acquity BEH C18, 1.7 µm, 2.1×50 mm column; gradient of 90:10 H$_2$O (0.025% TFA):CH$_3$CN (0.025% TFA) hold for 0.5 min to 10:90 H$_2$O (0.025% TFA):CH$_3$CN (0.025% TFA) in 2.5 min and hold for 2 min with flow rate of 0.4 mL/min]

Step 3

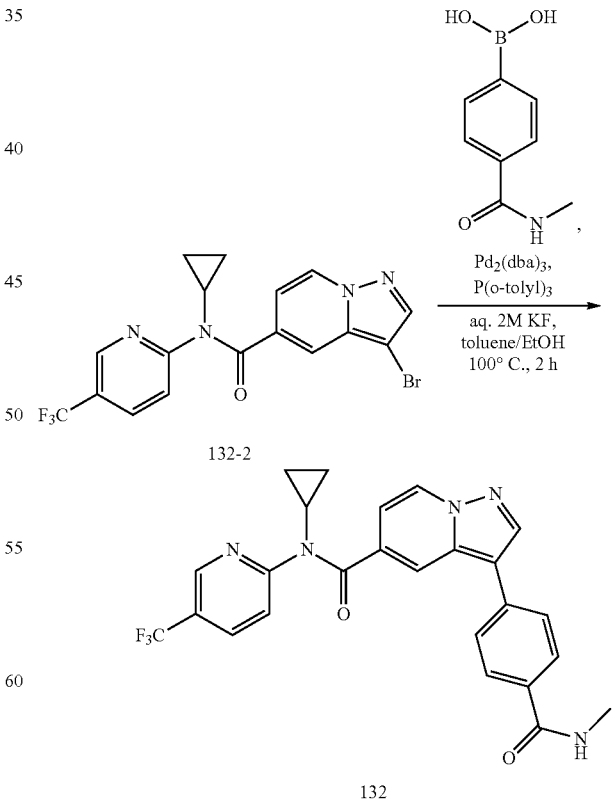

Compound 132 was prepared using the general procedure described in Suzuki Procedure H with the appropriate starting materials. Yield 3.7% (over two steps). Yellow solid. ¹H-NMR (DMSO-d$_6$): δ 8.80 (s, 1H), 8.74 (d, J=7.0 Hz, 1H), 8.51 (s, 1H), 8.46-8.48 (m, 1H), 8.31 (d, J=8.8 Hz, 1H), 7.96 (s, 1H), 7.92 (d, J=8.40 Hz, 2H), 7.80 (d, J=8.40 Hz, 1H), 7.60 (d, J=8.30 Hz, 2H), 7.02 (d, J=7.1 Hz, 1H), 3.28-3.34 (m, 1H), 2.81 (d, J=4.40 Hz, 3H), 0.86-0.91 (m, 2H), 0.63-0.65 (m, 2H). ESI-LC/MS: m/z 480.23 (M+H); R$_t$=2.55 min [Waters Acquity UPLC with Quattro micro TQD; Waters Acquity BEH C18, 1.7 μm, 2.1×50 mm column; gradient of 90:10 H$_2$O (0.025% TFA):CH$_3$CN (0.025% TFA) hold for 0.5 min to 10:90 H$_2$O (0.025% TFA):CH$_3$CN (0.025% TFA) in 2.5 min and hold for 2 min with flow rate of 0.4 mL/min]. HPLC purity: 99.0% at 292 nm; R$_t$=2.61 min [Waters Acquity UPLC with PDA detector; Waters Acquity HSS T3, 1.7 μm, 2.1×100 mm column; gradient of 70:30 H$_2$O (0.025% TFA):CH$_3$CN (0.025% TFA) to 20:80 H$_2$O (0.025% TFA):CH$_3$CN (0.025% TFA) in 4 min and hold for 2 min with flow rate of 0.4 mL/min].

Example 133

N-(5-Cyanopyridin-2-yl)-N-cyclopropyl-3-(5-(methylcarbamoyl)pyridin-2-yl)pyrazolo[1,5-a]pyridine-5-carboxamide Step 1

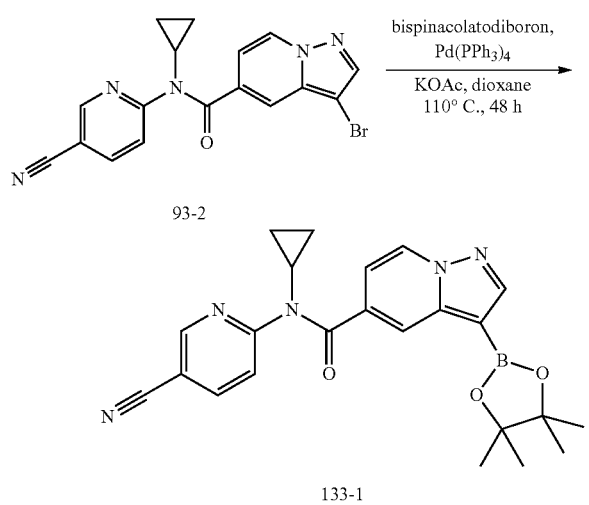

A solution mixture of 3-bromo-N-(5-cyanopyridin-2-yl)-N-cyclopropylpyrazolo[1,5-a]pyridine-5-carboxamide 93-2 (1.0 g, 2.617 mmol), bis(pinacolato)diboron (3.33 g, 13.110 mmol) and KOAc (900 mg, 9.183 mmol) in dioxane (80.0 mL) were taken in to a seal tube and degassed with argon for about 30 min. Then added Pd(PPh$_3$)$_4$ (727 mg, 0.629 mmol) and the reaction mixture was maintained at 110° C. for 48 h. The reaction mixture was filtered through celite and washed with ethyl acetate (100 mL). The filtrate was washed with water (50 ml), brine (50 mL), dried over anhydrous Na$_2$SO$_4$ and concentrated in vacuo to obtain 1.7 g (crude) of N-(5-cyanopyridin-2-yl)-N-cyclopropyl-3-(4,4,5,5-tetramethyl-1,3,2-dioxaborolan-2-yl)pyrazolo[1,5-a]pyridine-5-carboxamide 131-1 as a brown semi solid. The crude product was used as such for the next step without further purification. ESI-LC/MS: m/z 430.31 (M+H); R$_t$=2.93 min [Waters Acquity UPLC with Quattro micro TQD; Waters Acquity BEH C18, 1.7 μm, 2.1×50 mm column; gradient of 90:10 H$_2$O (0.025% TFA):CH$_3$CN (0.025% TFA) hold for 0.5 min to 10:90 H$_2$O (0.025% TFA):CH$_3$CN (0.025% TFA) in 2.5 min and hold for 2 min with flow rate of 0.4 mL/min].

Step 2

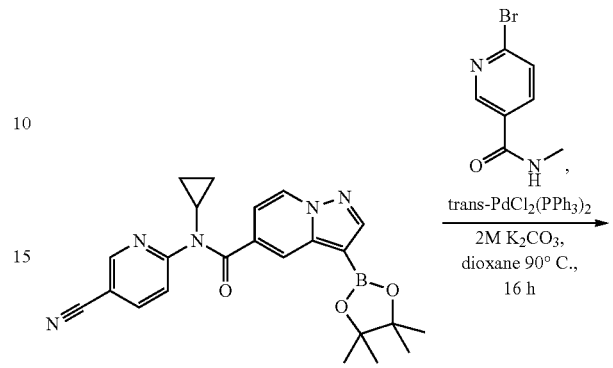

A solution of N-(5-cyanopyridin-2-yl)-N-cyclopropyl-3-(4,4,5,5-tetramethyl-1,3,2-dioxaborolan-2-yl)pyrazolo[1,5-a]pyridine-5-carboxamide 133-1 (900 mg, crude), N-methyl 6-bromonicotinamide (225 mg, 1.046 mmol) and 2M K$_2$CO$_3$ (4.194 mL, 4.194 mmol) in dioxane (80 mL) were degassed with argon for 30 min, added trans-PdCl$_2$(PPh$_3$)$_2$ (140 mg, 0.209 mmol) and stirred at 90° C. in sealed tube for 16 h. Reaction mixture was filtered through celite and washed the celite bed with ethyl acetate (100 mL). The combined filtrate was evaporated and the residue was purified by column chromatography over silica-gel (100-200 mesh) using a solvent gradient of 5% methanol in chloroform as eluant to obtain semi-pure product. This semi-pure compound was further purified by prep-HPLC gave 25 mg (1% over two steps) of N-(5-cyanopyridin-2-yl)-N-cyclopropyl-3-(5-(methylcarbamoyl)pyridin-2-yl)pyrazolo[1,5-a]pyridine-5-carboxamide 133 as yellow solid. ¹H-NMR (400 MHz, DMSO-d$_6$): δ 9.03 (d, J=1.7 Hz, 1H), 8.85 (s, 1H), 8.80 (d, J=2 Hz, 1H), 8.64-8.75 (m, 1H), 8.58-8.62 (m, 2H), 8.35 (dd, J=2.2, 8.3 Hz, 1H), 8.19 (dd, J=2.2, 8.4 Hz, 1H), 7.99 (d, J=8.4 Hz, 1H), 7.80 (d, J=8.3 Hz, 1H), 7.03 (dd, J=1.8, 7.1 Hz, 1H), 3.24-3.29 (m, 1H), 2.83 (d, J=4.4 Hz, 3H), 0.90-0.95 (m, 2H), 0.66-0.68 (m, 2H). ESI-LC/MS: m/z 438.29 (M+H); R$_t$=2.25 min [Waters Acquity UPLC with Quattro micro TQD; Waters Acquity BEH C18, 1.7 μm, 2.1×50 mm column; gradient of 90:10 H$_2$O (0.025% TFA):CH$_3$CN (0.025% TFA) hold for 0.5 min to 10:90 H$_2$O (0.025% TFA):CH$_3$CN (0.025% TFA) in 2.5 min and hold for 2 min with flow rate of 0.4 mL/min]. HPLC purity=97.2% at 254 nm; $R_t$=1.94 min [Waters Acquity UPLC with PDA detector; Waters Acquity BEH C18, 1.7 μm, 2.1×100 mm column; gradient of 70:30 H₂O (0.025% TFA):CH₃CN (0.025% TFA) to 20:80 H₂O (0.025% TFA):CH₃CN (0.025% TFA) in 4 min and hold for 2 min with flow rate of 0.3 mL/min].

Example 134

3-(4-carbamoylphenyl)-N-(4-cyanophenyl)-N-cyclopropylpyrazolo[1,5-a]pyridine-5-carboxamide

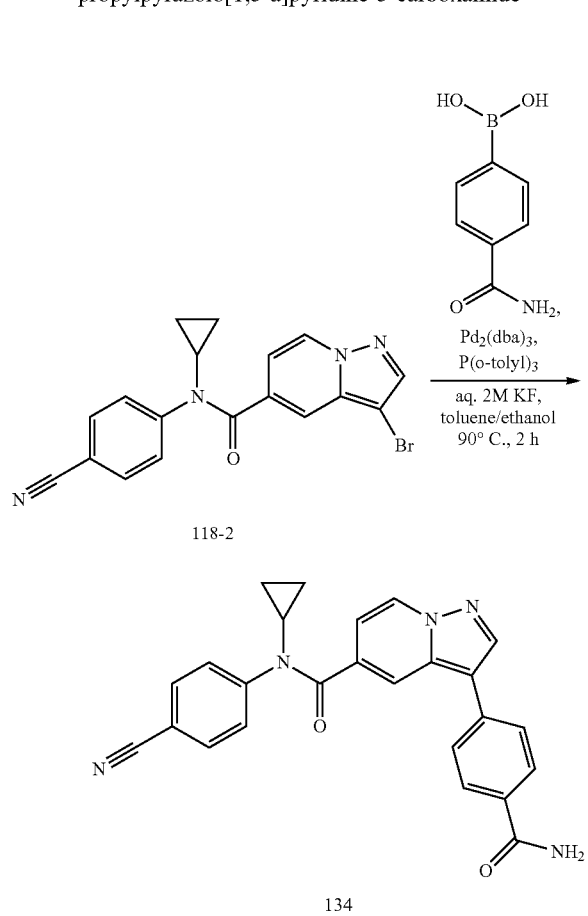

Compound 134 was prepared using the general procedure described in Suzuki Procedure H with the appropriate starting materials. Yield 24%. Yellow solid. ¹H-NMR (400 MHz, DMSO-d₆): δ 8.76 (d, J=7.1 Hz, 1H), 8.52 (s, 1H), 8.04-8.10 (m, 2H), 7.98 (d, J=8.3 Hz, 2H), 7.89 (d, J=8.4 Hz, 2H), 7.63-7.70 (m, 4H), 7.41 (s, 1H), 7.05 (d, J=7.4 Hz, 1H), 3.29 (m, 1H), 0.78-0.80 (m, 2H), 0.52-0.58 (m, 2H). ESI-LC/MS: m/z 422.20 (M+H); $R_t$=2.44 min [Waters Acquity UPLC with Quattro micro TQD; Waters Acquity BEH C18, 1.7 μm, 2.1×50 mm column; gradient of 90:10 H₂O (0.025% TFA):CH₃CN (0.025% TFA) hold for 0.5 min to 10:90 H₂O (0.025% TFA):CH₃CN (0.025% TFA) in 2.5 min and hold for 2 min with flow rate of 0.4 mL/min]. HPLC purity: 98.3% at 254 nm; $R_t$=2.19 min [Waters Acquity UPLC with PDA detector; Waters Acquity BEH C18, 1.7 μm, 2.1×100 mm column; gradient of 70:30 H₂O (0.025% TFA):CH₃CN (0.025% TFA) to 20:80 H₂O (0.025% TFA):CH₃CN (0.025% TFA) in 4 min and hold for 2 min with flow rate of 0.3 mL/min].

Example 135

3-(4-Carbamoyl phenyl)-N-cyclopropyl-N-(3,4-difluorophenyl)pyrazolo[1,5-a]pyridine-5-carboxamide

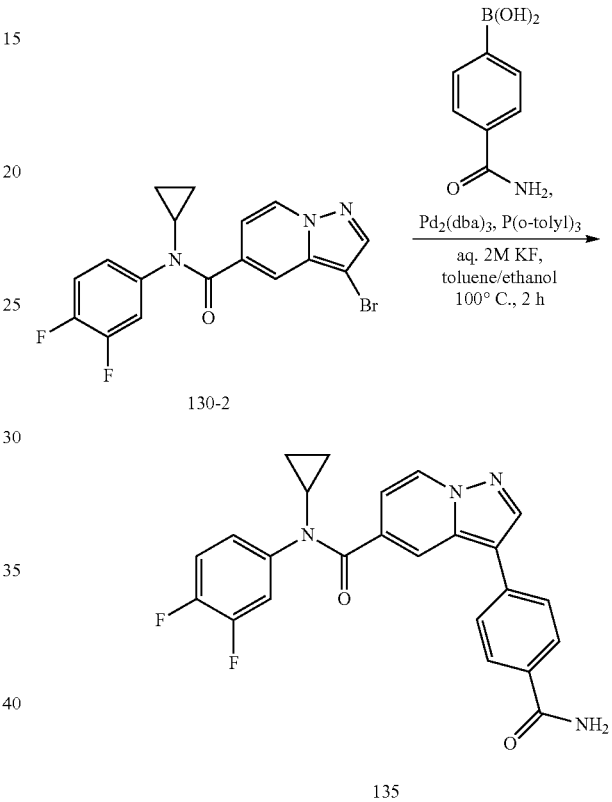

Compound 135 was prepared using the general procedure described in Suzuki Procedure H with the appropriate starting materials. Yield 18%. Yellow solid. ¹H-NMR (400 MHz, DMSO-d₆): δ 8.74 (d, J=7.0 Hz, 1H), 8.52 (s, 1H), 8.06 (d, J=10.1 Hz, 2H), 7.98 (d, J=7.9 Hz, 2H), 7.60-7.70 (m, 3H), 7.41-7.49 (m, 2H), 7.26 (d, J=8.3 Hz, 1H), 7.03 (d, J=7.0 Hz, 1H), 3.27-3.35 (m, 1H), 0.76-0.80 (m, 2H), 0.55-0.60 (m, 2H). ESI-LC/MS: m/z 433.21 (M+H); $R_t$=2.62 min [Waters Acquity UPLC with Quattro-micro detector; Waters Acquity BEH C18, 1.7 μm, 2.1×50 mm column; gradient of 90:10 H₂O (0.025% TFA):CH₃CN (0.025% TFA) hold for 0.5 min and to 10:90 H₂O (0.025% TFA):CH₃CN (0.025% TFA) in 3.0 min and hold for 2.0 min with flow rate of 0.4 mL/min]. HPLC purity: 98.2% at 254 nm; $R_t$=2.55 min [Waters Acquity UPLC with PDA; Waters Acquity BEH C18, 1.7 μm, 2.1×100 mm column; gradient of 70:30 H₂O (0.025% TFA):CH₃CN (0.025% TFA) to 20:80 H₂O (0.025% TFA):CH₃CN (0.025% TFA) in 4.0 min and hold for 2.0 min with flow rate of 0.3 mL/min.

Example 136

N-Cyclopropyl-3-(4-(methylcarbamoyl)phenyl)-N-(5-methylpyridin-2-yl)pyrazolo[1,5-a]pyridine-5-carboxamide Step 1

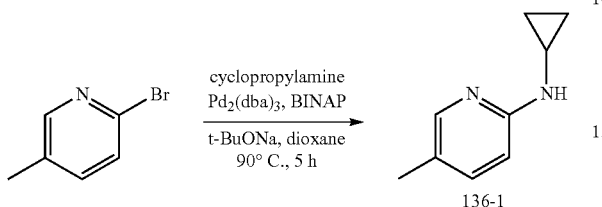

A solution mixture of 2-bromo-5-methylpyridine (500 mg, 2.906 mmol), t-BuONa (418 mg, 4.354 mmol) in toluene (20.0 mL) in sealed tube was degassed with argon for 15 min. $Pd_2(dba)_3$ (26 mg, 0.028 mmol), BINAP (54 mg, 0.086 mmol) and cyclopropylamine (0.40 mL, 5.77 mmol) were added. The reaction mixture was maintained at 100° C. for 4 h and cooled to room temperature. The reaction mixture was filtered through celite and washed with ethyl acetate (50 mL). The filtrate was concentrated under reduced pressure to afford 450 mg of crude N-cyclopropyl-5-methylpyridin-2-amine 136-1 as pale red oil. This material was used further without purification. ESI-LC/MS: m/z 149.0 (M+H); $R_t$=3.44 min [Agilent LC with Ion trap Detector; Xterra MS C18, 2.5 μm, 4.6×50 mm column; gradient of 80:20 $H_2O$ (0.01 M ammonium bicarbonate):$CH_3CN$ to 10:90 $H_2O$ (0.01 M ammonium bicarbonate):$CH_3CN$ in 4.0 min and hold for 3.0 min with flow rate of 1.0 mL/min].

Step 2

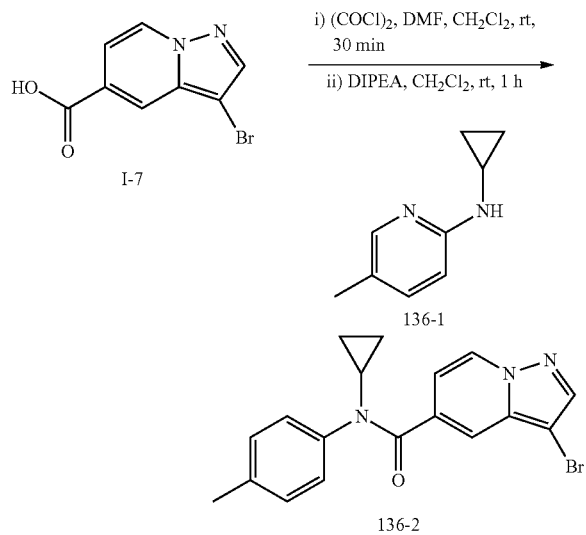

Compound 136-2 was prepared using the general procedure described in Amide Coupling-Method 1 with the appropriate starting materials. Yield 42% (over two steps). Yellow solid. $^1$H NMR (400 MHz, $CDCl_3$): δ 8.22-8.26 (m, 2H), 7.90 (s, 1H), 7.57 (s, 1H), 7.45 (dd, J=2.2, 7.9 Hz, 1H), 7.02 (d, J=8.0 Hz, 1H), 6.76 (dd, J=1.7, 7.4 Hz, 1H), 3.28-3.31 (m, 1H), 2.31 (s, 3H), 0.91-0.96 (m, 2H), 0.69-0.73 (m, 2H). ESI-LC/MS: m/z 371.1 (M+H) & 373.08 [(M+2)+H]; $R_t$=2.55 min [Waters Acquity UPLC with Quattro-micro detector; Waters Acquity BEH C18, 1.7 μm, 2.1×50 mm column; gradient of 90:10 $H_2O$ (0.025% TFA):$CH_3CN$ (0.025% TFA) hold for 0.5 min and to 10:90 $H_2O$ (0.025% TFA):$CH_3CN$ (0.025% TFA) in 3.0 min and hold for 2.0 min with flow rate of 0.4 mL/min].

Step 3

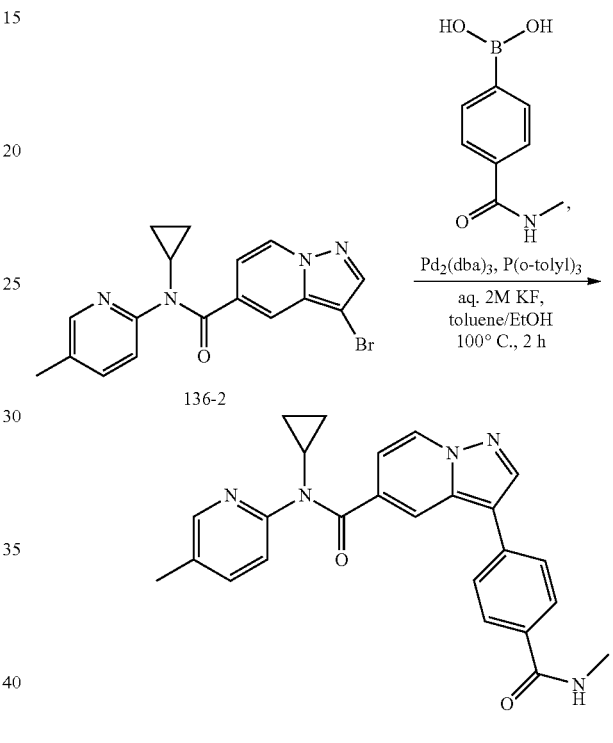

Compound 136 was prepared using the general procedure described in Suzuki Procedure G with the appropriate starting materials. Yield 35%. Yellow solid. $^1$H-NMR (400 MHz, DMSO-$d_6$): δ 8.67 (d, J=7.5 Hz, 1H), 8.49-8.55 (m, 1H), 8.46 (s, 1H), 8.26 (s, 1H), 7.93 (d, J=8.4 Hz, 2H), 7.73 (s, 1H), 7.67 (dd, J=2.2, 7.9 Hz, 1H), 7.54 (d, J=8.4 Hz, 2H), 7.34 (d, J=8.4 Hz, 1H), 6.93 (dd, J=1.8, 7.5 Hz, 1H), 3.18-3.22 (m, 1H), 2.82 (d, J=4.4 Hz, 3H), 2.22 (s, 3H), 0.80-0.84 (m, 2H), 0.64-0.67 (m, 2H). ESI-LC/MS: m/z 426.28 (M+H); $R_t$=1.84 min [Waters Acquity UPLC with Quattro-micro detector; Waters Acquity BEH C18, 1.7 μm, 2.1×100 mm column; gradient of 80:20 $H_2O$ (0.025% TFA): $CH_3CN$ (0.025% TFA) to 20:80 $H_2O$ (0.025% TFA):$CH_3CN$ (0.025% TFA) in 3.0 min and hold for 2.0 min with flow rate of 0.4 mL/min]. HPLC purity: 96.2% at 230 nm; $R_t$=2.91 min [Waters Acquity UPLC with PDA; Waters Acquity BEH C18, 1.7 μm, 2.1×100 mm column; gradient of 90:10 $H_2O$ (0.025% TFA):$CH_3CN$ (0.025% TFA) to 20:80 $H_2O$ (0.025% TFA):$CH_3CN$ (0.025% TFA) in 4.0 min and hold for 2.0 min with flow rate of 0.3 mL/min].

Example 137

N-(4-Cyanophenyl)-N-cyclopropyl-3-(6-(methylcarbamoyl)pyridin-3-yl)pyrazolo[1,5-a]pyridine-5-carboxamide

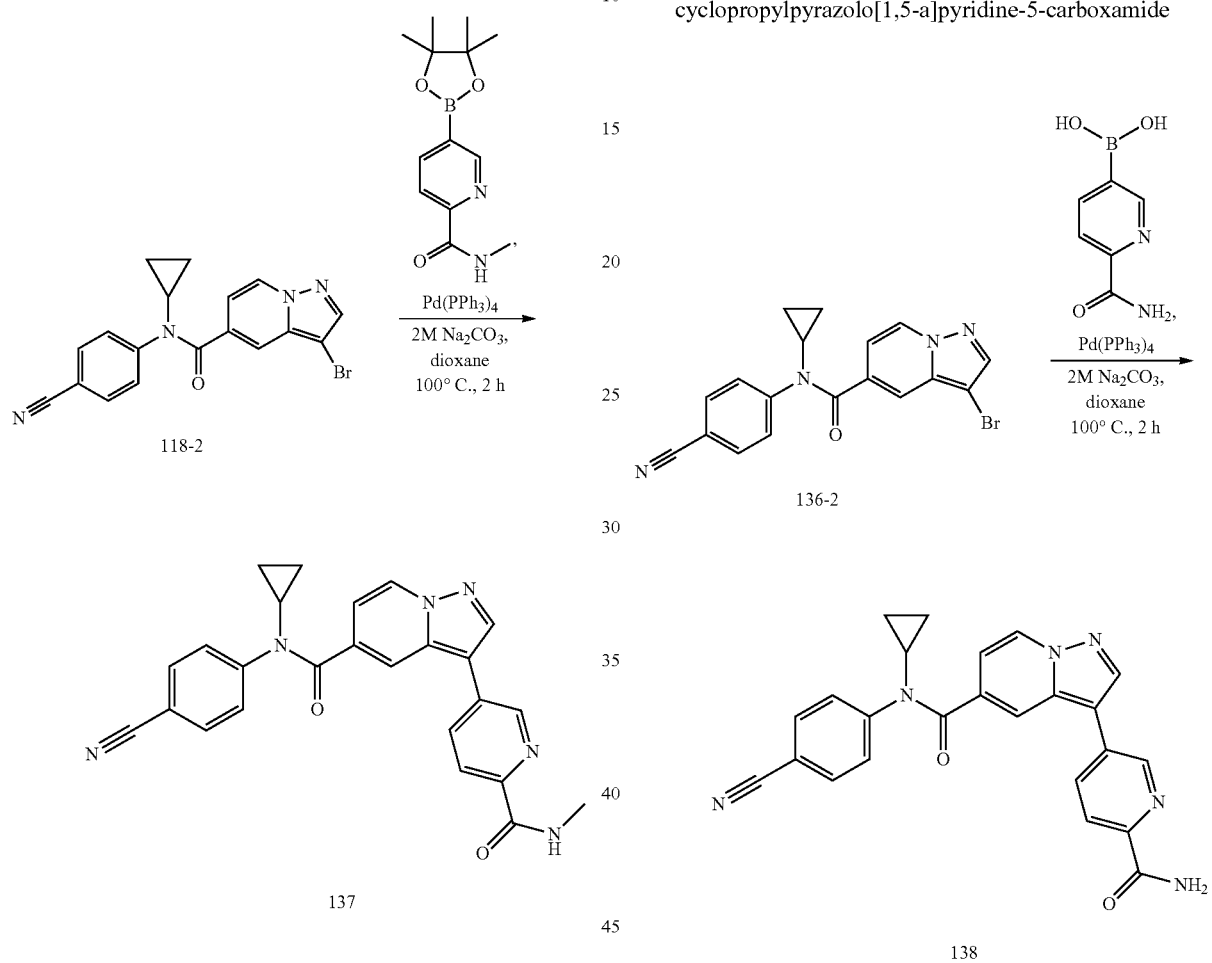

Compound 137 was prepared using the general procedure described in Suzuki Procedure G with the appropriate starting materials. Yield 31%. Yellow solid. $^1$H-NMR (400 MHz, DMSO-$d_6$): i 8.92 (d, J=1.7 Hz, 1H), 8.82 (d, J=6.8 Hz, 1H) 8.72-8.75 (m, 1H), 8.67 (s, 1H), 8.19-8.22 (m, 2H), 8.10 (d, J=8.4 Hz, 1H), 7.89 (d, J=8.8 Hz, 2H), 7.65 (d, J=8.8 Hz, 2H), 7.11 (dd, J=1.3, 5.7 Hz, 1H), 3.37-3.39 (m, 1H), 2.86 (d, J=4.8 Hz, 3H), 0.75-0.80 (m, 2H), 0.50-0.54 (m, 2H). ESI-LC/MS: m/z 437.16 (M+H); $R_t$=2.38 min [Waters Acquity UPLC with Quattro micro TQD; Waters Acquity BEH C18, 1.7 μm, 2.1×50 mm column; gradient of 90:10 $H_2O$ (0.025% TFA):$CH_3CN$ (0.025% TFA) hold for 0.5 min to 10:90 $H_2O$ (0.025% TFA):$CH_3CN$ (0.025% TFA) in 2.5 min and hold for 2 min with flow rate of 0.4 mL/min]. HPLC purity: 97.0% at 214 nm; $R_t$=1.27 min [Waters Acquity UPLC with PDA detector; Waters Acquity BEH C18, 1.7 μm, 2.1×100 mm column; gradient of 50:50 $H_2O$ (0.025% TFA):$CH_3CN$ (0.025% TFA) to 20:80 $H_2O$ (0.025% TFA):$CH_3CN$ (0.025% TFA) in 4 min and hold for 2 min with flow rate of 0.3 mL/min].

Example 138

3-(6-Carbamoylpyridin-3-yl)-N-(4-cyanophenyl)-N-cyclopropylpyrazolo[1,5-a]pyridine-5-carboxamide

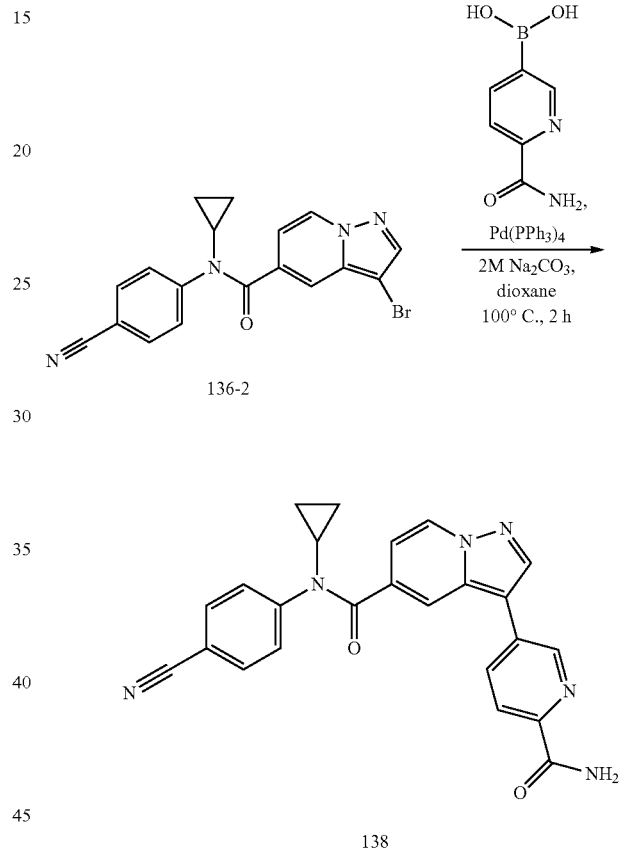

Compound 138 was prepared using the general procedure described in Suzuki Procedure G with the appropriate starting materials. Yield 7%. Yellow solid. $^1$H-NMR (400 MHz, $CD_3OD$): δ 8.81 (s, 1H), 8.60 (d, J=7.5 Hz, 1H), 8.43 (s, 1H), 8.19 (d, J=8.4 Hz, 1H), 8.10-8.13 (m, 1H), 8.02 (s, 1H), 7.75 (d, J=8.3 Hz, 2H), 7.55 (d, J=8.4 Hz, 2H), 7.07 (d, J=8.0 Hz, 1H), 3.36-3.38 (m, 1H), 0.89-0.91 (m, 2H), 0.600.62 (m, 2H). ESI-LC/MS: m/z 423.1 (M+H); $R_t$=2.37 min [Agilent LC with Ion trap Detector; Agilent Zorbax RRHT SB C18, 1.8 μm, 2.1×50 mm column; gradient of 90:10 $H_2O$ (0.1% FA):$CH_3CN$ (0.1% HCOOH) hold for 0.5 min to 10:90 $H_2O$ (0.1% HCOOH):$CH_3CN$ (0.1% HCOOH) in 2.5 min and hold for 2 min with flow rate of 0.4 mL/min]. HPLC purity: 99.7% at 254 nm; $R_t$=2.09 min [Waters Acquity UPLC with PDA detector; Waters Acquity BEH C18, 1.7 μm, 2.1×100 mm column; gradient of 70:30 $H_2O$ (0.025% TFA):$CH_3CN$

Example 139

3-(5-Carbamoylpyridin-2-yl)-N-(5-cyanopyridin-2-yl)-N-cyclopropylpyrazolo[1,5-a]pyridine-5-carboxamide

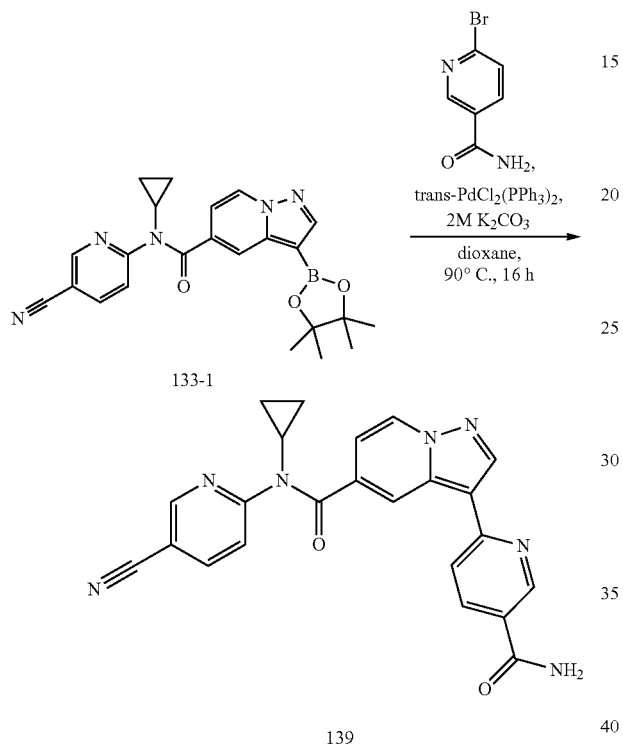

A solution of N-(5-cyanopyridin-2-yl)-N-cyclopropyl-3-(4,4,5,5-tetramethyl-1,3,2-dioxaborolan-2-yl)pyrazolo[1,5-a]pyridine-5-carboxamide 133-1 (2.0 g, crude), 6-bromonicotinamide (400 mg, 2.00 mmol) and 2M K$_2$CO$_3$ (8.0 mL, 8.0 mmol) in dioxane (80 mL) were degassed with argon for 30 min, added trans-PdCl$_2$(PPh$_3$)$_2$ (280 mg, 0.40 mmol) and stirred at 90° C. in sealed tube for 16 h. Reaction mixture was filtered through celite and washed the celite bed with ethyl acetate (100 mL). The combined filtrate was evaporated and the residue was purified by column chromatography over silica-gel (100-200 mesh) using a solvent gradient of 5% methanol in chloroform as eluant to obtain semi-pure product. This semi-pure compound was further purified by prep-HPLC gave 10 mg (1.5% over two steps) of Preparation of 3-(5-Carbamoylpyridin-2-yl)-N-(5-cyanopyridin-2-yl)-N-cyclopropylpyrazolo[1,5-a]pyridine-5-carboxamide 139 as yellow solid. $^1$H NMR (400 MHz, DMSO-d$_6$): δ 9.07 (d, J=1.7 Hz, 1H), 8.85 (s, 1H), 8.81 (d, J=2.2 Hz, 1H), 8.75 (d, J=7.1 Hz, 1H), 8.63 (s, 1H), 8.36 (dd, J=2.6, 8.8 Hz, 1H), 8.23 (dd, J=2.2, 8.3 Hz, 1H), 8.14 (s, 1H), 7.99 (d, J=8.3 Hz, 1H), 7.79 (d, J=8.7 Hz, 1H), 7.58 (s, 1H), 7.03 (dd, J=1.8, 7.5 Hz, 1H), 3.24-3.28 (m, 1H), 0.90-0.95 (m, 2H), 0.66-0.68 (m, 2H). ESI-LC/MS: m/z 424.34 (M+H); R$_t$=2.02 min [Waters Acquity UPLC with Quattro micro TQD; Waters Acquity BEH C18, 1.7 μm, 2.1×50 mm column; gradient of 90:10 H$_2$O (0.025% TFA):CH$_3$CN (0.025% TFA) hold for 0.5 min to 10:90 H$_2$O (0.025% TFA):CH$_3$CN (0.025% TFA) in 2.5 min and hold for 2 min with flow rate of 0.4 mL/min]. HPLC purity=97.8% at 254 nm; R$_t$=2.75 min [Waters Acquity UPLC with PDA detector; Waters Acquity BEH C18, 1.7 μm, 2.1×100 mm column; gradient of 90:10 H$_2$O (0.025% TFA):CH$_3$CN (0.025% TFA) to 20:80 H$_2$O (0.025% TFA):CH$_3$CN (0.025% TFA) in 4 min and hold for 2 min with flow rate of 0.3 mL/min].

Example 140

N-(5-cyanopyridin-2-yl)-N-ethyl-3-(4-[N-methylsulfamoyl]phenyl)pyrazolo[1,5-a]pyridine-5-carboxamide

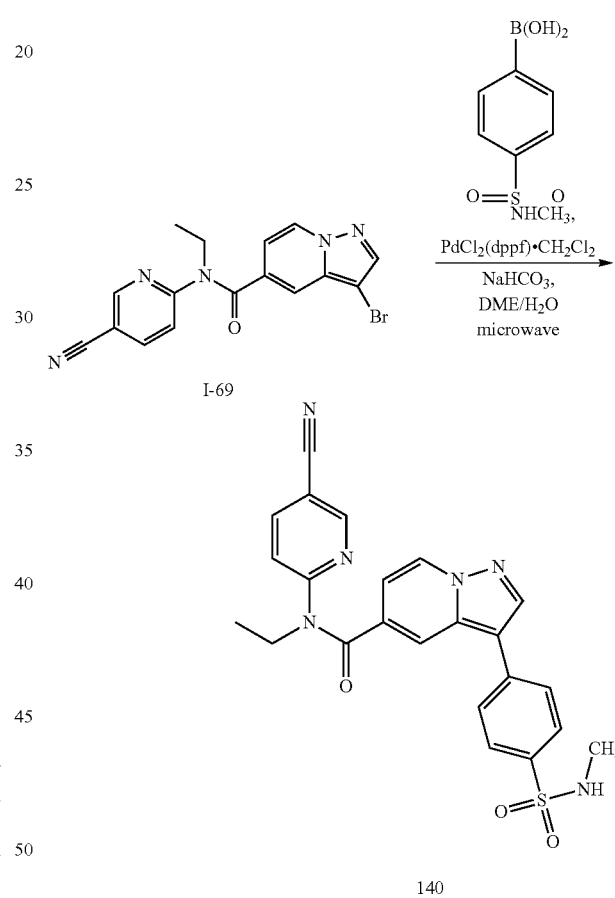

A mixture of 3-bromo-N-(5-cyanopyridin-2-yl)-N-ethyl-pyrazolo[1,5-a]pyridine-5-carboxamide I-69 (100 mg, 0.270 mmol) in DME:H$_2$O (3:1) (4 mL), (4-[N-methylsulfamoyl]phenyl)boronic acid (87 mg, 0.405 mmol) and NaHCO$_3$ (68 mg, 0.810 mmol) were added in to a 10 mL microwave vial and the mixture was degassed with argon for about 10 min. To this mixture was added PdCl$_2$(dppf)dichloromethane adduct (11 mg, 0.014 mmol) and sealed it, subjected to microwave at 140° C. for 30 min. The reaction mixture was diluted with ethyl acetate (20 mL) and filtered through celite. The filtrate was extracted with water (20 mL), brine (10 mL), dried over Na$_2$SO$_4$ and concentrated on rotavap to get brown residue. The residue was purified by column chromatography (ISCO purification system, 12 g silicagel column) with gradient mixture of 95% ethylacetate in cyclohexane to 100% ethylacetate as eluant to afford 14 mg (11%) of N-(5-cyanopyridin-2-yl)-N-ethyl-3-(4-(N-methylsulfamoyl)phenyl)pyrazolo[1,5-a]pyridine-5-carboxamide 140 as a yellow color solid. $^1$H NMR (400 MHz, DMSO-d$_6$): δ 8.87 (dd, J=0.63, 2.26 Hz, 1H), 8.70 (dd, J=0.82, 7.22 Hz, 1H), 8.57 (s, 1H), 8.24 (dd, J=2.26, 8.53 Hz, 1H), 8.00-8.06 (m, 1H), 7.82-7.88 (m, 2H), 7.76-7.81 (m, 2H), 7.54 (dd, J=0.63, 8.53 Hz, 1H), 7.49 (br. s., 1H), 6.78 (dd, J=1.76, 7.15 Hz, 1H), 4.12 (q, J=6.94 Hz, 2H), 2.46 (s, 3H), 1.21 (t, J=7.03 Hz, 3H). ESI-LC/MS: m/z 461.1 (M+H); R$_f$=0.82 min [Waters Acquity UPLC coupled with MS waters ZQ 2000; Acquity UPLC BEH C18 column, 1.7 μm, 2.1×50 mm; gradient of 98:2 H$_2$O (0.1% HCOOH):CH$_3$CN to 2:98 H$_2$O (0.1% HCOOH):CH$_3$CN for 2 minutes run time with 1.0 mL/min flow rate]. HPLC purity=97.6% at 254 nm; R$_t$=1.53 min [Waters Acquity UPLC equipped with a Acquity UPLC HSS T3 column, 1.8 μm, 2.1×50 mm; gradient of 95:5 H$_2$O (0.1% HCOOH):CH$_3$CN to 2:98 H$_2$O (0.1% HCOOH):CH$_3$CN for 2 min run time with 1.0 mL/min flow rate].

Example 141

N-(4-Cyanophenyl)-N-cyclopropyl-3-(5-(methylcarbamoyl)pyridin-2-yl)pyrazolo[1,5-a]pyridine-5-carboxamide

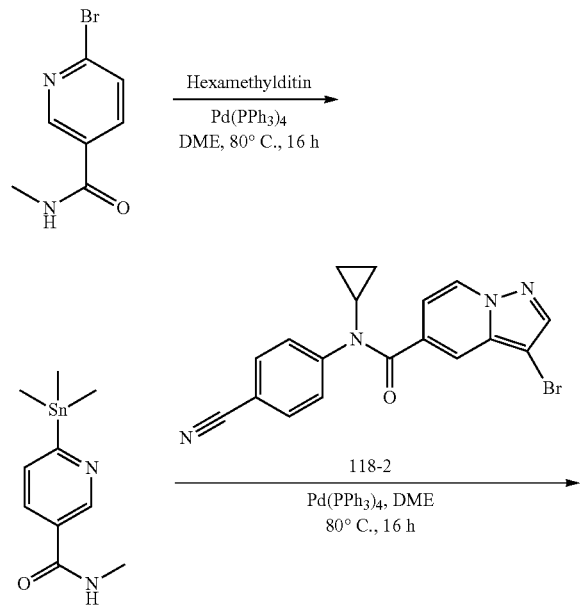

To a stirred solution of 6-bromo-N-methylnicotinamide (200 mg, 0.93 mmol), hexamethylditin (0.193 mL, 0.93 mmol) in 1,2-dimethoxyethane (20 mL) was degassed with argon for about 15 min. Pd(PPh$_3$)$_4$ (54 mg, 0.04 mmol) was added under argon atmosphere. The resulting reaction mixture was maintained at 80° C. for 16 h, allowed to room temperature and resulting solution was added to a mixture 3-bromo-N-(4-cyanophenyl)-N-cyclopropylpyrazolo[1,5-a]pyridine-5-carboxamide 118-2 (354 mg, 0.93 mmol) and Pd(PPh$_3$)$_4$ (54 mg, 0.04 mmol). The resulting reaction mixture was stirred at 90° C. for 16 h. The reaction was cooled and diluted with ethyl acetate (50 mL), washed with water (100 mL), brine (50 mL), dried over Na$_2$SO$_4$ and concentrated. The crude compound was purified by column chromatography over silica-gel (100-200) mesh with a solvent gradient mixture of 1% methanol in chloroform as eluant and then prep-HPLC to afford 20 mg (5%) of N-(4-cyanophenyl)-N-cyclopropyl-3-(5-(methylcarbamoyl)pyridin-2-yl)pyrazolo[1,5-a]pyridine-5-carboxamide 141 as a yellow color solid. $^1$H-NMR (400 MHz, CD$_3$OD): δ 9.02 (d, J=2.2 Hz, 1H), 8.69 (s, 1H), 8.62 (s, 1H), 8.57 (d, J=7.0 Hz, 1H), 8.16 (dd, J=2.2, 8.4 Hz, 1H), 7.86 (d, J=8.3 Hz, 1H), 7.73 (d, J=8.3 Hz, 2H), 7.54 (d, J=8.8 Hz, 2H), 7.08 (dd, J=1.7, 7.0 Hz, 1H), 3.37-3.40 (m, 1H), 2.96 (s, 3H), 0.89-0.94 (m, 2H), 0.61-0.65 (m, 2H). ESI-LC/MS: m/z 437.2 (M+H); R$_t$=2.36 min [Agilent LC-MS Infinity; Waters Acquity UPLC HSS T3, 1.8 μm, 2.1×50 mm column; gradient of 90:10 H$_2$O (0.05% HCOOH+3.75 mM ammonium acetate):CH$_3$CN (0.05% HCOOH) hold for 0.5 min and to 10:90 H$_2$O (0.05% HCOOH+3.75 mM ammonium acetate):CH$_3$CN (0.05% HCOOH) in 3.0 min and hold for 2.0 min with flow rate of 0.4 mL/min]. HPLC purity: 98.2% at 254 nm; R$_t$=3.08 min [Waters Acquity UPLC with PDA; Waters Acquity UPLC BEH C18, 1.7 μm, 2.1×100 mm column; gradient of 90:10 H$_2$O (0.025% TFA):CH$_3$CN (0.025% TFA) to 20:80 H$_2$O (0.025% TFA):CH$_3$CN (0.025% TFA) in 4.0 min and hold for 2.0 min with flow rate of 0.3 mL/min].

Example 142

3-(5-Carbamoylpyridin-2-yl)-N-(4-cyanophenyl)-N-cyclopropylpyrazolo[1,5-a]pyridine-5-carboxamide

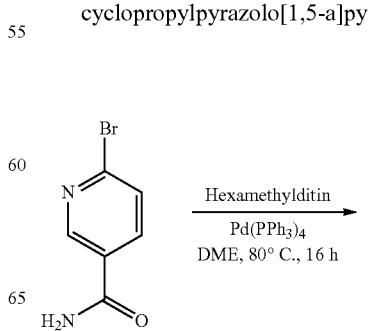

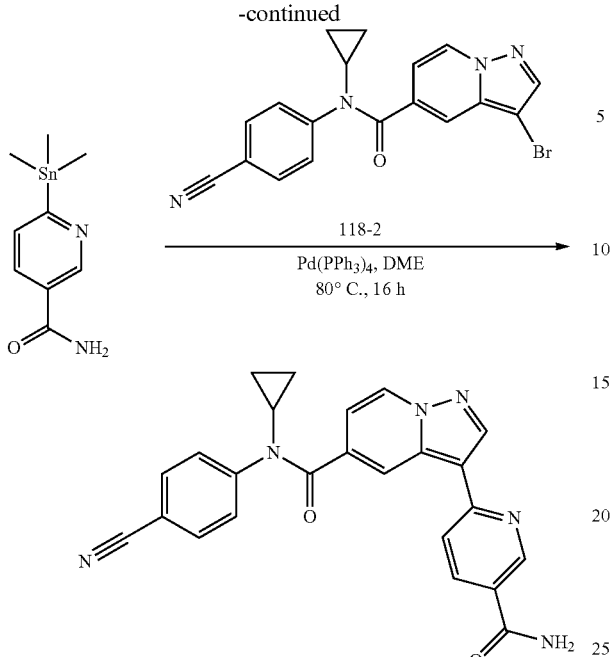

To a stirred solution of 6-bromonicotinamide (200 mg, 1.00 mmol), hexamethylditin (0.189 mL, 0.100 mmol) in 1,2-dimethoxyethane (20 mL) was degassed with argon for about 15 min. Pd(PPh$_3$)$_4$ (54 mg, 0.04 mmol) was added under argon atmosphere. The resulting reaction mixture was maintained at 80° C. for 16 h, allowed to room temperature and added to a mixture of 3-bromo-N-(4-cyanophenyl)-N-cyclopropylpyrazolo[1,5-a]pyridine-5-carboxamide 118-2 (380 mg, 1.00 mmol) and Pd(PPh$_3$)$_4$ (54 mg, 0.04 mmol). The resulting reaction mixture was stirred at 90° C. for 16 h. The reaction mass was diluted with ethyl acetate (50 mL), washed with water (100 mL), brine (50 mL), dried over Na$_2$SO$_4$ and concentrated. The crude compound was purified by column chromatography over silica-gel (100-200) mesh with a solvent gradient mixture of 1% methanol in chloroform as an eluant and then prep-HPLC to afford 25 mg (6%) of 3-(5-carbamoylpyridin-2-yl)-N-(4-cyanophenyl)-N-cyclopropylpyrazolo[1,5-a]pyridine-5-carboxamide 142 as a yellow color solid. $^1$H-NMR (400 MHz, DMSO-d$_6$): δ 9.08 (d, J=1.7 Hz, 1H), 8.83 (s, 1H), 8.77 (d, J=7.4 Hz, 1H), 8.67 (s, 1H), 8.23 (dd, J=2.2, 8.3 Hz, 1H), 8.13 (s, 1H), 7.98 (d, J=8.3 Hz, 1H), 7.86 (d, J=8.3 Hz, 2H), 7.62 (d, J=8.4 Hz, 2H), 7.57 (s, 1H), 7.13 (dd, J=1.7, 7.4 Hz, 1H), 3.36-3.40 (m, 1H), 0.79-0.83 (m, 2H), 0.50-0.54 (m, 2H). ESI-LC/MS: m/z 422.79 (M+H); R$_t$=2.13 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.0 min and hold for 2.0 min with flow rate of 0.4 mL/min]. HPLC purity: 98.8% at 254 nm; R$_t$=2.93 min [Waters Acquity UPLC with PDA; Waters Acquity UPLC BEH C18, 1.7 μm, 2.1×100 mm column; gradient of 90:10 H$_2$O (0.025% TFA):CH$_3$CN (0.025% TFA) to 20:80 H$_2$O (0.025% TFA):CH$_3$CN (0.025% TFA) in 4.0 min and hold for 2.0 min with flow rate of 0.3 mL/min].

Example 143

N-(4-Chlorophenyl)-N-cyclopropyl-3-(6-(methylcarbamoyl)pyridin-3-yl)pyrazolo[1,5-a]pyridine-5-carboxamide

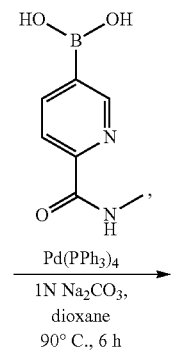

Compound 143 was prepared using the general procedure described in Suzuki Procedure G with the appropriate starting materials. Yield 11%. Yellow solid. $^1$H-NMR (400 MHz, DMSO-d$_6$): δ 8.91 (s, 1H), 8.73-8.78 (m, 2H), 8.64 (s, 1H), 8.09-8.16 (m, 3H), 7.39-7.45 (m, 4H), 7.04 (d, J=6.5 Hz, 1H), 3.31 (m, 1H), 2.85 (d, J=4.8 Hz, 3H), 0.75-0.80 (m, 2H), 0.52-0.58 (m, 2H). ESI-LC/MS: m/z 446.46 (M+H) & 448.50 [(M+2)+H]; R$_t$=2.63 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.5 min and hold for 1.5 min with flow rate of 0.4 mL/min]. HPLC purity: 98.5% at 254 nm; R$_t$=1.90 min [Waters Acquity UPLC with PDA; Waters Acquity UPLC BEH C18, 1.7 μm, 2.1×100 mm column; gradient of 50:50 H$_2$O (0.025% TFA):CH$_3$CN (0.025% TFA) to 20:80 H$_2$O (0.025% TFA):CH$_3$CN (0.025% TFA) in 4.0 min and hold for 2.0 min with flow rate of 0.3 mL/min].

Example 144

N-(5-Cyanopyridin-2-yl)-N-cyclobutyl-3-(6-(methylcarbamoyl)pyridin-3-yl)pyrazolo[1,5-a]pyridine-5-carboxamide

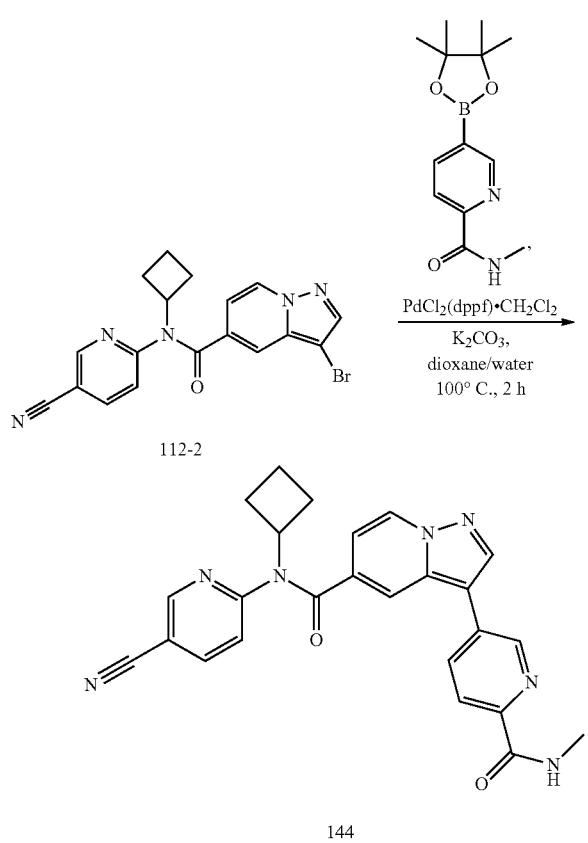

A solution mixture of 3-bromo-N-(4-cyanophenyl)-N-cyclobutylpyrazolo[1,5-a]pyridine-5-carboxamide 112-2 (3.0 g, 7.57 mmol), N-methyl-5-(4,4,5,5-tetramethyl-1,3,2-dioxaborolan-2-yl)picolinamide (3.99 g, 15.229 mmol), $K_2CO_3$ (2.3 g, 16.66 mmol) in dioxane:water (3:1) (60.0 mL) were degassed with argon for about 15 min. $PdCl_2$(dppf).$CH_2Cl_2$ complex (1.24 g, 1.518 mmol) was added to the reaction mixture under argon atmosphere. The reaction mixture was maintained at 100° C. for 2 h, cooled to room temperature and filtered through celite. The filtrate was partitioned between water (100 mL) and ethyl acetate (100 mL). The ethyl acetate layer was washed with water, brine, dried over anhydrous $Na_2SO_4$ and concentrated. The crude compound was purified by column chromatography over silica gel (100-200 mesh) using a solvent gradient of 70 ethyl acetate in pet-ether as eluant to afford 1.8 g (53%) of N-(5-cyanopyridin-2-yl)-N-cyclobutyl-3-(6-(methylcarbamoyl)pyridin-3-yl)pyrazolo[1,5-a]pyridine-5-carboxamide 144 as a Light yellow color solid. $^1$H-NMR (300 MHz, DMSO-$d_6$): δ 8.96 (d, J=2.4 Hz, 1H), 8.81 (s, 1H), 8.67-8.74 (m, 2H), 8.62 (s, 1H), 8.33 (dd, J=2.4 Hz, 8.1 Hz, 1H), 8.05-8.14 (m, 2H), 7.84 (s, 1H), 7.62 (d, J=8.4 Hz, 1H), 6.79 (dd, J=1.5, 7.2 Hz, 1H), 4.90-4.95 (m, 1H), 2.86 (d, J=4.8 Hz, 3H), 2.19-2.27 (m, 2H), 2.07-2.13 (m, 2H), 1.58-1.69 (m, 2H). ESI-LC/MS: m/z 452.39 (M+H); $R_t$=2.25 min [Waters Acquity UPLC with SQD; Waters Acquity UPLC BEH C18, 1.7 μm, 2.1×50 mm column; gradient of 95:05 $H_2O$ (0.1% HCOOH):$CH_3CN$ (0.1% HCOOH) hold for 0.5 min and to 50:50 $H_2O$ (0.1% HCOOH):$CH_3CN$ (0.1% HCOOH) in 1.7 min and to 0:100 $H_2O$ (0.1% HCOOH):$CH_3CN$ (0.1% HCOOH) in 3.0 min and hold for 2.0 min with flow rate of 1.0 mL/min]. HPLC purity: 98.5% at 254 nm; $R_t$=2.05 min [Waters Acquity UPLC with PDA; Waters Acquity UPLC BEH C18, 1.7 μm, 2.1×50 mm column; gradient of 98:02 $H_2O$ (0.025% TFA):$CH_3CN$ (0.025% TFA) to 10:90 $H_2O$ (0.025% TFA):$CH_3CN$ (0.025% TFA) in 2.5 min and hold for 3.5 min with flow rate of 0.3 mL/min].

Example 145

N-(4-Cyanophenyl)-N-cyclobutyl-3-(6-(methylcarbamoyl)pyridin-3-yl)pyrazolo[1,5-a]pyridine-5-carboxamide Step 1

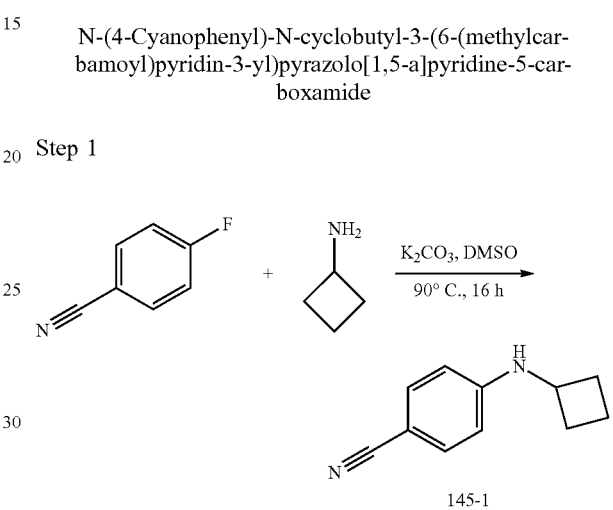

A solution mixture of 4-fluorobenzonitrile (2.0 g, 16.52 mmol), cyclobutylamine (1.69 mL, 19.79 mmol) and $K_2CO_3$ (4.56 g, 33.00 mmol) in DMSO (20 mL) was stirred at 90° C. for 16 h. The reaction mixture was partitioned between water (100 mL) and ethyl acetate (100 mL). The ethyl acetate was washed with brine (100 mL) and dried over anhyd. $Na_2SO_4$ and concentrated. The crude compound was purified by column chromatography over silica-gel (100-200 mesh) with a gradient mixture of 5% ethyl acetate in chloroform as an eluant to give 1.5 g (53%) of 4-(cyclobutylamino)benzonitrile 145-1 as a off-white solid. $^1$H NMR (400 MHz, DMSO-$d_6$): δ 7.43 (d, J=8.8 Hz, 2H), 6.96 (d, J=6.1 Hz, 1H), 6.55 (d, J=8.8 Hz, 2H), 3.84-3.92 (m, 1H), 2.32-2.34 (m, 2H), 1.71-1.84 (m, 4H).

Step 2

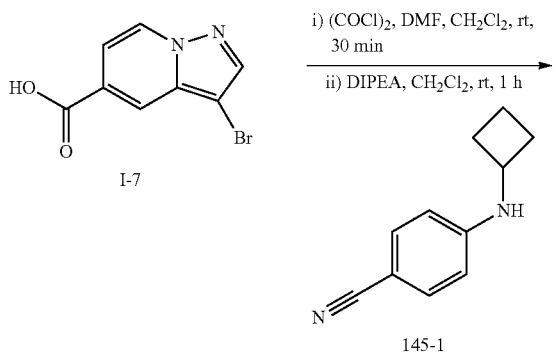

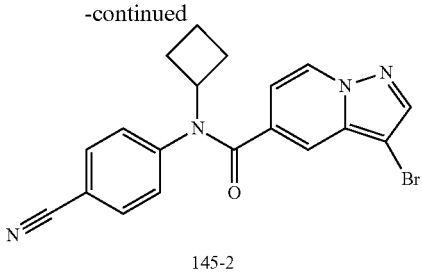

145-2

Compound 145-2 was prepared using the general procedure described in Amide Coupling-Method 1 with the appropriate starting materials. Yield 41%. Off-white solid. $^1$H NMR (400 MHz, DMSO-d$_6$): δ 8.60 (d, J=6.8 Hz, 1H), 8.17 (s, 1H), 7.84 (d, J=8.4, Hz, 2H), 7.45-7.55 (m, 3H), 6.81 (dd, J=1.6, 7.4 Hz, 1H), 4.86-4.91 (m, 1H), 2.13-2.19 (m, 2H), 1.78-1.89 (m, 2H), 1.50-1.65 (m, 2H). ESI-LC/MS: m/z 394.57 (M+H) & 396.61 [(M+2)+H]; R$_t$=2.97 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.0 min and hold for 2.0 min with flow rate of 0.4 mL/min].

Step 3

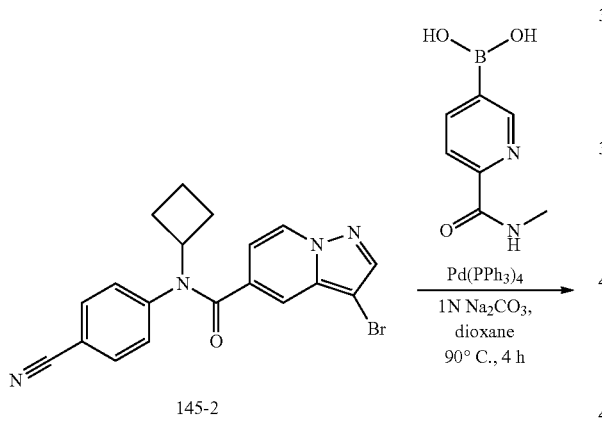

Compound 145 was prepared using the general procedure described in Suzuki Procedure G with the appropriate starting materials. Yield 13%. Yellow color solid. $^1$H-NMR (400 MHz, DMSO-d$_6$): δ 8.83 (s, 1H), 8.66-8.73 (m, 2H), 8.60 (s, 1H), 8.07-8.12 (m, 2H), 7.92 (s, 1H), 7.88 (d, J=8.3 Hz, 2H), 7.54 (d, J=8.4 Hz, 2H), 6.88 (dd, J=1.8, 7.0 Hz, 1H), 4.89-4.95 (m, 1H), 2.86 (d, J=4.8 Hz, 3H), 2.11-2.20 (m, 2H), 1.82-1.89 (m, 2H), 1.57-1.67 (m, 2H). ESI-LC/MS: m/z 451.54 (M+H); R$_t$=2.53 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.0 min and hold for 2.0 min with flow rate of 0.4 mL/min]. HPLC purity: 97.5% at 233 nm; R$_t$=1.71 min [Waters Acquity UPLC with PDA; Waters Acquity BEH C18, 1.7 μm, 2.1× 100 mm column; gradient of 50:50 H$_2$O (0.025% TFA):CH$_3$CN (0.025% TFA) to 20:80 H$_2$O (0.025% TFA):CH$_3$CN (0.025% TFA) in 4.0 min and hold for 2.0 min with flow rate of 0.3 mL/min].

Example 146

N-(4-Cyanophenyl)-N-isopropyl-3-(6-(methylcarbamoyl)pyridin-3-yl)pyrazolo[1,5-a]pyridine-5-carboxamide Step 1

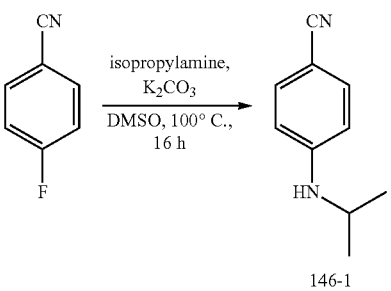

146-1

A solution mixture of 4-fluorobenzonitrilre (3.0 g, 24.79 mmol), isopropylamine (10 mL, 122.14 mmol) and K$_2$CO$_3$ (3.41 g, 24.72 mmol) in DMSO (10 mL) was stirred at 100° C. for 16 h. The reaction mixture was partitioned between water (50 mL) and ethyl acetate (2×50 mL). The ethyl acetate layer was washed with brine (100 mL), dried over anhydrous Na$_2$SO$_4$ and concentrated to afford 1.2 g (30%) of 4-(isopropylamino)benzonitrile 146-1 as a white solid. $^1$H NMR (400 MHz, DMSO-d$_6$): δ 7.42 (d, J=8.8 Hz, 2H), 6.60 (d, J=8.8 Hz, 2H), 6.53 (d, J=7.4 Hz, 1H), 3.56-3.64 (m, 1H), 1.13 (d, J=6.6 Hz, 6H).

Step 2

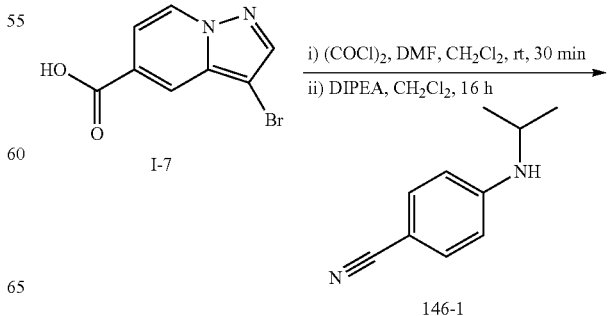

146-1

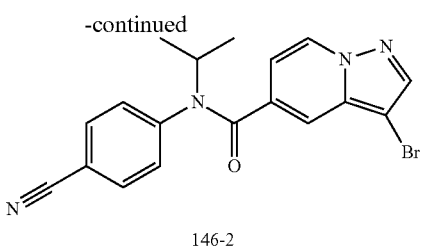

146-2

Compound 146-2 was prepared using the general procedure described in Amide Coupling-Method 1 with the appropriate starting materials. Yield 34%. Yellow solid. $^1$H-NMR (400 MHz, DMSO-$d_6$): δ 8.59 (d, J=7.0 Hz, 1H), 8.15 (s, 1H), 7.81 (d, J=8.4 Hz, 2H), 7.53 (d, J=8.3 Hz, 2H), 7.47 (s, 1H), 6.83 (dd, J=1.4, 7.1 Hz, 1H), 4.85-4.88 (m, 1H), 1.17 (d, J=6.6 Hz, 6H). ESI-LC/MS: m/z 383.38 (M+H) & 385.42 [(M+2)+H]; $R_t$=2.81 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025%

Step 3

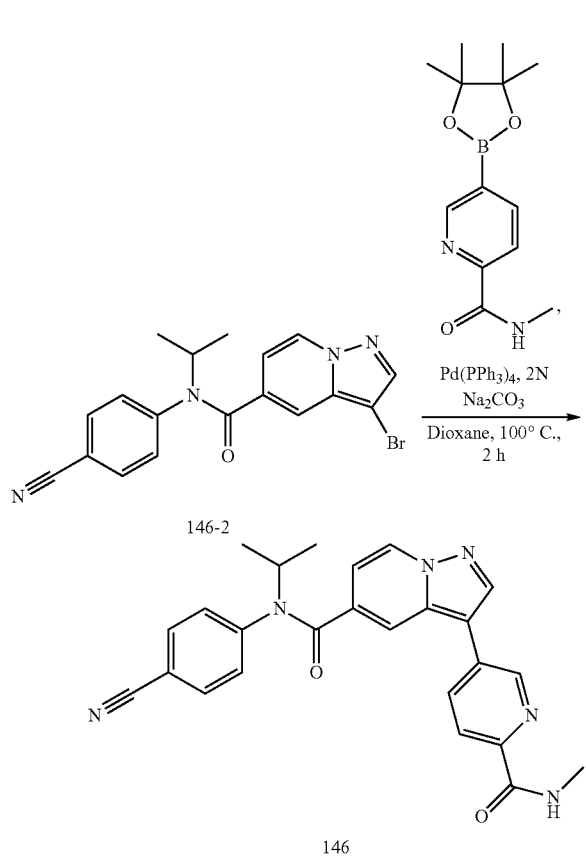

146

Compound 146 was prepared using the general procedure described in Suzuki Procedure G with the appropriate starting materials. Yield 20%. Yellow solid. $^1$H-NMR (400 MHz, DMSO-$d_6$): δ 8.83 (s, 1H), 8.73 (d, J=4.4 Hz, 1H), 8.66 (d, J=7.0 Hz, 1H), 8.59 (s, 1H), 8.06-8.13 (m, 2H), 7.91 (s, 1H), 7.85 (d, J=8.3 Hz, 2H), 7.57 (d, J=8.5 Hz, 1H), 6.90 (d, J=6.2 Hz, 1H), 4.89-4.91 (m, 1H), 2.86 (d, J=4.8 Hz, 3H), 1.18 (d, J=6.6 Hz, 6H). ESI-LC/MS: m/z 439.59 (M+H); $R_t$=2.42 min. [Waters Acquity UPLC with Quattro micro TQD; Waters Acquity BEH C18, 1.7 μm, 2.1×50 mm column; gradient of 90:10 H$_2$O (0.025% TFA):CH$_3$CN (0.025% TFA) hold for 0.5 min to 10:90 H$_2$O (0.025% TFA):CH$_3$CN (0.025% TFA) in 3.0 min and hold for 2 min with flow rate of 0.4 mL/min]. HPLC purity=97.49% at 233 nm; $R_t$=1.53 min [Waters Acquity UPLC with PDA detector; Waters Acquity BEH C18, 1.7 μm, 2.1×100 mm column; gradient of 50:50 H$_2$O (0.025% TFA):CH$_3$CN (0.025% TFA) to 20:80 H$_2$O (0.025% TFA):CH$_3$CN (0.025% TFA) in 4 min and hold for 2 min with flow rate of 0.3 mL/min].

Example 147

5-Cyano-N-cyclopropyl-N-(3-(4-(methylcarbamoyl)phenyl)pyrazolo[1,5-a]pyridin-5-yl) picolinamide Step 1

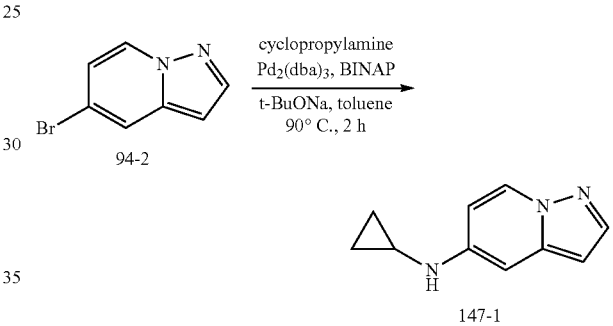

147-1

A solution mixture of 5-bromopyrazolo[1,5-a]pyridine 94-2 (900 mg, 4.59 mmol) and t-BuONa (661.2 mg, 6.88 mmol) in toluene (10 mL) was degassed with argon for about 10 min. To this mixture were added Pd$_2$(dba)$_3$ (84 mg, 0.091 mmol), BINAP (114.2 mg, 0.102 mmol) and cyclopropylamine (2 mL, 28.87 mmol) under argon atmosphere. The resulting reaction mixture was maintained at 90° C. for 2 h under microwave irradiation. The reaction mixture was diluted with water (30 mL) and extracted with ethyl acetate (2×50 mL). The combined organic layer was washed with water (30 mL), brine (25 mL), dried over anhydrous Na$_2$SO$_4$ and concentrated. The crude product was purified by column chromatography over silica-gel (100-200 mesh) using a solvent gradient of 25% ethyl acetate in pet-ether to afford 500 mg (62%) of N-cyclopropylpyrazolo[1,5-a]pyridin-5-amine 147-1 as a brown solid. $^1$H-NMR (400 MHz, CDCl$_3$): δ 8.18 (d, J=7.5 Hz, 1H), 7.78 (d, J=2.2 Hz, 1H), 6.72 (d, J=2.6 Hz, 1H), 6.15-6.18 (m, 2H), 4.28 (s, 1H), 2.44-2.49 (m, 1H), 0.78-0.80 (m, 2H), 0.54-0.58 (m, 1H). ESI-LC/MS: m/z 173.75 (M+H); $R_t$=1.99 min [Waters Acquity UPLC with Quattro-micro detector; Waters Acquity BEH C18, 1.7 μm, 2.1×50 mm column; gradient of 90:10 H$_2$O (0.025% TFA):CH$_3$CN (0.025% TFA) hold for 0.5 min and to 10:90 H$_2$O (0.025% TFA):CH$_3$CN (0.025% TFA) in 3.5 min and hold for 1.5 min with flow rate of 0.4 mL/min].

Step 2

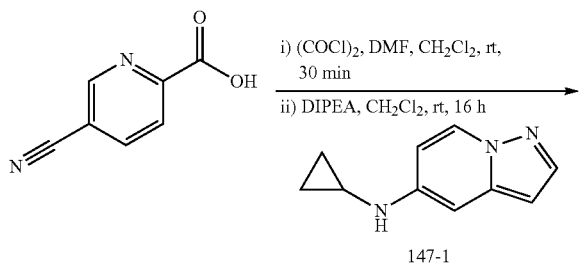

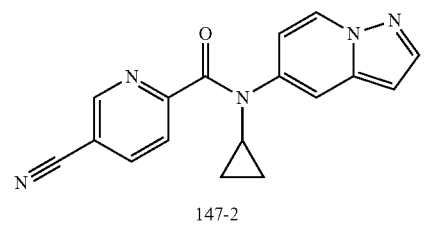

Compound 147-2 was prepared using the general procedure described in Amide Coupling-Method 1 with the appropriate starting materials. Yield 57%. Off-white solid. ESI-LC/MS: m/z 304.1 (M+H); $R_t$=3.04 min [Agilent LC with Ion trap Detector; Waters Xterra MS-C18, 2.5 µm, 4.6×50 mm column; gradient of 80:20 $H_2O$ (0.01 M Ammonium bicarbonate):$CH_3CN$ to 10:90 $H_2O$ (0.01 M Ammonium bicarbonate):$CH_3CN$ in 4 min and hold for 3 min with flow rate of 1.0 mL/min].

Step 3

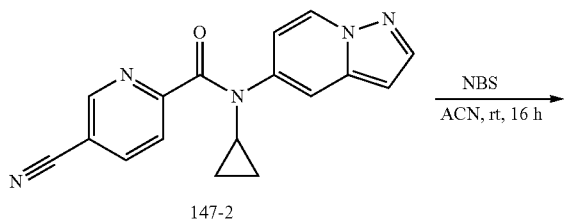

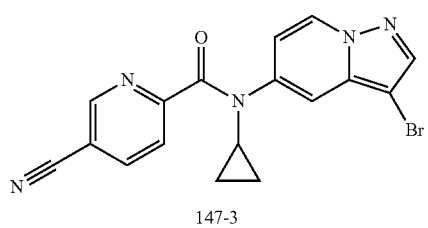

To a stirred solution of 5-cyano-N-cyclopropyl-N-(pyrazolo[1,5-a]pyridin-5-yl)picolinamide 147-2 (700 mg, 2.3 mmol) in aceotonitrile (10 mL) was added NBS (650 mg, 3.6 mmol) at room temperature and stirred for 16 h. Ethyl acetate (50 mL) was added to reaction mixture, and the organic layer was washed with water (25 mL), brine (25 mL), dried over anhyd. $Na_2SO_4$ and concentrated. The crude product was purified by silica (100-200 mesh) column chromatography with a solvent gradient mixture of 25% ethyl acetate in pet-ether to afford 500 mg (56%) of N-(3-bromopyrazolo[1,5-a]pyridin-5-yl)-5-cyano-N-cyclopropylpicolinamide 147-3 as an off-white solid. ESI-LC/MS: m/z 381.65 (M+H) & 383.69 [(M+2)+H]; $R_t$=2.57 min [Waters Acquity UPLC with Quattro-micro detector; Waters Acquity BEH C18, 1.7 µm, 2.1×50 mm column; gradient of 90:10 $H_2O$ (0.025% TFA):$CH_3CN$ (0.025% TFA) hold for 0.5 min and to 10:90 $H_2O$ (0.025% TFA):$CH_3CN$ (0.025% TFA) in 3.5 min and hold for 1.5 min with flow rate of 0.4 mL/min].

Step 4

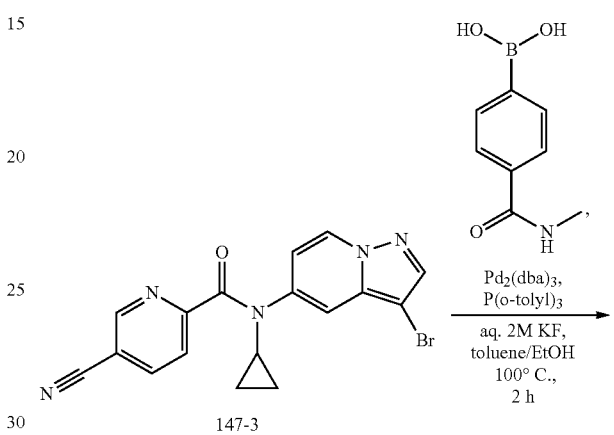

Compound 147 was prepared using the general procedure described in Suzuki Procedure H with the appropriate starting materials. Yield 9%. Yellow solid. $^1H$ NMR (400 MHz, DMSO-$d_6$): δ 8.99 (s, 1H), 8.76 (d, J=7.6 Hz, 1H), 8.46 (m, 3H), 7.90-7.95 (m, 4H), 7.63-7.65 (m, 2H), 7.05-7.07 (m, 1H), 3.30 (m, 1H), 2.81 (d, J=4.4 Hz, 3H), 0.70-0.74 (m, 2H), 0.55-0.60 (m, 2H). ESI-LC/MS: m/z 437.1 (M+H); $R_t$=3.90 min [Agilent LC with Ion trap Detector; Waters Xterra MS-C18, 2.5 µm, 4.6×50 mm column; gradient of 95:5 $H_2O$ (0.01 M Ammonium bicarbonate):$CH_3CN$ to 10:90 $H_2O$ (0.01 M Ammonium bicarbonate):$CH_3CN$ in 4 min and hold for 3 min with flow rate of 1.0 mL/min]. HPLC purity=90.1% at 226 nm; $R_t$=7.97 min [Waters HPLC with PDA; Xtimate C-18, 5.0 µm, 4.6×250 mm column; gradient of 80:20 $H_2O$ (0.01 M Ammonium acetate):$CH_3CN$ to 20:80 $H_2O$ (0.01 M Ammonium acetate):$CH_3CN$ in 20.0 minutes with flow rate of 1.0 mL/min].

Example 148

N-(5-Cyanopyridin-2-yl)-N-isopropyl-3-(6-(methyl-carbamoyl)pyridin-3-yl)pyrazolo[1,5-a]pyridine-5-carboxamide

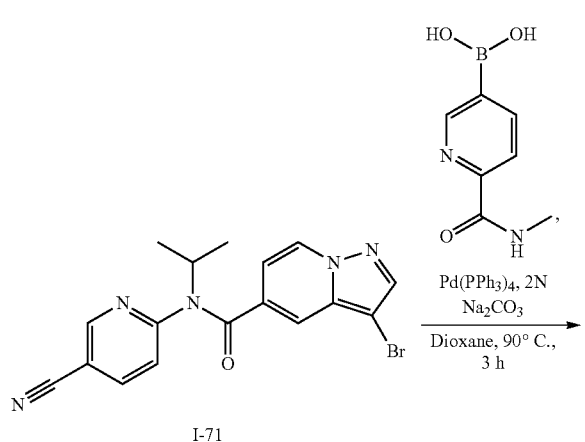

Compound 148 was prepared using the general procedure described in Suzuki Procedure G with the appropriate starting materials. Yield 12%. Yellow solid. $^1$H-NMR (400 MHz, DMSO-d$_6$): δ 8.97 (d, J=1.7 Hz, 1H), 8.77-8.80 (m, 2H), 8.68 (d, J=7.7 Hz, 1H), 8.62 (s, 1H), 8.26 (dd, J=2.7, 8.4 Hz, 1H), 8.05-8.13 (m, 2H), 7.83 (s, 1H), 7.54 (d, J=8.4 Hz, 1H), 6.76 (dd, J=1.7, 7.4 Hz, 1H), 4.90-4.93 (m, 1H), 2.86 (d, J=4.8 Hz, 3H), 1.32 (d, J=7.1 Hz, 6H). ESI-LC/MS: m/z 440.52 (M+H); R$_t$=2.36 min [Waters Acquity UPLC with Quattro micro TQD; Waters Acquity BEH C18, 1.7 μm, 2.1×50 mm column; gradient of 90:10 H$_2$O (0.025% TFA):CH$_3$CN (0.025% TFA) hold for 0.5 min to 10:90 H$_2$O (0.025% TFA):CH$_3$CN (0.025% TFA) in 3.0 min and hold for 2 min with flow rate of 0.4 mL/min]. HPLC purity=>99% at 254 nm; R$_t$=2.49 min [Waters Acquity UPLC with PDA detector; Waters Acquity BEH C18, 1.7 μm, 2.1×100 mm column; Gradient of 70:30 H$_2$O (0.025% TFA):CH$_3$CN (0.025% TFA) to 20:80 H$_2$O (0.025% TFA):CH$_3$CN (0.025% TFA) in 4 minutes and hold for 2 minutes with flow rate of 0.3 mL/min].

Example 149

N-(5-Cyano-6-methoxypyridin-2-yl)-N-cyclopropyl-3-(4-(methylcarbamoyl)phenyl)pyrazolo[1,5-a]pyridine-5-carboxamide Step 1

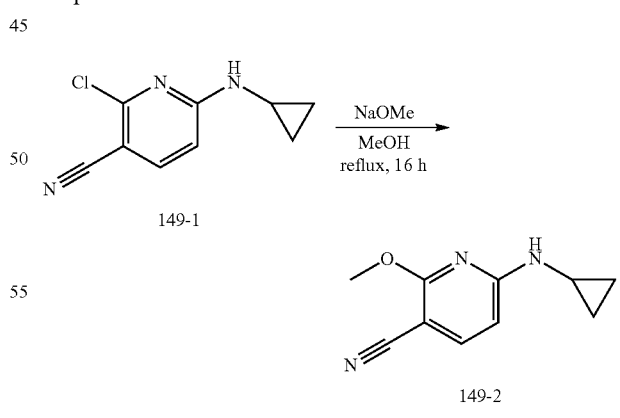

A solution mixture of 2,6-dichloronicotinonitrile (1 g, 5.78 mmol) and cyclopropylamine (1.82 mL, 26.27 mmol) in acetonitrile (10 mL) was stirred at room temperature for 16 h. The reaction mixture was diluted with water and extracted with ethyl acetate (2×50 mL). The combined organic layer was washed with water, brine solution, dried over anhydrous Na$_2$SO$_4$ and concentrated. The crude product was purified by column chromatography over silica-gel (100-200 mesh) using a solvent gradient mixture of 5% ethyl acetate in pet-ether to afford 500 mg (45%) of 2-chloro-6-(cyclopropylamino)nicotinonitrile 149-1 as a off white solid. $^1$H NMR (400 MHz, CDCl$_3$): δ 7.68 (d, J=8.4 Hz, 1H), 6.69 (d, J=8.8 Hz, 1H), 5.68 (br. s, 1H), 2.57-2.58 (m, 1H), 0.84-0.92 (m, 2H), 0.59-0.67 (m, 2H). ESI-LC/MS: m/z 194.0 (M+H) & 196.0 [(M+2)+H]; R$_t$=2.69 min [Agilent LC-MS Infinity; ZORBAX RRHT SB-C18, 1.8 μm, 2.1×50 mm column; gradient of 90:10 H$_2$O (0.1% HCOOH):CH$_3$CN (0.1% HCOOH) hold for 0.5 min and to 10:90 H$_2$O (0.1% HCOOH):CH$_3$CN (0.1% HCOOH) in 3.0 min and hold for 2.0 min with flow rate of 0.4 mL/min].

Step 2

A solution mixture of 2-chloro-6-(cyclopropylamino) nicotinonitrile (350 mg, 1.807 mmol) and sodium methoxide (979 mg, 18.13 mmol) in methanol (20 mL) was maintained at 80° C. for 16 h. The reaction mixture was diluted with water and extracted with ethyl acetate (2×150 mL). The combined organic layer was washed with water, brine solution, dried over anhydrous Na₂SO₄ and concentrated crude to afford 200 mg (58%) of 6-(cyclopropylamino)-2-methoxynicotinonitrile 149-2 as a off white solid. ¹H NMR (400 MHz, DMSO-d₆): δ 7.81 (s, 1H), 7.70 (br.s, 1H), 6.24 (br.s, 1H), 3.88 (s, 3H), 3.31 (br.s, 1H), 0.71-0.76 (m, 2H), 0.46-0.49 (m, 2H). ESI-LC/MS: m/z 189.69 (M+H); $R_t$=2.66 min [Waters Acquity UPLC with Quattro-micro detector; Waters Acquity BEH C18, 1.7 μm, 2.1×50 mm column; gradient of 90:10 H₂O (0.025% TFA):CH₃CN (0.025% TFA) hold for 0.5 min and to 10:90 H₂O (0.025% TFA):CH₃CN (0.025% TFA) in 3.5 min and hold for 1.5 min with flow rate of 0.4 mL/min].

Step 3

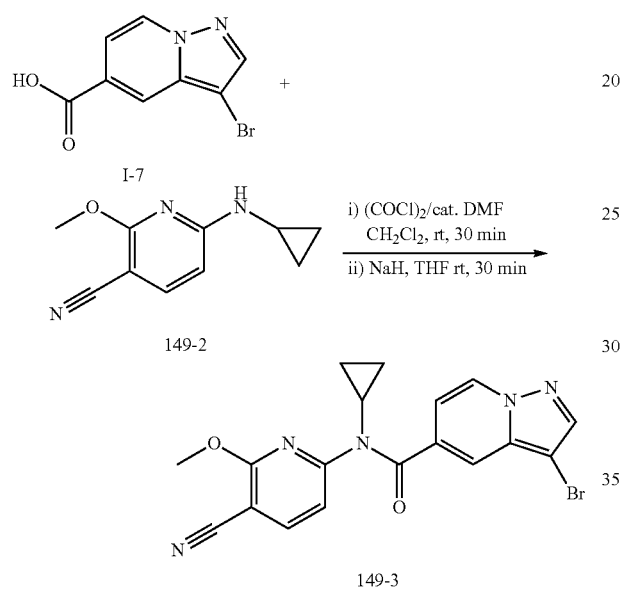

A solution of 3-bromopyrazolo[1,5-a]pyridine-5-carboxylic acid I-7 (500 mg, 2.074 mmol) in dichloromethane (10 mL) was added oxalyl chloride (0.5 mL, 5.82 mmol) followed by catalytic amount dimethylformamide at room temperature and stirred for 30 min. The resultant volatiles were distilled-off under reduced pressure to afford residue of acid chloride. The acid chloride was dissolved in dichloromethane (5 mL) was added to a mixture of NaH (60%) (829 mg, 20.708 mmol) and 6-(cyclopropylamino)-2-methoxynicotinonitrile 149-2 (395 mg, 2.087 mmol) in THF at 0° C. The resulting reaction mixture was stirred for 30 min at room temperature and diluted with ethyl acetate (50 mL). The organic layer was washed with water, brine, dried over anhydrous Na₂SO₄ and concentrated. The crude compound was purified by column chromatography over silica-gel (100-200 mesh) using a solvent gradient mixture of 30% ethyl acetate in pet-ether to afford 300 mg (35%) of 3-bromo-N-(5-cyano-6-methoxypyridin-2-yl)-N-cyclopropylpyrazolo[1,5-a]pyridine-5-carboxamide 149-3 as an off white solid. ¹H NMR (400 MHz, DMSO-d₆): δ 8.72 (d, J=2.4 Hz, 1H), 8.24-8.26 (m, 2H), 7.69 (s, 1H), 7.35 (d, J=8.4 Hz, 1H), 6.98 (dd, J=2.0, 7.2 Hz, 1H), 3.56 (s, 3H), 3.12-3.18 (m, 1H), 0.94-1.01 (m, 2H), 0.73-0.77 (m, 2H). ESI-LC/MS: m/z 412.41 (M+H) & 414.46 [(M+2)+H]; $R_t$=2.94 min [Waters Acquity UPLC with Quattro-micro detector; Waters Acquity BEH C18, 1.7 μm, 2.1×50 mm column; gradient of 90:10 H₂O (0.025% TFA):CH₃CN (0.025% TFA) hold for 0.5 min and to 10:90 H₂O (0.025% TFA):CH₃CN (0.025% TFA) in 3.5 min and hold for 1.5 min with flow rate of 0.4 mL/min].

Step 4

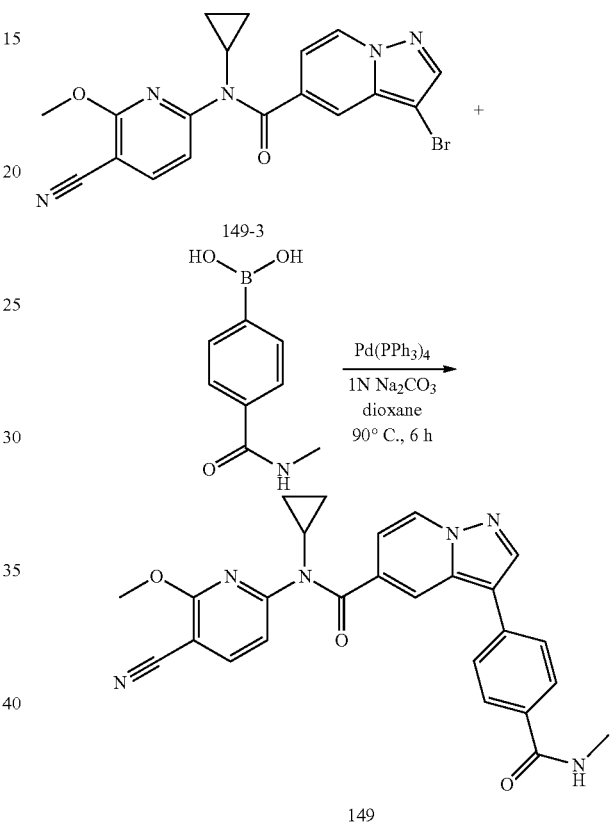

Compound 149 was prepared using the general procedure described in Suzuki Procedure G with the appropriate starting materials. Yield 23%. Yellow color solid. ¹H-NMR (400 MHz, DMSO-d₆): δ 8.75 (d, J=7.1 Hz, 1H), 8.54 (s, 1H), 8.47-8.51 (m, 1H), 8.26 (d, J=8.3 Hz, 1H), 8.09 (s, 1H), 7.92 (d, J=8.4 Hz, 2H), 7.69 (d, J=8.3 Hz, 2H), 7.37 (d, J=8.3 Hz, 1H), 6.98 (d, J=7.5 Hz, 1H), 3.59 (s, 3H), 3.16-3.18 (m, 1H), 2.80 (d, J=4.4 Hz, 3H), 0.95-0.99 (m, 2H), 0.75-0.87 (m, 2H). ESI-LC/MS: m/z 467.50 (M+H); $R_t$=2.46 min [Waters Acquity UPLC with Quattro-micro detector; Waters Acquity BEH C18, 1.7 μm, 2.1×50 mm column; gradient of 90:10 H₂O (0.025% TFA):CH₃CN (0.025% TFA) hold for 0.5 min and to 10:90 H₂O (0.025% TFA):CH₃CN (0.025% TFA) in 3.5 min and hold for 1.5 min with flow rate of 0.4 mL/min]. HPLC purity: 95.6% at 254 nm; $R_t$=2.63 min [Waters Acquity UPLC with PDA; Waters Acquity BEH C18, 1.7 μm, 2.1×100 mm column; gradient of 70:30 H₂O (0.025%

TFA):CH₃CN (0.025% TFA) to 20:80 H₂O (0.025% TFA): CH₃CN (0.025% TFA) in 4.0 min and hold for 2.0 min with flow rate of 0.3 mL/min].

Example 150

N-(5-cyanopyridin-2-yl)-N-ethyl-3-(6-[methylcarbamoyl]pyridin-3-yl)pyrazolo[1,5-a]pyridine-5-carboxamide

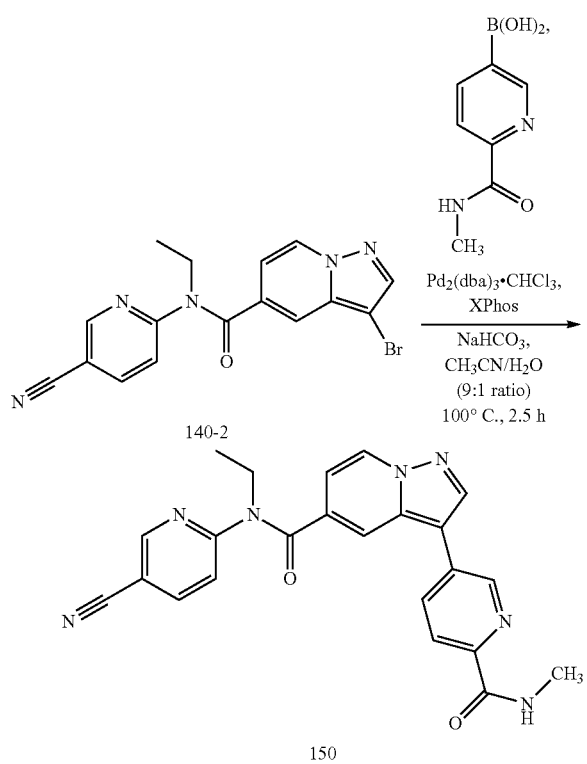

Compound 150 was prepared using the general procedure described in Suzuki Procedure I with the appropriate starting materials. Yield 63%. yellow solid. ¹H NMR (400 MHz, DMSO-d₆): δ 8.83-8.91 (m, 2H), 8.70-8.76 (m, 2H), 8.66 (s, 1H), 8.24 (dd, J=2.26, 8.53 Hz, 1H), 8.07-8.17 (m, 2H), 8.01-8.06 (m, 1H), 7.54 (dd, J=1.6, 8.53 Hz, 1H), 6.81 (dd, J=1.76, 7.15 Hz, 1H), 4.12 (q, J=7.03 Hz, 2H), 2.86 (d, J=4.89 Hz, 3H), 1.20 (t, J=7.2 Hz, 3H). ESI-LC/MS: m/z 425.8 (M+H); $R_t$=0.85 min [Agilent UHPLC 1290 coupled with API 3200; Acquity UPLC BEH C18 column, 1.7 µm, 2.1×50 mm; gradient of 98:2 H₂O (0.1% HCOOH):CH₃CN to 2:98 H₂O (0.1% HCOOH):CH₃CN for 2 min run time with 1.0 mL/min flow rate]. HPLC purity=>99% at 254 nm; $R_t$=1.44 min [Waters Acquity UPLC equipped with a Acquity UPLC HSS T3 column, 1.8 µm, 2.1×50 mm; gradient of 95:5 H₂O (0.1% HCOOH):CH₃CN to 2:98 H₂O (0.1% HCOOH):CH₃CN for 2 min run time with 1.0 mL/min flow rate].

Example 151

N-(5-fluoropyridin-2-yl)-N-isopropyl-3-(4-(methylcarbamoyl)phenyl)pyrazolo[1,5-a]pyridine-5-carboxamide Step 1

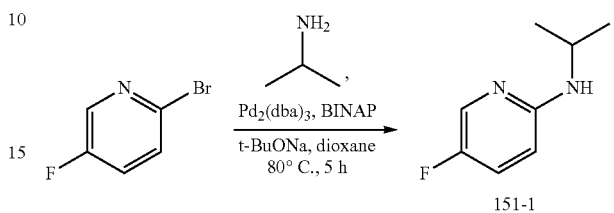

A solution mixture of 2-bromo-5-fluoropyridine (5.0 g, 28.40 mmol), t-BuONa (4.13 g, 43.02 mmol) in toluene (150 mL) was de-gassed with argon for 15 min. BINAP (622 mg, 0.999 mmol), Pd₂(dba)₃ (263 mg, 0.287 mmol) and isopropylamine (3.75 mL, 45.93 mmol) were added and stirred the reaction mixture at 90° C. for 4 h. The reaction mixture was partitioned between water (100 mL) and ethyl acetate (100 mL). The organic layer was washed with water (100 mL), brine (50 mL) and dried over anhyd. Na₂SO₄ and concentrated. The crude was purified by column chromatography over silica-gel (100-200 mesh) with a gradient mixture of 10% ethyl acetate in pet-ether as eluant to afford (3.5 g, 80%) of 5-fluoro-N-isopropylpyridin-2-amine 151-1 as a red color oil. ¹H NMR (400 MHz, DMSO-d₆): δ 7.90 (d, J=2.8 Hz, 1H), 7.27-7.32 (m, 1H), 6.41-6.44 (m, 1H), 6.27 (d, J=7.5 Hz, 1H), 3.85-3.93 (m, 1H), 1.11 (d, J=7.0 Hz, 6H). ESI-LC/MS: m/z 155.0 (M+H); $R_t$=3.56 min [Agilent LC with Ion trap Detector; Xterra MS-C18, 2.5 µm, 4.6×50 mm column; gradient of 80:20 H₂O (0.01 M ammonium bicarbonate):CH₃CN to 10:90 H₂O (0.01 M ammonium bicarbonate):CH₃CN in 5.0 min and hold for 2.0 min with flow rate of 1.0 mL/min].

Step 2

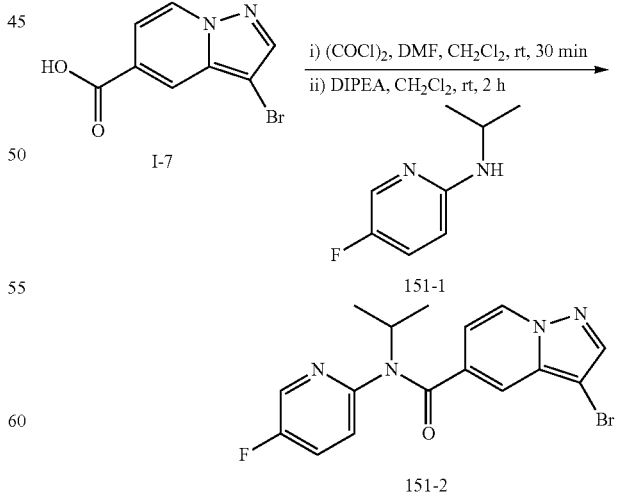

Compound 151-2 was prepared using the general procedure described in Amide Coupling-Method 1 with the appropriate starting materials. Yield 85%. Light yellow solid. ¹H NMR (400 MHz, DMSO-$d_6$): δ 8.57 (d, J=7.4 Hz, 1H), 8.46 (d, J=3.1 Hz, 1H), 8.14 (s, 1H), 7.64-7.69 (m, 1H), 7.34-7.40 (m, 1H), 7.26 (s, 1H), 6.71 (dd, J=1.7, 7.0 Hz, 1H), 4.81-4.88 (m, 1H), 1.21 (d, J=6.5 Hz, 6H). ESI-LC/MS: m/z 377.1 (M+H) & 379.1 [(M+2)+H]; $R_t$=2.85 min [Agilent LC-MS Infinity; Waters Acquity UPLC HSS T3, 1.8 μm, 2.1×50 mm column; gradient of 90:10 $H_2O$ (0.05% HCOOH+3.75 mM ammonium acetate):$CH_3CN$ (0.05% HCOOH) hold for 0.5 min and to 10:90 $H_2O$ (0.05% HCOOH+3.75 mM ammonium acetate):$CH_3CN$ (0.05% HCOOH) in 3.0 min and hold for 2.0 min with flow rate of 0.4 mL/min].

Step 3

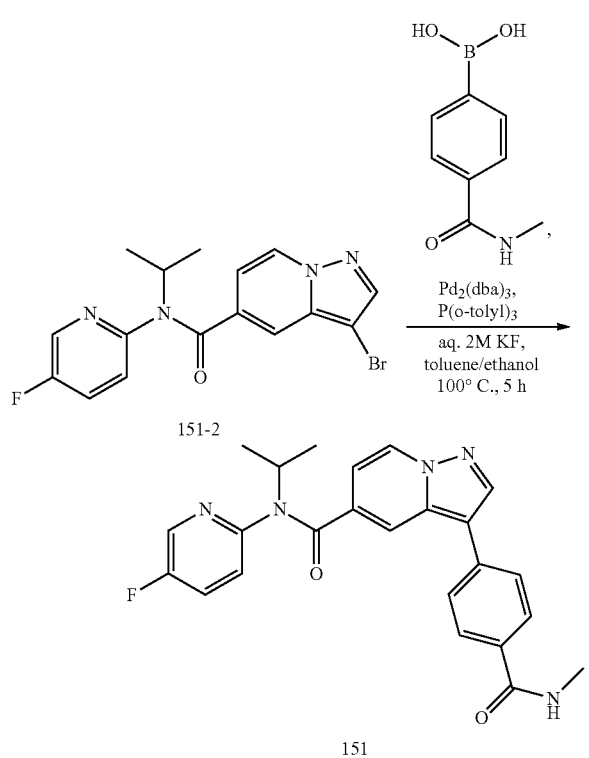 [SMILES: CNC(=O)c1ccc(B(O)O)cc1 ; CC(C)N(C(=O)c1ccn2ncc(Br)c2c1)c1ccc(F)cn1 ; CNC(=O)c1ccc(-c2cnn3ccc(C(=O)N(c4ccc(F)cn4)C(C)C)cc23)cc1]

Compound 151 was prepared using the general procedure described in Suzuki Coupling Procedure H with the appropriate starting materials. Yield 17%. Yellow solid. $^1$H-NMR (400 MHz, DMSO-$d_6$): δ 8.62 (d, J=6.4 Hz, 1H), 8.54 (d, J=3.2 Hz, 1H), 8.45-8.48 (m, 1H), 8.44 (s, 1H), 7.94 (d, J=8.4 Hz, 2H), 7.73 (td, J=3.2, 8.4 Hz, 1H), 7.67 (s, 1H), 7.54 (d, J=8.0 Hz, 2H), 7.44 (dd, J=4.4, 8.8 Hz, 1H), 6.77 (dd, J=1.2, 6.8 Hz, 1H), 4.88-4.92 (m, 1H), 2.82 (d, J=4.8 Hz, 3H), 1.24 (d, J=6.8 Hz, 6H). ESI-LC/MS: m/z 432.40 (M+H); $R_t$=2.16 min [Waters Acquity UPLC with Quattromicro detector; Waters Acquity BEH C18, 1.7 μm, 2.1×50 mm column; gradient of 90:10 $H_2O$ (0.025% TFA):$CH_3CN$ (0.025% TFA) hold for 0.5 min and to 10:90 $H_2O$ (0.025% TFA):$CH_3CN$ (0.025% TFA) in 3.0 min and hold for 2.0 min with flow rate of 0.4 mL/min]. HPLC purity: 98.8% at 254 nm; $R_t$=1.97 min [Waters Acquity UPLC with PDA; Waters Acquity BEH C18, 1.7 μm, 2.1×50 mm column; gradient of 98:02 $H_2O$ (0.025% TFA):$CH_3CN$ (0.025% TFA) to 10:90 $H_2O$ (0.025% TFA):$CH_3CN$ (0.025% TFA) in 2.5 min and hold for 3.5 min with flow rate of 0.3 mL/min].

Example 152

N-Isopropyl-3-(6-(methylcarbamoyl)pyridin-3-yl)-N-(5-(trifluoromethyl)pyridin-2-yl)pyrazolo[1,5-a]pyridine-5-carboxamide Step 1

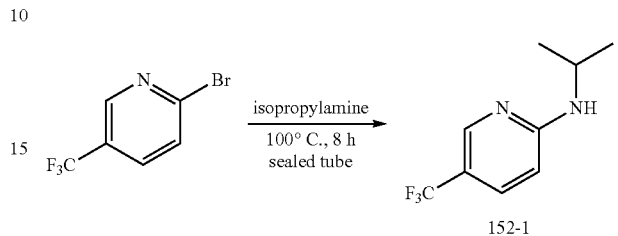

A solution of 2-bromo-5-(trifluoromethyl)pyridine (6.0 g, 26.55 mmol) and isopropyl amine (9.08 mL, 106.18 mmol) in sealed tube was maintained at 100° C. for 8 h. The reaction mixture was diluted with water (50 mL) and extracted with ethyl acetate (2×150 mL). The combined organic layer was washed with water (50 mL), brine (50 ml), dried over anhydrous $Na_2SO_4$ and concentrated. The crude product was purified by column chromatography over silica gel (100-200 mesh) using a solvent gradient of 20% ethyl acetate in pet-ether to afford 5.0 g (92%) of N-isopropyl-5-(trifluoromethyl)pyridin-2-amine 152-1 as an off white solid. $^1$H NMR (400 MHz, DMSO-$d_6$): δ 8.27 (s, 1H), 7.58 (dd, J=2.8, 9.2 Hz, 1H), 7.16 (d, J=6.8 Hz, 1H), 6.53 (d, J=8.8 Hz, 1H), 4.02-4.10 (m, 1H), 1.14 (d, J=6.4 Hz, 6H). ESI-LC/MS: m/z 205.0 (M+H); $R_t$=4.57 min [Agilent LC with Ion trap Detector; Xterra MS-C18, 2.5 μm, 4.6×50 mm column; gradient of 80:20 $H_2O$ (0.01 M Ammonium Bicarbonate):$CH_3CN$ to 10:90 $H_2O$ (0.01 M Ammonium Bicarbonate):$CH_3CN$ in 4.0 minu and hold for 3.0 min with flow rate of 1.0 mL/min].

Step 2

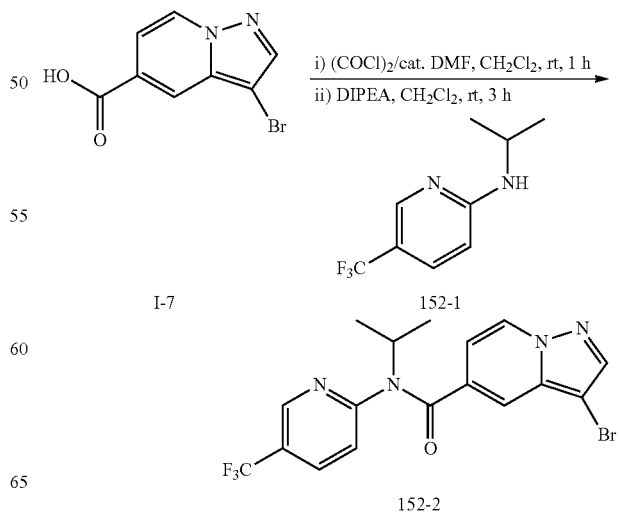

Compound 152-2 was prepared using the general procedure described in Amide Coupling-Method 1 with the appropriate starting materials. Yield 56%. Off-white solid. $^1$H NMR (400 MHz, DMSO-d$_6$) δ 8.88 (s, 1H), 8.62 (d, J=7.2 Hz, 1H), 8.13-8.17 (m, 2H), 7.52 (d, J=8.4 Hz, 1H), 7.30 (s, 1H), 6.76 (dd, J=1.6, 7.6 Hz, 1H), 4.87-4.94 (m, 1H), 1.31 (d, J=6.8 Hz, 6H).

Step 3

Example 153

N-Isopropyl-3-(4-(methylcarbamoyl)phenyl)-N-(5-(trifluoromethyl)pyridin-2-yl)pyrazolo[1,5-a]pyridine-5-carboxamide

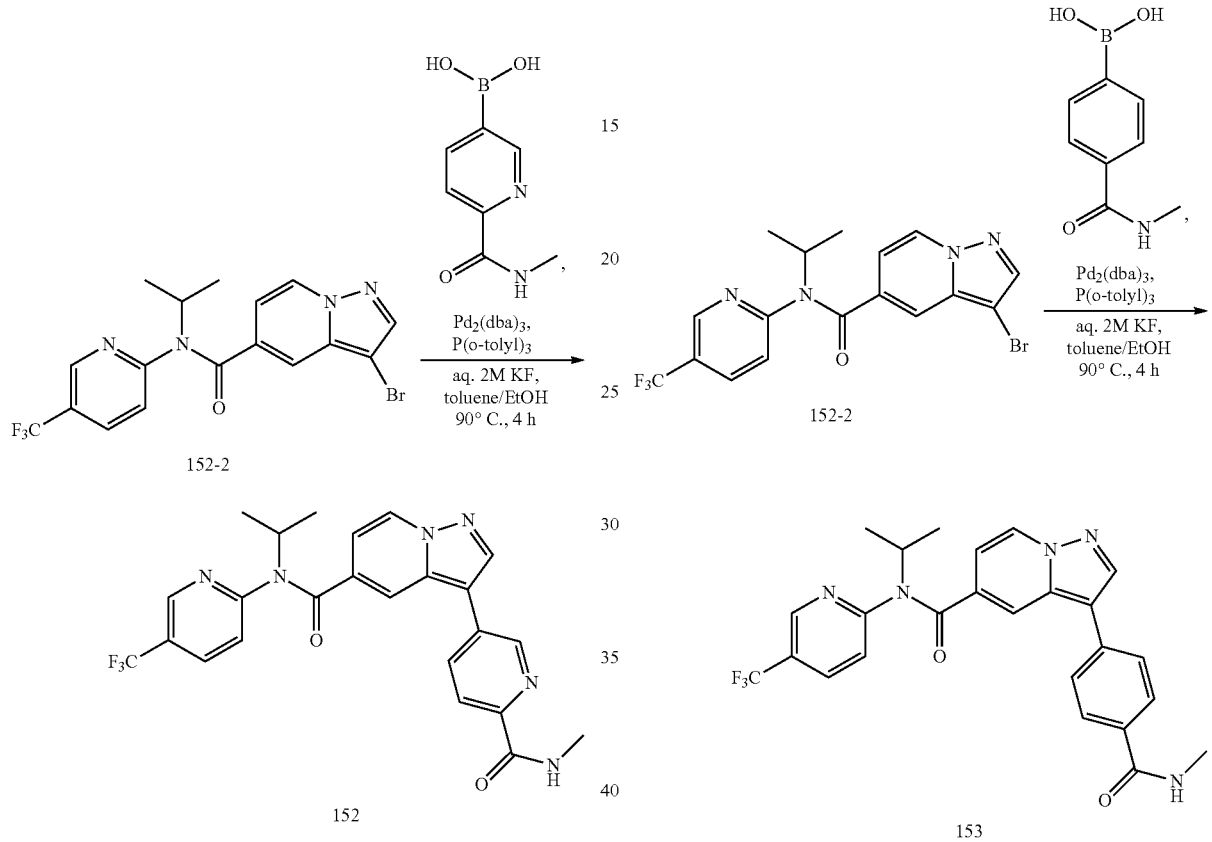

Compound 152 was prepared using the general procedure described in Suzuki Procedure H with the appropriate starting materials. Yield 13%. Light yellow solid. $^1$H NMR (400 MHz, DMSO-d$_6$): δ 8.97 (s, 1H), 8.67-8.78 (m, 3H), 8.59 (s, 1H), 8.16 (dd, J=2.5, 8.7 Hz, 1H), 8.11 (d, J=8.1 Hz, 1H), 7.97-8.01 (m, 1H), 7.74 (s, 1H), 7.56 (d, J=8.5 Hz, 1H4), 6.80 (dd, J=1.9, 7.3 Hz, 1H), 4.88-4.97 (m, 1H), 2.86 (d, J=4.7 Hz, 3H), 1.32 (d, J=6.5 Hz, 6H). ESI-LC/MS: m/z 483.3 (M+H); R$_t$=3.92 min [Agilent LC with Ion trap Detector; XBridge-C18, 3.5 μm, 4.6×75 mm column; gradient of 80:20 H$_2$O (0.005 M Ammonium Bicarbonate):CH$_3$CN to 10:90 H$_2$O (0.005 M Ammonium Bicarbonate):CH$_3$CN in 4.0 min and hold for 6.0 min with flow rate of 1.0 mL/min]. HPLC purity=98.9% at 230 nm; R$_t$=9.04 min [Waters HPLC with PDA; Symmetry Shield RP-18, 5.0 μm, 4.6×250 mm column; gradient of 90:10 H$_2$O (0.01% TFA):Methanol hold for 2.0 min and to 30:70 H$_2$O (0.01% TFA):Methanol in 3.0 min and to 10:90 H$_2$O (0.01% TFA):Methanol in 3.0 min and hold for 10.0 min with flow rate of 1.0 mL/min].

Compound 153 was prepared using the general procedure described in Suzuki Procedure H with the appropriate starting materials. Yield 13%. Light yellow solid. $^1$H NMR (400 MHz, DMSO-d$_6$): δ 8.95 (s, 1H), 8.65 (d, J=6.6 Hz, 1H), 8.40-8.55 (m, 2H), 8.19 (d, J=8.1 Hz, 1H), 7.92 (d, J=8.5 Hz, 2H), 7.65 (s, 1H), 7.56 (d, J=8.4 Hz, 1H), 7.47 (d, J=8.4 Hz, 2H), 6.81 (dd, J=1.8, 7.0 Hz, 1H), 4.90-5.00 (m, 1H), 2.82 (d, J=4.4 Hz, 3H), 1.32 (d, J=7.0 Hz, 6H). ESI-LC/MS: m/z 482.3 (M+H); R$_t$=3.84 min [Agilent LC with Ion trap Detector; XBridge-C18, 3.5 μm, 4.6×75 mm column; gradient of 80:20 H$_2$O (0.005 M Ammonium Bicarbonate):CH$_3$CN to 10:90 H$_2$O (0.005 M Ammonium Bicarbonate):CH$_3$CN in 4.0 min and hold for 6.0 min with flow rate of 1.0 mL/min]. HPLC purity=>99% at 254 nm; R$_t$=8.95 min [Waters HPLC with PDA; Symmetry Shield RP-18, 5.0 μm, 4.6×250 mm column; gradient of 90:10 H$_2$O (0.01% TFA):CH3CN hold for 2.0 min and to 10:90 H$_2$O (0.01% TFA):CH3CN in 4.0 min and hold for 12.0 minutes with flow rate of 1.0 mL/min].

Example 154

N-(5-cyanopyridin-2-yl)-N-isopropyl-3-(5-(methylcarbamoyl)pyridin-2-yl)pyrazolo[1,5-a]pyridine-5-carboxamide

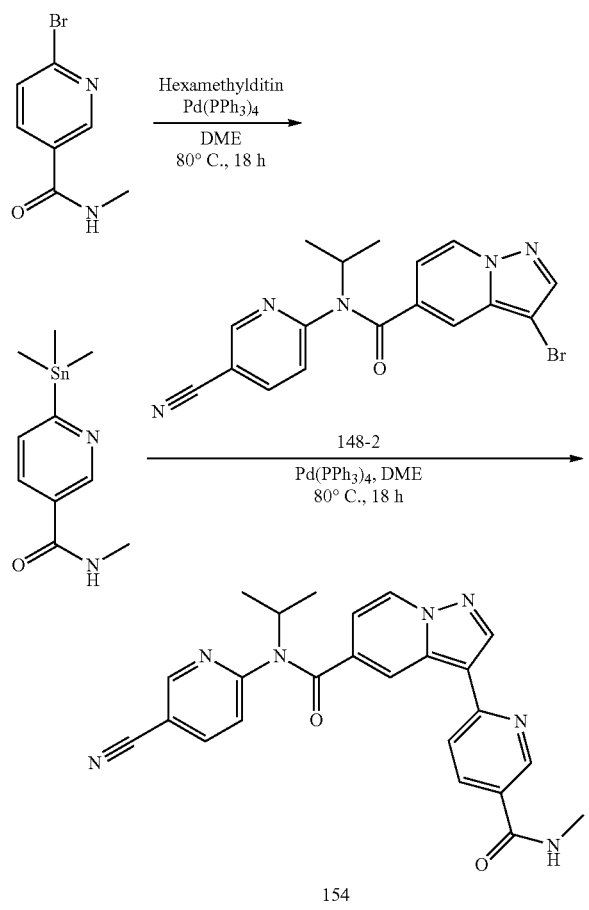

To a stirred solution of 6-bromo-N-methylpicolinamide (200 mg, 0.930 mmol), hexamethylditin (0.191 mL, 0.933 mmol) in 1,2-dimethoxyethane (20.0 mL) was degassed with argon for about 15 min. Pd(PPh$_3$)$_4$ (107.8 mg, 0.094 mmol) was added under argon atmosphere. The resulting reaction mixture was maintained at 80° C. for 16 h, allowed to room temperature and was added to a mixture of 3-bromo-N-(5-cyanopyridin-2-yl)-N-isopropylpyrazolo[1,5-a]pyridine-5-carboxamide 148-2 (357 mg, 0.929 mmol) and Pd(PPh$_3$)$_4$ (107.8 mg, 0.094 mmol). The reaction mixture was stirred at 90° C. for another 18 h. The reaction mixture was cooled to room temperature, extracted with ethyl acetate (100 mL). The organic layer was washed with water (2×100 mL), brine (50 mL), dried over Na$_2$SO$_4$ and concentrated. The crude compound was purified by column chromatography over silica gel (100-200 mesh) using a solvent gradient of 1-2% methanol in chloroform as an eluant followed by prep-TLC to afford 45 mg (11%) of N-(5-cyanopyridin-2-yl)-N-isopropyl-3-(5-(methylcarbamoyl)pyridin-2-yl)pyrazolo[1,5-a]pyridine-5-carboxamide 154 as a yellow color solid. $^1$H NMR (400 MHz, DMSO-d$_6$): δ 9.04 (d, J=2.0 Hz, 1H), 8.97 (d, J=2.0 Hz, 1H), 8.78 (s, 1H), 8.66 (d, J=7.4 Hz, 1H), 8.58-8.61 (m, 1H), 8.37 (s, 1H), 8.19-8.17 (m, 2H), 7.94 (d, J=8.3 Hz, 1H), 7.50 (d, J=8.3 Hz, 1H), 6.83 (dd, J=2.4 Hz, 7.4 Hz, 1H), 4.91-4.98 (m, 1H), 2.84 (d, J=4.4 Hz, 3H), 1.33 (d, J=6.8 Hz, 6H). ESI-LC/MS: m/z 440.3 (M+H); R$_t$=3.25 min [Agilent LC with Ion trap Detector; XBridge-C18, 3.5 µm, 4.6×75 mm column; gradient of 80:20 H$_2$O (0.005 M ammonium bicarbonate):CH$_3$CN to 10:90 H$_2$O (0.005 M ammonium bicarbonate):CH$_3$CN in 4.0 min and hold for 6.0 min with flow rate of 1.0 mL/min]. HPLC purity: 95.5% at 292 nm; R$_t$=4.29 min [Waters HPLC with PDA; XBridge C-18, 5.0 µm, 4.6×150 mm column; gradient of 80:20 H$_2$O (0.01 M ammonium bicarbonate):CH$_3$CN to 10:90 H$_2$O (0.01 M ammonium bicarbonate):CH$_3$CN in 6.0 min and hold for 6.0 min with flow rate of 1.0 mL/min].

Example 155

N-(5-Cyanopyridin-2-yl)-N-cyclobutyl-3-(5-(methylcarbamoyl)pyridin-2-yl)pyrazolo[1,5-a]pyridine-5-carboxamide

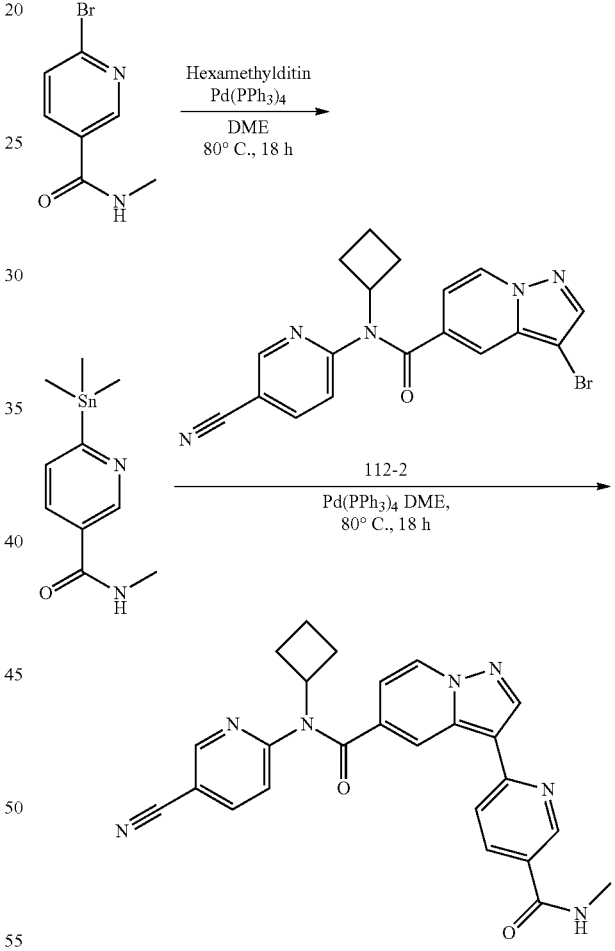

To a stirred solution of 6-bromo-N-methylpicolinamide (500 mg, 2.325 mmol), hexamethylditin (0.483 mL, 2.331 mmol) in 1,2-dimethoxyethane (50.0 mL) was degassed with argon for about 15 min. Pd(PPh$_3$)$_4$ (270 mg, 0.236 mmol) was added under argon atmosphere. The resulting reaction mixture was maintained at 80° C. for 16 h, allowed to room temperature and added to a mixture of 3-bromo-N-(5-cyanopyridin-2-yl)-N-cyclobutylpyrazolo[1,5-a]pyridine-5-carboxamide 112-2 (922 mg, 2.328 mmol) and Pd(PPh$_3$)$_4$ (270 mg, 0.236 mmol). The reaction mixture was stirred at 90° C. for 18 h. The reaction mass was cooled to room temperature, extracted with ethyl acetate (100 mL). The organic layer was washed with water, brine, dried over Na$_2$SO$_4$ and concentrated. The crude compound was purified by column chromatography over silica gel (100-200 mesh) using a solvent gradient of 1-2% methanol in chloroform as an eluant followed by prep-TLC to afford 60 mg (6%) of N-(5-cyanopyridin-2-yl)-N-cyclobutyl-3-(5-(methylcarbamoyl)pyridin-2-yl)pyrazolo[1,5-a]pyridine-5-carboxamide 155 as a yellow color solid. $^1$H NMR (300 MHz, DMSO-d$_6$): δ 9.04 (d, J=1.7 Hz, 1H), 8.97 (d, J=1.8 Hz, 1H), 8.79 (s, 1H), 8.67 (d, J=7.3 Hz, 1H), 8.58-8.60 (m, 1H), 8.39 (d, J=1.1 Hz, 1H), 8.29 (dd, J=2.6, 8.5 Hz, 1H), 8.18 (dd, J=2.6, 8.5 Hz, 1H), 7.95 (d, J=8.5 Hz, 1H), 7.60 (d, J=8.4 Hz, 1H), 6.86 (dd, J=2.2, 7.4 Hz, 1H), 4.85-5.00 (m, 1H), 2.84 (d, J=4.4 Hz, 3H), 2.25-2.27 (m, 2H), 2.08-2.15 (m, 2H), 1.63-1.67 (m, 2H). ESI-LC/MS: m/z 452.3 (M+H); R$_t$=3.32 min [Agilent LC with Ion trap Detector; XBridge-C18, 3.5 μm, 4.6×75 mm column; gradient of 80:20 H$_2$O (0.005 M ammonium bicarbonate):CH$_3$CN to 10:90 H$_2$O (0.005 M ammonium bicarbonate):CH$_3$CN in 4.0 min and hold for 3.0 min with flow rate of 1.0 mL/min]. HPLC purity: 98.2% At 254 nm; R$_t$=1.78 min [Waters Acquity UPLC with PDA; Waters Acquity UPLC BEH C18, 1.7 μm, 2.1×100 mm column; gradient of 80:20 H$_2$O (0.025% TFA):CH$_3$CN (0.025% TFA) to 20:80 H$_2$O (0.025% TFA):CH$_3$CN (0.025% TFA) in 3.0 min and hold for 3.0 min with flow rate of 0.3 mL/min].

Example 156

N-(5-fluoropyridin-2-yl)-N-isopropyl-3-(6-(methylcarbamoyl)pyridin-3-yl)pyrazolo[1,5-a]pyridine-5-carboxamide

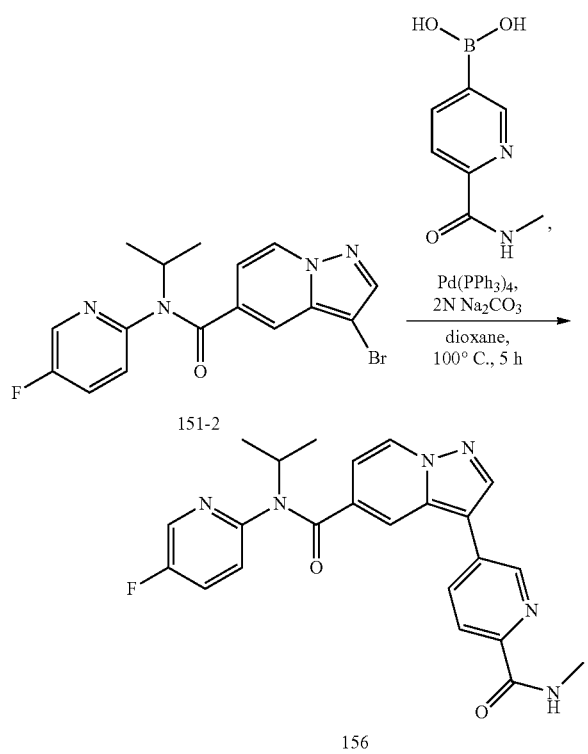 [SMILES: CNC(=O)c1ccc(B(O)O)cn1 ; CC(C)N(C(=O)c1ccn2ncc(Br)c2c1)c1ccc(F)cn1 ; CNC(=O)c1ccc(-c2cnn3ccc(C(=O)N(c4ccc(F)cn4)C(C)C)cc23)cn1]

Compound 156 was prepared using the general procedure described in Suzuki Procedure G with the appropriate starting materials. Yield 2%. Yellow solid. $^1$H-NMR (400 MHz, CDCl$_3$): δ 8.62 (d, J=1.4 Hz, 1H), 8.38 (d, J=2.8 Hz, 1H), 8.26-8.31 (m, 2H), 8.17 (s, 1H), 8.00 (brs, 1H), 7.85 (dd, J=2.4, 8.3 Hz, 1H), 7.73 (s, 1H), 7.29 (m, 1H), 6.94-6.99 (m, 1H), 6.77 (dd, J=2.0, 7.3 Hz, 1H), 5.01-5.07 (m, 1H), 3.08 (d, J=4.9 Hz, 3H), 1.31 (d, J=6.8 Hz, 6H). ESI-LC/MS: m/z 431.3 (M−H); R$_t$=3.41 min [Agilent LC with Ion trap Detector; XBridge-C18, 3.5 μm, 4.6×75 mm column; gradient of 80:20 H$_2$O (0.005 M ammonium bicarbonate):CH$_3$CN to 10:90 H$_2$O (0.01 M ammonium bicarbonate):CH$_3$CN in 4.0 min and hold for 3.0 min with flow rate of 1.0 mL/min]. HPLC purity: 94.6% at 234 nm; R$_t$=5.29 min [Waters HPLC with PDA; XBridge-C18, 5.0 μm, 4.6×150 mm column; gradient of 80:20 H$_2$O (0.01 M ammonium bicarbonate):CH$_3$CN to 10:90 H$_2$O (0.01 M ammonium bicarbonate):CH$_3$CN in 6.0 min and hold for 12.0 min with flow rate of 1.0 mL/min].

Example 157

N-ethyl-3-(6-(methylcarbamoyl)pyridin-3-yl)-N-(5-(trifluoromethyl)pyridin-2-yl)pyrazolo[1,5-a]pyridine-5-carboxamide

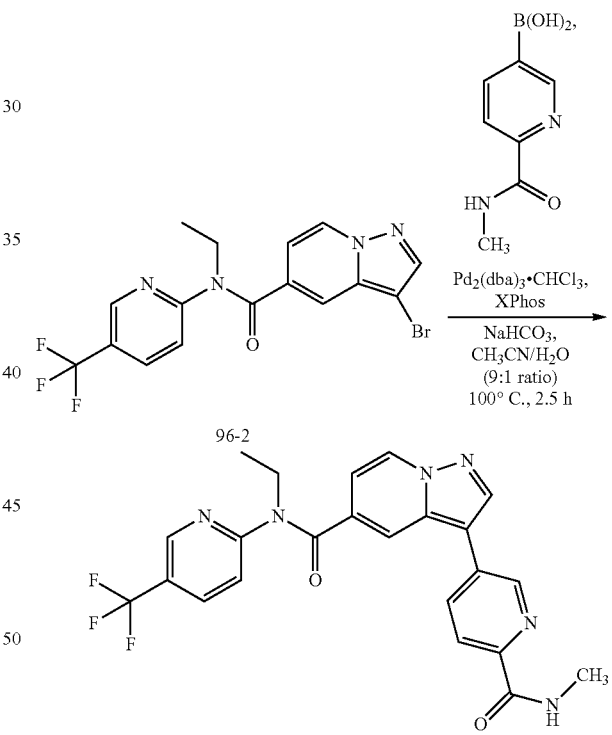

Compound 157 was prepared using the general procedure described in Suzuki Procedure I with the appropriate starting materials. Yield 58%. yellow solid. $^1$H NMR (400 MHz, DMSO-d$_6$): δ 8.81-8.88 (m, 2H), 8.70-8.77 (m, 2H), 8.65 (s, 1H), 8.18 (dd, J=2.26, 8.66 Hz, 1H), 8.03-8.11 (m, 2H), 7.93-7.98 (m, 1H), 7.56 (d, J=8.53 Hz, 1H), 6.84 (dd, J=1.76, 7.28 Hz, 1H), 4.13 (q, J=7.15 Hz, 2H), 2.86 (d, J=4.89 Hz, 3H), 1.22 (t, J=6.96 Hz, 3H). ESI-LC/MS: m/z 468.7 (M+H); R$_t$=0.97 min [Agilent UHPLC 1290 coupled with API 3200; Acquity UPLC BEH C18 column, 1.7 μm, 2.1×50 mm; gradient of 98:2 H$_2$O (0.1% HCOOH):CH$_3$CN to 2:98 H$_2$O (0.1% HCOOH):CH$_3$CN for 2 min run time with 1.0 mL/min flow rate]. HPLC purity=98.7% at 254 nm; R$_t$=1.68 min [Waters Acquity UPLC equipped with a Acquity UPLC HSS T3 column, 1.8 μm, 2.1×50 mm; gradient of 95:5 H$_2$O (0.1% HCOOH):CH$_3$CN to 2:98 H$_2$O (0.1% HCOOH):CH$_3$CN for 2 min run time with 1.0 mL/min flow rate].

Example 158

N-(5-cyanopyridin-2-yl)-N-ethyl-3-(4-(methylsulfonyl)phenyl)pyrazolo[1,5-a]pyridine-5-carboxamide

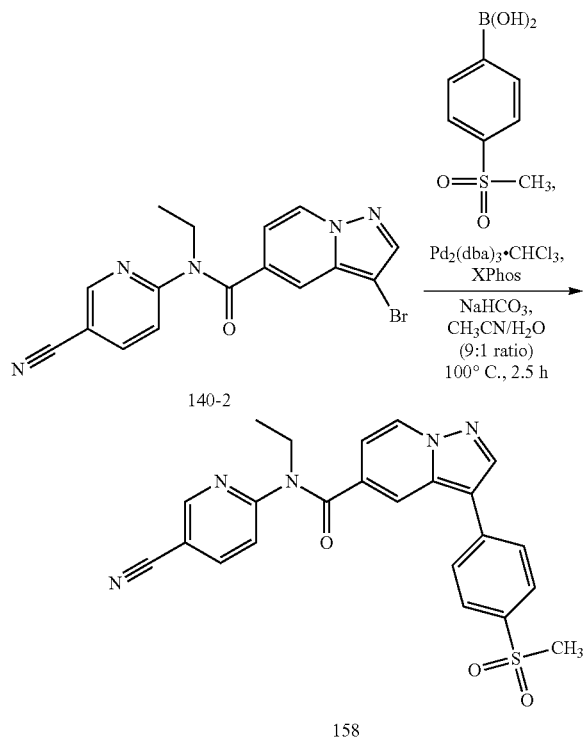

Compound 158 was prepared using the general procedure described in Suzuki Procedure I with the appropriate starting materials. Yield 53%. yellow solid. $^1$H NMR (400 MHz, DMSO-d$_6$): δ 8.88 (d, J=2.13 Hz, 1H), 8.71 (d, J=7.15 Hz, 1H), 8.59 (s, 1H), 8.25 (dd, J=2.26, 8.53 Hz, 1H), 8.01 (s, 2H), 7.99 (s, 1H), 7.82 (d, J=8.41 Hz, 2H), 7.55 (d, J=8.53 Hz, 1H), 6.81 (dd, J=1.63, 7.28 Hz, 1H), 4.12 (q, J=6.99 Hz, 2H), 3.26 (s, 3H), 1.21 (t, J=7.03 Hz, 3H). ESI-LC/MS: m/z 445.8 (M+H); R$_t$=0.89 min [Agilent UHPLC 1290 coupled with API 3200; Acquity UPLC BEH C18 column, 1.7 μm, 2.1×50 mm; gradient of 98:2 H$_2$O (0.1% HCOOH):CH$_3$CN to 2:98 H$_2$O (0.1% HCOOH):CH$_3$CN for 2 min run time with 1.0 mL/min flow rate]. HPLC purity=98.1% at 254 nm; R$_t$=1.57 min [Waters Acquity UPLC equipped with a Acquity UPLC HSS T3 column, 1.8 μm, 2.1×50 mm; gradient of 95:5 H$_2$O (0.1% HCOOH):CH$_3$CN to 2:98 H$_2$O (0.1% HCOOH):CH$_3$CN for 2 min run time with 1.0 mL/min flow rate].

Example 159

N-ethyl-N-(5-fluoropyridin-2-yl)-3-(6-(methylcarbamoyl)pyridin-3-yl)pyrazolo[1,5-a]pyridine-5-carboxamide

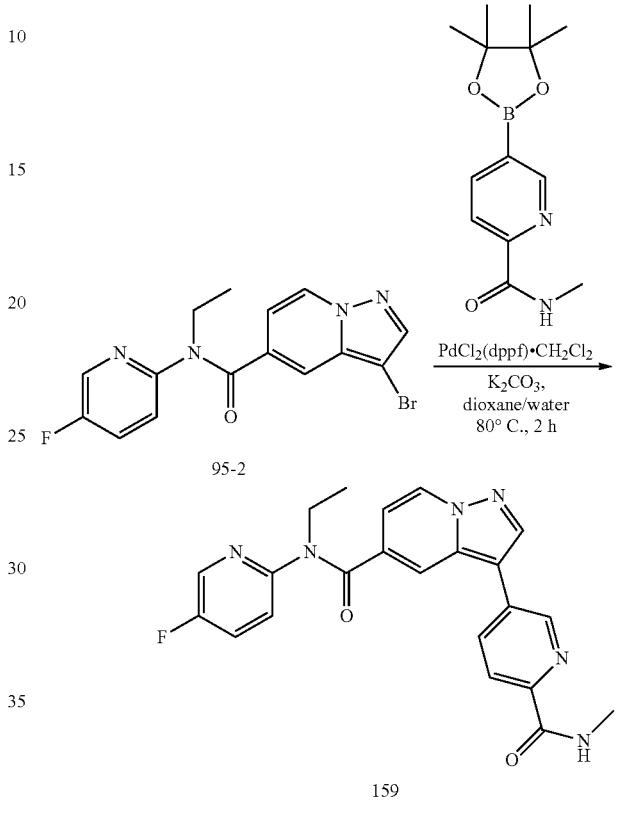

To a stirred solution of 3-bromo-N-ethyl-N-(5-fluoropyridin-2-yl)pyrazolo[1,5-a]pyridine-5-carboxamide 95-2 (500 mg, 1.377 mmol) in dioxane:water (3:1) (10.0 mL), N-methyl-5-(4,4,5,5-tetramethyl-1,3,2-dioxaborolan-2-yl) picolinamide (723.3 mg, 2.762 mmol), K$_2$CO$_3$ (419 mg, 3.036 mmol) were added and degassed with argon for about 15 min. PdCl$_2$(dppf)CH$_2$Cl$_2$ complex (225.3 mg, 0.275 mmol) was added under argon atmosphere. The resulting reaction mixture was maintained at 80° C. for 2 h, cooled to room temperature and filtered through celite. The filtrate was partitioned between water (100 mL) and ethyl acetate (100 mL). The ethyl acetate layer was washed with water, brine, dried over anhydrous Na$_2$SO$_4$ and concentrated. The crude compound was purified by column chromatography over silica gel (100-200 mesh) using a solvent gradient of 60-70 ethyl acetate in pet-ether as eluant to afford 300 mg (52%) of N-ethyl-N-(5-fluoropyridin-2-yl)-3-(6-(methylcarbamoyl)pyridin-3-yl)pyrazolo[1,5-a]pyridine-5-carboxamide 159 as a pale-yellow color solid. $^1$H-NMR (400 MHz, DMSO-d$_6$): δ 8.82 (s, 1H), 8.67-8.74 (m, 2H), 8.62 (s, 1H), 8.46 (d, J=3.0 Hz, 1H), 8.09 (s, 2H), 7.87 (s, 1H), 7.73 (td, J=3.3, 8.4 Hz, 1H), 7.42 (dd, J=3.6, 8.8 Hz, 1H), 6.77 (dd, J=1.8, 7.3 Hz, 1H), 4.01 (q, J=7.0 Hz, 2H), 2.86 (d, J=4.8 Hz, 3H), 1.17 (t, J=7.0 Hz, 3H). ESI-LC/MS: m/z 417.3 (M−H); R$_t$=3.23 min [Agilent LC with Ion trap Detector; XBridge-C18, 3.5 μm, 4.6×75 mm column; gradient of 80:20 H$_2$O (0.005 M ammonium bicarbonate):CH$_3$CN to 20:80 H₂O (0.01 M ammonium bicarbonate):CH₃CN in 4.0 min and hold for 3.0 min with flow rate of 1.0 mL/min]. HPLC purity: 98.1% at 254 nm; R$_f$=1.92 min [Waters Acquity UPLC with PDA; Waters Acquity UPLC BEH C18, 1.7 μm, 2.1×100 mm column; gradient of 90:10 H₂O (0.025% TFA):CH₃CN (0.025% TFA) to 10:90 H₂O (0.025% TFA):CH₃CN (0.025% TFA) in 4.0 min and hold for 2.0 min with flow rate of 0.3 mL/min].

Example 160

N-cyclobutyl-3-(4-(methylcarbamoyl)phenyl)-N-(5-(trifluoromethyl)pyridin-2-yl)pyrazolo[1,5-a]pyridine-5-carboxamide Step 1

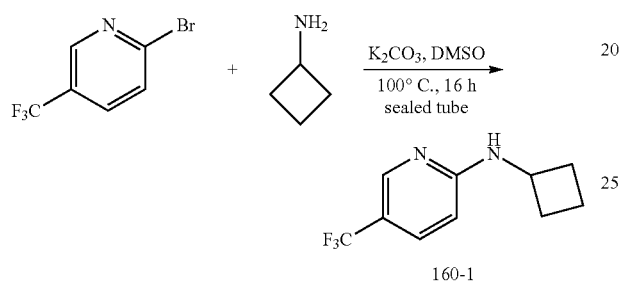

To a solution of 2-bromo-5-(trifluoromethyl)pyridine (10.0 g, 44.24 mmol), K₂CO₃ (8.3 g, 60.05 mmol) in DMSO (50 mL) was added cyclobutylamine (4.51 mL, 52.82 mmol) and maintained at 100° C. for 16 h in sealed tube. The reaction mixture was diluted with water and extracted with ethyl acetate (2×150 mL). The combined organic layers were washed with water, brine solution, dried over anhydrous Na₂SO₄ and concentrated. The crude product was purified by column chromatography over silica gel (100-200 mesh) using a solvent gradient of 20% ethyl acetate in pet-ether to afford 8.0 g (84%) of N-cyclobutyl-5-(trifluoromethyl)pyridin-2-amine 160-1 as a white solid. ¹H-NMR (400 MHz, DMSO-d₆): 8.26 (s, 1H), 7.55-7.63 (m, 2H), 6.50 (d, J=11.6 Hz, 1H), 4.30-4.33 (m, 1H), 2.23-2.31 (m, 2H), 1.82-1.93 (m, 2H), 1.64-1.72 (m, 2H). ESI-LC/MS: m/z 217.06 (M+H); R$_f$=2.85 min [Waters Acquity UPLC with SQD; Waters Acquity UPLC BEH C18, 1.7 μm, 2.1×50 mm column; gradient of 98:02 H₂O (0.1% HCOOH):CH₃CN (0.1% HCOOH) hold for 0.8 min and to 45:55 H₂O (0.1% HCOOH):CH₃CN (0.1% HCOOH) in 2.0 min and hold for 1.0 min and to 0:100 H₂O (0.1% HCOOH):CH₃CN (0.1% HCOOH) in 0.5 min and hold for 1.5 min with flow rate of 0.4 mL/min].

Step 2

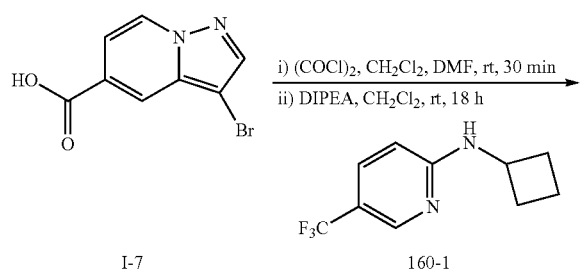

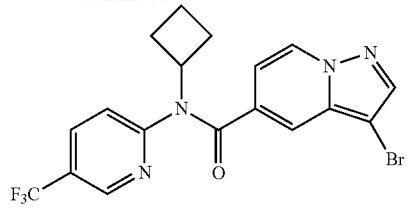

Compound 160-2 was prepared using the general procedure described in Amide Coupling-Method 1 with the appropriate starting materials. Yield 69%. yellow solid. ¹H NMR (400 MHz, DMSO-d₆): δ 8.92-8.87 (m, 1H), 8.63 (dd, J=13.08, 16.92 Hz, 1H), 8.24 (dd, J=2.36, 8.46 Hz, 1H), 7.61 (d, J=8.34 Hz, 1H), 7.36-7.32 (m, 1H), 6.78 (dd, J=1.77, 7.23 Hz, 1H), 4.99-4.88 (m, 1H), 2.28-2.19 (m, 2H), 2.09 (pd, J=2.59, 9.80 Hz, 2H), 1.74-1.55 (m, 2H).

Step 3

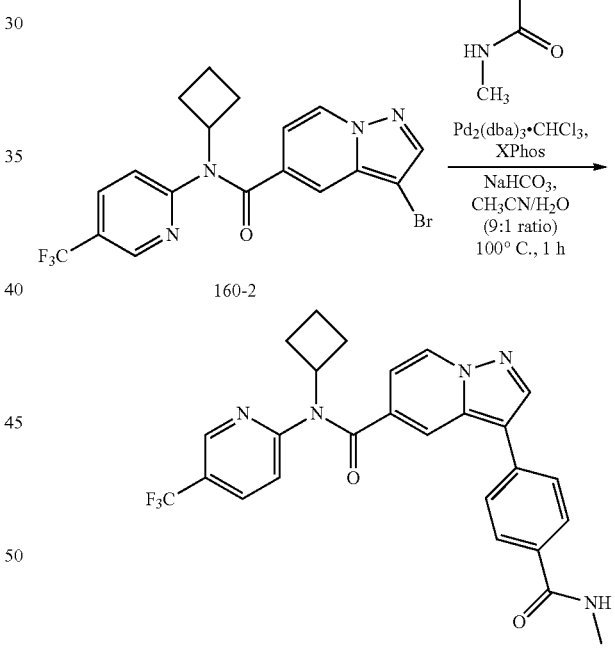

Compound 160 was prepared using the general procedure described in Suzuki Procedure I with the appropriate starting materials. Yield 72%. yellow solid. ¹H NMR (400 MHz, DMSO-d₆): δ 8.95 (s, 1H), 8.66 (d, J=6.99 Hz, 1H), 8.46 (s, 2H), 8.27 (d, J=9.21 Hz, 1H), 7.93 (d, J=7.58 Hz, 2H), 7.71-7.62 (m, 2H), 7.50 (d, J=7.61 Hz, 2H), 6.83 (d, J=7.16 Hz, 1H), 5.04-4.91 (m, 1H), 2.83 (s, 3H), 2.24 (d, J=7.62 Hz, 2H), 2.16-2.03 (m, 3H), 1.75-1.56 (m, 2H). ESI-LC/MS: m/z 494 (M+H); R$_f$=1.01 min [Agilent UHPLC 1290 coupled with API 3200; Acquity UPLC BEH C18 column, 1.7 μm, 2.1×50 mm; gradient of 98:2 H₂O (0.1% HCOOH):

CH₃CN to 2:98 H₂O (0.1% HCOOH):CH₃CN for 2 min run time with 1.0 mL/min flow rate]. HPLC purity=99.7% at 254 nm; R$_t$=1.74 min [Waters Acquity UPLC equipped with a Acquity UPLC HSS T3 column, 1.8 μm, 2.1×50 mm; gradient of 95:5 H₂O (0.1% HCOOH):CH₃CN to 2:98 H₂O (0.1% HCOOH):CH₃CN for 2 min run time with 1.0 mL/min flow rate].

Example 161

N N-cyclobutyl-3-(6-(methylcarbamoyl)pyridin-3-yl)-N-(5-(trifluoromethyl)pyridin-2-yl)pyrazolo[1,5-a]pyridine-5-carboxamide

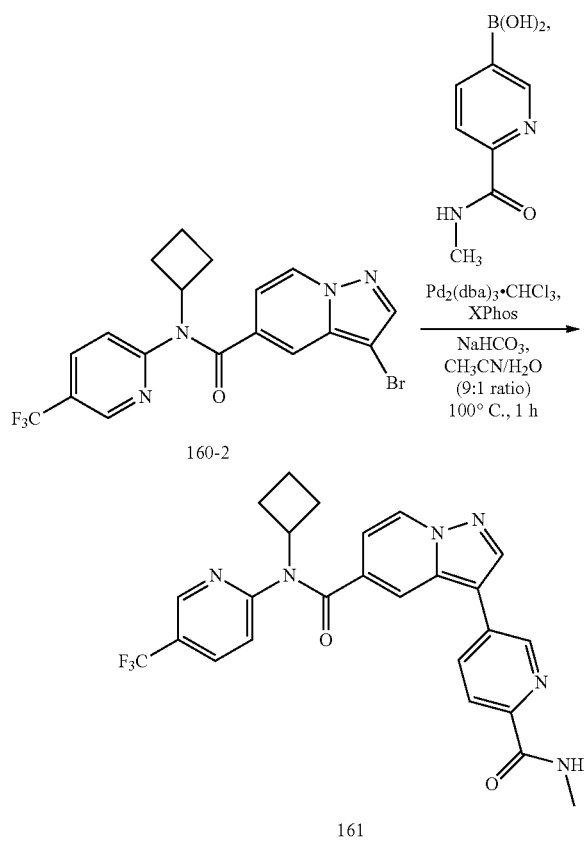 [SMILES: O=C(c1ccn2ncc(Br)c2c1)N(c1ccc(C(F)(F)F)cn1)C1CCC1 ; CNC(=O)c1ccc(B(O)O)cn1 ; CNC(=O)c1ccc(-c2cnn3ccc(C(=O)N(c4ccc(C(F)(F)F)cn4)C4CCC4)cc23)cn1]

Compound 161 was prepared using the general procedure described in Suzuki Procedure I with the appropriate starting materials. Yield 42%. yellow solid. ¹H NMR (400 MHz, DMSO-d₆): δ 8.94-8.92 (m, 1H), 8.81 (dd, J=0.86, 2.31 Hz, 1H), 8.76-8.69 (m, 2H), 8.62 (s, 1H), 8.27 (dd, J=2.52, 8.52 Hz, 1H), 8.11 (dd, J=0.85, 8.18 Hz, 1H), 8.02 (dd, J=2.25, 8.17 Hz, 1H), 7.77 (dd, J=0.97, 1.87 Hz, 1H), 7.64 (d, J=8.39 Hz, 1H), 6.86 (dd, J=1.81, 7.25 Hz, 1H), 5.03-4.90 (m, 1H), 2.87 (d, J=4.85 Hz, 3H), 2.29-2.18 (m, 2H), 2.16-2.03 (m, 2H), 1.75-1.56 (m, 2H). ESI-LC/MS: m/z 494.6 (M+H); R$_t$=1.01 min [Agilent UHPLC 1290 coupled with API 3200; Acquity UPLC BEH C18 column, 1.7 μm, 2.1×50 mm; gradient of 98:2 H₂O (0.1% HCOOH):CH₃CN to 2:98 H₂O (0.1% HCOOH):CH₃CN for 2 min run time with 1.0 mL/min flow rate]. HPLC purity=>99% at 254 nm; R$_t$=1.78 min [Waters Acquity UPLC equipped with a Acquity UPLC HSS T3 column, 1.8 μm, 2.1×50 mm; gradient of 95:5 H₂O (0.1% HCOOH):CH₃CN to 2:98 H₂O (0.1% HCOOH):CH₃CN for 2 min run time with 1.0 mL/min flow rate].

Example 162

N-(5-cyano-6-(2-hydroxyethoxy)pyridin-2-yl)-N-ethyl-3-(4-(methylcarbamoyl)phenyl)pyrazolo[1,5-a]pyridine-5-carboxamide Step 1

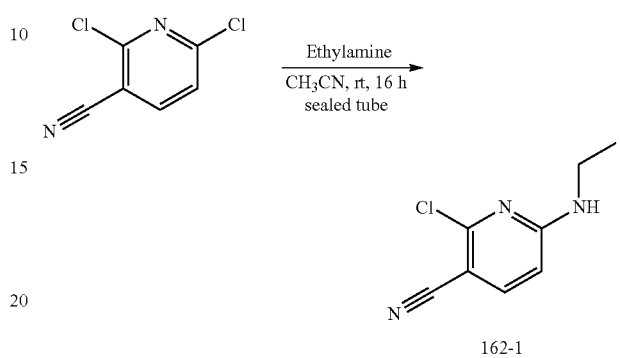

To a solution of 2,6-dichloronicotinonitrile (500 mg, 2.89 mmol) in acetonitrile, 2M ethanamine in THF (3.61 mL, 7.23 mmol) were added to a 20 mL microwave vial. The reaction mixture was stirred at room temperature for 16 h. The solvent was evaporated under vacuum. The crude compound was purified by column chromatography over silica gel (100-200 mesh) using a solvent gradient of 50% ethyl acetate in cyclohexane as eluant to afford 371 mg (71%) of yellow solid. The desired isomer was confirmed by 2D NOESY. ¹H NMR (400 MHz, CDCl₃): δ 7.56 (d, J=8.64 Hz, 1H), 6.27 (d, J=8.63 Hz, 1H), 5.14 (s, 1H), 3.37 (p, J=6.86 Hz, 2H), 1.26 (t, J=7.23 Hz, 3H).

Step 2

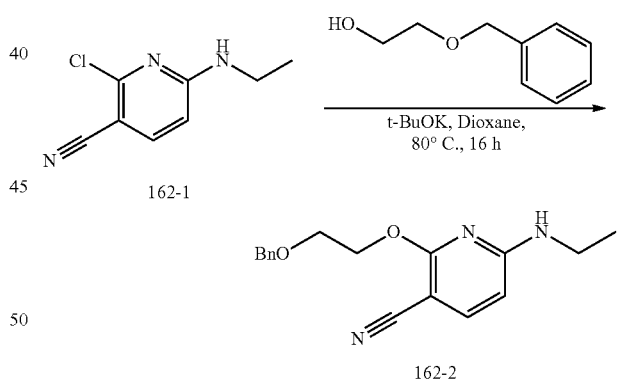

Potassium tert-butoxide (458 mg, 4.08 mmol) was added to 2-(benzyloxy)ethanol (0.726 ml, 5.10 mmol) in 15.0 mL of dioxane in a microwave vial and stirred at room temperature for 15 min. Subsequently, 2-chloro-6-(ethylamino) nicotinonitrile (370.7 mg, 2.041 mmol) in 15.0 mL of dioxane was added to the reaction mixture and it was stirred at 80° C. for 16 h. Reaction mixture was cooled to room temperature and diluted with water (50 mL) and extracted with ethyl acetate (2×50 mL). The organic layer was washed with water (50 mL), 1M hydrochloric acid (25 mL), sat. sodium bicarbonate solution (25 mL), sat. NaCl (25 mL) and dried with anhydrous sodium sulfate. The crude compound was purified by column chromatography over silica gel (100-200 mesh) using a solvent gradient of 50% ethyl acetate in cyclohexane as eluant to afford 228 mg (75%) of 2-(2-(benzyloxy)ethoxy)-6-(ethylamino)nicotinonitrile 162-2. ESI-LC/MS: m/z 299.7 [(M+2)+H]; R$_f$=1.13 min. [Agilent UHPLC 1290 coupled with API 3200; Acquity UPLC BEH C18 column, 1.7 μm, 2.1×50 mm; gradient of 98:2 H$_2$O (0.1% HCOOH):CH$_3$CN to 2:98 H$_2$O (0.1% HCOOH):CH$_3$CN for 2 min run time with 1.0 mL/min flow rate].

Step 3

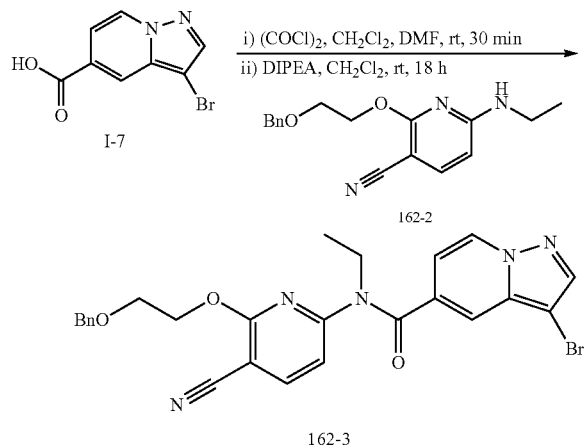

Compound 162-3 was prepared using the general procedure described in amide coupling-Method 1 with the appropriate starting materials. Yield 18%. $^1$H NMR (400 MHz, CDCl$_3$): δ 8.25 (d, J=7.23 Hz, 1H), 7.94 (s, 1H), 7.69 (d, J=8.08 Hz, 2H), 7.34 (d, J=4.49 Hz, 4H), 6.62-6.56 (m, 2H), 4.56 (s, 2H), 4.35 (t, J=11.35, 12.39 Hz, 2H), 4.12 (q, J=7.05 Hz, 2H), 3.71 (t, J=10.27, 12.81 Hz, 2H), 1.28 (t, J=7.06 Hz, 3H).

Step 4

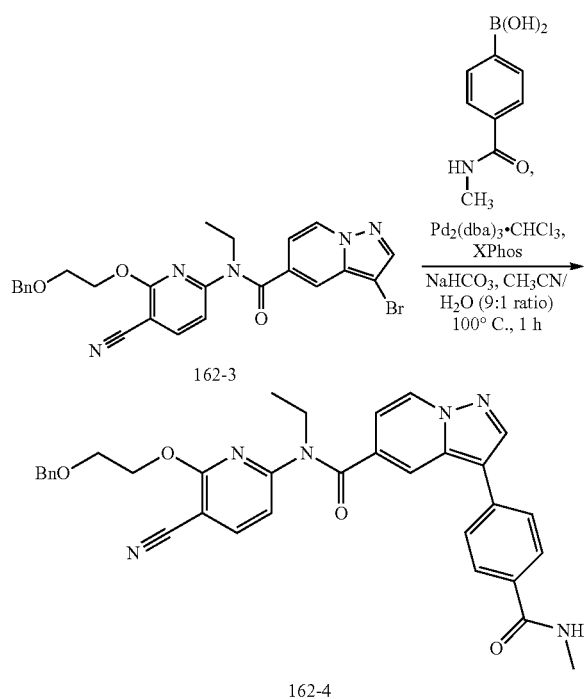

Compound 162-4 was prepared using the general procedure described in Suzuki Procedure I with the appropriate starting materials. Yield 55%. yellow solid. $^1$H NMR (400 MHz, CDCl$_3$): δ 8.34 (d, J=7.39 Hz, 1H), 8.18 (s, 1H), 7.88 (s, 1H), 7.83 (d, J=8.24 Hz, 2H), 7.70 (d, J=8.09 Hz, 1H), 7.46 (d, J=8.24 Hz, 2H), 7.33 (d, J=4.34 Hz, 4H), 7.28 (d, J=3.78 Hz, 3H), 6.70 (dd, J=1.65, 7.30 Hz, 1H), 6.57 (d, J=8.06 Hz, 1H), 6.24 (d, J=4.78 Hz, 1H), 4.58 (s, 2H), 4.39 (t, J=5.44, 8.70 Hz, 2H), 4.12 (q, J=7.04 Hz, 2H), 3.74 (dt, J=4.71, 9.43 Hz, 2H), 3.01 (d, J=4.79 Hz, 3H), 1.28 (t, J=7.05 Hz, 3H). ESI-LC/MS: m/z 575 (M+H); R$_f$=1.08 min. [Agilent UHPLC 1290 coupled with API 3200; Acquity UPLC BEH C18 column, 1.7 μm, 2.1×50 mm; gradient of 98:2 H$_2$O (0.1% HCOOH):CH$_3$CN to 2:98 H$_2$O (0.1% HCOOH):CH$_3$CN for 2 min run time with 1.0 mL/min flow rate].

Step 5

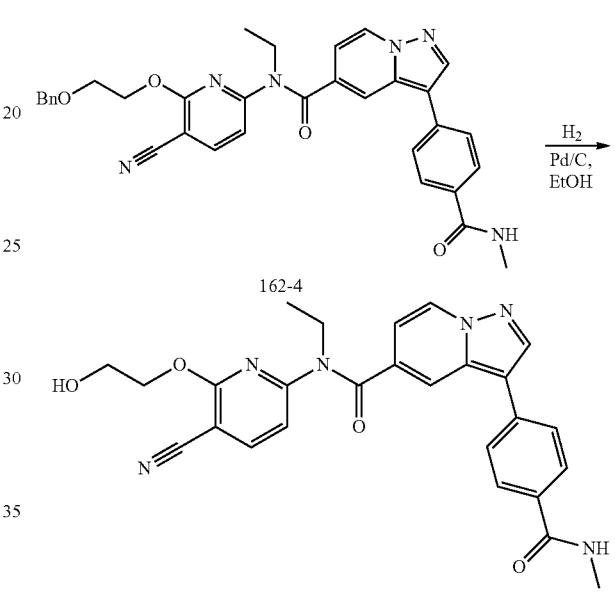

N-(6-(2-(benzyloxy)ethoxy)-5-cyanopyridin-2-yl)-N-ethyl-3-(4 (methylcarbamoyl)phenyl)pyrazolo[1,5-a]pyridine-5-carboxamide 162-4 (95 mg, 0.165 mmol) and palladium on carbon (1.759 mg, 0.017 mmol) were added to ethanol in a 8 ml vial. Hydrogen gas was bubbled into the reaction mixture for 16 h under constant stirring. Reaction mixture filtered through celite bed and the filterate was evaporated to get yellow residue. And the residue was purified by auto-prep (solvent system: 35-95% ACN in 8 mins, LOW pH SUNFIRE). The fractions were concentrated and lypholised to give 9.6 mg (12%) of N-(5-cyano-6-(2-hydroxyethoxyl)pyridin-2-yl)-N-ethyl-3-(4-(methylcarbamoyl)phenyl)pyrazolo[1,5-a]pyridine-5-carboxamide 162 as fluorescent yellow solid. $^1$H NMR (400 MHz, DMSO-d$_6$): δ 8.68 (d, J=7.18 Hz, 1H), 8.52 (s, 1H), 8.47 (d, J=4.57 Hz, 1H), 8.16 (d, J=8.17 Hz, 1H), 8.01 (s, 1H), 7.93 (d, J=8.36 Hz, 2H), 7.65 (d, J=8.35 Hz, 2H), 7.05 (d, J=8.18 Hz, 1H), 6.78 (dd, J=1.70, 7.22 Hz, 1H), 4.86 (t, J=5.35 Hz, 1H), 4.15 (t, J=9.98, 11.12 Hz, 2H), 4.08 (q, J=6.82 Hz, 2H), 3.53 (q, J=5.18 Hz, 2H), 2.82 (d, J=4.48 Hz, 3H), 1.23 (t, J=6.99 Hz, 3H). ESI-LC/MS: m/z 485.8 (M+H); R$_f$=0.81 min. [Agilent UHPLC 1290 coupled with API 3200; Acquity UPLC BEH C18 column, 1.7 μm, 2.1×50 mm; gradient of 98:2 H$_2$O (0.1% HCOOH):CH$_3$CN to 2:98 H$_2$O (0.1% HCOOH):CH$_3$CN for 2 min run time with 1.0 mL/min flow rate]. HPLC purity=98% at 254 nm; R$_t$=1.44 min [Waters Acquity UPLC equipped with a Acquity UPLC HSS T3 column, 1.8 μm, 2.1×50 mm; gradient of 95:5 H$_2$O (0.1% HCOOH):

CH₃CN to 2:98 H₂O (0.1% HCOOH):CH₃CN for 2 min run time with 1.0 mL/min flow rate].

Example 163

4-(5-(N-(5-Cyanopyridin-2-yl)-N-methylsulfamoyl)pyrazolo[1,5-a]pyridin-3-yl)-N-methyl benzamide Step 1

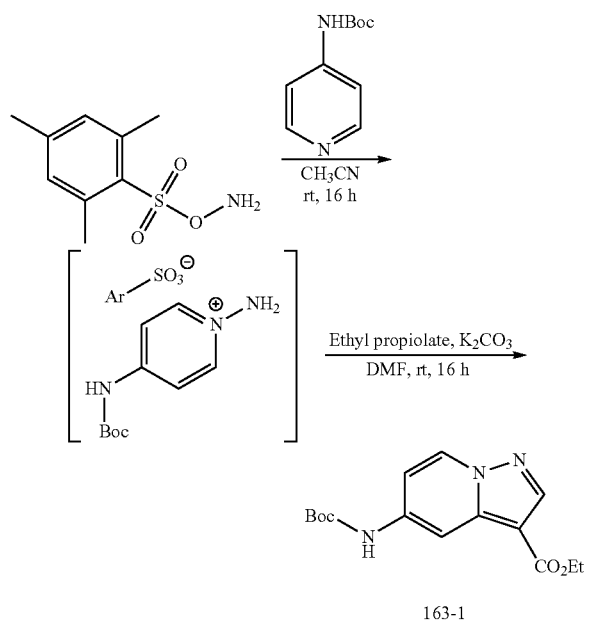

A solution mixture of tert-butyl pyridin-4-ylcarbamate (23.0 g, 118.55 mmol) was treated with O-(mesitylsulfonyl)hydroxylamine (25.49 g, 118.55 mmol) in acetonitrile (180 mL) at room temperature for overnight in a sealed tube and then solvent was evaporated under reduced pressure. The resulting crude compound was dissolved in DMF (250 mL), added to a mixture of K₂CO₃ (40.9 g, 296.37 mmol) and ethyl propiolate (11.99 mL, 118.55 mmol). The resulting reaction mixture was stirred at room temperature for 16 h. The reaction mixture was quenched with ice-cold water, the precipitated solid was collected by filtration and dried. The crude compound was purified by column chromatography over silica gel (100-200 mesh) using a solvent gradient of 20-30% ethyl acetate in pet-ether as eluant to afford 10.5 g (29%) of ethyl 5-((tert-butoxycarbonyl)amino)pyrazolo[1,5-a]pyridine-3-carboxylate 163-1 as an off-white solid. ¹H NMR (300 MHz, DMSO-d₆): 10.01 (s, 1H), 8.70 (d, J=7.2 Hz, 1H), 8.35 (d, J=2.1, 1H), 8.29 (s, 1H), 7.12 (dd, J=2.4, 7.5 Hz, 2H), 4.26 (q, J=6.9 Hz, 2H), 1.51 (s, 9H), 1.32 (t, J=6.9 Hz, 3H).

Step 2

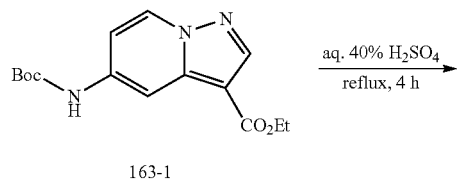

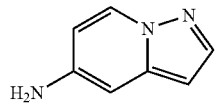

Ethyl 5-((tert-butoxycarbonyl)amino)pyrazolo[1,5-a]pyridine-3-carboxylate 163-1 (10.0 g, 32.751 mmol) was treated with 40% H₂SO₄ (80 mL) at reflux temperature for 4 h. The reaction mixture was taken up in water (100 mL), pH was adjusted to 8.0 with aq. 20% NaOH solution. The aq. layer was extract with ethyl acetate (3×100 mL). The combined extracts were washed with brine (2×50 mL), dried over anhyd. Na₂SO₄ and concentrated to afford 2.5 g (57%) of pyrazolo[1,5-a]pyridin-5-amine 162-2 as an pale brown solid. ¹H NMR (400 MHz, DMSO-d₆): δ 8.25 (d, J=5.4 Hz, 1H), 7.65 (d, J=1.5 Hz, 1H), 6.40 (d, J=1.8 Hz, 1H), 6.31 (dd, J=1.8, 5.4 Hz, 1H), 5.98 (d, J=1.2 Hz, 1H), 5.56 (s, 2H). ESI-LC/MS: m/z 133.9 (M+H); $R_f$=1.53 min. [Agilent LC with Ion trap Detector; XBridge-C18, 3.5 μm, 4.6×75 mm column; gradient of 80:20 H₂O (0.005 M Ammonium Bicarbonate): CH₃CN to 10:90 H₂O (0.01 M Ammonium Bicarbonate):CH₃CN in 4.0 minutes and hold for 3.0 min with flow rate of 1.0 mL/min].

Step 3

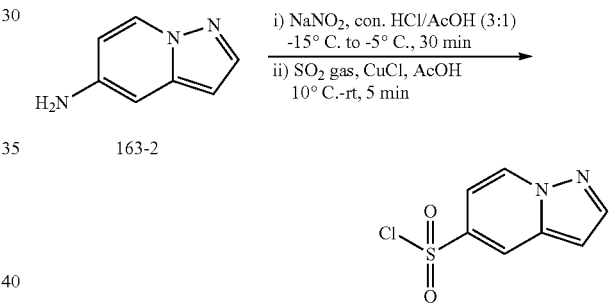

A solution of NaNO₂ (114 mg, 1.652 mmol) dissolved in water (0.3 mL) was added drop-wise to a suspension of pyrazolo[1,5-a]pyridin-5-amine 163-2 (200 mg, 1.503 mmol) in con. HCl:CH₃COOH (3:1) (1.0 mL) at −10° C. and the reaction mixture was maintained between −15° C. to −5° C. for 45 min. CuCl (37 mg, 0.373 mmol) was added to the solution of SO₂ gas in acetic acid (1.0 mL) (prepared by purging SO₂ gas in aceticacid for 20 min) and purged SO₂ gas further 10 more minutes. To this resulting solution was added above prepared solution (diazonium salt of 163-2) as drop-wise at 0° C. and the resulting reaction mixture was stirred for 5 min. The reaction mixture was poured to ice cold water (25 mL), extracted the product into ethyl acetate (2×20 mL), and the organic layer was washed with water, brine solution, dried over anhyd. Na₂SO₄, concentrated under reduced pressure to afford 130 mg (crude) of pyrazolo[1,5-a]pyridine-5-sulfonyl chloride 163-3 as a brown gummy mass. ESI-LC/MS: m/z 217.02 (M+H) & 218.97 [(M+2)+H]; $R_f$=1.88 min [Waters Acquity UPLC with Quattro-micro detector; Waters Acquity BEH C18, 1.7 μm, 2.1×50 mm column; gradient of 90:10 H₂O (0.1% HCOOH):CH₃CN (0.1% HCOOH) hold for 0.6 min and to 10:90 H₂O (0.1% HCOOH):CH₃CN (0.1% HCOOH) in 2.0 min and hold for 3.0 min with flow rate of 0.4 mL/min].

Step 4

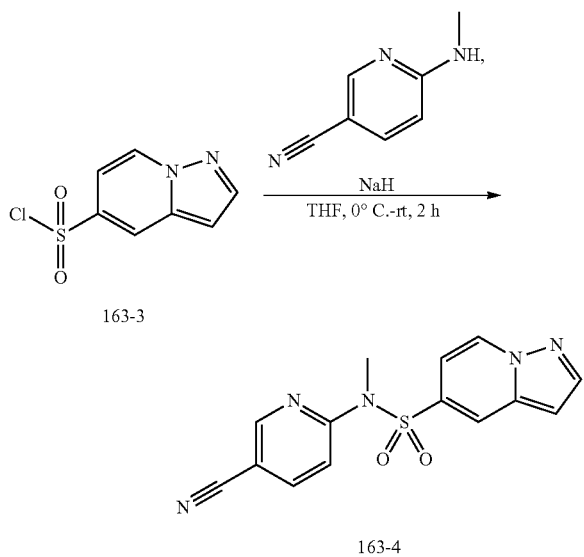

To a suspension of NaH (60%) (16.5 mg, 0.413 mmol) in THF (2.0 mL) at 0° C. was added 6-(methylamino)nicotinonitrile (50 mg, 0.375 mmol) and stirred for 5 min and then was added a solution of pyrazolo[1,5-a]pyridine-5-sulfonyl chloride 163-3 (97 mg, 0.447 mmol) in THF (1.0 mL). The resulting reaction mixture was stirred at rt for 2 h. Quenched the reaction mixture by adding brine solution (10 mL), extracted the product into ethyl acetate 2×25 mL). The combined extracts were washed with water (20 mL), brine solution (20 ML), dried over anhyd. $Na_2SO_4$, concentrated under reduced pressure. This crude compound on purification by pre-TLC gave 15 mg (13% over two steps) of N-(5-cyanopyridin-2-yl)-N-methylpyrazolo[1,5-a]pyridine-5-sulfonamide 164-4 as a off-white solid. ESI-LC/MS: m/z 314.06 (M+H); $R_t$=1.85 min. [Waters HPLC with SQD; Waters X-Bridge BEH C18, 2.5 μm, 3.0×50 mm column; gradient of 90:10 $H_2O$ (0.05% TFA):$CH_3CN$ (0.05% TFA) hold for 0.6 min and to 10:90 $H_2O$ (0.05% TFA):$CH_3CN$ (0.05% TFA) in 2.0 min and hold for 3.0 min with flow rate of 0.7 mL/min].

Step 5

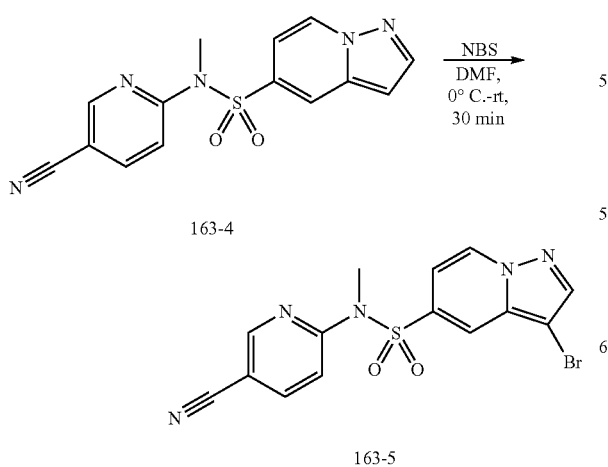

NBS (28.4 mg, 0.159 mmol) was added to a solution of pyrazolo[1,5-a]pyridine-5-sulfonyl chloride 163-4 (50 mg, 0.159 mmol) in DMF (1.0 mL) at rt and stirred for 30 min. The reaction mixture was diluted with water and extracted the product into ethyl acetate (2×20 mL). The organic layer was washed with water, brine, dried over anhydrous $Na_2SO_4$, and concentrated. The crude compound was purified by preparative-TLC to afford 45 mg (72%) of 3-bromo-N-(5-cyanopyridin-2-yl)-N-methylpyrazolo[1,5-a]pyridine-5-sulfonamide 163-5 as an off-white solid. $^1$H NMR (400 MHz, $CDCl_3$): δ 8.58 (d, J=2.0 Hz, 1H), 8.43 (d, J=7.6 Hz, 1H), 8.04-8.07 (m, 2H), 7.95 (dd, J=2.0, 8.8 Hz, 1H), 7.81 (d, J=8.8 Hz, 1H), 6.82 (dd, J=2.0, 7.2 Hz, 1H), 3.45 (s, 3H). ESI-LC/MS: m/z 392 (M+H) & 394 [(M+2)+H]; $R_t$=2.59 min. [Agilent RRLC; Waters Acquity CSH C18, 1.7 μm, 2.1×50 mm column; gradient of 98:02 $H_2O$ (0.1% HCOOH):$CH_3CN$ (0.1% HCOOH) hold for 0.5 min and to 55:45 $H_2O$ (0.1% HCOOH):$CH_3CN$ (0.1% HCOOH) in 1.2 min and to 25:75 $H_2O$ (0.1% HCOOH):$CH_3CN$ (0.1% HCOOH) in 2.5 min and to 0:100 $H_2O$ (0.1% HCOOH):$CH_3CN$ (0.1% HCOOH) in 3.2 min hold for 1.8 min with flow rate of 0.4 mL/min].

Step 6

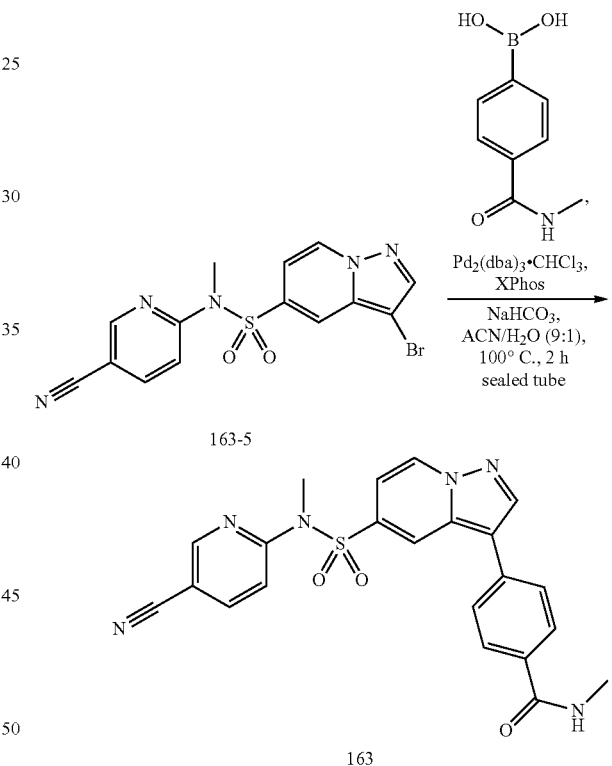

Compound 163 was prepared using the general procedure described in Suzuki Procedure I with the appropriate starting materials. Yield 49%. yellow solid. $^1$H NMR (400 MHz, DMSO-$d_6$): δ 8.90 (d, J=7.6 Hz, 1H), 8.81 (d, J=2.4 Hz, 1H), 8.66 (s, 1H), 8.44-8.50 (m, 1H), 8.32-8.36 (m, 2H), 7.98 (d, J=7.6 Hz, 2H), 7.77 (d, J=8.0 Hz, 2H), 7.73 (d, J=8.8 Hz, 1H), 7.08 (dd, J=2.0, 7.6 Hz, 1H), 3.45 (s, 3H), 2.82 (d, J=4.4 Hz, 3H). ESI-LC/MS: m/z 447.18 (M+H); $R_t$=1.81 min. [Waters Acquity UPLC with Quattro-micro detector; Waters Acquity BEH C18, 1.7 μm, 2.1×50 mm column; gradient of 90:10 $H_2O$ (0.1% HCOOH):$CH_3CN$ (0.1% HCOOH) hold for 0.6 min and to 10:90 $H_2O$ (0.1% HCOOH):$CH_3CN$ (0.1% HCOOH) in 2.0 min and hold for 3.0 min with flow rate of 0.4 mL/min]. HPLC purity=>99% at 254 nm; $R_t$=3.83 min [Waters HPLC with PDA; XBridge

Example 164

4-(5-(N-(5-Cyanopyridin-2-yl)-N-cyclopropylsulfamoyl)pyrazolo[1,5-a]pyridin-3-yl)-N-methylbenzamide Step 1

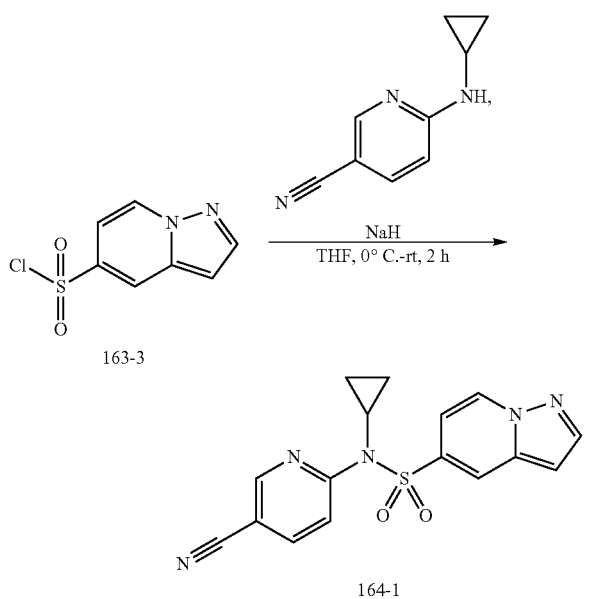

To a suspension of NaH (60%) (384 mg, 9.615 mmol) in THF (5.0 mL) was added a solution of 6-(cyclopropylamino)nicotinonitrile (913 mg, 5.73 mmol) at 0° C. and stirred for 10 min. To this reaction mixture was added a solution of pyrazolo[1,5-a]pyridine-5-sulfonyl chloride 163-3 (630 mg, 2.86 mmol) in THF (20.0 mL) and the resulting reaction mixture was stirred at rt for 2 h. The reaction mixture was quenched by adding brine solution (25 mL), extracted the product in to ethyl acetate (2×25 mL). The combined extracts were washed with 2 N HCl (25 mL), water (25 mL), brine (25 mL), dried over anhydrous Na₂SO₄, and the solvent was distilled off under reduced pressure. The crude compound was passed through a column of silica gel (100-200 mesh) using a solvent gradient of 30% ethyl acetate in pet-ether as eluant and obtained 200 mg (crude) of N-(5-cyanopyridin-2-yl)-N-cyclopropylpyrazolo[1,5-a]pyridine-5-sulfonamide 164-1 as a brown color gummy solid. The crude product was used as such in step without further purification.

Step 2

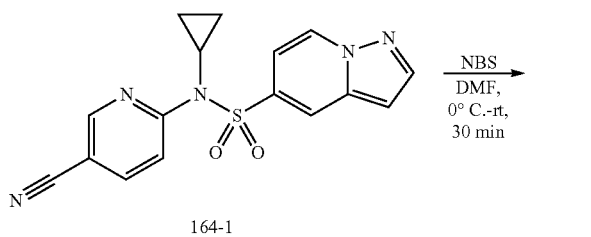

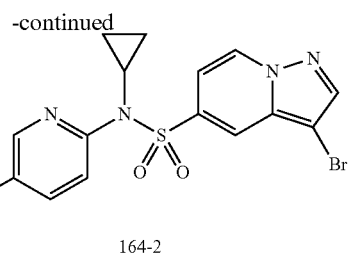

NBS (105 mg, 0.589 mmol) was added to a solution N-(5-cyanopyridin-2-yl)-N-cyclopropylpyrazolo[1,5-a]pyridine-5-sulfonamide 164-1 (200 mg, 0.589 mmol) in DMF (2.0 mL) at rt and stirred for 30 min. The reaction mixture was diluted with water and extracted the product into ethyl acetate (50 mL). The organic layer was washed with water (25 mL), brine (25 mL), dried over anhydrous Na₂SO₄, and concentrated to afford 300 mg (17% over three steps) of 3-bromo-N-(5-cyanopyridin-2-yl)-N-cyclopropylpyrazolo[1,5-a]pyridine-5-sulfonamide 164-2 as an off-white solid. ESI-LC/MS: m/z 418.09 (M+H) & 420.09 [(M+2)+H]; R$_f$=2.14 min. [Waters Acquity UPLC with Quattro-micro detector; Waters Acquity BEH C18, 1.7 μm, 2.1×50 mm column; gradient of 90:10 H₂O (0.1% HCOOH):CH₃CN (0.1% HCOOH) hold for 0.6 min and to 10:90 H₂O (0.1% HCOOH):CH₃CN (0.1% HCOOH) in 2.0 min and hold for 3.0 min with flow rate of 0.4 mL/min].

Step 3

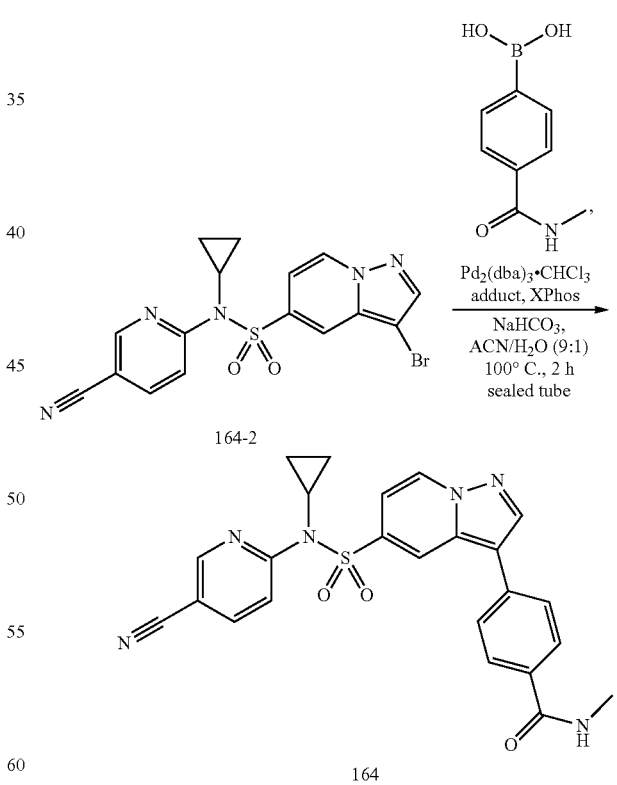

Compound 164 was prepared using the general procedure described in Suzuki Procedure I with the appropriate starting materials. Yield 21%. yellow solid. ¹H NMR (400 MHz, DMSO-d₆): δ 8.93 (d, J=7.6 Hz, 1H), 8.87 (s, 1H), 8.67 (s, 1H), 8.44-8.50 (m, 1H), 8.40 (dd, J=2.4, 8.8 Hz, 1H), 8.32

(s, 1H), 7.98 (d, J=7.6 Hz, 2H), 7.74 (d, J=8.0, 2H), 7.64 (d, J=8.8 Hz, 1H), 7.13 (dd, J=1.6, 7.6 Hz, 1H), 3.00-3.06 (m, 1H), 2.82 (d, J=4.4 Hz, 3H), 0.935-0.949 (m, 2H), 0.68-0.699 (m, 2H). ESI-LC/MS: m/z 473.0 (M+H); $R_t$=6.10 min [Agilent LC with Ion trap Detector; XBridge-C18, 3.5 μm, 4.6×75 mm column; gradient of 95:05 $H_2O$ (0.005 M Ammonium Bicarbonate):$CH_3CN$ hold for 1.0 min and to 85:15 $H_2O$ (0.005 M Ammonium Bicarbonate):$CH_3CN$ in 2.0 min and to 45:55 $H_2O$ (0.005 M Ammonium Bicarbonate):$CH_3CN$ in 4.5 min and to 0:100 $H_2O$ (0.005 M Ammonium Bicarbonate):$CH_3CN$ in 6.0 min hold for 3.0 min with flow rate of 1.0 mL/min]. HPLC purity=>99% at 254 nm; $R_t$=4.30 min [Waters HPLC with PDA; XBridge C-18, 3.5 μm, 4.6×100 mm column; gradient of 90:10 $H_2O$ (0.01 M Ammonium acetate):$CH_3CN$ to 05:95 $H_2O$ (0.01 M Ammonium acetate):$CH_3CN$ in 4.0 min and hold for 11.0 min with flow rate of 1.0 mL/min].

Example 165

4-(5-(N-(5-cyanopyridin-2-yl)-N-cyclopropylsulfamoyl)pyrazolo[1,5-a]pyridin-3-yl)benzamide

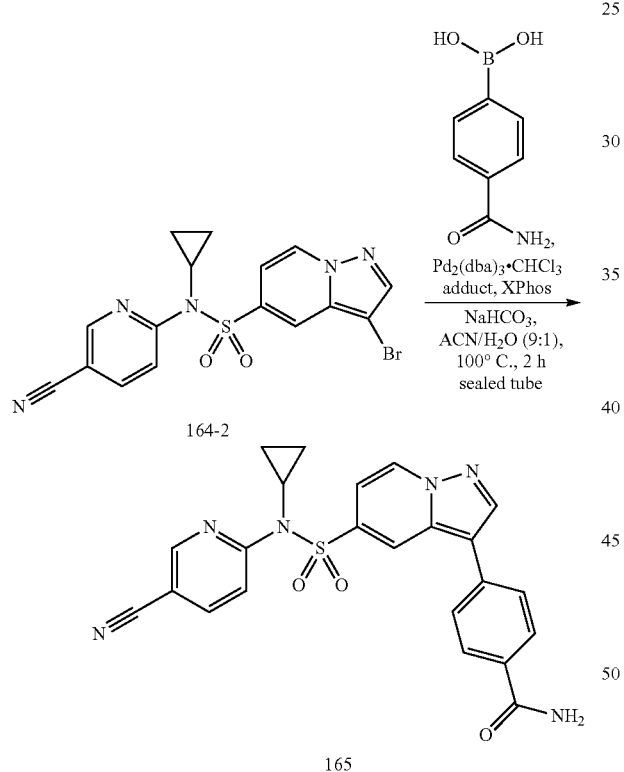

Compound 165 was prepared using the general procedure described in Suzuki Procedure I with the appropriate starting materials. Yield 46%. yellow solid. $^1$H NMR (400 MHz, DMSO-$d_6$): δ 8.93 (d, J=7.2 Hz, 1H), 8.87 (d, J=2.0 Hz, 1H), 8.67 (s, 1H), 8.40 (dd, J=2.0, 8.4 Hz, 1H), 8.32 (s, 1H), 7.98-8.06 (m, 3H), 7.74 (d, J=8.4 Hz, 2H), 7.64 (d, J=8.4 Hz, 1H), 7.38 (br s, 1H), 7.13 (dd, J=1.6, 8.0 Hz, 1H), 3.00-3.08 (m, 1H), 0.92-0.98 (m, 2H), 0.65-0.72 (m, 2H). ESI-LC/MS: m/z 459.21 (M+H); $R_t$=1.54 min [Waters Acquity UPLC with SQD; Waters Acquity UPLC BEH C18, 1.7 μm, 2.1×50 mm column; gradient of 97:03 $H_2O$ (0.05% TFA):$CH_3CN$ (0.05% TFA) hold for 0.2 min and to 65:35 $H_2O$ (0.05% TFA):$CH_3CN$ (0.05% TFA) in 1.0 min and to 02:98 $H_2O$ (0.05% TFA):$CH_3CN$ (0.05% TFA) in 2.0 min and hold for 1.85 min with flow rate of 0.6 mL/min]. HPLC purity=>99% at 254 nm; $R_t$=4.14 min [Waters HPLC with PDA; XBridge C-18, 3.5 μm, 4.6×100 mm column; gradient of 90:10 $H_2O$ (0.01 M Ammonium acetate):$CH_3CN$ to 05:95 $H_2O$ (0.01 M Ammonium acetate):$CH_3CN$ in 4.0 min and hold for 11.0 min with flow rate of 1.0 mL/min].

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:
1. A compound of Formula I,

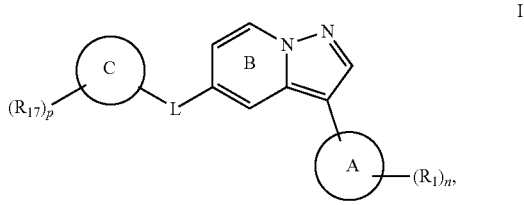

or a pharmaceutical acceptable salt, tautomer or stereoisomer thereof, wherein n is 0, 1, 2 or 3;

p is 0, 1, 2 or 3;

L is selected from the group consisting of *—$(CHR_3)_{1-3}$—, *—$CHR_3N(R_2)$—, *—$CHR_3O$—, *—$CHR_3S$—, *—$CHR_3S(O)$—, *—$CHR_3N(R_2)$ $CHR_3$—, *—C(O)—, *—$C(O)N(R_2)$—, *—C(O)N $(R_2)CHR_3$—, *—$N(R_2)$—, *—$N(R_2)CHR_3$—, *—$N(R_2)C(O)$—, *—$N(R_2)C(O)N(R_2)$—, *—N $(R_2)S(O)_2$—, wherein

* represents the point of attachment of L to the pyrazolo[1,5-a]pyridine fused ring depicted in Formula I;

each $R_2$ is independently selected from the group consisting of hydrogen, $C_{1-6}$alkyl, halo$C_{1-6}$alkyl, R—$C_{0-4}$alkylene, and R—$C_{0-4}$alkylene-C(O)—, wherein R is selected from the group consisting of hydroxyl, $C_{1-4}$alkoxy, amino, $C_{1-4}$alkylamino, $C_{3-6}$cycloalkyl, $C_{4-6}$heterocycloalkyl, and $C_{5-6}$heteroaryl, wherein the $C_{3-6}$cycloalkyl, $C_{4-6}$heterocycloalkyl, and $C_{5-6}$heteroaryl of R are each unsubstituted or substituted with 1-2 substituents independently selected from the group consisting of halo, amino, hydroxyl, $C_{1-4}$alkyl, $C_{1-4}$alkoxy, oxo, and $C_{5-6}$heteroaryl; and each $R_3$ is independently selected from the group consisting of hydrogen and $C_{1-4}$alkyl;

Ring A is selected from the group consisting of $C_{6-10}$aryl and $C_{5-10}$heteroaryl;

Ring C is selected from the group consisting of $C_{6-10}$aryl, $C_{6-10}$heteroaryl, $C_{5-7}$cycloalkyl, $C_{5-7}$heterocycloalkyl, and fused bicyclyl comprising a $C_{5-6}$heterocycloalky fused to a phenyl;

each $R_1$ is independently selected from the group consisting of halo, cyano, amino, $C_{1-4}$alkyl, $C_{1-4}$alkoxyl, halo-$C_{1-4}$alkyl, —C(O)N$R_7R_8$, —NHC(O)$R_{11}$, phenyl, and $C_{5-6}$heteroaryl; wherein the phenyl and $C_{5-6}$heteroaryl of $R_1$ are each unsubstituted or substituted with 1-2 substituents independently selected from the group consisting of $C_{1-4}$alkyl, amino, halo, and $C_{1-4}$alkylamino;

$R_7$ and $R_8$ are each independently selected from hydrogen, $C_{1-4}$alkyl and halo$C_{1-4}$alkyl;

$R_{11}$ is $C_{1-6}$alkyl, unsubstituted or substituted with 1-2 substituents independently selected from the group consisting of amino, $C_{3-6}$cycloalkyl and $C_{4-6}$heterocycloalkyl;

$R_{17}$ is selected from the group consisting of cyano, halo, $C_{1-4}$alkyl, halo-$C_{1-4}$alkyl, oxo, $C_{3-6}$cycloalkyl, and —SO$_2$—$C_{1-4}$alkyl.

2. The compound of claim 1, wherein L is selected from the group consisting of *—C(O)N($R_2$)— and *—N($R_2$)C(O)—, wherein each $R_2$ is independently selected from hydrogen, $C_{1-4}$alkyl, and R—$C_{0-4}$alkylene, and wherein R is selected from the group consisting of $C_{1-4}$alkylamino, $C_{3-6}$cycloalkyl, $C_{4-6}$heterocycloalkyl and $C_{5-6}$heteroaryl, each of which is unsubstituted or substituted with 1-2 substituents independently selected from the group consisting of halo, amino, hydroxyl, $C_{1-4}$alkyl, $C_{1-4}$alkoxy, oxo, and $C_{5-6}$heteroaryl.

3. The compound of claim 1, wherein L is selected from *—C(O)N(CH$_3$)—*—C(O)N(CH$_2$CH$_3$)—, *—C(O)N(CH(CH$_3$)$_2$)—, *—C(O)N(NH(CH$_3$))—, and *—N(CH$_3$)C(O)—.

4. The compound according to claim 1, wherein Ring A is selected from the group consisting of phenyl, pyridinyl, pyrimidinyl, pyrazinyl, pyridazinyl, pyrrolopyridinyl, and indazolyl, each of which is unsubstituted or substituted by $(R_1)_n$.

5. The compound according to claim 1, wherein Ring C is selected from the group consisting of

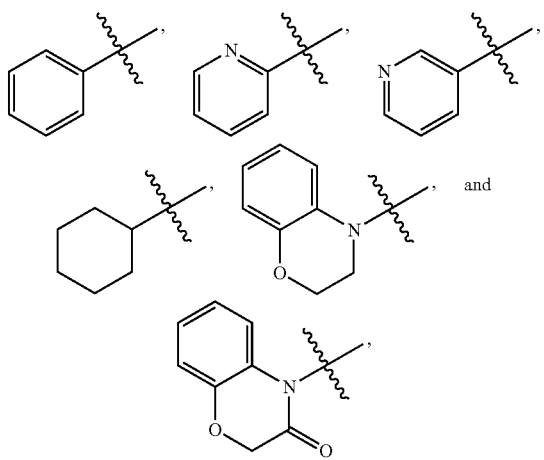

each of which is unsubstituted or substituted by $(R_{17})_p$.

6. The compound according to claim 1, wherein Ring C is selected from the group consisting of phenyl and pyridinyl, each of which is unsubstituted or substituted by $(R_{17})_p$.

7. The compound according to claim 1, wherein each $R_1$ is independently selected from the group consisting of trifluoromethyl, cyano, —NH$_2$—, —C(O)NH$_2$, —C(O)NHCH$_3$, —C(O)N(CH$_3$)$_2$, and —NHC(O)CH(NH$_2$)(CH$_3$).

8. The compound according to claim 1, wherein each $R_{17}$ is independently selected from the group consisting of cyano, halo, $C_{1-4}$alkyl, halo$C_{1-4}$alkyl, —SO$_2$—$C_{1-4}$alkyl, and $C_{3-6}$cycloalkyl.

9. The compound of claim 1, wherein the compound is of Formula Ia:

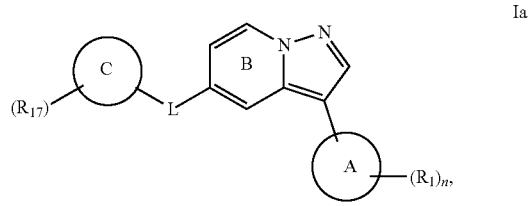

or a pharmaceutical acceptable salt, tautomer or stereoisomer thereof, wherein n is 1 or 2;

n is 1 or 2;

Ring A is phenyl, pyridinyl, or pyrimidinyl;

Ring C is phenyl or pyridinyl;

L is *—C(O)N$R_2$— or *—N$R_2$C(O)—, wherein $R_2$ is selected from hydrogen, $C_{1-4}$alkyl, $C_{1-4}$alkylamino-($C_{0-4}$)alkylene, $C_{3-6}$cycloalkyl-($C_{0-4}$)alkylene, $C_{4-6}$heterocycloalkyl-($C_{0-4}$)alkylene, wherein the $C_{4-6}$heterocycloalkyl is selected from the group consisting of piperazinyl, morpholinyl, thiomorpholinyl, tetrahydropyranyl, and oxetanyl, and wherein the $C_{3-6}$cycloalkyl is selected from cyclopropyl, cyclobutyl, cyclopentyl and cyclohexyl;

each $R_1$ is independently *—C(O)N$R_7R_8$ or —NH$_2$—, wherein $R_7$ and $R_8$ are each independently hydrogen or $C_{1-4}$alkyl; and $R_{17}$ is selected from the group consisting of cyano, halo, —NH$_2$—, —C(O)NH$_2$, —C(O)NH(CH$_3$), and —C(O)N(CH$_3$)$_2$.

10. The compound of claim 9, wherein L is selected from *—C(O)N(CH$_3$)—*—C(O)N(CH$_2$CH$_3$)—, *—C(O)N(CH(CH$_3$)$_2$)—, *—C(O)N(NH(CH$_3$))—, and *—N(CH$_3$)C(O)—.

11. The compound of claim 1, wherein the compound, or a pharmaceutical acceptable salt, tautomer or stereoisomer thereof, is selected from the group consisting of:

N-(4-cyanophenyl)-N-methyl-3-(4-(trifluoromethyl)phenyl)pyrazolo[1,5-a]pyridine-5-carboxamide;

4-fluoro-N-methyl-N-((3-(4-(trifluoromethyl)phenyl)pyrazolo[1,5-a]yridine-5-yl)methyl)aniline;

N-(4-chlorophenyl)-N-methyl-3-(4-(trifluoromethyl)phenyl)pyrazolo[1,5-a]pyridine-5-carboxamide;

N-(4-fluorophenyl)-N-methyl-3-(4-(trifluoromethyl)phenyl)pyrazolo[1,5-a]pyridine-5-carboxamide;

N-methyl-N-(5-methylpyridin-2-yl)-3-(4-(trifluoromethyl)phenyl)pyrazolo[1,5-a]pyridine-5-carboxamide;

4-chloro-N-methyl-N-((3-(4-(trifluoromethyl)phenyl)pyrazolo[1,5-a]yridine-5-yl)methyl)aniline;

N,5-dimethyl-N-((3-(4-(trifluoromethyl)phenyl)pyrazolo[1,5-a]yridine-5-yl)methyl)yridine-2-amine;

5-((4-fluorophenoxy)methyl)-3-(4-(trifluoromethyl)phenyl)pyrazolo[1,5-a]pyridine;

N-(4-cyanophenyl)-N-(2-methoxyethyl)-3-(4-(trifluoromethyl)phenyl)pyrazolo[1,5-a]pyridine-5-carboxamide;

N-(4-cyanophenyl)-N-(2-(dimethylamino)ethyl)-3-(4-(trifluoromethyl)phenyl)pyrazolo[1,5-a]pyridine-5-carboxamide;
N-(4-cyanophenyl)-N-((tetrahydro-2H-pyran-4-yl)methyl)-3-(4-(trifluoromethyl)phenyl)pyrazolo[1,5-a]pyridine-5-carboxamide;
N-(4-(methylsulfonyl)phenyl)-N-((tetrahydro-2H-pyran-4-yl)methyl)-3-(4-(trifluoromethyl)phenyl)pyrazolo[1,5-a]pyridine-5-carboxamide;
N-(5-cyanopyridin-2-yl)-N-methyl-3-(4-(trifluoromethyl)phenyl)pyrazolo[1,5-a]pyridine-5-carboxamide;
N-methyl-N-(5-methylpyridin-3-yl)-3-(4-(trifluoromethyl)phenyl)pyrazolo[1,5-a]pyridine-5-carboxamide;
5-(((5-methylpyridin-2-yl)oxy)methyl)-3-(4-(trifluoromethyl)phenyl)pyrazolo[1,5-a]pyridine;
5-(4-fluorophenethyl)-3-(4-(trifluoromethyl)phenyl)pyrazolo[1,5-a]pyridine;
N-(4-cyanophenyl)-N-methyl-3-(1-methyl-1H-indazol-5-yl)pyrazolo[1,5-a]pyridine-5-carboxamide;
3-(6-acetamidopyridin-3-yl)-N-(4-cyanophenyl)-N-methylpyrazolo[1,5-a]pyridine-5-carboxamide;
3-(4-carbamoylphenyl)-N-(4-cyanophenyl)-N-methylpyrazolo[1,5-a]pyridine-5-carboxamide;
3-(4-carbamoylphenyl)-N-(4-fluorophenyl)-N-methylpyrazolo[1,5-a]pyridine-5-carboxamide;
5-(((4-fluorophenyl)thio)methyl)-3-(4-(trifluoromethyl)phenyl)pyrazolo[1,5-a]pyridine;
5-(((4-fluorophenyl)sulfinyl)methyl)-3-(4-(trifluoromethyl)phenyl)pyrazolo[1,5-a]pyridine;
3-(4-(1H-pyrazol-5-yl)phenyl)-N-(4-cyanophenyl)-N-methylpyrazolo[1,5-a]pyridine-5-carboxamide;
N-(4-cyanophenyl)-N-methyl-3-(5-(trifluoromethyl)pyridine-2-yl)pyrazolo[1,5-a]pyridine-5-carboxamide;
N-(5-cyanopyridin-2-yl)-N-methyl-3-(5-(trifluoromethyl)pyridine-2-yl)pyrazolo[1,5-a]pyridine-5-carboxamide;
(S)-3-(4-(2-aminopropanamido)phenyl)-N-(4-cyanophenyl)-N-methylpyrazolo[1,5-a]pyridine-5-carboxamide;
3-(5-carbamoylpyridin-2-yl)-N-(4-cyanophenyl)-N-methylpyrazolo[1,5-a]pyridine-5-carboxamide;
4-cyano-N-methyl-N-(3-(4-(trifluoromethyl)phenyl)pyrazolo[1,5-a]yridine-5-yl)benzamide;
4-fluoro-N-methyl-N-(3-(4-(trifluoromethyl)phenyl)pyrazolo[1,5-a]pyridine-5-yl)benzamide;
4-cyano-N-methyl-N-(3-(4-(trifluoromethyl)phenyl)pyrazolo[1,5-a]pyridine-5-yl)benzenesulfonamide;
4-fluoro-N-methyl-N-(3-(4-(trifluoromethyl)phenyl)pyrazolo[1,5-a]pyridine-5-yl)benzenesulfonamide;
3-(4-carbamoylphenyl)-N-(5-cyanopyridin-2-yl)-N-methylpyrazolo[1,5-a]pyridine-5-carboxamide;
N-methyl-3-(4-(trifluoromethyl)phenyl)-N-(5-(trifluoromethyl)yridine-2-yl)pyrazolo[1,5-a]pyridine-5-carboxamide;
N-methyl-N-(5-(methylsulfonyl)pyridine-2-yl)-3-(4-(trifluoromethyl)phenyl)pyrazolo[1,5-a]pyridine-5-carboxamide;
N-(4-fluorobenzyl)-3-(4-(trifluoromethyl)phenyl)pyrazolo[1,5-a]yridine-5-amine
N-(4-fluorobenzyl)-3-(4-(trifluoromethyl)phenyl)pyrazolo[1,5-a]yridine-5-amine;
N-methyl-6-(trifluoromethyl)-N-(3-(4-(trifluoromethyl)phenyl)pyrazolo[1,5-a]yridine-5-yl)nicotinamide;
N-methyl-5-(trifluoromethyl)-N-(3-(4-(trifluoromethyl)phenyl)pyrazolo[1,5-a]yridine-5-yl)picolinamide;
4-cyano-N-((tetrahydro-2H-pyran-4-yl)methyl)-N-(3-(4-(trifluoromethyl)phenyl)pyrazolo[1,5-a]pyridine-5-yl)benzamide;
N-(4-cyanophenyl)-N-methyl-3-(1H-pyrrolo[2,3-b]pyridin-5-yl)pyrazolo[1,5-a]pyridine-5-carboxamide;
3-(6-aminopyridin-3-yl)-N-(4-cyanophenyl)-N-methylpyrazolo[1,5-a]pyridine-5-carboxamide;
3-(4-aminophenyl)-N-(4-cyanophenyl)-N-methylpyrazolo[1,5-a]pyridine-5-carboxamide;
3-(4-(2-aminoacetamido)phenyl)-N-(4-cyanophenyl)-N-methylpyrazolo[1,5-a]pyridine-5-carboxamide;
(R)-3-(4-(2-aminopropanamido)phenyl)-N-(4-cyanophenyl)-N-methylpyrazolo[1,5-a]pyridine-5-carboxamide;
(S)-3-(4-(2-amino-3-methylbutanamido)phenyl)-N-(4-cyanophenyl)-N-methylpyrazolo[1,5-a]pyridine-5-carboxamide;
(S)-3-(4-(2-amino-2-cyclohexylacetamido)phenyl)-N-(4-cyanophenyl)-N-methylpyrazolo[1,5-a]pyridine-5-carboxamide;
3-(4-fluorophenyl)-1-methyl-1-(3-(4-(trifluoromethyl)phenyl)pyrazolo[1,5-a]pyridin-5-yl)urea;
6-(1,1-difluoroethyl)-N-methyl-N-(3-(4-(trifluoromethyl)phenyl)pyrazolo[1,5-a]pyridin-5-yl)nicotinamide;
6-cyclopropyl-N-methyl-N-(3-(4-(trifluoromethyl)phenyl)pyrazolo[1,5-a]pyridin-5-yl)nicotinamide;
4-cyclopropyl-N-methyl-N-(3-(4-(trifluoromethyl)phenyl)pyrazolo[1,5-a]pyridin-5-yl)benzamide;
5-fluoro-N-methyl-N-(3-(4-(trifluoromethyl)phenyl)pyrazolo[1,5-a]pyridin-5-yl)picolinamide;
N-methyl-4-(methylsulfonyl)-N-(3-(4-(trifluoromethyl)phenyl)pyrazolo[1,5-a]pyridin-5-yl)benzamide;
N-(5-cyanopyridin-2-yl)-N-methyl-3-(1H-pyrrolo[2,3-b]pyridin-5-yl)pyrazolo[1,5-a]pyridine-5-carboxamide;
3-(6-aminopyridin-3-yl)-N-(5-cyanopyridin-2-yl)-N-methylpyrazolo[1,5-a]pyridine-5-carboxamide;
4-chloro-N-methyl-N-(3-(4-(trifluoromethyl)phenyl)pyrazolo[1,5-a]pyridin-5-yl)benzamide;
N-(3-(4-carbamoylphenyl)pyrazolo[1,5-a]pyridin-5-yl)-4-fluoro-N-methylbenzamide
4-fluoro-N-methyl-N-(3-(4-(5-(methylamino)-1,3,4-thiadiazol-2-yl)phenyl)pyrazolo[1,5-a]pyridin-5-yl)benzamide;
N-methyl-N-(5-(methylsulfonyl)pyridin-2-yl)-3-(1H-pyrrolo[2,3-b]pyridin-5-yl)pyrazolo[1,5-a]pyridine-5-carboxamide;
N-(5-cyanopyridin-2-yl)-N-methyl-3-(5-methylpyridin-2-yl)pyrazolo[1,5-a]pyridine-5-carboxamide;
N-(5-cyanopyridin-2-yl)-3-(5-methoxypyridin-2-yl)-N-methylpyrazolo[1,5-a]pyridine-5-carboxamide;
3-(5-carbamoylpyridin-2-yl)-N-(5-cyanopyridin-2-yl)-N-methylpyrazolo[1,5-a]pyridine-5-carboxamide;
3-(4-carbamoylphenyl)-N-methyl-N-(5-(trifluoromethyl)pyridin-2-yl)pyrazolo[1,5-a]pyridine-5-carboxamide;
3-(4-carbamoylphenyl)-N-methyl-N-(5-methylpyridin-2-yl)pyrazolo[1,5-a]pyridine-5-carboxamide;
N-(4-fluorophenyl)-N-methyl-3-(4-(methylcarbamoyl)phenyl)pyrazolo[1,5-a]pyridine-5-carboxamide;
4-(5-(1-(methyl(5-methylpyridin-2-yl)amino)ethyl)pyrazolo[1,5-a]pyridin-3-yl)benzamide;
4-(5-(1-(7-fluoro-3-oxo-2H-benzo[b][1,4]oxazin-4(3H)-yl)ethyl)pyrazolo[1,5-a]pyridin-3-yl)benzamide;
N-(4-cyanophenyl)-N-methyl-3-(4-(methylcarbamoyl)phenyl)pyrazolo[1,5-a]pyridine-5-carboxamide;
N-(4-(5-(1-(methyl(5-methylpyridin-2-yl)amino)ethyl)pyrazolo[1,5-a]pyridin-3-yl)phenyl)acetamide;
3-(4-acetamidophenyl)-N-(5-cyanopyridin-2-yl)-N-methylpyrazolo[1,5-a]pyridine-5-carboxamide;
4-(5-(7-fluoro-3,4-dihydro-2H-benzo[b][1,4]oxazine-4-carbonyl)pyrazolo[1,5-a]pyridin-3-yl)benzamide;

4-(5-(7-fluoro-3-methyl-3,4-dihydro-2H-benzo[b][1,4]
oxazine-4-carbonyl)pyrazolo[1,5-a]pyridin-3-yl)benzamide;

4-(5-(7-fluoro-3,4-dihydro-2H-benzo[b][1,4]oxazine-4-carbonyl)pyrazolo[1,5-a]pyridin-3-yl)-N-methylbenzamide;

4-(5-(7-fluoro-3-methyl-3,4-dihydro-2H-benzo[b][1,4]
oxazine-4-carbonyl)pyrazolo[1,5-a]pyridin-3-yl)-N-methylbenzamide;

N-(5-cyanopyridin-2-yl)-N-methyl-3-(4-(methylcarbamoyl)phenyl)pyrazolo[1,5-a]pyridine-5-carboxamide;

N-(5-cyanopyridin-2-yl)-3-(4-(methylcarbamoyl)phenyl)-N-(oxetan-3-yl)pyrazolo[1,5-a]pyridine-5-carboxamide;

N-(1-(1H-pyrazol-1-yl)propan-2-yl)-3-(4-carbamoylphenyl)-N-(5-cyanopyridin-2-yl)pyrazolo[1,5-a]pyridine-5-carboxamide;

3-(6-amino-5-fluoropyridin-3-yl)-N-(4-cyanophenyl)-N-methylpyrazolo[1,5-a]pyridine-5-carboxamide;

3-(4-amino-3,5-dimethylphenyl)-N-(4-cyanophenyl)-N-methylpyrazolo[1,5-a]pyridine-5-carboxamide;

3-(6-amino-5-methylpyridin-3-yl)-N-(4-cyanophenyl)-N-methylpyrazolo[1,5-a]pyridine-5-carboxamide;

3-(4-carbamoylphenyl)-N-(4-cyanocyclohexyl)-N-methylpyrazolo[1,5-a]pyridine-5-carboxamide;

3-(2-aminopyrimidin-5-yl)-N-(4-cyanophenyl)-N-methylpyrazolo[1,5-a]pyridine-5-carboxamide;

3-(6-amino-5-(trifluoromethyl)pyridin-3-yl)-N-(5-cyanopyridin-2-yl)-N-methylpyrazolo[1,5-a]pyridine-5-carboxamide;

3-(6-amino-5-cyanopyridin-3-yl)-N-(5-cyanopyridin-2-yl)-N-methylpyrazolo[1,5-a]pyridine-5-carboxamide;

3-(6-amino-5-chloropyridin-3-yl)-N-(5-cyanopyridin-2-yl)-N-methylpyrazolo[1,5-a]pyridine-5-carboxamide;

3-(6-amino-5-(dimethylcarbamoyl)pyridin-3-yl)-N-(5-cyanopyridin-2-yl)-N-methylpyrazolo[1,5-a]pyridine-5-carboxamide;

3-(6-amino-5-methoxypyridin-3-yl)-N-(5-cyanopyridin-2-yl)-N-methylpyrazolo[1,5-a]pyridine-5-carboxamide;

3-(4-carbamoylphenyl)-N-(4-chloro-2-formylphenyl)-N-methylpyrazolo[1,5-a]pyridine-5-carboxamide;

N-(5-Cyanopyridin-2-yl)-N-ethyl-3-(4-(methylcarbamoyl)phenyl)pyrazolo[1,5-a]pyridine-5-carboxamide;

N-(5-cyanopyridin-2-yl)-N-isopropyl-3-(4-(methylcarbamoyl)phenyl)pyrazolo[1,5-a]pyridine-5-carboxamide;

5-(5-(1-(4-cyanophenyl)-2-methylhydrazinecarbonyl)
pyrazolo[1,5-a]pyridin-3-yl)-N-methyl picolinamide;

N-(5-cyanopyridin-2-yl)-N-cyclopropyl-3-(4-(methylcarbamoyl)phenyl)pyrazolo[1,5-a]pyridine-5-carboxamide;

N-(5-cyanopyridin-2-yl)-N-methyl-3-(4-(methylcarbamoyl)phenyl)pyrazolo[1,5-a]pyridine-5-carboxamide;

N-ethyl-N-(5-fluoropyridin-2-yl)-3-(4-(methylcarbamoyl)phenyl)pyrazolo[1,5-a]pyridine-5-carboxamide; and N-ethyl-3-(4-(methylcarbamoyl)phenyl)-N-(5-(trifluoromethyl)pyridin-2-yl)pyrazolo[1,5-a]pyridine-5-carboxamide.

12. The compound of claim 1, wherein the compound, a pharmaceutical acceptable salt, tautomer, or stereoisomer thereof, is selected from the group consisting of:

3-(4-carbamoylphenyl)-N-(5-cyanopyridin-2-yl)-N-methylpyrazolo[1,5-a]pyridine-5-carboxamide;

N-(4-cyanophenyl)-N-methyl-3-(1H-pyrrolo[2,3-b]pyridin-5-yl)pyrazolo[1,5-a]pyridine-5-carboxamide;

3-(6-aminopyridin-3-yl)-N-(4-cyanophenyl)-N-methylpyrazolo[1,5-a]pyridine-5-carboxamide;

(R)-3-(4-(2-aminopropanamido)phenyl)-N-(4-cyanophenyl)-N-methylpyrazolo[1,5-a]pyridine-5-carboxamide;

N-(5-cyanopyridin-2-yl)-N-methyl-3-(1H-pyrrolo[2,3-b]pyridin-5-yl)pyrazolo[1,5-a]pyridine-5-carboxamide;

N-(5-cyanopyridin-2-yl)-N-methyl-3-(4-(methylcarbamoyl)phenyl)pyrazolo[1,5-a]pyridine-5-carboxamide;

3-(2-aminopyrimidin-5-yl)-N-(4-cyanophenyl)-N-methylpyrazolo[1,5-a]pyridine-5-carboxamide; and 3-(6-amino-5-(dimethylcarbamoyl)pyridin-3-yl)-N-(5-cyanopyridin-2-yl)-N-methylpyrazolo[1,5-a]pyridine-5-carboxamide.

13. The compound of claim 1, wherein the compound, a pharmaceutical acceptable salt, tautomer, or stereoisomer thereof, is selected from the group consisting of:

N-(5-Cyanopyridin-2-yl)-N-ethyl-3-(4-(methylcarbamoyl)phenyl)pyrazolo[1,5-a]pyridine-5-carboxamide;

N-(5-cyanopyridin-2-yl)-N-isopropyl-3-(4-(methylcarbamoyl)phenyl)pyrazolo[1,5-a]pyridine-5-carboxamide;

5-(5-(1-(4-cyanophenyl)-2-methylhydrazinecarbonyl)
pyrazolo[1,5-a]pyridin-3-yl)-N-methyl picolinamide;

N-(5-cyanopyridin-2-yl)-N-cyclopropyl-3-(4-(methylcarbamoyl)phenyl)pyrazolo[1,5-a]pyridine-5-carboxamide;

N-(5-cyanopyridin-2-yl)-N-methyl-3-(4-(methylcarbamoyl)phenyl)pyrazolo[1,5-a]pyridine-5-carboxamide;

N-ethyl-N-(5-fluoropyridin-2-yl)-3-(4-(methylcarbamoyl)phenyl)pyrazolo[1,5-a]pyridine-5-carboxamide;

N-ethyl-3-(4-(methylcarbamoyl)phenyl)-N-(5-(trifluoromethyl)pyridin-2-yl)pyrazolo[1,5-a]pyridine-5-carboxamide;

N-(4-Cyanophenyl)-N-methyl-3-(6-(methylcarbamoyl)
pyridin-3-yl)pyrazolo[1,5-a]pyridine-5-carboxamide 3-(5-Amino-6-chloropyridin-3-yl)-N-(5-cyanopyridin-2-yl)-N-methylpyrazolo[1,5-a]pyridine-5-carboxamide;

N-(4-Chlorophenyl)-N-methyl-3-(4-(methylcarbamoyl)
phenyl)pyrazolo[1,5-a]pyridine-5-carboxamide;

3-(4-Carbamoylphenyl)-N-(4-chlorophenyl)-N-methylpyrazolo[1,5-a]pyridine-5-carboxamide;

4-(5-((5-Cyanopyridin-2-yl)(methyl)carbamoyl)pyrazolo
[1,5-a]pyridin-3-yl)benzoic acid;

N-(5-Cyanopyridin-2-yl)-3-(4-((2-hydroxyethyl)carbamoyl)phenyl)-N-methylpyrazolo[1,5-a]pyridine-5-carboxamide;

N-Methyl-3-(4-(methylcarbamoyl)phenyl)-N-(4-(trifluoromethyl)phenyl)pyrazolo[1,5-a]pyridine-5-carboxamide;

3-(4-((2-Aminoethyl)carbamoyl)phenyl)-N-(5-cyanopyridin-2-yl)-N-methylpyrazolo[1,5-a]pyridine-5-carboxamide;

3-(4-Carbamoylphenyl)-N-(4-cyanophenyl)-N-(2-hydroxyethyl)pyrazolo[1,5-a]pyridine-5-carboxamide;

N-(5-Cyanopyridin-2-yl)-3-(4-(methylcarbamoyl)phenyl)pyrazolo[1,5-a]pyridine-5-carboxamide;

3-(6-Chloro-5-(methylsulfonamido) pyridin-3-yl)-N-(5-cyanopyridin-2-yl)-N-methylpyrazolo [1,5-a]pyridine-5-carboxamide;

3-(2-Aminopyridin-4-yl)-N-(5-cyanopyridin-2-yl)-N-methylpyrazolo[1,5-a]pyridine-5-carboxamide;

N-(4-Chlorophenyl)-N-methyl-3-(6-(methylcarbamoyl)
pyridin-3-yl)pyrazolo[1,5-a]pyridine-5-carboxamide;

N-(4-Cyanophenyl)-N-(2-hydroxyethyl)-3-(4-(methylcarbamoyl)phenyl)pyrazolo[1,5-a]pyridine-5-carboxamide;

N-(5-(2-Aminoethoxy)pyridin-2-yl)-N-methyl-3-(4-(methylcarbamoyl)phenyl)pyrazolo[1,5-a]pyridine-5-carboxamide;

N-(5-Cyanopyridin-2-yl)-N-cyclobutyl-3-(4-(methylcarbamoyl)phenyl)pyrazolo[1,5-a]pyridine-5-carboxamide;

N-(5-Cyanopyridin-2-yl)-N-methyl-3-(4-(piperidin-4-ylcarbamoyl)phenyl)pyrazolo[1,5-a]pyridine-5-carboxamide;

N-(5-Cyanopyridin-2-yl)-N-methyl-3-(4-((2-(methylamino)ethyl)carbamoyl)phenyl)pyrazolo [1,5-a]pyridine-5-carboxamide;

N-(5-cyanopyridin-2-yl)-3-(4-((2-(dimethylamino)ethyl)carbamoyl)phenyl)-N-methylpyrazolo[1,5-a]pyridine-5-carboxamide;

N-(4-Chlorophenyl)-N-cyclopropyl-3-(4-(methylcarbamoyl)phenyl)pyrazolo[1,5-a]pyridine-5-carboxamide;

N-(5-Cyanopyridin-2-yl)-N-(cyclopropylmethyl)-3-(4-(methylcarbamoyl)phenyl)pyrazolo[1,5-a]pyridine-5-carboxamide;

N-(4-Cyanophenyl)-N-cyclopropyl-3-(4-(methylcarbamoyl)phenyl)pyrazolo[1,5-a]pyridine-5-carboxamide;

N-(tert-Butyl)-N-(5-cyanopyridin-2-yl)-3-(4-(methylcarbamoyl)phenyl)pyrazolo[1,5-a]pyridine-5-carboxamide;

3-(4-Carbamoylphenyl)-N-(5-cyanopyridin-2-yl)-N-cyclopropylpyrazolo[1,5-a]pyridine-5-carboxamide;

N-(5-Cyanopyridin-2-yl)-N-cyclopropyl-3-(4-(isopropylcarbamoyl)phenyl)pyrazolo[1,5-a]pyridine-5-carboxamide;

N-(6-Methoxypyridin-3-yl)-N-methyl-3-(4-(methylcarbamoyl)phenyl)pyrazolo[1,5-a] pyridine-5-carboxamide;

N-(5-Cyanopyridin-2-yl)-N-cyclopropyl-3-(4-(cyclopropylcarbamoyl)phenyl)pyrazolo[1,5a]pyridine-5-carboxamide;

N-(5-Chloropyridin-2-yl)-N-cyclopropyl-3-(4-(methylcarbamoyl)phenyl)pyrazolo[1,5-a]pyridine-5-carboxamide;

N-Cyclopropyl-N-(5-fluoropyridin-2-yl)-3-(4-(methylcarbamoyl)phenyl)pyrazolo[1,5 a] pyridine-5-carboxamide;

N-(5-Cyanopyridin-2-yl)-N-cyclopentyl-3-(4-(methylcarbamoyl)phenyl)pyrazolo[1,5-a] pyridine-5-carboxamide;

N-(5-Cyanopyridin-2-yl)-N-cyclopropyl-3-(4-(ethylcarbamoyl)phenyl)pyrazolo[1,5-a]pyridine-5-carboxamide;

6-(N-Cyclopropyl-3-(4-(methylcarbamoyl)phenyl)pyrazolo[1,5-a]pyridine-5-carboxamido) nicotinic acid;

N-(5-Carbamoylpyridin-2-yl)-N-cyclopropyl-3-(4-(methylcarbamoyl)phenyl)pyrazolo[1,5-a]pyridine-5-carboxamide;

N-Cyclopropyl-N-(3,4-difluorophenyl)-3-(4-(methylcarbamoyl)phenyl)pyrazolo[1,5-a]pyridine-5-carboxamide;

N-(5-Cyanopyridin-2-yl)-N-cyclopropyl-3-(4-(oxetan-3-ylcarbamoyl)phenyl)pyrazolo[1,5-a]pyridine-5-carboxamide;

N-Cyclopropyl-3-(4-(methylcarbamoyl)phenyl)-N-(5-(trifluoromethyl)pyridin-2-yl)pyrazolo [1,5-a]pyridine-5-carboxamide;

N-(5-Cyanopyridin-2-yl)-N-cyclopropyl-3-(5-(methylcarbamoyl)pyridin-2-yl)pyrazolo[1,5-a]pyridine-5-carboxamide;

3-(4-carbamoylphenyl)-N-(4-cyanophenyl)-N-cyclopropylpyrazolo[1,5-a]pyridine-5-carboxamide;

3-(4-Carbamoylphenyl)-N-cyclopropyl-N-(3,4-difluorophenyl)pyrazolo[1,5-a]pyridine-5-carboxamide;

N-Cyclopropyl-3-(4-(methylcarbamoyl)phenyl)-N-(5-methylpyridin-2-yl)pyrazolo[1,5-a] pyridine-5-carboxamide;

N-(4-Cyanophenyl)-N-cyclopropyl-3-(6-(methylcarbamoyl)pyridin-3-yl)pyrazolo[1,5-a] pyridine-5-carboxamide;

3-(6-Carbamoylpyridin-3-yl)-N-(4-cyanophenyl)-N-cyclopropylpyrazolo[1,5-a]pyridine-5-carboxamide;

3-(5-Carbamoylpyridin-2-yl)-N-(5-cyanopyridin-2-yl)-N-cyclopropylpyrazolo[1,5-a]pyridine-5-carboxamide;

N-(5-cyanopyridin-2-yl)-N-ethyl-3-(4-[N-methylsulfamoyl]phenyl)pyrazolo[1,5-a]pyridine-5-carboxamide;

N-(4-Cyanophenyl)-N-cyclopropyl-3-(5-(methylcarbamoyl)pyridin-2-yl)pyrazolo[1,5-a] pyridine-5-carboxamide;

3-(5-Carbamoylpyridin-2-yl)-N-(4-cyanophenyl)-N-cyclopropylpyrazolo[1,5-a]pyridine-5-carboxamide;

N-(4-Chlorophenyl)-N-cyclopropyl-3-(6-(methylcarbamoyl)pyridin-3-yl)pyrazolo[1,5-a] pyridine-5-carboxamide;

N-(5-Cyanopyridin-2-yl)-N-cyclobutyl-3-(6-(methylcarbamoyl)pyridin-3-yl)pyrazolo[1,5-a]pyridine-5-carboxamide;

N-(4-Cyanophenyl)-N-cyclobutyl-3-(6-(methylcarbamoyl)pyridin-3-yl)pyrazolo[1,5-a]pyridine-5-carboxamide;

N-(4-Cyanophenyl)-N-isopropyl-3-(6-(methylcarbamoyl)pyridin-3-yl)pyrazolo[1,5-a]pyridine-5-carboxamide;

5-Cyano-N-cyclopropyl-N-(3-(4-(methylcarbamoyl)phenyl)pyrazolo[1,5-a]pyridin-5-yl) picolinamide;

N-(5-Cyanopyridin-2-yl)-N-isopropyl-3-(6-(methylcarbamoyl)pyridin-3-yl)pyrazolo[1,5-a]pyridine-5-carboxamide;

N-(5-Cyano-6-methoxypyridin-2-yl)-N-cyclopropyl-3-(4-(methylcarbamoyl)phenyl)pyrazolo [1,5-a]pyridine-5-carboxamide;

N-(5-cyanopyridin-2-yl)-N-ethyl-3-(6-[methylcarbamoyl]pyridin-3-yl)pyrazolo[1,5-a]pyridine-5-carboxamide;

N-(5-fluoropyridin-2-yl)-N-isopropyl-3-(4-(methylcarbamoyl)phenyl)pyrazolo[1,5-a]pyridine-5-carboxamide;

N-Isopropyl-3-(6-(methylcarbamoyl)pyridin-3-yl)-N-(5-(trifluoromethyl)pyridin-2-yl)pyrazolo [1,5-a]pyridine-5-carboxamide;

N-Isopropyl-3-(4-(methylcarbamoyl)phenyl)-N-(5-(trifluoromethyl)pyridin-2-yl)pyrazolo[1,5-a]pyridine-5-carboxamide;

N-(5-cyanopyridin-2-yl)-N-isopropyl-3-(5-(methylcarbamoyl)pyridin-2-yl)pyrazolo[1,5-a]pyridine-5-carboxamide;

N-(5-Cyanopyridin-2-yl)-N-cyclobutyl-3-(5-(methylcarbamoyl)pyridin-2-yl)pyrazolo[1,5-a]pyridine-5-carboxamide;

N-(5-fluoropyridin-2-yl)-N-isopropyl-3-(6-(methylcarbamoyl)pyridin-3-yl)pyrazolo[1,5-a]pyridine-5-carboxamide;

N-ethyl-3-(6-(methylcarbamoyl)pyridin-3-yl)-N-(5-(trifluoromethyl)pyridin-2-yl)pyrazolo[1,5-a]pyridine-5-carboxamide;

N-(5-cyanopyridin-2-yl)-N-ethyl-3-(4-(methylsulfonyl) phenyl)pyrazolo[1,5-a]pyridine-5-carboxamide;

N-ethyl-N-(5-fluoropyridin-2-yl)-3-(6-(methylcarbamoyl)pyridin-3-yl)pyrazolo[1,5-a]pyridine-5-carboxamide;

N-cyclobutyl-3-(4-(methylcarbamoyl)phenyl)-N-(5-(trifluoromethyl)pyridin-2-yl)pyrazolo[1,5-a]pyridine-5-carboxamide;

N N-cyclobutyl-3-(6-(methylcarbamoyl)pyridin-3-yl)-N-(5-(trifluoromethyl)pyridin-2-yl)pyrazolo[1,5-a]pyridine-5-carboxamide;

N-(5-cyano-6-(2-hydroxyethoxy)pyridin-2-yl)-N-ethyl-3-(4-(methylcarbamoyl)phenyl)pyrazolo[1,5-a]pyridine-5-carboxamide;

4-(5-(N-(5-Cyanopyridin-2-yl)-N-methylsulfamoyl)pyrazolo[1,5-a]pyridin-3-yl)-N-methyl benzamide;

4-(5-(N-(5-Cyanopyridin-2-yl)-N-cyclopropylsulfamoyl)pyrazolo[1,5-a]pyridin-3-yl)-N-methylbenzamide; and 4-(5-(N-(5-cyanopyridin-2-yl)-N-cyclopropylsulfamoyl)pyrazolo[1,5-a]pyridin-3-yl)benzamide.

14. A pharmaceutical composition comprising at least one compound of claim 1 or a pharmaceutically acceptable salt thereof, and a pharmaceutically acceptable carrier, diluent or excipient.

15. A method for treating or preventing malaria, comprising administering to a subject a therapeutically effective amount of a compound according to claim 1, wherein the administering may be in combination with a second agent.

16. A method for treating or preventing malaria, comprising administering to a subject a therapeutically effective amount of a pharmaceutical composition according to claim 14, wherein the administering may be in combination with a second agent.

17. The method according to claim 16, wherein the second agent is an antimalarial drug selected from artemisinin, artemether, artesunate, arteflene, dihydroartemisinin, chlorproguanil, trimethoprim, chloroquine, quinine, mefloquine, amodiaquine, atovaquone, proguanil, lumefantrine, piperaquine, pyronaridine, halofantrine, pyrimethamine-sulfadoxine, quinacrine, pyrimethamine-dapsone, quinidine, amopyroquine, sulphonamides, primaquine, ferroquine, tafenoquine, arterolane, and pyronaridine.

* * * * *